United States Patent
Moore et al.

(12)

(10) Patent No.: US 6,713,277 B1
(45) Date of Patent: Mar. 30, 2004

(54) METHODS AND COMPOSITION FOR THE DIAGNOSIS AND TREATMENT OF BODY WEIGHT DISORDERS, INCLUDING OBESITY

(75) Inventors: Karen Moore, Maynard, MA (US); Deborah Lynn Nagle, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/358,055

(22) Filed: Jul. 21, 1999

Related U.S. Application Data

(63) Continuation-in-part of application No. 09/245,041, filed on Feb. 5, 1999, now Pat. No. 6,274,339.
(60) Provisional application No. 60/104,978, filed on Oct. 20, 1998, and provisional application No. 60/093,630, filed on Jul. 21, 1998.

(51) Int. Cl.$^7$ .......................... C12P 21/06; C07H 17/00; C07K 14/00
(52) U.S. Cl. .................. 435/69.1; 536/23.1; 435/320.1; 435/252.3; 530/350
(58) Field of Search ............................. 435/69.1, 69.4, 435/320.1; 536/252.3, 254.2, 23.1; 530/350

(56) References Cited

U.S. PATENT DOCUMENTS

| | | | |
|---|---|---|---|
| 4,190,496 A | 2/1980 | Rubenstein et al. ........... 435/7 |
| 4,886,747 A | * 12/1989 | Derynck et al. ........... 435/69.4 |
| 5,075,217 A | 12/1991 | Weber ........................ 435/6 |
| 5,364,759 A | 11/1994 | Caskey et al. ............... 435/6 |

FOREIGN PATENT DOCUMENTS

| | | | |
|---|---|---|---|
| WO | 95/01802 | * | 1/1995 |
| WO | 96/24604 | * | 8/1996 |
| WO | 00/15651 | | 3/2000 |

OTHER PUBLICATIONS

Watson et al. Recombinant DNA, 2nd edition, pp. 453–455, 1994.*
Adams. GenEmbl Accession No. G20370, Jul. 1996.*
Falb et al. N_Geneseq_Accession No. T36030, Nov. 1996.*
Huynh et al. N_36 Accession No. Q82824, Aug. 1995.*
Deuel et al. N_Geneseq_36 Accession No. Q13151, Oct. 1991.*
Altschul, 1990, "Basic Local Alignment Search Tool", J. Mol. Biol. 215:403–410.
Börjeson, 1976, "The Aetiology of Obesity in Children", Acta Pediatr. Scand. 65:403–410.
Bork and Doolittle, 1994, "*Drosophila kelch* Motif is Derived from a Common Enzyme Fold", J. Mol. Biol. 236:1277–1282.

Bork and Beckmann, 1993, "The Cub Domain—A Widespread Module in Developmentally Regulated Proteins", J. Mol. Biol. 231:539–545.
Bray, 1992, "Genetic, Hypothalamic and Endocrine Features of Clinical and Experimental Obesity", Prog. Brain Res. 93:333–341.
Bray, 1989, "1989 McCollum Award Lecture. Genetic and Hypothalamic Mechanisms for Obesity—Finding the Needle in the Haystack", Am. J. Clin. Nutr. 50:891–902.
Coleman, 1978, "Obese and Diabetes: Two Mutant Genes Causing Diabetes–Obesity Syndromes in Mice", Diabetologia 14:141–148.
Dietrich et al., 1996, "A Comprehensive Genetic Map of the Mouse Genome", Nature 380:149–152.
Dinulescu et al., 1998, "Mahogany (mg) Stimulates Feeding and Increases Basal Metabolic Rate Independent of its Suppression of Agouti", Proc. Natl. Acad. Sci. USA 95:12707–12712.
Drickamer, 1995, "Multiplicity of Lectin–Carbohydrate Interactions", Struct. Biol. 2:437–439.
Duke–Cohan et al., 1998, "Attractin (DPPT–L), a Member of the Cub Family of Cell Adhesion and Guidance Proteins, is Secreted by Activated Human T Lymphocytes and Modulates Immune Cell Interactions", Proc. Natl. Acad. Sci. USA 95:11336–11341.
Ewing and Green, 1998, "Base–Calling of Automated Sequencer Traces Using *Phred*. I. Accuracy Assessment", Genome Res. 8:175–185.
Ewing and Green, 1998, "Base–Calling of Automated Sequencer Traces Using *Phred*. II. Error Probabilities", Genome Res. 8:186–194.
Friedman and Liebel, 1992, "Tackling a Weighty Problem", Cell 69:217–220.

(List continued on next page.)

*Primary Examiner*—Karen Cochrane Carlson
(74) *Attorney, Agent, or Firm*—Millennium Pharm. Inc.

(57) ABSTRACT

The present invention relates to mammalian mahogany genes, including the human mahogany gene, which are novel genes involved in the control of mammalian body weight. The invention encompasses nucleotide sequences of the mahogany gene, host cell expression systems of the mahogany gene, and hosts which have been transformed by these expression systems, including transgenic animals. The invention also encompasses novel mahogany gene products, including mahogany proteins, polypeptides and peptides containing amino acid sequences mahogany proteins, fusion proteins of mahogany proteins polypeptides and peptides, and antibodies directed against such mahogany gene products. The present invention also relates to methods and compositions for the diagnosis and treatment of mammalian body weight disorders, including obesity, cachexia, and anorexia, and for the identification of subjects susceptible to such disorders. Further, the invention relates to methods of using the mahogany gene and gene products of the invention for the identification of compounds which modulate the expression of the mahogany gene and/or the activity of the mahogany gene product. Such compounds can be useful as therapeutic agents in the treatment of mammalian body weight disorders, including obesity, cachexia, and anorexia.

28 Claims, 173 Drawing Sheets

OTHER PUBLICATIONS

Figure 1:
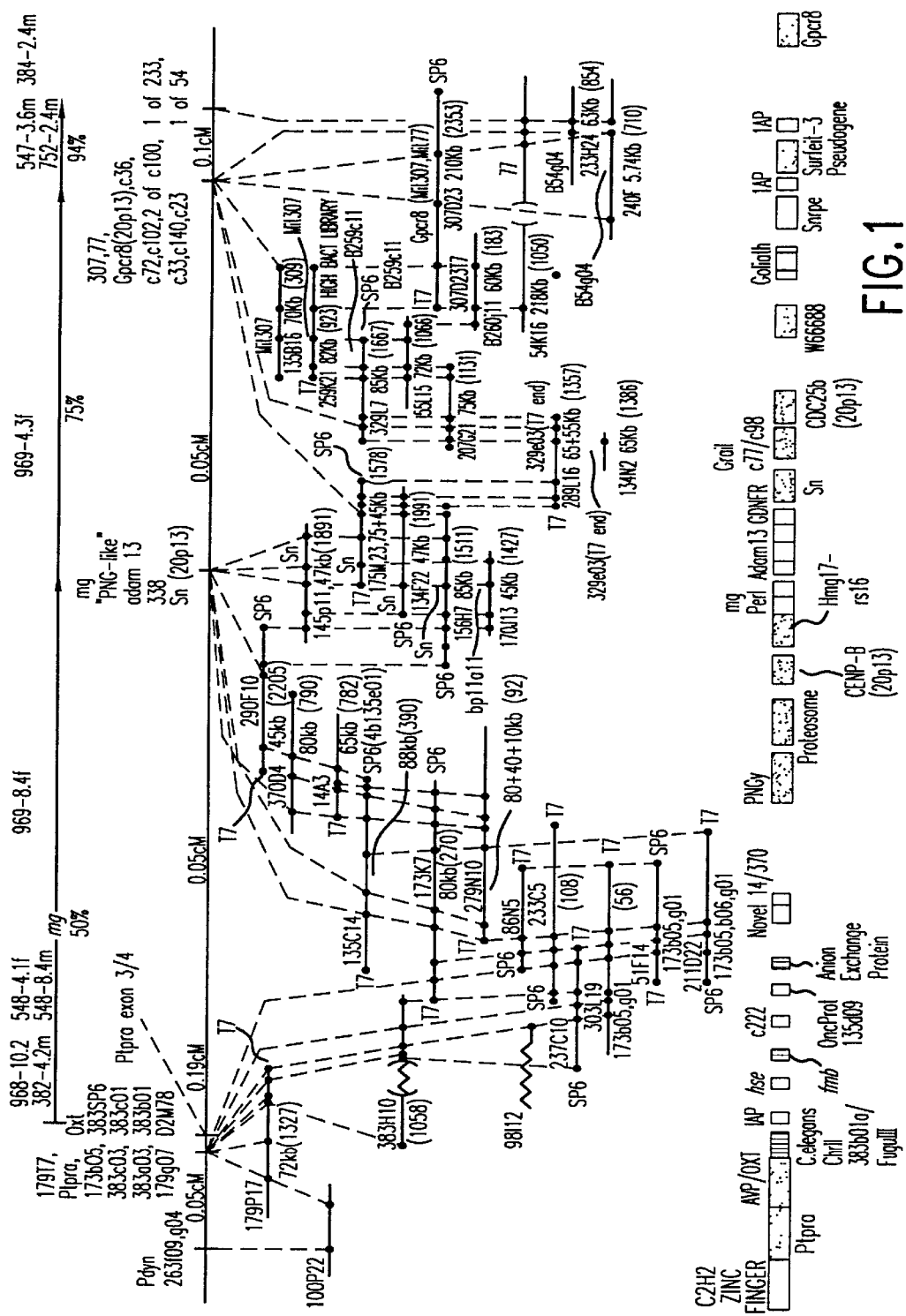

Friedman et al., 1991, "Molecular Mapping of Obesity Genes", Mammalian Genome 1:130–144.

Gordon et al., 1998, "Consed: A Graphical Tool for Sequence Finishing", Genome Res. 8:195–202.

Grundy and Barnett, 1990, "Metabolic and Health Complications of Obesity", Disease–a–Month 36:641–731.

Guan et al., 1991, "GRAIL: An Integrated Artificial Intelligence System for Gen eRecognition and Interpretation", Proc. 8$^{th}$ IEEE Conf. on Artificial Intelligence for Applications pp. 1–3.

Herberg and Coleman, 1977, "Laboratory Animals Exhibiting Obesity and Diabetes Syndromes", Metabolism 26:59–99.

Houghton et al., 1991, "Generation and Use of Synthetic Peptide Combinatorial Libraries for Basic Research and Drug Discovery", Nature 354:84–86.

Knoll et al., 1993, "Cytogenetic and Molecular Studies in the Prader–Willi and Angelman Syndromes: An Overview", Am. J. Med. Genet. 46:2–6.

Lam et al., 1991, "A New Type of Synthetic Peptide Library for Identifying Ligand–Binding Activity", Nature 354:82–84.

Lane and Green, 1960, "Mahogany, a Recessive Color Mutation in Linkage Group V of the Mouse", J. Hered. 51:228–230.

Lu et al., 1994, "Agouti Protein is an Antagonist of the Melanocyte–Stimulating–Hormone Receptor", Nature 371:799–802.

Maestrini et al., 1996, "A Family of Transmembrane Proteins with Homology to the MET–Hepatocyte Growth Factor Receptor", Proc. Natl. Acad. Sci. USA 93:674–678.

Michaud et al., 1994, "Differential Expression of a New Dominant Agouti Allele ($A^{iapy}$) is Correlated with Methylation State and is influenced by Parental Lineage", Genes & Dev. 8:1463–1472.

Miller et al., 1997, "Genetic Studies of the Mouse Mutations *mahogany* and *mahoganoid*", Genetics 146:1407–1415.

Moll et al., 1991, "Identification of High–Molecular–Weight Proteins with Multiple EGF–Like Motifs by Motif–Trap Screening", Genomics 51:27–34.

Nishina et al., 1994, "Atherosclerosis in Genetically Obese Mice: The Mutants Obese, Diabetes, Fat, Tubby, and Lethal Yellow", Metab. 43:554–558.

Robbins et al., 1993, "Pigmentation Phenotypes of Variant Extension Locus Alleles Result from Point Mutations that Alter MSH Receptor Function", Cell 72:827–834.

Schultz et al., 1998, "Smart, a Simple Modular Architecture Research Tool: Identification of Signaling Domains", Proc. Natl. Acad. Sci. USA 95:5857–5864.

Songyang et al., 1993, "SH2 Domains Recognize Specific Phospeptide Sequences", Cell 72:767–778.

Stunkard et al., 1990, "The Body–Mass Index of Twins Who Have Been Raised Apart", N. Eng. J. Med. 322:1483–1487.

Weis and Drickamer, 1996, "Structural Basis of Lectin–Carbohydrate Recognition", Ann. Rev. Biochem. 65:441–473.

www.ncbi.nlm.nih.gov (National Center for Biotechnology Informatio) GenBank Accession No. AA061169. Mj85g11.r1 Soares mouse p3NMF19.5 Mus musculus cDNA clone Image:482948 5' similar to WP:F33C8.1 CE05796 Perlecan–Like Glycoprotein: mRNA sequence (Marr, M. et al.). Database [Online]. Last update: Sep. 23, 1996. Accessed on: Jun. 14, 2000, Released from GenBank on Sep. 23, 1996.

www.ncbi.nlm.nih.gov (National Center for Biotechnology Information) GenBank Accession No. AA350292. EST57511 Infant brain *Homo sapiens* cDNA 3' end, mRNA sequence (Adams, M.D. et al.). Database [Online]. Last update: Apr. 21, 1997. Accessed on: Jun. 14, 2000. Released from GenBank on Apr. 21, 1997.

www.ncbi.nlm.nih.gov (National Center for Biotechnology Information) GenBank Accession No. R87660.Yp89g01.s1 Soares fetal liver spleen INFLS *Homo sapiens* cDNA clone Image:194640 3', mRNA sequence (Hillier, L. et al.). Database [Online]. Last update: Aug. 16, 1995. Accessed on: Jun. 14, 2000. Released from GenBank on Aug. 16, 1995.

www.ncbi.nlm.nih.gov (National Center for Biotechnology Information) GenBank Accessin No. T69367. Yc37g02.r1 Stratagene liver (#937224) *Homo sapiens* cDNA clone Database [Online]. Last update: Feb. 23, 1995. Accessed on: Jun. 14, 2000. Released from GenBank on Feb. 23, 1995.

www.ncbi.nlm.nih.gov (National Center for Biotechnology Information) GenBank Accession No. T92696. Ye26f05.r1 Strategene lung (#937210) *Homo sapiens* cDNA clone Image:118881 5', mRNA sequence (Hillier, L. et al.). Database [Online]. Last update: Mar. 22, 1995. Accessed on: Jun. 14, 2000. Released from GenBank on Mar. 22, 1995.

www.ncbi.nlm.nih.gov (National Center for Biotechnology Information) GenBank Accession No. H11351. Ym13b02.r1 Soares infant brain 1NIB *Homo sapiens* cDNA clone Image:47626 5', mRNA sequence. (Hillier, L. et al.). Database [Online]. Last Update: Jun. 26, 1995. Accessed on: Jun. 14, 2000. Released from GenBank on Jun. 26, 1995.

www.ncbi.nlm.nih.gov (National Center for Biotechnology Information) GenBank Accession No. AA350293. EST57512 Infant brain *Homo sapiens* cDNA 5' end, mRNA sequence (Adams, M.D. et al.). Database [Online]: Last update: Apr. 21, 1997. Accessed on Jun. 14, 2000. Released from GenBank on Apr. 21, 1997.

www.ncbi.nlm.nih.gov (National Center for Biotechnology Information) GenBank Accession No. AA297697. EST113254 Fetal heart II *Homo sapiens* cDNA 5' end, mRNA sequence (Adamsk, M.D. et al.). Database [Online]. Last update: Apr. 18, 1997. Accessed on: Jun. 14, 2000. Released from GenBank on Apr. 18, 1997.

www.ncbi.nlm.nih.gov (National Center for Biotechnology Information) GenBank Accession No. AB011120. *Homo sapiens* mRNA for KIAA0548 protein, partial cds (Nagase, T. et al.). Database [Online]. Last Update: Apr. 10, 1998. Accessed on: Jun. 14, 2000. Released from the DNA Data Bank of Japan (DDBJ) on Apr. 10, 1998.

www.ncbi.nlm.nih.gov (National Center for Biotechnology Information) GenBank Accession No. AA298732. EST114356 Supt cells *Homo sapiens* cDNA 5' end similar to laminin, B1 chain, mRNA sequence (Adams, M.D. et al.). Database [Online]. Last update: Apr. 18, 1997. Accessed on: Jun. 14, 2000. Released from GenBank on Apr. 18, 1997.

www.ncbi.nlm.nih.gov (National Center for Biotechnology Information) GenBank Accession No. AI076479. Oz28b04.x1 Soares_total_fetus_Nb2HF8_9w *Homo sapiens* cDNA clone Image:1676623 3' similar to contains L1.b1 L1 repetitive element;, mRNA sequence (NCI–CGAP http://www.ncbi.nlm.nih.gov/ncicgap). Database [Online]. Last update: Oct. 1, 1998. Accessed on: Jun. 14, 2000. Released from GenBank on Aug. 7, 1998.

www.ncbi.nlm.nih.gov (National Center for Biotechnology Information) GenBank Accession No. AA771958 ai37e06.s1 Soares_parathyroid_tumor_$_{NbHPA}$ *Homo sapiens* cDNA clone 1359202 3' similar to contains L1.t3 L1 repetitive element;, mRNA sequence (NCI–CGAP http://www.ncbi.nlm.nih.gov/ncicgap). Database [Online]. Last update: Dec. 31, 1998. Accessed on: Jun. 14, 2000. Released from GenBank on Jan. 29, 1998.

www.ncbi.nlm.nih.gov (National Center for Biotechnology Information) GenBank Accession No. R84298. Yp89g01.r1 Soares fetal liver spleen 1NFLS *Homo sapiens* cDNA clone Image:194640 5' similar to contains L1 repetitive element;, mRNA sequence (Hillier, L. et al.). Database [Online]. Last update: Aug. 14, 1995. Accessed on: Jun. 1, 2000. Released from GenBank on Aug. 14, 1995.

www.ncbi.nlm.nih.gov (National Center for Biotechnology Information) GenBank Accession No. D81046. HUM126G05B Human fetal brain (TFujiwara) *Homo sapiens* cDNA clone GEN–126G05 5', mRNA sequence (Fujiwara, T. et al.). Database [Online]. Last update: Feb. 9, 1996. Accessed on: Jun. 14, 2000. Released from the DNA Data Bank of Japan (DDBJ) on Feb. 6, 1996.

www.ncbi.nlm.nih.gov (National Center for Biotechnology Information) GenBank Accession No. AA378603. EST91322 *Synovial sarcoma Homo sapiens* cDNA 5' end, mRNA sequence (Adams, M.D. et al.). Database [Online]. Last update: Apr. 21, 1997. Accessed on: Jun. 14, 2000. Released from GenBank on Apr. 21, 1997.

www.ncbi.nlm.nih.gov (National Center for Biotechnology Information) GenBank Accession No. D60710. HUM126G05A Clontech human fetal brain polyA+ mRNA (#6535) *Homo sapiens* cDNA clone GEN–126G05 3', mRNA sequence (Fujiwara, T. et al.). Database [Online]. Last update: Apr. 28, 1995. Accessed on: Jun. 14, 2000. Released from the DNA Data Bank of Japan (DDBJ) on Aug. 27, 1995.

www.ncbi.nlm.nih.gov (National Center for Biotechnology Information) GenBank Accession No. D20236. HUMGS01210 Human promyelocyte *Homo sapiens* cDNA clone pm1235 3', mRNA sequence (Murakawa, K. et al.). Database [Online]. Last update: Oct. 7, 1996. Accessed on: Jun. 14, 2000. Released from the DNA Data Bank of Japan (DDBJ) on Jun. 18, 1994.

www.ncbi.nlm.nih.gov (National Center for Biotechnology Information) GenBank Accession No. AA345684, EST51733 Gall bladder I *Homo sapiens* cDNA 5' end, mRNA sequence (Adams, M.D. et al.). Database [Online]. Last update: Apr. 21, 1997. Accessed on: Jun. 14, 2000. Released from GenBank on Apr. 21, 1997.

www.ncbi.nlm.nih.gov (National Center for Biotechnology Information) GenBank Accession No. H45413. Yo66a08.s1 Soares breast 3NbHBst *Homo sapiens* cDNA clone Image:182870 3', mRNA sequence (Hillier, L. et al.). Database [Online]. Last update: Jul. 31, 1995. Accessed on: Jun. 14, 2000. Released from GenBank on Jul. 31, 1995.

www.ncbi.nlm.nih.gov (National Center for Biotechnology Information) GenBank Accession No. AA033305. Zk51d07.s1 Soares_pregnant_uterus_NbHPU *Homo sapiens* cDNA clone Image:486349 3', mRNA sequence (Hillier, L. et al.). Database [Online]. Last update: May 10, 1997. Accessed on: Jun. 14, 2000. Released from GenBank on Sep. 4, 1996.

Duke–Cohan et al., 1995, "A Novel Form of Dipeptidylpeptidase IV Found in Human Serum", J. Biol. Chem. 270:14107–14114.

Nagase et al., 1998, "Prediction of the Coding Sequences of Unidentified Human Genes. IX. The Complete Sequences of 100 New cDNA Clones from Brain Which Can Code for Large Proteins Proteins in vitro", DNA Research 5:31–39.

* cited by examiner

GAATTCCGGGCGAAGGGGAGCCGGCGTGCGGGGTGTGTATGTGTTCGCTGGGCGCGGCTCAGCCCCAGGAAGATGGTG

GCGGTGGCGGCGGCGGGCGACTGAGGCGCGGCTGAGGGGAGCACGAGGACGACAGAGCGCCTGCGGGCAGGAAGG

GCAGGCAGCACCGACCCTGCACCGCGACAGGGCCTGGAGGCCGGACCGCGCGCGGCCTGTGTCTCCGCGGGTGCT

GTCGCGGGCGCTGCCCCCGCCGCCGCTGCTGCCGCTGCTGCCGCTGCTCTTTCGCTGCTGCTGCCGCTGCCCCGGAGGCCGAG

GCCGCTGCGGTGGCGGCGGCGGTGTCCGGCTCGGCGCCGCGCAGCCGAGGCCAAGGAATGTGACCGGCCGTGTCAACGGCG

GCCGCTGCAACCCTGGCACCGGCCAGTGCGTCTGCCCCACGGGCTGGGCGAGCAATGCCAGCACTGCGCGGGGCCG

CTTCAGGACATCTGTCTCACGCCTATAATCACAGCTGTTCGGAAGGTGAGGCTGAGGAACAGTTCGAGGCAAGCTTCG

GCTACAGAATAAGTTCAAGAGTAACCTGGGGCAACTTGGGCTTGTCTCCAAAACCAAAATGAGCGAAAAGGAGCAAGCT

AGAGTCTTTTGGGAAAATTTAGCTGACTAATTTTCACCGAGAACTAACTGGCTCTTCTGGATTTGTAACAGATGGAC

CTGGGAATTATAAATATAAGACGAAGTGCACATGGCTCATTGAAGGACAGCCAAATAGAATAATGAGACTTCGCTTCAA

CCATTTTGCTACAGAATGTAGCTGGGACCATTTATATGTTATGATGGGACTCAATCTACGCACCTCTGATTGCTGCC

TTTAGTGGCCCTCATTGTTCCTGAAAGAGATGGCAATGAGACGGCTCCTGAGGTCACTGTCACTTCAGGTTATGCACTGC

TGCATTTTTCAGTGATGCTGCTTATAATCTGACTGGATTAATATCACTTACAATTTGACATGTGTCCGAATAATTG

FIG.2A(1)

CTCAGGGCCGAGGAGAGTGTAAGAGCAGTAACAGAGCAGCAGCGCTGTTGAGTGTGAATGTTCTGAAAACTGGAAAGGGGAG

TCGTGTGACATTCCTCACTGTACAGACAACTGTGGCTTTCCTCACCGAGGCATCTGTAATGCAAGCGATACCAGAGGGT

GCTCCTGCTTTCCTCACTGGCAGGGTCCTGGATGTTCAATTCCTGTGCCAGCTAACCAGTCTTTTGGACTCGAGAAGA

ATATTCTGATTTAAAGCTTCCCAGAGCCTCTCATAAAGCTGTGGTCAATGGAAATATAATGTGGGTTGTTGGGGATAT

ATGTTCAACCATTCAGATTACAGCATGTTTTAGCGTATGACCTGACTTCTAGGGAATGGCTTCCACTAAACCATTCTG

TGAACAGTGTGGTTGTAAGATATGGTCATTCTTTGGCATTACATAAGGATAAAATCTACATGTATGGAGGAAAAATTGA

TTCAACAGGGAACGTGACCAATGAGCTGAGAGTATTTCATATTCATAATGAATCATGGGTATTGTTAACTCCGAAAGCT

AAGGATCAGTATGCAGGTTGGACACTCAGCAGATATATAAGCGTTGTGCAGGAATATGACTTGGAAAAGAACACATGAGTATATTACA

TCGGTCATTGCCCACTCTATGGATATTGTTGCAAGGGGTTATGGCCACAGTAGTGTTTATGATGACCTCTACAGATACGATGTGGATACTCAGATGT

TACTCAGGGTGCTCTTGTGCAAGGCTTTCAGCGCCAACAAATACCGGCTTGAGATGACCTTCTACAGATACGATGTGGATACTCAGATGT

GGTGGCTACAAGGCTTTCAGCGCCAACAAATACCGGCTTGACAGATGACCTCTACAGATACGATGTGGATACTCAGATGT

GGACCATTCTTAAGGACAGCCGATTTTTCCGTTACTTGCATACAGCTGTGATAGTGAGTGGAACCATGCTGGTGTTGG

AGGGAACACACAATGACACTTCCATGAGCCACGGTGCCAAATGCTTCTCCTCGGACTTCATGGCTTATGACATTGCT

FIG.2A(2)

```
TGTGACCGATGGTCAGTGCTTCCCAGACCTGAGCTCCATCATGATGTCAACAGATTTGGCCATTCAGCAGTCTTGTACA
ACAGCACCATGTATGTTCGGCGGCTTCAACAGCCTCCTCCTCAGTGACGTCTTGGTCTTTACCTCGGAGCAGTGCGA
TGCACACCGCAGTGAAGCTGCTTGTGTGCAGCAGGACCTGGTATCCGGTGTCTGTGGGACACACAGTCGTCTCGATGT
ACCTCCTGGGAGTTGGCAACTGAAGAACAAGCAGAAGAAGTTAAAATCAGAGTGTTTTCTAAAGAACCCTTGACCATG
ACAGATGTGACCAGCACACAGATTGTTACAGCTGCACAGCCAATACCAATGACTGCCACTGGTGCAATGATCACTGTGT
CCCTGTGAACCACAGCTGCACAGAAGGCCAGATCTCCATTGCCAAGTATGAGAGTTGCCCCAAGGATAACCCCATGTAC
TACTGCAATAAGAAAACCAGCTGCCAGAGCTGTGCCCTAGACCAGAACTGCCAGTGGGAGCCCCGGAATCAAGAGTGCA
TCGCCCCTGCCGGAAAATATCTGTGGCAATGGCTGGCATTTGGTTGGAAACTCGTGTCTGAAAATCACTACTGCTAAGGA
GAATTATGACAATGCTAAATTGTCCTGTAGGAACCACACAATGCCTTTTGGCTTCCCTCACATCCCAGAAGAAGGTGGAG
TTTGTCCTTAAGCAGCTTCGATTAATGCAATCATCTCAAAGTATGTCCAAGCTCACTCTGACTCCATGGGTTGGTCTTC
GGAAGATCAAATGTCTTACTGGTGCTGGGAGGATATGTCTCCATTCACAAATAGTTGCTGCAGTGGATGCCATCTGA
GCCCAGTGATGCTGGCTTCTGTGGGATCTTGTCAGAGCCTAGTACTCGGGGATTAAAGGCTGCAACCTGCATCAACCCT
CTCAATGGCAGCGTCTGTGAAAGGCCTGCAAACCACAGTGCCAAGCAGTGCCGGACACCATGTGCCCTGCCGGACAGCGT
```

FIG.2A(3)

GTGGCGAGTGCACTAGCAGCAGCTCGGAGTGCATGTGGTGCAGTAACATGAAGCAGTGTGTGGACTCCAATGCCTACGT

GGCCTCCCTTCCCTTTTGGGCCAGTGTATGGAATGGTATACGATGAGCAGCTGCCCACCTGAAAATTGCTCTGGCTACTGT

ACCTGCAGCCATTGCTTGGAGCAGCCAGGCTGTGGTTGGTGTACTGATCCTAGCAATACTGGGAAAGGAAAATGTATTG

AGGGCAGCTATAAAGGACCTGTGAAGATGCCGTCACAGGCCTCGCAGGAAATGTGTATCCACAGCCCTTCTGAACTC

CAGCATGTGTCTAGAGGACAGCAGATACAACTGGTCTTTCATTCACTGTCCAGCTTGCCAGTGCAACGGACACAGCAAA

TGCATCAACCAGAGTATCTGTGAGAAGTGTGAGGACCTGACCACGGGCAAGCACTGCGAGACCTGCATATCTGGCTTCT

ATGGTGACCCGACTAATGGAGGCAAATGTCAGCCATGCAAGTGCAATGGGCACGCTATGTGAGGTAGAAAATCGATACCAAGGAAAC

CAAGTGCTTCTGTACCACCAAAGGTGTCAAGGGGACGAGTGCCAGCTATGTGAGGTAGAAAATCGATACCAAGGAAAC

CCTCTCAAAAGGAACATGCTACTATACCCTTCTCATTGACTATCAGTTCACCTTTAGCCTGTCCCAGGAAGACGACCGCT

ACTACACAGCCATCAACTTTGTGGCTACTCCTGATGAACAAAACAGGGATTTGGACATGTTCATCAATGCCTCCAAAAA

CTTCAACCTTCAACATCACCTGGGCCACCAGCTTCCCAGCCGGAACCCAGACTGGAGAAGAGGTGCCTGTTGTTTCAAAA

ACCAACATCAAGGAATACAAAGATAGCTTCTCTAATGAGAAATTTGATTTTCGCAACGATCCAAACATCACTTTCTTTG

TTTATGTCAGTAATTTCACTTGGCCCATCAAAATTCAGATTGCCTTCTCCCAGCACAGCAACTTCATGGACCTGGTACA

FIG.2A(4)

GTTCTTCGTGACTTTCTTCAGTTGTTCCTCTCGCTGCTTCTGGTGGCTGCAGTGGTCTGAAGATCAAGCAGAGCTGT

TGGGCATCCAGGCGGAGAGAGCAACTTCTTCGGGAGATGCAACAGATGGCCAGCCGCCCTTTGCTTCTGTAAACGTTG

CCTTGGAAACAGATGAGGAGCCTCCTGATCTTATTGGGGGAGTATAAAGACTGTTCCCAAACCCATTGCACTGGAGCC

GTGTTTTGGCAACAAAGCCGCTGTCCTCTCTGTGTTTGTGAGGCTCCCCTCGAGGCCTGGGTGGCATCCCTCCTCCTGGG

CAGTCAGGTCTTGCTGTGGCCAGCGCCCTGGTGGACATTTCTCAGCAGATGCCGATAGTGTACAAGGAGAAGTCAGGAG

CCGTGAGAAACCGGAAGCAGCAGCCCCTGCACAGCCTGGGACCTGCATCTGATGCTGGGGCCAGGGACTCTCCACGC

ACGAGCTAGTGAGTGGCACACCAGAGCCATCTGCAGGAAGGCGTGGCGGTGCGGTGCGGGACGGAA

GACTGGAAACCCTCAAAGCATCTGACTCACCTGCATGATCACAAGCTTTCTTTGACGGTTCTCCCATCCGTGTTCCAG

CATCTAACCTTTTACTTTTGCATAGGAAATACTTGATTTAATTACAGGTCCAGGGGATGAGCTGATGGTTGCTGGAGGAG

GCCAGTGTAGAGCCAGTGAGAGAACTAGGAATGACACTCAGGTTCACTGTGGAAAACTGTTCTTGGGACTGTCTCAACT

GTGCAAAAACAAAGATGGAGTGTTACAAGTAGACATTCGTCATCAGTTGTTCTTGAACATGGTCTTTTAAAAACTA

GTCAGATGAATTAACTTGTTTTCATCTGAAGCCTGCTATCTTTTTAAAAGATGTGCTATTTATTCTTGCACGATTTAG

GCAATTATCTCTCTTCCAGGGAGTACCTTTTTTCTAGTTGAGAATTAATAATGGTCCATCTCTTTTGATCATATCAAG

FIG.2A(5)

CTAGGATAGAAGGGGGCTATTTTAAATGTCAAGGTCAGCAGTGTTACTTTGAATGTAAACTGGTATAATAGGTAGTTT

TCTATAGTAACTTGATTAATTTAGTCTTAATCCATTTGAAACTCTCTCTTCCTTCTCTCTGCCTGTCCCTCTCCTTCT

CCATCTCACCCTCCCTCTCTCACACATACACACACAAACACATACACACAACACTAAGTGCCTAGACTTTAAATAGATC

TAGCAATTGGAAAGTTAGTAAGCCTAAGTTTTTACATAATTGCATTCCTACATTCTTGTAAAATTTAAATAGCTACCAT

TGGCAATCTGCTTTTTTCTAAATCTGATTTGCAGCCAGGAAAGAATTTCTCACCCAAGGAACATTTGATCTAGCAG

CAGGGATGAGAGGAAAGCAGAAATGAACTGTGAAAGCTCCTGTTTTATTATCAAAAAGGACACTGTCAAGAAGG

CGCCCCCTGCCCCCACCCCGTGTCACCCTAGGCCTGATAAGCGATCAGAGAGAGCATCTGTGTCCTGCAGCCTCCTCTGAACT

TGAGCAGAAAAGAGCACTGAGAGCACTTGGGACTCAGATGCCAGGAAAAGGGACAGCCTCCATTGTCAGGCAGAAGCTGCCCAA

TGTGGTTCATTCTCAGGCTGGGGTGGACTCAGATGCCAGGAAAAGGGACAGCCTCCATTGTCAGGCAGAAGCTGCCCAA

AGCCTGGAGAAGGACTTGTTTGCCCTCTTTCCCCAGGAGGGCTCGACCCACCCACCCTCCCTCTCAGACCAAGGTGG

TGGCTGTGAGGAGGCAGCAAATGCTGACAAGGATGAAAAGCACATGGAAAAAATGGACGAGGAGGGAAAACTCTGCC

AAATGGAAAATGACCAAATTTAAGAGGGTGGGACAGTCCCCTGCTCCTCTCCCAGAGGGCACTGCTTGGAAATTGTGTT

TTCCCCATTTATGGTGCTCTGTATTCGGCATTATGCAGCAGCCTCCCAGAAGCTCTCTTCTGCTTCAAAACCTGGGAT

FIG.2A(6)

CTCTGGCATTACCCTATTGGGATGGAACCGCTGGACAGCAATGCTCGAGTTTGTGAATTTGGAGAGATACTCAAAAGAGC

TAAAACTGCAGCATTTTACCTTTAAATGCAGTGCCTAGAGAGAGAGTATTGTCTCTTCCCCAACACTAACCCCACTCCC

ATGAAGAATTGCCTGGAAAGATGTTTCAAGGAATTTGAACCATAAAACACTATCTGATGCACAGAACACCTCTACTTT

GAGACTCACCTCTCATAAAGCTTCTTTTTCACATTACTGTTAAAGACCAGACGTTCTAGAAAAGACCCCTCCTCTCATG

AGCTCCCCCATCCCTGCTACAGAACACAGCACCCATGGCGCCTGCAGTGGACTGGCCCCTTAATTCCCACAGGCCCCCC

CAGCAAGGCCAAAGGGAGGCCCCTGGGTATTGTCCTCCTACAAGGAAGATCCTCTTTGTTGTTCAAAGGACCAGTTTT

CCTAGGCCAAAGAAGTCTCTTCCCCATGTTAGTCCTATGCCTTGAAATATCATGACCACACAGCCATCTGGTT

ATGTCTTATTTTTTCCTAAAAGATAATGTTTATTTTTAAAAAGGAAGGAAGCAAGTGAAGTTTCATTCTGCTCCA

GCGGTGGGGAAGCCGCTGAATCCACCTGCTTCTCCTTTGCAACCGACAGCAAACAGCTTTCTCCGGGCTCAGGGCAGAA

AAAGGGAATGGCAGGGAGTAAGAGGCCGCTGGGCTGGGCTGTTTCCAAGAAGGAATTGGTTGTCATCTGGCAGTGTT

GCGCGTCACAAGAGAGCCTGTATATAAATTAAAATAGTCAAGACAACACTGACCTTGCACTTGTACATAACTATACAGT

AGTGTCCAGAATGTTCAGACATTCGGAGTGTACATAAAACAGAAAAAATCTTCATGTATTTTATTAAATATAACAATG

TCTGAGTTTCACCTAAGATGTTTTGTGCCATATGCTGGATATCCAGGTTCTCGCCAGGCCCGATACATGAATAACAA

FIG.2A(7)

```
ACCCAAGAAACGCATCCCCATTGTGTGATGTGTTCAGATGCATCTGGCACCAATTAGGTATTCTTAAAACAGGACTCA
TCTGTCAGAGTGCACATGAAAAATCAGGCAGGGAATCGAAACGACAGCGCTGGAGGAGACTCAGGAAGCAGAGGCGTCC
CTGCCGCTGCCCTTGGCCCTGCAAGCACATCATGACCCTTTCTGGCAGCCTCTTGGTGCTCTGGGTAGTGAGGGATGAC
CAGTCTTGTCCTGAGAAATGTTTCTCTTAGTCTTTAAGTTCAAAGACTAACCTGTAGCAATCAGACTTTCCAAAAGGGG
GTTCTCCATTTTTGTAGTTTGTCTAAATTTTAATGACCATTTCCTGGAATCAGTTTATTATACTGAAAACTGGGGG
TGGGAGTAGGGAGCTAGTTTGTTGATAAATAGTTCCCATTTCCCCGTGAGAATTTGACATACCCTGGACTCCTGTGTG
CCTCCTGCCATCCCTGCACACAGCCTGGGAGAAGCCTGTGCCTCCCCGTGTGGAGAGAAGGCAACCCCAGATCCCCTG
AGCTAACCCGGAGGAAAGGCAGTCCTGGACAGAAGACTGTCAGCAGAAGGAAAGTACTGGACTACCCGTGGGTAAGTCC
TGCCATTCAAGACTGGAGACACCTGGGAAATAAAAAGAGCAGGGCACTGCTGGTGGGAAGAGGCATTTTACCTTCCAGT
GCAAATCCTGCTCTCTTTGATTTAATGGGGTGTACTGGGGCCAGGGGCTGATTCACTTCCTTGGGAGATGGTGGTGTTTT
CATGAACATCTTTGATCCTTCCATTTCATTTATTCATCCATTCAACAAGTATTGCTAAACACTAACTTAAGCTA
ATGCTAGGGTAGTGACTGAGATGTAAAAATAGATTTTAGAATTAAAACAAAATCCAAGTCCTCACACCCCTGTCATCCC
AGGAGATCTTTCCTGTGGTGGTTTCTGTGAGAATTGGCCATCCTGAGGACACAGCCAGGACGGCAGAGGCCTCCTGGC
```

FIG.2A(8)

CTCAGGGCATGCCCTGCCTACCTTCTGAAATGTTTACCCCATTGACCAAACTTGGCTCCAGCCATTGCGGTGGTTTCTA

GATAGCCAGGCCCACCAAGAGATATTGCCCCTTGATGAGAGTCAAACACCCTGCCTACAAGGAGATGTTTGAAATGGA

GAGGAAAATTGGCACCTCATCTTTAAAGGCAGTAATGAATTGATTTCAGTAACTGAATTGTGCACAAAACATTCT

AAACACTAGTGAAGCCTGTTCGTTGAACTAATTCTGGCTCTCTGGAAATGTTTGTTTTATAGTATTACGATTCGT

TTGTTTGGATTCAAGCTTAGTTTGTTAATATGTATAATTAGCATCTATTACACTCATGTAAATATGGAGTAAGTATTG

TAAACTATTTCATTGCGGGATTGTGGGGTGTTATACATACATTAGGACTGCAATTTTTGGTATTTTTGTATTGTAA

AATAACAGCTAATTTAAGCAGGAACAAGAGAACTAAGGGAGGTCTGTGCATTTTAAACACAAATGTGAAGAACTTGTAT

ATAAACAAAAGTAAATACTATAATACAAACTTCCTTCTGAAATAAAAGTAGATCTGGT

FIG.2A(9)

MRLRFNHFATECSWDHLYVYDGDSIYAPLIAAFSGLIVPERDGNETAPEVTVTSGYALLHFFSDAAYNLTGFNITYNFD

MCPNNCSGRGECKSSNSSSAVECECSENWKGESCDIPHCTDNCGFPHRGICNASDTRGCSCFPHWQGPGCSIPVPANQS

FWTREEYSDLKLPRASHKAVVNGNIMWVGGYMFNHSDYSMVLAYDLTSREWLPLNHSVNSVVVRYGHSLALHKDKIYM

YGGKIDSTGNVTNELRVFHIHNESWLLTPKAKDQYAVVGHSAHIVTLASGRVVMLVIFGHCPLYGYISVVQEYDLEKN

TWSILHTQGALVQGGYGHSSVYDDRTKALYVHGGYKAFSANKYRLADDLYRYDVDTQMMTILKDSRFFRYLHTAVIVSG

TMLVFGGNTHNDTSMSHGAKCFSSDFMAYDIACDRWSVLPRPELHHDVNRFGHSAVLYNSTMYVFGGFNSLLLSDVLVF

TSEQCDAHRSEAACVAAGPGIRCLWDTQSSRCTSWELATEEQAEKLKSECFSKRTLDHDRCDQHTDCYSCTANTNDCHW

CNDHCVPVNHSCTEGQISIAKYESCPKDNPMYYCNKKTSCRSCALDQNCQWEPRNQECIALPENICGNGWHLVGNSCLK

ITTAKENYDNAKLSCRNHNAFLASLTSQKKVEFVLKQLRLMQSSQSMSKLTLTPWVGLRKINVSYWCWEDMSPFTNSLL

QWMPSEPSDAGFCGILSEPSTRGLKAATCINPLNGSVCERPANHSAKQCRTPCALRTACGECTSSSSECMWCSNMKQCV

DSNAYVASFPFGQCMEWYTMSSCPPENCSGYCTCSHCLEQPGCGWCTDPSNTGKGKCIEGSYKGPVKMPSQASAGNVYP

QPLLNSSMCLEDSRYNWSFIHCPACQCNGHSKCINQSICEKCEDLTTGKHCETCISGFYGDPTNGGKCQPCKCNGHASL

CNTNTGKCFCTTKGVKGDECQLCEVENRYQGNPLKGTCYTLLIDYQFTFSLSQEDDRYYTAINFVATPDEQNRDLMF

INASKNFNLNITWATSFPAGTQTGEEVPVVSKTNIKEYKDSFSNEKFDFRNHPNITFFVYVSNFTWPIKIQIAFSQHSN

FMDLVQFFVTFFSCFLSLLLVAAVVWKIKQSCWASRRREQLLREMQQMASRPFASVNVALETDEEPPDLIGGSIKTVPK

PIALEPCFGNKAAVLSVFVRLPRGLGGIPPPGQSGLAVASALVDISQQMPIVYKEKSGAVRNRKQQPPAQPGTCI

FIG.2B

AGATTTTATGCCTTCGTACACGCCTCCCATAAGATGGACAAGGTGTACTA

ATTACTGCCATTACTGTTGCTGACCCCAGAGGTCAATGTCCTCACATGGC

CTCTACTGGCACTGTCTGGGCAGAAACTGTATATCCAACTGGTGAACCTG

AAAGCCCTATGACTACTTGGTGTCTCTGGTGCTAACCCTAGTCGTTGGGG

CATCTTACTGTATCCTGGTAAGGAAAGACATCCAGGCTCCCCACTTAYMK

WWACYRGYWMRGMYCAKGSYMGRGCYAAWKTKCTGTRRMRTCTGGCTGGC

ATAGAGACATTACTATTGAAAGTTTTGTCTTTCTAAATCCTTGGACTAAA

GAGAGCACAAGATTTTCTGGAAGATCTTGCTTTAAATTTTTTTTTTATTC

TTTTGAGATGCTACATATAATTAGAGGCCCTGCACATGGAGGCGAGAACC

CCACCTCTGGGCTACATCCTACGTCTTTTCCTTAGGGTATTTTTTTTTCT

TTCTTGTACCTATCAGTATTACTAAGTTGCAAATGTGCTCAGCAGTAAAT

TTAACATACATAGGCAAAAAGAAAAGTCTCAGGACACCCTGCCTCACACT

GTTTACTGTGCTCAGGAGTACTGAGCCATACTGTTTTCTTGCTGCTGCTT

TTTTTCTCTTGGTTGTTTACACACAGTGTTCAAGGTGTGTTAATCATAGT

TAGTATTTCAATTTTTTTCTTAGGTCAGCAAGAAAGCTCACAGAGGAAGAG

TGCTTTGCTGCCAGCCTGATGACCTGGGTGACCCAAGTGATCTCACCTAC

AGGGTGGGAGCACAGCACAGCATTCCAAGTCTTTTTCTGACCACACAGGC

ACTATGGCACACAAACACACAGGATACATAAATGTTAAAAAAAAAAAAAG

ACTTTTATATTTTTCTCCATATAATTTAAAAGATTCCTCTTTCAACATTC

CTTTTGCAAAGCAGTATCATTGTGTTTGTATATGTGTGTCCTTCCACATT

TTGTCTTCAATTCTAAATTTTTAGAATTGTTAGCCTGGTCCTCTCATTTC

FIG.3B(1)

```
TACTACTTTCTCTAGTAAACTGTCCTTTCATATTACACATCGCTCTCCTG

TCACCTGTTTTAGAGCTGTCATCCATTTTATAAGGTTACTTCACTGTTCT

ACACTACTTTGTGTCTTTTAATTACTATGCCTGGGGTGATTCAAAAACTG

TCTGTGATGGGTTGGTTGAGGATGGCTCCAATAGGTTCAACACTTGGTCC

TGATTGGTGGAACTGTTTTGGGAAGGATTAGGAGGTGTGACCTTGTGGGG

GAGTGTGTCACTGGGAGTGAGTGACCTTTGAGGTTTCAAAAGCCCATGCT

AGGCCCAGTGTCTGTCTGCCTGTCTGTCTGTCTCCTCCCTTTGCTCTTTC

TTCCCTCCCACTTGCTTGCAGATCAGATTCGAGCTCTTAGCTACTGCTCC

CGTGCTGTGCCTTGCTGCTACCATGCTTCTTGCCATGATGTTCATAGACT

TACTCTCTGAAACTGTAAATAAGCCCCCTAATAAAATGCTTTCTTTTAAA

ACTGCCTTGATCATGGTGTCTCTTCAAAGAAATAGAACATTAACAAAAAC

ACTATACCAAACTGCCTAATAGTCCTACTAATTTTATGATGAGTGCTAGT

GCTTTATAATCACTAGAAGAAAAAATTTCCAGGCCATAAAATTAACATGG

TTTTAAGTATGTATAAATCTTGTCTTGAAATCTGTTTTCTATAACTAACT

CTAATATGATAATGTATATTCTACCTTCAAAAAAGCACAAATAAGACTTC

AAACCCTGGGAATTGTTAGACAAAGGCCATTTAATACTAATAAGCTATAA

ACTGAAACCATCTGATATATGAAAACTATTAATAAAATCAAGATAAAATA

ACCCCTATTTATATAACTTACTATATACCTAAAGCAAAATATCAAAGAAA

GTACCTTAAAAAGATAAATTATTCTTATTTTGACAATGAATTCTTTGGGG

CGTTAAATTGTAGAATATCAACACATATCAAGAAAGTTTAGAAGAAAACT

ACCAAAGTTTAAACAGACTTTCCTCGGTAATTACTGGTGATTTCTTGGCT
```

FIG.3B(2)

```
TTTTTTTTTTTACACTGCAGTTTTTCAGGGTGGAAACTTAAGCTTTGTACA

GAAGCACTTACCACCACTCTCAGAGCTGGAAATGGCTCAAAGGGCAAAGC

ATTACAAGCCTGGCAACCTGAACCAAATACCCAAAACACTTGCAAAGGTG

AAAGGAGAAAACTAACTCCAGGAAGTTGTCCTTCGAGCTCCTCTTGCACA

CCACTGTATACACCCCCTTATATACACTCAGTTACCATAAATAAAATGTT

TCATTATAAAGACACTTACGCTAAAACCATGCTGTAATCTGAATGGTTGA

ACATATATCCGCCAACAACCCACATTATATTTCCATTGACCACAGCTTTA

TGAGAGGCTCTGGGAAGCTTTAAATCAGAATATTCTTCTCGAGTCCAAAA

AGACTGGTTAGCTGGCACAGGAATTGAGCATCCAGGACCTAATAAAAAAA

AAAAAAACAACAACAACAACAAATAGCTTCACAAAATGCAGCCTGAAAGT

TTATAGTATTCCAAGTTCCAATCTAAGTGCAAAGAATATTTAAAGACTTG

TGGGGCTAGAGAGATGGCTCAGTGGTTAAGAAAACTGACTGCTCTTCTTG

GAGGTCCTGAGTTCAAATCCCAGCAACTACATGGTGGCTCACAACCATAT

GTAATGGGGATCTGATGCCCTCTTCTGGTGTGTCTGAAGACAGCAACAAT

GTACTCACATGAAATAAATAAATTAATTTTTTAAAAAACAGACCAGAAAA

AAAAAAAAAAAAAGACTTGTGTTTCCTTTAGCACTTAAGCGCAAACATC

TTTAACTTGTGGGGTTTTAAAGGTTTTTACATGTACAGGTATTTTGTTTA

CATGTATGCCTATATACCACTTGCTTGCTTGGTACCCAATGATGTCAGGA

AAAGGCATTGAATCCCCTGGAACTAGAGTTACAGATCTTATGAGCTACTT

TGTGGATGCTAGGATCAAACCTGAGTCCTCTGGAAGAGCAACCAGTACTC

TTAACCAAGAAGCCATCTGCTTAGCACCTAACATGAGTTTTTAACTTACT
```

FIG.3B(3)

```
CAAGATACAGACCAAAACCAATCACTCCCTTATAAAATTTAATACTACAC

ACTTTCTGATAATTTGGCAATTTCTGATAATCAGGTTAAACTTTTTTAGA

GGTAAAAATCTTGCTGAAGCAACATTTAGTAGAAAGGGTAGACCAAGGGG

TTATTATATTAACTCATGTGGAAAAGGCATTAGGGTTGAAATATAATGAC

AGATCAAAATCGATCTTCTGGCAAGTCCAGGCGCTGAATAGATGAAAGAG

ACAAAGGGAGAATTGGACAAACTAAAAACATTTACATGAACACTTACTTT

CTGAGGACCTAAGCATAGAAGGAAAATCACTAAACCAACGATGACTGCTT

CCTCAATACCCCAGGGAATTCCCTACAGTACCTTAGTACCCGGTTGTGTT

GGGTAATGGCACTAGATGACAGCACTGAGACTCTAAGGAACGCTTGTCCT

CCTCTCAGCTTGAGTCTCTGCTTCTCTATCACCAGACCATGTTCCCTAAT

TCCCACGAATGAGTTGCAAAGGATTTGTCAAACCTTTCCACAATTCTAAG

CACATAGATAACAACCACATATATGTAAATTCAAAGAATCTGAATAAATG

GAGATGAATGCTTAAATGCCACCTGATACATGATTAACATAAGGCGTATG

GCTGCTAAAATAAACTCCCTACAGTTCACTAACTCAGAACTTTCTGTGAG

GGAAAGGACTTTGAAGGGCAGCTCCTACCCTGCCAGTGAGGAAAGCAGGA

GCACCCTCTGGTATCGCTTGCATTACAGATGCCTCGGTGAGGAAAGCCAC

AGTTGTCTGTACAGTGAGGAATGTCACACGACTCCCCTTTCCAGTTTTCA

GAACATTCACACTCAACAGCGCTGCTGCTGTTACTGCTCTTACACTCTCC

TCGGCCTGAGCAATTATTCGGACACATGTCAAAACTACAAAGACAGGAGA

AAACGAAGTCAACAATTTCAACTAAGCAACATTGCAACTAATGCAGACCT

TCCTCCTTCAGTTTAAGTTCAGTTCATTTGCAAGTGTGACTGCAGGACTT
```

FIG.3B(4)

ACCAGTTAGCCCAAGTGTGCTCACAGAGCTCTGTGTAGCTAGAGCCCCAG

GCTCAAGTAATGAAATCAAATCAACCTTGCTGCATTCACATATGAAGAAG

GAAGAATAAATAACTCACAAAGTTAGAGAAATTACAAAACAATAGACATT

TGTGCAAAATCACTTAGACTTAGCTCAAGACTGGCAACCAGGATCCTACT

CTTTCTGGTAGCTCATTAGTAAAGAGTTCTACAAAAGCAGCAAGGTCATG

CTAGGAAGTGGAGGAAGGAGAGGAAGCCAATGAGCTGCCAACATTCACGG

TATACATTTCTCTGTAAAGATTCTGAGAATTAACAGAATTTAAGATTATT

TTCCAGTGATGTAGTTAAAGGTCTTTAGTAACTTTTATCAGCTTAGAAGG

AGAAGAGCAGTTAACTTCATGTATGAGTTTAAGTGTCTCATGACTTAAGA

TAACAGTTTTGCTACAATTTGAAATGCCATACTTCAGACTTTTTAAAGGG

GTGCATTAGTGGACTATTACAATAGCTTAAAAATATAGATTTCTCCTACT

GATGATTATTACTGAGACACTACTAGTCTTTATTAAATTCACTTAGCAAA

ACTCCTGACATTTTCTTCCAGCAGCGGAAGAATGTCTCTCTCTTCTAGGA

GATCCTCAGTGACAAGATCTAGAAAGACCAAGAACTGTGGTCCCAACCAG

TGGGGCTGATATTTGTTTAACCTTTTAGCTCCTGTTTCTTCAATTATGAA

AAAAAAAAAAAAGAAGAAGAAGAAAATCCATGTTAAAATTTAGCAAGGAG

CCTGACTAGCTAGAAGCCTCCCTCCAATATATTAGTGTTATTAAGTCATT

TGAGTAGTATCACAAATATTAAATCTAAATATCTTACTTGTAAGTGATAT

TAAATCCAGTCAGATTATAAGCAGCATCACTGAAAAAATGCAGCAGTGCA

TAACCTGAAGTGACAGTGACCTCAGGAGCCGTCTCATTGCCATCTCTTTC

AGGAACAATGAGGCCACTGAAATGTAAACACAGACCAGATTACAGCAACT

FIG.3B(5)

```
TCAACAGAAACTGTCTATATGTTACTATTTGATCCTGCTGCTCCTGTTCC

AACACACACTGTAAATGTGACTCTAGCTGGCCTCAAATTCACAGACCCAC

CTGCTTCCACCTCCTGGGTTATAGGCATGCGCTACTATGCCCAACATCTA

AAAGGATTTGAAATCTATGACTTTGATTGAATTTTTGGTTTTTTGTTTTT

GCTATAAACTTTTTATTATAATACTCTCAAGTCTCTACAATAACATTATT

AACAAACTTTATGAATTGACAACTGTCAAATATATACTGTTGAAAGAAAA

TACTTTACATATTTTTGTAATATGTATCATATAATCTTTTTAATGTATTT

TATAGATGTCTTATATAAGTAAAAATAGAAAAGTTTACTGATTTATAATC

CTTATACTATTAGCTTTCAGACGTATTTTTGTTGTTAAACTGGTAACACA

TTTTATGTTTATAATTCACAATAAGCACTGCCACTGAAGGTGCCAAAGGC

TCCCTAGAATCTCAGTAAGAACCTAGTGGGTAATATTTGAAGTTTTGGAT

GCCAGTAAATTCATGTGTAAAGATTTATTGAGTAAGTGACTACCAGCGGG

ACAGTGGTGGTGCACGCCTTTAGTCCCAGCACTTGGGAGGCAGAGGCAGG

CGAATTTCTGAGTTCGAGGCCAGCCTGGTCTACAGAGTGAGTTCCCAGGA

TAACCAGGGCTACACAGAGAAACCCTGTCACCCTGTCTCAAAAAAAAAAA

AAAAAAAAAAAAGAATATACCATTTTTAAGGCATTTGATCCACAAAATCA

TACCACCTTGTTTTACAAAAGATATATATTAACTTGAAGGCTGGAAATGG

TGGCACATGTCTTTAGTCCCAGTATTGGGAAGACAGACCCAGATGGATCT

CTGAGTTCAAGACCAGCATGGTCTACATAGTGAATTCCATGTAAGTTTGT

CCGTGTGTGTAACTTGAAACCTCATTATAGAATGGAAGTGTCTACCCCAC

CCCACTTACCAACAGTAAGGAATATTATGTTGGTCCCGCTCATTTAATAC
```

FIG.3B(6)

ATGGTGTACTCCCAAGGTAAATCATTTTCATGTTTAGTCGCTCCTATTAT

TTTTTCCATTATCAATTCACTACAACTACTACCACCAATCACATTTAGCC

ACTAGAAAAGCCATGTGATTTGCTCCACACATACAACTTCACTCAATAAA

TAAACATCTTATCAGTACTACTCTCTTTCACTCACTCAATCCCTAGTC

CCCTAAGTTTTTGGACGATTACACCAGGTAAATTCCTACTTCAGGGTTAT

GACCATCTTAAAAACTACGACCTAGCAATTCTCTTTGTATAAGAAATACT

TCCCCGTATATACACAGAAAAACAAAGAACACTACTACAGCACTATTCAG

ATGACAACTGACTAAAAGTCACCTAATTGCTTATTTATGGGAGTTGATTA

AATTAGTCATTACAAATCTGTAGGTCTGCAAGACTAACCAAGAGCTTCGT

GAGGACAATAGGTAGGGCTACCCAGAGAAACCCTGTCACCCTGTCTCGAA

AAAAAAAAAAAAAAAGGGAGGCACAGAGAAAAAACAACAGGCCCGGGGTA

CCTGTACATCTATGTAAGCGTAGGTACATGCACATAAAAGTGACTACAAG

AGAACATAAACAGAGAGCGCCGATGAGAAGAGGATGGGATTTTTCATTTA

ATTTGCGTGTATGAGAGCACCTATATGTGCATGTTATCCGCACCAAAGTG

TGTAGGGTACATTATGTGAGTGTGCCTGCAGACGTCACTGTCAGGTGTCT

TCAATCACTCCCCTCCTTTTTCTTCTGGAGATAAGAGTTTCATGAAGTAG

TACTGGCTGGACTAGAACTCACTATGCAAACCAGGCTGGCCTTGAATTCT

CAGAGAGCCTCTTGAGTGCTGGAATTATATGCATGTGCCGCAACACAGCC

CACCTCATTTTGGGGGGTAGGATCTTTCACTGAACCTGAGCTCACTGATT

GGTTAGACCGGACTGGCCAGTAAGTTCCAGGACCTCTCTTGTCTCCGCCT

CTTCAGCACTGTGATCACAGGCTCACAACCACACCTGGACTTTTACTTGA

FIG.3B(7)

GTCCTGGAGATCTAAACTCAGCTCTCCATGCCTGTGCAGAAGGAATTAAA

CTGAGCCAGCTGTCTCAGTATCAAGAGAGAACATAGGAACTGTAAGATTC

TGACAGTACTCTAGGGCTTACAGAACACCGACACATTTTCTACTATGTAT

TCAGTTAATAAAAGAATAAATACAAACAAAAAAACATGAGAAACATATAG

AGGCAGAGACAGACAGACACACACACACACACACACACACGCACACAC

ACACACACACACACGCACTTAGACGGGTGTGGGGGAAGAAAGAGCAAG

GCCACCTAGAAACAGGTACGTTCCATGCAAATGATCACAGGAAAGGATTG

GGGATTTTTAACCACTTGTGGGAAATGCTGTACTCTCCTATTCTAGCACA

GATTTGAGGAAAAAGTAGACCAGAGAGTCTGTCCTTCCACATATCCTGGA

AAGTCACTGACATGTCCAAGTTTTGATTTCTTCATAGGGACAATGAGAGA

AACCCAGACTATCTCACAGCAGCACAGCAAGGACCAACCAGCAGAGCAGG

AGAAGTGCTTACAGCAGTGTGCTGCTAGAAGGTGCAACAGTCTTCTTACA

GAGGGCATTTAAATATGCAGGATGGATAAGTTTGCCAACTACAACTACAG

AGGCTGGACAAGGTAGGACAGCTTCTTCACTGTCAAAGACGTTTGGGCAG

TTGCTTCTATTTACCTTAAAATCAAACTGTGACAGCTGTGGCATATATAG

ATTTCTCCCAGAATGAAAACACATTAACTCACTTATGTCAATAATATGGA

GTAAACACAAACATAGTCTATCTAGCTCAGCATGCAAGACATGTGAGGAA

GAGGAGCTACTGTGAGTCCCTATCCCTGTCCCTAAGGAAACCAATATATG

TAAATGTAGTCTAAGCTGCAGGCAGTTCTTCAACTGCCTACCCCAGGCTG

CTCACCACTTCACATTCTAAGCACAGACTAGAAAGTATGATCAACCTCTG

AACACTGTGCTATAATGTTACCATCAATCTCACACACAAATTTCATAACA

FIG.3B(8)

TTTTAAGTAAGTCTATGATGATTCTATGTTGTGTCCCAGTTATATAAGAT

CCATAGGTCACAGGGTAGACATTCAAGGACACCAACATTTGGAATTTTGG

GTTTTTTTGGTGTACTGTATATACTTGCTAGTGCAGGTACCCATGCTCAT

GTGTGTAGAAGTTGGGCGTCTTTCTTCTATCACTGTCTACTTTATATTTT

CTTTATTGTTTCATTTGATATGTATAGGTGTTTTGCCTGCATATATGTGT

ATGTTTGTTGCCAGAAGAGGGTATTGAATTCCCTGGGACTAGAGTTACAG

GTGGTTGTGAGGCACCATTATGGGTACTGGGACTCAATCCTGGGTTCTCT

GGAAGGGCAGCCAGTACTTTTAATCACTGAGCCATCTCTTTAGCTTCCTT

CGTTCATTCGTTCGTTCATTCCTTCATTCCTTCATTCCTTCATTCAGAGG

ATTGAGATACCTTCCTCAGTTAGGCTGGCTAGCCAATGGACTCTGGGAAT

CTATCTGTTCAGCTATTCTCTCCTTCCCCATCCAAGTGCTGGGGATACAG

GCAGGTCCTACTGGGTTCATTTTGAAAAATTACAGAACTATGTATTTTCT

TCATAAATCTGAAACTCAGCATAACTGTCTCAGGCTAACATGGAATCCCT

AAATATATATGAGGCACAACCTGACTTTACCAACTGTACTATGTAAATTT

GCTAGTATATTAGTCAACACTTAATGGAAAAACATCTGATAAAAACAACT

TACAGGCCAATAGGCAAGGAGACACTTGGGGAGGTGGATTCAAGGCAGTC

ACTGGATTCTTGAATTTAAGTCCAGCCTAGGCTACATGAGATTCTGCTTC

AAAAAATAAACAATTAAATTTATGGGGGAAAGAATGATGTATTTTGGTTT

CAGAAATTCCATCCTATCATCCAAGGGAGATATTGTATAACAGCGAAGTT

CCTCAGCTCACAGCAGTCAGTAGCATATAGACAATCCTGGCTCCAAGCCT

ATGAAAACACAGCCTGTACTAAAGGTGTGTTCCTGTGTTTTTGAGTGAGAT

FIG.3B(9)

GTGCCCCCTAAGTCTTGTGTATTTGAATACTTGGCACTCACTTGGTGGCG

ATTTGGGAGGAATTAGGAGGTGTGGCCTTGGTGGAAAAGGAGCATCACTA

GGGTCAAGGTTTCAAAATCCTCCTGCCATCATCCCCAATATGTCCTCTCT

GCCTCCTGCTTGCAGTTCAAGCTATGAGCTCTTAGTTACTACTTCCACCA

CCTACCCCTGCTATCTCTGCTCCATCATCATGGACTCCTATTCTGGTGGA

ACTGTTAGTCCAAAAAAGTCCTTTCTTCTACAACTTGATTTGATGCCAGA

TCTAGCCCCCCAGCCTAGCTAGCAATATACCAAGGTATACCATCTTGAAC

TCTAGGTGTCTCTCAATCCAATCAAGCTACATAAGATTAACCATCATACC

TAGTCATCCCCAAATCAGTGTATCTCTCTCCTCCCAAGACTATAAGCTCC

TCAAGGGTCAAAATATGTAGAAAGGAAGAAAGATTCTCAAAGGTCAAGGA

TCAGACCTTGGTGAGGATTGAGCACTGTCTACACTTTGCCTGGTAAAGAA

GGGTCCACAATGTAAAAGAGAACTGACCTGAACAGTTTTCAATTAGGTGC

TAACAAATGTCTCATACGTATTGAGTTTCTTATAAATAAATAAATAAATA

AATAAATAAATAAGCAAGCAAGCAAGCAAGCACTTAAGAGCACTAGCTGC

TTTCTTCCTGAAGACCTGGTTTCAATTACCCAGCACTTATACAGAGGCTC

ATACCAATTGTAACTCCAGTTTGATGATATCCAACATCTTCTTCTAGCCT

TCAGACACCAAGCACCAAGCATGTAATGGTATAACACATGTATACCAAAC

ACCCATACAAACCAATTTTTAAAAAAATATTCGAGCCGGCGTGGTGGCGC

ACGCCTTTAATCCCAGCACTCGGGAGACAGAGGCAGGTGGATTTCTGAGT

TCGAGGCCAGCGTGGTCTACAGAGTGAGTTCCAGGACAGCCAGGGCTGCA

CAGAGAAACCCTGTCTCGAAAAACCAAAAAAAAAAAAAAAAAAAAAAAT

FIG.3B(10)

AGTCATTTTAGGGCTGGAGAGATGGCTCAGGGGTTAAGAGCACTGACTGT

TCTTCCAGAGGTCCTTAGTTCAATATCCAGCAACCACATGGTGGCTCACA

GCCATTTGTAATGGGGATCCAATATCCCATTCTGGTGTGTCTGAAGACAG

CTATAGTGTAAATAAAATAAAGAAATCATATAAATAAAATAAATAAATCT

TTTTAAAAATATTAATTAACCCAGGCTGAACCTAAACTTACAAACTTCCC

ACATTAGGCTCTTTAATGCGGGTGTTATAGGTCTGAATACCAGCTTAAGA

ATAATATTCTTCTGAAGAATGTGCCCTGGTCAATCACCATGACCACACCT

GCCAACAGGTCCTTCATAAAATACTTGGTATATGTTGAATGTTCCATAAA

ATTATGGAGCTAGAAAAGGTAGTGAGCTAGAAGGATATTAAAGATATAAA

CCATTGCCCCAGTGGTCCTCACATTTGTCTAGTAATAGAACGTTGTTAAA

CTGTTTTTATTTAGAATTTCAATATATAAAAGACAAATATGAAATAGTCC

GGAAGCAAATTAAGCTACAGCTTGCAGCAAAGCCAGATAGAATGCAGATT

AAACTAACACAGTACCTTTGTCTTATGTTTTAGATGCTAAAGTCTAGTCT

ACAACCCCAGCTGCCCTTGAACTCTTAGCAGTCCTCTTGCTTCAGCCTCT

CATGCTGCTAGGGTTAAAAGTATGTGCGACCACACACAGTTTTGAAGTTT

AGAGCACTTAAATGATCTATTCAGCAACTCAGGCAGGATTTACACTGAAA

GTAAATTATCTTATGAATCCTTTTTGGTTTTCCTTTTATTCATTTCATTC

ATGCACCTTACATGAACTATCTATTGCTAGGCTGTCTCTATACTGGATGC

TCAGCACATCACCAACATGCCGATTCTTCTACTGGTACAATGGCAATGCT

GAGAAAACCACACAACCTAAGACAGTAGGGAGGTGGTGCTCTGATTGTTG

GTGTTGTTGTTGTTGTTGTTTTGGTTTTTCGAGACAGGGTTTCTCTGTGT

FIG.3B(11)

```
AGCCCTGGCTGTCCTAGAACTCACTCTGTAGACCGGGCTGGCCTCAAACT

CAGAAATCCGCCTGCCTCTGCCTCCCAAGTGCTGGGATTAAAGGCGTGTG

CCACCACGCCGGGCTCTGGTGCTCTGATTTTTAAATACAACAATTTTCAG

CTAGCAATGTAACTCAGTAGTAAAATGCCTGCCCAGCATGCACAAGGCTC

CAGACTGGACCCTGAGCACCACAACACTTTTTAAAAGATGTGTTTATTTT

ATTTTATGTGCATGAGTGTTTTGCTTACATGAATGTCTGCACTGTGTTTA

CCTGGTGCCTGTGAAGGTTAGAAGGCAATGGAGCTATGGAGAGTTGTAAA

CTACCATGTGGAAATGGAGCTATGGAGAGTTGTAAACTACCATGTGGGTA

CTAGGAATTGAATCAGGGCACTCCTCTGCAAGAACAACAAAGGCTCTTAA

CAGCTAAAATATTACTACAAACCCACACCACAAAATTTTAAATTGATAGA

CATTATCACCTTAGTTCTAGATAGAGAATGTGCTTGGCATTGTAAGTACT

AAAAAGGTTTTGGGGTGGATCTTTTATATTATCTCACTATAATTTTATAA

AATTAATACTCAAATATGTTATAAGTTAAGGTTTTTATTTTTGTTTTTCA

TTTCTGTATTTTGTCTATGTAGCTCTGCCTGGCCTGAAACTCATGGGAAC

TTGACTGGCCTCAAACTCAGAGAGACCTGAACGGCCCTGCCTCCAAAGAG

CTGGGACTAACCATGCCCAACAGTAGGTAGCTTTAATACCTAACCAGTGT

ATTAGTTCATGCTCTCAATTAACCAACATTCTCTACATACAGAAATTTTT

ATGCCTATTTAATCAAATACACAGTCTAAGTAAACTCTAAGTACAACTGC

TTGGCTCATATTCTTACAATGGCTATGGCTAGCTAATTCAAAGGCCAGTC

ACATAAAAGGGTCTCTATGAATTCTGATTAACAAATGCAGTTAAATAGAT

GAATTCCTAAAAAGTAGTATCATAATAATATCATATTTAGTTTTTGTGCT
```

FIG.3B(12)

TCCATTATAGTTTGAGGTGCCTCCTCCCATAATGCAAGGTATATTTCAAA

TAATAGATATATACATGGTTAACACATGGCAAATGCCATTTTAAATGCTT

AGCACAGCCTGCTCTTTGGCTCCATTAAGTGAAACTCTTAAGTTCTCAGT

TAAAATAATTGTTGGAGAGCTATAGGAGCAATGGGTGGAGAACTAGTCTT

CTAATTTGTCCTTTGCCTCCTTGCGTACTAAGTAGTCCCTCCCTCACTAT

GTGGCATTCCAGCAGACTACCACCAAGAGAAGAACAGAAAAGTGTTGATT

TCTTTCTAAAGTAAAGAAATAAGGGGCCAGTGAGATACCTCAGCAGGTCA

AAGCCATTTGCCTAGAAACCAAAGTTCAATCCTTGGAAGCCCTGTAAAGG

TGGAATTAGAAAACAGACTCCACAAAACTGTCCTCTAACCTCCACTCGGG

CACACATGTGCCAACCCCTCCATTCTCCCTCCCCCACATACAAAGTAACA

ATAAACTTTCAGAAAATTTAAGTTGCTACGCATGGTGATTGATGAATGTC

TTTAATTCTAGCTCTTGGGAAGCAGAAGTGGGTGGATCTCTGTCAGTTCA

AGACCAACCTGGTCTATATAGTGTGTTCCAGGCATCCAGGACTACACACA

CACACACAAAATTACGTGAAGGAAGTAGAATGTTTGAAGGAAAGAAGTCT

GGAAATGGGGATGGAGAGAGACCTCAGCAATTAAGAAAAGGTCTTGCACC

GGACGTGGTGGTGCATGCCTTTAATCCCAGCACTCGGGAGGCAGAGGCAG

GCGGATTTCTGAGTTCGAGGCCAGCCTGGTCTACAAAGTGAGTTCCAGGA

CAGCCAGGGCTACACAGAGAAACCCAGTCTCGAAAAAACCAAAACCAAAA

ACAGAAAACCAGTATGATAGGTCAGGCAATTGGATCGAGACAGGACACTC

AAGATAGCTAGCCTGTGCAATATAGAAAGAAGTCTCATGGAAGAGAGAGG

GAAGGGAAGGAGGGGGGAGAGAGAGAGAGAGAGAGAGAGAGAGAGAGAGA

FIG.3B(13)

```
GAGAGAGAGAGAGAATGAGAGCGAGAGAGCGAGCGCACCTCAGTTGATAC

AAGATTGGGGCCCTGAGTTCCATCCCCAGCATCCCATAAATTGGGTGTAG

CAGCACACACCTGTATCCCAGCAGAGAGGCAAAAGACAAGTTCAAAGTCC

TATATGGAAAAAGTGTGAGATCAGCCTGGAGACCTGGTGTGTGGCAGTGG

GGTGAGGGGTGTCATCAAGGAGAAGGCTTAGTAAGTAAAGGACCTGCGTT

GGTTCTTGAGTTCAAGTCTCCAGCAATCAGAGAAAGCCAGAACCATTGCA

CAAACTTGTAAGCCAAGTGTTGGACTGGACAGAGACAGGCAAATGTTTGA

GGTCCAGGTTCAGTAAGAGACCCTATCTCAAAAAATCTGATGGAGAGTAA

CACTGGAAGAACTCAGAGTGAGTCACACATGCACACACAGGTGAATGTGT

ATACAAAGGGGCAGGGAGGGAGAATGAGAGGAGACTGGGAGATATCTGT

AGTTCATGTCTGTAATTCTAGCACTTCAGAGGCAGCTGGAGCTACACAGC

AAGACCCCGTCTCAAAAACAAACCCAAGCCTGACAGTGGTGAGGTACACC

TTTAAGCCCAGAGGCAGGAGAATCTCTGAGTTCAAGGGCAGCCTGAGTGA

GTTCCAGGACAACCAGGGCTCCACAAAGAAACACTGTCTTGAAAAAAACC

AAAACCAACCAAACAAAAAAGAATCAAAAACAACCACCACCACTACAACA

AAGCAAACAAGGGAGAAGGTATAAAATGCTTAGGAGAGTCTTCCTTTAGT

CTCCATCCTTTGGGTACTCCTTCCCCACAGAAAGCCACTACTACCAATTT

CTTACATAAGCTGCTGTTTTAGACACAGGTTTTTTTTTTTTTTAAATATA

GTAACATATTCATGTGTAGCTCATTTTTCTAGTGAGTGGTTGGTCCTTCT

TTTAACAGTTTAAAGGACCTCTATGTTTAAAGGCGATTGGCCCTTGTCTG

GAGTATGGGTTGTATTTTCCCAATTTGTGAGTTTTACCCAACCTATTGCC
```

FIG.3B(14)

```
TATTACCTATGGCCATTTATTCTTGTCGATAAGTAGTTTCCAATTGTATG

ACTATGGTCACAGTGTTCCATGGACTCTTCTGCCGCTAGACAGCCCCTGG

GTCTGAATTTGAGATGGTTACAAGGGTGATTGGCTCTGCTCCCTGGGTGC

TGGGATTAAAGGCGTGCACCTCCACACCCAATTTGTTCTGTTTTGTAAGA

AATGAGGTTTTATTGTGTTGCTCAGGCTGATCTCAGTCTCCTGGCCTCAA

GGTATCCTCCCATGTCGATACACAGCACAAGGCGTAGGAAAAGTGGCAGA

TTTTTTTAAATTAAGTTTTCTTTCCAAAATATAGATTCAGAAATGTGAGA

TTTTCACAAAGTGAACCTGCTCACTTCCCTGGCTCTMGAATCTCCATTGT

GGCTCCCGCCCATCCCTTTTGCCCACCAGTGGCTGTTGTATTGACTTCTA

TCCCATTCCTTAACTATACCTGTCCTTGGTCTTCGCTGTGAACTTGCTTG

GGCTGAGAATCACCTTGTTCCGGGCACATCAGGTCAGTGAGGGTGTTTCC

AGAGAGTTTTAACAGAGACCAGAAGACCCACTCCAAATGTGGGTGGCAAT

ACCTGATGTTCTGTCATCCTGGACTGGGTAGGAAGAGGAAAGTAAGAAGC

AAACGGCACCCCCACCTCTCTGTCTGCTTCCTCGCCGACACAAAGTGACC

AGGGCCTCCCACTCCTGCCCCCTCAGCTAGAGACACTTGCTGCCATCTTT

CCAACCACTCTGAGACTGTGCCTACTAACCGTGACCCAAAATAAATGTTT

CCTTCCTTAAGGTTGCCTTTGTTAGCTCCTTTAATAGAGCGGTAGGACAT

GTAACTGCCACAGGCAGCCATCGCTGCCAGCCCCTCCCACTGACCGTCTG

AGAACCACACTCAGCTGTAGGCACAGCTCTCATAGCTGTGTGGGCGTAGC

TCTGTCTACTCGGTCATTCCCCTGCTGCCGAGCATTTATTGTTTTCAGTT

CCTGGCTGATGGGTAGCACTGTTATGAACATCCTAGTACAAATCTCAGGG
```

FIG.3B(15)

```
TGACACGCGCCTTCATTTTTCCTGAGAAAATGCCCAAGGATAAAATGCTA

GGGCCAAGGGAAGAATATTTCACCATTAAGAGACACTGGTCAGGACTGGA

AAGATGGCCCAGTGGTTAAGAGCACTGACTACTCTTCCAGAGGTCCTGAG

TTCAATTCTCAGCAACCACATGGTGGCTCACAACCATCTGTAATGGGATC

CAATGTCCTCTTCTGGTGTGTCTGAAGACAGTGACAGTGTACCTACATAC

ATGAAATAAATAAATAAATATCTGAGAGAGACAGACAGACAGACACTGGC

TAGTCATCTCACAATGTTCTCATGTTTAAAATATGATACCATTTGTATAA

AGCAGAAACACAGGAAAAATAAAATCTGTGGTATTATATTTGATTTTTAA

ATTAACTTGATTAGTGAAGTTAGCAGCTACACTGGGCAGGGGTTGGGAGT

GGGGTACTCTGAAGTGCTGGTATTTCTGGTTTTGTTTTTTGTTTGTTTGT

TTTTTTATCTTATTTATATTACATAGAAAGCCATTTTGCTAATACACTTA

CCATGTGTATATATTGTGCTTGAATTACAGCTAAGTAATTATTTCTGAGG

GGCTTTAGACTACTGAAGATTGGGCCCAATGAGCCCCACCCCAAGTAGTC

TCCAACATCCCTCTTGGAAGTACTTGAGAGCAAAGATTCAAGTCACATGT

CCCCAAACCCTCAGCAGCCACCACCCTTTAGGTGTGGCTTTTGCTCTCGG

TCATCCTGGAACATCTTGCCATCTTTGGTTTGTTCTCTCCCTGTCTTGCC

TCTGGTAGAGCTGGGTTTCTGTGCTTCTATTCAACCATGTACAAGAACCA

TGTGCCACCTGCCATGTGCCAAGCCTGTGCCAGTCCCTGTGAGCGAGCAG

CCCACCCCGTGAGTTATCATGTGAGGAGCTATGAGGAGCAGGAAGGGGCC

CGGATGACTTCAGCAGACAGTATGAAGCAAGCACTGTGCGATTTATGCTC

CCTGGCCACATGCCCACAGATGGTGTCTGAGACACTAGCGTTTAATATTT
```

FIG.3B(16)

GAATTCTCCACATTCTAGCCTAGACATTTTGGTTGCAAGAAGAAAATTGA

CTCCAGTTGTATCCTGGAATGAAATTTATTGGAGGAAAATACTGGACAGG

CTCCCAGAGAAAATACGATATTCAGGCACAAAAAGAAATGGGGACTGAGG

ATCTGAAGTTCAAGGTCATCTGTAATGAGATTGAAGTCAGTTTGGGCTAC

ATGGGACCTGGTCTAGGGGGAATGGGGAAGAGAAGGGAAGGGATCGAGAT

AGGGAT

FIG.3B(17)

CAATGTGCTCTGACGATTAATGGGCTAGAAATGTGTGGCTGTTGATTAGT

GAAAAGATGTCATGGTTCAGGAGATTGGTAGTCTCTGTGGGAAGACAACT

CACTGAAAGGGAGGAAATAGCCTGGAAGAGATAAAGAGACAGTGATCAGC

TAGGAAGCTTAAAATTTAAATTTTGTTGGAAGTACTGTTAGGAATACTAG

CAGAGGCCAGATGAATGTATGGTTAAGTTATAGCAAAGGAAAAGATTGTT

AATGGTGAGGTTAGGAATGCAGGGTGACACCAACCTGTAATGTCAGCATT

AGCGAGATAGAAGCAGGTGTTTAAGGCCATTCTCTGCTACTTAGCAAGTT

GAGGCCAATCTGGACCACATGAGACCTTTTTTCAAAAATAAATCTCCTTA

AACAAAAGAGGCTGGGTTTTTTGATAGATTCTTCAAGATGTTAATGTAAA

TAAATGGAAGACCAAGGATGGCATGCTAATATCCTCAGTGTCTGAAGAAG

GACTATGTAGTGTTGGCTGCTGACTCTGAAGTAAGTGCTCATTACTGACA

GATAGTGTATCTTAGAGCCTGGCAGATGGGATGGAAGTGAGGAAGCAAGT

AGCACCTTTGTATATTATGTTCTAAGTAGCCAGAGATACTTGACACAAAA

CAAAGTTGAGAAAATGTATCTTCTAGAAAATACAGACATGGAAAGGTGTC

CTTTCTATAAAAGAGGTATTAAACATTAACCTGAAAAAAAAGTTAGCAAA

TTGGGCTTTGGCAAATGAATATAGTCAAGTTTCATTTTTATTTTGTTTTT

TGTATATGACTGTTTGGCTTGTTGTACCATGTGTGTTCCTGGTGCCTAGG

AAGTCAGCTGGAGTTACAGATGGTGTGAGTTGCCATGTGGGTGCTGAGAG

ATGAACCTAGGTCCTCTGGAAGAGCAGTTAGTGCTCTTAACCACTGAGCC

ATCTCTCTAGTTCCTTCTGTAGAATTTTCATTAATTTACAAAGGAGAAAG

TATAAATGATAAAACCATGAGAAGATAGACCGGCACTAGAATTAGTGGAG

FIG.3C(1)

```
TCAAAATGTTAATGATATGTCAGATACGCCTTATATGAGGAAGTTGCAAA

ATTATGAAAATCCAGGCACTCCACTGAGTTAGAAATCTAGGCTCTGATGC

ATACTGCTATGGTAAGGTAGCAAGTGGCCATTGAGTGCAGAAGTGAGTCT

GGATGGGTCTTCTGGTGTTGTGGAGCACACAGACTGCTGTCTTCTGCATT

GCAGTTTCACCTGTATTTCCTTGGAACTACTTAGCTTTGCAACTAGGCGT

TAAAAAAAACTTTATATTTATGGTTTTAAGTTATTTATTTGTTTTATTTT

ATTTTATGAGACATAGTCTCACTCTCTAACCTAGGCTGGCCTGGAACTGC

CTAGGTAACTTGAGCTGGTGATTCTCTTGCCATAGCCTTCTAAAATTTTA

GATTGCAGGCATAAGCCAGACCACTCCTGACTTTTGTAGCCATTTTTCTG

ACATGAAGTGTAACTTTGCTTTCATAACTAAAATGATTTAGTTGTTTTGT

TATTGTTTAATCCCTTTTGCTTTGAATGTATCCTTTTGTGTGGGTGGCAG

ATATATAACCACAGACTTTTCCACAGGCATCCTACCCTAGGTCCAGAAAT

GACTCTGAGACGTCTTATATATGAATGAATGCCTAGGCCAATAGCTTTGG

CTGATTTCCACGGGTTCATAGCTCAGTTATCCCATTTAAACTAGTCTAAG

TCATGCCATGAGGCTACATACCCCTCCTTCAGTTTCAGGCGACTGTCTTC

TCAGTTGTGTAATGTCCTATCCTCTGTTGCTGCTCCCCAACCCCCATCCT

TGCGTCATAGTCCGTCTGTCCTCGTCTCCCCCCATTTACTTGCACAACGG

ACTCTACTCTAGAAGTCCTCTCTGTGCTGGAGCTTGCACCTCCGCTCTCC

CCGTCTAAGCTAATAGGCAACAGCATTGTACAGACAGGTGATGCTTCCAT

ACATCGCACAGGAGATTCTCCCTACACAGATACTTATTCATCCAGCGTGA

ATGCAACCGTCCAGGCGTGTTCTCCTAGTTGTAGTACATGCTGTTGTATC
```

FIG.3C(2)

```
AGTCTGATGAATTTCTTTGTCTTTACAACCAAGAAAGATAATACTGTAAG

AAATTTTGACTAACATTTTTTCTTTATTTAAATTACAGACTAACTGGCTC

TTCTGGATTTGTAACAGATGGACCTGGGAATTATAAATATAAGACGAAGT

GCACATGGCTCATTGAAGGACAGTAAGTTATAATGGCTGACTTTATTTTA

ATTTATTATAAGAGCACAGTATAGCACAAAATACTTCCATGTGTGTTATT

GCTATTTCTTGAGACAGGACCTTTCTGACTGAGTAACTCAGGCTGACCTT

GAATTTTGCTATGCTACCTCTGCTTCCCAAGTGCTAGGGTGGTAGGTGTG

GACCACCATGCCCTGCTGCTAAAATACCGTTCATTGATGCTTTTCATTTG

GATAGTGTTCTTGCTTTTTAAAATTTACTTTTTGGGGGACCAGAGAGATG

GCTCAGTGGGTAAAGTGCTTGCTGAACAAGTCTGGTTATGTGAGTTAATC

CCTGGCTCCCACAGTGGAAGAGTGACTCCTGAAAGTTGTCTTCTGACTCC

CACGCTTGTGCATGCACGCACACACACAAATAATAAAATAAAAAATTAAA

AGGAAATTTTCTTTTTTTGGGTGATAGGGATTGAACCTATGACTTCACTAA

GCAAGTGCTCTATTGTTAAATAATTCCTTTAATTTGTGGGTTTTTTTTTT

TTAGGTTCCAAGTTGACTTAATGTTATAAATGAAAGATACATACCAGAAA

TTTGCATATTTCTAATAGTTTAAAAAACTTAGTTAAAATCTTTTTAATAG

TTTGCTTAAATCTTTATATAATAATGCTATTATATCATTTTTCTAAATAT

TGATTTTATTATCAGCAAAACAGTAAATGAGCCATCAGAATAACCACTGT

AGCCTGTTTCCCTGGCCCTCTGTCCTTCCATCTGTCTATCTTCTCTTTTT

TTTCCTTTTTTTGTGCCTGTCATTTAGGGCAAAGCATTTTAGTCTCTGAAC

AAAACTTTGAAATTTCCAAGTAACTCTTGTTTATTTGTTGTGTCTCATAT
```

FIG.3C(3)

```
TCAACCCAAGAAATATTATTTACTAACTCATTTAAAAGCAACAATTATAA

CCCACTACATGTTAGCAGAAAAACCTATTTGTTTTTATTGAGACGGGATC

ACACTAGTAAGCACTACATGGCATGGCGTTCACTGTGTAGATCAGGCAGG

CTGGCTTCGTGCTCTTGACAGTCCTCCTGTGTTTGTCTCTCACTTCTGAG

TGCTGGGATTATAGACATTACCAACACACCGATTTGGGGGGTTGGGGTAC

TGGGATCAGTCCAGAGTTGCATGGATGCTAGGCAAGCACTCCACCAACTT

AGCTATATCCCTGGTCATAAATGTCATAAGGAAAAAAATTCCTTATATTT

AAAGAAATTTTAAGAATTGCATTGTTTAAGATTTCACAGATCTCTTTGCT

ATCTGGCAATCTTTTTTGATATTTTGTTTTGTTTTTAAAAATATGTGGTA

TGTAAACAAACTTAAATATGAATGGGACAGTTCCAGATGAGAGTGAAAAG

TTAAATATTTGGGAGAAAAATTGATAGGTTTATCTATTATGGAAAATTTC

AGAGATTTTAGTAAAATTTGAAAATGGAGCTGGGAGGTCTGAGGTAGTCA

TCTAAAGCTGCCAGTTGTAGAGCGTGTTGGAGTGTGGAGTCAGAGGGAGT

TACTGATACACTTGTTGAAATTGCCCAGGCTTCATGGGAAGTGATGAGGG

GCTGTTACTGTGACTCTGGGCAGGGCTTGTTAGTTTCCTTTGGATTTAGT

CTCAGTCAGAGTTGATACATAGTTTCCTGAGGACGTGGCTTTTTGGTACA

GTGCTGTGAAAAGGCAGAGAAGCAGGTAAACTTAGAAAATGTGTGTTTTT

AAAGTGATGTGTTATGAAATCTTACGTAAGATGAATAAAGAAAGAAGTGG

GGACACTGAGGGCTCCTGTTTCTAAATGTTAAAAGCAAGGCTGGAAACAT

TCTTTGAAGGCCCCTGAAGTCAGAGCCCGTGTCTCTTTTGGTTCCCAGGA

CATTTTTGATATTCCCTTACACATAGCAAATACTAACTAGATCTCTGACA
```

FIG.3C(4)

```
AATGCAGGAAAGCTGTTTATATTTATATATATTTATATTGTATATTTTTC

TCCTTATAAATTCTTTAAAAGTCTGTTTTAGTAGTTAATGTTATGATTAT

TATAAATTACTTAATTATTTTTCTAGGCCAAATAGAATAATGAGACTTCG

CTTCAACCATTTTGCTACAGAATGTAGCTGGGACCATTTATATGTTTATG

ATGGGGACTCAATCTACGCACCTCTGATTGCTGCCTTTAGGTAAGCCCTG

CTGCATTTCATCTCAGGAAGTAAGTGTGTCTCCAGGATGGAGTCCGTGCT

GCATTTACTTTATTCTGCAGTCACACTCATCTCATGGAATTAGTTCTGTT

CTGGTGAGCTACAGTTCACTTGGTTTTTATGTACTGGGTCGTTTTCCATG

TATACTAGTATGTAGCCACGGTTAGTCTTGAACTTCTGGTTCTCCTGCCT

CCACCTTCCAAGTGCTAGGAGTATAGGCTTGTGCCACTGTGCCTGACTCA

TTTCACATTCTTGAACTGTGAAGTTTTGATAACACTATTAAATTTACCTG

CTATTTGTGATTTTGTTAAAGTTTGCATTAAAAAGTTTTTGACTATATTG

ATAATATTTTTGTGACAAATTTAAATCAGAAACCATACCTTTCTTGTTCT

TGTATGTATTTCATTCCATAGGCCCTTAGGAATAACTTTTTTTCAATAGTA

TATAGTTCTCTCAGTTTGTATATATGTATTATTAGGGATAGGAGGAGCTT

TCTGGAAGACTATTTATAAATTGGACAATGGCTAGCTGTTGAGAGTGAGG

AATTTGCTAGTTTTGTTTTGTAAATCCCTCCCCAATGCATCTGTATTAGT

GATTTAATAAAATAATGCAATTTTGTCAGTTATATGGGTTGCACTGAATT

TTTGCTATTTTATTTTAAGAAAGATTTTTGTGTGTCTACAGTGTATATGA

GTGTATGATATGTGTGCGTGTGCATGTGTGTGTACTTCTATGCAGGTA

CTCACATGCTATGGTGTGCACGTAAGGTTGGAGTGCAGCCTCACATGTTG
```

FIG.3C(5)

```
ATCATTATATTCCACCTTGTTAGAGATAGGTTGTCTTTGTTGTTTGCTGC

GGCCTGGAGCTGGAGCTGGAGCTAACGAGTCTCAGCCACCTGACATGGGT

ACTGGGAACCAAGAGCAGCAAGACCTCTTCTTCTTCTTCTTCTTTTTTCA

TTTTCGGTTTTTTCAAGACAGGGTTTCTCTGTATAGCCCTGGCTGTCCTGG

AACTCACTCTGTAGACCAGGCTGGCCTCGAACTCAGAAATCTGCCTGCCT

CTGCCTCCCAAATGCTGGGATTAAAGGTGTGTGCCACCACCACCCAGCCT

AAAAGATTTTCTTACTAAAATATATTTCTAAATTAATTAGTTGGAATCTG

GTTCATACTTCTTTTTGAAACAAAACCAGCATTTTTTTTCATTCTACATA

CAGAGACATTGACACTAGACACTGGTTATGAGTAGTTACTATAAGAATGG

GAAATTATTCCACCCTTGTAAAACTTAATACAACTCCTTATCAGGCTCTG

AAGACTTTTTAAAAGCAAGAATTGTATATAACACACAGAAATGATTTAGA

CTATTTAGATCTTTATTGCATGGGATTTTAAAATTATTATTGTATTTCGT

GGGCATGTTTTGTCTATGTAGCATATGTGCCTGTAGAGGCAACCACCAAG

TAGGTCCTGGGAATCAAACCTGGTACCCCTGCTCTTAGGTGTTCTTAACT

GCTGAGCCATCTCTCCAGTCCTC
```

FIG.3C(6)

AGGCAAGAAAGAGCCAGCGAGCCTCCAGACAGACCATTAGAAATTCCACA

GTCAGCACAATAGGGAGAACAGTAAATCTTACATTAAAAGAAGGCCAGGG

CCTGGTAGCAAAAGGTTTTAATTTAAGCACTTGAGAGGGAGAGGAGGCAA

ATCTCTCTGATTGGGGGTTGGGGTTAATGGTGAATGCCATGACACCCTGC

TCAGAGTTAGCCTTCTCCCCTAAAAAAATTTTAAATTCATTTTCAATGCT

GACACAGTTAATCATAGACATTGTATCTCAGACACCTCAACATACTCCAG

ACTGCAGCACCAGCCCACTGCTGAGGCTGTCGTTCAGTTGGTAGAAGGCA

TGCTCAGCATTCGCGAAGCACCAGACTTCATCCTTAGCACTACATAAAAC

TGGGTGTGGTCATGCACACTTATAACTTCAGCACCATGGAGGCAGAGGCA

GGATGATGAGAACTTGAGGATCATTCTCAGTTACATAGGGAGTTTGAGGT

TAAGCAGGGGTACAGGAGGCCTGTCTCAAACAAACAGACAAACAGACAAA

CAAACAAACTTCAAAAAACTCTTGAAGTACTAGGCCTAGTACGTGCTGAG

ATTGTAGGTATATGTCATCATGCCTGTTGTAGAATGAGTGAGAGCGGACT

CCATAGGCTTATAGATTTGAATCTTGGTGTCTGTCTATGTCATGTCATCC

CTGCACAAAAGCCCACACTAGGCCCACACATTCTCTCTGTCTGCTGCATG

TGGGTTAGATGTGAGCTCTCAGCTGCTGCTCCAGTGCCATGCCTGCCTGC

TGCCAGGCTCCAGCCATGACGGTCAGGGACTAACTCTCTGAAACTGTAAC

CAAGTTCCCAATGAAATGCTTTCTTTCATAAGTTGCCTTGGTCATGGTGT

CTGCTTCACAGCAATAACACGGTGACTAAGATACCTGGCTCCTCCCCTCC

CCACCCCACCATTATTTACCATAAAGTAAACAATACACAGTTGGATAACA

TGATACTGAAGTTATTTTCCTGTTTCCTGATGTAACCCAATTTTGGACAA

FIG.3D(1)

GATTAAGCCTTAAATAGCAAGCTGTGAGGCAGGATAAAGAAAAAGCTCGC

AGGCCAATGTCTGCTTTACCAAATTCTGTTCAGCAGTCTAAAGCTGCCGT

CACCTCGACTCCTGTGATGGCATTTCCATCACTATCTTAGATATTCCCTG

GGTCACAACCTTTTAGTACACAGATTGCAACTCTGATGGAATGGCTGACT

GCTTGGCTAATTAAAGCAAGCTAGAGTTTGTCTGGCTTCCTTGTCTGAAT

GGGGAGGTGGTATTTACAAAATTTTGTAAATAAACTACTATATTTGCATG

ATGTATATAAATTTGATGTGGCTGCTTTTAAATCATTTAACCTAAACTGT

CCCACAGAATCATCTGTTTGATTGGAAAGATTGTAGCTTCAAGAGAATTT

CTGCTGAACCTGAAATGATTCATAATGATGTGTCTGAAGAATGTGTGCTA

TCACCTACGGTTTTTGTTTTAGTTGATATTTGTACTTTAAGATTTCCTTT

ATGTATGTGTGTGTGTGTATTTATGTGAATGTATACCTCATGTATGTG

GTGCTCAAGGACACCTGAAGAAGGGCTCTGGAGCTGGAGTTACAGGGAGT

TGTGAGTGCTAGGAAAGAAAGCTGGGTACACTGGGAAATCAAAAGGTGCT

TCTAACCACTGAGAAATCCTGCCAGCCCCTTGGTTTATTAAAAATATCAA

ACAAAACCAACACTAGTTACATAAGTATCTCTCTCTCTTTCTTTCTCTCT

TTCTTTCTCTCTCTCTTTCTCTCTCTCTCTCTGTCACACACACACA

CACACACACACACACACACACACAAAGGATCCATAATAGTTCTTCTGT

ATCCCGGTTAAATATAAGTTCTTAGGGGCTAGAGAGATGGCTCAGCAGTT

AAGAGTGCTTGTTGTTCTTCCAGAGGACCCAAGTTCAGATCCTAGTACAC

ACATCAGGCAGCTCACAGCTACCCATATCTCCAGCTCCAGGAAGAACCAA

TCAATGCCTATGGCCCATGCAAGCACCAGCACACATATGCTCCACAAACA

FIG.3D(2)

```
TCCATATATATAGCTAAAAGTAATAAAAATAAATCTTCAAAAAATTAATT

CTGGTTGAACTGAAAAAGATCACCTAACATTTAGAAAAAGCAGTTTACTA

GTGAATAGGACATAAATCATGGTATCAAATATTCTGTTGTTAAAGGAAGC

AACTAGAAAAAGCATGTGTTTGAAATAACCAATGGATACAAAACAAATGA

GGCAACCCCAACATCTGTCAGTACCTTGCAAACCAACACAATAAATTTGA

TTTTATTTAAATCGTAGTTATTTTTCATGCTAGTAGTTTTGAAACACAAT

AAATTTGATTTTATTTAAATCGTAGTTATTTTTCATGCTAGTAGTTTTGA

AACCAAGATCTAGATTTTGTATAGCCACATAAATACACATTAGAATTGCA

AACTGATACGAGCTTCATCTTCATCAGTCTCTCTTCATGAAAAGCAGTTA

CAGGGACTGAGACATGACTCAGCAGTTACGGCATGGGCTGTTCTTCCATA

CGACATGGATTCAATTCTCAGTGCCCAAATGTTGGCTCACAACCATTTGT

AACTCTGGTCCCAGGGGATCTGACACTCTTCTTGGCTTCTATGGCCACTG

TATTCATACGGTACACAGACACATATGCAGGCAAAACTCAACAAAAAAAA

TAAGGTTTAAAAAAAAGAATTAGAACTTAAAGGCACTTCATTCCGTCAGC

ACTAAATCAGCCTCTCTGGAGTCTTCCCACTTCATGAGAAAATCGTCAGC

TCTCCACTGCTGTCTGTGGCTGAGGAGCAGGACCTGGACAACGTTCAGAG

ATTGTCAGTGCATCTCTTTTCTTCTTTGGTTTGCTGTCATCAGGTTCACT

GTCACATTCCCTTTGTACCATCCTTCCTTTAACAGCCTTTTGAAAATGCA

GAAATGTTGGATGCTGCCTTCAGTTCACACAGGCTGTCTTTTTAGCTCCT

CATCTATCTATGCTTAATTTGTTAGTGGTGCTCACCCATGTATGTGTTTA

TGTCATGAAGCCACAAGATGAGCCTTGATTGAGTCTTGCTGTCAGTGTGG
```

FIG.3D(3)

ATCACAGAAATGACACCCTATCATCTTTGCTTCCTGCTTGTTAGAAGTCA

TTGATTCTGCTTATACTCAAGGCCCACAGTATTATACTTGGGTGTGAACC

CCAGGAAGCAGGGAGGTGGGGGGTGTCATGGATACTACTCAGATATCTGA

CTGTTGTGATATTTCATCAGTTCTCATTGGTCCTATCTTTAAAATCTGCC

CTACATCTAGAGCTGGCTGTGGTGGTGTGTGTGGTGGCATCAGTATCAGA

ACTTGGATTACAGAGGCAGGAAGATTGTGATTTTTGAGGCCAGAATAGGT

GCATACAAAGATCCTGTCTGCAAAAGAAACAAATGTGCAAATAATTATAA

CTACTTTACTAATAGCCTAACTAATAACCACTGCTAGTGCTGTGTCCACG

AAAAGGTGAAGTAAACTGTGAAAATGACTTCCCCTTCTGTGTGACACACG

CCGTCATGTGATTTTACTTGTGTCTCATCATTGTTTTTCCTTCTGTTTGC

ATGTGTGAATGTTCACATGTGGAAGCCAGAAGTCAGTGTTGAGTGTCTTC

ATAATTGATCTCTATTCTCTTTGTTTTGAGACAGGGTTTTGAGACTAAGC

CCAGTGCTCAGTGATTCATCCAGTAAACTGTAGGGAGCTTCCTGTCTCTG

CCTCCACAGTGTTGGGATTACAAGCATGATCCAAATTATGTGACAAGCGC

TTTACTAACTTAGCCATGTCCTCAGCTCCCCACTCCCCTTTTCTTTTCTT

CTTCTTTTTTTTAGACTTACTTGTTTATTTTTATGAATGTCTTGCCTGCA

TGCATACACACACACACACACACACACACACACACACCCCACATGC

AAGCAATTCCAGAAGAGGGCATTGAATCCCTGAAACTGGAGTTCCAGTTA

ACTGTGAGCCTGTCATGTGCGTACTGGGAGCTAAATCCGGGTTCTCTGGA

AGGTCAGCAAGGTCTTACCTGGGAGCCGTCTCTTTAGCTCATGTGTTTCT

CTCTTGAAGCAAGAAACCTAGGAATCATTTTGAAACTTCCTTCACAGCCT

FIG.3D(4)

TTATCATAACTTCACGTCAATTTTTACCTACTCTTTCAACAAATACATGT

TATATTTACTTATTTTTATGTTTAGCCTGCTATTGGTTTCTACTTAGCCT

CTTGCAGTAGAGTTCTGTCAGATTTATGTTTCTATTGCTTTTAATTTATT

TGTAAAGGTGAATGGGAAAATATTTAAAAATTACAGATCCCATCATTTAC

TATATTCTTAAAAGCCATGGCTAGCCAGGCTTGGTTGTGCATGCTTGTAC

TCCCAGGACTCTGACAACTCAGTAAGGAGGAGAGTGAATCAGAAAATAGC

GCCAGCCTGTGCTGCTTAGCAAGAAACAGAAACAAGTACAATCACACACA

TAGAAAATCCCCCATTAATACCATCCCATTAGATATAATGGTCCTGTATG

ACCATTCAACCACTGTTTGTCCTCTGTACTGCAGTAACAGTCTTCTGCCC

TTGCCCGTGAAGCACGTGCGCACCCCGCCTCCAAGTGCTTTTGCACTGGT

GTCCTCCGTCTAGATGTCCTGTTACTATATGTAAGGACTGGTTTCTCCTC

CTCTTTACAGTTCAATCTAATTGTCTCATGAAAAGATCTTTCCTGACCAT

CTGGTTCAGACAGGTTCTCCCTGTTGTTGTTTTGTTTTTTGTTTTATAGT

TCTAAATTCCTTTCAGGAACTTTTGCTTATTTTAAATTCCCTGAGTGCAT

ACGTGTGCTTGTTGTTGCTCATGCTCGTTGTTTGGGCTTACTTTACTATC

AGCTCTGGATGTGGTTCACAGAAGGTGCTCAGGGGAGCACTCTCAGCCAC

TCATCTCACACGGGTTATAGATATATGTATTGATGCTACGTTTGCTTGTG

AGCCATGTTTTAAAGATTAGAATATCTTTTCTATGTGTACTCTATCAAAA

CACATGTTAGGGCTTTATCTATTTTATACAGATATTGGTGTTCTTGCTTT

ACTAATTTTCATGGAATTTCGGTGAATATTAGTATTTTAGATAGGAAGAC

TTGTCTCAAAATGTAGCTCAGCTGGTTGAGTGCCTGCCTGCATGTAGAAA

FIG.3D(5)

```
GCCCTGTATTCACTCTCCAGCACCTCAGAAGTGGGCCATGGTGCATATGC

TGTCATCTCAGCACTCCGGAGGGAGAGAAAAGAGAATCTGGAGTTCAAGG

TTATCCTTGGCTATATAACAAGTCCAAGATCAGCCTGGGCTACATGGCAT

CCTGCCTCAAAATCAAACACCAAATCAAAAAGCTCACATCTTGATCCAAA

AGAAGGTAGAGAGAATACACTGGGAAAGTCTTTGAAACCTCAAAGCTAAC

TCCAAGTGACAGTGACACCTCCTTAGCAGGGCCATAAATTCTAATCCTTC

CCCAAAGCCCACCAACTGGAGACCAAGTATTCAAAGATAAGAATCTATGC

AGTCCATTCTCCTTCAAACTACCACAGTAGGTTTTCTTAAAAAAAGAAAA

AAGAATATTTTAATTGATTGTGATTATTCAGTATTATTCATGAATAATCA

TGAACTACATGGCAGGACTATAAACTATTATTTTTTTTAAAGATTTATTT

ATTTATTTTATGTATGTGAGTACACTGTAGCTGTCTTCAGACACACCAGA

AGAGAGCATCAAATCCCATTACAGATGGTTGTGAGCCACCAAGTGGTTGC

TGGGAATTGAACTCAGGACCTCTGGAAGAACAGTCAGTTCTCTTAACCAC

TAAGCCATCTCTCCAGCCCCTATAAACTATTATTATATTTATAAAATATA

AATCCGTGAGTCTGTGCACCCCTGTGTGCACATGGATGGGACATCTTTGA

ACTGGATTATATCATACTTAGAAGAATACAAGATACTCTGTTTTGTCATT

TGGGTGAAAATATGGTCTGTTTATTTTGCAGGTATGACCTGACTTCTAGG

GAATGGCTTCCACTAAACCATTCTGTGAACAGTGTGGTTGTAAGATATGG

TCATTCTTTGGCATTACATAAGGTAAACTATCTCAACTCTTCACCAAGCA

AGAAGTTCAACTCTTCCTGTTGCTTTATGTCATTGAATACTATCGAGCTT

TGGTTTTAGTTGGTATAAGCTTTGTTTTGATGTCATGGAGGTATATAATT
```

FIG.3D(6)

```
CACCAAGTTGTCACCAAGTTGTAATTGGAAATTGAAGTTAGAACGATTTT

AATCCATGGTGTCTTGCATTTGGATACTCTGATCACAGTTAACAATGAAG

ATTAAATAGTGTCAGCAAGCCTATGCCCATTATCAAGTCTAGCATACTGC

ATGCGTGTGACTGAGTAGCCATTGTTATCTCCTTGTTTTGAGCGTATATT

GTAGAATGAGGCAACTGTATTTTCCACACCATTTTCGTTCTGTAACACGT

TTCATGTAGAGAAGGTGATTTAGAGAGGGGAAGAATGTGATTGTATTGGT

TGGTTCTTTCTCTATGCTATTCCTAGCAAGTCACCGAAGAGCTCATGTTA

CTCACACTTCTTAAGCTGGGATCACAATGAGATTGTGAACCACTCATTGT

TGTTTTCCAATATAATTTTTAAAAAGATGTATTTATTTTTATTTTATGTG

TGTGGGTGTTTTGCCTGCATGTATGCCTGTGTATACTGTTCCTCCAGAGG

TCAGAAGAGGATGGCATCAGAACTGGTGGCTGTTAGCTGCCATGTGGGTA

CTAGGAACTAAACCCGGGTCCTCTGCAAGAGCAGCAAGTGTTCATAAACT

CTCTCTCCAGCCCTAGAGTTGATTTCTTAATGGTTTTAAAAATCCTGTTT

ACATCTTTCTTATAGGATAAAATCTACATGTATGGAGGAAAAATTGATTC

AACAGGGAACGTGACCAATGAGCTGAGAGTATTTCATATTCATAATGAAT

CATGGGTATTGTTAACTCCGAAAGCTAAGGATCAGTATGCAGTGGTTGGA

CACTCAGCACACATTGTTACACTGGCATCTGGCCGTGTGGTCATGTTGGT

CATCTTCGGTCATTGCCCACTCTATGGATATATAAGCGTTGTGCAGGAAT

ATGACTTGGGTATGTATTTTTTTCCAGTGGAGGCATCTTGAATATCATACT

GAGAACCCCTGCCCTTATTATTAGGACACCGTAACAAAATTCAGCATGAT

CTTGATCCAGTACCTTGTCTTGAAATAGTATCAGTAGATAACTGGTGAGA
```

FIG.3D(7)

TTGAGGTTGTTGAAGTCCCTGTGCAACAGCTGTTTCTTACTTGTCAAGGT

CTAGTCTTGGCTTGGGAGGGGTTCTGAGGAAAGGGGTGTCAAAAAACCCA

AAAAGTCCAATTGTAGGTCCAAGCTGGCAGCTGTATATTGCATTAAGGAA

AGCTGAGGGAAATTTGGGATATTTATTTCATCTATTAGTCTACATCAAGC

AAGTCAAGCGCTCACAGTCAACGTTTGCACCCTCAAATTAGTAACAAAAG

AGGGGGAACTGAGGAGTCCAGCATGGTCCTGGTTGGGACAGAATGACATG

GTTCCAGCCCTGAGACAGGGGCAGCAGGTCCGGGCCTCCATGGATGTCAC

ACTATGGACATAAACCTGTTTGTATAATAATGTACATATTTCATGCTCCT

CTTCTGAGTAATGTCCTTCTGTTAATGTGAATGACTTCATGATAATCAGA

GCCAGTGTGAGTCTGGGAAGTAAATGGTGGGACCTTCAGGACAGCTCTTA

AGGCTGTGGAAAAGAACATGAGTTCAAAACCATATACTTCCTCAACTATA

CAAAAATAGAAGGATGCAATATGAATTGTATGAGGGGCTTCACAGATCTA

AAGGAACAAAAGCAGCTTCGCTGTGAGCCAACTTGTCAGAAAGATATTGA

GTAAGCAGTTAAAGAGATTTAGGGAGTGCTGATTGCTAGAGGAGGCCACC

CAGCTAAGTTTGTGCTTACAAAGGCAGACAAAGTCCTGAGTTCAGGGTGG

GCCTGGAACAGAGCAAGGTTAGTTAGACCTTGGTGTGGTAGAAATGGTAA

TTTCCAGACAGGATACCCAACTAGTTTTTGTGCTTAACAGAGGCAGGTAG

ATCTCTGAATTCTTTTGTAATGTTAAAAGGAAATGTGTGCTTGTTGTCTC

CCAAGGGGCCTGAGTCCCAGGATGCTGATTTATAGGAAACCTGGAGTAAC

TGGGTTTATGACCTGCAGGAGACGAGCTATCCAGAATGTTTTTTGCAATA

GCAAGAGAGAACTGCCTGGAGAACTGCCTTCAGCAAAGAATAGCAAGAGA

FIG.3D(8)

AAGCTGTCTAGAGAGAGAGCTGTCTGTAGAGAAAGCCGGTCAGAGAGAAA

GTAGACTGGAAAACTGTCTCCAGCTTGGACCCACAATTTGACTTTTTGTT

TTTGTTGACAAGTTGCCCTCCCCCAGAAACACCTTCCTCAGGACCCCTCC

CAAGCCAAGGCAGGGCCTTGGCCCTTCTTGTCAGCTTGCAAGGAGCCAAA

GATAGCATTAAATGCTTTGGATATCAAAATAAGCAAAATGCAAAACAGTA

AACACTCTAAAATAATTCTGGCTAGTCCTTTAAATATTAGGCCAGTGCAC

TGTTATTTTACCTTAATGTATAATCTTGTGTTACATTTTATTGTTTTTAT

TGTATAATAGGAATGTCAGAATTATAATTTTGTAACATTTGTTTGACATT

CCTGTGAAAATGCATCTAAAGATCATTAAAGTGCATCTGAAGATCATAAG

GACTCACTGAGGAGCACAGGGAATTAAGTGTCTGCTTAAGAGAACTTTGA

ATCTTTAATCTTTAGAATTTGTTTTAAAAATTTGAATCTTGCCAGTGTGG

TGGCGCATCCCTTTGGTCCCAGCACTCAAGGGGCAGAGGCAGGTGTATCT

CCATTAGTGTGAGGCCAGCCTGGTCTACAGAGCAAGTTCCAGGCCAGGCA

GGGTACACAGAGAAACCCTAGCTTAACAAAACAAAACAAAATATGAATCT

TTAAAAACTTGTTCTGTGAAAATTTCATACATGTATACAATATAGCTTGT

TCATATCCACCGCCATTCCTTCCAGCTCCTCTAGGCTTTCCCAGTGCATC

TCCTTCCTAGCCTTATGGCCTCCCTTTCAGGGTGAAGGTTAGCACACTGA

GTCCAGTTAGTGCTGATCCGATGCAGTCTTGTCTAGATGGTCTTCTTTAT

AATAAGGTGAAAGTATATCCTAAACTTCCGTCTTTTGCTCTAAGGTGTTT

AGACTTTAAACTAATGTTTAAATCGTTTAAATAATTTATTATTTCATAAG

AAGAGGAGCCTGCAACATTGACTTTAACTATTGTCTCTTATCCAGAAAAG

FIG.3D(9)

AACACATGGAGTATATTACATACTCAGGGTGCTCTTGTGCAAGGGGGTTA

TGGCCACAGTAGTGTTTATGATGACAGGACCAAGGCTCTGTACGTTCATG

GTGGCTACAAGGCTTTCAGCGCCAACAAATACCGGCTTGCAGATGACCTC

TACAGATACGATGTGGATACTCAGATGTGGTGGGTGTTTTCCTAGAGCTT

TCCCTTGGTAGTCTAGAATCTGCAGAGGCAATTGATTAAAAATACTGTGC

TATGGTTTGACTTTTGTTCAGCATTGTATGTAACAAAGTTAGGAGATCAA

TACAGTAATAGAGTTAAGGTACTAATGGTGCTGTTGCTGTCTGTTAGTGC

TTAGTGCTTTAGACCTGATTCACTGAACTCTAGCAAGGTTTCCTCTCTTC

AGAATTCTCAGCAATAAAAGCTGTGCTGATTTTATCCATACTTAAAAAGC

ATATCCTTCCTTTTCTCTTTTTGGTGTTGGGGATCAAACCTTGTACATGA

ATAGGCTATACCATCTTTATCCATTTACATCACCAAACAGGATGCTCTCG

TGCCTATTTGATAGGGTTTTCACTCACTTCGAACTGAAACTTGGGTTGTA

AGAGTATGGTACTTTTAGCAAATGGAAATAAATTTGAGTTATGATGCAAT

TATAAAGCACTGGTCTCTCTGTATTTCCCTCCTCCTTCTACTCCCTCCCT

CTTCCTTTCTGACCCCCTCTCTCAACATACATTAGAGACCATGCTTTGAC

TGTCAATTTATGCTGTGCTGAAGATCAGGTCTTTAGTGGCTGTGAACCAC

GGAGCCTATGCAGTGGAAGTTCTGGTCTCTGGCTTTTGCCTTACTAATAA

AACACTGAGCATAAATTTTGATTTGTATTTCACAATTCTTACCTGGAATT

CTTAAGTGGAATTATGGAGCCATAGAGAATGAACATTTTAGGGCTTTTAA

TATAGTTTCCCGAAATTTTAACAGATTTTCATGATTGTTAAAGGAAGTGG

CTTACGTATAGGGGGAAATCAAGTATTGCACATTTGAATCTAAAGTTATA

FIG.3D(10)

```
AAGTAATTACATTTAAATTGGCAAATAAGTATTCTTTTAAAACTAACCTT

ATATTTATTATTTCTAAATAAACTCAAAAGGACCATTCTTAAGGACAGCC

GATTTTTCCGTTACTTGCATACAGCTGTGATAGTGAGTGGAACCATGCTG

GTGTTTGGAGGGAACACACACAATGACACTTCCATGAGCCACGGTGCCAA

ATGCTTCTCCTCAGACTTCATGGCTTATGACATTGGTAAGCTTTCCAAAG

ATGTTTTAGCTTCAGGAATATTTTCTTTGCTGATGGAAAGATCACTATGT

TAAAATAATTGCACCATTTAAAAGAAGTCCAGGTGGTAGAATTTGCATTT

AATTTGAGTAGGGTTACACATCTATTGAAAAGCATTATTTTGGATTAAAC

TACATTAAATTCTTTGTGAAATCACTCTTCTTAATTGCTTTAATTCTTTT

TTTAGGTTGAGTTAATTGGTATCTTCTTTCTTATAAGTGCCTTACATAGT

AGTGGTGGTAGTTGTAACCACCAGTGTTATGTTAAGTTTGATGGGATATG

CTGTTTCCTAGAAACCTGGTTTTACACATGCTGTTGATGTCAATATACAT

GTGGCCAGAAGAGGGCAGTGTCTGTTTATTCCTGGAAAATAAACATCAGC

TGCTCTGTTGTGTAAATATCACCCATGTGATGTTCTTTCTGTTTATTTGT

CTTTGCATTTTGAGACAGCCTCACTATGTAGTCTAATTGGCTGAAGCTCA

GTATATAGATCAAGGTGACCTTGAACTTAGAGAAATCCTCCTGCCTCTTC

TGAGTGCTAAGATTAAAGATGTGTACTACGAATGAAAAAAAAAAATGTGT

ACTACCACACCTGACTAGAGATTCATTTTAAAAATTATTCTTATTGTGAT

AAAATGCTCAGAATAACACTCACCATCTTAATGTTTTAAGTAGTTTAGAT

TTAAATATATTCCTAGTGTTATTCATGTTATAATACCATCTGCTTGCCGA

CTTCTTGTAAAACTGAAACTCTGCCCTTAAACAATAGTTCCTCTCTTCAT
```

FIG.3D(11)

CCCTCACTCCAGCCTCTTGAAATCATTTTCTATATCTCTATGATTTTGAC

TAGTCTAAATTAGGCATTTTTTAAAAAAAAATATTTTGTTTACTTGTATGT

GTATGAGTGTTTTGCATGCATGTATGTTAAGCACACCATGTATATTCAGT

GCCCATAGAAGCCAAAAGTAGGCATAGATTCCCCAGAGCTGGAATTACAG

ACTTTTGTGAGCCACCATGTGGGTGCTGGATACTGTGCCCAAATCCTTTG

GAGGAATAGTGAGTCTTCTTAGCTGTTGAGCCATCTTGTCAGCCCTAGAT

GTTTGTTTTTAACAAACGTGTTTTTGCCAGCCATTGAGTTTTTAAATTGA

GAATGGGGGGTACACTATAGTTAGTCCTTAGCTTCAAGCTTGTGGAAGCA

GAAATGAGAAGACAATATAATCTTAACTCAGGAGGATTCTTGCTGGCTGA

AACAAAGATGTGAAATTACCTCCGAGCACTCCTAAGCCACTGGGGTGAGC

AGGGTGGTCTGGAGAGGCCTTGAAGAGAAGCTGTCTGAGCTTGTTCCTGG

GGACACTGGGAGTCAAATAGACCTCCTGGGCAGGGGGATTTAGTGCAGAC

AAGAGGCAGGAAAGTACATGTCAAATATTTAGGACTTTTGAACCGCTACC

TTTCTTTTGTCATGGTAACACAGAAGGTAGCAGGTGACTGTTAGACTAGA

ATGTTCAGATCTGATTCAGAGTGCCAGGGATCGTTGGTTGGTCTTGTGTA

AAGTCTCACAAGTGATAGAATCATATGTGTGTCTTAGACTTTTTTTGTTG

TAGGTATTTTAGATTTTTCTTGTTTTTCCTTTTTGTAAGTCTGGCCCTCA

CACTATGGTCCAGGCAGGCTTAAGACTTATGGTAACCATCCTACTCTGCC

TTTATGGGCCACCATGACCAATTTAAGAAGCTCTCTTGGGTGGCATTGTG

ATAAGTGATCTGGAAGGGGCATATTGACAGTTAGCAGGCTGCTACTGCAG

AAGTCCTAATTAGGTTTGTATCAAGGCCATGGAAGGAGCAGTGACTTCTA

FIG.3D(12)

GTACCTGGCTGTTGTGTGTCTTGACAAAAATATAACTGCCCTTTCTTCCC

AAGTGTCTACTATGGACCACCTTTGCCAAAACTAAAAGCAGATTCAGAGA

AAAACATATCATGATTGCACATGGCTATAATCCCTGAACTTAGGAGGATG

AGAAATATGGCAAGATTGAGACCAGTCTGAACTATCTAGTAAGACCGTGT

CTTTAATAAAAATAGTAAAAATTATAAAATCAGGGAGTAGGATCTGGGAA

GAAGAGAATGAAGTAAGTGTGGGGCATATCCAATTGGAGATGTCTTTAGG

ACAGAGCTGATTGCTGAGAGGTGGTTGTAGGAGAGGTGAGTTATTGTGGG

GCATAAAAGATGAGCAAGAGTCAGAGACAGTTGGAGAACAGAGTCTGAAC

AAGAGTAGAGACTAAAGAGAGTGTCAGAGAAGCAGGGAGAAAATAGGTGA

GATTGATGACCTGTGAGATATGTTAATGGCCAGAAGAGTGGCTAAAAATG

ACTGGAGAATCCTTCAGACTTGTCAACAAAGAAATCCTTTAGCCTAATTT

AGGGTGCAGGCGGCTGAGGAAGGACATAGGTGAAATATGTGCTCTGTGTG

TTCATTTTTATTAAAGCTTATCTGCAAAGGCCTCAGATTTGCTGTGTACT

TGTAGCTGAGGCTCTTTTTGAACTCCTGGTTCTCCTGGCTCCACCTTCCCA

AGTGCTAGGATTACAGATGTGTGCCCTAGTTAAAATAGCTGTATACCTAG

CATTAAAAATTTTAAGTTAGAAAATACTGTGGTGCTCCGGGGATGCATCT

CAGCAGTAGAGTGCTTGCCTGCTATACACAAGGCCCTGGGACTGATCCCT

AGCACCACAAATACTAAAGCAGACATTCTGGTAGGGAAAACTGGTAGACA

GCAGAGTGGTGACCATCAGGAGGGGGGTTGTGGGTGATGAATGACTACAT

TAATTAGAAGTTCTGTGCAGTATATTTATTTCATGCCCTGAAACATTGCT

GCTGCTGTTGCTGCTTTCCTTTACACATAATAACATAACTAAAAGACAGA

FIG.3D(13)

CAAGCATGTGGTATGAGGCTGTGGATGAGGCATTCTTTGTTTTCCTTTTT

TTTTTTTTTTTGAGACAGGGTTTCTCTGACCTGGCTGTCTGAAACTCAGT

AGGTAGAACAGGCTGGCCTTGAATGCACAGAGACCCTCCTGCTTCTGCCT

TCTGAGTGCTGGGTTCAAAATTTATGTTTTTTTCTATAAAGACTGAGAGT

TCACATGGACTATATATGACAACCTACTCTGAAATGTGTTTTTCTCCCCC

TTAGCTTGTGACCGATGGTCAGTGCTTCCCAGACCTGAGCTCCATCATGA

TGTCAACAGATTTGGCCATTCAGCAGTCTTGTACAACAGGTAATTGGAAA

GCAAAGGCTCTATTACTGTCTTACATCTTATATTCATTTTTAATATCAAC

TTCCTAACAGTTGTATCTGAATGGTAAGAGGTTTGGGGAGAAAAAAGGAG

AGAAGGCAGTTCTAAGTGCACGATAAGGTAAGGGGAATAGGACTGGGAGG

TTATGGGGTCAAAGAGCAAGTCTGAAGTCTGCACTATATCCAGGTGTGTG

CTCAGGAATACTTTTCTGACCAGCAGAGCTCTTTTTCCATTTGCTCCAGG

AACCTTAGTCCTGTAAAGGACATGCAAAGGACTAGGGTTGTGGGCCAGCA

ATAGAGTGTTTATCTAGCTTGCACAAGATCCTGAGTTCTGACCTCAGCAT

TTTGCCTTCTGCAAACACAGCATTTGCCATAAGGGACATGCAGAATGGCC

ATTTTACCTAGTCACTTGAAAGTGTGCTTTAAGATTGAGAAACTTAACAG

CCTGCTGATGCTGACTTTTCTTATTTTGCTTCTGTTACTGCTTTCTGCTT

CTTTCTTTAATACTCTAATGCTTACATTATATAGTCCTACAGGTATTCAA

ATTTTCTGTTGGAGTTTCCTAATACAAGTAATTTAACTTGCATTAGGAAA

AGGATAAAAGTGCCATTCTGGAGTTGTGAAGAATGACCGTTTAGAAGCTA

GATAGTGGGGAAAGATGATATCTTTAATCATGTGATTATTTAGTGTTTTA

FIG.3D(14)

CAAGTATATAGGGGATTGTGGCAAGACCATTGTATGATTAGAGACTAAAG

TGGAAAGATTTTTTAAATATCTTGTTAACTTGAGTGTTATCTTAAATTAC

AATCTGATGCTTTCCTTCAGAAAAAGCCCTAAATGCCTCTTGAGGTTTTC

ATCTGGCAAGTATCATGTCACCTGGCCTTGCTGGTGGAATCTGCCCCAGC

TCATGTGTGTTCTTAGTGTTCTCCTAGCACAGAGTTAGGCACGTGTGGGC

ATTTGCATACTAATGTATAGTAATAGTAACAATTGAATGAATTGTCTATT

AAAACATTCTTAAGTTTTACCCAAACACAGAGAGGTCGACAATTTGTCAT

AAAATGTAGTTTATCCATGAATCAAAATCAGGAATGACTGTCTGAACAGT

GTTTTTATTTTTTATTTTATTTTATTTTGTGTAATTTCTGTGATGTGTTT

GAATATCTCAGTTTTAGGCAGGATTGGAAATGTTAGAGGTTGGTAAGAGG

TCATGGTTGCAGTTTGATCATGAGAGAAATCGATGGCTCTCCCTTCATTG

CAGTGTTGTCAGTCAGCAGTGTGGGATCACCTATGTCTAACAGTTGTTCT

AATTGAGAGAGGATTACAGGAGGGAAAGCAGTGAGATTGTGAGGTGCTAG

ATGAGGAGATGGCATTTACCTAGCAGCCTTCTCTCCCGCCCTCCCATCAT

GTGACCTGAGAGATTCACAATTTCTGAAGATATCAGCTGTGCTTAGTTTA

AGCAATAGTTTTATTAACTAAATCCAACTTGATTCATGTTATTCCCAGGG

AACCAGTGGTAGGATTAAAAATGAATCCTAGTGTTCTTTTTGGTTATTGG

AATGTCAAGTTTTCAGACACTGTAACGAATACAGAGCCATACAATCACTA

TATTTATTTGGTCCTTTGTTGACTTAGAAAAATTGAAGCCCAGTTTAGGT

GAGCTACCAAATTTCTCATTGTGGATTAGTATTAAACTTGCGTGGAGTTG

TGGGATCTTGGAAGTGGGGGCTAAGCATCCGTGTTTGTCACAGCCCAGAA

FIG.3D(15)

GGAACAGATGAGGTTCCTTTTGAGGAGTCTTATGTCTTTATGAACTTGGA

CTTAGAAATATTTGATGTGTTTAATTCTGCTGTAGTTTTTTAAACTCTAG

CTAGTGAGCATCTTTTCACAGGAGCGCTTGAGTCTGACCTACAGCCATTG

TCTGTCTCTGGTGTGCATATTACAAATGCACTGGGAGCGTTTCTTGACCC

AAACATATAATTAGATTTTTCTTCTAAAAAGGTCTAGTTTGGGAAGGAAT

GAAAGGGATTAGAGAAATGTTGTGGGTTTGGTATTTATTTATTTATTTAT

TTATTTATTTAATGTATATGAATGATCTATCTTCATGTATACCTGCATGC

CAAAAGAGGACATCAGACTCATGATGGTGATGAACCATCATGTGGTTGCT

GGGAATTGAACTCAAGACCTCTGGAAAAACAGCTGGTGATCTTAACTGCT

GAGGCATCTCTCCAGCCCAATTGTTCTGTTTTAGTTTGAGGATGAACATC

TAATTTAGAGATGCCCTGCTTTTCCAAAAGTGAGTTTTAAACACTAATTT

CCATTGTCAGTGGATTGGTCTTTTAAGAATATAGGTAGTGGTGGCACACG

CCTTTAATCCCAGCACTTGGGAGGCAGAGGCAGGTGGATTTCTGAGTTCG

AGACCAGCCTGGTTTACAGAGTGAGTTCCAGGACAGCCAGGGATACACAG

AGAAACCCTGTCTCGAAAAGCAAACAAACAAAAACAAAACAAACAAACAA

AAACAAACAAAAAGAATATAGGTTGGAATAGGTTGGAAGCAGCCAATGAT

AGTGCATACCTTTAATCCCAGCACTTGAGAAGCAGAGGCAGGTGGAACTC

TGAGTTTGAGGCCAGCCTAGTTAGTCTACAGAGTATTTTCCTGGAGAGCC

AAGGCTATATATAGAAACCCTATCTTGAAAGGCCAAAAAAGGAGGAAAAA

AAAAAAAAGAAAAGAAAAAAGAAAAAAAGAATGCAGGTTGGGCAGTCAG

GGTAAGTGTCTAAGGTAAGAGGAATTCTTCAAGGTGGAAAGTCATGAGTT

FIG.3D(16)

CTGCGCCAGCCTAGGCTACAGAGTACTGAAAGGGGAAGAGACTGTCCATG

TGTCAGACCCTCATTTCTCCAAAAGTCACATGACTATATTTTTTCTGTAT

TGCCCACTCTTCCATACATGCACCTAACAATAAATATTGAAGTTCACTCT

GTGGCACTATATCTATGTGATAGACTTCTAGAAAAGTGATTTAAAGTTCA

AAAGGTAAATACGTAGTTTTGTTTCAAGTTGCCAAAATCCCTTTAGTAGA

CTCCTACAATCTTACATGCCCAGTAGCAGTATAGAAGCTTGCTTGTTGCC

TTGAAGCCTCACCAATTCAAATATTAGGTAACATTTGTTACATTTTTCTT

TGTCAGCTGGATAGGTAATGAATGACACAACAATGTGTTCCCATTTTCTC

TGCATTACTAATTGAAGTCCTATCACCCACAGCAGACTGAAGAGTTCCTT

TAATATTTTATGGACTTTGACAAACCTAGGATTCATAGCTTCCATACAGA

GAGGAATTTCACAAATAGCAAAGTTGGGCTGTTAGAAGAATAAAAAGAGA

ATTCTGAGTACAGCTTCTCAAAGAAGAGTCCCACGTAGGTGTCCTCTGGG

ATGTGCCTAGATGCAGGGTTATTGTACAGGAGCTCTTCTGTCTGCTCTCT

GATACTTGAGATTATAGGGTTGCAGGGAAATGCATTAGATGGCATTACAA

ACTGATAAGATAAAGTTAGGAGCTATCAGAGATTTAGGACATGGTTTTTC

TCTGTAAATGGGGCTTCTGGTGAGATTCCTAGAAAATGCTGTTTATAGCT

AGGAATGGGGTTATAGCTAGGAATGGGGAAAGACCTTAAGCAGTTGTGAG

CTGTGGTGGAATGCATGTGTTTTCAGTTTGCTAAGGCTTCCGGGAATACT

TTTCCTGTCGATAATTTTCTTTCACTCTCTTTGTAGCCTTCTTTGTATTA

AAATCCTCTCTGCTTGCTTTTGTGTGTGAATGTGTGTATGTGTGTGTTTG

TGTATGTGTGTGTATGCATGTGCATGTAGGTCCCTACATAGGACAGAACA

FIG.3D(17)

TATTTCCTGGAGTTATAGGTGCTTGTGAGCAGCCTTTTAGGGAACCAAAC

TCTGTCCTCTGGAAGAGTAGCCCCTTTAACTGCTGAGTCATTTCAGCCTC

AAGAATCTTCTCTTTTCCCTATTAGTAGAAGATGTCATCTTAGCTCTAGG

AACTACACCACCTCTGGCCTCAGTGGACACCCATTTACATATGCACATAC

AGCAGACAGACATATAACTAAAGATAAAATAAATCTTTTTAAAATGTCAT

TTCCCTGTGTACTAATTTTCCATGTACACACTCACAGGTAGATTTTTAAA

CTATTCTGAGTGATCACAAAGCAGAGCAGAAGGTGAAATTTGAGAGAATA

GATGATATTAGTGGATTTTGAGACCTTGAAAATAATGTCTCAGAGCATTA

AATTAATCACTCATGTATGTATGTATGTATATAAGTATGTATGCATGTAT

TATGTGGATGGGGGTGCTGTAGCACATGTGTGGAAGTCAGAGGACAACTT

TGTGAAGTCATGTTTCTCCTTCCATCTTTATATGGTTCCAGTGATTGAGC

TCAGATTGTCTACCTGTGTAGCAAGTGCCTTACCTGCTGACCTGTCGCAC

TAGCCCTCTCAGAGGACTTTTAATATTTGGAATATTTCTAACGATTGACA

GTCAAAAGTTTATTGTGAGCCAGGCACTTAAAATCCTAGCACTTGTGAGA

CACAAGATGGAGGTCAGTCCAGTCTACTGAGTTCTAGACCAGCAAGGGCT

ACACAGTGAAACCTGTCTCAAAAATTTCAAAAGCGGAGCTAGAGAAATTA

CCCAAGGAGCTAAAGGGAACTGCAACCCTATAGGTGGAACAACAATATGA

ACTAACCAGTACCTGGGAGCTCTTGTCTTTAGCTGCATATGTATCAAAAG

ATGGCCTAGTCGGCCATCACTGCAAAGAGAGGCCCATTGGACTTGCAAAC

TTTATATGCCCCAGTACAGGGGAACGCCAGGGCCAAAAAGGGGGAGTGGG

TGGGTAGGGGATTGGGGGGGTGGGTATGGGGAACCTTTGGGATAGCATTG

FIG.3D(18)

AAAATGTAAACGAGGAAAATACCTAATAATAAAAAAAAGAAATGATATCA

GAAAAAAATAAAAAAATAAAAAATAAAATAAAATAAAATTTCAAAAGCAA

CAACTCAAACCAGCCCTACGTCGTGCCTCTGAGTTCTCAGTAAATTCCTT

CTCTCTCTCCTCTCAGCACCATGTATGTGTTCGGCGGCTTCAACAGCCTC

CTCCTCAGTGACGTCTTGGTCTTTACCTCGGAGCAGTGCGATGCACACCG

CAGTGAAGCTGCTTGTGTGGCAGCAGGACCTGGTATCCGGTGTCTGTGGG

ACACACAGTCGTCTCGATGTACCTCCTGGGAGTTGGCAACTGAAGAACAA

GCAGAAAAGTTAAAATCAGAGTGTTTTTCTAAAAGAAGTATGTTTTTTCT

CTACTTAGAATTTAAAAATCTAATTTTATCTGAATTGTGAAGGAACCTAG

TCTCTGTACTTTCCTGTTCACCTTACTCTCTAGTTATTTCTTAATAAAAA

AATACACAAGATCTTTGGATGGGAGGAAGCATGTGGCTCCTGGAAGCTGT

TAGCAGGTAATAAGTTGTCTTTGAATTACACAGGCTTTGTGTACCAACTC

CTGGTCTGGCTGCAGGTGATCTGAAGCCATAGCACAATGAAATTTGTTTT

CATTTTGGTTTTATGAGACAGGGTCTTGCTCTATAGCTCATACTGGTCAA

GCTCCTTGTCAGCCTCCTCCTTCAGCCTCTTGAATGCTGGGGTTATAGGC

ATGCATCACTGGCCCTACTTGGGAAATATTTTGATGACAGACATGCTATA

TATTTCTTTGTTCAGTTTAGTAGCCACTAGCAATCTGTTATTATTAGATA

TTTGAAATGTGGCTATGTAACTAAGGGGCTAACTGTTTTCTTTTCTTTAG

TGTATGTAGTGAGGCAGATGTAGTAGCACACGCCTGCAATCCAGACACTC

ACGAGGCTGAGGCAAGAGGCAGTTCTAGGCCAGCCTGGGCTGTGTAATGA

GACCTTGTCTCAAGAGCCAAAACATCAACAATAAAAGAACAGTATGTGGC

FIG.3D(19)

TATTGGCTGTTATGTTGATGATGAAGGTCTAGTGTTAAGGATAAGAGCCT

CTAATGGTATGATCACATATAGCAAATTGCTCTGGTAGACAGCAGAGAGC

TGCTGTTCTTGAAAAGTATTTCCAGCCCCCTTTAGCTGTATATAGCAAGC

AGTACAGCATAACAGACAAACTATGGTCCCTTCTTCTAGAGCCCCTGGCG

TGCTCTTGTTATTTTTCTCTCCTTTGCTACTTGCTTAGTGGTTGCTCTGA

GCACCACTTCACCAACTCAGCGAAGTAACGTGCAAAAATGTTTGGAAAAT

AAGAATGCCTCCAAGATATTTGTCCATATCAATCTTTAAAGTATGAAACT

ACTTCCTTATCTAGTTGTTGCAGTTACATGAGAGTTATATTAGGCAGAGA

CTACTTCTGTTTTTCTGGTATGTGTTAAATAAAGTTGTGCAGGGACATAA

AGCTCCTGAGGCTGTGCTGTTGATTAGAATTTTGGTTCATTTATGGAAAA

CAGCTTACCAGAACCTGGTAGGATTCATAATTCTCCCGAAACAGTTAGAA

TTGGTAGAATAACCAAAATTTAAAGTTAAGCTTAAATATACAGTGCATTG

GAAATAATATTATCTTCTGAGGTTCAGTATGAGCCCATTAGTTTACCTCA

CTTTCTGGGTAGACCTAATCCTGTCAGAGTAAACTTGGCAAGAAAAGCAG

CCTACATGAAAACTGATCAGGCAGGGAAGTTTCTGTGGCCTCTCTTCCTG

CTTGTGTATGTCATATTCATGAAATGATTTATAGATGGCAACATGGCTTT

TAGCTTCTTGTTTGGGGATTTAATGAGAATTATGTTAGGTCTACAAAGAG

TGGAAGTTGTGAAATCCACAGGTTTGGAGTCACATGAGTATATAGAGTTC

GAGTTAGCAAGTGCCTCCTGTGGGGTTGTGGGTCACTGGGTATACCTGCA

CCCAGGTAGGCCTTGCATTTGTAACAAGGACAAATGTATTGGTCTCTCAT

ATTGCTTTCTTAGGCTTCTGCACAGCTTCTGGTGTTAATTCTGTTGCTAG

FIG.3D(20)

```
TTGATGTTTGTCGTGGGAAGAAAAGCATCCATTACTTCTTAGAAGCTATA

AAATTAACAGACCTTTGCTTTTCACTTTCTGGACACTATGGGAGGACAGT

TATAAAACAGTGTTTCTCGGATTGTCTGCTTATATCTGTTTTATTTTAAC

CTAAACATGGCACTGCTTTTTTCCTTTCAGTTTGACTATACACTTTGCTT

CCTGACTATTGTTAGGAGCTTTCCTACCTCAGATTATACATAAGAGAGGC

TGCCGCATAGTTGATGGGTTTGTCTTCTCTCTGTAGCCCTTGACCATGAC

AGATGTGACCAGCACACAGATTGTTACAGCTGCACAGCCAATACCAATGA

CTGCCACTGGTGCAATGATCACTGTGTCCCTGTGAACCACAGCTGCACAG

AAGGCCAGGTCAGATGCTGTTTTTCACGGATTTTAGGGAATAGAAAAATG

CTAGATGAGTGTGAGTGTAGGGCAAATAATGAGTAGAGTTCTTTTTAAAA

TGGGATATCGATTTGAATTCTACTGTTGCTCAGGTTTTCTCTTAGGAAGG

GATGCTATATACATCCTGATTCCAAGGATCGCTCCTGCTGCTGAGGTCTT

TGTGCAGTGTTTCCGAAAGCATGTTTTACAGAATGCCCTTGGCCCATATC

TGACTCAGCATGACATCTGGGCTAATCATGTATGATTTGTTATAGGTGAT

AATAGGCTATGAGTAAGGTGATCCAGCTTTTGCTGTCTTTGATGGCTTAT

GACATTTTTTTCTCAAAGTTTAATGCATTTCATAAGAAATAAGACTTGAG

ATTGCTATGGTGGGCACGGGCTGGGAGGAGCTCTGGAAAAGCAGCAGGTT

CAGCTTTCACGTTTTACAGATAAGCATTGGCTGAGGCTTGGTGGTGCCAG

TGGTTCCGTTGGGCTGCTAGCTTGCCAGCTAAAAGCATGTTAGTGAGAAT

ACACACTGTGGTATTCACATTGCAGTGCTGCTTCCTGTTCATTCTAATTC

TATCATTCATCCATCTACCTATCTCTATCTATCTATCTATCTATCTATCT
```

FIG.3D(21)

ATCTACCTACCTACCTACCTACCTACCTACCTACCTACCTACCTACCACT

TATCTAATTCTATCTGTCTGTCTGTCTGTCTTTCTGTCTATCTATCCTCC

ATCTAATTCTATCTATCTGTCCACCTATCTATCATCTAATTTTATACATC

CATCCATCTATCCATCTATCTGTCTGTCTATCATATATGTAATTCTAACC

ATTCATCTATCTATCCACTTATCTGTCTGTCATCTAATTCCATCCATTTA

TGTATCTATCTATATATCTAATTCTATCTATTCAATTCTTTTCTTTTTTT

CTATCTTTCTTTCTGCAGTTACCATTCTCAGTTAATTCTCACTGAGTTAT

TTGTGTGAATAACAAAACACTTCTCCCCTGTGTTCCAGATCTCCATTGCC

AAGTATGAGAGTTGCCCCAAGGATAACCCCATGTACTACTGCAATAAGAA

AACCAGCTGCAGGAGCTGTGCCCTAGACCAGAACTGCCAGTGGGAGCCCC

GGAATCAAGAGTGCATCGCCCTGCCGGGTAGGCCTTGCACAGGGATGTCC

TCTATAAGGTCCAAGCTTGGTCCTCCCTCCTCAGATCAAGGTGGACCTAG

GAACAAGATTGCTTATTCTGTCTATTTAGCCCTCTCACTATTGGGGGGGG

GGGGGGGCGATATTTTGTATGTTTTTAACTTAAATGTGGTTTTTATGTAT

GTATTTACTAGCCTTTGAAAGAAAGTGAAGTGTCAGCTCATGTTCTGGAG

AATTGGGGGGTAGCTTAGATCCATGTTACAAACTGTGTCCCACTGTCCTT

CCTTCTGCTGTGAAGGAGAACCTGGCACTAGAGCTCTGTGGTCTCAGCAG

CAGTCAGGAACCTGCAGGAAGCACTTACTGACAGTTGTGTGAGAAGAGAT

TTCTGTACCAGCATCATCTCCCATGTGACCTTCCTTCCCGACTATTTCAG

CAGAGGTTGTTCAGGGTATTAACTTAGGTCCTGAGGCCAGCTAGCCCTGA

CTAAATCTCTATGATGTATTTGCTTGATCAGGATATCCAGGAAGGGGAGC

FIG.3D(22)

TTCTGTGCTCTCCAACATCGAGGTTTGAGGGGAAGTTGGTCTGACTCTTT

TGAAAGCATTTTATTTAGTTTGCTGAATGGGCTTTAGTTTAGCCAGTGTT

CTATTGCTGTGAAGAGATACCATTTCCAACGTGTAACTTTTATGAAAGGA

AACATTTAAGTGGGGGCTTGCAGTCTCAGAAGCTATTATCATCATGACAG

GGAGCATAGAGGCACAAAGGCAGGCATTAGAGTGGTAGCTGAGAGCTACA

TCCTCATCTGTGAGCAGAGGCAGACAAGGTGTGAAAAAGACAGAACCTGG

CCTGGGCTTTTGAGACCTCAAAGTCTACCACCCCCAGTGAGACACTTCCT

CCAACAGCTCCTGCAACAAAGCTCCATCCCCGATCCTTCTCCAGTCCTG

CCACTCCCTGGTGAATGAGCACTCACATATATGAGCCTATGGGGGTCATT

CTTACTCAAGCCACTACAGGCTTTGTTTTGTGTCTCAGACTTTATGTCAA

TAGAATACCTAGACACCTTGTTACAAGACAGGCCTGGAAAGCCTGCAGTG

CTGACTCCCTGCCAGTAGCACATTCTGAGGAGCAAGTCCCTTAAGTCGCT

TACCTGCTCTTACATTACGCCTTTCCCTGACCATTTAGTGAGCACTGTTG

GTGTCCCCAACCTGAACCTGGTTCTGGGGAAACACTTGCTTATTCACTTC

CGTGCTAATGGCCAGGGAGCAAGCATGCTTTCATGCAACACTGTGAGTTC

AGTACAACCACAGGAGGAGATTGCAGACTTCCTTCGTGTACTGTATCACT

ATGAGGTTTTCCAAACCAGTCTCCCTTTCACCTCATTTTTTGGCATGCCT

TATGTACTTGCTTATACTTTCTATCTTATGACATGAAAACAGAGTGGCAT

TTGGAGGCTTAAATTTATCACATTCCCAATTCAATTCCATTTTCAGTTTA

CTCTTTCTGTATATACATCAGTGTGCAGATAAATATCTCTTTGTGTGAGC

ATTGGAGGCCAGAGGTTAACCTCTGGTATATTCTTCCTCTATCACTCTTC

FIG.3D(23)

```
ACAGGGTCCTTTGATGAATGTGGAGCTCACTGATTACATAGACTAGCTGA

CTCAACCCTCAGGCCTCATAACCCTGCCTCTAGCCCTCAGATGAGATTAC

AAGCAAGCAAAACTACGCCTGGCCTTTTATGTGGGTGCTTGGAATTTGAA

CTGGGTACTTATGCTTGACACAAGTATTTTATCCACTGAACCATCTCCCA

AGCCTCCATTTGCAGTTTTTTACCTCACCCTTCCAATATATATATTTATT

TGTATGCCCTTTGTTCAAGATTTTAGTCACCTTTTACATTTTTCTTCAAA

AATAATTGCACCAATTTCTTAATAATGGCACCCAAAAGTAGGAACATTAG

CCTAGAGTATACCCTGTGAGCCAGGAAATGTGACTGGTGAGACTTGTAAA

AGGGTCTTTTTATTCTGGCCCTCAGCGGAGGCTCAGCAGTGGAGCATGCA

TGCTGTTCCTCTGGAGGACCCGAGGTCCCCAGGGGCCAGGTCACAACCAC

TTGTAACTTTAACTCTGATCTAATGCCCTCTATGGCTTTTGTGCTATAGT

CTCTTGCACTAACCCACACTCAAGGCACACATACACACATTCTTTAAAAG

ATAAATTATTTTATTTTCAAAGGTTTTTTTCTGCATATAGAAGTTAATAA

TTTGTCTGTTATGCTCACCAGATCCTAACAAAGCACCTGAAATTCAAATC

AGGATGAGTTCAGATGTTCAGTATTTTGAACTAGTAAACCGAACTGCATA

ATTCCTAAAACTTTGTTTTCTTTCCTCTTCCCCTTTAAAAAAGAAAATAT

CTGTGGCAATGGCTGGCATTTGGTTGGAAACTCGTGTCTGAAAATCACTA

CTGCTAAGGAGAATTATGACAATGCTAAATTGTCCTGTAGGAACCACAAT

GCCTTTTTGGCTTCCCTCACATCCCAGAAGAAGGTGGAGTTTGTCCTTAA

GCAGCTTCGATTAATGCAATCATCTCAAAGTATGGTGAGTTAATGTGTTC

AGAACTTTGGTTTCTAGGGCACAACAGCAGCTCTTATGTAGAAGGCCACA
```

FIG.3D(24)

GTTGTATGTTATTTGCCTGGTAAGAGAAAGAATTACAATAAATGATTAAT

AATATACTGTGGGCCTCTATTTCAGAGGCTCTTCTTTTGATACCTTTCTT

CTTGTCTTAAAAAGTTCAGTACTTTGCATATTTTATTAGTTGTTATTATT

AAGTAAATTATAAGGTATGAACATATGGAATGAATGGTAATATGTGTACA

TATTCTGGTGACATCAGATTATTTTGTACTTGATTTATATCTAGATTCTG

CTTGGGAAAAGGGAGAGTAAAATGTTAGTTACCTAGGTGTCATTAAAGCC

ATCTACAGCCCCTGGAGGTATTATTATAGCACATAGTGTAATCGTCAGTA

AGAAATGTAAAATCTGCCCAGGTTTTATAGCCTTCTTCCTAAGGCTTCTG

AACTCAGAAAGTTCTCTTACTCTAGAGCCAAACTCTCAAATGGCTTGTAG

TTACTATATAGTCTCATTTGGTATTTTTCTTGGTAAGTCTAATTCTAAGA

CTTGTGATTTGACTGTGATGCTTCAGTCAATTAGATATTCACAGAGCAGC

TTTTCTGTCTATGCTGGCTGTGGTACAGAGAGATGTGAGGGACATGTTTT

TGTCTAGCCAGGAGAAGACAGAATGCAGCTCAGCATCTCTCATTTGGCAC

CACCTTCATGTGATGGGATGCCGGTATGGTGTGGGTCCTGGTTGTTAAAT

CTCAGGAAGTCCATATATCCAGAAATGACCTCAACTATAGGTGGATTTCT

GGCAATTAGGTAAAAGTCAGCATTCCTTGGGCACTTGGGAAACTGGTTAC

CATCTGCATAAAGGAGTCATTTCCCTTCTATCTGGCAGAAGGGACATATG

GCTATCTATTGTGCCTGTCAGCATGGAAGCACATGCTAGTCTCCAGGTCC

CCCCAATATCACAAGTACCTATAGCAGTGAATTAGTTAAACTGATTTGGC

TCCCAATGGGTCAAGTACAGCTGCACCTGCCCAAGAGCTCTTTGGGTTTG

CAAATGAGAGACACATAGTTAATTTTTATATGCTTTGACTAGTTCAGTTG

FIG.3D(25)

```
CTGGACATTTCTAATCCTCCCTGCAGTAGCATACATTAACCCCTCCAACT

TTCCTGAGTCAACTTACTAACTCAACATTTCATCTCTGACACCCCAGACC

TAATGGCAGAGTGGCCCTTAGAGCCACTTTCCCAATTTTTTTTTTATCAG

ATATTTTCTTTATTTTCATTTCCAATGTCCCCTTTCCTAGTTTCCCTGTC

CTCTCCCCCTGCTCCCCAACCCACCCACTCCCTCTTCCTGGCCTTGGCAT

TCCCCTATACTGGGGCATAGAGCCTTCACAGGACCAAGGACCTCTCCTCC

CATTGATGACCGACTAGGCCATCCTCTGCTGAATATACAGCTAGCACCAC

GAGTCCCACCATGTGTTTTCTTTGATTGGTGGTTTAGTCTCAGGGAGCTC

TGGGGTACTGGTTAGTTCATATTGGTGTTCACTTTCCCAAATTCTTACAT

GGCTGGTTTAGTTCTTTCCTGCAGCTCTTAGGTCTAATCCCTTTCCTTCC

TCTGTCATGGTGATTGCCTTCCTCTCCTATCTCAGTTCCTTGCCTGCTCA

ATCTAAAAGTCCCACCTCCATCTTTCTGCCCAGCCACTGGCTGTATGCAG

TTCTTTATTATCAGTTGAAGCCAGCTAGGGGCAGAGACCTTCAGGTCTGT

AAGTGCTTTGGGGAGCAGAATTAAGACAAAGCATTAGAACCAATTCCCAA

CAAGTACCTGCTATACATTTCAAAGTCCATATTAGTCTCCTGGGTCTTCC

CTTCCCCAGCTACTTGTCCTCCTTGTAATCCAAATGACAAGCTTTTTCAC

ACATCTCTTTATCTCACATTTCCCTAGCCCTGGCCATGTCCACTTGTTCT

TTTACTCTCTGCTCTGCTCTCTTTCCAATGCCTCTGGATATTTTCTCTCT

CTTATTCACAATAAAAACCAAACCAAACCAAACAAAAAACCTTACCCTAA

TAATGGAGTGGTCACGCCTGAGGTTTCCTTACTGCTCCCCCTTGCACACG

TCTTGTGTCTGACACACTGGCAGGCTTTTATTAGCAGCAGGCTCTAGGAG
```

FIG.3D(26)

CTGAGAGAAGCAGCAGGCACCTCTGAGGTGGTAGTTACTAGAGTGATTAG

AACAGACAGTGGAGACGTGGCTGGAAATATGGACTCTGGTGTTTGGAGCC

AAGTATGGTAGGCGGCAGAAGCCAGCAGAAGCATGATCCACACCTTCACC

AGGTTGCTTCCATTGGGAAAGGCTGGACCCCTTGGGAAGGGGTCCCTTTG

TGCCTTCCTAGGTGTTCGGAGCCAGGTGTGTGAGGGATACAGTAAAGGGA

CTGACTGCATGACTGCTCCATTAGGGTGAAGGGTTTTGTTGTGAATAGGA

GAAACAAAATGTGCAGAGGCATCTGGGAGAGAGCAGAGCAGAGTGAAAAG

GAAGCAGTGTAGGCATGGTCAGGGCTAGGGACAGCGGAGACAGCAAGATA

GCGAGTGGGTGATAAGGTGAGAGAGAGTGTGTGTGTGCGGTGCACACATC

ACGTGCATTATAAGGAGGCTGAGTAGCTAGCTGGGGGGAGGGAAGGGCCA

GAAAACTAGCATGCACTCTGAAACGGGTACTTGTGATGCTGAGGGAGCTT

GGGGGAGAAGGGCATGCCTCAAGACCAGAAGAGGGAGTTGGAGTTACAGT

TTGTAAGATGCCTAATTTGAATGCTGAGATCCAAACTCTGATCCTTTGGC

TGAACATCATATCTGCTGAGCCATCTCTCCAGCCCCTAGAAAGGTGGTGA

TGGTGGTTGTTCTTGTTTTGTTTTATTTTGTTTAAATGGGGAGCCAGGTA

CAGTACATCATGCCTTTAATCCCAGCAGGAGATTCAGGAGATAGAGACAG

GTAGATCTCTTTGAGTTCAAGGGCACCTTGGTGTGTATAGGAAATTCCAT

CCACCCAGGGCTACAGAAGGGTACCTTGTCTTTAAAAAAAAAAAAAAGAA

AGAAAGAAAGAAAAAGAAAAAAAAAAGAGAATGAAATTTCAGAGTTATGC

AAGATAGGAGCTCAGTGGTAGAGTGTGTGCCCAGGAAGTGCTGGGTTTGA

CTCCTCAGAACAACAGCAGGGGCAGAAACTAGTCTACAGGTTCATGAGTG

FIG.3D(27)

GTGTTTTGTTTTGTTTTACATAAAATGTGTTGAATTAGATAAGTAGATAA

AATGTGACTCATACACAGATAAATAGATAAAATGTGATACATGTACCTGT

ACATAGAAGATTATGATCTCACCTTTAAAAAGGAGGAAATAGAGAGTTTT

GGTAGTTACACCACAGGAAAACTGGAAAAGAAAATGTATATATGAGGCTG

TGCCCCATGGCTAAAGGAACATGTTTTTAAGTCATTTGAATTCACCAAAC

AGTTTTAGGTAATGATATATGGTTTTGCATACAACCAGTATTTTATAAAT

ATTAGCAAGGTCACATCATTTATGAACCAACATTTAAACTAAATTTGTAA

ATCATCATTTCTTTATAGCACTTGTCATAGAACATAAGTAGTTTAAAATG

TGATTATTGCTTTGCTCTTGATGTCTGAAAATCTTCATGTATTCTCTTCT

TTGAGCCATTTTTATGCTTTGCAGTACTGGATGCATATTGAAGTGATCAC

TTATTTTAATCTACCTTGCCTGAGTTTGGGGAATAGATGGTTTCCACATG

TCTGTGGGTTATGCCTAAGCTAGTGGTTTTTATGTTAGAGCTTGTTTTGG

GGAAGGCACTGGTTGCATTCATAGCTGTGTTTCTTTTGCCTGTAGTCCAA

GCTCACTCTGACTCCATGGGTTGGTCTTCGGAAGATCAATGTGTCTTACT

GGTGCTGGGAGGATATGTCTCCATTCACAAATAGTTTGCTGCAGTGGATG

CCATCTGAGCCCAGTGATGCTGGCTTCTGTGGGATCTTGTCAGAGCCTAG

TACTCGGGGATTAAAGGCTGCAACCTGCATCAACCCTCTCAATGGCAGCG

TCTGTGAAAGGCCTGGTAAGGACATGGGTGCATATAGTGCTCCAGGAGGA

GCCAAGACAGCAAAGGAGGCACAGCTGAATGAGCGCTGAGGTGATGAAGT

ACTTATGGCAGCAGGGAGAGGAGCACCAATTTAGGCATATGTATTTCAAA

CAGAACCCGATTCCAGATAGTCTTTCTTGGCCTCTGACTGCTTTAAGCCA

FIG.3D(28)

TACTGAAAACCAAAAATAAAATTGCTGAAAGAACCCAGTTTATATTGAGC

TGCACTGTTTCGTTGGTCTCAAAGTGTTGAGAATTGTTCTAGAAGATTAT

TTCCTTGGTGTTGGCAGAGAAGTGCTATGGAGGAAACAACAACCTGAAAC

CAAAGAAACATTTAGAAAAGCAGCAAGTCAGGACACTATTCAGACACTGC

TGGGGTGGGGGGAGAGGGGCATGGCCAAAGAAGCCGACAGAGCCAACACC

AGGCTGTGGCAATGTCCTGCGCTGAGGTTAAGGTTAGACTCCATGAGGCC

AGGCCCAGAACAGCCATACACAAATGAGGACTCCAAAACAAGAGGTGCAA

GTGTAGTGGAGACTCCATCCCTGCAGGTCCTGTTTCAGGAAATGATTGTA

CTTTGCCTGAGTAATACAGCCTAGGAGCTACTTTCTGATAGGGTTTTTTA

AATACTTACAAAGAATTATTTATCTTTAATCATGTGGTTTTGTATGTGTG

TGCTTGCACATGCAGTGCTTGTGAGAGAGAGTATGTGTGAGAGCATGCAT

GTATGAGAGTGTGAGAATATATGTGAGAGAGTGTGAGTGCATGTGTGCGT

GTGTGCATCTGTGTGTACAGGTGTGTGTACATGCATGTGTGTATAAGAGT

ATGTGAGAGTGTGGGTGTGTGTGTGAGAGTATGTGAGAATATATGTATGA

GTGTGTGTGAGTATGAGTGTATGTGCGTGCCTGCATGTGTGTGTGTGTGT

GTGTGTGTGTGTGTGTGTGTGTGTGTGTAGAAGTGGCCTTGGAAAACA

GAGTTGTCAGATCTCTTAGAGATATAGTTGCAGTTGGTTGTGAGCCATCT

CATATGAGCGCTGGAAGTTGAAATTGGGTTCTCTGGAATCCTCTGGGTTC

CTTGTTGAAGCCTGAATATTTTGATAAATATTTATGTCATTATCCCTCAA

AATTGTAAATGTAGAATTTAACAAACTCAGGTCTTGAGTCATCTTTGTCC

CAAGGTTTGTTTGTTTGGTTTTTTGTTCCCCCACCTTTTCTTCAGTGCTT

FIG.3D(29)

TTAAAAAAGAGAGTCCATTTTTTCCTAAATGTTTAAATACAGTTGAGGAA

TAGAACATCTGACTCCAATTTCCTGGGTTTCCCTCCATGTAGTGTAGTGC

TGACCTGATTTCAGTGTGCATTGAAAACTTTGATCACTTGGAAGGCAGCT

ATGCTCACCACTATACTACCAATGTCTGCAATCCTATAGGAGAAACAACA

ATATGAACTAACTAGTACCCCCCAGAGCTGTGTCTCTAGTTGCATATGTA

GCAGAGGATGGCCTAGTCAGCCATCATTGGGAGGAGAGGCCCTTGGTATT

GCGAAGATCATATGCCCCAGTACAGGGGAATGCCAGGACCAGGAAGCAAG

AGTGGGTGGGTTGGGGAGCAGTGCGGGGGGGGGGGGTATAGGGGGTTTTG

GGGATAGCATTTGAAATGTAAATGAAGAAAATAACTAATAAAAATTGCCT

TAAAAAAAAACAAAAAAGAAAAGTTTTTGATCTTAGCTGACCAGTGTCTC

TTTGGGTCTTAATTTCCAGCAAACCACAGTGCCAAGCAGTGCCGGACACC

ATGTGCCCTGCGGACAGCGTGTGGCGAGTGCACTAGCAGCAGCTCGGAGT

GCATGTGGTGCAGTAACATGAAGCAGTGTGTGGACTCCAATGCCTACGTG

GCCTCCTTCCCTTTTGGCCAGTGTATGGAATGGTATACGATGAGCAGCTG

CCCACGTAAGTGGAAGGAGCTTTTGAACATTTGCAGGCAAGTTGGGCTTG

ACTTTCTGCTCAAGTCCATGCAGAAGCTGGTCGGGCCGGCCCTTCCAGAT

TAACATGTATGTATAGAATGCAGCACAGTGTTCCATGCAGTAAATCAGTT

ACATCAAGGAGAAGGCACAGGGTACAGAAATACCTTTTCTTCTTCAGGGT

AATATTATAATTCAATCTGTATAATGTTTCTACATCTTAATCTACCAGTA

TGTAAAGTGCTTTCTAGTAGAGGCCTCCCCAGCTCCCTTTTTCATCCAAC

ATCCTGATATTAAAAGGTTGGAAAAGTCCCTGTTATATATTATGTAAAAT

FIG.3D(30)

GTGGGGCCCTTTAAATTATTTCAGTTCAATAATCACTATAGGGTACTATT

TTTAATTCATGGAAGTTAAATCATCTGTTAAAAGAAAAGGTAATAACAGT

AAATTCAAATCTTGTGATAGTGAATTACAAGTTGGATTGTTTTGCCTTGT

TTTTTAATAGCTGAAAATTGCTCTGGCTACTGTACCTGCAGCCATTGCTT

GGAGCAGCCAGGCTGTGGTTGGTGTACTGATCCTAGCAATACTGGGAAAG

GAAAATGTATTGAGGGCAGCTATAAAGGACCTGTGAAGATGCCGTCACAG

GCCTCTGCAGGAAATGTGTATCCACAGCCCCTTCTGAACTCCAGCATGTG

TCTAGAGGACAGCAGATACAACTGGTCTTTCATTCACTGTCCAGGTAAGA

TGCCTGTGTATCCTAGTTCAAATCTCGTACATAAACTAGACGCCCAGATC

CCTTGGCTCACTTGTTTTCTTGACTGTGTTTGAGTTCTTTCTGTGTTCTG

CATCACCTTGTTGGATCATAGCTGGCAAAGGTGCTCTCCTTTCTGTGGGC

TTTTTCTTTACTTGATTGATTGTTTCTTTGGTTGCACAGAAGCTTTTTAG

CTTTCTGAAGTCCCATTTGCCAGTTGTCCTTAATTCCTGGGCGAGTAGAA

GCCTCATAAAAAAAAGTTCCTTCCTACACATGTATCATGTAGGGCACTGC

CTATGTTTTATTCCAGAAGTTTCAGAGGTTCGGGTTATGTCTTTGATCCA

TTTAGGGTTACTTTTTGTGAAAGGTAATGGACACAGTTCTGTTTCATTCA

TTATTCTACATGTGGACATCTACTTTTCCCAGCACCAGTTTTGAAGATGT

TATCTTTTCTGCAGGTTGTTTGTTTGCTTGTTTTGTCTCTTCAGAAAATC

CCAGATGGCGGTAGCTGTGAGTGCTTAGGCTTGGCCTACCTGTTTCATTA

TGTTGGCTTGCATGTCTGTTTTGTGCAGTGCCACCATATTGTCTTAATTG

CTATAGCTCTGCAATCTATCTTGACATCTGTGTTGGCAATCCTGCAGTTT

FIG.3D(31)

```
CGACCCTTCTGCTCAGCAGTGCTTTGGCCATCTGGGGTCTTTTCTGGGTT

CATAATGAATTTTAGGATTTTTTTTTCTATTTCTGAGAAAGTATTGTTGA

TATTTTGATTGCGATTGAATTGAATCTGTAAATTGCTTTTGGTAGAATGG

TCATTTTCACAATATTAATTTTACTGATCCATGAACATAGGATGACTCCA

GTCTCTCATGTCTCCCTATAGCCCTGTCTTAAGAGATTTGGAGTCTTCAT

TGTAGAAGTCCTTCACCTCCTTGGTTAAGTTTATTTCTAGATATTGTATT

GTCTTTGGTATTATAAATGGTAGTATGTCCATGATCTTGTTCTCAGTGTT

TTTTTAGTTTAGTTTTTTTTAATTTATGTGTATGAGTGTTTGTTTTATAT

ATGTGTATATGTGCATTCATGTCCTCTGGGCATCAGATCCCCTGGGACTG

GATTTACAGACAGCTTTGAGCTGCCTGTAGGTGCTGAGAATTGAACCCAG

GTCCTCTGCAAGAACAGCCAGTGCTCCTACTCCCCAGCCCCAGAAGTACT

AATTTTTAAGAGCTGATTTTCTACCTTTGCTGACATTGTTGATTGTTTCT

AGAAGTTTAGTGATAGAGTTTTTGAGATTTCTTATATATCTTATGTTATC

TGTAAAAAGGGATAATTTGACTCCTTTTCCTATTTATATCCTTTTATTTC

TTTCATTTGCCATATTGTTCTAGCTAGTGCTTCCCGCTCAGTATTGAAAA

GAGTGGTGATTGTGAACAGCTTTTCTTATTTCTTATTTTAATGGGATTAT

TCACCCATTTAAGATAATGTTGGTTATGGGTTTGTCATACACAGCCCTTC

TTATATTGAGGTATGTTCCTTCCAGTCCTGTTCTCTCTAGGACTTTTTTT

TTTTTAATCAAGAAAGCATATTGGGTTTTTTGTTGTTGTTATTTTGTTTT

GTTTTTCTAGACAAGGTTTCTCTGTGCAGCCCTGGCTGTCCTGGAATTCA

CTCTGTAGACCAGGCTGGCCTTGAACTCAGAAATCCACCTGCCTCTGCCT
```

FIG.3D(32)

CCCGAGTGCTGGGATTAAAGGCGTGCACCACCACTGCCTGGCACATGTTG

GTTATTTTGCAAGCCCTTTCTACATCTACTAAGATGAGCATGTGGTTTCA

TCTTTGTCTGTTTATATTGTCTGTTGTATTTATTGACTTATGTGTGTTGA

GCCAACCTGAAGTTCTGGGATAAAACCCACATGCTTTGGATGATTTTTGT

GCTATGTGCTTATATTGTGTTTGTTAGTGCTTTATTGAGGACGTCTGCAT

CCGTGTTCATCTGGGGTACTGTCTGTAGTTTGCTTATTTTGTTGTCTTTA

CCTGCTCTGCATTTTAGAGTAATCCTGGATTTATAGAAAGCATTTGGGAG

TAGTCCTTCTGTTTATTAAAAAAAAAAATTAAGAATGATTGGTTGTTGTG

TGGTGGAATTCTGCTGTGAACCCATCTGGTTCTGGACTCTATTCGGAAGG

CTTTTTATTACTGTTTCAGTCTCCTTGTTTGCAGTGATCTATTTAGGTTG

CTAATCTCCTTATGATTCATTTGGATGAATCAAGAAATTAATCCATCTCT

TTAGATTTCCAGCTTAATGGAATATGAGTGTTAAAGTATTTCTTTATAGC

ATTCTGTATTTTTTGGCATCTGTTGTAATATTTCCCTGTTCTTTCTGTTA

ATCTCTTTCTTTCTTGTGGTTAGTTGGGCTAAGAGGCTCTTGGTTTTTTT

TTTTTTTTTTTATCTTTTTAAAGGACCAGCTCTTAGATTCATTAATTCTT

TGTATTATTTTCCTTGTTTCTTTTTCACTGATTTCATTTTAGATTTTATT

ATTTCTTGCCATCTACTGCGTTTGGGTTGGTTTTAGTTATTTTTCCAAGA

TTTTCAGTTTCATCACTAAGTCATTCATTTGGGCTCTTTTGGGTTTCTTC

ACGAGAACCCACTTGGGACTGTTACCTTCCCTTTTAGACCTGCTTTTAAT

GTGCCCCAGAGATTTGTTACATTGTCTTTTCGATTTAACTTAGTTTCAGG

AATATTTTGATTTCTTCTTTGACCCATTCATCATTCGGTAATGAGTTGTT

FIG.3D(33)

TAATCTCTAGTGAGTTTATACATTTATTAGAATTTTGTTTACTGATGATT

TTAAGGTGTTTGGCTTTGTTTGTTTGTTTGTTTGTTTGTTTTTCGAGACA

GGGTTTCTCTGTTGTAGCTCTGGCTTTCTCTATGTAGAACAGTCTGACCT

CAAATTCACAGAGATCCACCTGCCTCTGCCACTGAAGTTCTGGGATTAAA

GGTGTGTGCCACCACTACCTGGCTGATTTTAAGTTTTATTACATAATAGA

CAGGTAGGGTACATAGATTTTCTACATTTGTGAAGGTTTGCGTTGTTTGT

CAGCATGTAATTCTGTGTGCTGCTGAGGGAATGTATGTTGTTTTGACAGT

TAGGTGGAAAAGTCTGTAGACATCTGTTAGATCCATTTTACATTTCAAGA

AGCCATTTAATTCTGAAGTTTCTCTGCTTATTTTTTCCCAGGTGACTTAC

CTATTGGAGAAAATAGGGTGCTAAAATCATTTACTATTATTGTTTTTTTT

AAGAAGAAAATAATTAATTTAAAAAACCCTGGAAAGAAAGATACCAAATG

TGAATCATGTTTCCTGGATAGTGGGGTTATATTTGATCATTTATTTTTCC

TCTCAAATACTGTGAGTTTTTACAATGAATAACAACATAAATATTTTTAT

GTTGCTGTGGACTTTAACTTTGCTTTGATAATATATTTGGTTTTTTGAGA

CTAATTTCTTTTTGATATTTTATTTTCTCATACTAGTTTTTAGTAAACTT

TGGTTTTGTTTTGTTTGTATTTTTTAGACTGGCCACCAACTTGCTATGTT

GTCAAGGGTGGCCTTAAAATCCACACCCAATACTTTGTCCTCTCTTTCTT

TCTTTCTTTTTTTTTTTTATTGGAACAAAATTTCTAGGTGGGAATCTCAC

TATGTTACCCAGGCTGACCTGAAACTTCTGGGCTTAAGCAAGATGGGTGC

ACATGATCAGAGACGCTGCGCTGCCCGCCTCAGCCCCTGCTAGTTGGAAC

TATAGGCACAGACAGCTGTACTTCACTCATTTCAATGATTTAACATTTAG

FIG.3D(34)

```
ACTATATGCAAATAAATATGAAATGTATTCACCAAGTTCTCCTATGGGAG

AAACAGAGCCCTTAAGATTTTTTCCTTTCAGCTTGCCAGTGCAACGGACA

CAGCAAATGCATCAACCAGAGTATCTGTGAGAAGTGTGAGGACCTGACCA

CGGGCAAGCACTGCGAGACCTGCATATCTGGCTTCTATGGTGACCCGACT

AATGGAGGCAAATGTCAGCGTAAGTCACACAGGTCAAGTTAGTCACAAGT

CAGGTACAATAGTACAGTACCTGCAGTTGACTTAAATATCTTAAAGGGAA

AAGGCCTCTTGGTTTGGGATATTGCCTTTCTTAATTATGTTAAATTGTTA

AAAGTTTAACTGAGGGGCTAGAAATGTGGCTCAGTTGGCTAAGAACACTG

ACTGTTCTTCTAGAGGACCGAGGTTCAATTCCCAGCACCCACATGGCAGC

TCACAAGTGCTTGTAACACCTGGGATCCAACAACCTCATACAGACATACA

TGCATGCAAAACACTAATATACATAAAATAAATCCATTAAAAAGTGTTTG

ATGATGCTGGAAGAGGAAAAAAGGCTCAACTTGTGGGTTTGGGAGCAGTT

AGTTAAAGCAACAAACCGACAGTAAAGGAGCTAAGCTTTTATTTCTTCAG

CAGAGGCATAAACAAGGGGCCGAAGTCACTGAGGCACCAGCTGCCTTTAT

TCCATTTCCCTCCCATGGAAGCACATCAGCTCAAGTCAAGCAGAGCAGCC

TGGGATGGGAGGTCATCTCATTGGAGAAGGAGGCAGGAGGCATTGTGAGG

GGAGGGAGGACAAGGCTGGGAATGGGAAGTCCTGAGCTCAGAATCAGAAT

GAGGACAAGATCTTCAGTTTCCTTCTTAATATAAAGAGGTATCACAGAGG

TCTCTATAGAAGTCTACTGGAAGCCTCACACAGGCACAAGGGTACATTTG

AAAAACTGTGACAGCCAGGGAGAGTCCCCTTCTGAAGTGTCCTTCCTCAG

AGACTGCAGCACCTGACTGTGCCCCAGTCTGCAAGAGGTTTGGGGAGAGC
```

FIG.3D(35)

```
AACTGACCTCCTGAGGACCCCAGATGAATCTTTAAGATGGCCTGCTTTTG

GTTTTGGTTGGTTGGTTTTTAGACAGATCTAGGAGAGTTGGTGATGAGCT

TGAATTCTCTGTCCTCCTGCCTGACCTCCAAATGCCCAGCTTCACATGGG

CTCCCATTAAGTTGTGAGTTTCGGTGTCTGGCTCCTGCTCTCACAGCCAG

TGCAGTACATTGAGCTCCATAGAGATAGCGCCGGGGCAAATGAGAGCTGG

ACGGGCACTGGGTGACTCTGTGCCTTGTGCCGGAAAATCAACTAAACATG

GGCAAAGGAGATCCTAAGAAGCCGAGAGGCAAAATGTCCTCATATGCACT

CTTTGTGAAAACCTGCTGGGAGGAGCACAAGAAGAAGCACCCGGATGCTT

CTGTCAACTTCTCAGAGTTCTCCAAGAAGTGCTCAGAGAGGTGGAAGACC

ATGTCTGCTAAAGAAAAGGGGAAATTTGAAGATATGGCAAAGGCTGACAA

GGCTCGTTATGAAAGAGAAATGAAAACCTACATCCCCTGCCCCCAAACAG

GAGACCAAAACGAAGTACTAGGACCCCAATGCACCCAATGCCTTCTTCGG

CCTTCTTGTTCTGTTCTGAGTACCTCCCCAAAATCAAAGGTGAGCACCCA

GCTTATCCATTGGTGATGTTGCAAAGAAACTAGGAGAGATGTGAACAACG

CTGCAGCAGATGACAAGCAACCCTAGGAGAAGAAGGCTGCCAAGCTGAAG

GAAAAGTACGAGAAGGATATTGCTGCCTACAGAGCTAAAGGAAAACCTGA

TGCAGCAAAAAAAAAAAAAAGGGGGGTGGCCAAGGCTGAAAAGAGCAAGA

AAAAGAAGGAAGAGGAAGATGGGAGGAGTATGAGGAAGAGGAGGAAGAAG

AAAGATGAAGAAGAATATGATGATGATGAATAAGCTGGTTCTAGTTTTTT

TCTCATCTATAAAGCATTTAACCCCCCTGTATACAATTCACTCCTTTTAA

AGAAAAAAATTGAAATGTAAGCCTGTGTTAGATTTGTTTTTAAACTTTAC
```

FIG.3D(36)

AGTGTCTTTTTTTTGTATAATTAACATACTGCCGAATATGTCTTTAGATA

GCCCTGTTCTGGTGGTATTTTCAATAGCCAGTAACCTTGCCTGGTACAGT

CTGGGGGTTGTAAATTGGCATGGAAATTTAAAGCAGGTTCTTGTTGGTGC

ACAGCATAAATTAGTTATATATGGGGACAGTAGTTTGGTTTTGGTTTTAT

TTTTGGGTTTTTTTTTTTTCATCTTCAGTCGCCTCTGATGCAGCTTATATG

AATATGATTGTTGTTCTGTTAACTGAATACCACTCTGTAATTGAAAAAAA

AAAATCGTGGCTGTCTTGACATCCTGAATGTTTCTAAGTAAATACAGTTT

TGTTTTTATTAATATTGTCCTTTCGACAGGTCTGAAAGTTTTCTTCTTGA

GGGAAAGCAGTCTTTTGCTTTTGTCCCTTTTGGGTCACATGGGTTACTGC

AGTGTGTATCTTTTCATATAGTTAGCTGGAAGAAAGCTTTTGTCCACACA

CCCTGCATATTGTGGTAGGGGTAACACTTTCATCCATATTCAAAGAATCT

CCAAAATCGTGATCAGTTGGATAAGAAATATTATATAACCTACTTGGCAA

AGCAAGGTGTGATCAATTCTGTCACACCATGGGATCATTAGAATCAAGCA

ATCTGAAAATCTGTCCTTAAAGGACTGATAGAAAAGTATTTTCTAATCCT

TATACAAAGGCTCTCCTTTAACTGCCACTGCTATGTAATGACAGTTATGT

TTTGCAGTTTCCCTACTAAAGAAGACCTGAGAATGTATCCCCAAAAGCGT

GAGCCTAAACTACACAACTGCAGTACTATTTGTTGACCTTAGTCCCAGCG

AAGGCTATCACGAGAATGCTAGCTATAATATAATGCCTCTGCCCCTCTAT

CTAAATATGGATTGCTCAGGAAACTTGACTGCTTAAAGGTATTTTTTTCA

TATTGTTGTTCCTCCTATAGGGTTGCAGACCCCTTTAGCTCCTTGGGTAC

TCTCTCTATCTATCTATCTATCTATCTATCTATCTATCTATCTATCTATC

FIG.3D(37)

```
TATCTCTTGTCAGATTTCTTTTTTTCTTTTCTCTTTCTTTCTTTCTTTTTT

TAAGATTTATTTATTATTATTTCTAAGTACACTGTAGCTGTCTTCAGATG

CACCAGAAGAGGGTGTCAGATCTCATTACGGATGGTTGTGAGCCACCATG

TGGTTGCTGGGCTTTGAACTCAGGACCTTAGGAAGAGCAGTCGGTGCTCT

TAACCACTGAGCCATCTCTACAACCCTTAAAGGTATTTTTAAGTAGTTGA

GTCAGCTTTTAAAATTATGCCAGAAGTGTCAAAAGTTCAAAAGTTTAGGA

CCATCCTCTATTGAAGTACAGGGTCATCCTGGGCTACATGAGACCCTGCC

TTAAAACCAAAATCAAACAAACAACAGGAAAAACAAGAGTTAAGAAAGAG

AAAAAGAAGCACTTGGAAACAAAGATCTGTGGAGTATGTATAGGCTTCTC

TACAACAGGTGTATGTAGGATCTTGATGGCTTTTGAGTCTATTACCCTCA

AAGAGGTACTGAGAAACCTAAATGTGATCACCGTGGTCTCTGAGGGGCAC

CTGGCAGGATTATGGGAGATAACTAAAGCTTGCTAATCACAGAGTTTAGG

GAGGGAGGACGTCTCTAAGGCAAGTTAACTGTCTGGTTTGAGATGCTTAG

GTGATGTCTGAGGAAGTAATAAGGCCTGTCCATTTTCATACACACTCAGG

CCTTAAGTCTGGGTAATGGCTACTTGAACATAAAATAGTCCTCTATGAAA

GGAATAATATCTCTGTGTCAGCAGCCTTCACGGCTAATGTTAATTGTGCA

GGAACCCTGCTTCTCAGTCAGACAGAAGCTCAATCAGGCAGGGGCAGGAC

TTCTTTGCCTTTCCCATGTCCTTGTAATTTCCCTGGCTTTTCATCTTGGT

TCAAACATACTTACCTGTTAGGTAATTATAAGAACACCAAATATTACTGA

ATAAAATGTGTTTATGACTTTGTGGTGACTGCCATTCAAGAATTAGATGC

CTTAGCCAGCAATGATGGCACACGCCTTTAATCCCAGCACTTGGGAGGCA
```

FIG.3D(38)

```
GAGATAGGCAGATTTCTGAGTTCCAGGACAGCCAGGGCTACACAGAGAAA

CCCTGTCTCGAAAAAACAAAACAAACAAACAAAAAGATTTCGATGTCTTT

ATCACCCAAATCAAGTAACTTTCCAAAGTCTCACAGTGAGATGTAGCCTA

GTTGGGAGCCACATCTAATATATGCTGATGATCTTAACAAGTAGCCTGCT

TGTGTCTTCAGGTGACCACCCCGGTGTCCTCAGCTACCTCTAGAAAGATC

ACACTTTCCTCTGTGGTCTCTGCAGGGTCCCTGTATGATTCTGGAACCTT

GCTGTACTTCTCAGAGTCCTGATTCATAAAGCACTGAGTTTTTGCTTGTT

TGTTTGTTTTGATACTATTGGTAAGAATATATATTGAACCTTGACATGCC

TTTTTAAAATAACATTATTTTTACAATAGTACTTTAGCCTTGATTATGTT

AACTGCTTACTGTTTCAGATGACATTCGTACATCTTTTAATCCTCAAACC

AGTCCTATGAGATGGCTAGCATCATTGTCACATCATTTAGGCAAGGAAAC

AGGTCTTGGGTTAAGCTTCATGCTCAGAGCTCCTTGGAACACAGTGGACT

CAAGTGCAAGCAGACTGACGCGACTGGGTTTTACTAATTCAGTAAGCCTG

TACTCTATGGAGGAAGAGTTTCTGACCACTGGATGCAGTCTGATGACCTC

TGACTGTTCTGTTTGAAAGGTTTCTTTCAGTGATTTTATTTTTCTCCATG

TGGACTTTTTTTTCCAGCTTTTAAAATATATATATATATCTTATTCGCTTC

ACATCCTGCTCACTGTCCTCCCTCCCCTGTCATCCCCTCCTACAATCCTT

CATATCCCCCCTTACCTTCTGAGCAGCTGGGAGCCCCTCTGGGTATCCCC

ACACTCGGGCACATCAAGTCTGTGAGGCTGGACGCATCTTCCCCCACTGT

GGCCAGACAAGGCAGCCCAACTAGAACATATCCCACAGACAGGCAACAGC

TTTTAGGATAGCCCCTGCTCCAGTTGTTCAGCACCCACATGAAGACCAAG
```

FIG.3D(39)

```
CTGCACATCTGCTACATATGTGCAGGGAGGCCTAAGTTCAGCCCATGTAT

GTTCTTTGGTTTGTGGTTCAGTCTCTGAGAACCCCAAGGATACAAGTTAT

CTGACTCTCTTAATCTTCCTATAGAGTTCCTATCTCCTCTGGGGCCCACG

ATTGGTGTCCCTATTGCTTCACTGGGATTCCTGCCTGGCTACACCCACTA

TGACCAAGGCAAGTCTTAGAAAAGACAACATTTAACTGGGGCTGGCTTAC

AGGTTCAGAGGTTCAGTTCAGTATCATCAAGGCAGGAACATGGCATCATC

CAAGCAGGCATAGTATAGAAAGAGCTGAGAGTTCTACAACTTATCTGAAG

GCTGCTAGCAGAATACCGACTTCCAGGCAGCTAGGATGGGGGTCTTCAGA

CCCACACCCACAGTTGGTGTCCCTATTGCTTCACTGGGGTTCCTGCCTGG

CTACAGGAGGTAGCCTCTTCAGGTTCCATATCCCCAATGCTGTGAGCCAC

AGTTAAGGTCACCCACTATTGATTCTAGGGTGTCTCCCTCATCCCAGGTC

TCTTTCATTGTGGAGATGCCCCCCACTTCCCCACCACTGTCAGTTGCAGA

TTTCCATTCTCGGGACCATCTGGCCATGCCTTCTGTTTCTCCTCACACCT

GATCCCGACACCCCGCCCATTCCTTCTCCTACCTAGTTCCCTCCCTCCA

TATGCTTCCTATGACTATTTTATTCCCCCTTCTAAGTGAGATTCAAGCAT

CCTCACTTGGGCCGGCCTTCTTGTTTTGTTTCTTTGGGACTGTGGAGTGT

AGCTTGGGTATCCCATTTTTTTATGGCTAATATCTGCTTATAAGTGAGTA

CATACCATTCGTGTCCTTTTGGGATTGAGTTACCTCACTCAGGATGGTAT

TCTTAAGTTCTATTCATTTGCCTGCAAAATTCATGATGTTTTTGTTTTTA

GTAACTGAATAGTAGTCCACTGTATAGATGTACCACAGTTTCTTTATCCA

TTCTTCAGTTGAGTGAAATCTAGGTTGTTTCCAGTTTCTGGCTATTACAA
```

FIG.3D(40)

ATAAAGCTGCTATGAACATAGTGGAGCATGTGTCCTTGTGGGATGGTAGA

GCATCTTTTGGGCATATGCCCAGGAGTGATGATATAGCTGAGTCTTGAAG

TAGAACTATTCTTAGTTTTCTAAAAAACCACGAAATTGATTTCCAAAGTA

GTTGTACAAATTTGCACTCCCTCTAACCAAGCAAGTGAAAGATCTGTATG

ACAAGAACTACAAGTCCCTGAAGAAATAAACTGAAGAAGATATCAAAAGA

TGGAAAGATCTCCCATGATCGTGAATAGGTAGGATTAACAAGGTGAAACT

GGACATCTTACCAAAAGCAATCTAGAGATTCAGTGCAATCCCCATCAAAA

TTCCAACACAATTTTTCTGTAGACCTTGAAAGAGCAATTCTCAGTTTCAT

ATAGGAAAACATAAAGCCCAGGAGAGCCAAAACAGTTCTGAGCCATAAAC

GAACTTGTGGAGGAATCACCATCCCTGACCTTAAAGCCGCACTACAGAGC

AGTCGTGATTAAAACAACAACAAAGGCTGCGCACTTTTGGTACAGAAACA

GACGTGCTGACCAATGGCATCCAATCCAAGATCCAGAAAGAAACCCACAC

ACTATAGTTTTTTTTTTAAATATAAAGTTCTTCAGCTTAATGCTTCTCATT

ATTCATGAGAGAAGAAGACTCAACAGCAAAGAAGGTGAAACAAGGGTGAC

AAGTACCACAGGGCTCTCGAGTGTCTCTTGTGATGGACTAGGGAGCCCGT

CAGTTCTGAATGCTCAGGAATGTGGTTCACAGTGTGGCCACAGTACAGAA

GATCCCCGAGATAAGGCAGAAGACAGTCACCACAGGTCATCTCCACAGGG

CAAGGACTCAGTATATGGCATATTACTAATGCTCTTAAATATTTACTGAA

CAAAGGAACAAAATGCTGAGTCTGTCACAGAGATGAAAATAGCCGTTGCT

TCAGGGGACAGCAGAAGATAGCCTTTTTTTTCTCCTTGAATGGTAGTTAAT

TTAATGTTGCCTCTATATTATTAGAAATAAATTACAAGCTGAAAAATAAT

FIG.3D(41)

```
GAGTCATACGCAGTGATTTCTCTTGCTTTAGGCTGTCTTTACTACAAACC

CATTTCAGGCTAAATGATTTTGTCTTAATCACAGTCTATGGTAATCTGTC

AAGCCAGTTGTGACCTGTCTTCCTTTCCTTCTTCCCAGCATGCAAGTGCA

ATGGGCACGCATCACTGTGCAACACCAACACCGGCAAGTGCTTCTGTACC

ACCAAAGGTGTCAAGGGGGACGAGTGCCAGCTGTGAGTACCACACACACT

CTGTGTCTCCAGTGGGGGACTGGGCCTTGCAGCTGCCTGGGCCCTGTCGG

CCACCTGCTTGCCTGGGCATTGTTGCCCTTCACTCCCAGGGTCTTTGAGT

GGACTAGTGTGGAGGTTTACCTTTTTTCCTTCAGACAGGTTATCTCAGTT

ACTTTAATATTGCTCTGATAAAACATATGACCAAGGCAACTTACAAAATA

AAGCCTTTAATTGGGCTTATGACTTAAGAGCATTGGAGTCTACATTGAGT

TCCAGGGCAATAGAGCTACATAGTAAGACTGTATCAATCAATCAATAAAT

AGGACTACATAGTAAGACTGTATCAATCAATCAGTAGATGAAGAGAAAGA

AAGAAAGAAAGAAAGAAAGAAAGAAAGGAAGGAAGGAAGGAAGGAA

GGAAGGAAGGAAGGGGAAGAACAAAACAAGCTTAGATAGGAAGAAC

AGGATAGAATGAATGACAAATGCTTGAAAAATGTTTTAGCTGTACTTTTA

GAAGCATACTCAATCCACACAGAAGTAAAAATGTTGTTCCTTATGAGTAG

TACCTAGCATTATTACATATGTACTTGCCTGTGTCCTTGGGCAAGTATTT

GTTTATTTGTTGTTTTTATACTGTTGCTGGTGTAAATTACTGAGCAGTTA

GCAGAAACATTCCTGCAAATGGGATAGTCTCTCTGATCTGAATAATGATA

TAGTTTATGTAAAAGGATTTACTTGGTTTAAAAATAAATATAGAGTCTGT

GCTTTAAATGTCAATAGAAGATAATTTCTTTTTTCCCTAGATGTGAGGTA
```

FIG.3D(42)

GAAAATCGATACCAGGGAAACCCTCTCAAAGGAACATGCTACTGTAAGTT

TTTGTAATTGTTTCTAGAGAGTAATTGAACAAAACGACATTGCTTTTTTT

TTTTACCATTGTCTGAGAATGATAAATGCTTGGGGGATGAAGCAAATACT

CATAGCCATGCCCCTGACTTGGTGAACACTGTTCTAACTGAGGCATGGTC

TCTGCTGGTCATCCAGAGCAGTTAGCAGGGGTGCTGTCCTGCCTGTCCTT

GTTCAGCTCCCGCGGAGGCGTGCTCATTCACCATTGCCCAGTGTAGCTTA

TCATGTCCAATCTTCAGACAGCCAGGAAGGAGTTTCTAAGATAGAGGTGC

GTTCCACCATTCTCTCTGCAGCTGATTTGTGCTCACAAACAAGTAAATAA

AACACCAAATTAATACCTTGGTGTGAAAGTGAATCTGGTAAGCTTACAGC

TTTATCATAAATATATTTTTTGTCTATGAGAATCTACATAGTAGGTTCTA

GACTATAGAACAATAAAAAAAGGAATTAACATTTGGCATATGCAGCATAA

TGGTATATATAAATTGTAGAAGAAAATGGATGGTTCTAGACCTGAAAAGA

CAAGAAAATTGCTTGTGTGTAATCTGGGCAGGTCTTAAGTTGTGACCTTC

AACATCTGCTTCCCAAGCAGCTGGAACCACCAGGCCTACAGAATTCTTAG

CTATGATTCTAAAGGTCATTCATCAAATATAATGTTAATGTGTATTTTAT

TAAAGTTTCAAACTTCTATCTTTAATAATCTGCAAATGTAGCTCAGTAGA

GGAGAGCTCTCGCTGTAAGGTCCTGTGTTCTATCCCCAGCACAACAAAAC

AAGACATTTAAGAAAAAATTAAAACAAGTTGGCTGTATTGTCTCAGTATC

TCATCCTTGAGATAGTGAGGCAGGAGGACTTTTAGTTTGAGGCCTATGTG

GGTTATGTAGTGTGAAACCTTTCTCAAATAATATTTACACTTTTTTCTTT

AAAAAACAACTTTTTTTCTTAATTTATGTGTTTTGCAACATGTAAGTCTGT

FIG.3D(43)

```
GCAATGTGAACATATCTGTTGCCTTTGAATGCCAGAGAGGGTTTCAGTTT

TCCTGGATCTGGAGTTACCAAGGGTTGTGAGCTGCCATAGTGGGTGCTGG

TAATGAACTGAGTCCTCTGGAAGAGCAGCCAGTGCTCTTAACTGCTGAGC

CATCTCTGCTGCTAGGTACTCCCCCTTCCCCCCTTAAATTTAAGACAAAG

GTCTCACTGTGTAGCCTCAGATGGTCTAGAACTCAATTTGTAGAATGGTT

GACCTTTGAACTCACAAAACTCTGCCTGCTTCTGCCTCCTGAGTGTTGAG

ATTAAAGTTGTATGTCACCACACCTGCCCCTATGATTTCTATATTTAATA

AAGATCATGACTAGGATATAGAGAACACTTTTAGAACTGAAGAAGAAGAC

AGTTACAGTTAAAAGCAAAACAAAAACAAAAACAAAACAAAACCCAGAAA

AAAAAAGAATGAAAACTAGCACTGAAGAAAAAATAAATTTTAAAAATAGG

CAAAGAGTCACTATTATATTGTGATGGATGTGTTATATGTTTAAAACCAC

AAGTGAGATACAGGCCTGAAATGACTTTAATCGAAGCTACACCAGCCTGG

GGTGGTAGTTCAGTTGGTAAAGTTCTTGCTATGCAAGCACAAGAAGCTGG

GTTTGATGCCCAGGACCCATGCTGAAACCCAGGAGTGCTGCTGAGTGCTT

CAGCTCTGGGGTGGCAGGGCTCACTGGCAGGAAGCCTAGGCTAAGAGAGA

CTCTGTCTCGAAAAACAAGGCCGATGGCACCTGATGAACGGCATCTCAGC

ATGACCTTTGCTCGGCATATAATGTGTACACACAAATTCATAGTTTAGTA

GAAGACAAGTATGATCTGCTTTTCATGAAGTCTGTTGTAATACGCCTTCT

TTAGTTAACCATAGTTGCTTAAAAAAAGAAAAAAATCGACCTCACTGGAC

AGAAAATGGATAGAGTGTTCTAATAGCCAATTCAATTCATCATCATTATC

AAAACCTATAACTTAGGGGGCTGGAGAGATGGCTCAGCGGGTAAGAGCAC
```

FIG.3D(44)

```
TGACTCCTCTTCTGAAGGTCCTGAGTTCAAATCCCAGCAACCAGATGGTG

GCTCACAACCATCCATAAAGAGATCTGATGCCCTCTTCTGGAGTGTCTGA

AGACAGCTACAGTGTACTTACATAAAATAAATAAATAAATCTTTAAAAAA

AAACACCTATAACTTAAACTTATCAATAACTTTAACTTTCCTACCCCATG

CTTCCTAGTTACCCATTCTGCTTTCTGTTTGTATGATCCTGGGTATGGCA

TCTTAATGGAACCACAGTGTTTGACTTTGTATCTACTTAATATTAGGCAT

GATGCCTCTGACTCTCATCCCTGATATAGCACAGTTCAAAATTGCCTTTC

TTTGGTGCTGTACATATAGCTGAGCGTTTGAGTGCTTCCCTGCATGCACA

GGTTTCTGAATTCAATCCCCAGCACAAAAAATGATAAAAAGAAAGCAAAA

AGGCTTATTTTTACAGCTGGACAGATCATCCTGCATTGTGCCTGTCATGT

TTTGCTTGTTTCTTCTGTCAGTGGACACTGTGTTACTTCTACCTTTTGGT

TGTTGTCAGGAATATTGTAAACATGAGTGAATATACACCCAGAAGTACAA

CTGGATGTGGTAATTCTATGAGTGTTTTGTTTTTTGAGGGATGGTTATTA

TTGTTTCCATACAATAAATTACATTTCCTTACAGTTCATTACATTTCCAA

AAGCCATGCATAGCATTTCTGTTGTTCTACATTCTTATTGACACCAGTTT

TCAATTTACATTTATTTTGTGAGTTTTTTAATTGGTAACCATCATAATGG

ACATAAAAAATAGCTCATTGTAGTTTTGGTATTTGTATTTCAGTAATGCT

TGGTGTGATTATCTTTTTATATTCTTATTAACCATTAGTGTGTATCTTTT

TTTGGAAAAACACCTCTTCAAGGGTTTTACTATGTAGCTCTGGCTGGCCT

GGAACTTGTGCAGACCAGGCTTGCCTCCGGTTCCCACTGTCTTAGGTAGG

TTTCCATTGCTGTGAAGAGGCACCATGACCAGAGCAACTCTTACGAAGGA
```

FIG.3D(45)

CATTTAATTGGGGCTGGCTTACAGTTTCAGAGGTTTAATCCATTATCATC

ATGGCAGGAAGCATGGCAGCATCCAGGCAGATGTGGTGCTGGAGGAGCCG

AGAGAGTTCTATATCTTGATTCAAAAATAGCCAGGAAAAGACTGTCTACA

GCAGGCAACCAGGAGGAGACTGTCTTCCATATTGGGCAGAACTTGAGCAC

TAGGAGTGTTCCAAAGCCACCTACACAGTGACACAGTACATCCAAAAAGG

CCACACCTATTCCAACAAGGCCACACCTCCTAATAGTTCTACTTCTCATG

GGCCAAGCATACTCAAACCACTACATCCACCTACTTCTGTCTCCCGAATG

CTGGGATTAAAGGCATATGTTGCCATTACCCAATTTTAAACCAGATTATT

ATTGTTTTTTTGTACAACAGACTTTTAAGGTTAAAGTTTGCAGCAATAGG

CATTCTTTGAAGCTGTATCACACTGATATATGTCTGTTGTTTTCTTCCTT

CCTAGATTAAAATAGTACAGTATATTCAAGTTTCAATTGTCCCTTTCCAT

AAGAAGTCCTGGTTTCTGTTCCATTATTAGTTTATATCTTAGTGTTCTTA

AGTAAAAATACTCAGTATTTATAGATGAGTTAGATTAGAGCCAAACCCCA

ATCAGGGTATTGGTAATGAAGGTTTGCTGGATAATTCAAAGGATACTGCA

AAGATCTGGTTTCTAATGGAAAGAACATGTAAGTTGGCCATTAGTGGACC

ACACATCTGTATTTCTTATTCTTTGGAACCTTGGGCAGGATAGACAGATG

AGCTAAGATTCCTTCATAGCTATTGAATTTGTGAGAAAAACAAATTGTGT

TTCCAGAAACCTGCTTTAGTTTGTATCAACACTTACTTTCTTTCTGTGTG

TGGTGTGTGTGATGTGCCTGTACCATTTTCAAGTTTTTCTTCCTTCTTTC

CATAGATACCCTTCTCATTGACTATCAGTTCACCTTTAGCCTGTCCCAGG

AAGACGACCGCTACTACACAGCCATCAACTTTGTGGCTACTCCTGATGAA

FIG.3D(46)

GTAAGCTTTTCTTTTAAGCTGTCTTATTTTGTGTTAAATTTTGTATAGGT

TTTTTTCTTGGTCATCCTGGACAAAAGTACTACATAGAAGCAGACAGTAT

CAGGGTGGGAATATAAAAGGCAACCAGTTTTTAAGTATTTTTTTATTTAC

TTGTTGACAGTTTTATATGATTATATAATGTGCTTGATGATATTCAACCT

GTGACCTTTTGTCTCCCTCATACTTAGTTCCTTCTCTCCCCACCAAGTCA

CCTTCACTCCCTCTCGTGTGTGTGTGTGTGTGTGTGTGTGTGTGTGTGTG

TGTGTGTGAGAGAGAGAGAGAGAGAGAGAGAGAGAGAGAGAGAGAGAGAA

AGACAGACAGACAGATAGACAGAGAGACAGAGATTGATTGATTGATTGAT

TGATTGATTGATTGATTGATTTACCTACCTAGTTTACCAGCTGACTGCAG

GAGCATGCTGGGTGGGAAGTTCTTACTGGAGCATAGACACATTACAGTGA

CTACACCACTGAAGAAAGTGACTCCCTCTCAGGTAGTCTTCACTGCCACT

AGGTCCTCAGGGATCAAGAGAATGTTTGGAGTCTACATTTTATCTTTTTT

CCACTCAGAAGGCAAACATTACTGAATGTTTTTAAGTAGTAGAATAATGT

TCATGATAGTCTGTTTAATATTAAATTAAGAATTTGTTCCTAATTATAAA

ATTTTTAGAAGATAGACAAGAAGACAAAATTTTTGAGTTAACAGTTTGAA

AGGTTTATTTTTATTTTATTTTATATGTATGAATATTTTAGCTTCTTGTA

TCCCTGTGCATCATGTGTGTGCAGTGCCTGTGGAGGCCAGAAATAGATAT

TGGATCCCTGGAACTAGAGTGATAGATCATTGTGAGCCATCATATGGGTG

CTAGAACCAACCCAGGGTCCTCTGCAAGAGCAGTGAGTGCTCTTAACTGC

TAGGCCATTTCTTTAGCCCCTAAATGTGAACAACTCTTTAAATAAATGTA

AGTGATCTTAAATACTCTGGAGAAAAATCTGTAGCTATACCTTACTTTTT

FIG.3D(47)

AAAAATTATTTTGTTTTATATTATGAGTGTTTTGCCTACATATATGTGTG

TCTGATGCCTGCAGAGGTCAGAAGAGGGTGTTGGATCCCCTAGAACTGGG

GTTACAGATGGCTGTGAGCAGCTATGTGGTGCCTGGGAGTTGAACCCTGG

TTCTCTGTTAGGGCAACAACTGCTTTTAACCATCAACCCATCTCTTTGGC

ACATGGGTGCATTGTTGGTTTGGCTGCTTGAGTTGTGTGTGAGGGGTGTG

TGTGCATACATATGTGGGTCCATGCTTATCCAGTGGAGGCCAGAGGTCAG

AGTCATGTATCTCTCTGTTACTTTCTACCTTATGTTTTGGAAGCAAGATT

AGATAGACCCCTGGGACCTTCCTGTCTTCTCCTCAGCACTAGGACTACAA

GTCCACACCTGACTTTTTACATGGGGCTTCAGATCTAACTCAGTCCCAAC

ACTTGTTTCATTTCCTTAGCACCTTGGCTAGATTCTTAGGATTTTAGAAG

GAGCTTATAGCAAAATACCACAAGTGAAATTTACTACTGCCTTAGTCATA

AGCAAATATTGAAGGCTCAGTCTTTAAGGGTATAATTGATAGTGTTCTTT

TTTTTTTTTAAGTAAACAAATAGCCTGTCATGGTAACTATCGCTGTAGTCC

CATTACTTGTGAGAGATGTCAGCTCAAGGCCAGCCTCCGCTACATAAGTA

AGGGAAGACCAGCCTGAGCTATATGGGACTCTATCAAAACAAATAAACAT

TGTAGAATTTTTGTAATACTTATTAGAAGGTAGCTGATGATCATGAGAGT

CTTTAGACATTTCTTCATTCCACTGTTTTGTGTGTGTGTGTTTCATGACA

GATTTCTTACTAGATTTATCTCTTTGTGTGTGTGTGTGTGTGTGTGTGTT

TTACAAAATGACAAAGATTTTAGTCCTTCTCGTGGAAAGTAGTTGCTAGT

GGTCAGCAGATACTTGCTAGTATAAATAAATGAGCATAGATCTGCGCTTG

CAAAGGAAGACAAAGGGAAAAAAGGTTTTCTTGAACATAATTCCTACTTT

FIG.3D(48)

```
GTGAAAGAAACTTCTCATTTGGAAATTACATTTTGAAAATAGGTATTGTG

AATGTTTCCATTGTGGTTTGTGGTATAACTATCAAATAACACTTTTTTAA

AAAGAAAAATCTTAATTTTCTAAGATTTTTAAATACCCTTTTAAAATGAG

CATTTCCAGCATGGTTTGATTAATTTGTAAAATGTAAGAATATAGTATCT

AAGGCTACAGAAATGACTCAGTGGTTAAGAGCACTGGCTGCTTTACAGAG

GACCCAGGTTCCATCCCCAGCACCCTCATGACAGTTCACAGCCATCTGTA

TTTCTAGTTCCAGGGCATCTGATGCCCTTCTCTGATTTTCTCCAGTACTA

GTGACACACAGCATACATTTGAACAAAACCACTGATACACATAAAATAAA

TTGTTTTCAAGAAACAATATAGCATCTAATTAGCTTACAAAACTAATTAT

TTGTTTCTGTACTAATTACGTTTCTATTGGCATGACTAAGGCAACTTATA

AGAGAAAGCATTTAATTTGGGGTTCACACTTCTAGTGCCTTAGATTCTAT

GAGCATCATGGTAGGGAGTGTGGCAGTAGGCAGGCAGGCATGGTGCTGGA

GCAGAGGCTGAGAGCTCACATTTGATTTTCTACTAGAAGACACAGAGAGA

GCTAACTGGAAAAGGCATGGGCTTTTCAAACCTCAAAGCCCCCCTCTAGG

AACACACACCTCCACCAAGGCCATACCTCCTAATCAAACAGTCCTACCAA

CTGAGGACTAACCATTCAGAGATAGATGAGTCTATGGAGGCCATTGTCAT

CCAAACCACCACAGGCCCCAAGAAAGATTTGTTAGTGAAATTTCAGTGAA

AACTAAAACAGCATTAGAATTTACCTGGCATAGCCAGCAATGATCTCTTC

TGTTCAGTGCCACAGATTTCTTTGAGTTAAAACTCAGTTGTTAAAACCAA

AAATCAAAATGTAATTGGCACTTTAAATTGCTATAAGGGGAAACAAGGTT

TTCAAAGCCATGAAACCATATTCAGAATAATTTTAGCGAGAGAAATATTT
```

FIG.3D(49)

```
TTTCTTTTTTTTGTCGTTTCTTTTTTTTCTTGGAGAGAAATATTTTTATT

ATTTTATATTATTTTAATTACATATTTAATTATTAACCATTTCTGACAGA

GGGCAAAAGGTGAGGATCTTCATGGAACTAATATCTGATAAAGCACCAAA

TTCTTCCCAACTCTGGGATGCAAATGACAGTTCAACTTCAGTTTATTGCT

TGTATTGAAGAAAATTGACAAGAAATGTCATGTCTTAACATAAGCATGGA

TTTCTTTTAAGATGTAGAATAGTCTATAATTAATGTTTTTGAGACTAGTA

AGACCTGATTATTGTTGTATCTTAAAATCTAGAAGGTACTAACAATTTTC

TAATGTGTATTTTTTTTTTTCATCAGCAAAACAGGGATTTGGACATGTTCA

TCAATGCCTCCAAAAACTTCAACCTCAACATCACCTGGGCCACCAGCTTC

CCAGGTACAGACACACCTAGAGAGATGGATTGGCAAGTTTAGTGTAGGAG

TTGGGGAAGGAGGCTCTGAAGGCTGGTGAGTGAGTTCAGAGCCCACCTCT

GCCTCTTAGTAGCCATGGCACCTTGAACAAGCCATGCTTGAACAAGCATG

TACAATTCCCTCTCTACCTTAGGCTACTCAGAGTGAGGAGTCACAGCTCT

TGCCTCCAGCGTTGCTGGTTCAGGTTGGTTGGATGGCTGCTCCCTGCTTT

GCCACCACCTTCCAGCACTATGACTATCTCTATGTTTGTGCTTCACAGGG

GAAAAACTAAAGTGACTCATAGTTTTAAGAAATGAAAACTCTTTAAGGGA

AGGGGGATAACTCTAATATGTAGAGGTATTCATACTTTGGGATAACTCCT

AAAAGTACAGCTTTTCCATTCTTGTTTATCTTATAGTGACTATAAAATTC

TGATGGCCCTAATGTAGCAGTTACTATAAATAACCACTCCATAACTTGAT

AGCCCTGAAGATAGACCTAGGTTTGAATTTACCTGCACGGTGTTGAACAA

GTTACTGAAGCTTTCTTTTCTTTGTTTTTTAAGTTTGTTTTATTTTATGT
```

FIG.3D(50)

```
GTGTGTTTGCCTTTGCCTGTATGTGTATAAGTGTACCATGTATGTGCAGT

GCTTGAGAAGGTCAGAAGAGGACATCAGCTCCCCACCCTCAACGAGTTAC

AGACAATTATGAACTACTATATCTGTGCTGGCAACAGAACCCAGGTCTTC

TGAAAGAGCAACCAGTGCTCTTAACTGCTGAGCCATCTCTCTCTAGCCCC

CAAGTTACCTAAACTTTCTGATCCAGTTTCCTTCTTTATAAAATGATACA

GTGAAAATAGCTTTGCTATGTACAGAGATATTCCAACTTTTTAATATTAC

AACATGACATCTACAAATATGTTAGCCCTCATTCATAATCTTGCCTGAAT

TGTAGAGTGTTGCAAGGAATAAATGAAATAAAGGAGGTACTTATTATAGA

GTTTGAGGTTTGCCTTCATGCATAAAGAGAAGCTTTTTTGAGTCTGTACT

ACTCATGTTCTTAGCCAATGGAGTATATAAAATATGGTAGAACCATTTAG

AAATGGAGTCTCACTGGGTACAGGCCTGAATGCAGTGGTAGCAGGTAGCA

GAAAGAAGGCCTGAGTGGCTGCTTGAGCACCTTCTCCATCAAGACTTGAG

GACCTTTCTGCTTAGGAAGTGATGAGCGAGTAAGTGTCCCTGAACAGGAG

CCTTGAGCATATTCTACAGTGTGAAGCAGAAATACAAAGGAGTTGAGGTA

TCATGTGCAAAATGAATGCAGTGTCTGTTTTATATGTATGATTGTTTTAC

ATACATGTATGTCTGTGCATCGCTTATATATCTGGAGCCTCTGAGACAGA

TTACTTAATCTATTGGGACTTGAGTTTTTCCAATCTGTAGATGGAGATAG

GAAGGTGTTGTGTGGGTTAGAGACTGAAGCTCATAAGGCTATATTCTTTT

GACACTGTAAGTGCTCAATAAACTTTTACCCTCATTACTAGTGCGCAAAG

ATTCTTTCTGATTGGCATACCCGCCTCCCAAGTCTTTATTTTTATTCTTG

CTTCTTTCTAGCCGGAACCCAGACTGGAGAAGAGGTGCCTGTTGTTTCAA
```

FIG.3D(51)

AAACCAACATCAAGGAATACAAAGATAGCTTCTCTAATGAGAAATTTGAT

TTTCGCAACCATCCAAACATCACTTTCTTTGTTTATGTCAGTAATTTCAC

TTGGCCCATCAAAATTCAGGTAAGAACTGCTTTTTAACTTCATTCCCGTA

AAGATGGTGACATCTCTTTAGTGGAGACTAACTTCACTCATTTGGAATCT

GTGGTGACTGAAAGATAGTGTTGCTTTGCCTTTGAGGGATCTTTGCCATA

GACTGAGTAGCAGGTGAGTGCTGTTCTTAGGTTGGAGAGATGTTCAGTGA

GTGGAGTGCTTGCTACACAAGCCTGAGGACATGCAGTTCATCTGCAGCCT

CTCATACAAAGCGGGACACGCAGGGTGTGCCTGTCACCTCAGCACTGGAC

ATGCAGTGTGTGCCTGTCACCCCAGCACAGGACACGCAGGGTGTGCCTGT

CACCTCAGCACTGGACATGCAGTGTGTGCCTGTCACCCCAGCACAGGACA

CGCAGTGTGTGCCTGTCACCCCAGCACTGGACACGCAGTGTGTGCCTGTC

ACCCCAGCACTGGGAAGCAGGGGACAGAAAGATCTTGCTTGCTGGCCAGC

CACTCAAAGCTGGATCTGTGAGTTCTAGATTCAGTTAGAGACCCTGTCTC

AAGTAAAATAAGGTAGAGAGGAATTGAGGAAGACACCTGATTACCTCTGG

CTTCTGTATGCATGTGCACATATATATACCTTCACACATATACACACTCA

GAGAAAAAATTCTGAGAGTGTCATATCACTTGTGAAGAAAGTTTTAAAGC

ACTTTTAAAAGCAAGATGAAAGCTATGCAAGGTATGCAAGGTAGTATACT

TTTGTAATCCCAGGATGTGGAAGACCAATGCAGGAGGATCACCCTGAGTT

TGAGGCCATAGGAAGACCCTGCCTCAAAAGGAGGGAAGGAGGGAGGGAGG

GAGAGAGAGAAAGAGAAAGAGAAAGAGAGAGAGAAAGAGAAAGAGAAAAA

GAAAGAAAGAAAGAAAGAAGGAAGGAAGGAGAAAGAAAATCAAATTGATT

FIG.3D(52)

```
GGCATATAGTTATGTGTTTATTTTTTGAGTAATTGCTATGTAAAAGCCTT

TAGAAATACACAGTTTTAATTATGGAATTGAGTATAAATAAAACAAGTAC

ATGTTTGTAACCAATAAAGTATAAAAATGACACATAAGATGTCAAAGTGG

TATGATGGCTATAATGTGGAGTCCATAGAGGAAGCAGTAGGCAGTATGAG

GTACTGTGTAAAAACACATAGCTTTACTATTGCACAGACAAGTGTGGATT

CTTGTTCTGTGTGTGGTTCATGGAGGCTCTCCAGTTTGCAGATTCTCTGT

GCATGTGTCCTGAAGGATTGGTCTTCCTGCTATGACCTCTGGTGTTATTA

GCCTGAACTGAGTCCTAAGGAGACAGGTAGTGGAAATGTTTGTATTGCAA

AGACAGTATGGGTAGTTGTTTTTAGAAACAGGAGTTCAACAGAATTGATA

GAACTTGTGATCAAGAAGCTAACAGCTGGACTGGGATGTAGCTCAGTTGA

AAGAACGCTTGTCTAACATTAAGAAGCCCTGGGTACCATCACTACCACAG

CATAAACTGAGAGTAGTGACAGACTCATGTGTCCCAGCACTGGGAAGGTA

GAGGTAGGAGGATCAGAGGCTGCCCAGGGAGGTTGAGAGTGACTTACGCT

AGGAGATAGATCTAAAAATGAAAAGGAAAAAGAACTTGGTAGCTGCTAGA

GCTACCATGAAGAGAGTGGAGCTTAAGGATTCAGCTGAAGAATGTAAACT

GCCTTCTGATGACAACTGAGAGTCGCTGAGTTATTTAAAGTCAGGAAGTG

AACAAAGATCAGTGTTTCAGAAAGACCTCTGTGGCAACAGTATTGACTAG

AAGTAGCCCCTCCTATGTCAGGTACTGGTTTAGACTGTATTTGGAAGTGT

CCTCTTTCTTGATGGCCCTCAGACACCTTTCATGGCCACTCCTCTGCATT

TGTACCCCATAGCCACACACTTGATGGTTCTTTATTACATAAATAGCTCC

TTATAGGCAATGATAGATTTTATATTTTTGATAATTTTAAGATAAACTCT
```

FIG.3D(53)

```
ATGTCATTGCATAGAATTTAGTAGTTGTAGGTACTCAGTAAATGTATATA

GGATGAATACAAAAGCTTTAGGGTAACAGTATTTTGTTCTTCTTCCCCCG

CATTTTTAACTATCTCATAGTAGCACAGACTAACCCATAACTGACCATGA

AGCCAAGGATGACCTTGAACTCCTGTACCTTCTACCTCTTCCCCGAAAGT

GCTGAAGTTACTGGCATGTGCTGCTCACCCAACTAATAGCAAGTTTTTCT

TATAAAGGTGCTGATGCCCTTTCCCTGTTTGTGTTAATTGCTGACACTTA

AAAGCTCTTTATCCCAACCCACAGTGTTAAAGAGTTTAGTTAAATTTTGT

GGAAATTTTGTCCCAAATGAAGTGGTTGATGGCAGGCCTGGTGGCTCCTT

CCTATAATTCCAACACTCAGGAGACAGAGTCAGGACGATGGCCAAGAATT

CAAGGCCTTGGGCCTACAGAGTAGAAGAGAGAAGAATGAGGATTCGAACA

CCTGATTAAATAGATACCATTTCCTGCTACCAACCTGTGCCTTAGCTACT

CTTCTATTGCCGTGACAAAACATCATACCCAAGGCAGCTTATAAAAGAAA

GCATTTATTAGGACTCACAGTTTCAAGGGTTATACTCCAAAACCATCATG

GCCGGGAGCAGGCAGCAGGCAGGAACATCTGCTGTGAGGAAGAGCTGAGA

GCTCACTTCTTTATCCACAAATAGGAGGCAGAGAGAAAGCTAACTAGGAA

TAGAATGAGCTTTGCAGACCTCAAAGCCCACCTCCTTCCCAAACATTTCC

ACCAATTGGGAACTAAGTATTCTAATCTGTGAGCCTCTGGAGGCCCATTC

TTATTTAAACTACCACACTTTATAAGTTAATACTACATGTGATGAGGAAA

CTGGTATGGGAATTCTGAAAAGTAGTTCACAGGAGTGGGAGGGGCTGAAC

GTGAGTAGATGCTAGCATGTGTGTCAGGAGTGAAGTGTTCAGAGCATTGC

CTGGTTTGACTTCTCTCCAGAGCTGAGGTGAACATGCTTTGTGCCAATAC
```

FIG.3D(54)

```
AAACCCGTATTAAAGCGGTGGTAGTTACTGAAAATCAGTGCAGGGCTGTG

GTCTCAACACAATGTTTGAAAAAGAAAACAGGGCATCCACATCAGGCAGT

GTACAGCTGCTTATAATTCCAGTCCTCTGGCCTCTGCTCACATGCACATA

CCCCCCCATACATACACACATGATTAAACATAATGAAAAATTAAAAATTA

ATGCTATAAAAATGGAAAGAGCCGGGCGTGGTGGTGCATGCCTTTAATCC

CAGCACTTGGGAGGCAGAGGCAGGCGGATTTCTGAGTTCGAGGCCAGCCT

GATCTACAGAGTGAGTTCCAGTACAGCTAGGGCTACACAGAGAAACCCTG

TCTCGAAAAACAAAAACAAAAACAAAAACAAAAAAAAAAGTGGAAAGAAA

GGTTCACTGTTTCACAGGAAAACTCTGAGAGGTGATAATCCAATCCCAGT

TTAAAATATACTCCATAGTGCACACAGCCTCTCCCATCCTTGGCAACTGA

GGCCTGTGAGAAGACTCAGTCCTCTCCTGGCTTCCAACCTTACAGTGTTC

AAAACTCTTCTGCAAGATCCACATGGTCCTACCAAGACCCTGAAGGTCAG

GCATGCTGATTAGGCTGTCTCTGGGCCTGAAGTGAAAGGTAAACACTTCC

GAGATCTCCAAAGCCTTGGGAAGATTCTGAAATGTATGGGTGTTGGTTCA

GGTAGACTCTCAGCCTTGGTGAAGCTGCCCCCGGAGCTGTAGGGTTATCT

GCAGAAAGTCAGCCAGGTGCACTTACCCTGGAATCCTCTCCCATTCACAG

ACACCTCCCTGAGGCTTTGTGGCTTCACCTCACTGTGCAGCTAGCTCCTG

TTTTACATGCTTATATAATGAATGGTCTTGGTAAAGAAGATGATAAAGGC

AAGCTAGAGGCCTTTTTTTTTCCCCTCTTCAAATTTTGATTGGCCTTTCCC

TACTGTTACACTGTCTACTCAAGGTTTTGAGCATTTACTTTGTGTACATA

GTAAAAGCAAAGTACATATTTTTTAAGTAGAAAAGAAAGCATCTGTGGTCT
```

FIG.3D(55)

```
TTGATATAGGTGCTTTTCTTTATTTTAATAGTAATACTTATTCCATGCTT

GTTAAGAAATTCATTCACAGCGTGTTTTCATAGAGACTTTCTCTATAGAG

ATATATAGAAATCTAGACATGAGGACAGCCCACTAACCCACTCTTCAGAC

ACTAGCTGCTTCTCTTAGAGCCCTGGGCTCTCACCCTTTGGAGGACAGCC

ATCCTCACTCATATGTGACAAGCTTAGACACAGAATAATCACAGAGACTC

CAGCCTCCCCCACAAACCCACAATGCCAATATCCCATATTCCCAGGAACT

TTTAATAAGCCATCCACTCTAATACTCCATCTCTTATCTCAGGCATAGGC

CCTGGTTTTGGTTTGCTTCAGAGTACTGCCTTTTCTCTACCACGCCCTTC

CCACTCTTTGCTGACCCTCCAGAGATGTCATTTCCAAATGAAGGGGGTTT

TTGGTTCTGTGGGTGTTTTGTTTTTCAGTGCAGTTCCTTAACTGCTATTC

AGGGGACGGAGCAGGCAAACCAGATCTCTAACTTCTGAGGCCTGTGAAGA

GAAGCATCAGAACCTCCCAGGGGAGCTGTAGGAGCAGGAGTCAGGCCTAG

ATATGACTGTGAGAGAGTGGGGACCATTACCAGTGTCTTACAAATGAGGG

GAAGGACTACCGTGCTGGGCCCTGAAAGATAAGGAGGACCAGGCTTCAGG

AAGGTAGGACACATTCTGCTGACTGTCTGGGATTGAGGACAGTAACACAA

CTACTTAGACATACTTTGAATGAAGGACAGACTTAGTGCTTCAGAACTGT

AAATCCATTATATCTTTCCCAAGTCTTAGGCTAGCCAAGTTTCTCAACAT

TTATCTACCTCATCCCAAAGGGTTCCCAGGACAAATATTTCTTACTCAAA

CATTTGATGGGAGTTGGAATCAGGTTGAGGAAATGCAGGGGTGTAGATTT

TAGATTTCTGGGAATATGTATAGATAGCTACCTTCTGTTGGATAGAAAAT

GAGATTGTAAGTTTTTCAGTGTTTTTTTACACGAGTTTGTGTGCCCATGT
```

FIG.3D(56)

ATGCACATGTGGAGGCCACGGGTCTACCTTAGGTGTCTTCTTCAGGAACC

AGCCATCTTATTTTTAAGATGATCTCTCTCCAGACCTCAGGGCTATCAAC

ACACCTCAGGGATCCATCCTCCTGACTGTATGTCCCTAGCATTTGGGTTA

CTGTACCACCATGCTCAGGTCTTTGTGTAGGTCCTGGGGATCACAGTTAG

GTTCTCATACTGCAGGGCAAGCACTTTGTAAACAACTATCTCCCCTGCAT

ATGGAAGTATTACCACTAAATTACAACAAGATTTTCTTCTATTAAAATTA

TATTTTAGAAGCTGGATATAGTAATGCGTTGGGGCAAAAGGAGGGAGGGA

AATGAAGAGGATAGGAAGAGGGGGAGGGAGAAGGGAAAGAGTGGAGGCGG

GATCAGAAGTCCAATGTTATTCAAGGGCAGCCTGACCTAGATAAATCCCT

ATTAAAAAGTTTTCAGTATAGAAACTTCTCATCACCTTCATTATCAGAAA

AGCCCCTAAATTCAGAACACTTTTTAATCTTAATTAGTTGACAATTTCAT

AAATGTATTATTTATATATATGAATAACATTTTCCTCCTACCTTTTTTTC

CCTTCCCCTCTGATGATTCCCATCCTCCCAACCAAGCCCCCCTTCTGCAT

TTGTTTGTTGCTTTAATGACCCACTGAGTTCCATTGGGCTCACTTCCATG

AGTGTGACTAGAAGAGCTATTTATCAGAATGTGGGCAACTTACCAGTAGT

GACACTGATGAAGAAAGTGTTTCCCTCTTACCCAGTAACCATTAATGGCC

AGGAGCTCCTGGGAGGGGTGGGCGCCTTATGAGCCCCTTCTCCAAAATGC

TTTCAAACTGTGACCAGCTATATTTAATGTTTTTATTATGCCTGTGTATC

CATGTGGGACAAGAAAGCTTGAGAGTATCATAGCATGCATGTGGAGGTCA

AAGAACAACTGTGTAAAGTCAGATCTCACTTCCCACCTTCACATGGGCTC

TGGCACTGAACTCATGTCAGTGACCTGAGAGGCACTTTATCCTCTAACAC

FIG.3D(57)

GCACCCTGTGCCCAGCCTAAAATTTGACCTTTGCAAGGTTTAGTGTGTGT

TATCTGACTGTCTGAGTAAGGATGACAAAATGAAACCAAACTTATGGGAT

AAAGCTTGGTGGTTGTATCAGTACATTTTTATTGTTGTGATAAAACATTA

TGACCAAGACAGCTTATAGAAGAGTTTATTTGGGTGTATAGTTCCAGAGA

GGTAAGAGTCTGTCCTGACAAGGAAGCTGTGGCAGCAAGTGGCAGGTATG

GCTACAGGAGCAGGAAGCAGAAAGAGCAAACTAGAAACAGTTGAGGTTTT

TTAATAGGAAAGCCCACTCCCCTAATGATGTCCTTCCCCTAGCAGACCAC

AAGTCCTAACCCTCCCTACACAGCACCACCAGCTGGGGAGTTCAAATGTC

TGGGACTGCAGGGGACATCTCATTCAGACCACCTCAGTGGGAGAATGCTT

GCCTTCATAGTATGTGCAAGGCCCTAGGTTCAATTCTAGCCAAGAAAAGA

GAACATGAGGAAAGAAAAGAAGGTGGGAGAGAGTAGAGAAAGAAGAGAAG

AAGAGGAAAAAGGAAGGGAAGGGGGAGACAGAGGAAAGCAGGGAAGCAGA

GGAGAGGAGAAGAGAAAGAAAAGATTAACCAGCCTGGTTTTTAATAGCAC

CCCTCCCACTCTCAGTAGTTCCCAATTTGAGCATTAAGTTCAAGACTGAT

AGATATTTCTGGGTGGGTGACCAGTGTGGTCATAAACATGGTGACTTTTG

CTCTCCGTACAACTTGTGATTATGAACTTGTTAGATGATCAGCTTCAACA

GGAGAGGGCCTCCTTTAGTCTCAGGTGCCCCCTCCAGCCACCCTGGGACT

CGCAGCCTCTCTGTGATGAGACACAGGACATTAACTGGTATGGTTCTGCT

TTGCCAAAACGTCAGTCCATGGTTGAACTCTCCACAATGAGAAAGAAGCT

TTGAGAATCATTACATGGCATCAGGCAAGCCAGGACTGATGGAGCCTGAG

AAAGGGCCAGGAGCATCCGCAGGTTTTGGCACCCAGTACTAACTAGTAAA

FIG.3D(58)

```
AGCACCTCATAGGTTTCTTTAAAATGCAAACACTAAGGAAAATCTAACTT

TTTTTTATTTATTAAGGCCATTCATTTTATTTTATAAGTATTTTGCCTGT

ATACATATGTACCACATGCATACAAGGTCAAAAGATAGTATTGGGTCTTC

GAACTGGAGGTACAGATGATTGTGAGCTGCCATGTGGATCCTCGAAATTG

AACCTAGGTCGTCTACAAGAGCAGGAAGTGCTCTTAACTTCTGAGCCATC

TCTCCAGCTCCAGAAAAGCTACTCATAAAAGTCAAATCTAAGCCATGTGT

CTGGTGATGTACACCTTTAATTGTAGCACATGGAAGGCGGAAGTAGGCGG

ATTGTTATTCATCCAAGGCCAGTCTTCTCTTAACAGTGACAAAAACAAAA

CCAAACCCGAAACCTGTTACTTTGCACTTTAGAGTATAAGTGATAGAGAA

AAGACACAGAAATTTTAGAATCTATACCTTAAAATACCTTATGGCTTATA

TGATACTGTTGGGACCATATTTACTTATGGAATGCAAAAAAAAAAAAAAA

AAAAAAAGATGGGGGGGGGAGCTGAAGGTCTCCTTTCTATTCTGTTGTAAA

TCTAGCTATAAAAAGAGTAAGAGGCATGAGTGTGTCTCAGTGGTAGAGCA

CCTGCTTAGCTTGTGTGGGATTGAATGATCCTCAGCACCACAGAAGAAGG

GTGGGGCAATAAATTTAGGAAAATAAGATGCTAATCATTGACTTTCTTGA

TTTTTTTAAAAAAAGTTATTATTTTATGTTTATTGTATATGTTTATATTT

TCTATGTGTGTTTTTGATGTGTGCTGGAGGGATGGGGGCCACTTGCTGAA

CTTCCCAATTGTTATCATAACTACCATCTTTAGTGAAACAGTTACCATCT

ACTTAGTAATTGTTTCATTCGAATAGATACTGAACACTCTTAATCTGAAA

CTAATGCTCAGAAAGTTCCACTTTGCCAAGCAAGCAGGATAATGTAAGCC

TATAATTTTAGCACTGGGAGGGTGAGGCAGAATTGTGAGCTCAAGGGCAC
```

FIG.3D(59)

CCTGAGCTTTTGAGATCCTGTCTCAAATAAAATTAAATTATATAGATATC

AGATTTTCAGAATAGGTGTGTTCAGCTGCTGAATAAATCTAAGCAAATAT

CCCCAAAGAACCCTGAAATCTGAAACGTATTAGTTCTAAGCCCTATGTTG

TGTGTGTGTGTGTGTGTGTGTGTGTGTGTGTGTGTGTGTGTGTGTGTG

TAAGATAGATTCTCACTATGTAACCCTAGCTTGCCTGGATCTTGCTATAT

AGAGAGACCAGGCATATGCTATCGTGCCTGGGAGTCCCAAACGTTTTAGA

TGAAAGATTTCAGTTGTACCATTATCTTCCTAATGAGGGCTCTGGTCTAG

TGAGGCAGGTGACATTAGGCCAGTAGTAAGTATTAGGAATTGGTGATGAC

GGTCAATTCTGAGACACACAGTAGATACATCTAATCTACCAATACAACCA

ATGATTTAGAAAGAATTAGGCCATAGTTAAATTTGCAGTGTTTTTCTTCT

CCACAAAATAATGTTACTTCTTTCAGTTCTTAGTTCAAATACAGTAGGAA

TTTTTTATATTCTTGGTGCTAAACACTATTATTTTATAGTAAAGTTAGTA

AGATAGAAATGACGCCCTGTGGGTTGTCTGGTCGTAGTCTGTAGCTGAGG

CCATTTTGCTGAGAAGCAGCGTAGGCTGTCACTGGCTTTGTCACCCATAT

TTTCTGTATTTTTGCTGCAGATTGCCTTCTCCCAGCACAGCAACTTCATG

GACCTGGTACAGTTCTTCGTGACTTTCTTCAGGTAATTTCTCTATGCTAA

TTGTACACATTCCATCGAGACAGTCCCTTAACTGCAGCTTGCTTTGTATA

TCCCTACAAAGCTGCTTTTCACTCACAGTGATGTAAATTTAGTCTGATGT

GATAAAACTCTCCGTTTGTATGATTCGGCTCTTTGCATGGGGAGAGGTTT

GGGCTCAAGCAGTTATTAATAATATAGCTACTGCTGTGAGCTACATGTCT

TAATCTGTCTTAATCAAGATATGACTGTGATTTTCCATAGGGAAAGGTAA

FIG.3D(60)

```
GGTTTACTTGCAAACTCCTGGGGTTCTCCTTTTTTTATAGTTTTCTTATT

AGTAGGGTTTTTTTTTTTTTTGAGAATACTATGCAGAAATGATTGAAAAG

AACAAATTAGTCATTGCATATTGGTAAGAGAAGCAGCAAGAGCCACCTCA

CCTCCCTCTGCTCTCCCCAAATAGAAACTGCTCTGCTGTGCTGCTTCTCT

ACCTTCACACCAATGCTCGGCCTGCCAACTCAGTTATCTTTCCTTTCCTT

TTAAGATAGGGTCTCTCCTTATAGTAGTTATGACTGTCCTGGAATTCTAA

ATAGAAGAGGTTGGCTTTCAAATCACAGATCCTCCTGCCTCTGCCTTCTG

AGTACTGGAAGTATGGTGTATGCCACCGTGCCACAGCTAACTCAGTTATT

TTTTGGTGTTCTATAACTGCCTTACATACATACAGACCAGGTACACACAA

AATTCCTTTCCATTAATTTAATAGTTATATCACAATGCATTGACCAACTA

AAAAATCCTAAATTGACTTATGATTCTACTTGCTCATGTTTTAAAGGAAA

GGTTACTCTTTGCTTATCTTAAATGTAATATTTTTCCTTTGCAGTTGCTG

TTTAAATTTTCCCTATAAGTCGACCCCAAATTTACATCTATAATCTGGCA

AAACAAAAAGACCTCTAGTGATGGTTGTCTCTTAGCTTTAGTCTCTCTTG

GACTCCATTCCCTCCACCCATAATGTTCCATCCTCTGTCCTTAAGTGTAC

TAGTCTCCAAGGCCTGCTATGTGGTTGTCATTGTTGTAGTTACTTTTCTA

TGTTGTGACAAAGCACCCTGACAGTGGCAATTTAGAAAGCATATAATTTG

AGGATCACAGTTCCTGGTTAGAATCCATGACCATCTTAGCAAAGGCAGAC

AGGCAGGCCTGGCACTGAACAAGTAGCTGAGATCGTCCATCTGGTCCACA

AGCATAAGGCAGAGAAGCTAATTGGGAATGGCATGGGCTTTGGAAACCTC

AGAGTCCACTCTTAGTGATACCTCCTTATCCTTCCAAACAGTATTACACA
```

FIG.3D(61)

```
TTCAAACTTCAAATGTGTGAGCCTCTGGGGACCACTCTCATTTAAACCAC

CACAGTGATCTTGGCAACTTCTTTTGTGTTCGTCCCATGCCACAGTCTTT

CCATGTATTTCTCCTTTTGCTGGAACTTTTTCCCTCGAAGGTTCCTGAGG

AAAGAAACATAGATAACTTTTGTATGTACTTCTACAACTGAAAGTATCTT

AATTTTTGCCCTAACAAATTTTTGTTTGCTTACTTGCTTGCTTACTTGAT

TCTGCGTGCATGCATTTATTTGTTTGTTTGTTTGTTTGTTTGTTTGAGAC

AAGATCTCTCTTTGTAGTTCTGGCTGCCTCAAACTCAGAGAGATTCATCT

GCCTCTGCCTCCAGAATGCTGGGATAAAGGCATGCTCCACCATACCTAAT

CCAACCTCACAATTTTTTAAGTGTGTATTTATATGTGTGTGTGGTATATG

TAAAGGTGTGTGTGTTCATGCACACATGTGCAGAGATCAGAGGAGTCAGG

TTTTCTCATCTATCACTCTCTGCCTTATTATTTTGAGACAGGGTCTCTTG

TTCGATATTACATATACTAGGTGAGATAGCCCAGGAGCTTGTAGGAATTC

TCTCCCATTTCTACCTTCCAAATGTGTGCTACTGCATCTGGCTTTAAGCA

AGTTCTGGGAATCTGAGGTCAGGTCCTTACACCTATGTAGCAACTCTGCC

TACTGAGTCATCTTACTAGTATTCACAAGGTCAAAGGTTGGGACCAACAG

CCAAGGTTGTCCTCAGATCTCCACACAGATGTACCCACAATTATACAAAC

ACTCAACATAAACCTATTTACACACCCACATCACACGCACACACATACAT

GCACATACAAAAAAATGCTTTTTGAAAGAAGTAGAGAATGCTAGATATGG

TATTACACGTATATAATCCAAGCCACTCTGGAAGCTGAGGCAGGAGGATT

TCAAGTTTGAAACCAGCTTGACCACATAATTATACCATGCCTCAAAAATT

GTATAGAGAATAAGAATGAATATGAATGAGACTAAAGTCATATCTCAGTT
```

FIG.3D(62)

ACTTTTCTATTGCTGTGGCAAAACACCATGACAAAGGTAATTTACAGAAG

AGATTATTGGGGCATATAGTTTCAGAGGGTGAGTCCATGACAATTATGAT

ATGGCACTGAAGTAATAGCTGAGAGCTTAAATCTGGTCCACAACATTAGG

CAGACAGAGAGCTAACTGGAAATAGCCATGAGATTTTGAAACCTCAAGCC

CCACTCCTAGTGATGTCCCACACCTCCTAATCCTTCCCAAACAGTTCCAT

CAGCTGGGAACAAGATATTCAACATATAAGCCTATGGGGGTCATTCTCAT

TCAAACCACCAGTAGTAATTATTAGAGCCCAGCAAAGAAGGAAGGGATAG

AAAGAAATGATTGATGGGAACTGGGGTGAAGTCTGATACAGAGAGATCTT

TATGTACTGCAGCGTAGCTCAGGAAGATAACTATGGTTAAGGACAATTAG

CTAAGTGATTAGTAGAGAGGATTTTAATATTTCCAATACAAAGAAATGCT

GCAGGCCTGAAATAGGGTACGTTTCAGTGACCCAGATCTGATTATTACAA

CTCATACACTTGTACCAACCACATAAATATGTACAATAATTGTGTCAGTT

TTATATTAAATAAAAATGTGGAGCAAGTTAAAAAATGCCTGTTTTAAACT

GATCACAGTTATATGCCAGCTTTTCTTTGCTGTGACAAAATACCATAGGG

AGTAGTTTATAAGGAAAGAGATTTCCTCCAGCTCATAATTCCAGAATTTT

CAGTCTAGAGTCAGTTAGTTCTATCATATTGGGCCCACAGCTAGACCAAA

TACAATGATGGGGAGAATGTGGTAAAGAAAAGTATTTACCTCAGAGTGGT

CAGGAGGAACACAAGACAAAATATACATTTCAGTCCCATACCTCCAGTGA

CTTGCTTCATCCAAACAGACGCCACCATCCAATAGCCATTAAAATACAAG

TCAACCAGTTGATTGACATCCATTGATCTTAGTCATATCCCTAAATTCAA

CCTCTAAGCTCTGATGCTCTGGGGGCCAAGCCTCTATTGCATAAATCTCT

FIG.3D(63)

```
GGAGCATATTTCATAATATGAAATATTAAACAGGTCTCTCAGGAGCTGTT

TGGTAGACTTAGTTGTTTTTTTTTTTTTTTTGTTTAAGGTTTTTTTGGTT

GGGTTTTGTTTTGTTTTGTTTTGTTTTGTTGTTTGTTGTTGTTTTT

TTCGAGACCGGGTTTCTCTGTATAGCCCTGGCGGTCCTGGAACTCACTTG

TAGACCAGGCTGGCCTCGGACTCAGAAATTTACCTGCCTCCTCCTCCCAA

GTGCTGGGATTAAAGGTGTGCGACACCACTGCCTGGCCTAGACTTATTTT

TTTAATCAGATTTGAGTCTTTGCCTCTGGAATCACAGTAGCTTTTCCCAT

TCAACACCTAGTTTACAGAAGAAAGAAAACCCAATTTTTTTTTTTATAAT

CATTAGACAACTAGAAGTTTTCCCTCCTATTAAGAAAACATATTAACGGG

CTGGCGAGATGGCTCAGTGGGTAAGAGCACCCGACTGCTCTTCCCAAGGT

CCAGAGTTCAAATCCCAGCAACCACATGGTGGCTCACAACCATCCGTAAC

GAGATCTGACTCCCTCTTCTGGAGTGTCTGAAGACAGCTACAGTGTACTT

ACATATAATCAATAAATAAATCTTTTTAAAAAAAAAAAAAAAAGAAAAAGA

AAAAGAAAACATATTAACAGTATTGAGAAAACTGTTGGCTTAAATTTGAT

GATTTGAATTTTATTTTACTAATAAATGCATGTATTGCTGGGCATGGCAG

CACATCCCAGCACTCAGGATTCCGAGATAAGAGATCATAAGTCCACGCTA

GCTGGAATAGCAAAATAAAATCTTTTTTTAAAAAATATACATACATACAT

ACATACATACATACATACATACACACACACACACTTTTCTCAGT

AGTACGGCCAATTAGTTGACTTGTCTAACGGAGGGAGGAAGAGGAGGCAG

AGAGCATGCTGTTCAGATCACGTTCTCTTTTGCATTCAGTCTGGGACCCC

AGCCCATAGTGTGGTGCTGCCCACATTGATTATTGGTATTCAGTTAACCC
```

FIG.3D(64)

AGTGTAGAAACTCTCTCAGAGACATGCCCAGATGCTTGCCTCATAACCAC

TGTGTATGTATATATGCTTACAGAAAATATACTCATCATTACACATAAAT

TTCATCCACTTACCTCTTATGAAAAGTTGATTATTTACTGAGATTTTTCT

CATTCTGAAAATCCATAAAGTCTACCACATTGATTAAATTACTTGTTTTT

TACCTGTTATTGCTCATGTTAGAATTGCTTTCCTTATTTGGGGTAAGCTG

TCGTTGGCCACTGTGAGGGGCTTATCAAGAAGTCAGAAATGGGAACACCT

TCTAGGAAGTCAGGACTGGAAGCTTAGCTGAGCCAGCAAGTGTTTCTCAC

ACTGCACTTCCTGTGAGCCTACCTGTGCGGCATCAGGAACTGGAGTTGGG

ACCTTGAGGATTGTTCCCTGGAGGCAGGGGTGGAGTCAGGCAGGGGTGAA

GCTGACTCACAAGATGGTCTTGCCTTTCAGTTGTTTCCTCTCGCTGCTTC

TGGTGGCTGCAGTGGTCTGGAAGATCAAGCAGAGCTGTTGGGCATCCAGG

CGGAGAGAGGTAAGCCCAAGTAGACAAACTCCACATAAAACTCATTTTTT

TCCTTCTTTCTAGGCAGATCACTTTTACCTGTTGAGTGATGACTAATATT

CATATGAGAAGCATGCTGTTTAACCTGCATTCTGTGGTTCCACTATGTGC

CATCAGTAGATTTTAATTATTCTTGCATAAAGTGTCATTAGTTTTGCCAC

TGCTTGATTCAAGTCTTCCTAAGAGTCTTTCCTAAGAATATGAGTGTAGA

GACAAGTTCAGCTCAGTGACAGAGCACTTGCCTGGCATAAACTGAGTCCC

TGGATTCTAGTCTCAGCACCCTCTAATAGCACAACACTAGAGACAAAGCT

TCTAACCTGTGGGTCTTGGGCAGCAGGTAGGGGAGGGGGATTTAAAAAAC

AAAAACAAACCTCTAGCTGTAGCCTGTGTCATTTGTTATGACTAAGCACT

AGAGTGGGTACTAGTAGACATGCCATGTGGACATTGAGCACCTCTCCATC

FIG.3D(65)

```
CCAGGCACTGATCCAGGTGGTTCTGCTTTATCTTCATCTCCACCCTAGGA

TATAAGGGAGGCTACGTAACTACCCATCACCACACAGATGCTGAGGTACA

GAACTGAGGGGTAACTAGTGCCTCTGCCTTCACAGCACAGGTTCCTAAAC

ACGTTTTCTACAAACACTTCATTTGTTCTAGTCTGTTCATTTAAGAATCT

CATGTTCTGACTGAATGAGCTAGACAACTCACCCTAGACTATACATTCTA

AAGAAGGGCAACAAGGCAGTTTTGTTACTGTTGAGAAGAAAACAAAGTTA

TTTCCGTATGAGTTATTGAGATAGAATAGTAGAGATTTGTCTGAATACAA

AATAGAAAGTATATAAAAGTATATAAGTGGATCATAAAGAAAGCAACAAT

CAACTGGAAAATATTTGCAGTATCATGAGAGAGAGAAAACTAGAAGATGA

ACCCCCTCAAAAAAGGATTTTTAAAATATGCTTAGACTGTATTCAGTCAG

CTAATAAACTTTTTTTACCTTTATTTGGAATTTACGAATAGCACTGAACC

TGACCATTGTAAATGCACGAGGTCAGGCATGACTTGTTCCCAGTAGGAAG

TTGTTTTTAGTTCTTGCTGTGGCCTGGGTCCTGATGGAAGTTCTTTACCC

ACCTTATCTCCTGTCCTCTTGGCAGAGGTTCTAGAATAGTGCTGTGATGG

GGTAGCAACTGTCTTCCTGTGACCCTGCACCTAGATTATTACAGAACCCA

GACTGGGTTTGCTGAGTTAATGGAAATTCTTTCTAGGTTCAGTAGAGAGA

TGTGCTGACACATACTAGGCCATCTAGTTTTTTCAGTAATGCTCAGAGACC

GCAATAGGATATGTAACAGCAACAAAATTTTTTAACATAAAATTTCCCTTC

TAAAACAGAGTGATGATTTATGTAGCTTCAGGATCCTGCCTCCTAGAAGA

TGGTTTGAAGCAAGGCCAGTTTGTCTTCCCTAGCATAACCTCAGAAGACC

TCTCATATTATTGATGGTATAGGAATGAATGCCCACATTCTGTATTTGAG
```

FIG.3D(66)

```
ATGTGTGCTATAGTATCTCATCTGACCCAACATGAAAACATTTCAAGCCA

TGTGTGCTTGGGTAAGGTAGGAGTTCAAAGTCATCCAGTGAGTTCAAGGC

CAGCCTGGGCTGCATGAGACACTGTCTCATAAACAGACACTTGAATCTCA

TTTAAAGAAGACATTGAAGACTTGATACTTTGAACACCTATCCTAACGTA

TCCACCCCCAAATCCAGAGTCCTTCATGTTCTTGTCCTCTGCAGTTCCAC

TTTCATTGTGTTCTCAGCAGCAGCTCTCTCCGAGGAGAGTTGTCTCCCAT

CCTATCAGCCATCTTTTTTATTGTTGTTGCTCTGACAATGTCTGGTTCAG

GTTTTAACACAAAGCAAGCTAGAGTGATTTTAATCTAGCAACAAAAATAT

AAAAAGGTAAGTTTTTGCCCTTTTATATATTCAATCAACAGATATCATAG

CATTATATCCTCCACTTTAACTTTTATTTCTTACTGGTAAGGGCTTTTTA

TAAAAATATAATAGTGTTACCACATGTAACAAAATTTGATACCTTGTGCT

ACCTAGCACCTTGTCATGTCCAGTTTTCCTCAGCTGTCACAGAAGCGACA

CTGCATCTGATCAGTTTGAATCAGAGAGAGTGTAGCATGTCTAATATCTA

GTATTCACTAATAAAATCTCAGTACTAAGCATATTAATAATACTATATTA

TTCATTAGCAACTTCTTCGGGAGATGCAACAGATGGCCAGCCGCCCCTTT

GCTTCTGTAAACGTTGCCTTGGAAACAGATGAAGAACCTCCTGATCTCAT

TGGGGGAAGTATAAAGGTGAGAAGTGGCTCAAAGGTCCATATAGCTTTTC

AGAACTCAGGCCTCAGTTTGCTAGGCTACAGACAGCAAGCGCTCTGTGTG

TCACTCCTGTCTCCTCTCTAACAGTTAGTCAGCAGAAGCAACCCCGAGCG

ACCGTAAGGGGCTCTGTGTGTGGCTTTACTTTTCGAGTTGTTGCATGTCA

GATTTTAACATGCAAATTAAGCTTGTTATTCTTACTTTGTGGCATAATAC
```

FIG.3D(67)

```
TTTATAGTTTTTATTTGGAAATATCTAATCTGGGCTAGGTGTGATGGTGC

ACATCTTTAATCTCAGTTCAGAGGAGGCAGAGACAGAGGCAGGCAGGATC

TCCTTGAGTTCTAGAACAGCTGGTCTACATAATGAGACCCTATATGTTAG

AAAAAAAGAAAGAGGGGGTGGGGGAAGGCAGCTAACTTTAACCATTAATT

GAACCAACACACACACATTTTGTTCAGAGCCCCAGTACTCAATTAAAAGC

CAGGCAGGCATGGTAACAGTACTTAGGGAGTCAGAAACAGGATTCCCAGA

GTAAGCAGTCTGACTAGGCTAGCAGGAAATGGTGAGTTTCAGGTTCAGCA

AGAGGCCCTGCCTCAGTAAGTAAATTGAAGAACAACTGAGGGAGACTTGC

ATGTGCACTTGTGCATGCACCCACACATGCACTTGCACACATACCATATG

TCACCATGCTTAGACTATAAAATGTAGTCACTACTGGCAGCACATGCCTA

CAATACAGATGCAGGAGAATCACTGCAAATTTGAGATCAGCCTGGGCTAC

TGGACAAGATTTTGTCTCAAGAAAACTAAAACAATACAAAAGTGTACTGG

GGGGGTTATTCTAATGCCAGTGTTTATGACAGCACATTCAGAACTGACAG

TAAAGGCAATCAAGGACTGTCAGTGGTGGGTATATACATAGGCAGAGGAG

CAACTGCTACTAGAAACTGTTTATCCTTTAAAAGACTAATGTATGCTGCA

GCATAGACAAACGTTAAGTTGTGTTAAGTAAAAGATGCTGTATCATTCCA

CTTACCCATCGAGAATAATCAAATACAAGACAGAGTAAAATAGTGACTGC

TAGAGGCTTAAAAGAAAAGACCAGGGGGTGGGGAAAGGGAGGGAAGGAAG

TGGGAGAGGGAGGAAGGGAGAGAGGGAGGGAGGGAGCCAGACTTTGTGGC

TTACAGCATCAAGAGGCTGAGGCAGAAGGGTTACAAATTCAAGGCCCTAC

TGGGCTACATAGTGAGAAGTAGGATTTCCTTGAGCTGTCTTTCTAGGTCA
```

FIG.3D(68)

```
TAATCTCTCATTGGGGGAAGTCAGGGCAGGGACTTGAGGCAGAAACCATG

GGGAATGCTATTTGCTGGCTCCTTCCCAGGCTCCTCTCTAGCTTTGTTTT

CTCATTTTGTTTTTACTGTCTATGGGTGTTTTACCTGCTTGTTTTTCTGT

GTACCATATACATGCCTGCTACCCACAGAGGCACTGATGCCTGGAACTGG

AGTTACAGATGGTTGCAGGCTGCCCTGTGAGTGCTGGGAACTAAACTCGG

GTCCTCTACATGAGCAAGTGTTCTTAACCATTGAGCCATCTCTCCAGCCT

ATAAAATTCTTTTTTAAAAATAAAGTCTGCAACAGAAAATGAATATTTTC

TAGAGCTGAAGCATTCAATGAGTGGATAAAGAATCCATTTGATGAGCTAT

CTACCTTTCACAAGCTCTTAACCCCTACAGACTCAGGACTTAGTGGCTGG

AAGATGAATGTAAAACAGGTAGCTCTCTCCATAATATCTGGTCTGTTTGT

GCCAGGTGTGCAGAACTGTGCAACAGGTCACCATACAAACCGGCGTGGGC

CTTTCCTGACACTCACACAGCTCTCGGGACAGTGCCCGTGGGGACCTCTT

ATTGACCTTATAAGCACCTGACTGTGCAGTGTAGCAGGGAGTTAAGGTGC

TTCTGTTTTCTTCCTCCAGACCGTTCCTAAGCCCATTGCCCTGGAGCCCT

GCTTTGGTAACAAAGCCGCAGTCCTCTCTGTATTCGTGAGGCTCCCTCGA

GGACTGGGAGGAATCCCTCCTCCTGGTCAGTCAGGTGAGTAGACAGGAGA

CAATGACAGATATTGGTCTGTGAAGGACTGAGTCTTAGACACTTCTTCTG

GTATAGAACCTGGGTCTGGGCACAGTGCTTAGTGGTACAGAGCTTTGGTG

GAACAATTCTATAGTCCCCAAACTGTGTTCTGAGCACTGACATTCCTGTC

CTGGGGTGGAAGTTCAGGACCTTCCTCACGGTGCACAGCGTCCTCAGACA

TTCATGCTCTGGTCCCCTTGACTCTATTGATCCCTGCTTTCTTTTTTTTT
```

FIG.3D(69)

TTAACCCCTTGTTCTTATCTCAAATTTAGGCTTTTTCTTCCTTGATACAA

GCTCCTATTCATCTCCATGCCTCTGGCTTCCAGCCATGTCCTCAAAGCTT

GTGTTGCCAAGTACAGAGTTCTAGTCATGCTCCACATCTTCTTAAGGTCT

TGCTATGCAGCCTTAGCTGGACGAGTGCTCGTTATAGGCCAGGCAGTGGT

GGTACACGCCTTATGTCCTAGCACTGAGGAGGCAGAGGCAGGCAGATCTC

TGAGTTCAAGACCACCCTGGTCTACAGAGTAAATTCCAGGACAACCAGAG

CTACATAGGGAAACCCTGTCTCAAAAAAATAAAAACAACAACAGGAACAA

CCCCAAAAACTCATTATATTGCCCAGGCTGGCTTCAAACTCATAGTTATC

CTCCTACTTCAGCCTCCAAAGTGCTGGGATTATGGGTGTGACCCTTCATG

CCCAGATTGTCTTAAATATGAGGCATGAAGAAGTATTATGAAAACATAAA

GGATATTTTGAAAATTATAATTCTACTGGGTTAATGCAGATCCATTTTCA

TTTCATTGAAATAATGATACAGCCTTTGGAGGTTAGGGGAGCCTCTCCTG

TTTTCAAACTGACTTTGAACTTCTGATCATCCCGCCACCACCGCCACCTC

CTCCTCCTCCTCCTCCTCCCCAGTGCTGAGATACATCACTACTCCTGGTT

TATGTGGCACAGAGGCTCAAACCCAGGGCCTCATGCATGCTAGGCAGACA

CTCTACCAGCCAACCTACCCACAGCTCCTAGATGTGCACCGTATTACAAA

CATTTATTCTTCAGCATGTTTTTTTTTTTTTTCCTAAAAATCATCTCTA

CAGGAAACAAGTACCAGTGGTGTTTTAGGGCAGGAATAGGAAGAAAATAT

TTTTACTATATACTCTTTTTTTTTAATCATTTTTTAGATTTTATTTATTT

TAAAATTTATTTACTATTATTAATAAGTACACTGTAGCTGTCTTCAGACA

ACCCAGCAGAGGGCATCAGATCTCATTACGGATGGTTGTGAGCCACCACG

FIG.3D(70)

```
TAGTTGCTGGGATTTGAACTCAGGACCTTTGGAAGAGCAGTCAGTGCTCT

TAACTGGTGAGCCATCTCTCCAGCCCCTACTATATACTCTTTTAAATGAC

TTATTTGCTTTTATTTTTATGTGCATTGGTAATCTGCCTGCATGTATGTC

TCTGAGAGAGGATCAGATTCCTTGGAATTTGAGTTACCTTGTGGGTGCTG

GGAATTGAACCCAGGTCCTCTGGAAGAACAGCCAGTGCTCATAACTGCTG

AGCCGTCTCTGCAGCCCCTACTATATACTTTTTTTATAGTTTTGAATTTT

TTTTTCTTTTTGGGTATTGCTAAGGATCAAATATAGATCTACTATTTATT

TTTTATAACATCCATTAGTATTTTTATAACTTACTACATAGTTTGCCAAT

TCTTTTATACATGTCCATCAAACATGTAAGTCATAATTTATATAAACCTT

GTGTTAAAGCTGGAGGCACAGAAGGAAGATTGCTACAGAGTGAAGTCTAG

ACTAGCCAGGGCTATATAGTGGGACCCTGTTGCAAAGAAAAAGTTCTCTC

TTTAAACACAAAGGCAGTATGAAAAGACATACCTTGATTCTGAAGCTGTG

CATAGGAATGCCTCACACAGTGTTCTGCTCAGGACTATACTCAGATGCAG

TGGTCTGAGGGACTTGGTGGTGTCTCAGCCAAAATAACCTGGAGTTTAGT

AGGAAAGTCTCCTTTATCCGTGTCCAGTCCTGAAGGGAAGCCTTATTTAT

GTATGATGAGTCAGGACCCATTGTCTTCATCTTACTTGGCATCCCCCCAG

CACTGAGTCTCTGAGTTAGCCTTACTTGGACAGAGTGACTCTCTGGGCAC

TCTGGACAGCATCTCCTGCTTCAAAAGGGCAAGATCTTTAGAAGACACAG

AGATGGAGCAGGTCTTACATGGAGATATAGCAGCTTTTCCTTCCTGACCC

TTGACCCAATGCTTCTTTGGAAATCCTCATGAAACCCTGCTCCTTTCTGG

AGACCCACCCCACAGCAGGGTTATCCATGCCAAGCTTCCTGTACTTTCTC
```

FIG.3D(71)

```
TTTTTGAGGAAGCACATACACACAAAGTTTTAGTAGCTCGCACATCTCAC

TGTGAAGTAGTGATACTTTCATTGCTATCTTCTGGAAACAGGCAGGAGTA

GGCACACGCTCAGAGCATAGCTGCACTCTCATTCACTTGCCACCCTGAGG

CAGAGCACACGACTTTGTGATCTGCTATGGAGGAGAGAGAAATGAGTAGT

TAGGTGTGTATAAATAAGCTAACACCATCACCCCTTTATCTTTCACTAGG

GAAATGTAAAAAGAAATCTGAAATTATTTTGTAAAAAAGTAAGCTGCTTC

ATGACACATGTCCCCTCTTGTGGGTTCTTCCAAGGTCTCGCTGTGGCCAG

TGCCCTGGTGGACATTTCTCAGCAGATGCCAATAGTGTACAAGGAGAAGT

CAGGAGCTGTAAGAAACCGGAAGCAGCAGCCGCCTGCACAGCCTGGAACC

TGCATTTGATACTGGGGCAGGAATTCGCCCTCACAGAGGGCGTGTGGTCC

ACGAAGCTGTCTACAGGGGAGGCTGCAGGCAGGAAGCAGGCGTGGGGCAG

AAGACTGGGGACCCTTGAAGCGTCCAACTCATGTGCATGATCATGCAAGC

TGTTTTCATGGCTCACCCCTCTGTGTCCAGCATCTAACCTTTTACTTCTG

TGTAGGAAATAATTTAATTACAAGTCCAGGAATGGTCTGCTCTACTCATG

GGTGGAGGAGACCAGTGCCGACCCCGTGAGAGCTGAAGGTGATGCTGAGG

TCCCTTGTGGAAGCCTCTCTTGGGAATCTCAACTGCAGAGGAGCTGCCCT

CTGTCAGCAGCTCTCCAGCATGGTCCTCTGACACTCCTCAGATGAACTGT

TCTCATCGGAAGCTTGCTGTCTTTTTACAAGATGAGCTTTTACTCTCTTC

CAGGAAGTAGCTTTTTTTTCTAGCTGAGAATTAATAATGGTCTTTCTCTTT

GGAAGTCATATCAAAGTATAATTGATGGGGGCCTTGTTTTGTTTTGTTTT

GGTTTTTGGAGACAGGGTCTCACTGTGTAGTCCTAGCTGGCCTGGAACTC
```

FIG.3D(72)

ACTATGTAGATCAGGCTGGACTGAACTCACAAAGATCCACCTGCCTCTGC

CTCACAAATGCTGGGATAAAAAGCATGAACCACCAGGCCCAGCAAAGAGG

GCTATTCTAAATGTCAAGGTCAATGGAGTTAGAATATATATAAAAAAATG

CAATTGATAATTCTCTATAGAAACTTGATTAATTTTAATCCATTCTTTCC

TTCTCTTTCTCTCACTCTGTCTTACACACATGCACACATACACACACACT

AAGTGCCTAGACTTTGAATAGATCTAGCAATTGGACATTAGTAAGCCTAA

GTTTTTACATGATTGCATTCCTACATTCTTGTAAACTTTAAGTAACTACC

ATTGCAGTTTGTTCTTTTTTTAAAGTCTAATTTGCAGCCAAGAACGAGTA

ATTCTCACCCCAAGCAACATCTAATAGGGACTGAGTGACCCCAGCCCAGC

CTAGTGTCACTTTAGGCCTGACGTTTGAGCAACCCTCGGCTCTTGCCAAG

GCACCACAGAATGCACTTGCTCATGCCCTGTGCCTCTTGAGCAGAAAAGA

GCACTGACAACTGGGACACCTGGCTCTGTCTTCCTACAGCTGCTCGCACT

GACCTGTGGGAACCTGTGGGTCATCCCCAGGCTGAATGGAGTACACACTA

GAAGAGGGATGATGCCTAGCATTGGGGCAGCATCTGCTCAGCACATGGAA

AGGGACCTGGTTCCATCTCCCCTGGGCAGGAGTTGGTCCAGCCTCCTCCC

AGACCCAGCTGGTGGCTGTGAGGAGGTGGGGAATGCTAATGAGAATGAAA

AGCACATGGGTTGATGGGAAGGGACAAGATTACCACGTTAGGAGGGTGAG

CAGCCCTCTGCTATGTGCCCAGGACCCTGCCTGGACATTGCATTTCCCCA

TTTATGGTGCTCCGTATTCTGGCATTATGCAGCAGCCTCACACACCTGTC

CTCTCCTTCTTCATGTCCTACAGTTCTGCTATCACCTGACTAGAATAGCC

CTCTAGGCAACAGTGCTCAAATGTATGAGTTTGGAGAAGTTAACAATCAG

FIG.3D(73)

```
AAGAACAAAAACTGTAGTGTTTCACCTTTAAATGCAGTGTTGAAGAGGGA

GCCTTTCTCTAAGCCCTGCACTAACCCACTCCTCCCAAGACTCTTGTGGA

GTGACAGTTCCAAGCTGAACCATAAATCACTGATGCACAAAACACTGCTA

GAAGGCTCACCTCTCAAAACACGACTCTTTGCATCACTATTAAAGAGCAG

AAAGTTCTAGAAATGATCCCAGCCTCATCCCCTATACAGTTAGGAGCTCC

CCACATCTCTACCAAAACCCAGCACATAAGTATCTGCGTGGTCTAGCCTT

TCATCTCCGTAACAAGCCAGGGGACTCTTGGCCAAAAGAAAGAAAGGGAA

GTTGCACTAGGGCTTGTCCGTCCATAAGGAATTCCCCTCTGCTTTGCTCA

AAGGACCAAATTTCTTTGGCCAAAGAAGTTGCTTCTATGTTAGTCCCATA

CCCTGAAGTAATATGTACCATGGCTCCCACCTACCTGTTTATGCTCTCCC

TGCCCCCAGGGAAACTGTTTATTCTTTCAAAAGAAGCAAACAGCGTTCAT

TTCTGCTCCTGTAATGGAGAAACAGCCAGCTCCCCTGCATCCCTTACAGC

CAACAGCTCCCTTCAGGCTTAGAGCAGGGGGAATGGCAGGGATTAAGAGC

TCAGCTCAGAGCCAGTTACCAAGATGGAATGGAGTTGTGACCCAGTAACT

GTGTCACGAGAGACCATGTATATAAAATAGTCATGACGACACTGACCTCT

TGCACTTGTACATAACTATACTGTAGTGTCCAGAATGTTCAGACATTCAG

GGTGTACATAAACAGAAGAGTATCATAATGTATTTTTATTAAACACTAAC

ATCTGAGTTTCACCTAATCTGTTTCTGTGCCATATACTGGGTATCCAAGC

TCTGGGAAGTTATCCTACCAGGCCCTGATCTGTTGATAAGGCACTATACA

CCATGCTGGTGTGTTCTGTAGCCTTGTGCCCATTAGGTAACTGAACAATG

ATTCAGCTCTTAGAATACCTAGGAAGACAGCAAGCAGGGTGACACACGGC
```

FIG.3D(74)

```
TGTGATCTAAGCATTCAGAAGACAGAGGCAGGAAGAAAATTCAAAAATGG

GGCTGGAGAGATGGCTCAGTGGTTAAAAGCACTGGCTGCTCTTGGTCAGG

ACACTAGTTCAGTTCCCAGTACCCACATGGTGGCTCACAACCTTCTGTGA

CTACAGTTCCAGATAACCTGACACCCTCCTCTGGCCTCCTCGGGTGCCTG

TGGTGGTCCACCTGGTGCACAGACAAACACCCAATACACACAAAACAAAA

GTAACTCAAGAATAGCCTGGGCTACATAGCAAGAGCCTGTCTCAAAACAA

ACGAACCTATGAAGAGCCAGGCAGTCTATCTATTTACATGGCAGTATACT

AGAGAAACTCAGGAAGCAAGAGTGTTCATCACTGTTGTAATTTCAAATGC

TCCTTGTGATTTCTGGCATCTCTGTGGGGTGAGGTGTTCTGTTACTCTTC

ACATTCAAAGACTGTCACCCATGAACGTCAGACTTTGCAAAGGGGCTCTC

TAAGCTGCACTGTTGTGGCTTTGTCTAAAATTTTAATGACGTTTCTGAGA

ACCATGTTCTTTTTTATACTAAAATCTGGGGATGGGAGGGCTCATTTGTTG

ATAAATAGCACTATTTTCCCACACCTCAGCCTCCTGTCCCCGTCCTGGTC

TTCCCTACACAGTCTGGAGAGGGCTCTGAAAGGTCCACAGAGTTTGACAG

ACACGAAAGCAACCCATTGCCCCGTTGACCTGACCTGGAAGAAGACTGTC

AGCAAAAGGAAAATACCAGAATATCTGGAAAGCTTGAAGTGTAAGATGGG

ATCTCGTTGGGGAATTGGATGAAGAAAAGCAGAGCGCCTCTGGTAGGTGA

CTCTGCAGCCTGCCAGCGCCCGCCCTCTTTCTACACAGCAGAGTGTGCAT

GGCAAGGAAATGAGTCACCTCCTTGGGGGATGGTGCTGTTTTTATGAAAA

CCTCTGATCCTTGGTGTCCTTTAATTGATCTGTTCAACAAATATTTACTA

AACACTTCTAAGCTAACATTAGGGCAGTGACTGAGGTGGAAACCCAGCTC
```

FIG.3D(75)

TTTAGACAGCTGTCATCCTAGGATAGCTTCCTGGAAGCAGAACCAAGAAG

CCAGAAGGTTCTTCCTAGGGTGGCCTTGGCTCCCTGAAGGAATCTGAAAT

GCTGACCCTGTCACAACCTCCCAGCACAGCTTTGGAATGAGACATCAGCC

TGGCCTCCAGCAGAGCAGAGGCTCTGGAGCTCCACATCCTGCCTGCAGGG

AGCCCTCAGGGTGCCCTCCAGAGTACAGGGAGAAACTAAAGGCAATAACA

GAAGCTGCTCTCAGAGCCTGACTGTGCACAAAACACTAGTGAAGCCTGCT

GAACTAATTCTGCCTCTGGAAATCTTTTCTGGTTCTTTACAGTTTGTTGT

TTTGTTTTGATCCAAGCTTAGTTTGTTACTATGTGTGATTTAGCATCTGT

CGCACTTGTGTAAATATGGAGTAAGTATTGTAAACTATTTAATTGCTGCG

ATTGTTGGGTTATACATACATTTAGGACTGCAATTTTTTGGTATTTTTTG

TATTGTAAAATAACAGCTAATTTCATCAGGAACAAGAGAATTAAGGGGGT

CTGCATTTTAAATGCAGATGTGAAGCACTTGTATATAAATAAAAGTAAAT

ACTATAATACAAAGTTCCTTCTGAAATAAAAGTAGATCTGGTAAAAATGT

GCGTGCGTTTCGTTCTGAATGTTCAATGCTAATTTTGTTTTATTTTATAT

TTACATTTTAGTCCTTATTTTAGCAGTGAGGAGACAGGCACAGCAGTGCA

TTCTCACCTTGGCAGCTGAGGAATCCCCTAGAGTAGACTGCAACTCAAGA

CTCTTGGCTTCCACACTGAAAAGAGTTTCAGTTTATGAAGCAGAGTTTAG

GAAGTTTAGTGAGGAATTTAAGGACTTCTTTTAATGTTTGTGTCTACATA

TGTGGGTACATATATGACACAGCATGCATGTGGAAGGCAAACAACACCTT

AATGGAAGTGGCCTGAAGAACAAACTCAGGACTTCAATCTTGGCAGCATA

AACCTTTACCTAATGAGTCATCTCCAGTCTATACGGGGTGTGTGTGTGAA

FIG.3D(76)

```
CACATGTGCAACAGCACACAGTGGAGGTCAGCACAACTCTTGCGAGTCAA

TTCTCCCTTACCTTGTAAGACCTAGAATTCCACATTGCCCAGGCTCTGAA

AGTTAGGTTGGGTCCACACTGGGCCATGGCTGATGAAATGTTGGAAAAGT

GATAACACCAAACTTTTGCACAGAAAATATTTTCATCTGGGGCCTTCCCT

GGAGTTCACAGGCTAAAGTGTTGGAAGGAACATGGGTCCCTGAGCCACCA

CTTTCACAAAAACTACCTGATCAAGAAGAACTATTCTGGGTTTCTGTTGC

TAAAATTCCTTCCCAGAGAGAAATGTAAGCAATGTCTGCCCCTTCAAGGG

TCCCAGCAAGAAACCAAGGCACAATTCCACCAAAGTTCACTAGAAAACCA

GTGAGTTTATTGGGCTTCCGTGCAGAACATACATGAGGGGTTACTTAGAG

AAGTGTGGATACTCCTCCCCCTAACAATCCACACCCTGAAAAAGCCTTAC

CCAGCAGGGATGAGGGCTTCCCCAGACCCACATTGATGGTGCTCCCATTC

CATTTTTCCCTGGCATGCAAAGAGATAGACAGAAAAATAGATTATATATA

ATATACACATAAATTAGAAAAATAGATTATATAATATACACATAAATTAT

ATATTATATATAATATATAATACACAGATAGATTATATATGATATATA

AAACACACAGAAATAGGGTATATATAATATATAATACACAAACTACTCAG

CTATTAAAAACAGTGGATTCATGAAATTCTTAGGCAAATGGATGGAACTA

GAAAATATTCTGAGTGAGGTAACCCAATCACAAAAGAACACACATGGTAT

GCACTCACTGATAAGTGGATATTAGCCCAGAAGCTTGGAATACCCAAGAT

ACCATTCACAGACCACATGAAGCTCAAGAAAGGAAGATCAACGTGTGGGT

GCTTCTGTTCTTCTTAGAGGAACACCCTCATAAAGTAGTGGTGGGGGGTG

GGGGGAGACAGAATAGGTGGTTTCCAGGAGAGGAGGAAAACAGGAAAGGG
```

FIG.3D(77)

```
AATAAATAACATTTGAAATGTAAATAAAGAAAATACCCAATAATAAAAGA

AAAAGAATTTTGAAACAGAGGGTAAAAAATAATACACAAACCAGGTAGAT

AGATTATATATAATATATATAACACAGAGATAGATAGATAGATAGATAGA

TAGATAGATAGATAGATAGATAGATAGATAGATAGATAGGTCAACTGCTC

GCCCCTCCACTAGGTAACATGCAGTTAAGGCAGAGCTGCATACAACAGAT

GTTAGGGATACTCAGGTGAGAATCTCAGGCTTTGCTCCATCCATCTATGC

TGGGGTGTAAGCTGTCAACAAGTTTAGCTGGGATGATGCTTTGCAAGAGG

GCACAGCTGAATGCCCTAAGATGGTAGATGCTTGGCTCAAAGGAGACACT

ACAGCTCTGCATCAAGGCAAACTAACTGAGATGAGGGCCTTTATTTTCCA

GATCTGTATCCTGGAGCATCATTCACCTGTTACTACACTGAAAACATTTG

GTGTTGGTTTCATGGCAGATGACAGGCAGTGAGAGAAGTACAGCAGCGGA

CTGCTAGAGGTGGGGGTTCTGTCAGGACGTGGGAGGCTGTTTGGTTAGTA

ACTTGGAAAGCAACAAGTTTTTAGCTAGAGGGAGAAAAGCTGGAGATAAC

TGTACTTGCTTGATTTCTTAAATATCAAATTTTATTTTATGCATATGGGT

ATTTTGCTTGCATGTATGGCTATACACTACATGCTTGTGGTGCCCACAGA

GACCAGAGGAAGTAGTGTGAGCCTCTGAAACTGAAGTTACAGACATTACG

ACTTGAGTGCCTGAAACTGAACCTTGGTCCTCTGGAAGAACAGCCAGGGC

TCCTAACCACTGAGCTATCTCTCCAGCCCTGACAGAACATCATGTACTCC

AGGCTGGTCTCAAATTTGCTTTATAGCCAAGAACGGTCTTAAATTCTGAT

CCTCCTGTTCTCTCAAGTAGTGGGGTTACAGGTCTACACTGCCGTTTTCT

TGAGCAAATCATTACAAATTGAGTTCTAAGCCAGGTGTAATAGTTCATGT
```

FIG.3D(78)

AGTAACAATCTGGAATTTTGGTCTCTTAAAAAAACAAATATTATAAGAAT

GTATTTTCATTTTAATCCCAGGTGTATGGCATATATCGAACTGCTTTGGA

CTGACTACAGCAGCTATGATTTTTTCTTGTTCTAGCAGAGGTATGGTTTT

GCCAGCTACAGATAGTTTCTGTGATTGTGTGACATTTGGAATTCTGGAAA

CTTTTCAGATGGTATATAAATATTAGAGCCCCAATAGGCAGAGTTGATGA

TTGTTGGTCATTCAGGGGTATTGGTTGTGGTTAGTAGTCTTGCTTGAAGA

AGAAACAAGAACAAATTAGATTCAGAGATCTCTATATCTCTCTCTATCTT

CCTTTCTGTCCTATCTAGTAATAGGGGGTAAAACCAGGATGATAAAGGGT

TGGGGGAACCCACAAAGTAACAAAGACTGGCTACAAGTGGCACCCAACTT

GGAACTCAAAATTGCCATAGAGGAAGCAGCAGGGGATGAAGGAATGGATT

GTGGCTGTTGTTGCTGGGATATTCCTCACTTTGCTCCCAGAGGGGATTTT

TCTGAGGTTTTGTTGTTTTGCTTTGCTTTGCTTTGGTTTTCTTCTACATA

TTCTGTTTTTTAAGTAAGTTGAAATAATAGCCGAGAAGCTGGAAAAGTTT

GGTGTGGAAATGGAGCAGCCTGAGAAACAAACAATGTATGAAATGGGAAA

ACTAAAGGGGCCACTCTTCTCTCTTTTCTGAAAGGCTTGCAGACTTGGTG

GTGCACCTGGAGAGTTTATGGATGGAGATGGAAGCTCTTAGGAGACAAGA

AGCATGGAAAAAGAGAACAAAGGCTCAGTCCCAGTGACTGAAGAGAGCAG

GAGTTTTCCAAAGAAGGTGCATGGGAGGGCCACTGGTCAGAAAAAAAAGG

CTGAAAAATACCAAAGGACAATGTGCTGAAATAGCCCATTTCAAGAGAAA

GGGTTCATCTCAAACCAGCATTCTGACAGAGTGGAAGGAGGGGTGGCTCA

GGGTTATGAGATCACCATCAGCTTTTCCAGTTTTCCCATATAGCATATGC

FIG.3D(79)

```
CTGCTAATGGTATGGAACAAGAGTAAGGCAAAATAGGATGGTGTCCTATA

GAAATGATAGCTCTAAGGTGTTTTTAAAAGGCCTTGATTTCATATGGAAT

GCACTCTCCTTATGTGGAACGGATATTAAATAACCGGGGTACACAAACTA

GAATCCCTTCCCAAGATTGGAAGGGATTGGTAACAGCTGTACTAGAGACT

GTCAGCCGTTGCAATGGTTAACATGCTGGAGGAAAGAAGCTGTGAACATT

GAACAGTAAAACAGAGCAAGGGGTATTAATATAGTGAACGAACAGCTGCT

AGGTGAAGGGCGGTACTCTAGTGTACAAGCACAGACTCGGTGTCATGAAA

CTACTATAGAACAAGGTTGCCTCAGTGGCTATAACACCTTGGGACAAAGG

AGGAGCCAGGAAAAAGTCCAGTTCATTTACAAAGATTATATAAGGCTCTG

GAGAAGCCTTCACTGATTTTTTTTTTTACAAAGATTAGTCTCAGCTATGA

ACAAAGCCATATCAGACCCTGACACAAGGCAGGTGTTGATAGAGACCTTG

GTGTATGACAATGCAAATACCAAATATAAAAATGTCATTAGACTTTTAAA

GGCACAAGTAATGCCTATGGATGAGTGGATAAGGGATAAGACCAATATTA

GTTCTAATGTGTACTGTGCTAATATCATTGATCAAGCTATAGCTAGAGAT

CTCTGATGTCAAAATGCCTTGTGCTTCAGTTGCAGCAAATACAGTAATTT

GCAAGGAGTCATTGTGGCCAAAACTAAAGGTCTCAGATCTCAAAATGCCT

GATGCTTTGTGGGAAATAGGGTCATTTGCAACAAAAATGTGAACAAGACA

TCTTTAAGGGCAATGGTTTTTCTAAATATAAACCAGAAAGACGGCCTAGG

CTTCCAAGGTTGTGCTGGCGATGTGGCCAGGGTTGCCACTGGACCAATGA

GTGTAGGTCCAAAAGAGATATTCAAGGTAACGTATTACCATCATGAAATG

GTCTTGGGGGCCTATCTTGAGGCCCTGCAGCAAAGAGTATGAGCCATTCC
```

FIG.3D(80)

AACCAGAGAGTGGCATGGAGACTCAAAACCTTCACTGGGCACTGGAGATT

TAATGCACACTAGCTATTGCAGGCAGCATGGCTCTAGACTTGGCCACAGA

TAAACATCTTGCTCTATCCCCCAAAATTCAAAGTTATAACATAGCTACTG

GAGTGTATGGTCTTTTTCCCTCAGGGACAGTAAGGATAATCTTGGGAAGG

AGTGGATTGACTTCCTAAGAATTCACTGTGCATCAGGAAGTATAGATGAA

TATTTCAAAGGAGAAATTAAAATTGTGGCATATGTAAAGGTAGAGCTGCA

ACTTAACACAGGCGATAGGGTTGCTCAGCTGCTGCTGTTTCCCTATATCA

AAGGCAAAGCAACTGCAGCAGAAAGAGGAGAGGCCTGAAAACCTTGGGCA

CTGACACAAAAATTGCTTATTTCATTGAAAATGTCTGTTTATAACTTCCC

ACTATACAGCACAACAGGAGGGGGCTTAAAACATAATGGGGAAAATGTCA

CAATTCTGCAATTTTTGTTTCCTTAAAAAAAACACACACAGAATTTTA

ATAATGTGTTCTCATCTTAATCCCGGGTGTGGGAATTAGGGCTGCTTTGG

ACCATTCCCAGCAGCTGACTATGATTTGCCTCATGCTCTAGCAGAAGTAT

GATTTTTGCCACCTGCAGATAGTTTCTGGGATTGTGTGACATTTGGAATT

TTGGGAACTTTTTCTGAAGGTATATAAATGCTAAGGCCCTGGTGGGGAGGG

TTGGTGGTTGGTGGTCATTCAGGGGGGTGGTTGTGGTTAGTGGTCTTGCT

CAAAGAACAAACAAGAAAGTCATTTGATTCAGATGTATCTTTCTTCCTTC

CCCCACTCTTTCTCTCCTCCCCCCGGCACCCTGCCCCCTGCCCCGACCTC

TACCCTTCTTTTTTCTATCTAGTGACAAGGATGAAACCAGGGGGATAAAGG

GTGGGAAAAAGAAGAGCCCACAAAGTAACTCAGGTTGGCTACAAGTTCAT

GCCAAGAATCCTAGGACCTTGTTGTTTAAAGGCTTGTTTTATTTTGTGAA

FIG.3D(81)

```
CATGAATGTTAAATGTACATACATGTTAAGTGTATGTATGTACACCATAT

GCATGCATACAGAATCCAGAAGAAAGTACATTATACCCTGGAATGGAACT

TAGAGTTGTGAGACAGCATGAGGATGCTGGGAACTGAACCCAGTTTCTCC

ACAAGAGGAGTAGTTGCTCTTCACTGCTTAACCTTTCCTCCAGCCCCAAT

CCTAGCATTTTGGAGGCTGATGTAGGAAGATTATCCCAAGTGTGAGGTCA

TCTTGGGCTCCATAATAAGTTTAAGACCAATCTCAGCTCCAGAGTAGGAC

CCTGCCTCAAAAACACACAGGTGGAAAGATGGGTCGGCAATGAAGAGCAC

ACACTGTGCCTCCAGGGGACCCAAGCTTGGGTCCAAGCACCCTTGTTGGG

CAGCTCACAACTGCCTGTAACTCCACCTCCAGAGGATCCTAAGCCACCTT

CTGGCTTGGCTTCATGGAGGGAACAGGTATGTGGGTATCTGAGTGTGACG

AATGAGCAGCAAGTGAGTCTCGCTGTGGCTAGCACAAAGTATGGGCTGAA

GAGCAGGAGGACAGCTGAAAAGTGGCCTTTCCTGGTGACTAAGTTGGTCT

GAGCAGCTGAGTCAGTTTCTTCCTGGCTGCTTGGCTGGTCTCAGTGCTTA

TAAGCTGCTCACTTGTAAGTCTTTTCCTAGGAGCCCAGCTTGTCTAGGGG

TTGTCTTTGCAACTGGCCTTGTCTGACAGTGACTTTCAGCAGTCTTAGCT

GCTTATATACACAGTCTTAGGAAAGAAGGCTGGTGAATCTGATCCATTTC

AGGAACTTTCTGAAGCTATTCTGAATTTACTTTACAAGCTTACCTGCAGG

ATAGAGGATCTCAGCTCTTTATAAACATCCTGTCCTAAAACACCCTGTTG

TTCCTCTTCTCTTTTACATCCTGTGTCTTGAGAAGTTTGCCTCCAGGATG

GAAGTTGTTCAATTCAGAGGACACTGTTGCACAAGCTCCCAGCACCCACA

TGTGAGCTCAGTGCTCTCCTTGGCTCTAGCTCTGCCCTATGAGGTTTTTT
```

FIG.3D(82)

```
ATTTTGTCATCATAATCTTTTCCTATATCCTTCCTTGTTCTGGGAACTCA

TCTGGTTCATTTTTTTGGCATTTTGAGAAAAGCTCTCACTATACAAATCA

GGCTGCCTCCAAATCATCTTTTTGCCTTAACCTCCTCAGTACCAAGATCA

CGAGTGGATCTTAACACTTGACTGACTCGTTTAAGTGTGAGGAAATGTGG

ACCAATAAGAGAGCCCAGGAAAGCCCAGGAGAATCTGTAGCCCCATGGCT

GTTGTGTCAGAACCCAGAGTTTTGTCAACAGAATTTGGTTCCTAATTTCT

CCACTTTATAAAAACGAGTGAGAGAAACAGGAACCTATTCAGATCTGGCG

TCTGAGCAATCAGTGGGTGAACATCTAGAGATCTGTTCTGCATCTCCTCG

CCAGCTGGCAGAGCATGCGTAAGGCGGGAGGGAACAAGGGCAATCACTCA

CTCTGGGGCTCAGGCTTGCCCCTTGGGTCAGGTGTTTCTGAGAGACGTGA

TGTCTGCTTCTCTTGTTACCATCCCTCATCCTCTCCCCTCCTTCTGTCCC

CTACTTACCAATTTCACTGGCCAGTGTCCATATTTCCTGCAAAAGCGATT

TGGTTTAATGAGCTTGACTATGCCCGACTCCTTTAGGGAGGGTGGGGAAA

GGGCAACGAGGGCAGTAAGTGGTTTCCACAACCACTTTGCACCCGGCTGC

TGGGCCCCAAGCCAGAGGAACGTGCATGAGCCATGAAGTTTCCACTGATA

AATCCACAGATGCTTCTAGCACCTGCCTTTCTGACTCAGCCTCACCGTGC

CGCCTGCCAGCTGTGAAATCAGTGCCAACAACAGGTAACCGAGACCCAGG

CGCAGGGCCAGGACAGCTGTCTGACACTTCCAGACAGGATGTGGAGGCTG

ACAGTTGTGATGGAGAGGAGATGGGGAGGACAGAGACGGGCTCAGCTTTA

AGACACCGAGCCACAGAGCACCAAACAAAAGCCAGGGCCTTCTGAGGTAG

AAGTAACAGAAACCAAACAGGCAATTCTACTAGTTTCCTGGGACTGTTTG
```

FIG.3D(83)

CTGCATTTGCCAATCTTGGTAGTTTTAAAAAACAAAAACAGTTTGTTCTC

AGCACTGGCAGAGCTTTCCTCCTCTGGAGGCTCCAGGGGTCCAGACTCTC

CTCTGTGGTACACTGGCTTCAGACATATCTCTTGCCTATGGCTGCCTCAC

TCTAAACTCTGCCTGTCCTTGAATTACCTCTCTCTGCACTGGCTTTATAA

AGGAAACATGAGATTGTGTTTAGGGCCTGTTTGGGTGACCTCCTCAGGAT

CTATAACATAATCACATCTCTACCGTATGAAGTGACGCTTCCGTCCCAGT

GTGTAATACATTTGCCGGCGCCTGTCCTTAGGACAGTGACCACCACCAAC

TGTGGAACTTGACTATGTCCACGTCATCTTCCTACTAGCTTTAGAAGGCT

TATACCCACACTTTCTATCCAGAATTGTATTTTTATTTAGAATCATTCCT

ACTTTTAAAAAAGTCTCTGTGGTTAAAAGCATTGCAGAGGGCTTGGGTTT

TGGTCCCCAGGACCCACATCAAGTGGCTCACAGTGTCCTGGAACTCTTGT

TCCAATACCCTCTTCTGGTCTCCATAGGCACTACATACATATGGCACATA

TATGTATACTCAGGCACACGTGTAAATTTTAATGTCTACTTTTTATGCTA

AATATCAAAGTCACTCGAGCAGTGGAGTTGAGCACACTCACATAAGGAAA

TCATCAGACAGACACTTCATCCTGTGTTGGAGCCACTTTGTGGCTGGAGT

AAGCAGGGCAGAGTGATGTTTTCATTACTCTCTGGCCCCAGCACCCCCTG

CCTCTCCCCACCCATTCGTCCATGCAGGTGGGGAAGAGAATTCTCTTTGT

GAAATTGGAAGTTTGGACCCAGCTTCACTCTTACTCTGCCCAGTACCTCC

TGTGAGAAACCCTCCTATCCCAGGTGACCTGCTGGCTGTGACTCTCCTCA

GCAAAAGGCCCGTGACCCACACTGCGCCACTAATGTATCATCCCCAAATG

CTGAAAAGGAAGCGTGTCTTCCTCTCTCTCTTTTTCTTTTGGTCTTTT

FIG.3D(84)

TGAGACAGAGTTTCTCTGTATAGCCCTGGCTGTCCTGGAACTCACTTTGT

AGACCAGGCTGGCCTCGAACTCAGAACTCCGCCTGCCTCTGCCTCCCGAG

TGCTGGGATTAAAGGCGTGCATCACCACTGCCCGGCTGCGTGTCTTTCTC

TTAGCGGTCTCTGTGGAGATGCTGAGTATGAAGCTCATCCTACCCACCCT

TCAGTGGGGCCTTTTCTAGCTACTGAGCAGCTGTGTGAGGACTCGTGATC

ACAAGGTCCTTTGAACCCTTGAGACAGATGTGCCTGAGCCCAGTTTGACC

TGACAAAAGCCTAGAGCTCACTGATAATGCCAGCAAACACCATCTTTGAG

TTTGCAAAGGAATCGCAACACATGCATTCAGTTTCCGTTGCTGGCTGCTG

CTCCAGAGATGGCTATATTCATTCTCAGGTACTCAGACTCAAGAGTAGTT

CTGGCCACACAGGTCTCCACATTTCGAGGTCAAATGACAGAAAACCAGGT

TGGTCTCAGTGCACATGGGTTTATTGAGCCACTGCAGGTGCTGGGGAAAC

CATGGCAGGGAGATCCTGGGAAGCCAGTGGGGTGCTGAGCAGGAGGGACC

TCAGTCTCTCCTTAATGTCTACACACTGTGTCATAGGTGACAAGCCACGT

CAGTGCTGTGACACGGGTAAGCTTAATGGTGAGTAATGGCTAACTGGGAG

GGTATTTAGGCAGCCTTGTCTGTCAGCCTGTTCATATGATCTCCTTAGTG

CCTTGTCATCTTGGAAAAGGACAGTTCCAAATTCTAGGAGCGGGGGCTAG

TCTCTGTCCTGCTCTGTAAGCCCAGGGGACCCAATGAGGCCTCATCTATG

GGTGCTCAGCTCTAGGATGGGGAAGAAAATGGACAAGATGCCTACTGACG

GGAACACAGGCTTTTCAGTCAGACCCTAGCCTCCAGCCCCCAATCCAGAG

GACAGCCACACAGGGGTCCAGGCCTGCAAAGGGCAGCAGACCTGAGGGCA

AGGGAGTTTCAGCTCAGTGAGCAGTCATCGGGAGACATGGCAGTCAGCTG

FIG.3D(85)

```
TGTCGTCCACGGTTCATGTTCCTAATCAGAGCAGGGCCTGGAGAGCCAGG

GCAGTGAGTGCATACAGCCAGGACACCTTGGGCGTTAGGACAAAACAAGG

ACTGTTTCTGCCTCCAGCTCTTCTCAGGCCACTCGTGCCTTGCCTAGGAA

GGGTAAGAGAGCACAGATGGGAAGGATTCGGAAACTGTCAACTCCCTGTC

CTCTCCCCATACCTACCCGCGGGAAACAGCACCCAGCAGTCTGGTCCTGC

AGAACTGATGGCTGCAAGCTGTCAAAGGCTTGTATGGCACCATCTGCGGA

GTGCAGAGATCCAGAGAAGGCTTGGCCAGGAAACCCTAGAAACTACCCCA

CTCCCTTGGGACAAAAAATAAGACACCCTGGAACCTGCAAGGCATGGCCT

GAGATGGAAGGTCACTGTGCTAAGAATGACCCACAAACTGCTAGTGAGGT

TGACAAGGGCTGCCCCCTCTCCCTTTACAGGTGAACACAATCGGGATTAA

TAAGAGTTTAACTCTCAGCTACTAAGTGGCAGAGACAGGCTTCAAACAGA

CCCCCAGAAATCTGGAACTGAGCCATTCCACCCAGAGGCAAGAACAGCAG

AGGTAAGTTGGGCACACATGGAAGAAAGGGCCACCCCATTAGTGTCAAAA

GGGAGGCCAACTTCAGGCCATTGGACACGTTTTAACGCTGACTTCCACCC

ATGTACCATGGCATGTGCACACTGTCCATCGCCCACACCAAACATGATGC

GACGTAAATAAGACCCACGGGCCAGGCAGCTTGGATTGGGCCACAGACAT
```

FIG.3D(86)

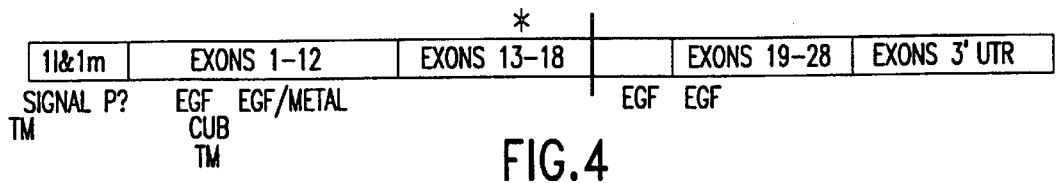

FIG.4

| | | |
|---|---|---|
| Exon 1 | CelegE106 | TCTCCTAGTTGTAGTACATGCTGTTG |
| | CelegE108 | AGGTCCTGTCTCAAGAAATAGCAATAAC |
| Exon2 | CelegE33 | TTTGAAGGCCCCTGAAGTCAGAG |
| | CelegE36 | TTGAGTCCCCATCATAAACATATAAATGG |
| | CelegE37 | TTCTAGGCCAAATAGAATAATGAGACTTC |
| | CelegE40 | AGAACTAATTCCATGAGATGAGTGTG |
| Exon 3 | CelegE41 | TGAAGTTGCTGTAATCTGGTCTGTG |
| | CelegE44 | AAGGAGCCTGACTAGAAGCCTC |
| Exon4 | CelegE69 | TAAACTCCCTACAGTTCACTAACTCAG |
| | CelegE72 | AGCGCTGTTGAGTGTGAATGTTCTG |
| | CelegE73 | AAAGCCACAGTTGTCTGTACAGTGAG |
| | CelegE76 | AGGTCTGCATTAGTTGCAATGTTGC |
| Exon5 | CelegE77 | TATACACCCCCTTATATACACTCAG |
| | CelegE80 | AGAGCCTCTCATAAAGCTGTGGTC |
| | CelegE81 | TTGAACATATATCCGCCAACAACCC |
| | CelegE84 | CTTGGAATACTATAAACTTTCAGGCTGC |
| Exon6 | CelegE101 | TAAAGCAACAGGAAGAGTTGAACTTCTTG |
| | CelegE104 | TGCACCCTGTGTGCACATGG |
| Exon7 | CelegE109 | TTACGGTGTCCTAATAATAAGGGCAG |
| | CelegE111 | AATCATGGGTATTGTTAACTCCGAAAGC |
| | CelegE114 | TGTAACAATGTGTGCCGAGTGTCC |
| | CelegE116 | TCTCTCTCCAGCCCTAGAGTTG |
| Exon8 | CelegE86 | AGAAGAGGAGCCTGCAACATTGAC |
| | CelegE88 | TTTGTTGGCGCTGAAAGCCTTG |
| | CelegE89 | TGGCCACAGTAGTGTTTATGATGAC |
| | CelegE91 | TTAATCAATTGCCTCTGCAGATTCTAG |

FIG.5(1)

| | | |
|---|---|---|
| Exon9 | CelegE93 | TGGCTTACGTATAGGGGGAAATCAAG |
| | CelegE95 | TTGTGTGTGTTCCCTCCAAACACC |
| | CelegE98 | GGACCATTCTTAAGGACAGCCGAT |
| | CelegE100 | ACATAGTGATCTTTCCATCAGCAAAG |
| Exon10 | CelegE117 | TGAATGCACAGAGACCCTCCTG |
| | CelegE120 | CCTCTTACCATTCAGATACTGTTAGG |
| Exon11 | CelegE121 | AGCAACAACTCAAACCAGCCCTAC |
| | CelegE124 | TTCTTCAGTTGCCAACTCCCAGG |
| | CelegE125 | AAGCTGCTTGTGTGGCAGCAG |
| | CelegE128 | AGTAAGGTGAACAGGAAAGTACAGAG |
| Exon12 | CelegE130 | TACATAAGAGAGGCTGCCGCATAG |
| | CelegE132 | CCCTACACTCACACTCATCTAGC |
| Exon13 | CelegE30 | CCCTGTGTTCCAGATCTCCATTG |
| | CelegE32 | TTCCTAGGTCCACCTTGATCTGAG |
| Exon14 | CelegE14 | AGCACCTGAATTCAAATCAGGATGAG |
| | CelegE15 | AAACCAAAGTTCTGAACACATTAACTCAC |
| Exon15 | CelegE17 | CTGGTTGCATTCATAGCTGTGTTTC |
| | CelegE20 | ACAGAAGCCAGCATCACTGGG |
| | CelegE21 | TTACTGGTGCTGGGAGGATATGTC |
| | CelegE24 | ATAAGTACTTCATCACCTCAGCGCTC |
| Exon16 | CelegE1 | TTGATCTTAGCTGACCAGTGTCTC |
| | CelegE4 | TCTGCATGGACTTGAGCAGAAAGTC |
| Exon17 | CelegE6 | CAAATCTTGTGATAGTGAATTACAAGTTGG |
| | CelegE8 | TTTATAGCTGCCCTCAATACATTTTCC |
| | CelegE9 | TGTACCTGCAGCCATTGCTTGG |
| | CelegE12 | GGATCTGGGCTCTAGTTTATGTACG |

FIG.5(2)

| | | |
|---|---|---|
| Exon18 | CelegE25 | TTGAACTATAGGCACAGACAGCTG |
| | CelegE27 | AACTTGACCTGTGTGACTTACGC |
| Exon19 | CelegE193 | TCACAGTCTATGGTAATCTGTCAAGC |
| | CelegE194 | AAGGGCAACAATGCCCTGGCAA |
| Exon20 | CelegE195 | TTCCTGCAAATGGGATAGTCTCTCTG |
| | CelegE196 | ATCCCCCAAGCATTTATCATTCTCAG |
| Exon21 | CelegE197 | TGTGTTTCCAGAAACCTGCTTTAGTTTG |
| | CelegE198 | TAGTACTTTTGTCCAGGATGACCAAG |
| Exon22 | CelegE199 | TGACAAGAAATGTCATGTCTTAACATAAGC |
| | CelegE200 | TTCAGAGCCTCCTTCCCCAACT |
| Exon23 | | |
| Exon24 | CelegE203 | TAGTCTGTAGCTGAGGCCATTTTGC |
| | CelegE204 | AAGCAAGCTGCAGTTAAGGGACTGT |
| Exon25 | CelegE205 | TTGGGACCTTGAGGATTGTTCCC |
| | CelegE206 | CACTCAACAGGTAAAAGTGATCTGCC |
| Exon26 | CelegE207 | TGCATCTGATCAGTTTGAATCAGAGAG |
| | CelegE208 | AAACTGAGGCCTGAGTTCTGAAAAGC |
| Exon27 | CelegE181 | CACCAAAGCTCTGTACCACTAAGC |
| | CelegE182 | TGACTGTGCAGTGATGCAGGG |
| Exon28 ÕUTR? | CelegE171 | TTGACCTTGACATTTAGAATAGCCCTC |
| | CelegE172 | GCTGAGAATTAATAATGGTCTTTCTCTTTG |
| | CelegE173 | TACACAGTGAGACCCTGTCTCC |
| | CelegE174 | TAGCTGAGGTCCCTTGTGGAAG |
| | CelegE175 | AGTGTCAGAGGACCATGCTGG |
| | C.elegE176 | CTTGAAGCGTCCAACTCATGTGC |

FIG.5(3)

| | |
|---|---|
| CelegE161 | AACTCATACATTTGAGCACTGTTGCC |
| CelegE162 | TGAGGAGGTGGGGAATGCTAATG |
| | |
| CelegE163 | ACATAGCAGAGGGCTGCTCAC |
| CelegE164 | ACTGACCTGTGGGAACCTGTG |
| | |
| CelegE165 | AATGCTAGGCATCATCCCTCTTCTAG |
| CelegE166 | AACATCTAATAGGGACTGAGTGACCC |
| | |
| CelegE167 | TTCTGTGGTGCCTTGGCAAGAG |
| CelegE168 | CACACATACACACACACTAAGTGCC |
| | |
| CelegE169 | TGGTAGTTACTTAAAGTTTACAAGAATGTAGG |
| CelegE170 | AAATGCTGGGATAAAAAGCATGAACCAC |
| | |
| C.elegE145 | TTCAGTTACCTAATGGGCACAAGGC |
| CelegE148 | ACGACACTGACCTCTTGCACTTG |
| | |
| CelegE150 | TGTACACCCTGAATGTCTGAACATTC |
| CelegE152 | GCGTTCATTTCTGCTCCTGTAATGG |
| | |
| CelegE153 | TGAGCTCTTAATCCCTGCCATTCC |
| CelegE154 | TAGGGCTTGTCCGTCCATAAGG |
| | |
| CelegE157 | TGTTACGGAGATGAAAGGCTAGACC |
| CelegE158 | TAAGCCCTGCACTAACCCACTC |
| | |
| CelegE159 | TGTTTTGAGAGGTGAGCCTTCTAGC |
| CelegE160 | CATGTCCTACAGTTCTGCTATCACC |
| | |
| CelegE141 | CTTTTCTTCATCCAATTCCCCACGAG |
| CelegE144 | TCTCTAAGCTGCACTGTTGTGGCT |
| | |
| C.elegE129 | TGGAAGCCAAGAGTCTTGAGTTGC |
| CelegE132 | GTCTGCATTTTAAATGCAGATGTGAAGC |
| | |
| CelegE134 | CGAAACGCACGCACATTTTTACCAG |
| CelegE136 | GTGTGATTTAGCATCTGTCGCACTTG |
| | |
| CelegE137 | TGTATGTATAACCCAACAATCGCTGC |
| CelegE140 | TCCAGAGTACAGGGAGAAACTAAAGG |

FIG.5(4)

AGCGCTATTCAGCTGTGCCTCCTTTGCTGTCTTGGCTCCTCCTGGAGCACTAT
ATGCACCCATGTCCTTACCAGGCCTTTCACAGACGCTGCCATTGAGAGGGT
TGATGCAGGTTGCAGCCTTTAATCCCCGAGTACTAGGCTCTGACAAGATCCCA
CAGAAGCCAGCATCACTGGGCTCAGATGGCATCCACTGCAGCAAACTATTTG
TGAATGGAGACATATCC

FIG.6

```
GAATTCCGGGCGAAGGGGAGCCGGCGTGCGGGGTGTGTATGTGTTCGCTGGGCGCCGGCTCAGCCCCAGGAAGATGGTG

GCGGTGGGCGGCGGCGGGCTGAGGCGCGGCTGAGGGGAGCACGAGGACGACAGCAGCGCCTGCGGGCAGGAAGG

GCAGGCAGCACCGACCCTGCACCGGACGGGGCCTGGAGGCCGGGACCGCGCGCGCCGGCTGTGTCTCCCGCGGGTGCT

GTCGCGGGGCGCTGCCCCCGCCGCTGCCGCTGCTCTTTTCGCTGCTGCTGCCGCTGCCCCGGGAGGCCGAG

GCCGCTGCGGTGGGCGGCGGGTGTCCGGCTCGGCCCCAGCCGAGGCCAAGGAATGTGACCGGCGTGTGTCAACGGCG

GCCGCTGCAACCCTGGCACCGGCGTCTGCGCCCACGGGCTGGGCGAGCAATGCCAGCACTGCGGGGGCCG

CTTCAGGACATCTGTCTCACGCCTATAATCACAGCTGTTCGGAAGGTGAGGCTGAGGAACAGTTCGAGGCAAGCTTCG

GCTACAGAATAAGTTCAAGAGTAACCTGGGGCAACTTGGGCTTGTCTCCAAAACCAAAATGAGCGAAAAGGAGCAAGCT

AGAGTCTTTGGGAAAATTTTAGCTGACTAATTTTCACCGAGAACTAACTGGCTCTTCTGGATTTGTAACAGATGGAC

CTGGGAATTATAAATATAAGACGAAGTGCACATGGCTCATTGAAGGACAGCCAAATAGAATAATGAGACTTCGCTTCAA

CCATTTTGCTACAGAATGTAGCTGGGACCATTTATATGTTTATGATGGGACTCAATCTACGCACCTCTGATTGCTGCC

TTTAGTGGCCTCATTGTTCCTGAAAGAGATGGCAATGAGACGGCTCCTGAGGTCACTGTCACTTCAGGTTATGCACTGC

TGCATTTTTTCAGTGATGCTGCTTATAATCTGACTGGATTAATATCACTTACAATTTGACATGTGTCCGAATAATTG
```

FIG.8A

```
CTCAGGCCGAGGAGAGTGTAAGAGCAGTAACAGCAGCAGCGCTGTTGAGTGTGAATGTTCTGAAAACTGGAAAGGGGAG

TCGTGTGACATTCCTCACTGTACAGACAACTGTGGCTTTCCTCACCGAGGCATCTGTAATGCAAGCGATACCAGAGGGT

GCTCCTGCTTCCTCCTCACTGGCAGGGTCCTGGATGTTCAATTCCTGTGCCAGCTAACCAGTCTTTTTGGACTCGAGAAGA

ATATTCTGATTTAAAGCTTCCCAGAGCCTCTCATAAAGCTGTGGTCAATGGAAATATAATGTGGGTTGTTGGCGGATAT

ATGTTCAACCATTCAGATTACAGACATGGTTTTAGCGTATGACCTGACTTCTAGGGAATGGCTTCCACTAAACCATTCTG

TGAACAGTGTGGTTGTAAGATATGGTCATTCTTTGGCATTACATAAGGATAAAATCTACATGTATGGAGGAAAAATTGA

TTCAACAGGGAACGTGACCAATGAGCTGAGAGTATTTCATATTCATAATGAATCATGGGTATTGTTAACTCCGAAAGCT

AAGGATCAGTATGCAGTGGTTGGACACACTCAGCACACATTGTTACTGGCATCTGGCCGTGTGGTCATGTTGGTCATCT

TCGGTCATTGCCCACTCTATGGATATATAAGCGTTGTGCAGGAATATGACTTGGAAAAGAACACATGGAGTATATTACA

TACTCAGGGTGCTCTTGTGCAAGGGGTTATGGCCACAGTAGTGTTTATGATGACAGGACCAAGGCTCTGTACGTTCAT

GGTGGCTACAAGGCTTTCAGCGCCAACAAATACCGGCTTGCAGATGACCTCTACAGATACGATGTGGATACTCAGATGT

GGACCATTCTTAAGGACAGCCGATTTTTCCGTTACTTGCATACAGCTGTGATAGTGAGTGGAACCATGCTGGTGTTTGG

AGGGAACACACAATGACACTTCCATGAGCCACGGTGCCAAATGCTTCTCCTCGGACTTCATGGCTTATGACATTGCT
```

FIG.8B

TGTGACCGATGGTCAGTGCTTCCCAGACCTGAGCTCCATCATGATGTCAACAGATTTGGCCATTCAGCAGTCTTGTACA

ACAGCACCATGTATGTGTTCGGCGGCTTCAACAGCCTCCTCCTCAGTGACGTCTTGGTCTTTACCTCGGAGCAGTGCGA

TGCACACCGCAGTGAAGCTGCTTGTGTGGCAGGAGGACCTGGTATCCGGTGTCTGTGGGACACACAGTCGTCTCGATGT

ACCTCCTGGGAGTTGGCAACTGAAGAACAAGCAGAAAAGTTAAAATCAGAGTGTTTTCTAAAAGAACCCTTGACCATG

ACAGATGTGACCAGCACACAGATTGTTACAGCTGCACAGCCAATACCAA

FIG.8C

MRLRFNHFATECSWDHLYVYDGDSIYAPLIAAFSGLIVPERDGNETAPEVTVTSGYALLHFFSDAAYNLTGFNITYNFD

MCPNNCSGRGECKSSNSSSAVECECSENWKGESCDIPHCTDNCGFPHRGICNASDTRGCSCFPHWQGPGCSIPVPANQS

FWTREEYSDLKLPRASHKAVVNGNIMWVGGYMFNHSDYSMVLAYDLTSREWLPLNHSVNSVVVRYGHSLALHKDKIYM

YGGKIDSTGNVTNELRVFHIHNESWVLLTPKAKDQYAVVGHSAHIVTLASGRVVMLVIFGHCPLYGYISVVQEYDLEKN

TWSILHTQGALVQGGYGHSSVYDDRTKALYVHGGYKAFSANKYRLADDLYRYDVDTQMWTILKDSRFFRYLHTAVIVSG

TMLVFGGNTHNDTSMSHGAKCFSSDFMAYDIACDRWSVLPRPELHHDVNRFGHSAVLYNSTMYVFGGFNSLLLLSDVLVF

TSEQCDAHRSEAACVAAGPGIRCLWDTQSSRCTSWELATEEQAEKLKSECFSKRTLDHDRCDQHTDCYSCTANTX

FIG. 8D

GAATTCCGGAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAGGAGGGCGAAGGGGAGCCGG
CGTGCGGGGTGTGTATGTGTTCGCTGGGCGCCGGCTCAGCCCCAGGAAGATGGTGCCGGTGGCGGCGGCGGCGACT
GAGGGCGCGGCTGAGGGGGAGCACGACGACAGCGCCTGCGGGCAGGAAGGGCAGGCAGCACCGACCCTGCACCG
CGACAGGGGCCTGGAGGCCGGGACCGCGCGCCCGGCTGTGTCTCCCGGGGTGCTGTCGCGGGCGCTGCCCCGCCGCC
GCTGCTGCCGCTGCTCTTTCGCTGCTGCTGCTGCCGCTGCCCGGGAGGCCGAGGCCGCTGCGGTGGCGGCGGGTG
TCCGGCTCGGCCGCAGCCGAGGCCAAGGAATGTGACCGGCGTGTGTCAACGGCGGCCGCTGCAACCCTGGCACCGGCC
AGTGCGTCTGCCCCACGGGCTGGGTGGGCGAGCAATGCCAGCACTGCGGGGGCCGCTTCAGACTAACTGGCTCTTCTGG
ATTTGTAACAGATGGACCTGGGAATTATAAATATAAGACGAAGTGCACATGGCTGGGACTGGGACTCAATCTACG
ATGAGACTTCGCTTCAACCATTTTGCTACAGAATGTAGCTGGGACCATTTATATGTTTATGATGGGGACTCAATCTACG
CACCTCTGATTGCTGCCTTTAGTGGCCTCATTGTTCCTGAAAGAGATGGCAATGGAGACGGCTCCTGAGGTCACTGTCAC
TTCAGGTTATGCACTGCTGCATTTTTTCAGTGATGCTGCTTATAATCTGACTGGATTTAATATCACTTACAATTTTGAC
ATGTGTCCGAATAATTGCTCAGGCCGAGGAGGAGAGTGTAAGAGCAGTAACAGCAGCAGTGTTGAGTGTGAATGTTCTG
AAAACTGGAAAGGGGCCGGAATTC

FIG.9A

EFRKKKKKKKKKKKKKKKKKKKKKKKKKKKKKKGGRRGAGVRGVYVFAGRRLSPRKMVAVAAAAT

EARLRGSTTTTAAPAGRKGRQHRPCTATGAWRPGPRARLCLPRVLSRALPPPPLLPLLFSLLLLPLPREAEAAAVAAAV

SGSAAAEAKECDRPCVNGGRCNPGTGQCVCPTGWVGEQCQHCGGRFRLTGSSGFVTDGPGNYKYTKCTWLIEGQPNRI

MRLRFNHFATECSWDHLYVYDGDSIYAPLIAAFSGLIVPERDGNETAPEVTVTSGYALLHFFSDAAYNLTGFNITYNFD

MCPNNCSGRGECKSSNSSSAVECECSENWKGAGIX

FIG.9B

SIGNAL PEPTIDE PREDICTIONS

| METHOD | PREDICT | SCORE | Mat@ |
|---|---|---|---|
| SignalP (eukaryote) | MAYBE | | 127 |

TRANSMEMBRANE SEGMENTS PREDICTED BY MEMSAT

| START | END | ORIENT | SCORE |
|---|---|---|---|
| 102 | 120 | INS--->OUT | 2.1 |
| 234 | 250 | OUT--->INS | 1.7 |
| 262 | 279 | INS--->OUT | 0.5 |

ATGTACTACTGTAACAAGAGACCAGCTGCCCTGGACCAGAACTGCCAGTGGGAGCCCGGAATCAGG

AGTGCATTGCCCTGCCCGAAAATATCTGTGGCATTGGCTGGCATTTGGTTGGAAACTCATGTTTGAAAATTACTACTGC

CAAGGAGAATTATGACAATGCTAAATTGTTCTGTAGGAACCACACAATGCCCTTTTGGCTTCTCTTACAACCCAGAAGAAG

GTAGAATTTGTCCTTAAGCAGCTGCGAATAATGCAGTCATCTCAGAGACATGTCCAAGCTCACCTTAACCCCATGGGTCG

GGCCCTTCGGGAAAGGTYCAATGTGTCCTACTKGGGTGCTGGGGAAGGATATGKTCCCCATTTTACAAATAGTTTTACTACA

GTGGGATGSCCGTCTTGAGGCCCAGTGTTGCTTGGRATTCTGTGGGAATTTT:ATTCAGGAACCCAGTACTTCGGGGA

CTGAAGGCTGCAACCTGCATTCAACCCACTYMAATGGTAGTGTCTGTGAAAGGCCTGCAAACCACAGTGCTAAGGCAGT

GCCGGACACCATGTGCCTTGAGGACAGCATGTGGAGATTGCACCAGCGGCAGCTCTGAGTG:CATGTGGTGCAGCAACA

TGAAG::CAGTGTGTGTGACTCCAATGCCTATGTGCCTCCTTCCCTTTTGG::CCAGTGTATGGAATGGTATACGATGAGC

ACCTGCCCCCTGAAAATTGTTCAGGCTACTGTACCTGTAGTCATTGCTTGGAGCAACCAGGCTGTGGCTGGTGTACTG

ATCCCAGCAATACTGGCAAAGGGAAATGCATAGAGGGTTCCTATAAAGGACCAGTGAAGATGCCTTCGCAAGCCCTAC

AGGAAATTTCTATCCACAGCCCCTGCTCAATTCCAGCATGTGTCTAGAGGACAGAGATACAACTGGTCTCTTTCATTCAC

TGTCCAGCTTGCCAATGCAACGGCCACAGTAAATGCATCAATCAGAGCATCTGTGAGAAGTGTGAGAACCTGACCACAG

FIG.10A(1)

```
GCAAGCACTGCGAGACCTGCATATCTGGCTTCTACGGTGATCCCACCAATGGAGGGAAATGTCAGCCATGCAAGTGCAA

TGGGCACGGCGTCTCTGTGCAACACCAACACGGGCAAGTGCTTCTGCACCACCAAGGGCGTCAAGGGGGACGAGTGCCAG

CTATGTGAGGTAGAAAATCGATACCAAGGAAACCCTCTCAGAGGAACATGTTATTATACTCTTCTTATTGACTATCAGT

TCACCTTTAGTCTATCCAGGAAGATGCTATTACACAGCTATCAATTTGTGGCTACTCCTGACGAACAAAACAG

GGATTTGGACATGTTCATCAATGCCTCCAAGAATTTCAACCTCAACATCACCTGGGCTGCCAGTTTCTCAGCTGGAACC

CAGGCTGGAGAAGAGATGCCTGTGTTTCAAAAACCAACATTAAGGAGTACAAAGATAGTTTCTCTAATGAGAAGTTTG

ATTTTCGCAACCACCCAAATATCACTTTCTTTGTTTATGTCAGTAATTCACCTGGCCATCAAAATTCAGATTGCCTT

CTCTCAGCACAGCAATTTTATGGACCTGGTACAGTTCTTCGTGACTTTCTTCAGTTGTTCCTCTCTTTGCTCCTGGTG

GCTGCTGTGGTTTGGAAGATCAAACAAAGTGTTGGGCCTCCAGACGTAGAGAGCAACTTCTTCGAGAGATGCAACAGA

TGGCCAGCCGTCCCTTGCCTCTGTAAATGTCGCCTTGGAAACAGATGAGGAGCCTCCTGATCTTATTGGGGGGAGTAT

AAAGACTGTTCCCAAACCCATTGCACTGGAGCCGTGTTTTGGCAACAAAGCCGTGTCCTCTCTGTGTTTGTGAGGCTC

CCTCGAGGCCTGGGTGGCATCCCTCCTCCTGGGCAGTCAGGTCTTGCTGTGCCAGCGCCTGGTGGACATTTCTCAGC

AGATGCCGATAGTGTACAAGGAGAAGTCAGGAGCCGTGAGAAACCGGAAGCAGCAGCCCCTGCACAGCCTGGGACCTG
```

FIG. 10A(2)

```
CATCTGATGCTGGGGCCAGGGACTCTCCCACGCACGAGCTAGTGAGTGGCACACCAGAGCCATCTGCAGGGAAGGGCGT

GGCGGGGAAATGGCTGTGCGGTGCGGGACGGAAGACTGGAAACCCTCAAAGCATCTGACTCACCTGCATGATCACAAGC

TTTCTTTGACGGTTTCTCCCATCCGTGTTCCAGCATCTAACCTTTTACTTTTGCATAGGAAATACTTGATTTAATTACA

GGTCCAGGGATGAGCTGATGGTTGCTGGAGGAGGCCAGTGTGAGAGCAACTAGGAATGACACTCAGGTTCA

CTGTGGAAAACTGTTCTTGGGACTGTCTCAACTGTGCAAAAACAAAAGATGGAGTGTTTACAAGTAGACATTCGTCAT

CAGTTGTTCTTGAACATGGTCTTTTAAAAACTAGTCAGATGAATTAACTTGTTTTCATCTGAAGCCTGCTATCTTTTT

AAAAGATGTGCTATTTATTCTTGCACGATTTAGGCAATTATCTCTCTTCCAGGGAGTACCTTTTTTTCTAGTTGAGAAT

TAATAATGGTCCATCTCTTTGATCATATCAAGCTAGGATAGAAGGGGGCTATTTAAATGTCAAGGTCAGCAGTGTT

ACTTTGAATGTAAACTGGTATATAATAGGTAGTTTTCTATAGTAACTTGATTAATTTAGTCTTAATCCATTTGAAACTCTC

TCTTCCTTTCTCTGCCTGTCCCTCCTCCTTCTCCATCTCACCCTCTCCACACATACACACACACAAACACATACA

CACAACACTAAGTGCCTAGACTTTAAATAGATCTAGCAATTGGAAAGTTAGTAAGCCTAAGTTTTTACATAATTGCATT

CCTACATTCTTGTAAAATTTAAAATAGCTACCATTGGCAATCTGCTTTTTTTCTAAAATCTGATTTGCAGCCAGGAAAGA

ATTTTCTCACCCAAGGAACATTTGATCTAGCAGCAGGGATGAGAGGAAAGCAGAAATGAATGAACTGTGAAAGCTCCTG
```

FIG. 10A(3)

```
TTTTTATTATCAAAAAGGACACTGTCAAGAAGGCGCCCCTGCCCCACCCGTGTCACCCTAGGCCTGATAAGCGAT
CAGAGGAAAGGACTCATTCATGTCACGCTTCCTTGAGCAGAAAAGAGCACTGAGAGCACTGGGACCCTGGATCAGAG
AGCATCTGTGTCCTGCAGCCTCCTCTGAACTTGTGGTTCATTCTCAGGCTGGGGTGGACTCAGATGCCAGGAAAGGG
ACAGCCTCCCATTGTCAGGCAGAAGCTGCCCAAAGCCTGGAGAAGGACTTGTTTGCCCTCTTTCCCCAGGAGGGCTC
GACCCCACCCACCCTCCCTCTCAGACCAAGGTGGCTGCTGTGAGGAGGGCAGCAAATGCTGACAAGGATGAAAAGCACAT
GGAAAAAAATGGACGAGGAGGGGAAAAACTCTGCCAAATGGAAAATTGACCAAATTTAAGAGGGTGGGACAGTCCCTGCTC
CTCTCCCAGAGGGCACTGCTTGGGAAATTGTGTTTCCCCATTTATGGTGCTCTGTATTCTGGCATTATGCAGCAGCCTC
CCAGAAGCTCTCTTCTGCTTCAAAACCTGGGATCTCTGGCATTACCCTATTGGGATGGACCGCTGGACAGCAATGCTCG
AGTTTGTGAATTGGAGAGATACTCAAAAGAGCTAAAACTGAGCATTTTACCTTTAAATGCAGTGCCTAGAGAGAGAG
TATTGTCTCTTCCCAACACTAACCCCACTCCCATGAAGAATTGCCTGGAAAGATGTTTTCAAGGAATTTGAACCATAA
AACACTATCTGATGCACAGAACACCTCTACTTTGAGACTCACCTCTCATAAAGCTTCTTTTTCACATTACTGTTAAAGA
CCAGACGTTCTAGAAAAGACCCCTCCTCTCATGAGCTCCCCCATCCCTGCTACAGAACACAGCACCCATGGCCCTGCA
GTGGACTGGCCCCTTAATTCCCACAGGCCCCCAGCAAGGCCAAAGGGAGGCCCCTGGGTATTGTCCTCCTACAAGGA
```

FIG. 10A(4)

AGATCCTCTCTTTGTTTGTTGTCAAAGGACCAGTTTCCTAGGCCAAAGAAGTCTCTTCCCCATGTTAGTCCTATGCCTTGAA

ATATCATGCACCATGACCCACAGCCATCTGGTTATGTCTTATTTTTTCCTAAAAGATAATGTTTATTTTAAAAAGGA

AGGAAGAAGCAAGTTGAAGTTTCATTCTGCTCTCCAGCGGTGGGGAAGCCGCTGAATCCACCTGCTTCTCCTTGCAACCGA

CAGCAAACAGCTTTCTCCGGCCTCAGGGCAGAAAAAGGGAATGGCAGGAGTAAGAGGGCGCTGGGCTCGGAGCCTGTTT

CCAAGAAGGAATTGGTTGTCATCTGGCAGTGTTGCGCGTCACAAGAGAGCCTGTATATAAATTAAAATAGTCAAGACAA

CACTGACCTTGCACTTGTACATAACTATACAGTAGTGTCCAGATGTTCAGACATTCGGAGTGTACATAAAACAGAAAA

AATCTTCATGTATTTTATTAAATATAACAATGTCTGAGTTTCACCTAAGATGTTTTTGTGCCATATGCTGGATATCCA

GGTTCTCGCCAGGCCCGATACATGAATAACAAACCCAAGAAACGCATCCCCATTGTGTGATGTGTTCAGATGCATCTG

GCACCAATTAGGTATTTCTTAAAACAGGACTCATCTGTCAGAGTGCACATGAAAAATCAGGCAGGAATCGAAACGACA

GCGCTGGAGGAGACTCAGGAAGCAGAGAGGCGTCCCTGCCGCCTTGGCCCTGCAAGCACATCATGACCCTTTCTGGC

AGCCTCTTGGTGCTCTGGGTAGTGAGGGATGACCAGTCTGTCCTGAGAAATGTTTCTCTTAGTCTTCTTAAGTTCAAAGA

CTAACCTGTAGCAATCAGACTTTCCAAAGGGGTTCTCCATTTTTGTAGTTTTGTCTAAATTTTAATGACCATTTC

CTGGAATCAGTTTATTATACTGAAAACTGGGGGTGGGAGTAGGAGCTAGTTTGTTGATAAATAGTTCCCATTTCCCCG

FIG. 10A(5)

```
TGGAGAATTTGACATACCCTGGACTTCCTGTGTGCCTCCTGCCATCCCTGCACACAGCCTGGGAGAGAAGCCTGTGCCTCC
CCGTGTGGAGAGAAGGCAACCCCAGATCCCCTGAGCTAACCCGGAGGAAAGGCAGTCCTGGACAGAAGACTGTCAGCAG
AAGGAAAGTACTGGACTACCCGTGGGTAAGTCCTGCCATTCAAGACTGGAGAGACACCTGGGAAATAAAAAGAGCAGGGCA
CTGCTGGTGGGAAGAGGCATTTTACCTTCCAGTGCAAATCCTGCTCTTTGATTAATGGGGTGTACTGGGGCCAGGGG
CTGATTCACTTCCTTGGGAGATGGTGGTGTTTTCATGAACATCTTTGATCCTTCCATTCATTTATTCATCCATCCATT
CAACAAGTATTTGCTAAACACTAACTTAAGCTAATGCTAGGGTAGTGACTGAGATGTAAAATAGATTTAGAATTAAA
ACAAAATCCAAGTCCTCACACCCCTGTCATCCCAGGAGATCTTTCCTTGTGGTGGTTTCTGTGAGAATTGGCCATCCTG
AGGACACAGCCAGGACGGGCAGAGGCCTCCTGGCCTGGGTGGTTTCTAGATAGCCAGGCCCACCAAGAGATATTGCCCCTTGATGAGAGTCAAA
CAAACTGGCTCCAGCCATTGCGGGTGGTTTCTAGATAGCCAGGCCCACCAAGAGATATTGCCCCTTGATGAGAGTCAAA
CACCCTGCCTACAAGGAGATGTTTGAAATGGAGAGGAAAATTGGCACCTCATCTTTTAAAGGCAGTAATGGAATTGAT
TTTCAGTAACTGAATTTGTGCACAAAACATTCTAAACACTAGTGAAGCCTGTTTCGTTGAACTAATTCTGGCTCTGGAA
ATGTTTTGTTTTATAGTTATTTACGATTTCGTTTGTTTGGATTCAAGCTTAGTTTGTTAATATGTATAATTAGCATC
TATTACACTCATGTAAATATGGAGTAAGTATTGTAAACTATTTCATTGCGGGGATTGTGGGTGTTATACATACATTAG
```

FIG.10A(6)

GACTGCAATTTTTGGTATTTTTGTATTGTAAATAACAGCTAATTTAAGCAGGAACAAGAGAACTAAGGGAGGTCTG

TGCATTTTAAACACAAATGTGAAGAACTTGTATATAAACAAAGTAAATACTATAATACAAACTTCCTTCTGAAATAAA

AGTAGATCTGGTAAAAAAAAAAAGAAAAAAAAAAAAAGGGCGGCCGC

FIG.10A(7)

MYYCNKKTSCRSCALDQNCQWEPRNQECIALPENICGIGWHLVGNSCLKITTAKENYDNAKLFCRNHNALLASLTTQKK

VEFVLKQLRIMQSSQSMSKLTLTPWVGPSGRXNVSYXVLGKDMXPILQIVLLQWDXRLEAQCCLXFCGNFXSGTQLLRG

LKAATCIQPTXMVVSVKGLQTTVLRQCRTPCALRTACGDCTSGSSEXHVVQQHEXSVWTPMPMWPPSLLXQCMEWYTMS

TCPPENCSGYCTCSHCLEQPGCGWCTDPSNTGKGKCIEGSYKGPVKMPSQAPTGNFYPQPLLNSSMCLEDSRYNWSFIH

CPACQCNGHSKCINQSICEKCENLTTGKHCETCISGFYGDPTNGGKCQPCKCNGHASLCNTNTGKCFCTTKGVKGDECQ

LCEVENRYQGNPLRGTCYYTLLIDYQFTFSLSQEDDRYYTAINFVATPDEQNRDLDMFINASKNFNLNITWAASFSAGT

QAGEEMPVVSKTNIKEYKDSFSNEKFDFRNHPNITFFVYVSNFTWPIKIQIAFSQHSNFMDLVQFFVTFFSCFLSLLLV

AAVVWKIKQSCWASRRREQLLREMQQMASRPFASVNVALETDEEPPDLIGGSIKTVPKPIALEPCFGNKAAVLSVFVRL

PRGLGGIPPPGQSGLAVASALVDISQQMPIVYKEKSGAVRNRKQQPPAQPGTCI

```
                                                                    Transmembrane
obe2       FRNHPNITFFVYYSNFTWP------IKIQIAFSQHSNFMDLVQFFVTFFSCFLSLLLVA
KIAA0534   FRSNPNITFYYYSNFSWP------IKIQIAFSQHNTIMDLVQFFVTFFSCFLSLLLVA
YC81_CAEEL FGPDSNTTFFVRVYNFNTP------VQIVVSFAQSPPIN-WVLFFVIFAACFIVLLVVA
MEGF8      LKSSRFYLLLLGVGDPSGPGANGSADSQGLLFFRQDQAHIDLFVFFSVFFSCFFLFLSLC
                                     Site
obe2       AVVWKIKQSCWASRREQLLREMQQMASRPFASVETLPWNR-----------------
KIAA0534   AVVWKIKQTCWASRREQLLRERQQMASRPFASVDVALEVGAEQTEFLRGPLEGAPKPIA
YC81_CAEEL GLLWMIKVRIEAYRRNQRRIDEIEHMASRPFASTKMELSMLSQFSSAG---------
MEGF8      VLLWKAKQALDQRQEQRRHLQEMTKMASRPFAKVTVCFPPDPTAPASAWKP-AGLPPP-A

FIG. 16A
```

```
                10        20        30        40        50        60
inputs  MVAVAAAAATEARLRGSTTTTAAPAGRKGRQHRPCTATGAWRPGPRARLCLPRVLSRALP
        :::  ::::::::::: :..::: ::: :                  :::
        MVA- AAAATEARLRRRTAATAALAGRSG-------------GPH------------
              10        20    [   EGF          30
                                                           EGF 1
                70        80        90       100       110       120
inputs  PPPLLPLLFSLLLLPLPREAEAAAVAAAVSGSAAAEAKECDRPCVNGGRCNPGTGQCVCP
                                                    ::::::::::::::::
        ---------------------------------------------CVNGGRCNPGTGQCVCP
                                                              40

130   CUB 140       150    CUB 160        170       180
inputs  TGWVGEQCQHCGGRFRLTGSSGFVTDGPGNYKYKTKCTWLIEGQPNXIMRLRFNHFATEC
        ::::::::::::::::::::::::::::::::::::::::::::::: ::::::::::::
        AGWVGEQCQHCGGRFRLTGSSGFVTDGPGNYKYKTKCTWLIEGQPNRIMRLRFNHFATEC
         50    J L 60        70         80   CUB 90       100

190       200       210       220       230       240
inputs  SWDHLYVYDGDSIYAPLIAAFSGLIVPERDGNETAPEVTVTSGYALLHFFSDAAYNLTGF
        :::::::::::::::::: :::::::::::::: :: :::::::::::::::::::::::
        SWDHLYVYDGDSIYAPLVAAFSGLIVPERDGNETVPEVVATSGYALLHFFSDAAYNLTGF
         110       120       130       140       150       160
                    EGF2                                        EGF3
               250       260       270       280       290       300
inputs  NITYNFDMCPNNCSGRGECKSSNSSSXVECECSENWKGXACDIPHCTDNCGFPHRGICNX
        :::: :::::::::::::::: ::::: :::::::::::: ::::::::::::::::::
        NITYSFDMCPNNCSGRGECKISNSSDTVECECSENWKGEACDIPHCTDNCGFPHRGICNS
         170   J L 180  EGF2 190       200      J 210       220
                                                   Kelch1        Kelch2
               310       320       330       340       350       360
inputs  SDXRGCSCFSDWQGPGCSVPVPANQSFWTREEYSNLKLPRASHKAVVNGNIMWVVGGYMF
        :: ::::::::::::::::::::::::::::::::::::::: :::::::::::::::::
        SDVRGCSCFSDWQGPGCSVPVPANQSFWTREEYSNLKLPRASHKAVVNGNIMWVVGGYMF
         230       240       250       260       270       280
                                                       Kelch3
               370       380       390       400       410       420
inputs  NHSDYNMVLAYDLASREWLPLNRSVNNVVVRYGHSLALYKDKIYMYGGKIDSTGNVTNEL
        ::::::::::::::::::::::::::::::::::::::::::::::::::::::::::
        NHSDYNMVLAYDLASREWLPLNRSVNNVVVRYGHSLALYKDKIYMYGGKIDSTGNVTNEL
         290       300       310       320       330       340
```

FIG.17A

```
                                        kelch4
            430       440       450       460       470       480
inputs  RVFHIHNESWVLLTPKAKEQYAVVGHSAHIVTLKNGRVVMLVIFGHCPLYGYISNVQEYD
        ::::::::::::::::::::::::::::::::::::::::::::::::::::::::::::
        RVFHIHNESWVLLTPKAKEQYAVVGHSAHIVTLKNGRVVMLVIFGHCPLYGYISNVQEYD
        350       360       370       380       390       400
                                        Kelch5
            490       500       510       520       530       540
inputs  LDKNTWSILHTQGALVQGGYGHSSVYDHRTRALYVHGGYKAFSANKYRLADDLYRYDVDT
        ::::::::::::::::::::::::::::::::::::::::::::::::::::::::::::
        LDKNTWSILHTQGALVQGGYGHSSVYDHRTRALYVHGGYKAFSANKYRLADDLYRYDVDT
        410       420       430       440       450       460
                                Kelch 6nt
            550       560       570       580       590       600
inputs  QMWTILKDSRFFRYLHTAVIVSGTMLVFGGNTHNDTSMSHGAKCFSSDFMAYDIACDRWS
        ::::::::::::::::::::::::::::::::::::::::::::::::::::::::::::
        QMWTILKDSRFFRYLHTAVIVSGTMLVFGGNTHNDTSMSHGAKCFSSDFMAYDIACDRWS
        470       480       490       500       510       520
                                        kelch 1ct
            610       620       630       640       650       660
inputs  VLPRPDLHHDVNRFGHSAVLHNSTMYVFGGFNSLLLSDILVFTSEQCDAHRSEAACLAAG
        :::::::                 ::::::::::::::::::::::::::::::::::::
        VLPRPDSTMMSTDLAIPAVLHNSTMYVFGGFNSLLLSDILVFTSEQCDAHRSEAACLAAG
        530       540       550       560       570       580
                                        plexin 1
            670       680       690       700       710       720
inputs  PGIRCVWNTGSSQCISWALATDEQEEKLKSECFSKRTLDHDRCDQHTDCYSCTANTNDCH
        ::::::::::::::::::::::::::::::::::::::::::::::::::::::::::::
        PGIRCVWNTGSSQCISWALATDEQEEKLKSECFSKRTLDHDRCDQHTDCYSCTANTNDCH
        590       600       610       620       630       [640
                                                ligand-binding γcytokine chain
            730       740       750       760       770       780
inputs  WCNDHCVPRNHSCSEGQISIFRYENCPKDNPMYYCNKKTSCRSCALDQNCQWEPRNQECI
        ::::::::::::::::::::::::::::::::::::::::::::::::::::::::::::
        WCNDHCVPRNHSCSEGQISIFRYENCPKDNPMYYCNKKTSCRSCALDQNCQWEPRNQECI
        650       660       670       680       690       700
                                c-type lectin
            790       800       810       820       830       840
inputs  ALPENICGIGWHLVGNSCLKITTAKENYDNAKLFCRNHNALLASLTTQKKVEFVLKQLRI
        ::::::::::::::::::::::::::::::::::::::::::::::::::::::::::::
        ALPENICGIGWHLVGNSCLKITTAKENYDNAKLFCRNHNALLASLTTQKKVEFVLKQLRI
        710 [     720       730       740       750       760
```

FIG.17B

```
              850        860        870        880        890        900
inputs  MQSSQSMSKLTLTPWVGLRKINVSYWCWEDMSPFTNSLLQWMPSEPSDAGFCGILSEPST
        ::::::::::::::::::::::::::::::::::::::::::::::::::::::::::::
        MQSSQSMSKLTLTPWVGLRKINVSYWCWEDMSPFTNSLLQWMPSEPSDAGFCGILSEPST
        770        780        790        800        810        820
                                          plexin repeat 2
              910        920        930        940        950        960
inputs  RGLKAATCINPLNGSVCERPANHSAKQCRTPCALRTACGDCTSGSSECMWCSNMKQCVDS
        ::::::::::::::::::::::::::::::::::::::::::::::::::::::::::::
        RGLKAATCINPLNGSVCERPANHSAKQCRTPCALRTACGDCTSGSSECMWCSNMKQCVDS
        830        840        850        860        870        880

970        980        990       1000       1010       1020
inputs  NAYVASFPFGQCMEWYTMSTCPPENCSGYCTCSHCLEQPGCGWCTDPSNTGKGKCIEGSY
        ::::::::::::::::::::::::::::::::::::::::::::::::::::::::::::
        NAYVASFPFGQCMEWYTMSTCPPENCSGYCTCSHCLEQPGCGWCTDPSNTGKGKCIEGSY
        890        900        910        920        930        940
                                                              lamin-like EGF-1
              1030       1040       1050       1060       1070       1080
inputs  KGPVKMPSQAPTGNFYPQPLLNSSMCLEDSRYNWSFIHCPACQCNGHSKCINQSICEKCE
        ::::::::::::::::::::::::::::::::::::::::::::::::::::::::::::
        KGPVKMPSQAPTGNFYPQPLLNSSMCLEDSRYNWSFIHCPACQCNGHSKCINQSICEKCE
        950        960        970        980        990       1000
                                                              lamin-like EGF-2
              1090       1100       1110       1120       1130       1140
inputs  NLTTGKHCETCISGFYGDPTNGGKCQPCKCNGHASLCNTNTGKCFCTTKGVKGDECQLCE
        ::::::::::::::::::::::::::::::::::::::::::::::::::::::::::::
        NLTTGKHCETCISGFYGDPTNGGKCQPCKCNGHASLCNTNTGKCFCTTKGVKGDECQLCE
        1010       1020       1030       1040       1050       1060

1150       1160       1170       1180       1190       1200
inputs  VENRYQGNPLRGTCYYTLLIDYQFTFSLSQEDDRYYTAINFVATPDEQNRDLDMFINASK
        ::::::::::::::::::::::::::::::::::::::::::::::::::::::::::::
        VENRYQGNPLRGTCYYTLLIDYQFTFSLSQEDDRYYTAINFVATPDEQNRDLDMFINASK
        1070       1080       1090       1100       1110       1120

1210       1220       1230       1240       1250       1260
inputs  NFNLNITWAASFSAGTQAGEEMPVVSKTNIKEYKDSFSNEKFDFRNHPNITFFVYVSNFT
        ::::::::::::::::::::::::::::::::::::::::::::::::::::::::::::
        NFNLNITWAASFSAGTQAGEEMPVVSKTNIKEYKDSFSNEKFDFRNHPNITFFVYVSNFT
        1130       1140       1150       1160       1170       1180
```

FIG.17C

```
                            TM
         1270      1280      1290      1300      1310      1320
inputs  WPIKIQIAFSQHSNFMD[LVQFFVTFFSCFLSLLLVAAVVWK]KQSCWASRRREQLLREMQ
        : : : : : :.                               :.        ::
        WPIKIQV-------------------------------------QT       EQ-----
        1190

1330      1340      1350      1360      1370      1380
inputs  QMASRPFASVNVALETDEEPPDLIGGSIKTVPKPIALEPCFGNKAAVLSVFVRLPRGLGG

------------------------------------------------------------

1390      1400      1410      1420
inputs  IPPPGQSGLAVASALVDISQQMPIVYKEKSGAVRNRKQQPPAQPGTCIN

------------------------------------------------
```

FIG.17D

ATGGTGGCGGTGGCCGCAGCGGCGGCAACTGAGGCAAGGCTGAGGAGGAGGACGCGGCGGCGACGCGCTCGCGGGCAGGAGCGCGGGCC

GCACCGACCCTGCACACGCGACAGGGCCTGGAGGCCGGGACCGCGCGCCCGGCTGTGTCTCCCGCGGGTGCTGTCGCGGGGCGCTGCCCCGC

CGCCGCTGCTGCCGCTGCTCTTTTCGCTGCTGCTGCCGCTGCCCCGGGAGGCCGAGGCCTGCGGTGGCGGCGGGGTGTCCGGCTCG

GCCGCAGCCGAGGCCAAGGAATGTGACCGGCCGTGTGTCAACGGGCGGTCGCTGCAACCCTGGCACCGGCCAGTGCGTCTGCCCCGCCGGCTG

GGTGGGCGAGCAATGCCAGCACTGCGGGGGCCGCTTCAGACTAACTGGATCTTCTGGGTTTGTGACAGATGACCTGGAAATTATAAATACA

AAACGAAGTGCACGTGGCTCATTGAAGGACAGCCAAATAGAATAATGAGACTTCGTTCAATCATTTGCTACAGAGTGTAGTTGGGACCAT

TTATATGTTTATGATGGGACTCAATTTATGCACCGCTAGTTGCTGCATTTTTTAGTGATGCTGCTTATAATTTGACTGGATTAATATTACTTACAGTT

CCCTGAGGTTGTTGCCACATCAGGTTATGCCTTGCTGCGCATTTTTAGTGATGCTGCTTATAATAGCAGATACTGTTGAATGTGAATGG

TTGATATGTGTCCAAATAACTGCTCAGGCCGAGGAGAGTGTAAGATCAGTAATAGCAGATACTGTTGAATGTGAATGTTCTGAAAACTGG

AAAGGTGAAGCATGTGACATTCCTCACTGTACAGACAACTGTGGTTTCCTCATCGAGGCATCTGCAATTCAAGTGATGTCAGAGGATGCTC

CTGCTTCTCAGACTGGCAGGGTCCTGGATGTCAGTTCCTGTACCAGCTAACCAGTCATTTGGACTCGAGAGGAATATTCTAACTTAAAGC

TCCCCAGAGCATCTCATAAAGCTGTGTCAATGGAAACATTATGTGGGTTGTTGGAGGATATATGTTCAACCACTCAGATTATAACATGGTT

CTAGCGTATGACCTTGCTCTAGGGAGTGGCTTCCACTAAACCGTTCTGTGAACAATGTGGTTGTTAGATATGGTCATTCTTTGGCATTATA

FIG.18A(1)

```
CAAGGATAAAATTTACATGTATGGAGGAAAAATTGATTCAACTGGGAATGTGACCAATGAGTTGAGAGTTTTTCACATTCATAATGAGTCAT
GGGTGTTGTTGACCCCTAAGGCAAAGGAGCAGTATGCAGTGGTTGGGCACTCTGCACACATTGTTACACTGAAGAATGCCGAGTGGTGTCATG
CTGGTCATCTTTGGTCACTGCCCTCTCTATGATATATAAGCAATGTGCAGGAATATGATTTGATAAGAACACATGGAGTATATTACACAC
CCAGGGGTGCCCTTGTGCAAGGGGGTTACGGCCATAGCAGTGTTTACGACCAGTGTTTACGACCAGTGTTTACGACCATAGGACCAGGGCCCTATACGTTCATGGCTACAAGGCTT
TCAGTGCCAATAAGTACCGGCTTGCAGATGATCTCTACCGATATGTGGATACCCAGATGTGGACCATTCTTAAGGACAGCCGATTTTTC
CGTTACTTGCACACAGCTGTGATAGTGAGTGGAACCATGCTGGTGTTTGGGGGAAACACACAATGACACATCTATGAGCCATGGCGCCAA
ATGCTTCTCTTCAGATTTCATGGCCTATGACATTGCCTGTGACCGCTGGTGTTTCGGTGGTTTCAATAGTCTCCTCCTCAGCGACATCCTGGTATTCACCTCG
TTGGCCATTCAGCAGTCTTACACAACAGCACCATGTATGTGTTCGGTTAGCAGCAGGACCTGGTATTCGGTGTGTGGAACACAGGGTCGTCTCAGTGTAT
GAACAGTGTGATGCCATCGGAGTGAAGCCGCTTGTTTAGCAGCAGGACCTGGTATTCGGTGTGTGGAACACAGGGTCGTCTCAGTGTAT
CTCGTGGGCGCTGGCAACTGATGAACAAGAAGAAAAGTTAAAATCAGAATGTTTTTCCAAAAGAACTCTTGACCATGACAGATGTGACCAGC
ACACAGATTGTTACAGCTGCACACAGCCAACACCAATGACTGCCACTGGTGTGCAATGACCATTGTCCCCAGGAACCACAGCTGCTCAGAGGC
CAGATCTCCATTTTTAGGTATGAGAATTGCCCCAAGGATAACCCTATGTACTGTAACAAGAAGACCAGCTGCAGGAGCTGTGCCCTGGA
CCAGAACTGCCAGTGGGAGCCCCGGAATCAGGAGTGCATTGCCCTGCCCGAAAATATCTGTGGCATTGGTTGGAAACTCAT
```

FIG. 18A(2)

GTTTGAAAATTACTACTGCCAAGGAGAATTATGACAATGCTAAATTGTTCTGTAGGAACCACAATGCCCTTTGGCTTCTCTTACAACCCAG

AAGAAGGTAGAATTTGTCCTTAAGCAGCTGCGAATAATGCAGTCATCTCAGAGCATGTCCAAGCTCACCTTAACCCCATGGGTCGGCCTTCG

GAAGATCAATGTGTCCTACTGGTGCTGGGAAGATATGTCCCCATTTACAAATAGTTACTACAGTGGATGCCGTCTGAGCCCAGTGATGCTG

GATTCTGTGGAATTTTATCAGAACCCAGTACTCGGGGACTGAAGGCTGCAACCTGCATCAACCCACTCAATGTAGTGTCTGTGAAAGGCCT

GCAAACCACAGTGCTAAGCAGTGCCGGACACCATGCCTTGAGGACAGCATGTGGAGATTGCACCAGCGGCAGCTCGAGTGCATGTGGTG

CAGCAACATGAAGCAGTGTGTGGACTCCAATGCCTATGGCCTCCTTCCCTTTGGCCAGTGTATGGAATGGTATACGATGAGCACCTGCC

CCCCTGAAAATTGTTCAGGCTACTGTACCTGTAGTCATTGCTTGGAGCAACCAGGCTGTGGCTGGTGTACTGATCCCAGCAATACTGGCAAA

GGGAAATGCATAGAGGGGTTCCTATAAAGGACCAGTGAAGATGCCTTCGCAAGCCCCTACAGGAAATTTCTATCCACAGCCCTGCTCAATTC

CAGCATGTGTCTAGAGGACACAGCAGATACAACTGGTCTTTCATTCACTGTCCAGCTTGCCAATGCAACGGCCACAGTAAATGCATCAATCAGA

GCATCTGTGAGAAGTGTGAGAACCTGACCACAGGCAAGCACTGCGAGACCTGCATATCTGGCTTCTACGGTGATCCCACCAATGGAGGGAAA

TGTCAGCCATGCAAGTGCAATGGGCACGCGTCTCTGTGCAACACCAACAGGGCAAGTGCTTCTGCACCACCAAGGGCGTCAAGGGGGACGA

GTGCCAGCTATGTGAGGTAGAAAAATCGATACCAAGGAAAACCCTCTCAGAGGAACATGTTATTATACTCTTCTTATTGACTATCAGTTCACCT

TTAGTCTATATCCCAGGAAGATGATGCTATTACACAGCTATCAATTTTGTGGCTACTCCTGACGAACAAAACAGGGATTTGGACATGTTCATC

FIG.18A(3)

```
AATGCCTCCAAGAATTTCAACCTCAACATCACCTGGGCTGCCAGTTTCTCAGCTGGAACCCAGGCTGGAGAAGAGATGCCTGTTGTTTCAAA

AACCAACATTAAGGAGTACAAAGATAGTTTCTCTAATGAGAAGTTTGATTTCGCAACACCCAAATATCACTTTCTTGTTTATGTCAGTA

ATTTCACCTGGCCCATCAAAATTCAGATTGCCTTCTCTCAGCAGCAATTTATGGACCTGGTACAGTTCTTCGTGACTTTCTTCAGTTGT

TTCCTCTCTTTGCTCCTGGTGCTGTGGTTGGAAGATCAAACAAAGTTGTGGGCCTCCAGACGTAGAGAGCAACTTCTTCGAGAGAT

GCAACAGATGGCCAGCCGTCCCTTGCCTCTGTAAATGTCGCCTTGGAAACAGATGAGGAGCCTCCTGATCTTATTGGGGGAGTATAAAGA

CTGTTCCCAAACCCATTGCACTGAGCCGTGTTTGGCAACAAAGCCGCTGTCCTCTCTGTTGTGAGGCTCCCTGAGGCCTGGGTGGC

ATCCCCTCCTCCTGGGCAGTCAGGTCTTGCTGTGGCCAGCGCCCCTGGTGGACCTGTGGGCCAGGACTCTCCACGCACGAGCTAGTG

AGCCGTGAGAAACCGGAAGCAGCAGCCATCTGCAGGGAAGGGCGTGGCGGGGAAATGGCTGTGCGGTGCGGGACGGAAGACTGGAAACCCTCAAAGCATCTG

AGTGGCACACCAGAGCTTTCTTTGACGGTTCTCCCATCCGTGTTCCAGCATCTAACCTTTACTTTGCATAGGAAATACTTGAT

ACTCACCTGCATGATCACAAGCTTTCTTTGACGGTTGCTGGAGGAGCCAGTGTAGAGCCAGTGAGAGAACTAGGAATGACACTCAGGTTCACTGT

TTAATTACAGGTCCAGGGATGAGCTGATGGTTGCTGGAGGAGCCAGTGTAGAGCCAGTGTTTACAAGTAGACATTGTCATCAGTGTTCTTGAACAT

GGAAAACTGTTCTGGGACTGTCTCAACTGTGCAAAAAACAAAGATGGAGTGTTTACAAGTAGACATTGTCATCAGTGTTCTTGAACAT

GGTCTTTTAAAAACTAGTCAGATGAATTAACTTGTTTCATCTGAAGCCTGCTATCTTTTTAAAAGATGTGCTATTATTCTTGCACGATT
```

FIG.18A(4)

```
TAGGCAATTATCTCTCTTCCAGGGAGTACCTTTTTTCTAGTTGAGAATTAATAATGGTCCATCTCTTTGATCATATCAAGCTAGGATAGA
AGGGGGGCTATTTAAATGTCAGTTCAGCAGTGTTACTTTGAATGTAAACTGGTATAATAGGTAGTTTTCTATAGTAACTTGATTAATTTA
GTCTTAATCCATTTGAAACTCTCTCTTCCTTCTCTCGCTGTCCCTCTCCATCTCACCCTCCCTCTCACACATACACACACA
AACACATACACACAACTAAGTGCCTAGACTTTAAATAGATCTAGCAATTGGAAAGTTAGTAAGCCTAAGTTTTACATAATTGCATTCCT
ACATTCTGTAAATTTAAATAGCTACCATTGGCAATCTGCTTTTTTCTAAAATCTGATTTGCAGCCAGGAAAGAATTTCTCACCCAAGG
AACATTTGATCTAGCAGCAGGGATGAGAGGAAAGCAGAAATGAATGTGAAAGCTCCTGTTTTATTATCAAAAAGGACACTGTCAAG
AAGGCGCCCCCTGCCCCCCACCCCCGTGTCACCCTAGGCCTGATCAGAGAGCATCTGTGTGTCCTGCAGCCTCCTCTGAACTTGTGGTTCATTCTCAGGCTGGG
AAGAGCACTGAGAGCACTTGGGACCCCTGGATCAGAGAAAGGACAGCCTCCATTGTCAGGCAGAAGCTGCCCAAAGCCTGGAGAAGGACTTGTTTGCCCTCTTTCCCC
GTGGACTCAGATGCCAGGAAGGGACAGCCTCCATTGTCAGGCAGAAGCTGCCCAAAGCCTGGAGAAGGACTTGTTTGCCCTCTTTCCCC
AGGAGGGGCTCGACCACCCACCCCCTCCCTCAGACCAAGGTGGTGGCTGTGAGGAGGGCAGCAAATGCTGACAAGGATGAAAAGCACATGG
AAAAAAATGGACGAGGAGGGAAAACTCTGCCAAATGGAAAATGACCAAATTTAAGAGGGTGGGACAGTCCCCTGCTCCTCTCCCAGAGGGCA
CTGCTTGGAAATTGTGTTTCCCCATTTATGGTGTCTCGTATTCTGGCATTATGCAGCAGCCTCCCAGAAGCTCTCTTCTGCTTCAAAACCT
GGGATCTCTGGCATTACCCTATTGGGATGGACCGCTGGACAGCAATGCTCGAGTTTGTGAATTGGAGAGATACTCAAAGAGCTAAAACTG
```

FIG. 18A(5)

```
CAGCATTTTACCTTTAAATGCAGTGCCTAGAGAGAGTATTGTCTCTTCCCCAACACTAACCCCCACTCCCATGAAGAATTGCCTGGAAAGA
TGTTTTCAAGGAATTTGAACCATAAAAACACTATCTGATGCACAGAACACCTCTACTTTGAGACTCACCTCTCATAAAGCTTCTCTTTTCACAT
TACTGTTAAAGACCAGACGTTCTAGAAAAGACCCCTCTCTCATGAGCTCCCCATCCCTGCTACAGAACACAGCACCCATGGCGCCTGCAG
TGGACTGGCCCCTTAATTCCCACAGGCCCCCCAGCAAGGCCAAAGGGAGGCCCCTGGGTATTGTCCTCCTACAAGGAAGATCCTCTTTGTT
TGTTCAAAGGACCAGTTTCCTAGGCCAAAGAAGTCTCTTCCCCATGTTAGTCCTATGCCTTGAAATATCATGCACCATGACCACAGCCAT
CTGGTTATGTCTTATTTTTTCCTAAAGATAATGTTTATTTTAAAAAGGAAGAAGCAAGTGAAGTTTCATTCTGCTCCAGCGGTGG
GGAAGCCGCTGAATCCACCTGCTTCTCCTTTGCAACCGACAGCAAACAGCTTTCTCCGGCCTCAGGGCAGAAAAAAGGGAATGGCAGGGAGTA
AGAGGCGCTGGGCTCGGAGCCTGTTCCAAGAAGGAATTGGTTGTCATCTGGCAGTGTTGCGCGTCACAAGAGAGCCTGTATATAAATTAAA
ATAGTCAAGACAACACTGACCTTGCACTTGTACATAACTATACAGTAGTGTCCAGAATGTTCAGACATTCGGAGTGTACATAAAACAGAAAA
AATCTTCATGTATTTTATTAAATATAACAATGTCTGAGTTTCACCTAAGATGTTTTGTGCCATATGCTGGATATCCAGGTTCTCGCCAGG
CCCCGATACATGAATAACAAACCCAAGAAACGCATCCCCATTGTGTGATGTGTTCAGATGCATCTGGCACCAATTAGGTATTTCTTAAAACA
GGACTCATCTGTCAGAGTGCACATGAAAAATCAGGGAATCGAAACGACAGCGCTGGAGGAGACTCAGGAAGCAGAGGCGTCCCTGCCG
CTGCCCTTGGCCCTGCAAGCACATCATGACCCTTTCTGGCAGCCTCTTGGTGCTCTGGGTAGTGAGGGATGACCAGTCTTGTCCTGAGAAAT
```

FIG. 18A(6)

```
GTTTCTCTTAGTCTTCTTAAGTTCAAAGACTAACCTGTAGCAATCAGACTTTCCAAAAGGGGGTCTCCATTTTTTGTAGTTTTGTCTAAATTT

TTAATGACCATTTCCTGGAATCAGTTTATTATACTGAAACTGGGGGTGGGAGTAGGGAGCTAGTTTGTTGATAAATAGTTCCCATTTCCCC

GTGGAGAATTTGACATACCCTGGACTCCTGTGTGCCTCCTGCCATCCCTGCACACAGCCTGTGCCTCCCGTGTGGAGAG

AAGGCAACCCCAGATCCCCTGAGCTAACCGGAGGAAAGGCAGTCCTGGACAGAAGACTGTCAGCAGAAGGAAAGTACTGGACTACCCGTGG

GTAAGTCCTGCCATTCAAGACTGGAGACACCTGGGAAATAAAAGAGCAGGGCACTGCTGGTGGGAAGAGGCATTTACCTTCCAGTGCAAA

TCCTGCTCCTTTGATTAATGGGGTGTACTGGGGCCAGGGCTGATTCACTTCCTTGGGAGATGGTGGTGTTTTCATGAACATCTTTGATCC

TTCCATTTCATTTATTCATCCATTCAACAAGTATTTGCTAAACACTAAGCTAACTTAAGCTAATGCTAGGGTAGTGACTGAGATGTAAAAATA

GATTTTAGAATTAAAACAAAATCCAAGTCCTCACACCCCTGTCATCCCAGGAGATCTTTCCTTGTGGTGGTTTCTGTGAGAATTGGCCATCC

TGAGGACACAGCCAGGACGGCAGAGGCCTCCTGGCCTCTAGATAGCCAGGCCCACCAAGAGATATTGCCCCTTGATGAGAGTCAAACACCCTGCTACAAGGAGATGTTT

CCAGCCATTGCGGGTGGTTTCTAGATAGCCAGGCCCACCAAGAGATATTGCCCCTTGATGAGAGTCAAACACCCTGCTACAAGGAGATGTTT

TGAAATGGAGGGAAAATTGGCACCTCATCTTTAAAGGCAGCAGTAATGAATTGATTTCAGTAACTGAATTGTGCACAAAACATTCTAAAC

ACTAGTGAAGCCTGTTTCGTTGAACTAATTCTGGCTCTGGAAATGTTTTGTTTATAGTTATTACGATTCGTTTGTTGGATTCAAGCT

TAGTTTGTTAATATGTATAATTTAGCATCTATTACACTCATGTAAATATGGAGTAAGTATTGTAAACTATTTCATTGCGGGGATTGTGGGTG
```

FIG.18A(7)

TTATACATACATTTAGGACTGCAATTTTTTGGTATTTTTTGTATTGTAAAATAACAGCTAATTTAAGCAGGAACAAGAGAACTAAGGGAGGT
CTGTGCATTTTAAACACAAATGTGAAGAACTTGTATATAAACAAAGTAAATACTATATAATACAAACTTCCTTCTGAAATAAAAGTAGATCTG
GTAAAAAAAAAAAGAAAAAAAAAAAAA

FIG.18A(8)

MVAVAAAAATEARLRRRTAATAATAALAGRSGGPHRPCTATGAWRPGPRARLCLPRVLSRALPPPPLLPLLFSLLLLPLPREAEAAAVAAAVSGS

AAAEAKECDRPCVNGGRCNPGTGQCVCPAGWVGEQCQHCGGRFRLTGSSGFVTDGPGNYKYKTKCTWLIEGQPNRIMRLRFNHFATECSWDH

LYVYDGDSIYAPLVAAFSGLIVPERDGNETVPEVVATSGYALLHFFSDAAYNLTGFNITYSFDMCPNNCSGRGECKISNSSDTVECECSENW

KGEACDIPHCTDNCGFPHRGICNSSDVRGCSCFSDWQGPGCSVPVPANQSFWTREEYSNLKLPRASHKAVVNGNIMWVVGGYMFNHSDYNMV

LAYDLASREWLPLNRSVNNVVVRYGHSLALYKDKIYMYGGKIDSTGNVTNELRVFHIHNESWVLLTPKAKEQYAVVGHSAHIVTLKNGRVVM

LVIFGHCPLYGYISNVQEYDLDKNTWSILHTQGALVQGGYGHSSVYDHRTRALYVHGGYKAFSANKYRLADDLYRYDVDTQMMTILKDSRFF

RYLHTAVIVSGTMLVFGGNTHNDTSMSHGAKCFSSDFMAYDIACDRWSVLPRPDLHHDVNRFGHSAVLHNSTMYVFGGFNSLLLSDILVFTS

EQCDAHRSEAACLAAGPGIPCVWNTGSSQCISWALATDEQEEKLKSECFSKRTLDHDRCDQHTDCYSCTANTNDCHWCNDHCVPRNHSCSEG

QISIFRYENCPKDNPMYYCNKKTSCRSCALDQNCQWEPRNQECIALPENICGIGWHLVGNSCLKITTAKENTDNAKLFCRNHNALLASLTTQ

KKVEFVLKQLRIMQSSQSMSKLTLTPWVGLRKINVSYWCWEDMSPFTNSLLQWMPSEPSDAGFCGILSEPSTRGLKAATCINPLNGSVCERP

ANHSAKQCRTPCALRTACGDCTSGSSECMWCSNMKQCVDSNAYVASFPFGQCMEWYTMSTCPPENCSGYCTCSHCLEQPGCGWCTDPSNTGK

GKCIEGSYKGPVKMPSQAPTGNFYPQPLLNSSMCLEDSRYNWSFIHCPACQCNGHSKCINQSICEKCENLTTGKHCETCISGFYGDPTNGGK

CQPCKCNGHASLCNTNTGKCFCTTKGVKGDECQLCEVENRYQGNPLRGTCYYTLLIDYQFTFSLSQEDDRYYTAINFVATPDEQNRDLDMFI

FIG. 18B

NASKNFNLNITWAASFSAGTQAGEEMPVVSKTNIKEYKDSFSNEKFDFRNHPNITFFVYVSNFTWPIKIQIAFSQHSNFMDLVQFFVTFFSC
FLSLLLVAAVVWKIKQSCWASRRREQLLREMQQMASRPFASVNVALETDEEPPDLIGGSIKTVPKPIALEPCFGNKAAVLSVFVRLPRGLGG
IPPPGQSGLAVASALVDISQQMPIVYKEKSGAVRNRKQQPPAQPGTCICWGQGLSHARASEWHTRAICREGRGGEMAVRCGTEDWKPSKHLT
HLHDHKLSLTVSPIRVPASNLLLLHRKYLILQVQGADGCWRRPVSQENEHSGSLWKTVLGTVSTVQKTKDGVFTSRHSSSVVLEHGLLKTSQ
MNLVFISLLSFLKDVLFILARFRQLSLFQGVPFFLVENWSISFDHIKLGKGGYFKCQGQQCYFECKLVVVFYSNLINLVLIHLKLSLPFSLP
VPLLLHLTLPLSHIHTQTHTHNTKCLDFKIQLESAVFTLHSYILVKFKLPLAICFFSKIFAARKEFSHPRNISSSRDERKAEMNELKLLFLL
SKRTLSRRRPLPPPPCHPRPDKRSEERTHSCHASLSRKEHEHLGPLDQRASVCPAASSELVVHSQAGVDSDARKGTASHCQAEAAQSLEKDL
FALFPPGGARPTHPPSQTKVVAVRRAANADKDEKHMEKNGRGGKTLPNGKPNLRGWDSPLLLSQRALLGNCVFPIYGALYSGIMQQPPRSSL
LLQNLGSLALPYWDGPLDSNARVCEFGEILKRAKTAAFYLMQCLEREYCLFPNTNPTPMKNCLERCFQGITIKHYLMHRTPLLDSPLIKLLF

HITVKDQTFKRPLLSAPPSLLQNTAPMAPAVDWPLNSHRPPQQGQREAPGYCPPTRKILFVCSKDQFSAKEVSSPCSYALKYHAPPTAIWLC

LIFFLKDNVYFKGRKKQVKFHSAPAVGKPLNPPASPLQPTANSFLRPQGRKREWQGVRGAGLGACFQEGIGCHLAVLRVTREPVYKLKSRQH

PCTCTLYSSVQNVQTFGVYIKQKKSSCIFIKYNNVVSPKMFLCHMLDIQVLARPRYMNNKPKKRIPIVCVQMHLAPIRYFLKQDSSVRVHMK

NQAGNRNDSAGGDSGSRGVPAAALGPASTSPFLAASWCSGGMTSLVLRNVSLSLVQRLTCSNQTFQKGVLHFLFCLNFPFPGISLLYKLGVG

FIG.18C

VGSFVDKFPFPRGEFDIPWTPVCLLPSLHTAWGEACASPCGEKATPDPLSPGGKAVLDRRLSAEGKYWTTRGVLPFKTGDTWEIKRAGHCWW

EEAFYLPVQILLLFNGVYWGQGLIHFLGRWWCFHEHLSFHFIYSSIHSTSICTLTANARVVTEMKILELKQNPSPHTPVIPGDLSLWWFLEL

AILRTQPGRQRPPGLRACPAYLLKCLPHPNLAPAIAVVSRPGPPRDIAPESNTLPTRRCFEMERKIGTSSFKGSNGIDFQLNLCTKHSKHSL

FRTNSGSGNVFVLLFTISFVWIQAFVNMYNLASITLMIWSKYCKLFHCGDCGCYTYIDCNFLVFFVLNNSFKQEQENGRSVHFKHKCEELVY

KQKILYKLPSEIKVDLVKKKEKKKKK

FIG. 18D

ATGGTGGCGGTGGCCGCAGCGGCGGCCAACTGAGGCAAGGCTGAGGAGGAGGACGGCGGCGCAGGAGCGGCGGCCGCACCGACCCTGCACC

GCGACAGGGGCCGGGACCGCGCCGGCTGTGTCTCCCGCGGGTGCTGCCCCCGCCGCTGCCCGCTGCTCTTTTCGCTGCTG

CTGCTGCCGCTGCCCGGGAGGCCGAGGCCGCGGTGGCGGGCCGCTGCGGTCGCGCCAGCCGCGAGGCCAAGGAATGTGACCGGCCGTGTCAACGGCGGT

CGCTGCAACCCTGGCACCGGCCAGTGCGTCTGCCCCGCCGGCTGGGTGGGCGAGCACTGCGGGGGCCGCTTCAGACTAACTGGATCTTCTGGGTTTGTG

ACAGATGGACCTGGAAATTATAAATACAAAACGAAGTGCACGTGGCTCATTGAAGGACAGCCAAATAGAATAATGAGACTTCGTTCAATCATTTTGCTACAGAGTGT

AGTTGGGACCATTTATATGTTATGGGGACTCAATTGCTGCATTTTTTAGTGATGCTAGTTGCTGCGCTAGTTGCTGCAATGAGACTGTCCCT

GAGGTTGTGCCACATCAGGTTATGCCTTGCTGCATTTTTTAGTGATGCTCTTATAATTGACTGGATTTAATATTACTTACAGTTTTGATATGTGTCCAAATAAC

TGCTCAGGGCCGAGGAGAGTGTAAGATCAGTAATAGCAGCGATACTGTTGAATGTGAATGTTCTGAAAACTGGAAAGGTGAAGCATGTGACATTCCTCACTGTACAGAC

AACTGTGGTTTCCTCATCGAGGCATCTGCAATTCAAGTGATGTCAGAGGATGCTCCTGCTTCTCAGACTGGCAGGGTCCTGGATGTTCAGTTCCTGTACCAGCTAAC

CAGTCATTTTGGACTCGAGAGGAATATTCTAACTTAAAGCTCCCCAGAGCATCTCATAAAGCTGTGGTCAATGAAACATTATGTGGGTTGTTGGAGGATATATGTTC

AACCACTCAGATTATAACATGTTCTAGCGTATGACCTTGCTTCTTAGGGAGTGGCTTCCACTAAACGTTCTGTGAACAATGTGGTTGTTAGATATGGTCATTCTTTG

GCATTATACAAGGATAAAATTTACATGTATGGAGGAAAAATTGATTCAACTGGGAATGTGACCAATGAGTTGAGAGTTTTCACATTCATAATGAGTCATGGGTGTTG

TTGACCCCCTAAGGCAAAGGAGCAGTATGCAGTGGTTGGGCACTCTGCACACATTGTTACTGAAGAATGGCCGAGTGGTCATGCTGGTCATCTTTGGTCACTGCCCT

FIG. 19A

```
CTCTATGGATATATAAGCAATGTGCAGGAATATGATTTGGATAAGAACACATGGAGTATATTACACACCCAGGGTGCCCTTGTGCAAGGGGGTTACGGCCATAGCAGT

GTTTACGGACCATAGGACCAGGGCCCTATACGTTCATGTGGCCAATAAGTCTTTCAGTGCCAATAAGTACCGGCTTGCAGATGATCTCTACGATATGATGTGGATACC

CAGATGTGGACCATTCTTAAGGACAGCCGATTTTTCCGTTACTGCACACAGCTGTGATAGTGAGTGGAACCATGCTGGTGTTTGGGGGAAACACACACAATGACACA

TCTATGAGCCATGGGCCAAATGCTTCTCTTCAGATTTCATGGCCTATGACATTGCCTGTGACCGCTGGTCAGTGCTTCCCAGACCTGATCTCCACCATGATGTCAAC

AGATTTGGCCATTCAGCAGTCTTACACAACAGCACCATGTATGTGTTCGGTGGTTTCAATAGTCTCCTCCTCAGCGACATCTGGTATTCACCTCGGAACAGTGTGAT

GCGCATCGGAGTGAAGCCGCTTGTTTAGCAGCAGGACCTGGTATTCGGTGTGTGGAACACAGGGTCGTCTCAGTGTATCTCGTGGGCGCTGGCAACTGATGAACAA

GAAGAAAAGTTAAAATCAGAATGTTTTCCAAAAGAACTCTTGACCATGACCAGCACAGATGTTACAGCTGCACAGCCAACACCAATGACTGCCAC

TGGTGCAATGACCATTGTGTCCCCAGGAACCACAGCTGCTCAGAGAAGGCCAGATCTCCATTTTTAGGTATGAGAATTGCCCCAAGGATAACCCTATGTACTACTGTAAC

AAGAAGACCAGCTGCAGGAGCTGTGCCCTGGAGCCCAGTGGGAGCCCAGAGTGCATTGCCCTGCCGAAAATATCTGTGCATTGGCTGGCAT

TTGGTTGGAAACTCATGTTTGAAAATTACTACTGCCAAGGAGAATTATGACAATGCTAAATTGTTCTGTAGGAACCACAATGCCCTTTGGCTTCTCTTACAACCCAG

AAGAAGGTAGAATTTGTCCTTAAGCAGCTGCGAATAATGCAGTCATCTCAGAGCATGTCCAAGCTGATGCCGTGATTCTGTGAATTTTATCAGAACCCAGTGTCC

TACTGGTGCTGGGAAGATATGTCCCCATTTACAAATAGTTTACTACAGTGTCTGTGAAAGGCCTGCAAACCACAGTGCCGGACACCATGTGCCTGAGGACA

CGGGGACTGAAGGCTGCAACCTGCATCAACCCACTCAATGTGTAGTGTCTGAAAGGCCTGCAAACCACAGTGCAAGCAGTGCCGGACACCATGTGCCTGAGGACA
```

FIG.19B

GCATGTGGAGATTGCACCAGCGGCAGCTCTGAGTGCATGTGGTGCAGCAACATGAAGCAGTGTGTGGACTCCAATGCCTATGTGGCCTCCTTCCCTTTTGGCCAGTGT

ATGGAATGGTATACGATGAGCACCTGCCCCCTGAAATTGTTCAGGCTACTGTAGTCATTGCTTGGAGCAACCAGGCTGTGGCTGGTGTACTGATCCAGC

AATACTGGCAAAGGGAAATGCATAGAGGGGTTCCTATAAAGGACCAGTGAAGATGCCTTCGCAAGCCCCTACAGGAAATTTCTATCCACAGCCCCTGCTCAATTCCAGC

ATGTGTCTAGAGGACAGCAGATACAACTGGTCTTTCATTCACTGTCCAGCTTGCCAATGCAACGGCCACAGTAAATGCATCAATCAGAGCATCTGTGAGAAGTGTGAG

AACCTGACCACCAGGCAAGCACTGCGAGACCTGCATATCTGGCTTCTACGGTGATCCCACCAATGGAGGGAAATGTCAGCCATGCAAGTGCAATGGGCACGCGTCTG

TGCAACACCAACACGGGCAAGTGCTTCTGCACCACCAAGGGCGTCAAGGGGGACGAGTGCCAGCTATGTGAGGTAGAAAATGATACCAAGGAAACCCTCTCAGAGGA

ACATGTTATTATACTCTTCTTATTGACTATCAGTTCACCTTTAGTCTATCCCAGGAAGATGATCGCTATTACACAGCTATCAATTTGTGGCTACTCCTGACGAACAA

AACAGGGATTTGGACATGTTCATCAATGCCTCCAAGAATTTCAACCTCACCTGGGCTGCCAGTTCTCAGCTGGAACCCAGGCTGGAGAAGAGATGCCTGTT

GTTTCAAAAACCAACATTAAGGAGTACAAAGATAGTTTCTCTAATGAGAAGTTTGATTTTCGCAACCACCCAAATATCACTTCTTTGTTTATGTCAGTAATTTCACC

TGGCCCATCAAAATTCAGGTGCAAACTGAACAATGAGGACGCATGGACACAGGAAGGGAACATCACACACCAGGGCCTGTTGTGGGGTGGGGGAAGGGGAAGGGAT

AGCATTAGGGGATATACCTAATGTTAAATGACGAGTTAAATGGGTGCAGCACACAACATGGCATATGTATACATATGTAACAAACCTGCATGTGTGCACATGTACCC

TAAAACTTAAAGTATAATTAAAAAAAAAAAAAAAGAAAAAAAAAAAAAAAAAAAAAAAAAAAAAAAA

FIG. 19C

MVAVAAAATEARLRRRTAATAALAGRSGGPHRPCTATGAWRPGPRARLCLPRVLSRALPPPPLPLLFSLLLLPLPREAEAAAVAAAVSGSAAAEAKECDRPCVNGG
RCNPGTGQCVCPAGWVGEQCQHCGGRFRLTGSSGFVTDGPGNYKYTKCTWLIEGQPNRIMRLRFNHFATECSWDHLYVYDGDSIYAPLVAAFSGLIVPERDGNETVP
EVVATSGYALLHFFSDAAYNLTGFNITYSFDMCPNNCSGRGECKISNSSDTVECECSENWKGEACDIPHCTDNCGFPHRGICNSSDVRGCSCFSDWQGPGCSVPVPAN
QSFWTREEYSNLKLPRASHKAVVNGNIMWVVGGYMFNHSDYNMVLAYDLASREWLPLNRSVNNVVVRYGHSLALYKDKIYMYGGKIDSTGNVTNELRVFHIHNESWVL
LTPKAKEQYAVVGHSAHIVTLKNGRVVMLVIFGHCPLYGYISNVQEYDLDKNTWSILHTQGALVQGGYGHSSVYDHRTRALYVHGGYKAFSANKYRLADDLYRYDVDT
QMWTILKDSRFFRYLHTAVIVSGTMLVFGGNTHNDTSMSHGAKCFSSDFMAYDIACDRWSVLPRPDLHHDVNRFGHSAVLHNSTMYVFGGFNSLLLLSDILVFTSEQCD
AHRSEAACLAAGPGIRCVWNTGSSQCISWALATDEQEEKLKSECFSKRTLDHDRCDQHTDCYSCTANTNDCHWCNDHCVPRNHSCSEGQISIFRYENCPKDNPMYYCN
KKTSCRSCALDQNCQWEPRNQECIALPENICGIGWHLVGNSCLKITTAKENYDNAKLFCRNHNALLASLTTQKKVEFVLKQLRIMQSSQSMSKLTLTPWVGLRKINVS
YWCWEDMSPFTNSLLQWMPSEPSDAGFCGILSEPSTRGLKAATCINPLNGSVCERPANHSAKQCRTPCALRTACGDCTSGSSECMWCSNMKQCVDSNAYVASFPFGQC
MEWYTMSTCPPENCSGYCTCSHCLEQPGCGWCTDPSNTGKGKCIEGSYKGPVKMPSQAPTGNFYPQPLLNSSMCLEDSRYNWSFIHCPACQCNGHSKCINQSICEKCE
NLTTGKHCETCISGFYGDPTNGGKCQPCKCNGHASLCNTNTGKCFCTTKGVKGDECQLCEVENRYQGNPLRGTCYTLLIDYQFTFSLSQEDDRYTAINFVATPDEQ
NRDLDMFINASKNFNLNITWAASFSAGTQAGEEMPVVSKTNIKEYKDSFSNEKFDFRNHPNITFFVYVSNFTWPIKIQVQTEQGRMDTGRGTSHTRACCGVGGRGRDS
IRGYTCMTSWVQHTNMAYVYICNKPACCAHVPNLKYNKKKKKKKKKKKKKKKKK

FIG. 19D

ATGGTGGCGGTGGCCGCGCAGCGGCGGCAACTGAGGCAAGGCTGAGGAGGAGGACGGCGGGACGGCGCTCGCGGGCAGGAGGCGGGCCGCACCGACCCTGCACC

GCGACAGGGGCCTGGAGGCCGGGACGCGCCGGCTGTGTCTCCCGGGTGCTGTCGCGGGGCGCTGCCCCCGCGCGCTGCCGCTGCTCTTTTCGCTGCTG

CTGCTGCCGCTGCCCCGGGAGGCCGCTGCGGTGGCGGCGGGCCGAGGCCGCTGCGGTCGGCCTCGGCGCAGCCGAGGCCAAGGAATGTGACCGGCGTGTCAACGGCGGT

CGCTGCAACCCTGCACCGGCCAGTGCGTCTGCCCCGCGCTGGGTGGGCGAGCAATGCCAGCACTGCGGGGCCGCTTCAGACTAACTGGATCTTCTGGGTTTGTG

ACAGATGGACCTGGAAATTATAAATACAAAACGAAGTGCACGTGGCTCATTGAAGGACAGCCAAATAGAATAATGAGACTTCGTTCAATCATTTTGCTACAGAGTGT

AGTTGGGACCATTTATATGTTTATGATGGGACTCAATTTATGCACGCGCTAGTGTGCTGCATTTAGTGGGCCTCATTGTTCCTGAGAGAGATGGCAATGAGACTGTCCCT

GAGGTTGTTGCCACATCAGGTTATGCCTTGCTGCATTTTTTAGTGATGCTGCTTATAATTGACTGGATTTAATATTACTAGTTTTGATATGTGTCCAAATAAC

TGCTCAGGCCGAGGAGAGTGTAAGATCAGTAATGCAGGCGATACTGTTGAATGTTCTGAAAACTGGAAAGGTGAAGCATGTGACATTCCTCACTGTACAGAC

AACTGTGGTTTCCTCATCGAGGCATCTGCAATTCAAGTGATGTCAGAGGATGCTCCTGCTTCTCAGACTGGCAGGGTCCTGGATGTTCAGTTCCTGTACCAGCTAAC

CAGTCATTTTGGACTCGAGAGGAATATTCTAACTTAAAGCTCCCCAGAGCATCTCATAAAGCTGTGGTCAATGGAAACATTATGTGGGTTGTTGGAGGATATATGTTC

AACCACTCAGATTATAACATGGTTCTAGCGTATGACCTTGCTTCTAGGGAGTGGCTTCCACTAAACCGTTCTGTGAACAATGTGGTTGTTAGATATGGTCATTCTTTG

GCATTATACAAGGATAAAATTTACATGTATGGAGGAAAAATTGATTCAACTGGGAATGTGACCAATGAGTTGAGAGTTTTCACATTCATAATGAGTCATGGGTGTTG

TTGACCCCTAAGGCAAAGGAGGCAGTATGCAGTGGTTGGGCACTCTGCACACATTGTTACACTGAAGAATGGCCGAGTGGTCATGCTGGTCATCTTTGGTCACTGCCCT

FIG. 20A

```
CTCTATGGATATATAAGCAATGTGCAGGAATATGATTGGATAAGAACACATGGAGTATATTACACACCCAGGGTGCCCTTGTGCAAGGGGTTACGGCCATAGCAGT
GTTTACGACCATAGGACCAGGGCCCTATACGTTCATGGTGGCTACAAGGCTTTCAGTGCCAATAAGTACCGGCTTGCAGATGATCTCTACCGATATGATGTGGATACC
CAGATGTGGACCATTCTTAAGGACAGCCGATTTTTCCGTTACTTGCACACAGCTGTGATAGTGAGTGGAACCATGTGGTGTTTGGGGGAAACACACACAATGACACA
TCTATGAGCCATGCGCCAAATGCTTCTCTCTTCAGATTTCATGGCCTATGACATTGCCTGTGTGACCGCTGGTCAGTGCTTCCCAGACCTGATCTTCCACCATGATGTCAAC
AGATTTGGCCATTCAGCAGTCTTACAACAGCACCATGTATGTTCGGTGGTTTCAATAGTCTCCTCCTCAGCGACATCCTGTATTCACCTCGGAACAGTGTGAT
GCGCATCGGAGTGAAGCCGCTTGTTAGCAGCAGGACCTGGTATTCGGTGTGTGGAACACAGGGTCGTCTCAGTGTATCTCGTGGGCGCTGCAACTGATGAACAA
GAAGAAAAGTTAAAATCAGAATGTTTTCCAAAGAACTCTTGACCATGACAGATGTGACCAGCAGCTGCACACAGATTGTTACAGCTGCACACCAACATGACTGCCAC
TGGTGCAATGACCATTGTGTCCCCAGGAACCACAGCTGCTCAGAAGGCCAGATCTCCATTTTTAGGTATGAGAATTGCCCCAAGGATAACCCTATGTACTGTAAC
AAGAAGACCAGCTGCAGGAGCTGCCCTGGACCAGAACTGCCAGTGGGAGCCCCGGAATCAGGAGTGCATTGCCCTGCCCGGTAGGCCTTGCAGGGTCATCTTGGTG
TGTGTGGGTCCATTACTTCAGCCTGCTCCCCAACACTGTGCAGCCTAAGTTGAACCTAGCAGAGGGGAAGAGCTAATTCTGTCCATTCATCCCCCACACGAGTATT
ATGGGCTTTTTGTTTTTAACTAAAATACAGTTCTTAAGTATTTGTTCCTACTGTCCTTTGAAATAAAGTGAAACATCCTTTGCTGCTCTGTAAAAAAAAAAAAAA
AAAAAAAAAAAAAAAAAAAAAAAAAAAAAAAAAA
```

FIG.20B

MVAVAAAAATEARLRRRTAATAALAGRSGGPHRPCTATGAWRPGPRARLCLPRVLSRALPPPPLLPLLFSLLLLPLPREAEAAVAAVSGSAAAEAKECDRPCVNGG

RCNPGTGQCVCPAGWVGEQCQHCGGRFRLTGSSGFVTDGPGNYKYTKCTWLIEGQPNRIMRLRFNHFATECSWDHLYVYDGDSIYAPLVAAFSGLIVPERDGNETVP

EVVATSGYALLHFFSDAAYNLTGFNITYSFDMCPNNCSGRGECKISNSSDTVECECSENWKGEACDIPHCTDNCGFPHRGICNSSDVRGCSCFSDWQGPGCSVPVPAN

QSFWTREEYSNLKLPRASHKAVVNGNIMWVGGYMFNHSDYNMVLAYDLASREWLPLNRSVNNVVVRYGHSLALYKDKIYMYGGKIDSTGNVTNELRVFHIHNESWVL

LTPKAKEQYAVVGHSAHIVTLKNGRVVMLVIFGHCPLYGYISNVQEYDLDKNTWSILHTQGALVQGGYGHSSVYDHRTRALYVHGGYKAFSANKYRLADDLYRYDVDT

QMWTILKDSRFFRYLHTAVIVSGTMLVFGGNTHNDTSMSHGAKCFSSDFMAYDIACDRWSVLPRPDLHHDVNRFGHSAVLHNSTMYVFGGFNSLLLSDILVFTSEQCD

AHRSEAACLAAGPGIRCVWNTGSSQCISWALATDEQEEKLKSECFSKRTLDHDRCDQHTDCYSCTANTNDCHWCNDHCVPRNHSCSEGQISIFRYENCPKDNPMYYCN

KKTSCRSCALDQNCQWEPRNQECIALPGRPCRVILVCVGPLLQPASPNTVQPKLNLAEGKSFCPFIPHTSIMGFFVFNNTVLKYLFLLSFEIKNILCCSVKKKKKKK

KKKKKKK

FIG. 20C

METHODS AND COMPOSITION FOR THE DIAGNOSIS AND TREATMENT OF BODY WEIGHT DISORDERS, INCLUDING OBESITY

This is a continuation-in-part of U.S. patent application Ser. No. 09/245,041, filed on Feb. 5, 1999, now U.S. Pat. No. 6,274,339 which is incorporated herein by reference in its entirety. Priority of provisional application No. 60/093,630 filed on Jul. 21, 1998, and of provisional application No. 60/104,978 filed on Oct. 20, 1998, each of which is incorporated herein by reference in its entirety, is also claimed under 35 U.S.C. §119(e) (1).

1. INTRODUCTION

The present invention relates to mammalian mahogany genes, including the human mahogany gene, which are novel genes involved in the control of mammalian body weight. The invention encompasses nucleotide sequences of the mahogany gene, host cell expression systems of the mahogany gene, and hosts which have been transformed by these expression systems, including transgenic animals. The invention also encompasses novel mahogany gene products, including mahogany proteins, polypeptides and peptides containing amino acid sequences mahogany proteins, fusion proteins of mahogany proteins polypeptides and peptides, and antibodies directed against such mahogany gene products.

The present invention also relates to methods and compositions for the diagnosis and treatment of mammalian body weight disorders, including obesity, cachexia, and anorexia, and for the identification of subjects susceptible to such disorders. Further, the invention relates to methods of using the mahogany gene and gene products of the invention for the identification of compounds which modulate the expression of the mahogany gene and/or the activity of the mahogany gene product. Such compounds can be useful as therapeutic agents in the treatment of mammalian body weight disorders, including obesity, cachexia, and anorexia.

2. BACKGROUND OF THE INVENTION

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa, which together affect approximately 0.2% of the female population of the western world, also pose serious health threats. Further, such disorders as anorexia and cachexia (wasting) are also prominent features of other diseases such as cancer, cystic fibrosis, and AIDS.

Obesity, defined as an excess of body fat relative to lean body mass, also contributes to other diseases. For example, this disorder is responsible for increased incidence of diseases such as coronary artery disease, hypertension, stroke, diabetes, hyperlipidemia, and some cancers (See, e.g., Nishina, P. M. et al., 1994, Metab. 43: 554–558; Grundy, S. M. & Barnett, J. P., 1990, Dis. Mon. 36: 641–731). Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity (Friedman, J. M. et al., 1991, Mammalian Gene 1: 130–144).

The epidemiology of obesity strongly shows that the disorder exhibits inherited characteristics (Stunkard, 1990, N. Eng. J. Med. 322: 1438). Moll et al. have reported that, in many populations, obesity seems to be controlled by a few genetic loci (Moll et al., 1991, Am. J. Hum. Gen. 49: 1243). In addition, human twin studies strongly suggest a substantial genetic basis in the control of body weight, with estimates of heritability of 80–90% (Simopoulos, A. P. & Childs, B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65: 279–287).

In other studies, non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake. In addition, it is a commonplace experience in animal husbandry that different strains of swine, cattle, etc., have different predispositions to obesity. Studies of the genetics of human obesity, and of animal models of obesity demonstrate that obesity results from complex defective regulation of both food intake, food induced energy expenditure, and of the balance between lipid and lean body anabolism.

There are a number of genetic diseases in man and other species which feature obesity among their more prominent symptoms, along with, frequently, dysmorphic features and mental retardation. For example, Prader-Willi syndrome (PWS; reviewed in Knoll, J. H. et al., 1993, Am. J. Med. Genet. 46: 2–6) affects approximately 1 in 20,000 live births, and involves poor neonatal muscle tone, facial and genital deformities, and generally obesity.

In addition to PWS, many other pleiotropic syndromes have been characterized which include obesity as a symptom. These syndromes are genetically straightforward, and appear to involve autosomal recessive alleles. Such diseases include, among others, Ahlstroem, Carpenter, Bardet-Biedl, Cohen, and Morgagni-Stewart-Monel Syndromes.

A number of models exists for the study of obesity (see, e.g., Bray, G. A., 1992, Prog. Brain Res. 93: 333–341; and Bray, G. A., 1989, Amer. J. Clin. Nutr. 5: 891–902). For example, animals having mutations which lead to syndromes that include obesity symptoms have also been identified. Attempts have been made to utilize such animals as models for the study of obesity, and the best studied animal models to date for genetic obesity are mice. For reviews, see, e.g., Friedman, J. M. et al., 1991, Mamm. Gen. 1: 130–144; Friedman, J. M. and Liebel, R. L., 1992, Cell 69: 217–220.

Studies utilizing mice have confirmed that obesity is a very complex trait with a high degree of heritability. Mutations at a number of loci have been identified which lead to obese phenotypes. These include the autosomal recessive mutations obese (ob), diabetes (db), fat (fat), and tubby (tub).

The dominant Yellow mutation (Ay) at the agouti locus causes a pleiotropic syndrome which causes moderate adult onset obesity, a yellow coat color, and a high incidence of tumor formation (Herberg, L. and Coleman, D. L., 1977, Metabolism 26:59), and an abnormal anatomic distribution of body fat (Coleman, D. L., 1978, Diabetologia 14:141–148). The mutation causes the widespread expression of a protein which is normally seen only in neonatal skin (Michaud, E. J. et al., 1994, Genes Devel. 8:1463–1472). The agouti protein has been reported to be a competitive antagonist of α-MSH binding to the melanocortin receptors MC1-R and MC4-R in vitro (Lu et al., 1996, Nature 371:799–802), and the authors speculated that de-regulated ubiquitous expression of agouti may lead to obesity by antagonism of melanocortin receptors expressed outside the hair follicles.

Mahogany (mg) and mahoganoid (md) are mutations that suppress the phenotypic effects of agouti protein in vivo (Lane and Green, 1960, J. Hered. 51: 228–230). The mahogany and mahoganoid mutation have been-mapped to mouse chromosomes 2 and 16, respectively (Green, 1989, "Catalog of mutant genes and polymorphic loci", pp. 12–403 in Genetic Variants and Strains of the Laboratory Mouse, Lyon, M. F. and Searle, A. G., eds., Oxford University Press, Oxford). Mutations of both mg and md have been shown to suppress the effects of agouti on obesity as well as on coat color (Miller et al., 1997, Genetics 146: 1407–1415).

In summary, therefore, obesity, which poses a major, worldwide health problem, represents a complex, highly heritable trait. Given the severity, prevalence, and potential heterogeneity of such disorders, there exists a great need for the identification of those genes that participate in the control of body weight.

3. SUMMARY OF THE INVENTION

The present invention relates to the identification of novel nucleic acid molecules and proteins encoded by such nucleic acid molecules that are involved in the control of mammalian body weight, and which, further, are associated with mammalian body weight disorders such as obesity, cachexia, and anorexia. The nucleic acid molecules of the present invention represent the genes corresponding to the mammalian mahogany gene, including the human mahogany gene.

In particular, the compositions of the present invention include nucleic acid molecules which comprise the following sequences: (a) nucleotide sequences of the mahogany gene, including, e.g., murine mahogany sequences as shown in FIGS. 2A, 3B–D, 6A–B, 8A, and 9A, as well as allelic variants and homologs thereof, and human mahogany sequences, as shown, e.g., in FIGS. 10A, 18A, 19A and 20A, as well as allelic variants and homologs thereof; (b) nucleotide sequences that encode the mahogany gene product amino acid sequences, as shown, e.g., in in FIGS. 2B, 8B, 9B, 10B, 17, 18B, 19B and 20B; (c) nucleotide sequences that encode portions of the mahogany gene product corresponding to its functional domains and individual exons; (d) nucleotide sequences comprising the novel mahogany gene sequences disclosed herein that encode mutants of the mahogany gene product in which all or a part of one or more of the domains is deleted or altered, as shown, e.g., in FIG. 6; (e) nucleotide sequences that encode fusion proteins comprising the mahogany gene product, or one or more of its domains fused to a heterologous polypeptide; (f) nucleotide sequences within the mahogany gene, as well as chromosome sequences flanking the mahogany gene, see, e.g., FIG. 3, which can be utilized as part of the methods of the present invention for the diagnosis of mammalian body weight disorders, including obesity, cachexia, and anorexia, which are mediated by the mahogany gene, as well as for the identification of subjects susceptible to such disorders; (g) nucleic acid sequences that hybridize to the above described sequences under stringent or moderately stringent conditions, particularly human mg homologs. The nucleic acid molecules of the invention include, but are not limited to, cDNA and genomic DNA sequences of the mahogany gene.

The present invention also encompasses expression products of the nucleic acid molecules listed above; i.e., proteins and/or polypeptides that are encoded by the above mahogany nucleic acid molecules.

Agonists and antagonists of the mahogany gene and/or gene product are also included in the present invention. Such agonists and antagonists will include, for example, small molecules, large molecules, and antibodies directed against the mahogany gene product. Agonists and antagonists of the invention also include nucleotide sequences, such as antisense and ribozyme molecules, and gene or regulatory sequence replacement constructs, that can be used to inhibit or enhance expression of the mahogany gene.

The present invention further encompasses cloning vectors, including expression vectors, that contain the nucleic acid molecules of the invention and can be used to express those nucleic acid molecules in host organisms. The present invention also relates to host cells engineered to contain and/or express the nucleic acid molecules of the invention. Further, host organisms which have been transformed with these nucleic acid molecules are also encompassed in the present invention. Host organisms of the invention include organisms transformed with the cloning vectors described above, e.g., transgenic animals, particularly non-human transgenic animals, and particularly transgenic non-human mammals.

The transgenic animals of the invention include animals that express a mutant variant or polymorphism of a mahogany gene, particularly a mutant variant or polymorphism of a mahogany gene that is associated with a weight disorder such as obesity, cachexia, or anorexia. The transgenic animals of the invention further include those that express a mahogany transgene at higher or lower levels than normal. The transgenic animals of the invention further include those which express the mahogany gene in all their cells, "mosaic" animals which express the mahogany gene in only some of their cells, and those in which the mahogany gene is selectively introduced into and expressed in a specific cell type(s). The transgenic animals of the invention also include "knock-out" animals. Knock-out animals comprise animals which have been engineered to no longer express the mahogany gene.

The present invention also relates to methods and compositions for the diagnosis of mammalian body weight disorders, including obesity, cachexia, and anorexia, as well as for the identification of subjects susceptible to such disorders. Such methods comprise, for example, measuring expression of the mahogany gene in a patient sample, or detecting a mutation in the mahogany gene in the genome of a mammal, including a human, suspected of exhibiting such a weight disorder. The nucleic acid molecules of the invention can also be used as diagnostic hybridization probes, or as primers for diagnostic PCR analysis to identify of mahogany gene mutations, allelic variations, or regulatory defects, such as defects in the expression of the mahogany gene. Such diagnostic PCR analyses can be used to diagnose individuals with a body weight disorder associated with a particular mahogany gene mutation, allelic variation, or regulatory defect. Such diagnostic PCR analyses can also be used to identify individuals susceptible to such body weight disorders and hyperphagia.

Methods and compositions, including pharmaceutical compositions, for the treatment of body weight disorders such as obesity, cachexia, and anorexia are also included in the invention. Such methods and compositions are capable of modulating the level of mahogany gene expression and/or the level of activity of the mahogany gene product. Such methods include, for example, modulating the expression of the mahogany gene and/or the activity of the mahogany gene product for the treatment of a body weight disorder which is mediated by some other gene, for example by the agouti gene.

The invention still further relates to methods for identifying compounds which modulate the expression of the mammalian mahogany gene and/or the synthesis or activity of mammalian mahogany gene products. Such compounds include therapeutic compounds which can be used as pharmaceutical compositions to reduce or eliminate the symptoms of mammalian body weight disorders such as obesity, cachexia, and anorexia. Cellular and non-cellular assays are described that can be used to identify compounds that interact with the mahogany gene and/or gene product, e.g., modulate the activity of the mahogany gene and/or bind to the mahogany gene product. Such cell-based assays of the invention utilize cells, cell lines, or engineered cells or cell lines that express the mahogany gene product.

In one embodiment, such methods comprise contacting a compound to a cell that expresses a mahogany gene, measuring the level of mahogany gene expression, gene product expression, or gene product activity, and comparing this level to the level of mahogany gene expression, gene product expression, or gene product activity produced by the cell in the absence of the compound, such that if the level obtained in the presence of the compound differs from that obtained in its absence, a compound that modulates the expression of the mammalian mahogany gene and/or the synthesis or activity of mammalian mahogany gene products has been identified.

In an alternative embodiment, such methods comprise administering a compound to a host, e.g., a transgenic animal that expresses a mahogany transgene or a mutant mahogany transgene, and measuring the level of mahogany gene expression, gene product expression, or gene product activity. The measured level is compared to the level of mahogany gene expression, gene product expression, or gene product activity in a host that is not exposed to the compound, such that if the level obtained when the host is exposed to the compound differs from that obtained when the host is not exposed to the compound, a compound that modulates the expression of the mammalian mahogany gene and/or the synthesis or activity of mammalian mahogany gene products, and/or the symptoms of a mammalian body weight disorder, such as obesity, cachexia, or anorexia, has been identified.

The Example presented in Section 6, below, describes the genetic and physical mapping of the mahogany gene to a specific 700 kb interval of mouse chromosome 2. The example presented in Section 7, below, describes the identification of a transcription unit within this chromosome interval, referred to herein as the MG gene, which represents the mahogany gene. The expression and sequence analysis of this candidate mahogany gene is described in the example presented in Section 8, below. These experiments prove that the candidate gene MG is indeed the mahogany gene. The example presented in Section 9, below, presents data demonstrating that the mechanism of mahogany action is specific for diet-induced obesity, therefore supporting the use of mahogany antagonists as a specific therapeutic for treatment of diet-induced body weight disorders. The example presented in Section 10, below, presents the identification and characterization of the human mg gene, variants thereof and polypeptides encoded by the human mahogany sequences.

DEFINITIONS

As used herein, the following terms shall have the abbreviations indicated.

BAC, bacterial artificial chromosomes
bp, base pair(s)
EST, expressed sequence tag
mg, mahogany gene
RFLP, restriction fragment length polymorphism
RT-PCR, reverse transcriptase PCR
SSCP, single-stranded conformational polymorphism
SSLP, simple sequence length polymorphisms
STS, short tag sequence
YAC, yeast artificial chromosome

4. BRIEF DESCRIPTION OF THE FIGURES

FIG. 1. Physical map of the mahogany interval of mouse chromosome 2.

FIGS. 2A(1)–2A(9). Panel A(1)–A(3): cDNA nucleotide sequence of the wild-type (C57BL/6J) murine mahogany gene (SEQ ID NO: 1), including the 5' and 3' untranslated regions, and Panel B: the derived amino acid sequence (SEQ ID NO: 2) of the mahogany gene product.

Figure 3A:
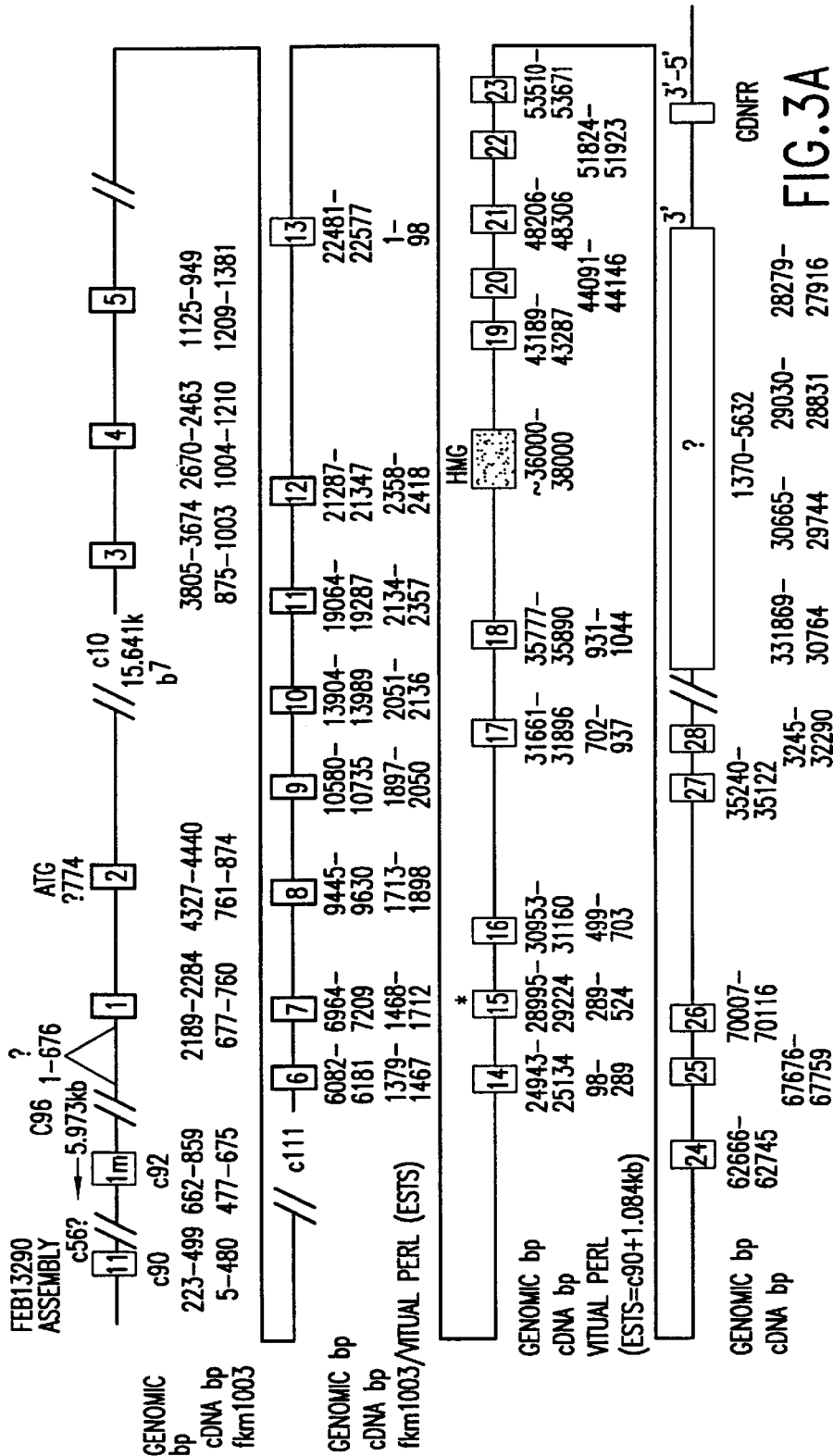

FIGS. 3A and 3B(1)–3B(97) and 3C(1)–3C(6) and 3D(1)–3D(86). Genomic structure and nucleotide sequences derived from the wild-type (C57BL/6J) mouse genomic regions containing the mg gene. Panel A, genomic structure; Panel B(1)–B(9), genomic sequence c56 (SEQ ID NO: 3); Panel C(1)–C(4), genomic sequence c96 (SEQ ID NO: 4); Panel D(1)–D(37), genomic sequence of c110/111 (SEQ ID NO: 5).

FIG. 4. Structural depiction of MG cDNA without introns. CUB=CUB domain, metal=metallothionin domain; T-transmembrane domain.

FIGS. 5(1)–5(4). Nucleotide sequence of primers (SEQ ID NOS.20–124) used to amplify each of the exons in the mg gene.

FIG. 6. Nucleotide sequence of the wild-type (SEQ ID NO: 6) and mahogany mutant (SEQ ID NO: 7) sequences in exon 15 of the MG gene. Bases shown in bold are deleted in Mg3J mutant mg.

Figure 7:
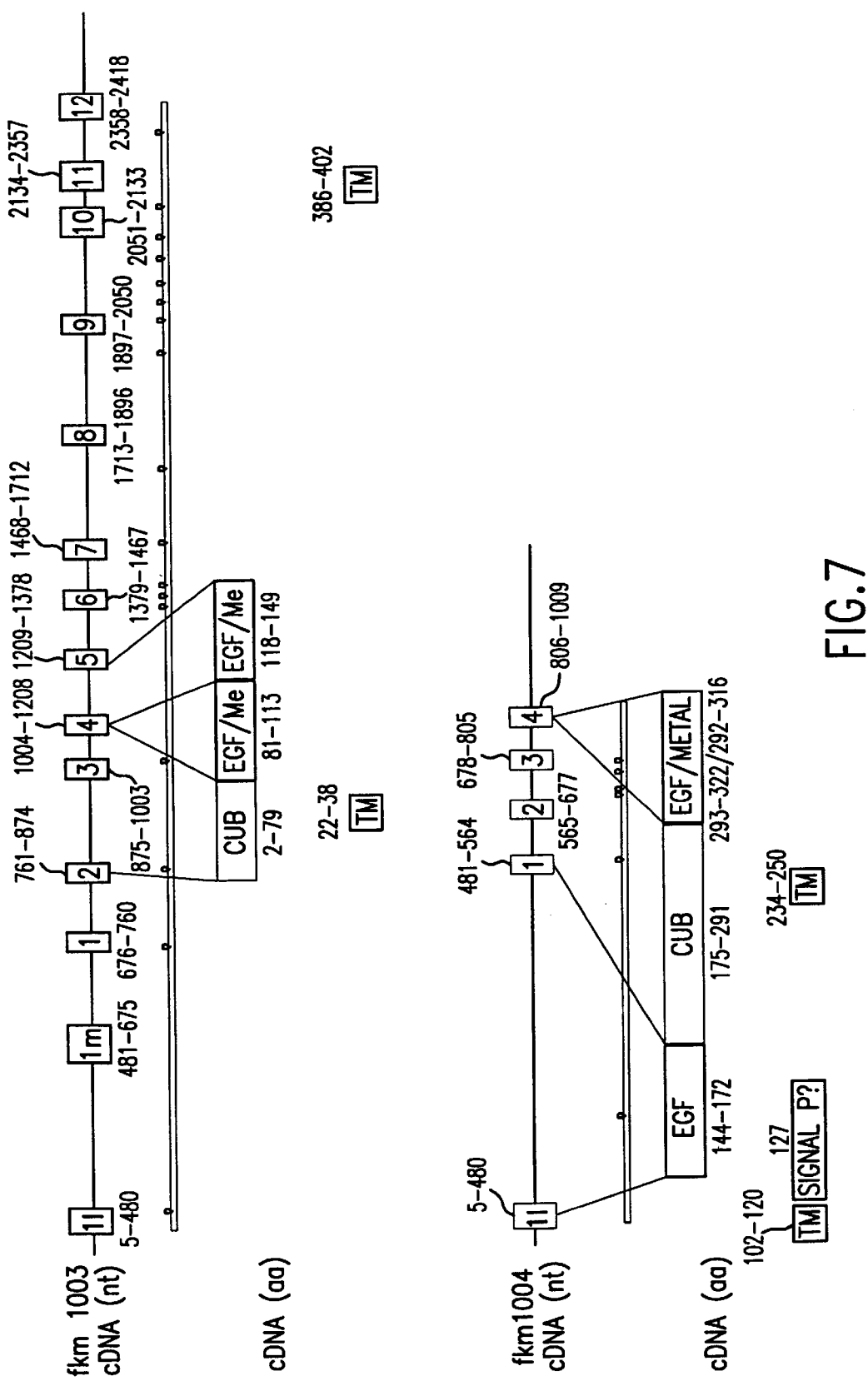
Figure 8E:
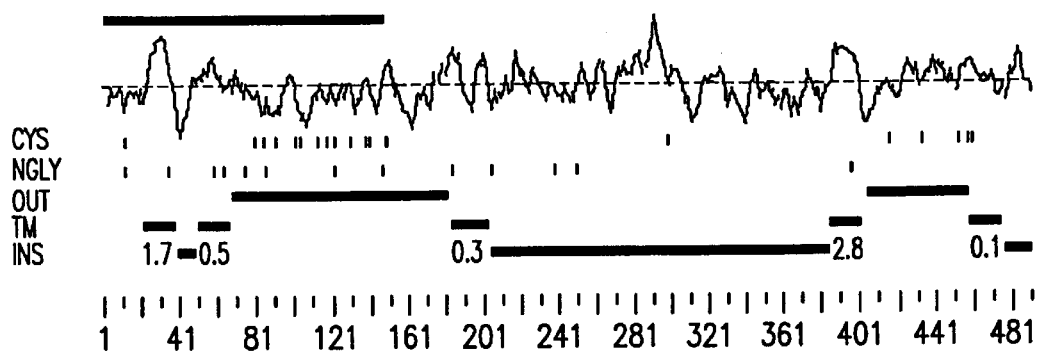

FIG. 7. Differential 5' start sequences in the murine mahogany gene showing splice forms akm1003 and akm1004.

FIGS. 8A–8E. Panel A, cDNA sequence (SEQ ID NO: 8) from one form of the differential 5' start site found in the murine (akm1003), Panel B, amino acid sequence (SEQ ID NO: 9) encoded by the cDNA of Panel A; Panel C, hydropathy plot of the akm1003 amino acid sequence.

Figure 9C:
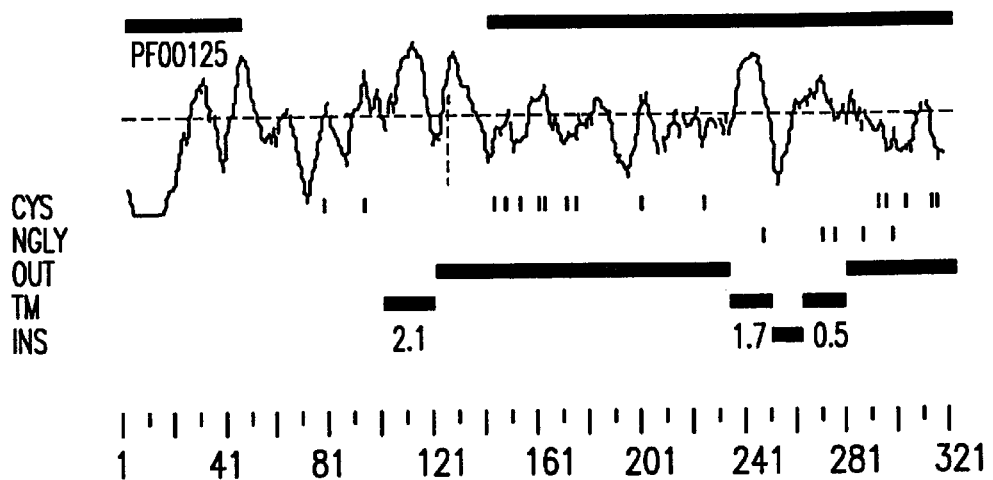

FIGS. 9A–9C. Panel A, cDNA sequence (SEQ ID NO: 10) from one form of the differential 5' start site found in the murine (akm1004); Panel B, amino acid sequence (SEQ ID NO: 11) encoded by the cDNA of Panel A; Panel C, hydropathy lot of the akm1004 amino acid sequence.

FIGS. 10A(1)—10A(7), and 10B. Nucleotide sequence (SEQ ID NO: 12) of a contig containing a portion of the human MG cDNA, panel A(1)–A(3) and the translated amino acid sequence (SEQ ID NO: 13), panel B.

Figure 11A:
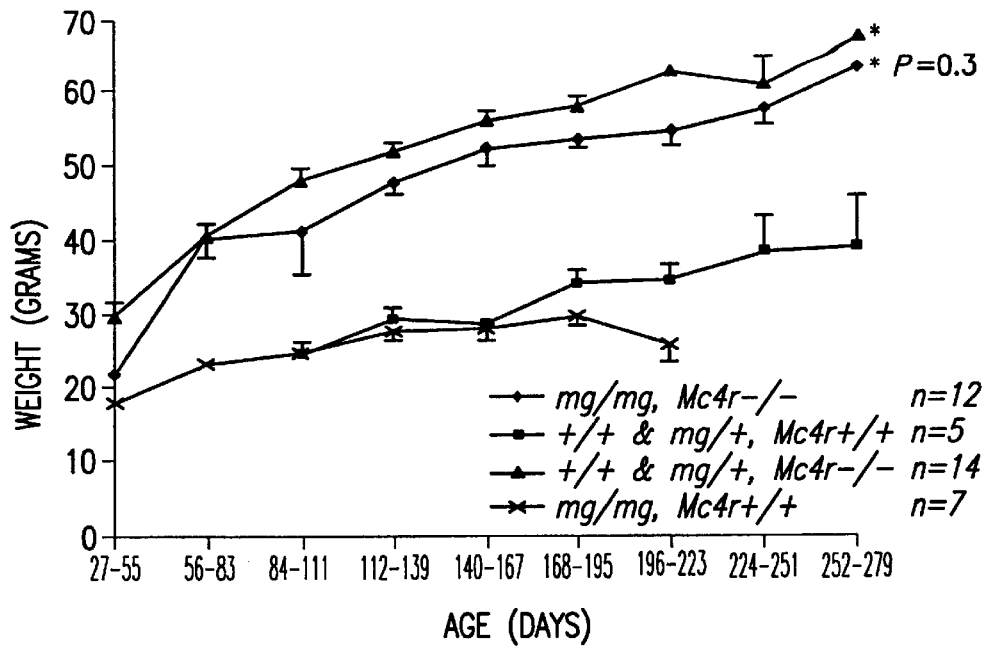
Figure 11B:
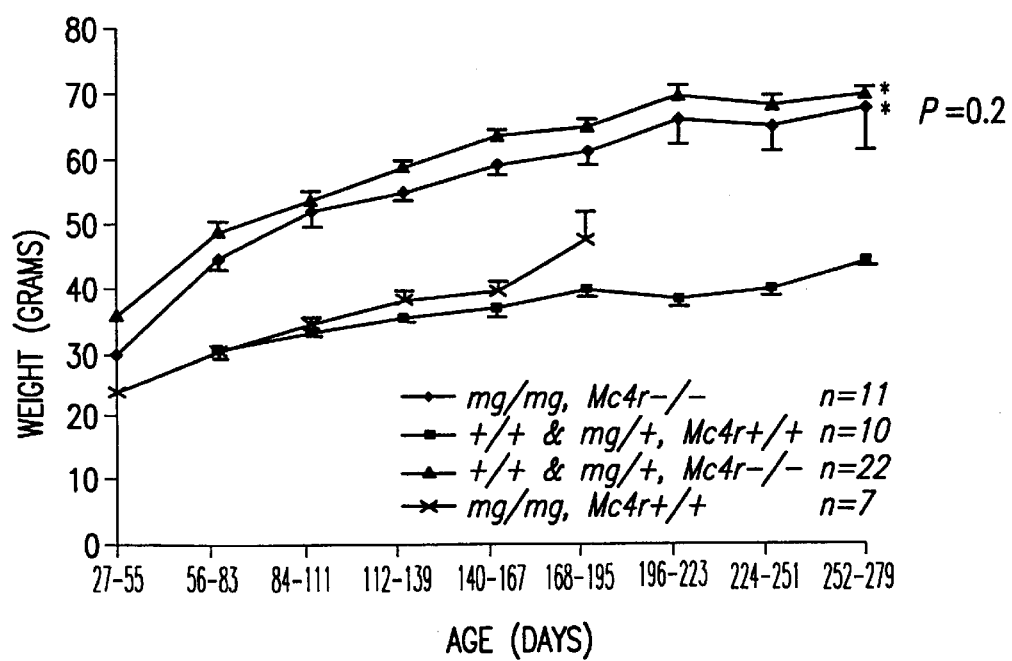

FIGS. 11(B) and 11B. Effect of mg on MC4r −/− induced weight gain in females (FIG. 11A) and males (FIG. 11B); values depicted are the mean +/− SD within a designated time interval.

FIGS. 12A–12D. Effect of mg on monogenic obese mutants $Lepr^{db}$ (FIG. 12A), tub (FIG. 12B), $Cpe^{fat}$ (FIG.

12C), and on high fat diet induced obesity (FIG. 12D); the values indicated are the mean +/− SD of the weight length ratio for each animal.

FIGS. 13A–13D. Genetic and physical map of the region surrounding the mg locus; all MIT markers are presented with shortened names, e.g., D2MIT77 is indicated as D2M77; locations of loci which also mapped on the human cytogenetic map are indicated in parentheses after the gene symbol.

FIG. 13A. The genetic map of the mg gene region on the Millennium BSB mapping panel (Misumi, D. J. et al., 1997, *Science* 278:135–138);

FIG. 13B. The genetic map obtained from crosses segregating mg mutant alleles;

FIG. 13C. The ~1 Mb BAC contig across the mg gene region of mouse Chromosome 2;

FIG. 13D. The transcriptional units identified in the mg region; the filled box indicates the mg gene, whereas the hatched box is a member of the High Mobility Group (HMG) gene family which sits between coding exons 21 and 22 of the mg gene.

Figure 14:
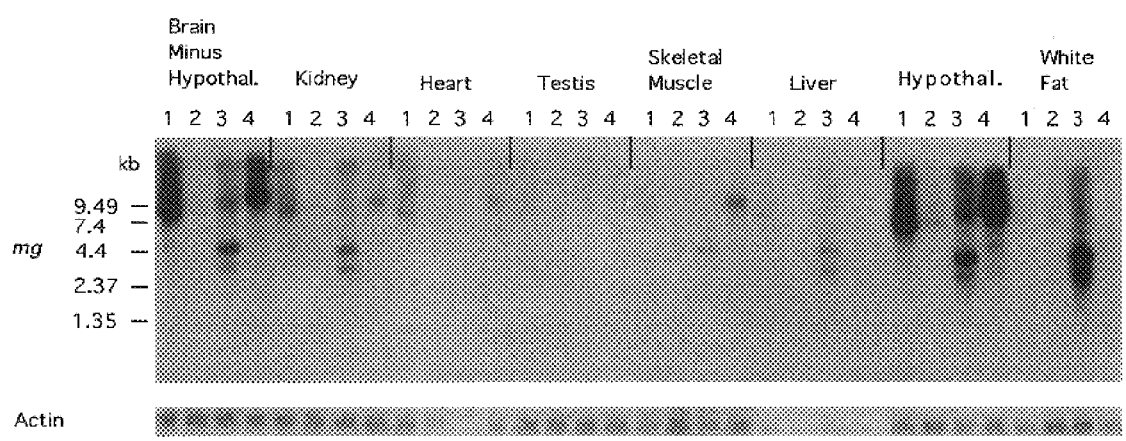

FIG. 14. Northern blot analysis with C3H/HeJ (lane 1), and three mutant alleles of mg: C3HeB/FeJ-mg$^{3J}$ (Lane 2), LDJ/Le-mg (Lane 3), and C3H/HeJ-mg$^J$ (Lane 4); the size marker is shown on the left, and hybridization with actin is shown below for loading comparisons.

Figure 15A:
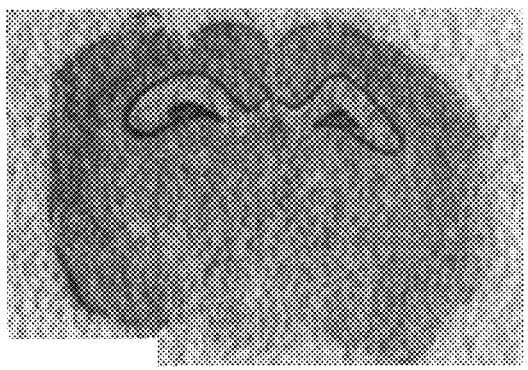
Figure 15B:
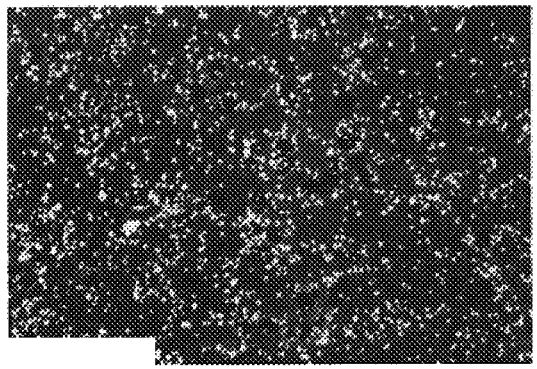
Figure 15C:
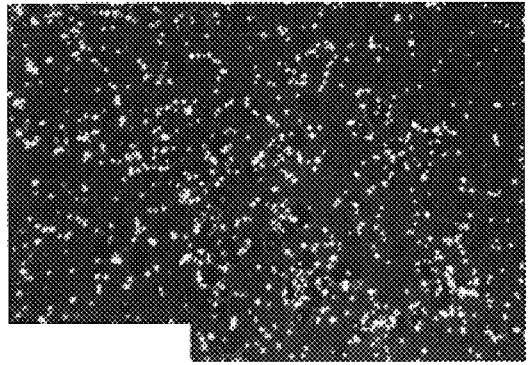
Figure 15D:
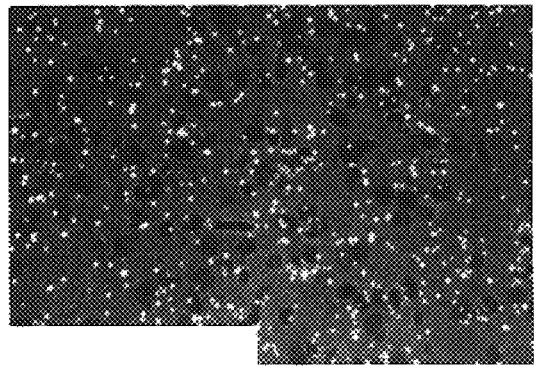

FIGS. 15A–15D. In situ hybridization data: FIG. 15A demonstrates widespread expression of mg throughout the mouse brain is seen in an antisense autoradiographic image of a C3H/HeJ brain at the level of the 3rd ventricle; decreased expression in mg mutants is documented in selected antisense darkfield images of 10 µm whole mount cross sections of the ventromedial hypothalamic nucleic (VMH) of C3H/HeJ (FIG. 15B), LDJ/Le-mg (FIG. 15C), and C3HeB/FeJ-mg$^{3j}$ (FIG. 15D).

Figure 16B:
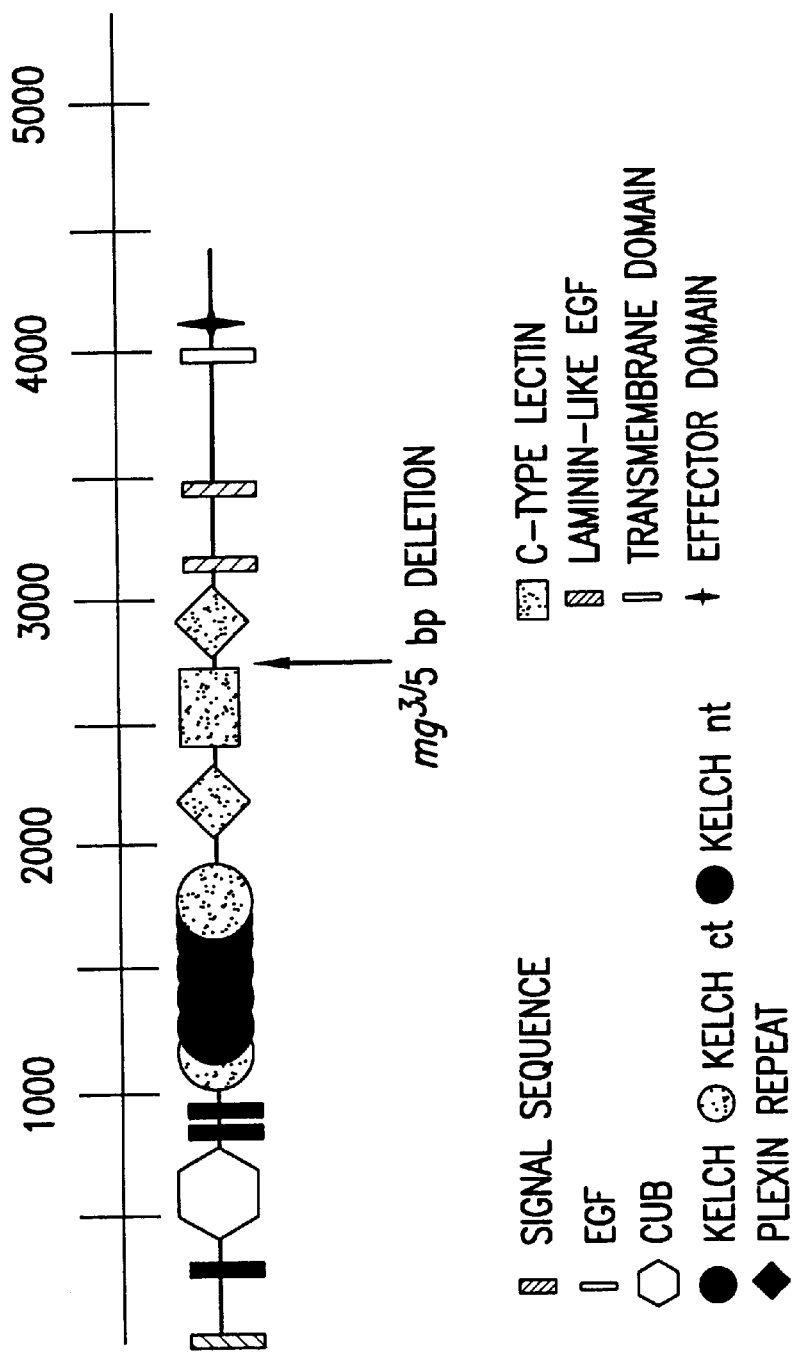

FIGS. 16A–16B. Alignment of the MG protein sequence (SEQ ID NOS:128) with its family members (SEQ ID NOS:125–127) showing the transmembrane region (indicated in brackets) and cytoplasmic tail (FIG. 16A); and a schematic of the molecular modular architecture of MG (FIG. 16B).

FIGS. 17A–17D. Sequence alignment of the predicted MG protein sequence (SEQ ID NO:131) (top) with the Attractin protein sequence (SEQ ID NO:132). Characteristic MG domains are as indicated. See Section 10.2 for details.

FIGS. 18A(1)–18A(8), 18B, 18C, and 18(D). Panel A: cDNA nucleotide sequence (SEQ ID NO: 14) of the long splice variant of the human ortholog of the mahogany gene, and Panel B: the derived amino acid sequence (SEQ ID NO: 15) of the mahogany gene product which it encodes. FIGS. 19A–19D. Panel A: cDNA nucleotide sequence (SEQ ID NO: 16) of a shorter splice variant of the human ortholog of the mahogany gene, and Panel B: the derived amino acid sequence (SEQ ID NO: 17) of the mahogany gene product which it encodes.

FIGS. 20A–20C. Panel A: cDNA nucleotide sequence (SEQ ID NO: 18) of a second shorter splice variant of the human ortholog of the mahogany gene, and Panel B: the derived amino acid sequence (SEQ ID NO: 19) of the mahogany gene product which it encodes.

5. DETAILED DESCRIPTION OF THE INVENTION

Described herein is the identification of the novel mammalian mahogany (mg) gene, including the human mahogany gene, which is involved in the control of mammalian body weight. Also described are recombinant mammalian, including human mahogany DNA molecules, cloned genes, and degenerate variants thereof. The compositions of the present invention further include mg gene products (e.g., proteins) that are encoded by the mg DNA molecules of the invention, and the modulation of mg gene expression and/or mg gene product activity in the treatment of mammalian body weight disorders, including obesity, cachexia, and anorexia. Also described herein are antibodies against mg gene products (e.g., proteins), or conserved variants or fragments thereof, and nucleic acid probes useful for the identification of mg gene mutations, and the use of such nucleic acid probes in diagnosing mammalian body weight disorders, including obesity, cachexia, and anorexia. Further described are methods for the use of the mg gene and/or mg gene products in the identification of compounds which modulate the activity of the mg gene product.

5.1. The Mahogany Gene

The mahogany genes are novel mammalian genes involved in the control of body weight. The nucleic acid sequences of the mahogany genes, including the murine mahogany gene sequences shown in FIGS. 2A, 3B–D, 6A–B, 8A, and 9A, as well as allelic variants and homologs thereof, and human mahogany sequences, as shown, e.g., in FIGS. 10A, 18A, 19A and 20A, as well as allelic variants and homologs thereof. The genomic sequence and structure, i.e., the intron/exon structure, of the mahogany genes have also been elucidated, FIG. 3.

The mahogany gene nucleic acid molecules of the present invention comprise: (a) the DNA sequence shown in FIGS. 2A, 3, 6A–B, 8A, 9A, 10A, 18A, 19A or 20A, or any DNA sequence that encodes the amino acid sequence of the mahogany gene product shown in FIGS. 2B, 8B, 9B, 10B, 17, 18B, 19B or 20B; (b) nucleotide sequences comprising the novel mahogany sequences disclosed herein that encode mutants of the mahogany gene product in which all or a part of one or more of the domains is deleted or altered, as shown, e.g., FIG. 6; (c) nucleotide sequences that encode fusion proteins comprising a mahogany gene product, or one of its domains fused to a heterologous polypeptide; and (d) nucleotide sequences within a mahogany gene, nucleotide sequences on the chromosome flanking the mahogany gene, see, e.g., FIG. 3 and human genomic sequences syntenic to the sequences depicted in FIG. 3, which can be utilized as part of the methods of the invention for identifying and diagnosing individuals who exhibit or are susceptible to weight disorders, including obesity, cachexia, and anorexia.

The mahogany nucleotide sequences of the invention further comprise: (a) any nucleotide sequence that hybridizes to the complement of a nucleic acid molecule that encodes a mahogany gene product under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) particularly human mg sequences, FIG. 10; and (b) any nucleotide sequence that hybridizes to the complement of a nucleic acid molecule that encodes a mahogany gene product under less stringent conditions, such as moderately stringent conditions, e.g., washing in 0.2×SSC/0.1% SDS at 42° C. (Ausubel et al., 1989, supra), yet which still encodes a functionally equivalent mahogany gene product.

"Functionally equivalent", as utilized herein, refers to a gene product (e.g., a protein) capable of exhibiting a substantially similar in vivo activity as the endogenous mg gene products encoded by the mg gene sequences described above. The in vivo activity of the mg gene product, as used herein, refers to the ability of the mg gene product, when present in an appropriate cell type, to ameliorate, prevent, or delay the appearance of the mahogany phenotype relative to its appearance when that cell type lacks a functional mahogany gene product.

The invention also includes nucleic acid molecules, preferably DNA molecules, that are the complements of the nucleotide sequences described above. Among the nucleic acid molecules of the invention are deoxyoligonucleotides ("oligos") which hybridize under highly stringent or moderately stringent conditions to the mahogany nucleic acid molecules described above. Exemplary highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as antisense molecules, useful, for example, in mahogany gene regulation, and/or as antisense primers in amplification reactions of mahogany gene nucleic acid sequences. With respect to mahogany gene regulation, such techniques can be used to regulate, for example, weight disorders such as obesity, cachexia, or anorexia. Such sequences may also be used as part of ribozyme and/or triple helix sequences, which are also useful for mahogany gene regulation. Still further, such molecules may be used as components of diagnostic methods whereby, for example, the presence of a particular mahogany allele associated with a weight disorder, such as obesity, cachexia, or anorexia, may be detected. Among the molecules which can be used for diagnostic methods, such as those which involve amplification of genomic mahogany sequences, are primers or probes that can routinely be obtained using the genomic and cDNA sequences disclosed herein.

In one embodiment, the nucleic acid molecules of the invention do not include nucleic acid molecules that consist solely of the nucleotide sequence that encodes the attractin protein sequence depicted in FIGS. 17A–C.

The mahogany nucleic acid sequences of the invention further include fragments of the nucleic acid sequences described above. For example, mahogany nucleic acid fragments can include fragments of at least 10, 12, 15, 20, 30, 40, 50, 100, 150, 200, 300, 400, 500, 600, 700, 800, 900, 1000, 1100, 1200, 1300, 1400, 1500, 1600, 1700, 1800, 1900, 2000 or more nucleotides.

The nucleotide sequences of the present invention also include (a) DNA vectors that contain any of the foregoing mahogany coding sequences and/or their complements; (b) DNA expression vectors that contain any of the foregoing mahogany coding sequences operatively associated with a regulatory element that directs the expression of the coding sequences; and (c) genetically engineered host cells and organisms that contain any of the foregoing mahogany coding sequences operatively associated with a regulatory element that directs the expression of the coding sequence in the host cell. As used herein, regulatory elements include, but are not limited to inducible and non-inducible promoters, enhancers, operators, and other elements known to those skilled in the art that drive and regulate gene expression. Such regulatory elements include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3'-phosphoglycerate kinase, the promoters of acid phosphatase, and the promoters of the yeast alpha-mating factors.

In addition to the mahogany gene sequences described above, homologs of such sequences, exhibiting extensive homology to one or more domains of the mahogany gene product can be present in other species. In a preferred embodiment, the mahogany gene homologue maps to a chromosomal region that is syntenic to the chromosomal region of the mahogany gene. In a particularly preferred embodiment, a human mahogany gene homologue sequence maps to a human chromosome region that is syntenic to the region of mouse chromosome 2 to which the murine mahogany gene maps, namely 20p15, and comprises the contiged human MG cDNA provided herein. Further, there can also exist homologue genes at other genetic loci within the genome of the same species which encode proteins having extensive homology to one or more domains of the mahogany gene product. Such mahogany homologs can include, for example, secreted forms of the mahogany sequences, see, e.g., Duke-Cohan, J. S. et al. (1998, *Proc. Natl. Acad. Sci. U.S.A.* 95:11336–11341). Such sequences, can be used, for example, in the screening assays, described in Section 5.4.2 below, for compounds that interact with the mahogany gene and/or its gene product and that may therefore be useful in treating and ameliorating body weight disorders.

Other mahogany homologs can be identified and readily isolated, without undue experimentation, by molecular biological techniques well known in the art, and are therefore within the scope of the present invention. As an example, in order to clone a human mahogany gene homologue using isolated murine mahogany gene sequences, such murine mahogany gene sequences may be labeled and used to screen a cDNA library constructed from mRNA obtained from appropriate cells or tissues derived from the organism (in this case, human) of interest. With respect to the cloning of such a human mahogany homologue, a human cDNA library may, for example be used for screening, such as a cDNA library obtained from mRNA isolated from brain tissues, particularly containing hypothalamic regions.

The hybridization washing conditions used should be of a lower stringency when the cDNA library is derived from an organism different from the type of organism from which the labeled sequence was derived. With respect to the cloning of a human mahogany homologue, for example, hybridization can be performed for 4 hours at 65° C. using Amersham Rapid Hyb™ buffer (Cat. #RPN1639) according to manufacturer's protocol, followed by washing, with a final washing stringency of 1.0×SSC/0.1% SDS at 50° C. for 20 minutes being preferred.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled fragment may be used to screen a genomic library derived from the organism of interest, again, using appropriately stringent conditions.

Further, a mahogany gene homologue may be isolated from nucleic acid of the organism of interest by performing PCR using two degenerate oligonucleotide primer pools designed on the basis of amino acid sequences within the mahogany gene product disclosed herein. The template for the reaction may be cDNA obtained by reverse transcription of mRNA prepared from, for example, human or non-human cell lines or tissue known or suspected to express a mahogany gene allele.

The PCR product may be subcloned and sequenced to ensure that the amplified sequences represent the sequences of a mahogany gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library. This method has been used to isolate sequences encoding each of the murine MG gene exons as well as to isolate contigs containing the human MG sequences provided herein, FIG. 10.

PCR technology may also be utilized to isolate full length cDNA sequences. For example, RNA may be isolated, following standard procedures, from an appropriate cellular or tissue source (i.e., one known, or suspected, to express the mahogany gene). A reverse transcription reaction may be performed on the RNA using an oligonucleotide primer specific for the most 5' end of the amplified fragment for the priming of the first strand synthesis. The resulting RNA/DNA hybrid may then be "tailed" with guanines using a standard terminal transferase reaction, they hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989 supra.

Mahogany gene sequences may additionally be used to isolate mutant mahogany alleles. Such mutant alleles may be isolated from individuals either known or proposed to have a phenotype which contributes to the symptoms of body weight disorders such as obesity, cachexia, or anorexia or disorders associated with hyperphagia. Mutant alleles and mutant allele products may then be utilized in the therapeutic and diagnostic systems described below. Additionally, such mahogany gene sequences can be used to detect mahogany gene regulatory (e.g. promoter) defects which can affect body weight.

A cDNA of a mutant mahogany gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant mahogany allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant mahogany allele to that of the normal mahogany allele, the mutation(s) responsible for the loss of alteration of activity of the mutant mahogany gene product can be ascertained.

Alternatively, a genomic library can be constructed using DNA obtained from an individual suspected of or known to carry the mutant mahogany allele, or a cDNA library can be constructed using RNA from a tissue known, or suspected to express the mutant mahogany allele. The normal mahogany gene or any suitable fragment thereof may then be labeled and used as a probe to identify the corresponding mutant mahogany allele in such libraries. Clones containing the mutant mahogany gene sequences may then be purified and subjected to sequence analysis according to methods well known to those of skill in the art.

Additionally, an expression library can be constructed utilizing cDNA synthesized from, for example, RNA isolated from a tissue known, or suspected to express a mutant mahogany allele in an individual suspected of or known to carry such a mutant allele. In this manner, gene products made by the putatively mutant tissue may be expressed and screened using standard antibody screening techniques in conjunction with antibodies raised against the normal mahogany gene product as described, below, in Section 5.3. For screening techniques, see, for example, Harlow, E. and Lane, eds., 1988, "Antibodies: A Laboratory Manual", Cold Spring Harbor Press, Cold Spring Harbor. In cases where a mahogany mutation results in an expressed gene product with altered function (e.g., as a result of a missense or a frameshift mutation) a polyclonal set of anti-mahogany gene product antibodies are likely to cross-react with the mutant mahogany gene product. Library clones detected via their reaction with such labeled antibodies can be purified and subjected to sequence analysis according to methods well known to those of skill in the art.

5.2. Protein Products of the Mahogant Gene

Mahogany gene products (e.g., proteins), polypeptides and peptide fragments, mutant, truncated, or deleted forms of the mahogany gene product, and/or fusion proteins of the mahogany gene product can be prepared for a variety of uses. For example, such gene products, or peptide fragments thereof, can be used for the generation of antibodies in diagnostic assays, or for the identification of other cellular or extracellular products involved in the regulation of mammalian body weight.

Mahogany gene products, also referred to herein as mahogany proteins, of the present invention include those gene products encoded by the mahogany gene sequences described in Section 5.1, above. For example, FIGS. 2B, 8B and 9B depict murine mahogany amino acid sequences. Mahogany gene products also include human mahogany gene products as shown, e.g., in FIGS. 10B, 17B, 18B, 19B, and 20B.

In addition, mahogany gene products may include proteins that represent functionally equivalent gene products. Such an equivalent mahogany gene product may contain deletions, including internal deletions, additions, including additions yielding fusion proteins, or substitutions of amino acid residues within and/or adjacent to the amino acid sequence encoded by the mahogany gene sequences described, in Section 5.1, above, but that result in a "silent" change, in that the change produces a functionally equivalent mahogany gene product. Such amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Functionally equivalent", as utilized herein, refers to a gene product (e.g., a protein) capable of exhibiting a substantially similar in vivo activity as the endogenous mg gene products encoded by the mg gene sequences described in Section 5.1, above. The in vivo activity of the mg gene product, as used herein, refers to the ability of the mg gene product, when present in an appropriate cell type, to ameliorate, prevent, or delay the appearance of the mahogany phenotype relative to its appearance when that cell type lacks a functional mahogany gene product.

Alternatively, where alteration of function is desired, deletion or non-conservative alterations can produce altered, including reduced-activity, mahogany gene products. Such alterations can, for example, alter one or more of the biological functions of the mahogany gene product. Further, such alterations can be selected so as to generate mahogany gene products that are better suited for expression, scale up, etc. in the host cells chosen. For example, cysteine residues can be deleted or substituted with another amino acid residue in order to eliminate disulfide bridges.

As another example, altered mahogany gene products can be engineered that correspond to mutants or variants of the mahogany gene product associated with mammalian weight disorders, such as obesity, cachexia, or anorexia. Altered mahogany gene products can also be engineered that correspond to mutants or variants of the mahogany gene product known to neutralize or ameliorate the symptoms of body weight disorders, such as obesity, cachexia, or anorexia, which are mediated by some other gene, including, but not limited to, body weight disorders mediated by the agouti gene.

Also within the scope of the present invention are peptides and/or proteins corresponding to one or more domains of the mahogany protein or any one of the individual exon encoded regions of the MG protein, as well as fusion proteins in which the full length mahogany protein, a mahogany peptide, or a truncated mahogany protein or peptide is fused to an unrelated heterologous protein. Such proteins and peptides can be designed on the basis of the mahogany nucleotide sequence disclosed in Section 5.1, above, and/or on the basis of the mahogany amino acid sequence disclosed in the Section.

The mahogany gene products of the invention further include fragments of the gene products described herein. For example, mahogany gene product fragments can include fragments of at least 10, 12, 15, 20, 30, 40, 50, 100, 150, 200, 300, 400, 500, 600, 700, 800, 900, 1000, 1100, 1200, 1300 or more amino acids in length.

In one embodiment, it is understood that the gene products of the present invention do not include a gene product that consists solely of the amino acid sequence of the attractin polypeptide depicted in FIG. 17.

Fusion proteins of the invention include, but are not limited to, IgFc fusions which stabilize the mahogany protein or peptide and prolong half life in vivo; or fusions to any amino acid sequence that allows the fusion protein to be anchored to the cell membrane; or fusions to an enzyme, fluorescent protein, or luminescent protein which provides a marker function.

The mahogany gene products, peptide fragments thereof and fusion proteins thereof, may be produced by recombinant DNA technology using techniques well known in the art. Thus, methods for preparing the mahogany gene products, polypeptides, peptides, fusion peptide and fusion polypeptides of the invention by expressing nucleic acid containing mahogany gene sequences are described herein. Methods that are well known to those skilled in the art can be used to construct expression vectors containing mahogany gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding mahogany gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the mahogany gene product coding sequences of the invention. Such host-expression systems represent vehicles by which the coding sequences of interest may be produced and subsequently purified, but also represent cells that may, when transformed or transfected with the appropriate nucleotide coding sequences, exhibit the mahogany gene product of the invention in situ. These include but are not limited to microorganisms such as bacteria (e.g., *E. coli, B. subtilis*) transformed with recombinant bacteriophage DNA, plasmid DNA or cosmid DNA expression vectors containing mahogany gene product coding sequences; yeast (e.g., Saccharomiyces, Pichia) transformed with recombinant yeast expression vectors containing the mahogany gene product coding sequences; insect cell systems infected with recombinant virus expression vectors (e.g., baculovirus) containing the mahogany gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing mahogany gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the mahogany gene product being expressed. For example, when a large quantity of such a protein is to be produced, for the generation of pharmaceutical compositions of mahogany gene product or for raising antibodies to mahogany gene product, for example, vectors that direct the expression of high levels of fusion protein products that are readily purified may be desirable. Such vectors include, but are not limited, to the *E. coli* expression vector pUR278 (Ruther et al., 1983, EMBO J. 2, 1791), in which the mahogany gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhidrosis virus (AcNPV) is used as a vector to express foreign genes. The virus grows in *Spodoptera frugiperda* cells. The mahogany gene product coding sequence may be cloned individually into non-essential regions (for example the polyhedrin gene) of the virus and placed under control of an AcNPV promoter (for example the polyhedrin promoter).

Successful insertion of mahogany gene product coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, the mahogany gene product coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing mahogany gene product in infected hosts. (e.g., See Logan and Shenk, 1984, Proc. Natl. Acad. Sci. USA 81, 3655–3659). Specific initiation signals may also be required for efficient translation of inserted mahogany gene product coding sequences. These signals include the ATG initiation codon and adjacent sequences. In cases where an entire mahogany gene, including its own initiation codon and adjacent sequences, is inserted into the appropriate expression vector, no additional translational control signals may be needed. However, in cases where only a portion of the mahogany gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the mahogany gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the mahogany gene product. Such engineered cell lines may be particularly useful in screening and evaluation of compounds that affect the endogenous activity of the mahogany gene product.

A number of selection systems may be used, including but not limited to the herpes simplex virus thymidine kinase (Wigler, et al., 1977, Cell 11, 223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, the expression characteristic of an endogenous mahogany gene within a cell line or microorganism my be modified by inserting a heterologous DNA regulatory element into the genome of a stable cell line or cloned microorganism such that the inserted regulatory element is operatively linked with the endogenous mahogany gene. For example, an endogenous mahogany gene which is normally "transcriptionally silent", i.e., a mahogany gene which is normally not expressed, or is expressed only a very low levels in a cell line or microorganism, may be activated by inserting a regulatory element which is capable of promoting the expression of a normally expressed gene product in that cell line or microorganism. Alternatively, a transcriptionally silent, endogenous mahogany gene may be activated by insertion of a promiscuous regulatory element that works across cell types.

A heterologous regulatory element may be inserted into a stable cell line or cloned microorganism, such it is operatively linked with an endogenous mahogany gene, using techniques, such as targeted homologous recombination, which are well known to those of skill in the art, and described e.g., in Chappel, U.S. Pat. Nos. 4,215,051; 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

The mahogany gene products can also be expressed in transgenic animals. Animals of any species, including, but not limited to, mice, rats, rabbits, guinea pigs, pigs, micropigs, goats, sheep, and non-human primates, e.g., baboons, monkeys, and chimpanzees may be used to generate mahogany transgenic animals. The term "transgenic," as used herein, refers to animals expressing mahogany gene sequences from a different species (e.g., mice expressing human mahogany gene sequences), as well as animals that have been genetically engineered to over express endogenous (i.e., same species) mahogany sequences or animals that have been genetically engineered to no longer express endogenous mahogany gene sequences (i.e., "knock-out" animals), and their progeny.

Any technique known in the art may be used to introduce a mahogany gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115, 171–229)

Any technique known in the art may be used to produce transgenic animal clones containing a mahogany transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals that carry a mahogany transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the mahogany transgene be integrated into the chromosomal site of the endogenous mahogany gene, gene targeting is preferred. Briefly, when such a technique is to be utilized, vectors containing some nucleotide sequences homologous to the endogenous mahogany gene are designed for the purpose of integrating, via homologous recombination with chromosomal sequences, into and disrupting the function of the nucleotide sequence of the endogenous mahogany gene. The transgene may also be selectively introduced into a particular cell type, thus inactivating the endogenous mahogany gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant mahogany gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of mahogany gene-expressing tissue, may also be evaluated immunocytochemically using antibodies specific for the mahogany transgene product.

5.3. Antibodies to Mahogant Gene Products

Described herein are methods for the production of antibodies capable of specifically recognizing one or more mg gene product epitopes, or epitopes of conserved variants, or peptide fragments of the mg gene products. Further, antibodies that specifically recognize mutant forms of mg gene products, are encompassed by the invention.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a mg gene product in an biological sample and may, therefore, be utilized as part of a diagnostic or prognostic technique whereby patients may be tested for abnormal levels of mg gene products, and/or for the presence of abnormal forms of such gene products. Such antibodies may also be utilized in conjunction with, for example, compound screening schemes, as described, below, in Section 5.4.2, for the evaluation of the effect of test compounds on mg gene product levels and/or activity. Additionally, such antibodies can be used in conjunction with the gene therapy techniques described, below, in Section 5.4.3.2, to, for example, evaluate the normal and/or engineered mahogany-expressing cells prior to their introduction into the patient.

Anti-mg gene product antibodies may additionally be used in methods for inhibiting abnormal mg gene product activity. Thus, such antibodies may, therefore, be utilized as part of weight disorder treatment methods.

For the production of antibodies against a mg gene product, various host animals may be immunized by injection with a mg gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a mg gene product, or an antigenic functional derivative thereof. For the production of polyclonal antibodies, host animals such as those described above, may be immunized by injection with mg gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against mahogany gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse, et al., 1989, Science, 246, 1275–1281) to allow rapid and easy identification of monoclonal Fab fragments with the desired specificity.

5.4. Uses of the Mahogany Genes, Gene Products, and Antibodies

Described herein are various applications of the mahogany genes, of the mahogany gene products, including peptide fragments thereof, and of antibodies directed against mahogany gene products and peptide fragments thereof. Such applications include, for example, prognostic and diagnostic evaluation of body weight disorders and the identification of subjects with a predisposition to such disorders, as described below, in Section 5.4.1. Additionally, such applications include methods for the treatment of body weight and body weight disorders, as described, below, in Section 5.4.2, and for the identification of compounds which modulate the expression of the mahogany gene and/or the activity of the mahogany gene product, as described in Section 5.4.3, below. Such compounds can include, for example, other cellular products which are involved in body weight regulation. These compounds can be used, for example, in the amelioration of body weight disorders, including obesity, cachexia, and anorexia.

While, for clarity, the uses described in this section are primarily uses related to body weight disorder abnormalities, it is to be noted that each of the diagnostic and therapeutic treatments described herein can additionally be utilized in connection with other defects associated with the mahogany gene, such as hyperpigmentation, hyperphagia and other disorders resulting in increased metabolic rates.

5.4.1. Diagnosis of Body Weight Disorder Abnormalities

A variety of methods can be employed for the diagnostic and prognostic evaluation of body weight disorders, including obesity, cachexia, and anorexia, and for the identification of subjects having a predisposition to such disorders.

Such methods may, for example, utilize reagents such as the mahogany gene nucleotide sequences described in Section 5.1, and antibodies directed against mahogany gene products, including peptide fragments thereof, as described, above, in Section 5.3. Specifically, such reagents may be used, for example, for:

(1) the detection of the presence of mahogany gene mutations, or the detection of either over- or under-expression of mahogany gene relative to levels of mahogany expression in a wild-type, non-body weight disorder state which correlates with certain body weight disorders or susceptibility toward such body weight disorders;

(2) the detection of over- or under-abundance of mahogany gene product relative to the abundance of mahogany gene product in a wild-type non-body weight disorder state which correlates with certain body weight disorders or susceptibility toward such body weight disorders; and (3) the detection of an aberrant level of mahogany gene product activity relative to mahogany gene product activity levels in a wild-type, non-body weight disorder state which correlates with certain body weight disorders or susceptibility toward such body weight disorders.

Mahogany gene nucleotide sequences can, for example, be used to diagnose a body weight disorder using, for example, the techniques for detecting mutations in the mahogany gene described above in Section 5.1, above.

The methods described herein may be performed, for example, by utilizing pre-packaged diagnostic kits comprising at least one specific mahogany gene nucleic acid or anti-mahogany gene product antibody reagent described herein, which may be conveniently used, e.g., in clinical settings, to screen and diagnose patients exhibiting body weight disorder abnormalities, and to screen those individuals exhibiting a predisposition to developing a body weight disorder abnormality.

For the detection of mahogany gene mutations, any nucleated cell can be used as a starting source for genomic nucleic acid. For the detection of mahogany gene expression or mahogany gene products, any cell type or tissue in which the mahogany gene is expressed may be utilized, such as, for example, tissues or cells shown herein to express the MG gene.

Nucleic acid-based detection techniques are described, below, in Section 5.4.1.1. Peptide detection techniques are described, below, in Section 5.4.1.2.

5.4.1.1. Detection of Mahogany Gene Nucleic Acid Molecules

Mutations or polymorphisms within the mahogany gene can be detected by utilizing a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving mahogany gene structure, including point mutations, insertions, deletions and chromosomal rearrangements. Such assays may include, but are not limited to, Southern analyses, single stranded conformation polymorphism analyses (SSCP), and PCR analyses.

Diagnostic methods for the detection of mahogany gene-specific mutations can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described in Section 5.1, above, under conditions favorable for the specific annealing of these reagents to their complementary sequences within or flanking the mahogany gene. Preferably, the lengths of these nucleic acid reagents are at least 15 to 30 nucleotides.

After incubation, all non-annealed nucleic acids are removed from the nucleic acid:mahogany molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled mahogany nucleic acid reagents is accomplished using standard techniques well-known to those in the art. The mahogany gene sequences to which the nucleic acid reagents have annealed can be compared to the annealing pattern expected from a normal mahogany gene sequence in order to determine whether a mahogany gene mutation is present.

In a preferred embodiment, mahogany gene mutations or polymorphisms can be detected by using a microassay of mahogany nucleic acid sequences immobilized to a substrate or "gene chip" (see, e.g. Cronin, et al., 1996, Human Mutation 7:244–255).

Alternative diagnostic methods for the detection of mahogany gene specific nucleic acid molecules, in patient samples or other appropriate cell sources, may involve their amplification, e.g., by PCR (the experimental embodiment set forth in Mullis, 1987, U.S. Pat. No. 4,683,202), followed by the analysis of the amplified molecules using techniques well known to those of skill in the art, such as, for example, those listed above. The resulting amplified sequences can be compared to those that would be expected if the nucleic acid being amplified contained only normal copies of the mahogany gene in order to determine whether a mahogany gene mutation exists.

Among those mahogany nucleic acid sequences which are referred for such amplification-related diagnostic screening analyses are oligonucleotide primers which amplify mahogany exon sequences. The sequences of such oligonucleotide primers are, therefore, preferably derived from mahogany intron sequences so that the entire exon, or coding region, can be analyzed as discussed below. Primer pairs useful for amplification of mahogany exons are preferably derived from adjacent introns. Appropriate primer pairs can be chosen such that each of the 25 mahogany exons are amplified. Primers for the amplification of mahogany exons can be routinely designed by one of ordinary skill in the art by utilizing the exon and intron sequences of mahogany shown in Figures, particularly FIGS. 3 and 5.

Additional mahogany nucleic acid sequences which are preferred for such amplification-related analyses are those which will detect the presence of a mahogany polymorphism which differs from the consensus mahogany sequence depicted in Figures, particularly those that detect the polymorphism identified in exon 15 (FIG. 7). Such polymorphisms include ones which represent mutations associated with body weight disorders such as obesity, cachexia, or anorexia.

Further, well-known genotyping techniques can be performed to type polymorphisms that are in close proximity to mutations in the mahogany gene itself, including mutations associated with weight disorders such as obesity, cachexia, or anorexia. Such polymorphisms can be used to identify individuals in families likely to carry mutations in the mahogany gene. If a polymorphism exhibits linkage disequilibrium with mutations in the mahogany gene, the polymorphism can also be used to identify individuals in the general population who are likely to carry such mutations. Polymorphisms that can be used in this way include restriction fragment length polymorphisms (RFLPs), which involve sequence variations in restriction enzyme target sequences, single-base polymorphisms, and simple sequence length polymorphisms (SSLPs).

For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the mahogany gene, and the diagnosis of diseases and disorders related to mutations in the mahogany gene.

Also, Caskey et al. (U.S. Pat. No. 5,364,759) describe a DNA profiling assay for detecting short tri and tetra nucleotide repeat sequences. The process includes extracting the DNA of interest, such as the mahogany gene, amplifying the extracted DNA, and labelling the repeat sequences to form a genotypic map of the individual's DNA.

A mahogany probe could additionally be used to directly identify RFLPs. Further, a mahogany probe or primers derived from the mahogany sequence could be used to isolate genomic clones such as YACs, BACs, PACs, cosmids, phage, or plasmids. The DNA contained in these clones can be screened for single-base polymorphisms or SSLPs using standard hybridization or sequencing procedures.

The level of mahogany gene expression can also be assayed. For example, RNA from a cell type or tissue known, or suspected, to express the mahogany gene, such as muscle, brain, kidney, testes, heart, liver, lung, skin, hypothalamus, spleen, and adipose tissue may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the mahogany gene. Such analyses may reveal both quantitative and qualitative aspects of the expression pattern of the mahogany gene, including activation or inactivation of mahogany gene expression.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the mahogany gene nucleic acid reagents described in Section 5.1. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

As an alternative to amplification techniques, standard Northern analyses can be performed to determine the level of mRNA expression of the mahogany gene, if a sufficient quantity of the appropriate cells can be obtained.

Additionally, it is possible to perform such mahogany gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

5.4.1.2. Detection of Mahogany Gene Products

Mahogany gene products, including both wild-type and mutant mahogany gene products, conserved variants, and polypeptide fragments thereof, which are discussed, above, in Section 5.2, may be detected using antibodies which are directed against such mahogany gene products. Such antibodies, which are discussed in Section 5.3, below, may thereby be used as diagnostics and prognostics for a body weight disorder. Such methods may be used to detect abnormalities in the level of mahogany gene expression or of mahogany gene product synthesis, or abnormalities in the structure, temporal expression, and/or physical location of mahogany gene product. The antibodies and immunoassay methods described herein have, for example, important in vitro applications in assessing the efficacy of treatments for body weight disorders such as obesity, cachexia, and anorexia. Antibodies, or fragments of antibodies, such as those described below, may be used to screen potentially therapeutic compounds in vitro to determine their effects on mahogany gene expression and mahogany gene product production. The compounds that have beneficial effects on body weight disorders, such as obesity, cachexia, and anorexia, can thereby be identified, and a therapeutically effective dose determined.

In vitro immunoassays may also be used, for example, to assess the efficacy of cell-based gene therapy for a body weight disorders, including obesity, cachexia, and anorexia. Antibodies directed against mahogany gene products may be used in vitro to determine, for example, the level of mahogany gene expression achieved in cells genetically engineered to produce mahogany gene product. In the case of intracellular mahogany gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the mahogany gene. The protein isolation methods employed herein may, for example, be such those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the mahogany gene.

Preferred diagnostic methods for the detection of mahogany gene products, conserved variants or peptide fragments thereof, may involve, for example, immunoassays wherein the mahogany gene products or conserved variants or peptide fragments are detected by their interaction with an anti-mahogany gene product-specific antibody.

For example, antibodies, or fragments of antibodies, such as those described, above, in Section 5.3, may be used to quantitatively or qualitatively detect the presence of mahogany gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for mahogany gene products that are expressed on the cell surface.

The antibodies (or fragments thereof) useful in the present invention may, additionally, be employed histologically, as in immunofluorescence or immunoelectron microscopy, for in situ detection of mahogany gene products, conserved variants or peptide fragments thereof. In situ detection may be accomplished by removing a histological specimen from a patient, and applying thereto a labeled antibody that binds to a mahogany polypeptide. The antibody (or fragment) is preferably applied by overlaying the labeled antibody (or fragment) onto a biological sample. Through the use of such a procedure, it is possible to determine not only the presence of the mahogany gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of a mahogany gene product.

Immunoassays for mahogany gene products, conserved variants, or peptide fragments thereof will typically comprise: (1) incubating a sample, such as a biological fluid, a tissue extract, freshly harvested cells, or lysates of cells in the presence of a detectably labeled antibody capable of identifying mahogany gene products, conserved variants or peptide fragments thereof; and (2) detecting the bound antibody by any of a number of techniques well-known in the art.

The biological sample may be brought in contact with and immobilized onto a solid phase support or carrier, such as nitrocellulose, that is capable of immobilizing cells, cell particles or soluble proteins. The support may then be washed with suitable buffers followed by treatment with the detectably labeled mahogany gene product specific antibody. The solid phase support may then be washed with the buffer a second time to remove unbound antibody. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which the mahogany gene product-specific antibody can be detectably labeled is by linking the same to an enzyme, such as for use in an enzyme immunoassay (EIA) (Voller, A., "The Enzyme Linked Immunosorbent Assay (ELISA)", 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect mahogany gene products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4.2. Screening Assays for Compounds that Interact with the Mahogany Gene or Gene Product The following assays are designed to identify compounds that bind to a mahogany gene product, compounds that bind to proteins, or portions of proteins that interact with a mahogany gene product, compounds that interfere with the interaction of a mahogany gene product with proteins and compounds that modulate the activity of the mahogany gene (i.e., modulate the level of mahogany gene expression and/or modulate the level of mahogany gene product activity). Assays may additionally be utilized that identify compounds that bind to mahogany gene regulatory sequences (e.g., promoter sequences; see e.g., Platt, 1994, J. Biol. Chem. 269, 28558–28562), which is incorporated herein by reference in its entirety, and that can modulate the level of mahogany gene expression. Such compounds may include, but are not limited to, small organic molecules, such as ones that are able to cross the blood-brain barrier, gain to and/or entry into an appropriate cell and affect expression of the mahogany gene or some other gene involved in the body weight regulatory pathway, or intracellular proteins.

Methods for the identification of such proteins are described, below, in Section 5.4.2.2. Such proteins may be involved in the control and/or regulation of body weight. Further, among these compounds are compounds that affect the level of mahogany gene expression and/or mahogany gene product activity and that can be used in the therapeutic treatment of body weight disorders, including obesity, cachexia, and anorexia, as described, below, in Section 5.9.

Compounds may include, but are not limited to, peptides such as, for example, soluble peptides, including but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L-configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Compounds identified via assays such as those described herein may be useful, for example, in elaborating the biological function of the mahogany gene product and for ameliorating body weight disorders, such as obesity, cachexia, or anorexia. Assays for testing the effectiveness of compounds identified by, for example, techniques such as those described in Sections 5.4.2.1–5.4.2.3, are discussed, below, in Section 5.4.2.4.

5.4.2.1. In Vitro Screening Assays for Compounds that Bind to the Mahogany Gene Product In vitro systems may be designed to identify compounds capable of binding the mahogany gene products of the invention. Compounds identified may be useful, for example, in modulating the activity of unimpaired and/or mutant mahogany gene products, may be useful in elaborating the biological function of the mahogany gene product, may be utilized in screens for identifying compounds that disrupt normal mahogany gene product interactions, or may in themselves disrupt such interactions.

The principle of the assays used to identify compounds that bind to the mahogany gene product involves preparing a reaction mixture of the mahogany gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring a mahogany gene product or a test substance onto a solid support and detecting mahogany gene product/test compound complexes formed on the solid support at the end of the reaction. In one embodiment of such a method, the mahogany gene product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for mahogany gene product or the test compound to anchor any complexes formed in solution, and a labeled antibody specific for the other component of the possible complex to detect anchored complexes.

5.4.2.2. Assays for Proteins that Interact with the Mahogany Gene Product

Any method suitable for detecting protein-protein interactions may be employed for identifying mahogany gene product-protein interactions.

Among the traditional methods that may be employed are co-immunoprecipitation, cross-linking and co-purification through gradients or chromatographic columns. Utilizing procedures such as these allows for the identification of proteins that interact with mahogany gene products. Such proteins can include, but are not limited, the mahoganoid gene product.

Once isolated, such a protein can be identified and can be used in conjunction with standard techniques, to identify proteins it interacts with. For example, at least a portion of the amino acid sequence of a protein that interacts with the mahogany gene product can be ascertained using techniques well known to those of skill in the art, such as via the Edman degradation technique (see, e.g., Creighton, 1983, "Proteins: Structures and Molecular Principles," W. H. Freeman & Co., N.Y., pp.34–49). The amino acid sequence obtained may be used as a guide for the generation of oligonucleotide mixtures that can be used to screen for gene sequences encoding such proteins. Screening may be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with a mahogany gene product. These methods include, for example, probing expression libraries with labeled mahogany gene product, using mahogany gene product in a manner similar to the well known technique of antibody probing of λgt11 libraries.

One method that detects protein interactions in vivo, the two-hybrid system, is described in detail for illustration only and not by way of limitation. One version of this system has been described (Chien, et al., 1991, Proc. Natl. Acad. Sci. USA, 88, 9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the mahogany gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, mahogany gene products may be used as the bait gene product. Total genomic or cDNA sequences are fused to the DNA encoding an activation domain. This library and a plasmid encoding a hybrid of a bait mahogany gene product fused to the DNA-binding domain are co-transformed into a yeast reporter strain, and the resulting transformants are screened for those that express the reporter gene. For example, a bait mahogany gene sequence, such as the open reading frame of the mahogany gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait mahogany gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait mahogany gene-GAL4 fusion plasmid into a yeast strain that contains a lacZ gene driven by a promoter that contains GAL4 activation sequence. A cDNA encoded protein, fused to a GAL4 transcriptional activation domain that interacts with bait mahogany gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait mahogany gene product-interacting protein using techniques routinely practiced in the art.

5.4.2.3. Assays for Compounds that Interfere with Mahogany Gene Product Macromolecule Interaction The mahogany gene products may, in vivo, interact with one or more macromolecules, such as proteins. For example, the mahogany gene products may, in vivo, interact with the mahoganoid gene products. Other macromolecules which interact with the mahogany gene products may include, but are not limited to, nucleic acid molecules and those proteins identified via methods such as those described, above, in Sections 5.4.2.1–5.4.2.2. For purposes of this discussion, the macromolecules are referred to herein as "binding partners". Compounds that disrupt mahogany gene product binding to a binding partner may be useful in regulating the activity of the mahogany gene product, especially mutant mahogany gene products. Such compounds may include, but are not limited to molecules such as peptides, and the like, as described, for example, in Section 5.4.2.1 above.

The basic principle of an assay system used to identify compounds that interfere with the interaction between the mahogany gene product and a binding partner or partners involves preparing a reaction mixture containing the mahogany gene product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of mahogany gene product and its binding partner. Control reaction mixtures are incubated without the test compound or with a compound which is known not to block complex formation. The formation of any complexes between the mahogany gene product and the binding partner is then detected. The formation of a complex in the control reaction, but not in the reaction mixture containing the test compound, indicates that the compound interferes with the interaction of the mahogany gene product and the binding partner. Additionally, complex formation within reaction mixtures containing the test compound and normal mahogany gene product may also be compared to complex formation within reaction mixtures containing the test compound and a mutant mahogany gene product. This comparison may be important in those cases wherein it is desirable to identify compounds that disrupt interactions of mutant but not normal mahogany gene product.

The assay for compounds that interfere with the interaction of the mahogany gene products and binding partners can be conducted in a heterogeneous or homogeneous format. Heterogeneous assays involve anchoring either the mahogany gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds that interfere with the interaction between the mahogany gene products and the binding partners, e.g., by competition, can be identified by conducting the reaction in the presence of the test substance; i.e., by adding the test substance to the reaction mixture prior to or simultaneously with the mahogany gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the mahogany gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the mahogany gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes an be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. In this approach, a preformed complex of the mahogany gene product and the interactive binding partner is prepared in which either the mahogany gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt mahogany gene product/binding partner interaction can be identified.

In another embodiment of the invention, these same techniques can be employed using peptide fragments that correspond to the binding domains of the mahogany gene product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, a mahogany gene product can be anchored to a solid material as described, above, in this Section by making a GST-1 fusion protein and allowing it to bind to glutathione agarose beads. The binding partner can be labeled with a radioactive isotope, such as $^{35}$S, and cleaved with a proteolytic enzyme such as trypsin. Cleavage products can then be added to the anchored GST-1 fusion protein and allowed to bind. After washing away unbound peptides, labeled bound material, representing the binding partner binding domain, can be eluted, purified, and analyzed for amino acid sequence by well-known methods. Peptides so identified can be produced synthetically or produced using recombinant DNA technology.

5.4.2.4. Assays for the Identification of Compounds that Ameliorate Body Weight Disorders Compounds, including but not limited to binding compounds identified via assay techniques such as those described, above, in Sections 5.4.2.1–5.4.2.3, can be tested for the ability to ameliorate body weight disorder symptoms, including obesity, cachexia, and anorexia. It should be noted that the assays described herein can identify compounds that affect mahogany activity by either affecting mahogany gene expression or by affecting the level of mahogany gene product activity. For example, compounds may be identified that are involved in another step in the pathway in which the mahogany gene and/or mahogany gene product is involved, such as, for example, a step which is either "upfield" or "downfield" of the step in the pathway mediated by the mahogany gene. Such compounds may, by affecting this same pathway, modulate the effect of mahogany on the development of body weight disorders. Such compounds can be used as part of a therapeutic method for the treatment of the disorder.

Described below are cell-based and animal model-based assays for the identification of compounds exhibiting such an ability to ameliorate body weight disorder symptoms.

First, cell-based systems can be used to identify compounds that may act to ameliorate body weight disorder symptoms. Such cell systems can include, for example, recombinant or non-recombinant cell, such as cell lines, that express the mahogany gene.

In utilizing such cell systems, cells that express mahogany may be exposed to a compound suspected of exhibiting an ability to ameliorate body weight disorder symptoms, at a sufficient concentration and for a sufficient time to elicit such an amelioration of such symptoms in the exposed cells. After exposure, the cells can be assayed to measure alterations in the expression of the mahogany gene, e.g., by assaying cell lysates for mahogany mRNA transcripts (e.g., by Northern analysis) or for mahogany gene products expressed by the cell; compounds that modulate expression of the mahogany gene are good candidates as therapeutics.

In addition, animal-based systems or models for a mammalian body weight disorder, for example, transgenic mice containing a human or altered form of mahogany gene, may be used to identify compounds capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of body weight disorder symptoms. The response of the animals to the exposure may be monitored by assessing the reversal of the symptoms of the disorder.

With regard to intervention, any treatments that reverse any aspect of body weight disorder-like symptoms should be considered as candidates for human therapeutic intervention in such a disorder. Dosages of test agents may be determined by deriving dose-response curves, as discussed in Section 5.5.1, below.

5.4.3. Compounds and Methods for the Treatment of Body Weight Disorders

Described below are methods and compositions whereby body weight disorders, including obesity, cachexia, and anorexia, may be treated. Such methods can comprise, for example administering compounds which modulate the expression of a mammalian mahogany gene and/or the synthesis or activity of a mammalian mahogany gene product, so that symptoms of the body weight disorder are ameliorated. Alternatively, in those instances whereby the mammalian body weight disorder results from mahogany gene mutations, such methods can comprise supplying the mammal with a nucleic acid molecule encoding an unimpaired mahogany gene product such that an unimpaired mahogany gene product is expressed and symptoms of the disorder are ameliorated.

In another embodiment of methods for the treatment of mammalian body weight disorders resulting from mahogany gene mutations, such methods can comprise supplying the mammal with a cell comprising a nucleic acid molecule that encodes an unimpaired mahogany gene product such that the cell expresses the unimpaired mahogany gene product, and symptoms of the disorder are ameliorated.

Because a loss of normal mahogany gene function results in the restoration of a non-obese phenotype in individuals exhibiting an agouti mutation (e.g. individuals that ectopically express the agouti gene in all tissues) a decrease or elimination of normal mahogany gene product would facilitate progress towards a normal body weight state in such individuals. Methods for inhibiting or reducing the level of mahogany gene product synthesis or expression can include, for example, methods such as those described in Section 5.4.3.1.

Alternatively, symptoms of certain body weight disorders such as, for example, cachexia and anorexia, which involve a lower than normal body weight phenotype, may be ameliorated by increasing the level of mahogany gene expression and/or mahogany gene product activity. Methods for enhancing the expression or synthesis of mahogany can include, for example, methods such as those described below, in Section 5.4.3.2

5.4.3.1. Inhibitory Antisense, Ribozyme and Triple Helix Approaches

In another embodiment, symptoms of body weight disorders may be ameliorated by decreasing the level of mahogany gene expression and/or mahogany gene product activity by using mahogany gene sequences in conjunction with well-known antisense, gene "knock-out," ribozyme and/or triple helix methods to decrease the level of mahogany gene expression. Among the compounds that may exhibit the ability to modulate the activity, expression or synthesis of the mahogany gene, including the ability to ameliorate the symptoms of a mammalian body weight disorder, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the mahogany gene could be used in an antisense approach to inhibit translation of endogenous mahogany mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. U.S.A. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-O-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff and Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been and Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.4.3.2. Gene Replacement Therapy

Mahogany gene nucleic acid sequences, described above in Section 5.1, can be utilized for the treatment of a mammalian body weight disorders, including obesity, cachexia, and anorexia. Such treatment can be in the form of gene replacement therapy. Specifically, one or more copies of a normal mahogany gene or a portion of the mahogany gene that directs the production of a mahogany gene product exhibiting normal mahogany gene function, may be inserted into the appropriate cells within a patient, using vectors that include, but are not limited to adenovirus, adeno-associated virus, and retrovirus vectors, in addition to other particles that introduce DNA into cells, such as liposomes.

Because the mahogany gene is expressed in the brain, such gene replacement therapy techniques should be capable delivering mahogany gene sequences to these cell types within patients. Thus, in one embodiment, techniques that are well known to those of skill in the art (see, e.g., PCT Publication No. WO89/10134, published Apr. 25, 1988) can be used to enable mahogany gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such mahogany gene sequences to the site of the cells in which the mahogany gene sequences are to be expressed.

Additional methods that may be utilized to increase the overall level of mahogany gene expression and/or mahogany gene product activity include using target homologous recombination methods, discussed in Section 5.2, above, to modify the expression characteristic of an endogenous mahogany gene in a cell or microorganism by inserting a heterologous DNA regulatory element such that the inserted regulatory element is operatively linked with the endogenous mahogany gene in question. Targeted homologous recombination can be thus used to activated transcription of an endogenous mahogany gene that is "transcriptionally silent", i.e., is not normally expressed, or to enhance the expression of an endogenous mahogany gene that is normally expressed.

Further, the overall level of mahogany gene expression and/or mahogany gene product activity may be increased by the introduction of appropriate mahogany-expressing cells, preferably autologous cells, into a patient at positions and in numbers that are sufficient to ameliorate body weight disorder symptoms. Such cells may be either recombinant or non-recombinant.

Among the cells that can be administered to increase the overall level of mahogany gene expression in a patient are normal cells, preferably brain cells, that express the mahogany gene. Alternatively, cells, preferably autologous cells, can be engineered to express mahogany gene sequences, and may then be introduced into a patient in positions appropriate for the amelioration of the body weight disorder symptoms. Alternately, cells that express an unimpaired mahogany gene and that are from a MHC matched individual can be utilized, and may include, for example, brain cells. The expression of the mahogany gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.4.2, that are capable of modulating mahogany gene product activity can be administered using standard techniques that are well known to those of skill in the art. In instances in which the compounds to be administered are to involve an interaction with brain cells, the administration techniques should include well known ones that allow for a crossing of the blood-brain barrier.

5.5. Pharmaceutical Preparations and Methods of Administration

The compounds that are determined to affect mahogany gene expression or gene product activity can be administered to a patient at therapeutically effective doses to treat or ameliorate body weight disorders, such as obesity, anorexia, or cachexia. A therapeutically effective dose refers to that amount of the compound sufficient to result in amelioration of symptoms of such a disorder.

5.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in.order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.5.2. Formulations and use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

Genetic and Physical Mapping of the Mahogany Locus

In the Example presented herein, studies are described which, first, define the genetic interval on mouse chromosome 2 within which the mahogany gene lies, and second, successfully narrow the interval to approximately 0.29 cM. Further, the physical mapping of this interval is described.

Mouse crosses were performed to obtain homozygous mg/mg mice. First, LDJ-Le-mg mice were crossed with CAST/Ei mice. The F1s were back-crossed with LDJ-Le-mg mice and the resulting litters scored for coat color. Mice showing coat color of mg/mg homozygotes were genotyped to using D2/NDS3 and D2/MIT19 markers to identify meiotic events. Mice showing recombinant events were fine structure mapped using various markers shown in FIG. 1. All genotyping was performed using PCR-SSLP and then analyzed using PAGE.

After 2300 meiosesis, the mahogany gene was mapped to a 0.99 cM interval FIG. 1. This corresponded to an interval width of 700 kb.

Physical Mapping of the Genetic Interval

The 700 kb mahogany region on mouse chromosome 2 is shown in FIG. 1. Genetic markers, clones spanning the region and open reading frames in the interval are shown in the figure.

7. EXAMPLE

Identification of a Candidate Mahogany Gene

In the Example presented herein, a gene is identified within the cloned DNA described in the Example in Section 6, above, which corresponds to a candidate mahogany gene.

Clones spanning the 700 kb region were sequenced and open reading frames were identified and analyzed through this interval. Nucleic acid sequencing was performed using ABI sequencers and the manufactures recommended procedures. Many novel sequences encoding proteins are located in this interval, see the bottom of FIG. 1. With each open reading frame identified, mutational analysis, primarily via SSCP analysis, was used with the three alleles of the mahogany phenotype mice to identify which of the open reading frames within this interval contain a mutation in an mg mouse.

A mutation was found in one of the genomic/cDNA sequences found in the integral in mg3J mice. FIGS. 3 and 2 provide the genomic and cDNA sequences surrounding the mutation, FIG. 6 shows the mutation in mg3J, and FIGS. 8 and 9 show splice variants in the 5' end of the murine mg gene. The mutation in mg3J mice is a deletion of a GCTGC sequence which results in the creation of a frameshift. Based on the chromosomal location and mutation identification, the cDNA provided in FIG. 2 and the corresponding genomic DNA which contains the contigs provided in FIG. 3 represent the mg gene/locus.

Further analysis of cDNA clones identified two distinct splice variants in the 5' end of the mg gene. FIG. 7 provides an analysis of the structure of the two splice variants, denoted akm1003 and akm1004. FIGS. 8 and 9 provide the nucleic acid and amino acid sequence of the 5' ends of these splice variants and structural analysis of the protein encoded by the 5' regions.

Analysis of libraries of human cDNA sequences led to the identification of three forms of the human ortholog of the mg gene: a long form (FIG. 18) and two shorter splice forms, each of which is shown in FIGS. 19 and 20.

8. EXAMPLE

Characterization of the Mahogany Gene

In the example presented herein, the nucleic acid sequence of the mahogany gene transcript identified in the example presented in Section 7, above, is used to generate Northern analysis data which characterize the expression of the mahogany transcript in a number of tissues both of wild type mice, and of mice exhibiting the mahogany phenotype. The results presented in this example are consistent with the mg gene being the mahogany gene.

For Northern analysis, polyA RNA was isolated from wild-type and the original mg mutant, mg3J and mg-Lester mice and utilized from the Northern analysis following standard protocols. Northern blots prepared from this mRNA were hybridized with a probe obtained from sequences common to the akm1003 and akm1004 sequences. Specifically PCR primers TTCCTCACTGG and GGACACACAG (SEQ ID NOS:129–130) were use o amplify cDNA from the akm1003 sequence which had been radiolabelled by random priming using a Gibco-BRL kit according to the manufacturer's recommended protocol.

An mg transcript was found in all mice examined in MRNA isolated from brain (minus the hypothalamus), kidney, heart, testes, liver, skin, and hypothalamus. No expression was seen in muscle.

In a Northern blot run on RNA samples from mahogany mice, the mg transcript was found to be expressed at a reduced level in all tissues in mRNA isolated from mg3J mice, as a varied size fragment in mg-Lester derived mRNA, and at different levels and sizes in original mg mutant mice derived mRNA.

These results are consistent with the mg gene disclosed herein as being the mahogany gene.

9. EXAMPLE

Effects of the Mahogany Gene on Genetic and Dietary Obesity

This section describes experiments which examine whether the mg gene acts specifically within the agouti pathway. Specifically, these experiments test whether mg can suppress the obesity of other monogenic obese mutants as well as whether it can suppress diet-induced obesity. The results show that mg does not suppress obesity in any of the monogenic obese mutants. However, mg can suppress diet-induced obesity. Thus, the mg gene and its corresponding gene product and compounds that modulate mg expression and/or activity have implications in the treatment of diet-induced obesity disorders, as well as in the treatment of disorders related directly to the mg or agouti gene.

9.1. Materials and Methods

Genetic Crosses

Figure 13:
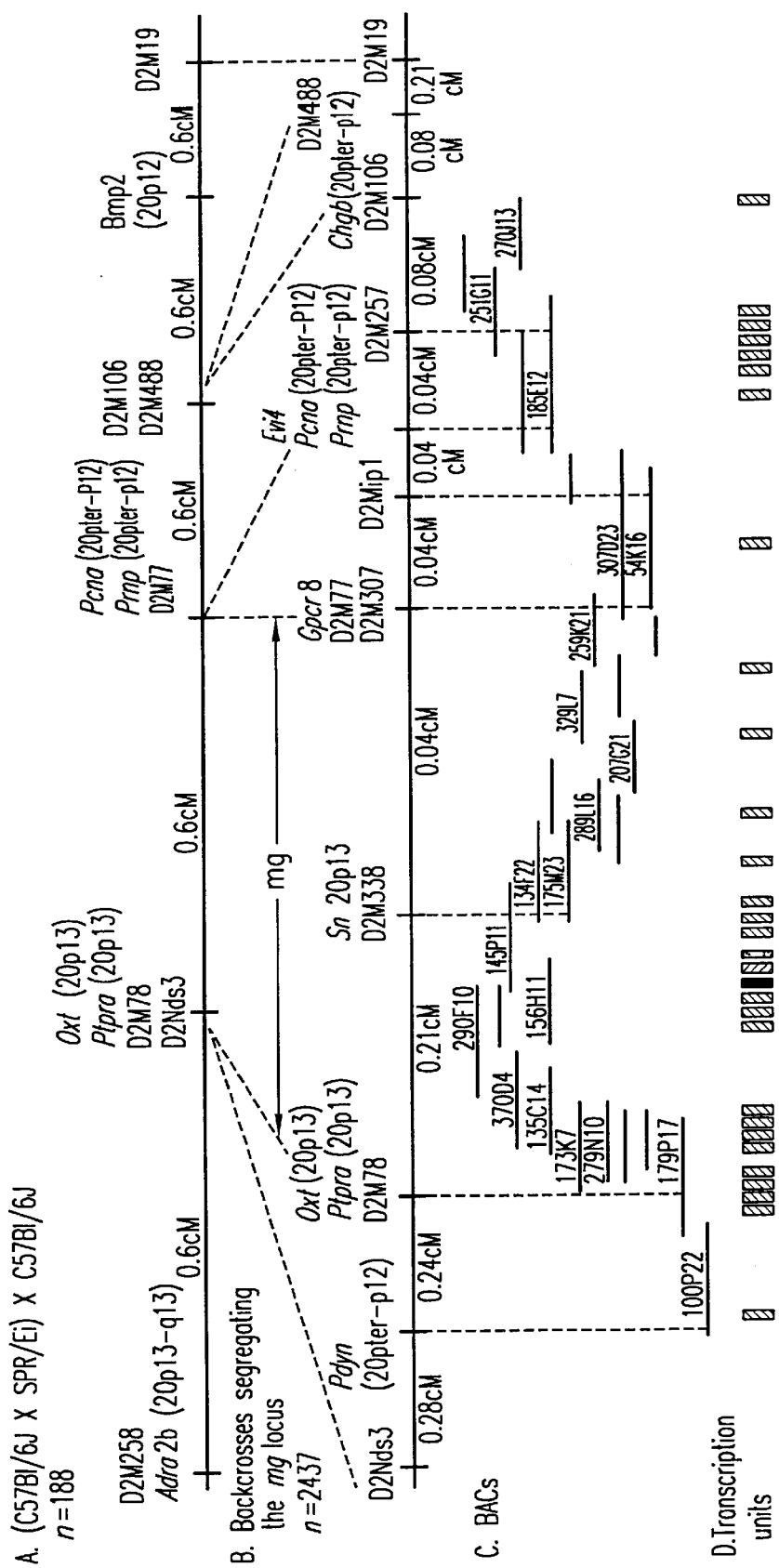

The crosses, and the number of animals for each (n) were (LDJ/Le-mg/mg X CAST/Ei) X LDJ/Le-mg/mg (n=1588), (C3HeB/FeJ-mg$^{3J}$/mg$^{3J}$ X CAST/Ei) X C3HeB/FeJ-mg$^{3J}$/mg$^{3J}$ (n=324), (C3HeB/FeJ-mg$^{3j}$/mg$^{3J}$ X MOLF/Ei) X C3HeB/FeJ-mg$^{3J}$/mg$^{3J}$ (n=216) and (C3HeB/FeJ-mg$^{3J}$/mg$^{3J}$ X C57BL6/J) X C3HeB/FeJ-m$^{3J}$/mg$^{3J}$ (n=309). The 2437 N$_2$ mice were analysed by coat colour to determine their genotype at the mg locus. As mice change color slightly at each hair molt and because the phenotype of mg/mg vs. mg/+ can be subtle, all mice were phenotyped at the same age by a single person. Genomic DNA was made from a tail biopsy of each mouse and analysed for multiple simple sequence length repeat polymorphism (SSLP) markers. The first ~100 mice were typed for a series of polymorphic Mit genetic markers (Deitrich, W. F. et al., 1996, *Nature* 380:149–152) from distal mouse chromosome 2 in order to accurately delimit the position of mg. With the first ~100 mice it was determined that mg mapped approximately 15 cM proximal of Agouti between markers D2Mit19 and D2Nds3 (FIG. 13). All remaining animals were genotyped for D2Mit19 and D2Nds3. Animals recombinant in that interval were typed with all available Mit markers between and for the ever growing number of markers developed during the project which, finally totaled 265 markers.

9.2. Results

The murine mahogany (mg) gene is known to act in a dosage dependent manner within the agouti pathway, to compensate for the agouti overexpression and for lack of signaling from the nul allele Mc1r (Miller, K. A. et al., 1997, *Genetics* 146:1407–1415; Dinulescu, D. M. et al., *Proc. Natl. Acad. Sci.*, in press; Robbins, L. S. et al., 1993, *Cell* 72:827–834). The phenotype of mice homozygous for both mg and a null allele of Mc1r (recessive yellow, Mc1r$^e$) is yellow, the same as the phenotype of Mc1r$^e$/Mc1r$^e$ mice, indicating that mg is not acting downstream of Mc1r. A similar experiment was performed with obese Mcr4 knock out mice (FIG. 11). For both sexes, all the animals homozygous for Mc4r−/− were approximately equally obese and were heavier than the mice wild-type at Mc4r independent of the genotype for mg. This data strengthens and confirms the Mc1r data previously published, strongly suggesting that mg acts at or upstream of both melanocortin receptors.

Figure 12A:
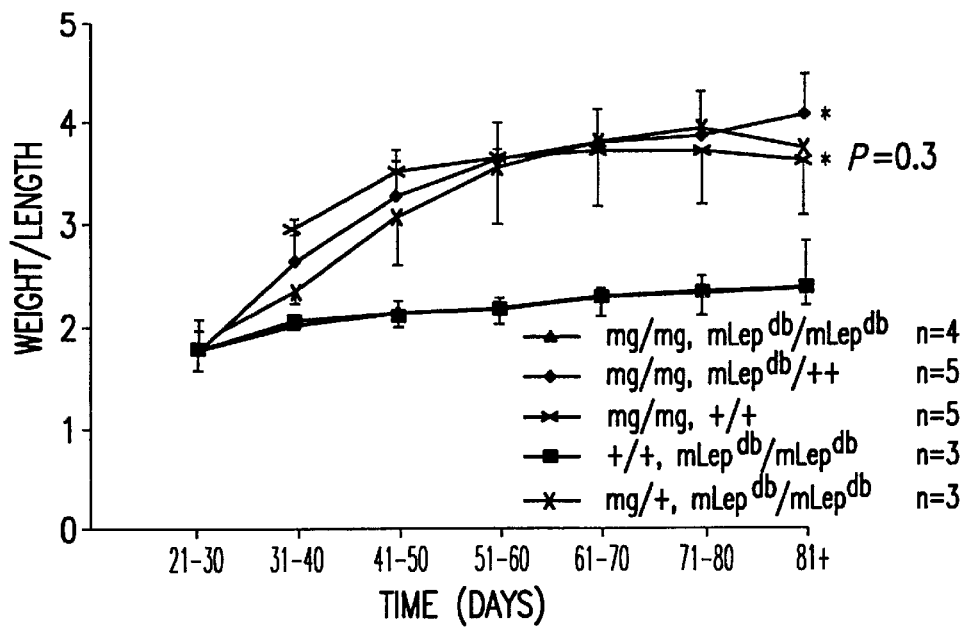
Figure 12B:
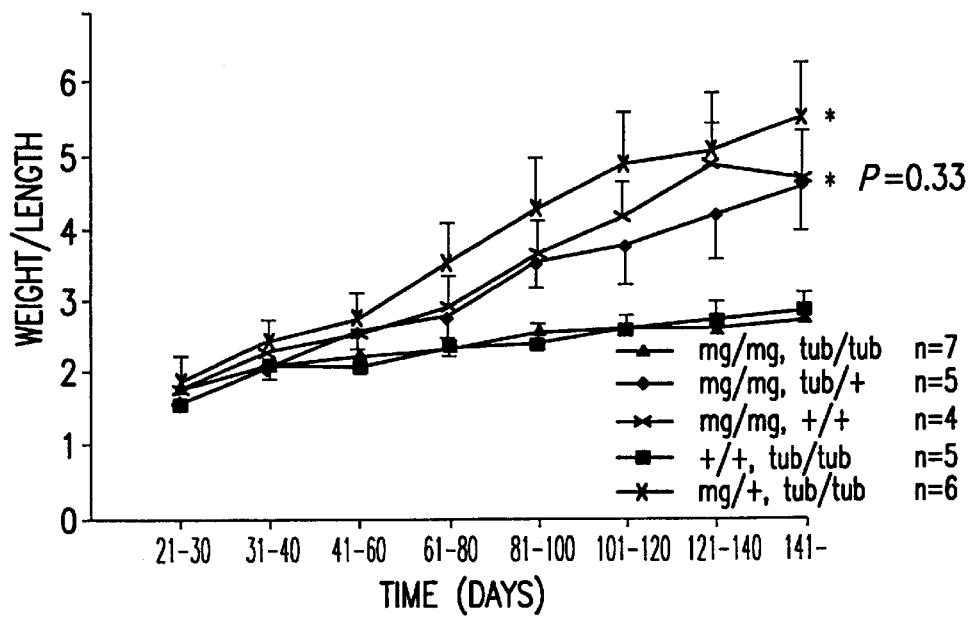
Figure 12C:
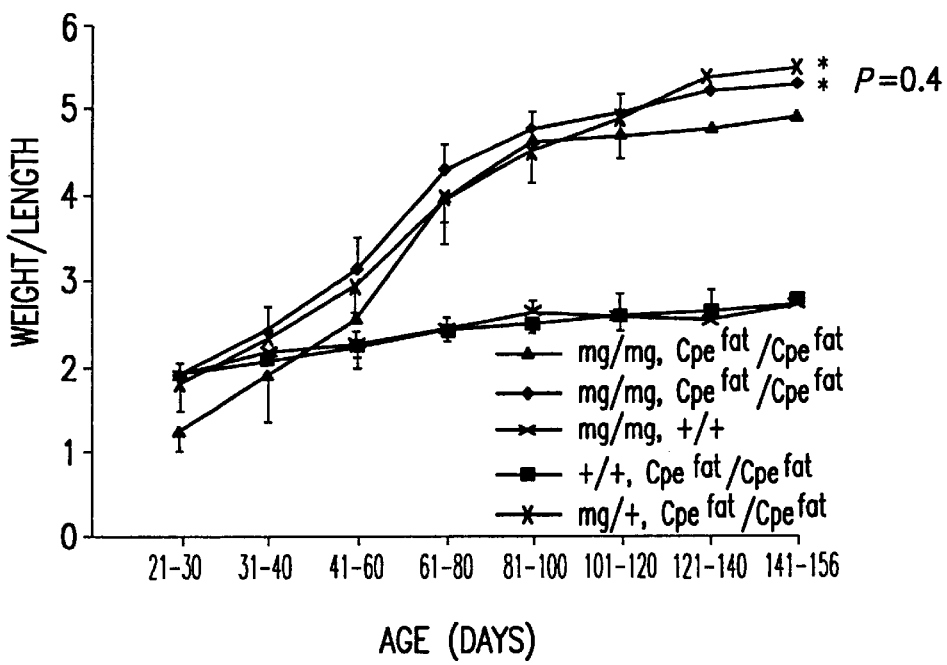
Figure 12D:
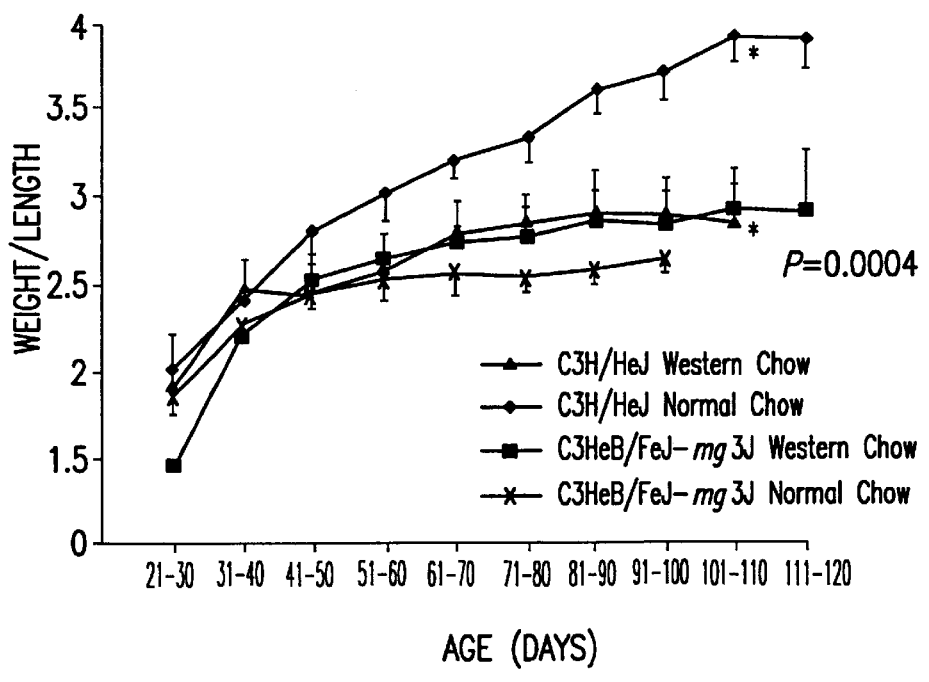

To test whether mg acts specifically within the agouti pathway, experiments were performed to determine whether mg can suppress the obesity of other monogenic obese mutants of the mouse and whether it could suppress diet-induced obesity. Appropriate genetic crosses were set up to produce mice segregating mg and one of the mouse obesity mutations Cpe$^{fat}$, tub, or Lepr$^{db}$ such that all combinations of homozygous and heterozygous animals were on the same mix of genetic background. No suppression of obesity was seen for any of the monogenic obese mutants (FIG. 12) lending credence to the assumed specificity of action within the agouti pathway. To ask whether mg can suppress diet induced obesity C3HeB/FeJ-mg$^{3J}$ and C3H/HeJ mice were placed, at weaning, either on normal chow having a physiological fuel value (PFV) of 3.63 kcal/gm with 9% fat, or onto a high fat diet having a PFV of 4.53 kcal/gm with 42.2% fat. Food consumption and body weight were measured weekly. Converting the grams of food consumed to calories indicated that C3H/HeJ mice on normal how and high fat diet consumed ~97 kCal/week and ~96 kCal/week, respectively. C3HeB/FeJ-mg$^{3J}$ mice on normal chow and high fat diet consumed ~83 kCal/week and ~81 kCal/week, respectively. Despite the equal calorie intake, the C3H/HeJ mice on the high fat diet readily gained more weight than the C3H/HeJ mice on normal chow (p=0.0004). In stark contrast, the C3HeB/FeJ-mg$^{3J}$ mice on either diet showed no statistically significant difference in weight (FIG. 12D). Female data showed the same trends, although there was no statistical significance between any of the mice on either diet.

10. EXPERIMENT

Mapping and Sequencing of the Mahogany Gene

This section describes experiments wherein the murine mahogany gene was genetically and physically mapped to an approximately 0.6 cM interval, and then sequenced. The murine mg sequence obtained was then used to isolate and sequence the human mg gene. Northern and in situ analyses of mg expression in mouse tissue are also described, and sequence motifs of the predicted MG polypeptide are discussed.

10.1. Materials and Methods

Physical Mapping

More than 36,000 individual sequences from the region were compared by BLAST (Altschul, S. F. et al., 1990, *J. Mol. Biol.* 215:403–410) to publicly available sequence databases and analyzed using GRAIL (Guan, X. et al., 1992, *Proc. Eighth IEEE Conference on AI Applications:*9–13) to identify potential coding sequence. In addition, sequences from overlapping BACs were assembled using phrap (Sing, C. F. et al., 1998, Genome Res. 8:175–185; Ewing B. and Green, P., 1998, *Genome Res.* 8:186–194; Gordon, D. et al., 1998, *Genome Res.* 8:195–202), and the resulting contigs were also analyzed using BLAST and GRAIL to aid in gene prediction. This data was displayed in ACEdb (Durbin, Richard and Mieg, Jean Thierry, 1991, A C. elegans Database, Documentation, code, and data available from anonymous FTP servers at lirmm.lirmm.fr, cele, mrc-lmb.cam.ac.uk, and ncbi.nlm.nih.gov) to further visualize predicted exons and their relationships to each other.

Northern Blot Analysis

PolyA+ RNA was extracted from the tissues indicated from wild-type, C3H/HeJ and the three mutant alleles of mg, C3HeB/FeJ-mg$^{3J}$, LDJ/Le-mg, and C3H/HeJ-mg$^L$, according to the manufacturer's instructions. RNA STAT-60 (Tel-Test, Inc., 1511 Sounty Rd. 129, Friendswood, Tex. 77546) was used to isolate total RNA. PolyA+ was isolated using Poly(A)Pure™ mRNA purification kit (Ambion, Inc., 2130 Woodward St. #200, Austin, Tex. 78744). 2 µg of each mRNA was separated on a 1% agarose-formaldehyde gel, transferred to nylon, and hybridized with a probe for mg corresponding to nt 990–1406 of the murine cDNA sequence with Rapid-hyb Buffer (Amersham LIFE SCIENCE, Gaithersberg, Md.). Filters were washed with 0.11×SSC, 0.1% SDS and exposed to KODAK X-omat film overnight.

10.2. Results

A positional cloning strategy was undertaken to identify the mg gene. Multiple genetic crosses were set up to produce second generation mice (n-2437) segregating mg which were used to genetically localise the.mg locus (FIG. 13B). When the genetic map critical interval for mg was resolved to ~0.6 cM physical mapping was initiated. Approximately 1 Mb was contiged with 30 BACs (FIG. 13C), most of which were made into random sheared libraries for shot gun sequencing. At completion of the project it was estimated that 85% sequence coverage across the interval had been achieved and that all genes within the region had been found. Twenty-nine genes were identified, 15 of which are novel genes. Within the final minimal interval for mg, indicated by the arrows in FIG. 13, there were eleven genes of which nine were unknown. All of these genes were tested as candidates for mg by examining the three mutant alleles of the mahogany locus, the original allele, mg, that arose in a stock of Swiss×C3H mice, and two alleles that have independently arisen on the C3H background, C3HeB/FeJ-$mg^{3J}/mg^{3J}$ and C3H/He-$mg^L$/mg. Each gene was examined by Northern blot analysis and RT-PCR analysis of RNA from tissues from wild-type and mg mutant mice, by Southern blot analysis of DNA from wild-type and mg mutant mice, and by SSCP analysis of genomic PCR products designed to cover the intron-exon boundaries of much of each of the genes. In all, 20 genes were analyzed in this manner, one of which showed a northern blot difference between the wild type and mutant alleles (FIG. 14).

The wild type expression pattern of this gene gives three bands of size ~9 kb, 4.5 kb, and 3.8 kb, of which the larges message is the most prominent (FIG. 14). The smaller two bands can be seen in all tissues but, depending upon tissue, may require extended exposure. Each of the different mg alleles gave a different expression pattern. C3HeB/FeJ-$mg^{3J}/mg^{3J}$ has extremely low expression, the 9 kb message only being very faint in brain, hypothalamus, and fat on northerns. C3H/He-$mg^L/mg^L$ expresses a single aberrant band of approximately 9.5–10 kb in kidney, heart, muscle, fat, and, most prominently, brain and hypothalamus. The LDJ/Le-mg/mg shows an altered ratio of the three wild type messages: the 9 kb message is reduced, while the two smaller messages are more highly expressed, in particular being very abundant in fat and hypothalamus. In situ analysis was used to look more closely at mg expression in the brain and specifically the hypothalamus. Overall hybridization in LDJ/Le-mg/mg looks equivalent to that of wild type, and the C3HeB/FeJ-$mg^{3J}/mg^{3J}$ shows an overall reduction of expression. Close examination of the hypothalamic region in both wild type and mutant alleles revealed differences in the ventromedial hypothalamic nucleus (VMH). Both C3HeB/FeJ-$mg^{3J}/mg^{3J}$ and the LDJ/Le-mg/mg have reduced VMH expression (FIG. 15) which is particularly interesting as many neuropeptides and receptors known to be involved in body weight regulation are expressed in the VMH, including Mc4r.

Initially, two overlapping mouse cDNAs of 1051 bps and 2419 bps were identified. Using these cDNAs as a starting point it was possible to build over 7990 bps of human sequences, using both the public EST database and an in house database, as well as identifying one cDNA clone from a human liver library. The 23 ESTs used in the contiging are listed in Table I below. Using the derived human sequence, it was then possible to estimate the intron-exon boundaries within the mouse genomic sequence. These were verified by PCR amplification and sequencing. In total, 4079 bps of mouse sequence was obtained, of which 4011 bp are coding sequence. The mouse genomic locus spans over 160 kb, and has 31 identified exons, at least one of which is differentially spliced.

TABLE I

| Gene Bank Accession # | SEQ ID NO. | Clone ID # | Clone Source |
| --- | --- | --- | --- |
| NA | | NA | Human Endothelial Cell (MPI) |
| AA062169 | 133 | 482948 | Soares mouse P3NMF19.5 |
| NA | | NA | Human Liver (MPI) |
| AA350292 | 134 | 151062 | Infant Brain |
| R87660 | 135 | 194640 | Soares Fetal Liver Spleen 1 NFLS |
| T69367 | 136 | 82898 | Stratagene Liver |
| T92696 | 137 | 118881 | Stratagene Lung |
| H11351 | 138 | 47626 | Soares Infant Brain 1 NIB |
| AA350293 | 139 | 151062 | Infant Brain |
| AA297697 | 140 | 149184 | Fetal Heart II |
| AB011120 | 141 | NA | Human Male Brain |
| AA297214 | 142 | 129808 | Embryo, 12 week I |
| AA298732 | 143 | 184690 | T-Lymphocyte |
| AI076479 | 144 | 1676623 | Soares Total Fetus Nb2HF8 9W |
| AA771958 | 145 | 1359202 | Soares parathyroid tumor NbHPA |
| R84298 | 146 | 194640 | Soares Fetal Liver Spleen 1NFLS |
| D81046 | 147 | 1178923 | Human Fetal Brain (Tfujiwara) |
| AA378603 | 148 | 183010 | Synovial Sarcoma |
| D60710 | 149 | 962349 | Clontech Human Fetal Brain (#6535) |
| D20236 | 150 | pm1235 | Human Promyelocyte |
| AA345684 | 151 | 147210 | Gall Bladder I |
| H45413 | 152 | 182870 | Soares Breast 3NbHBst |
| AA044305 | 153 | 486349 | Soares Pregnant Uterus NbHPu |

The mutant mahogany alleles were also sequenced, checking all intron-exon boundaries. A 5 bp deletion at 2809 nt was found in the coding sequence of the mg gene from C3HeB/FeJ-$mg^{3J}/mg^{3J}$ which introduces a stop codon a position 937, two codons 3' of the deletion. This mutation will result in a seriously truncated protein lacking many interesting domains, as discussed below. The $mg^{3J}$ allele is the same allele that showed extremely low expression levels. The combined Northern blot analysis, in situ hybridization analysis, and sequence analysis of the mutant $mg^{3J}$ allele strongly suggest that this gene is the mouse mahogany gene.

The 4011 bp of open reading frame (ORF) of mouse MG predicts a 1336 amino acid polypeptide with molecular mass of 148,706 D (FIG. 17, top sequence). BLAST searches of the NCBI and SwissProt protein databases identified two human paralogues with a similar modular architecture (KIAA0534, Genbank accession no. 3043592; and MEGF8, Genbank accession no. AB011541), as well as a C. elegans homologue (YC81_CAEEL, Genbank accession no. Q19981).

Another human protein, Attractin or DPPT-L (Duke-Cohen, J. S. et al., 1998, Proc. Natl. Acad. Sci. U.S.A. 95:11336–11341), appears to be a 1198 amino acid residue, approximately 134,000 D, secreted splice variant of the MG polypeptide. An alignment of the predicted MG (top) and Attractin (bottom) amino acid sequences is shown in FIG. 17. Attractin has not identified as being involved in the regulation of body weight. Rather, the protein is reported to mediate an interaction between T lymphocytes and monocytes that leads to the adherence and spreading of monocytes that become foci for T lymphocyte clustering (see Duke-Cohen et al., supra).

Searching the MG polypeptide with the SMART domain tool (Schultz, J. et al., 1998, Proc. Natl. Acad. Sci. U.S.A. 95:5857–5864) revealed sequence motifs that may provide further clues to its biological function (FIG. 16B, FIG. 17). The single transmembrane spanning MG protein has a large extracellular sequence of 1289 amino acids containing three EGF domains (Nakayama, M. et al., 1998, Genomics 51:27–34), two laminin-like EGF repeats, a CUB domain (Bork, P. and Beckmann, G., 1993, Mol. Biol. 231:539–545), a C-type lectin domain (Drickamer, K., 1995, Nat. Struct.

Biol. 6:437–439; Weis W. I., and Drickamer, K., 1996, *Ann. Rev. Biochem.* 65:441–473), two plexin-like repeats (Maestrini, E. et al., 1996, *Proc. Natl. Acad. Sci. U.S.A.* 93:674–678), and six consecutive kelch repeats (Bork, P. and Doolittle, R. F., 1994, *J. Mol. Biol.* 236:1277–1282). Multiple EGF domains are commonly found in Type-1 membrane proteins involved in cell adhesion and receptor-ligand interactions (Schultz, J. et al, 1998, *Proc. Natl. Acad. Sci. USA* 95:5857–5864). Laminin-EGF-like modules are found in a variety of proteoglycans such as perlecan and heparin sulphate proteoglycan. As CUB domains also frequently occur in glycosylated proteins and c-type lectins are known to be carbohydrate binders, it is likely that MG is heavily glycosylated and that carbohydrate interactions are essential for its function. Many kelch motif containing proteins have been found that, like MG, have multiple consecutive domains. Such consecutive four-stranded α-sheet Kelch motifs form a bladed beta "propeller fold" that is common in many sialidases and other enzymes (Maestrini, E. et al., supra). Unlike the other well recognized domains, the "plexin" repeat is less well defined. It was first recognized as a triple repeat in the Xenopus gene plexin that has similarity to MET (Bork, P. and Beckmann, G., 1993, *Mol. Biol.* 231:539–545). Since then, this cysteine rich repeat has been found in 6 MET gene family members, three of which signal via tyrosine kinase and three of which are hypothesized to have putative signaling function via a novel conserved cytoplasmic domain. However, it is fascinating that there is an eight amino acid stretch that is 100% conserved in the four proteins shown in FIG. 16A from human, mouse, and *C. elegans*. The conservation of sequence across such widely evolutionary divergent species strongly indicates a functional domain, possible a putative signaling motif.

The multi-domain structure of MG is complex, but draws many similarities from receptor and receptor-like proteins. The full-length MG polypeptide is predicted to be a large membrane-spanning protein with multiple extracellular domains that may have a binding or gathering function as well as a highly conserved putative signaling motif in the cytoplasmic tail.

The present invention is not to be limited in scope by the specific embodiments described herein, which are intended as single illustrations of individual aspects of the invention. Functionally equivalent methods and components are within the scope of the present invention. Indeed, various modifications of the invention, in addition to those shown and described herein, will become apparent to those skilled in the art from the foregoing description and accompanying drawings.

All publications and patent applications mentioned in the specification are herein incorporated by reference to the same extent as if each individual publication or patent application was specifically and individually indicated to be incorporated by reference.

What is claimed is:

1. An isolated nucleic acid molecule comprising at least 30 contiguous nucleotides of the nucleotide sequence of SEQ ID NO: 1 (FIG. 2A), SEQ ID NO: 7, or SEQ ID NO: 8 (FIG. 8A), wherein said nucleic acid molecule does not consist entirely of either a nucleotide sequence of SEQ ID NO: 141 or a fragment thereof, and wherein expression of said nucleic acid molecule suppresses obesity.

2. An isolated nucleic acid molecule comprising at least 500 contiguous nucleotides of the nucleotide sequence of SEQ ID NO: 12 (FIG. 10A), wherein said nucleic acid molecule does not consist entirely of a either a nucleotide sequence of SEQ ID NO: 141 or a fragment thereof, and wherein expression of said nucleic acid molecule suppresses obesity.

3. An isolated nucleic acid molecule comprising at least 150 contiguous nucleotides of the nucleotide sequence of SEQ ID NO: 10 (FIG. 9A), wherein expression of said nucleic acid molecule suppresses obesity.

4. An isolated nucleic acid molecule comprising at least 600 contiguous nucleotides of SEQ ID NOs: 14, 16, or 18, with the proviso that the nucleic acid molecule does not consist entirely of either the nucleotide sequence of SEQ ID NO: 141, or a fragment thereof, wherein expression of said nucleic acid molecule suppresses obesity.

5. An isolated nucleic acid molecule comprising at least 30 contiguous nucleotides of the nucleotide sequence of SEQ ID NO: 1 (FIG. 2A) or SEQ ID NO: 8 (FIG. 8A), wherein said nucleic acid molecule does not consist entirely of a either a nucleotide sequence of any of the following sequences or a fragment thereof: SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, or SEQ ID NO: 152, and wherein expression of said nucleic acid molecule suppresses obesity.

6. The isolated nucleic acid molecule of claim 5 which comprises at least 100 nucleotides.

7. The isolated nucleic acid molecule of claim 5 which comprises at least 300 nucleotides.

8. The isolated nucleic acid molecule of claim 5 which comprises at least 500 nucleotides.

9. The isolated nucleic acid molecule of claim 5 which comprises at least 600 nucleotides.

10. An isolated nucleic acid molecule comprising at least 30 contiguous nucleotides of the nucleotide sequence of SEQ ID NO: 12 (FIG. 10A), SEQ ID NO: 14 (FIG. 18A), SEQ ID NO: 16 (FIG. 19A), or SEQ ID NO: 18 (FIG. 20A), wherein said nucleic acid molecule does not consist entirely of a nucleotide sequence of the following sequences or a fragment thereof: SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, or SEQ ID NO: 152, and wherein expression of said nucleic acid molecule suppresses obesity.

11. The isolated nucleic acid molecule of claim 10 which comprises at least 100 nucleotides.

12. The isolated nucleic acid molecule of claim 10 which comprises at least 300 nucleotides.

13. The isolated nucleic acid molecule of claim 10 which comprises at least 500 nucleotides.

14. The isolated nucleic acid molecule of claim 10 which comprises at least 600 nucleotides.

15. The isolated nucleic acid molecule of any one of claim 1, 2, 3, 4, 5, 6, 7, 8, 9, 10, 11, 12, 13, or 14, wherein said nucleotide sequence encodes a polypeptide comprising a transmembrane domain.

16. A vector comprising the isolated nucleic acid molecule of any one of claim 1, 2, 3, 4, 5, 6, 7, 8, 9, 10, 11, 12, 13, or 14.

17. A host cell genetically engineered to contain the nucleic acid of any one of claim 1, 2, 3, 4, 5, 6, 7, 8, 9, 10, 11, 12, 13, or 14.

18. The nucleic acid molecule of any one of claim 1, 2, 3, 4, 5, 6, 7, 8, 9, 10, 11, 12, 13, or 14, further comprising a heterologous sequence.

19. A host cell genetically engineered to express the nucleic acid of any one of claim 1, 2, 3, 4, 5, 6, 7, 8, 9, 10, 11, 12, 13, or 14.

20. A method of producing a polypeptide comprising culturing the genetically engineered host cell of claim 19 so that the polypeptide is expressed in cell culture, and recovering the polypeptide from the cell culture.

21. An isolated nucleic acid molecule comprising at least 30 contiguous nucleotides of the nucleotide sequence of SEQ ID NO: 7, wherein said nucleic acid molecule does not consist entirely of a either a nucleotide sequence of any of the following sequences or a fragment thereof: SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, or SEQ ID NO: 152, and wherein expression of said nucleic acid molecule suppresses obesity.

22. The isolated nucleic acid molecule of claim 21, which comprises at least 100 nucleotides.

23. The isolated nucleic acid molecule of claim 21 or 22 wherein said nucleotide sequence encodes a polypeptide comprising a transmembrane domain.

24. A vector comprising the isolated nucleic acid molecule of claim 21 or 22.

25. A host cell genetically engineered to contain the nucleic acid of claim 21 or 22.

26. The nucleic acid molecule of claim 21 or 22, further comprising a heterologous sequence.

27. A host cell genetically engineered to express the nucleic acid of claim 21 or 22.

28. A method of producing a polypeptide comprising culturing the genetically engineered host cell of claim 27 so that the polypeptide is expressed in cell culture, and recovering the polypeptide from the cell culture.

* * * * *

SEQUENCE LISTING

<160> NUMBER OF SEQ ID NOS: 153

<210> SEQ ID NO 1
<211> LENGTH: 8827
<212> TYPE: DNA
<213> ORGANISM: Mus musculus

<400> SEQUENCE: 1

```
gaattccggg cgaaggggag ccggcgtgcg gggtgtgtat gtgttcgctg ggcgccggct        60
cagccccagg aagatggtgg cggtggcggc ggcggcggcg actgaggcgc ggctgagggg       120
gagcacgagg acgacagcag cgcctgcggg caggaagggc aggcagcacc gaccctgcac       180
cgcgacaggg gcctggaggc cgggaccgcg cgcccggctg tgtctcccgc gggtgctgtc       240
gcgggcgctg ccccgccgc cgctgctgcc gctgctcttt tcgctgctgc tgctgccgct       300
gccccgggag gccgaggccg ctgcggtggc ggcggcggtg tccggctcgg ccgcagccga       360
ggccaaggaa tgtgaccggc cgtgtgtcaa cggcggccgc tgcaaccctg gcaccggcca       420
gtgcgtctgc cccacgggct gggtgggcga gcaatgccag cactgcgggg gccgcttcag       480
gacatctgtc tcacgcctat aatcacagct gttcggaagg tgaggctgga ggaacagttc       540
gaggcaagct tcggctacag aataagttca agagtaacct ggggcaactt gggcttgtct       600
ccaaaaccaa aatgagcgaa aaggagcaag ctagagtctt ttgggaaaat tttagctgac       660
taatttttca ccgagaacta actggctctt ctggatttgt aacagatgga cctgggaatt       720
ataaatataa gacgaagtgc acatggctca ttgaaggaca gccaaataga ataatgagac       780
ttcgcttcaa ccattttgct acagaatgta gctgggacca tttatatgtt tatgatgggg       840
actcaatcta cgcacctctg attgctgcct ttagtggcct cattgttcct gaaagagatg       900
gcaatgagac ggctcctgag gtcactgtca cttcaggtta tgcactgctg catttttttca       960
```

-continued

```
gtgatgctgc ttataatctg actggattta atatcactta caattttgac atgtgtccga    1020
ataattgctc aggccgagga gagtgtaaga gcagtaacag cagcagcgct gttgagtgtg    1080
aatgttctga aaactggaaa ggggagtcgt gtgacattcc tcactgtaca gacaactgtg    1140
gctttcctca ccgaggcatc tgtaatgcaa gcgataccag agggtgctcc tgctttcctc    1200
actggcaggg tcctggatgt tcaattcctg tgccagctaa ccagtctttt tggactcgag    1260
aagaatattc tgatttaaag cttcccagag cctctcataa agctgtggtc aatggaaata    1320
taatgtgggt tgttggcgga tatatgttca accattcaga ttacagcatg gttttagcgt    1380
atgacctgac ttctagggaa tggcttccac taaaccattc tgtgaacagt gtggttgtaa    1440
gatatggtca ttctttggca ttacataagg ataaaatcta catgtatgga ggaaaaattg    1500
attcaacagg gaacgtgacc aatgagctga gagtatttca tattcataat gaatcatggg    1560
tattgttaac tccgaaagct aaggatcagt atgcagtggt tggacactca gcacacattg    1620
ttacactggc atctggccgt gtggtcatgt tggtcatctt cggtcattgc ccactctatg    1680
gatatataag cgttgtgcag gaatatgact tggaaaagaa cacatggagt atattacata    1740
ctcagggtgc tcttgtgcaa ggggggttatg gccacagtag tgtttatgat gacaggacca    1800
aggctctgta cgttcatggt ggctacaagg cttttcagcgc caacaaatac cggcttgcag    1860
atgacctcta cagatacgat gtggatactc agatgtggac cattcttaag gacagccgat    1920
ttttccgtta cttgcataca gctgtgatag tgagtggaac catgctggtg tttgagggga    1980
acacacacaa tgacacttcc atgagccacg gtgccaaatg cttctcctcg gacttcatgg    2040
cttatgacat tgcttgtgac cgatggtcag tgcttcccag acctgagctc catcatgatg    2100
tcaacagatt tggccattca gcagtcttgt acaacagcac catgtatgtg ttcggcggct    2160
tcaacagcct cctcctcagt gacgtcttgg tctttacctc ggagcagtgc gatgcacacc    2220
gcagtgaagc tgcttgtgtg gcagcaggac ctggtatccg gtgtctgtgg gacacacagt    2280
cgtctcgatg tacctcctgg gagttggcaa ctgaagaaca agcagaaaag ttaaaatcag    2340 agtgttttc taaaagaacc cttgaccatg acagatgtga ccagcacaca gattgttaca    2400
gctgcacagc caataccaat gactgccact ggtgcaatga tcactgtgtc cctgtgaacc    2460
acagctgcac agaaggccag atctccattg ccaagtatga gagttgcccc aaggataacc    2520
ccatgtacta ctgcaataag aaaaccagct gcaggagctg tgccctagac cagaactgcc    2580
agtgggagcc ccggaatcaa gagtgcatcg ccctgccgga aaatatctgt ggcaatggct    2640
ggcatttggt tggaaactcg tgtctgaaaa tcactactgc taaggagaat tatgacaatg    2700
ctaaattgtc ctgtaggaac cacaatgcct ttttggcttc cctcacatcc agaagaagg    2760 tggagtttgt ccttaagcag cttcgattaa tgcaatcatc tcaaagtatg tccaagctca    2820
ctctgactcc atgggttggt cttcggaaga tcaatgtgtc ttactggtgc tgggaggata    2880
tgtctccatt cacaaatagt ttgctgcagt ggatgccatc tgagcccagt gatgctggct    2940
tctgtgggat cttgtcagag cctagtactc ggggattaaa ggctgcaacc tgcatcaacc    3000
ctctcaatgg cagcgtctgt gaaaggcctg caaaccacag tgccaagcag tgccggacac    3060
catgtgccct gcgacagcg tgtggcgagt gcactagcag cagctcggag tgcatgtggt    3120
gcagtaacat gaagcagtgt gtggactcca atgcctacgt ggcctccttc ccttttggcc    3180
agtgtatgga atggtatacg atgagcagct gcccacctga aaattgctct ggctactgta    3240
cctgcagcca ttgcttggag cagccaggct gtggttggtg tactgatcct agcaatactg    3300
```

```
ggaaaggaaa atgtattgag ggcagctata aaggacctgt gaagatgccg tcacaggcct    3360
ctgcaggaaa tgtgtatcca cagccccttc tgaactccag catgtgtcta gaggacagca    3420
gatacaactg gtctttcatt cactgtccag cttgccagtg caacgacac agcaaatgca     3480 tcaaccagag tatctgtgag aagtgtgagg acctgaccac gggcaagcac tgcgagacct    3540
gcatatctgg cttctatggt gacccgacta atggaggcaa atgtcagcca tgcaagtgca    3600
atgggcacgc atcactgtgc aacaccaaca ccggcaagtg cttctgtacc accaaaggtg    3660 tcaagggggga cgagtgccag ctatgtgagg tagaaaatcg ataccaagga aaccctctca    3720
aaggaacatg ctactatacc cttctcattg actatcagtt caccttttagc ctgtcccagg    3780 aagacgaccg ctactacaca gccatcaact ttgtggctac tcctgatgaa caaaacaggg    3840
atttggacat gttcatcaat gcctccaaaa acttcaacct caacatcacc tgggccacca    3900
gcttcccagc cggaacccag actggagaag aggtgcctgt tgtttcaaaa accaacatca    3960
aggaatacaa agatagcttc tctaatgaga aatttgattt tcgcaaccat ccaaacatca    4020 ctttcttttgt ttatgtcagt aatttcactt ggcccatcaa aattcagatt gccttctccc    4080
agcacagcaa cttcatggac ctggtacagt tcttcgtgac tttcttcagt tgtttcctct    4140
cgctgcttct ggtggctgca gtggtctgga agatcaagca gagctgttgg gcatccaggc    4200
ggagagagca acttcttcgg gagatgcaac agatggccag ccgcccctt gcttctgtaa     4260 acgttgcctt ggaaacagat gaggagcctc ctgatcttat tggggggagt ataaagactg    4320
ttcccaaacc cattgcactg gagccgtgtt ttggcaacaa agccgctgtc ctctctgtgt    4380
ttgtgaggct ccctcgaggc ctgggtggca tccctcctcc tgggcagtca ggtcttgctg    4440
tggccagcgc cctggtggac atttctcagc agatgccgat agtgtacaag gagaagtcag    4500
gagccgtgag aaaccggaag cagcagcccc ctgcacagcc tgggacctgc atctgatgct    4560 gggggccaggg actctcccac gcacgagcta gtgagtggca caccagagcc atctgcaggg    4620
aagggcgtgg cggggaaatg gctgtgcggt gcgggacgga agactggaaa ccctcaaagc    4680
atctgactca cctgcatgat cacaagcttt cttttgacgtt ttctcccatc cgtgttccag    4740
catctaacct tttacttttg cataggaaat acttgattta attacaggtc cagggatgag    4800
ctgatggttg ctggaggagg ccagtgtaga gccagtgaga gaactaggaa tgacactcag    4860
gttcactgtg gaaaactgtt cttgggactg tctcaactgt gcaaaaaaca aaagatggag    4920
tgtttacaag tagacattcg tcatcagttg ttccttgaaca tggtctttta aaaactagtc    4980
agatgaatta acttgttttc atctgaagcc tgctatcttt tttaaaagat gtgctatttta   5040 ttcttgcacg atttaggcaa ttatctctct tccaggagt accttttttt ctagttgaga     5100
attaataatg gtccatctct tttgatcata tcaagctagg atagaagggg ggctatttta    5160
aatgtcaagg tcagcagtgt tactttgaat gtaaactggt ataataggta gttttctata    5220
gtaacttgat taatttagtc ttaatccatt tgaaactctc tcttcctttc tctctgcctg    5280
tccctctcct tctccatctc accctccctc tctcacacat acacacacaa acacatacac    5340
acaacactaa gtgcctagac tttaaataga tctagcaatt ggaaagttag taagcctaag    5400
tttttacata attgcattcc tacattcttg taaaatttaa atagctacca ttggcaatct    5460 gcttttttttc taaaatctga tttgcagcca ggaaagaatt ttctcaccca aggaacattt    5520
gatctagcag cagggatgag aggaaagcag aaatgaatga actgtgaaag ctcctgttttt   5580 tattatcaaa aaggacactg tcaagaaggc gcccctgcc cccaccccg tgtcaccccta     5640 ggcctgataa gcgatcagag gaaggactc attcatgtca cgcttccttg agcagaaaag     5700
```

-continued

```
agcactgaga gcacttggga ccoctggatc agagagcatc tgtgtgtcct gcagcctcct    5760
ctgaacttgt ggttcattct caggctgggg tggactcaga tgccaggaaa gggacagcct    5820
cccattgtca ggcagaagct gcccaaagcc tggagaagga cttgtttgcc ctctttcccc    5880
caggaggggc tcgacccacc caccctccct ctcagaccaa ggtggtggct gtgaggaggg    5940
cagcaaatgc tgacaaggat gaaaagcaca tggaaaaaaa tggacgagga gggaaaactc    6000
tgccaaatgg aaaatgacca aatttaagag ggtgggacag tccctgctc ctctcccaga     6060 gggcactgct tggaaattgt gttttcccca tttatggtgc tctgtattct ggcattatgc    6120
agcagcctcc cagaagctct cttctgcttc aaaacctggg atctctggca ttaccctatt    6180
gggatggacc gctggacagc aatgctcgag tttgtgaatt tggagagata ctcaaaagag    6240
ctaaaactgc agcattttac ctttaaatgc agtgcctaga gagagtat tgtctcttcc      6300 ccaacactaa ccccactccc atgaagaatt gcctggaaaa atgttttcaa ggaatttgaa    6360
ccataaaaca ctatctgatg cacagaacac ctctactttg agactcacct ctcataaagc    6420 ttcttttca cattactgtt aaagaccaga cgttctagaa aagacccctc ctctcatgag     6480
ctcccccatc cctgctacag aacacagcac ccatggcgcc tgcagtggac tggcccctta    6540
attcccacag gccccccag caaggccaaa gggaggcccc tgggtattgt cctcctacaa     6600
ggaagatcct ctttgtttgt tcaaaggacc agttttccta ggccaaagaa gtctcttccc    6660
catgttagtc ctatgccttg aaatatcatg caccatgacc cacagccatc tggttatgtc    6720
ttattttttt cctaaaagat aatgtttatt tttaaaaagg aaggaagaag caagtgaagt    6780
ttcattctgc tccagcggtg gggaagccgc tgaatccacc tgcttctcct ttgcaaccga    6840
cagcaaacag ctttctccgg cctcagggca gaaaaggga atggcaggga gtaagaggcg     6900
ctgggctcgg agcctgtttc caagaaggaa ttggttgtca tctggcagtg ttgcgcgtca    6960
caagagagcc tgtatataaa ttaaaatagt caagacaaca ctgaccttgc acttgtacat    7020
aactatacag tagtgtccag aatgttcaga cattcggagt gtacataaaa cagaaaaaat    7080
cttcatgtat ttttattaaa tataacaatg tctgagtttc acctaagatg tttttgtgcc    7140
atatgctgga tatccaggtt ctcgccaggc cccgatacat gaataacaaa cccaagaaac    7200
gcatccccat tgtgtgatgt gttcagatgc atctggcacc aattaggtat ttcttaaaac    7260
aggactcatc tgtcagagtg cacatgaaaa atcaggcagg gaatcgaaac gacagcgctg    7320
gaggagactc aggaagcaga ggcgtccctg ccgctgccct tggccctgca agcacatcat    7380 gacccttct ggcagcctct tggtgctctg ggtagtgagg gatgaccagt cttgtcctga     7440
gaaatgtttc tcttagtctt taagttcaaa gactaacctg tagcaatcag actttccaaa    7500 aggggttct ccatttttg tagttttgtc taaattttta atgaccattt cctggaatca     7560
gtttattata ctgaaaactg ggggtgggag tagggagcta gtttgttgat aaatagttcc    7620
catttccccg tggagaattt gacatacct ggactcctgt gtgcctcctg ccatccctgc     7680
acacagcctg gggagaagcc tgtgcctccc cgtgtggaga aaggcaacc ccagatcccc     7740 tgagctaacc cggaggaaag gcagtcctgg acagaagact gtcagcagaa ggaaagtact    7800
ggactacccg tggtaagtc ctgccattca agactggaga cacctgggaa ataaaaagag     7860
cagggcactg ctggtgggaa gaggcatttt accttccagt gcaaatcctg ctcctttgat    7920
ttaatggggt gtactgggc cagggctga ttcacttcct tgggagatgg tggtgttttc      7980
atgaacatct ttgatccttc catttcattt attcatccat ccattcaaca agtatttgct    8040
```

```
aaacactaac ttaagctaat gctagggtag tgactgagat gtaaaaatag attttagaat    8100
taaaacaaaa tccaagtcct cacaccctg tcatcccagg agatctttcc ttgtggtggt     8160
ttctgtgaga attggccatc ctgaggacac agccaggacg gcagaggcct cctggcctca    8220
gggcatgccc tgcctacctt ctgaaatgtt taccccattg accaaacttg gctccagcca    8280
ttgcggtggt ttctagatag ccaggcccac caagagatat tgcccttga tgagagtcaa     8340 acaccctgcc tacaaggaga tgttttgaaa tggagaggaa aattggcacc tcatctttta    8400
aaggcagtaa tggaattgat tttcagtaac tgaatttgtg cacaaaacat tctaaacact    8460
agtgaagcct gtttcgttga actaattctg gctctggaaa tgttttttgtt ttatagttat   8520 ttacgatttc gtttgtttgg attcaagctt agtttgttaa tatgtataat ttagcatcta    8580
ttacactcat gtaaatatgg agtaagtatt gtaaactatt tcattgcggg gattgtgggt    8640
gttatacata catttaggac tgcaatttt tggtattttt tgtattgtaa ataacagct       8700 aatttaagca ggaacaagag aactaaggga ggtctgtgca ttttaaacac aaatgtgaag    8760
aacttgtata taaacaaaag taaatactat aatacaaact tccttctgaa ataaaagtag    8820
atctggt                                                              8827
```

<210> SEQ ID NO 2
<211> LENGTH: 1260
<212> TYPE: PRT
<213> ORGANISM: Mus musculus

<400> SEQUENCE: 2

```
Met Arg Leu Arg Phe Asn His Phe Ala Thr Glu Cys Ser Trp Asp His
  1               5                  10                  15

Leu Tyr Val Tyr Asp Gly Asp Ser Ile Tyr Ala Pro Leu Ile Ala Ala
             20                  25                  30

Phe Ser Gly Leu Ile Val Pro Glu Arg Asp Gly Asn Glu Thr Ala Pro
         35                  40                  45

Glu Val Thr Val Thr Ser Gly Tyr Ala Leu Leu His Phe Phe Ser Asp
     50                  55                  60

Ala Ala Tyr Asn Leu Thr Gly Phe Asn Ile Thr Tyr Asn Phe Asp Met
 65                  70                  75                  80

Cys Pro Asn Asn Cys Ser Gly Arg Gly Glu Cys Lys Ser Ser Asn Ser
                 85                  90                  95

Ser Ser Ala Val Glu Cys Glu Cys Ser Glu Asn Trp Lys Gly Glu Ser
            100                 105                 110

Cys Asp Ile Pro His Cys Thr Asp Asn Cys Gly Phe Pro His Arg Gly
        115                 120                 125

Ile Cys Asn Ala Ser Asp Thr Arg Gly Cys Ser Cys Phe Pro His Trp
    130                 135                 140

Gln Gly Pro Gly Cys Ser Ile Pro Val Pro Ala Asn Gln Ser Phe Trp
145                 150                 155                 160

Thr Arg Glu Glu Tyr Ser Asp Leu Lys Leu Pro Arg Ala Ser His Lys
                165                 170                 175

Ala Val Val Asn Gly Asn Ile Met Trp Val Val Gly Gly Tyr Met Phe
            180                 185                 190

Asn His Ser Asp Tyr Ser Met Val Leu Ala Tyr Asp Leu Thr Ser Arg
        195                 200                 205

Glu Trp Leu Pro Leu Asn His Ser Val Asn Ser Val Val Arg Tyr
    210                 215                 220

Gly His Ser Leu Ala Leu His Lys Asp Lys Ile Tyr Met Tyr Gly Gly
```

```
                225                 230                 235                 240

Lys Ile Asp Ser Thr Gly Asn Val Thr Asn Glu Leu Arg Val Phe His
                245                 250                 255

Ile His Asn Glu Ser Trp Val Leu Leu Thr Pro Lys Ala Lys Asp Gln
                260                 265                 270

Tyr Ala Val Val Gly His Ser Ala His Ile Val Thr Leu Ala Ser Gly
                275                 280                 285

Arg Val Val Met Leu Val Ile Phe Gly His Cys Pro Leu Tyr Gly Tyr
                290                 295                 300

Ile Ser Val Val Gln Glu Tyr Asp Leu Glu Lys Asn Thr Trp Ser Ile
305                 310                 315                 320

Leu His Thr Gln Gly Ala Leu Val Gln Gly Gly Tyr Gly His Ser Ser
                325                 330                 335

Val Tyr Asp Asp Arg Thr Lys Ala Leu Tyr Val His Gly Gly Tyr Lys
                340                 345                 350

Ala Phe Ser Ala Asn Lys Tyr Arg Leu Ala Asp Asp Leu Tyr Arg Tyr
                355                 360                 365

Asp Val Asp Thr Gln Met Trp Thr Ile Leu Lys Asp Ser Arg Phe Phe
                370                 375                 380

Arg Tyr Leu His Thr Ala Val Ile Val Ser Gly Thr Met Leu Val Phe
385                 390                 395                 400

Gly Gly Asn Thr His Asn Asp Thr Ser Met Ser His Gly Ala Lys Cys
                405                 410                 415

Phe Ser Ser Asp Phe Met Ala Tyr Asp Ile Ala Cys Asp Arg Trp Ser
                420                 425                 430

Val Leu Pro Arg Pro Glu Leu His His Asp Val Asn Arg Phe Gly His
                435                 440                 445

Ser Ala Val Leu Tyr Asn Ser Thr Met Tyr Val Phe Gly Gly Phe Asn
                450                 455                 460

Ser Leu Leu Leu Ser Asp Val Leu Val Phe Thr Ser Glu Gln Cys Asp
465                 470                 475                 480

Ala His Arg Ser Glu Ala Ala Cys Val Ala Ala Gly Pro Gly Ile Arg
                485                 490                 495

Cys Leu Trp Asp Thr Gln Ser Ser Arg Cys Thr Ser Trp Glu Leu Ala
                500                 505                 510

Thr Glu Glu Gln Ala Glu Lys Leu Lys Ser Glu Cys Phe Ser Lys Arg
                515                 520                 525

Thr Leu Asp His Asp Arg Cys Asp Gln His Thr Asp Cys Tyr Ser Cys
                530                 535                 540

Thr Ala Asn Thr Asn Asp Cys His Trp Cys Asn Asp His Cys Val Pro
545                 550                 555                 560

Val Asn His Ser Cys Thr Glu Gly Gln Ile Ser Ile Ala Lys Tyr Glu
                565                 570                 575

Ser Cys Pro Lys Asp Asn Pro Met Tyr Tyr Cys Asn Lys Lys Thr Ser
                580                 585                 590

Cys Arg Ser Cys Ala Leu Asp Gln Asn Cys Gln Trp Glu Pro Arg Asn
                595                 600                 605

Gln Glu Cys Ile Ala Leu Pro Glu Asn Ile Cys Gly Asn Gly Trp His
                610                 615                 620

Leu Val Gly Asn Ser Cys Leu Lys Ile Thr Thr Ala Lys Glu Asn Tyr
625                 630                 635                 640

Asp Asn Ala Lys Leu Ser Cys Arg Asn His Asn Ala Phe Leu Ala Ser
                645                 650                 655
```

-continued

```
Leu Thr Ser Gln Lys Lys Val Glu Phe Val Leu Lys Gln Leu Arg Leu
            660                 665                 670

Met Gln Ser Ser Gln Ser Met Ser Lys Leu Thr Leu Thr Pro Trp Val
            675                 680                 685

Gly Leu Arg Lys Ile Asn Val Ser Tyr Trp Cys Trp Glu Asp Met Ser
            690                 695                 700

Pro Phe Thr Asn Ser Leu Leu Gln Trp Met Pro Ser Glu Pro Ser Asp
705                 710                 715                 720

Ala Gly Phe Cys Gly Ile Leu Ser Glu Pro Ser Thr Arg Gly Leu Lys
            725                 730                 735

Ala Ala Thr Cys Ile Asn Pro Leu Asn Gly Ser Val Cys Glu Arg Pro
            740                 745                 750

Ala Asn His Ser Ala Lys Gln Cys Arg Thr Pro Cys Ala Leu Arg Thr
            755                 760                 765

Ala Cys Gly Glu Cys Thr Ser Ser Ser Glu Cys Met Trp Cys Ser
            770                 775                 780

Asn Met Lys Gln Cys Val Asp Ser Asn Ala Tyr Val Ala Ser Phe Pro
785                 790                 795                 800

Phe Gly Gln Cys Met Glu Trp Tyr Thr Met Ser Ser Cys Pro Pro Glu
            805                 810                 815

Asn Cys Ser Gly Tyr Cys Thr Cys Ser His Cys Leu Glu Gln Pro Gly
            820                 825                 830

Cys Gly Trp Cys Thr Asp Pro Ser Asn Thr Gly Lys Gly Lys Cys Ile
            835                 840                 845

Glu Gly Ser Tyr Lys Gly Pro Val Lys Met Pro Ser Gln Ala Ser Ala
            850                 855                 860

Gly Asn Val Tyr Pro Gln Pro Leu Leu Asn Ser Ser Met Cys Leu Glu
865                 870                 875                 880

Asp Ser Arg Tyr Asn Trp Ser Phe Ile His Cys Pro Ala Cys Gln Cys
            885                 890                 895

Asn Gly His Ser Lys Cys Ile Asn Gln Ser Ile Cys Glu Lys Cys Glu
            900                 905                 910

Asp Leu Thr Thr Gly Lys His Cys Glu Thr Cys Ile Ser Gly Phe Tyr
            915                 920                 925

Gly Asp Pro Thr Asn Gly Gly Lys Cys Gln Pro Cys Lys Cys Asn Gly
930                 935                 940

His Ala Ser Leu Cys Asn Thr Asn Thr Gly Lys Cys Phe Cys Thr Thr
945                 950                 955                 960

Lys Gly Val Lys Gly Asp Glu Cys Gln Leu Cys Glu Val Glu Asn Arg
            965                 970                 975

Tyr Gln Gly Asn Pro Leu Lys Gly Thr Cys Tyr Tyr Thr Leu Leu Ile
            980                 985                 990

Asp Tyr Gln Phe Thr Phe Ser Leu Ser Gln Glu Asp Asp Arg Tyr Tyr
            995                 1000                1005

Thr Ala Ile Asn Phe Val Ala Thr Pro Asp Glu Gln Asn Arg Asp Leu
            1010                1015                1020

Asp Met Phe Ile Asn Ala Ser Lys Asn Phe Asn Leu Asn Ile Thr Trp
1025                1030                1035                1040

Ala Thr Ser Phe Pro Ala Gly Thr Gln Thr Gly Glu Glu Val Pro Val
            1045                1050                1055

Val Ser Lys Thr Asn Ile Lys Glu Tyr Lys Asp Ser Phe Ser Asn Glu
            1060                1065                1070
```

```
Lys Phe Asp Phe Arg Asn His Pro Asn Ile Thr Phe Val Tyr Val
        1075                1080                1085

Ser Asn Phe Thr Trp Pro Ile Lys Ile Gln Ile Ala Phe Ser Gln His
        1090                1095                1100

Ser Asn Phe Met Asp Leu Val Gln Phe Val Thr Phe Ser Cys
1105                1110                1115                1120

Phe Leu Ser Leu Leu Leu Val Ala Ala Val Val Trp Lys Ile Lys Gln
            1125                1130                1135

Ser Cys Trp Ala Ser Arg Arg Arg Glu Gln Leu Leu Arg Glu Met Gln
        1140                1145                1150

Gln Met Ala Ser Arg Pro Phe Ala Ser Val Asn Val Ala Leu Glu Thr
        1155                1160                1165

Asp Glu Glu Pro Pro Asp Leu Ile Gly Gly Ser Ile Lys Thr Val Pro
        1170                1175                1180

Lys Pro Ile Ala Leu Glu Pro Cys Phe Gly Asn Lys Ala Ala Val Leu
1185                1190                1195                1200

Ser Val Phe Val Arg Leu Pro Arg Gly Leu Gly Ile Pro Pro Pro
        1205                1210                1215

Gly Gln Ser Gly Leu Ala Val Ala Ser Ala Leu Val Asp Ile Ser Gln
            1220                1225                1230

Gln Met Pro Ile Val Tyr Lys Glu Lys Ser Gly Ala Val Arg Asn Arg
        1235                1240                1245

Lys Gln Gln Pro Pro Ala Gln Pro Gly Thr Cys Ile
        1250                1255                1260

<210> SEQ ID NO 3
<211> LENGTH: 17056
<212> TYPE: DNA
<213> ORGANISM: Mus musculus

<400> SEQUENCE: 3
agattttatg ccttcgtaca cgcctcccat aagatggaca aggtgtacta attactgcca      60
ttactgttgc tgaccccaga ggtcaatgtc ctcacatggc ctctactggc actgtctggg     120
cagaaactgt atatccaact ggtgaacctg aaagccctat gactacttgg tgtctctggt     180
gctaacccta gtcgttgggg catcttactg tatcctggta aggaaagaca tccaggctcc     240
ccacttaymk wwacyrgywm rgmycakgsy mgrgcyaawk tkctgtrrmr tctggctggc     300
atagagacat tactattgaa agttttgtct ttctaaatcc ttggactaaa gagagcacaa     360
gattttctgg aagatcttgc tttaaatttt ttttttattc ttttgagatg ctacatataa     420
ttagaggccc tgcacatgga ggcgagaacc ccacctctgg gctacatcct acgtcttttc     480
cttagggtat tttttttttct ttcttgtacc tatcagtatt actaagttgc aaatgtgctc     540
agcagtaaat ttaacataca taggcaaaaa gaaaagtctc aggacaccct gcctcacact     600
gtttactgtg ctcaggagta ctgagccata ctgttttctt gctgctgctt tttttctctt     660
ggttgtttac acacagtgtt caaggtgtgt taatcatagt tagtatttca atttttttctt     720
aggtcagcaa gaaagctcac agaggaagag tgctttgctg ccagcctgat gacctgggtg     780
acccaagtga tctcacctac agggtgggag cacagcacag cattccaagt cttttttctga     840
ccacacaggc actatggcac acaaacacac aggatacata aatgttaaaa aaaaaaaaag     900
acttttatat ttttctccat ataatttaaa agattcctct ttcaacattc cttttgcaaa     960
gcagtatcat tgtgtttgta tatgtgtgtc cttccacatt ttgtcttcaa ttctaaattt    1020
ttagaattgt tagcctggtc ctctcatttc tactactttc tctagtaaac tgtcctttca    1080
```

-continued

```
tattacacat cgctctcctg tcacctgttt tagagctgtc atccatttta taaggttact    1140
tcactgttct acactacttt gtgtctttta attactatgc ctggggtgat tcaaaaactg    1200
tctgtgatgg gttggttgag gatggctcca ataggttcaa cacttggtcc tgattggtgg    1260
aactgttttg ggaaggatta ggaggtgtga ccttgtgggg gagtgtgtca ctggagtga     1320
gtgacctttg aggtttcaaa agcccatgct aggcccagtg tctgtctgcc tgtctgtctg    1380
tctcctccct ttgctctttc ttccctccca cttgcttgca gatcagattc gagctcttag    1440
ctactgctcc cgtgctgtgc cttgctgcta ccatgcttct tgccatgatg ttcatagact    1500
tactctctga aactgtaaat aagcccccta ataaaatgct ttcttttaaa actgccttga    1560
tcatggtgtc tcttcaaaga aatagaacat taacaaaaac actataccaa actgcctaat    1620
agtcctacta attttatgat gagtgctagt gctttataat cactagaaga aaaaatttcc    1680
aggccataaa attaacatgg ttttaagtat gtataaatct tgtcttgaaa tctgttttct    1740
ataactaact ctaatatgat aatgtatatt ctaccttcaa aaagcacaa ataagacttc     1800
aaaccctggg aattgttaga caaaggccat ttaatactaa taagctataa actgaaacca    1860
tctgatatat gaaaactatt aataaaatca agataaaata acccctattt atataactta    1920
ctatataacct aaagcaaaat atcaagaaaa gtaccttaaa aagataaatt attcttattt    1980
tgacaatgaa ttctttgggg cgttaaattg tagaatatca acacatatca agaaagttta    2040
gaagaaaact accaaagttt aaacagactt tcctcggtaa ttactggtga tttcttggct    2100
ttttttttt acactgcagt ttttcagggt ggaaacttaa gctttgtaca gaagcactta    2160
ccaccactct cagagctgga aatggctcaa agggcaaagc attacaagcc tggcaacctg    2220
aaccaaatac ccaaaacact tgcaaaggtg aaaggagaaa actaactcca ggaagttgtc    2280
cttcgagctc ctcttgcaca ccactgtata cacccctta tatacactca gttaccataa     2340
ataaaatgtt tcattataaa gacacttacg ctaaaaccat gctgtaatct gaatggttga    2400
acatatatcc gccaacaacc cacattatat ttccattgac cacagcttta tgagaggctc    2460
tgggaagctt taaatcagaa tattcttctc gagtccaaaa agactggtta gctggcacag    2520
gaattgagca tccaggacct aataaaaaaa aaaaaaacaa caacaacaac aaatagcttc    2580
acaaaatgca gcctgaaagt ttatagtatt ccaagttcca atctaagtgc aaagaatatt    2640
taaagacttg tggggctaga gagatggctc agtggttaag aaaactgact gctcttcttg    2700
gaggtcctga gttcaaatcc cagcaactac atggtggctc acaaccatat gtaatgggga    2760
tctgatgccc tcttctggtg tgtctgaaga cagcaacaat gtactcacat gaaataaata    2820
aattaatttt ttaaaaaaca gaccagaaaa aaaaaaaaa aaaagacttg tgtttccttt    2880
agcacttaag cgcaaacatc tttaacttgt ggggttttaa aggttttac atgtacaggt     2940
attttgttta catgtatgcc tatataccac ttgcttgctt ggtacccaat gatgtcagga    3000
aaaggcattg aatcccctgg aactagagtt acagatctta tgagctactt tgtggatgct    3060
aggatcaaac ctgagtcctc tggaagagca accagtactc ttaaccaaga agccatctgc    3120
ttagcaccta acatgagttt ttaacttact caagatacag accaaaacca atcactccct    3180
tataaaattt aatactacac actttctgat aatttggcaa tttctgataa tcaggttaaa    3240
cttttttaga ggtaaaaatc ttgctgaagc aacatttagt agaaagggta gaccaagggg    3300
ttattatatt aactcatgtg gaaaaggcat tagggttgaa atataatgac agatcaaaat    3360
cgatcttctg gcaagtccag gcgctgaata gatgaaagag acaaagggag aattggacaa    3420
```

```
actaaaaaca tttacatgaa cacttacttt ctgaggacct aagcatagaa ggaaaatcac   3480
taaaccaacg atgactgctt cctcaatacc ccagggaatt ccctacagta ccttagtacc   3540
cggttgtgtt gggtaatggc actagatgac agcactgaga ctctaaggaa cgcttgtcct   3600
cctctcagct tgagtctctg cttctctatc accagaccat gttccctaat tcccacgaat   3660
gagttgcaaa ggatttgtca aacctttcca caattctaag cacatagata acaaccacat   3720
atatgtaaat tcaaagaatc tgaataaatg gagatgaatg cttaaatgcc acctgataca   3780
tgattaacat aaggcgtatg gctgctaaaa taaactccct acagttcact aactcagaac   3840
tttctgtgag ggaaaggact ttgaagggca gctcctaccc tgccagtgag gaaagcagga   3900
gcaccctctg gtatcgcttg cattacagat gcctcggtga ggaaagccac agttgtctgt   3960
acagtgagga atgtcacacg actcccccttt ccagttttca gaacattcac actcaacagc   4020
gctgctgctg ttactgctct tacactctcc tcggcctgag caattattcg gacacatgtc   4080
aaaactacaa agacaggaga aaacgaagtc aacaatttca actaagcaac attgcaacta   4140
atgcagacct tcctccttca gtttaagttc agttcatttg caagtgtgac tgcaggactt   4200
accagttagc ccaagtgtgc tcacagagct ctgtgtagct agagcccag gctcaagtaa   4260 tgaaatcaaa tcaaccttgc tgcattcaca tatgaagaag gaagaataaa taactcacaa   4320
agttagagaa attacaaaac aatagacatt tgtgcaaaat cacttagact tagctcaaga   4380
ctggcaacca ggatcctact ctttctggta gctcattagt aaagagttct acaaaagcag   4440
caaggtcatg ctaggaagtg gaggaaggag aggaagccaa tgagctgcca acattcacgg   4500
tatacatttc tctgtaaaga ttctgagaat taacagaatt taagattatt ttccagtgat   4560
gtagttaaag gtctttagta acttttatca gcttagaagg agaagagcag ttaacttcat   4620
gtatgagttt aagtgtctca tgacttaaga taacagtttt gctacaattt gaaatgccat   4680
acttcagact ttttaaaggg gtgcattagt ggactattac aatagcttaa aaatatagat   4740
ttctcctact gatgattatt actgagacac tactagtctt tattaaattc acttagcaaa   4800
actcctgaca ttttcttcca gcagcggaag aatgtctctc tcttctagga gatcctcagt   4860
gacaagatct agaaagacca agaactgtgg tcccaaccag tggggctgat atttgtttaa   4920
ccttttagct cctgtttctt caattatgaa aaaaaaaaa aagaagaaga agaaaatcca   4980
tgttaaaatt tagcaaggag cctgactagc tagaagcctc cctccaatat attagtgtta   5040
ttaagtcatt tgagtagtat cacaaatatt aaatctaaat atcttacttg taagtgatat   5100
taaatccagt cagattataa gcagcatcac tgaaaaaatg cagcagtgca taacctgaag   5160
tgacagtgac ctcaggagcc gtctcattgc catctctttc aggaacaatg aggccactga   5220
aatgtaaaca cagaccagat tacagcaact tcaacagaaa ctgtctatat gttactattt   5280
gatcctgctg ctcctgttcc aacacacact gtaaatgtga ctctagctgg cctcaaattc   5340
acagacccac ctgcttccac ctcctgggtt ataggcatgc gctactatgc ccaacatcta   5400
aaaggatttg aaatctatga ctttgattga atttttggtt ttttgttttt gctataaact   5460
ttttattata atactctcaa gtctctacaa taacattatt aacaaacttt atgaattgac   5520
aactgtcaaa tatatactgt tgaaagaaaa tactttacat atttttgtaa tatgtatcat   5580
ataatctttt taatgtattt tatagatgtc ttatataagt aaaaatagaa aagtttactg   5640
atttataatc cttatactat tagctttcag acgtattttt gttgttaaac tggtaacaca   5700
ttttatgttt ataattcaca ataagcactg ccactgaagg tgccaaaggc tccctagaat   5760
ctcagtaaga acctagtggg taatatttga agttttggat gccagtaaat tcatgtgtaa   5820
```

```
agatttattg agtaagtgac taccagcggg acagtggtgg tgcacgcctt tagtcccagc   5880
acttgggagg cagaggcagg cgaatttctg agttcgaggc cagcctggtc tacagagtga   5940
gttcccagga taaccaggc tacacagaga accctgtca ccctgtctca aaaaaaaaaa     6000
aaaaaaaaa aagaatatac cattttttaag gcatttgatc cacaaaatca taccaccttg   6060
ttttacaaaa gatatatatt aacttgaagg ctggaaatgg tggcacatgt ctttagtccc   6120
agtattggga agacagaccc agatggatct ctgagttcaa gaccagcatg gtctacatag   6180
tgaattccat gtaagtttgt ccgtgtgtgt aacttgaaac ctcattatag aatggaagtg   6240
tctaccccac cccacttacc aacagtaagg aatattatgt tggtcccgct catttaatac   6300
atggtgtact cccaaggtaa atcattttca tgtttagtcg ctcctattat tttttccatt   6360
atcaattcac tacaactact accaccaatc acatttagcc actagaaaag ccatgtgatt   6420
tgctccacac atacaacttc actcaataaa taaacatctt atcagtacta ctctctcttt   6480
cactcactca atccctagtc ccctaagttt ttggacgatt acaccaggta aattcctact   6540
tcagggttat gaccatctta aaaactacga cctagcaatt ctctttgtat aagaaatact   6600
tccccgtata tacacagaaa acaaagaac actactacag cactattcag atgacaactg    6660
actaaaagtc acctaattgc ttatttatgg gagttgatta aattagtcat tacaaatctg   6720
taggtctgca agactaacca agagcttcgt gaggacaata ggtagggcta cccagagaaa   6780
ccctgtcacc ctgtctcgaa aaaaaaaaa aaaagggag gcacagagaa aaaacaacag     6840
gcccggggta cctgtacatc tatgtaagcg taggtacatg cacataaaag tgactacaag   6900
agaacataaa cagagagcgc cgatgagaag aggatgggat ttttcattta atttgcgtgt   6960
atgagagcac ctatatgtgc atgttatccg caccaaagtg tgtagggtac attatgtgag   7020
tgtgcctgca gacgtcactg tcaggtgtct tcaatcactc ccctcctttt tcttctggag   7080
ataagagttt catgaagtag tactggctgg actagaactc actatgcaaa ccaggctggc   7140
cttgaattct cagagagcct cttgagtgct ggaattatat gcatgtgccg caacacagcc   7200
cacctcattt tgggggtag gatctttcac tgaacctgag ctcactgatt ggttagaccg    7260
gactggccag taagttccag gacctctctt gtctccgcct cttcagcact gtgatcacag   7320
gctcacaacc acacctggac ttttacttga gtcctggaga tctaaactca gctctccatg   7380
cctgtgcaga aggaattaaa ctgagccagc tgtctcagta tcaagagaga acataggaac   7440
tgtaagattc tgacagtact ctagggctta cagaacaccg acacattttc tactatgtat   7500
tcagttaata aaagaataaa tacaaacaaa aaaacatgag aaacatatag aggcagagac   7560
agacagacac acacacacac acacacacac acgcacacac acacacacac acacgcgac   7620
ttagacgggt gtgggggaag aaagagcaag gccacctaga aacaggtacg ttccatgcaa   7680
atgatcacag gaaaggattg gggatttta accacttgtg ggaaatgctg tactctccta   7740
ttctagcaca gatttgagga aaaagtagac cagagagtct gtccttccac atatcctgga   7800
aagtcactga catgtccaag ttttgatttc ttcataggga caatgagaga acccagact    7860
atctcacagc agcacagcaa ggaccaacca gcagagcagg agaagtgctt acagcagtgt   7920
gctgctagaa ggtgcaacag tcttcttaca gagggcattt aaatatgcag gatggataag   7980
tttgccaact acaactacag aggctggaca aggtaggaca gcttcttcac tgtcaaagac   8040
gtttgggcag ttgcttctat ttaccttaaa atcaaactgt gacagctgtg gcatatatag   8100
atttctccca gaatgaaaac acattaactc acttatgtca ataatatgga gtaaacacaa   8160
```

```
acatagtcta tctagctcag catgcaagac atgtgaggaa gaggagctac tgtgagtccc   8220
tatccctgtc cctaaggaaa ccaatatatg taaatgtagt ctaagctgca ggcagttctt   8280
caactgccta ccccaggctg ctcaccactt cacattctaa gcacagacta gaaagtatga   8340
tcaacctctg aacactgtgc tataatgtta ccatcaatct cacacacaaa tttcataaca   8400
ttttaagtaa gtctatgatg attctatgtt gtgtcccagt tatataagat ccataggtca   8460
cagggtagac attcaaggac accaacattt ggaattttgg gttttttttgg tgtactgtat  8520
atacttgcta gtgcaggtac ccatgctcat gtgtgtagaa gttgggcgtc tttcttctat   8580
cactgtctac tttatatttt ctttattgtt tcatttgata tgtataggtg ttttgcctgc   8640
atatatgtgt atgtttgttg ccagaagagg gtattgaatt ccctgggact agagttacag   8700
gtggttgtga ggcaccatta tgggtactgg gactcaatcc tgggttctct ggaagggcag   8760
ccagtacttt taatcactga gccatctctt tagcttcctt cgttcattcg ttcgttcatt   8820
ccttcattcc ttcattcctt cattcagagg attgagatac cttcctcagt taggctggct   8880
agccaatgga ctctgggaat ctatctgttc agctattctc tccttcccca tccaagtgct   8940
ggggatacag gcaggtccta ctgggttcat tttgaaaaat tacagaacta tgtattttct   9000
tcataaatct gaaactcagc ataactgtct caggctaaca tggaatccct aaatatatat   9060
gaggcacaac ctgactttac caactgtact atgtaaattt gctagtatat tagtcaacac   9120
ttaatgaaaa aacatctgat aaaaacaact tacaggccaa taggcaagga gacacttggg   9180
gaggtggatt caaggcagtc actggattct tgaatttaag tccagcctag gctacatgag   9240
attctgcttc aaaaaataaa caattaaatt tatggggaa agaatgatgt attttggttt    9300
cagaaattcc atcctatcat ccaagggaga tattgtataa cagcgaagtt cctcagctca   9360
cagcagtcag tagcatatag acaatcctgg ctccaagcct atgaaaacac agcctgtact   9420
aaaggtgtgt tcctgtgttt tgagtgagat gtgccccta agtcttgtgt atttgaatac     9480
ttggcactca cttggtggcg atttgggagg aattaggagg tgtggccttg gtggaaaagg   9540
agcatcacta gggtcaaggt ttcaaaatcc tcctgccatc atccccaata tgtcctctct   9600
gcctcctgct tgcagttcaa gctatgagct cttagttact acttccacca cctacccctg   9660
ctatctctgc tccatcatca tggactccta ttctggtgga actgttagtc caaaaaagtc   9720
ctttcttcta caacttgatt tgatgccaga tctagccccc cagcctagct agcaatatac    9780
caaggtatac catcttgaac tctaggtgtc tctcaatcca atcaagctac ataagattaa    9840
ccatcatacc tagtcatccc caaatcagtg tatctctctc ctcccaagac tataagctcc    9900
tcaagggtca aaatatgtag aaaggaagaa agattctcaa aggtcaagga tcagaccttg   9960
gtgaggattg agcactgtct acactttgcc tggtaaagaa gggtccacaa tgtaaaagag   10020
aactgacctg aacagttttc aattaggtgc taacaaatgt ctcatacgta ttgagtttct   10080
tataaataaa taaataaata aataaataaa taagcaagca agcaagcaag cacttaagag   10140
cactagctgc tttcttcctg aagacctggt ttcaattacc cagcacttat acagaggctc   10200
ataccaattg taactccagt ttgatgatat ccaacatctt cttctagcct tcagacacca   10260
agcaccaagc atgtaatggt ataacacatg tataccaaac acccatacaa accaattttt   10320
aaaaaaatat tcgagccggc gtggtggcgc acgcctttaa tcccagcact cgggagacag   10380
aggcaggtgg atttctgagt tcgaggccag cgtggtctac agagtgagtt ccaggacagc   10440
cagggctgca cagagaaacc ctgtctcgaa aaaccaaaaa aaaaaaaaaa aaaaaaaat    10500
agtcatttta gggctggaga gatggctcag gggttaagag cactgactgt tcttccagag   10560
```

```
gtccttagtt caatatccag caaccacatg gtggctcaca gccatttgta atgggatcc    10620
aatatcccat tctggtgtgt ctgaagacag ctatagtgta aataaaataa agaaatcata   10680
taaataaaat aaataaatct ttttaaaaat attaattaac ccaggctgaa cctaaactta   10740
caaacttccc acattaggct ctttaatgcg ggtgttatag gtctgaatac cagcttaaga   10800
ataatattct tctgaagaat gtgccctggt caatcaccat gaccacacct gccaacaggt   10860
ccttcataaa atacttggta tatgttgaat gttccataaa attatggagc tagaaaggt    10920
agtgagctag aaggatatta aagatataaa ccattgcccc agtggtcctc acatttgtct   10980
agtaatagaa cgttgttaaa ctgttttat ttagaatttc aatatataaa agacaaatat    11040
gaaatagtcc ggaagcaaat taagctacag cttgcagcaa agccagatag aatgcagatt   11100
aaactaacac agtacctttg tcttatgttt tagatgctaa agtctagtct acaaccccag   11160
ctgcccttga actcttagca gtcctcttgc ttcagcctct catgctgcta gggttaaaag   11220
tatgtgcgac cacacacagt tttgaagttt agagcactta aatgatctat tcagcaactc   11280
aggcaggatt tacactgaaa gtaaattatc ttatgaatcc tttttggttt tccttttatt   11340
catttcattc atgcacctta catgaactat ctattgctag gctgtctcta tactggatgc   11400
tcagcacatc accaacatgc cgattcttct actggtacaa tggcaatgct gagaaaacca   11460
cacaacctaa gacagtaggg aggtggtgct ctgattgttg gtgttgttgt tgttgttgtt   11520
ttggtttttc gagacagggt ttctctgtgt agccctggct gtcctagaac tcactctgta   11580
gaccgggctg gcctcaaact cagaaatccg cctgcctctg cctcccaagt gctgggatta   11640
aaggcgtgtg ccaccacgcc gggctctggt gctctgattt taaatacaa caattttcag    11700
ctagcaatgt aactcagtag taaatgcct gcccagcatg cacaaggctc cagactggac    11760
cctgagcacc acaacacttt ttaaaagatg tgtttatttt attttatgtg catgagtgtt   11820
ttgcttacat gaatgtctgc actgtgttta cctggtgcct gtgaaggtta aaggcaatg    11880
gagctatgga gagttgtaaa ctaccatgtg gaaatggagc tatggagagt tgtaaactac   11940
catgtgggta ctaggaattg aatcagggca ctcctctgca agaacaacaa aggctcttaa   12000
cagctaaaat attactacaa acccacacca caaaattta aattgataga cattatcacc    12060
ttagttctag atagagaatg tgcttggcat tgtaagtact aaaaaggttt tggggtggat   12120
cttttatatt atctcactat aattttataa aattaatact caaatatgtt ataagttaag   12180
gttttttattt ttgtttttca tttctgtatt ttgtctatgt agctctgcct ggcctgaaac   12240
tcatgggaac ttgactggcc tcaaactcag agagacctga acggccctgc ctccaaagag   12300
ctgggactaa ccatgcccaa cagtaggtag ctttaatacc taaccagtgt attagttcat   12360
gctctcaatt aaccaacatt ctctacatac agaaattttt atgcctattt aatcaaatac   12420
acagtctaag taaactctaa gtacaactgc ttggctcata ttcttacaat ggctatggct   12480
agctaattca aaggccagtc acataaaagg gtctctatga attctgatta acaaatgcag   12540
ttaaatagat gaattcctaa aaagtagtat cataataata tcatatttag ttttttgtgct   12600
tccattatag tttgaggtgc ctcctcccat aatgcaaggt atatttcaaa taatagatat   12660
atacatggtt aacacatggc aaatgccatt ttaaatgctt agcacagcct gctctttggc   12720
tccattaagt gaaactctta agttctcagt taaaataatt gttggagagc tataggagca   12780
atgggtggag aactagtctt ctaatttgtc ctttgcctcc ttgcgtacta agtagtccct   12840
ccctcactat gtggcattcc agcagactac caccaagaga agaacagaaa agtgttgatt   12900
```

```
tctttctaaa gtaaagaaat aaggggccag tgagatacct cagcaggtca aagccatttg    12960
cctagaaacc aaagttcaat ccttggaagc cctgtaaagg tggaattaga aaacagactc    13020
cacaaaactg tcctctaacc tccactcggg cacacatgtg ccaaccctc cattctccct     13080 cccccacata caaagtaaca ataaactttc agaaaattta agttgctacg catggtgatt    13140
gatgaatgtc tttaattcta gctcttggga agcagaagtg ggtggatctc tgtcagttca    13200
agaccaacct ggtctatata gtgtgttcca ggcatccagg actacacaca cacacacaaa    13260
attacgtgaa ggaagtagaa tgtttgaagg aaagaagtct ggaaatgggg atggagagag    13320
acctcagcaa ttaagaaaag gtcttgcacc ggacgtggtg gtgcatgcct ttaatcccag    13380
cactcgggag gcagaggcag gcggatttct gagttcgagg ccagcctggt ctacaaagtg    13440
agttccagga cagccagggc tacacagaga aacccagtct cgaaaaaacc aaaaccaaaa    13500
acagaaaacc agtatgatag gtcaggcaat tggatcgaga caggacactc aagatagcta    13560
gcctgtgcaa tatagaaaga agtctcatgg aagagagagg aagggaagg aggggggaga     13620 gagagagaga gagagagaga gagagagaga gagagagaga gagaatgaga gcagagagc     13680 gagcgcacct cagttgatac aagattgggg ccctgagttc catccccagc atcccataaa    13740
ttgggtgtag cagcacacac ctgtatccca gcagagaggc aaaagacaag ttcaaagtcc    13800
tatatggaaa aagtgtgaga tcagcctgga gacctggtgt gtggcagtgg ggtgagggt     13860 gtcatcaagg agaaggctta gtaagtaaag gacctgcgtt ggttcttgag ttcaagtctc    13920
cagcaatcag agaaagccag aaccattgca caaacttgta agccaagtgt tggactggac    13980
agagacaggc aaatgtttga ggtccaggtt cagtaagaga ccctatctca aaaaatctga    14040
tggagagtaa cactggaaga actcagagtg agtcacacat gcacacacag gtgaatgtgt    14100
atacaaaggg ggcagggagg gagaatgaga ggagactggg agatatctgt agttcatgtc    14160
tgtaattcta gcacttcaga ggcagctgga gctacacagc aagacccgt ctcaaaaaca     14220 aacccaagcc tgacagtggt gaggtacacc tttaagccca gaggcaggag aatctctgag    14280
ttcaagggca gcctgagtga gttccaggac aaccagggct ccacaaagaa acactgtctt    14340
gaaaaaaacc aaaaccaacc aaacaaaaaa gaatcaaaaa caaccaccac cactacaaca    14400
aagcaaacaa gggagaaggt ataaaatgct taggagagtc ttcctttagt ctccatcctt    14460
tgggtactcc ttccccacag aaagccacta ctaccaattt cttacataag ctgctgtttt    14520
agacacaggt ttttttttt tttaaatata gtaacatatt catgtgtagc tcattttct     14580 agtgagtggt tggtccttct tttaacagtt taaaggacct ctatgtttaa aggcgattgg    14640
cccttgtctg gagtatgggt tgtattttcc caatttgtga gttttaccca acctattgcc    14700
tattacctat ggccatttat tcttgtcgat aagtagtttc caattgtatg actatggtca    14760
cagtgttcca tggactcttc tgccgctaga cagcccctgg gtctgaattt gagatggtta    14820
caagggtgat tggctctgct ccctgggtgc tgggattaaa ggcgtgcacc tccacaccca    14880
atttgttctg ttttgtaaga aatgaggttt tattgtgttg ctcaggctga tctcagtctc    14940
ctggcctcaa ggtatcctcc catgtcgata cacagcacaa ggcgtaggaa aagtggcaga    15000
tttttttaaa ttaagttttc tttccaaaat atagattcag aaatgtgaga ttttcacaaa    15060
gtgaacctgc tcacttccct ggctctmgaa tctccattgt ggctcccgcc catccctttt    15120
gcccaccagt ggctgttgta ttgacttcta tcccattcct taactatacc tgtccttggt    15180
cttcgctgtg aacttgcttg ggctgagaat caccttgttc cgggcacatc aggtcagtga    15240 gggtgttttcc agagagttttt aacagagacc agaagaccca ctccaaatgt gggtggcaat   15300
```

```
acctgatgtt ctgtcatcct ggactgggta ggaagaggaa agtaagaagc aaacggcacc    15360
cccacctctc tgtctgcttc ctcgccgaca caaagtgacc agggcctccc actcctgccc    15420
cctcagctag agacacttgc tgccatcttt ccaaccactc tgagactgtg cctactaacc    15480
gtgacccaaa ataaatgttt ccttccttaa ggttgccttt gttagctcct ttaatagagc    15540
ggtaggacat gtaactgcca caggcagcca tcgctgccag cccctcccac tgaccgtctg    15600
agaaccacac tcagctgtag gcacagctct catagctgtg tgggcgtagc tctgtctact    15660
cggtcattcc cctgctgccg agcatttatt gttttcagtt cctggctgat gggtagcact    15720
gttatgaaca tcctagtaca aatctcaggg tgacacgcgc cttcattttt cctgagaaaa    15780
tgcccaagga taaaatgcta gggccaaggg aagaatattt caccattaag agacactggt    15840
caggactgga agatggccc agtggttaag agcactgact actcttccag aggtcctgag     15900
ttcaattctc agcaaccaca tggtggctca caaccatctg taatgggatc caatgtcctc    15960
ttctggtgtg tctgaagaca gtgacagtgt acctacatac atgaaataaa taataaata    16020 tctgagagag acagacagac agacactggc tagtcatctc acaatgttct catgtttaaa    16080
atatgatacc atttgtataa agcagaaaca caggaaaaat aaaatctgtg gtattatatt    16140
tgatttttaa attaacttga ttagtgaagt tagcagctac actgggcagg ggttgggagt    16200
ggggtactct gaagtgctgg tatttctggt tttgttttt gtttgtttgt tttttatct     16260 tatttatatt acatagaaag ccatttgct aatacactta ccatgtgtat atattgtgct    16320
tgaattacag ctaagtaatt atttctgagg ggctttagac tactgaagat tgggcccaat    16380
gagccccacc ccaagtagtc tccaacatcc ctcttggaag tacttgagag caaagattca    16440
agtcacatgt ccccaaaccc tcagcagcca ccacccttta ggtgtggctt ttgctctcgg    16500
tcatcctgga acatcttgcc atctttggtt tgttctctcc ctgtcttgcc tctggtagag    16560 ctgggttct gtgcttctat tcaaccatgt acaagaacca tgtgccacct gccatgtgcc    16620
aagcctgtgc cagtccctgt gagcgagcag cccaccccgt gagttatcat gtgaggagct    16680
atgaggagca ggaaggggcc cggatgactt cagcagacag tatgaagcaa gcactgtgcg    16740
atttatgctc cctggccaca tgcccacaga tggtgtctga cactagcg ttaatattt      16800 gaattctcca cattctagcc tagacatttt ggttgcaaga agaaaattga ctccagttgt    16860
atcctggaat gaaatttatt ggaggaaaat actggacagg ctcccagaga aaatacgata    16920
ttcaggcaca aaagaaatg gggactgagg atctgaagtt caaggtcatc tgtaatgaga    16980
ttgaagtcag tttgggctac atgggacctg gtctagggg aatggggaag agaagggaag    17040
ggatcgagat agggat                                                    17056
```

<210> SEQ ID NO 4
<211> LENGTH: 5973
<212> TYPE: DNA
<213> ORGANISM: Mus musculus

<400> SEQUENCE: 4

```
caatgtgctc tgacgattaa tgggctagaa atgtgtggct gttgattagt gaaagatgt       60 catggttcag gagattggta gtctctgtgg gaagacaact cactgaaagg gaggaaatag     120
cctggaagag ataaagagac agtgatcagc taggaagctt aaaatttaaa ttttgttgga    180
agtactgtta ggaatactag cagaggccag atgaatgtat ggttaagtta tagcaaagga    240
aaagattgtt aatggtgagg ttaggaatgc agggtgacac caacctgtaa tgtcagcatt    300
```

-continued

```
agcgagatag aagcaggtgt ttaaggccat tctctgctac ttagcaagtt gaggccaatc        360
tggaccacat gagaccttt ttcaaaaata aatctcctta aacaaaagag gctgggtttt        420
ttgatagatt cttcaagatg ttaatgtaaa taaatggaag accaaggatg gcatgctaat        480
atcctcagtg tctgaagaag gactatgtag tgttggctgc tgactctgaa gtaagtgctc        540
attactgaca gatagtgtat cttagagcct ggcagatggg atggaagtga ggaagcaagt        600
agcacctttg tatattatgt tctaagtagc cagagatact tgacacaaaa caagttgag         660 aaaatgtatc ttctagaaaa tacagacatg gaaaggtgtc ctttctataa aagaggtatt        720
aaacattaac ctgaaaaaaa agttagcaaa ttgggctttg gcaaatgaat atagtcaagt        780 ttcatttta ttttgttttt tgtatatgac tgtttggctt gttgtaccat gtgtgttcct         840
ggtgcctagg aagtcagctg gagttacaga tggtgtgagt tgccatgtgg gtgctgagag        900
atgaacctag gtcctctgga agagcagtta gtgctcttaa ccactgagcc atctctctag        960
ttccttctgt agaattttca ttaatttaca aaggagaaag tataaatgat aaaaccatga       1020
gaagatagac cggcactaga attagtggag tcaaatgtt aatgatatgt cagatacgcc        1080
ttatatgagg aagttgcaaa attatgaaaa tccaggcact ccactgagtt agaaatctag       1140
gctctgatgc atactgctat ggtaaggtag caagtggcca ttgagtgcag aagtgagtct       1200
ggatgggtct tctggtgttg tggagcacac agactgctgt cttctgcatt gcagtttcac       1260
ctgtatttcc ttggaactac ttagctttgc aactaggcgt taaaaaaaac tttatattta       1320
tggttttaag ttatttattt gttttatttt attttatgag acatagtctc actctctaac       1380
ctaggctggc ctggaactgc ctaggtaact tgagctggtg attctcttgc catagccttc       1440 taaaattta gattgcaggc ataagccaga ccactcctga cttttgtagc cattttctg         1500 acatgaagtg taactttgct ttcataacta aaatgattta gttgttttgt tattgtttaa       1560 tccctttgc tttgaatgta tccttttgtg tgggtggcag atatataacc acagactttt        1620
ccacaggcat cctaccctag gtccagaaat gactctgaga cgtcttatat atgaatgaat       1680
gcctaggcca atagctttgg ctgatttcca cgggttcata gctcagttat cccatttaaa       1740
ctagtctaag tcatgccatg aggctacata cccctccttc agtttcaggc gactgtcttc       1800
tcagttgtgt aatgtcctat cctctgttgc tgctccccaa cccccatcct tgcgtcatag       1860
tccgtctgtc ctcgtctccc cccatttact tgcacaacgg actctactct agaagtcctc       1920
tctgtgctga agcttgcacc tccgctctcc ccgtctaagc taataggcaa cagcattgta       1980
cagacaggtg atgcttccat acatcgcaca ggagattctc cctacacaga tacttattca       2040
tccagcgtga atgcaaccgt ccaggcgtgt tctcctagtt gtagtacatg ctgttgtatc       2100
agtctgatga atttctttgt ctttacaacc aagaaagata atactgtaag aaattttgac       2160
taacattttt tctttatta aattacagac taactggctc ttctggattt gtaacagatg       2220
gacctgggaa ttataaatat aagacgaagt gcacatggct cattgaagga cagtaagtta       2280
taatggctga cttatttta atttattata agagcacagt atagcacaaa atacttccat       2340
gtgtgttatt gctatttctt gagacaggac ctttctgact gagtaactca ggctgacctt       2400
gaattttgct atgctacctc tgcttcccaa gtgctaggt ggtaggtgtg gaccaccatg        2460
ccctgctgct aaaataccgt tcattgatgc ttttcatttg gatagtgttc ttgcttttta       2520
aaatttactt tttgggggac cagagagatg gctcagtggg taaagtgctt gctgaacaag       2580
tctggttatg tgagttaatc cctggctccc acagtggaag agtgactcct gaaagttgtc       2640
ttctgactcc cacgcttgtg catgcacgca cacacacaaa taataaaata aaaattaaa       2700
```

-continued

```
aggaaatttt cttttttggg tgatagggat tgaacctatg acttcactaa gcaagtgctc    2760
tattgttaaa taattccttt aatttgtggg tttttttttt ttaggttcca agttgactta    2820
atgttataaa tgaaagatac ataccagaaa tttgcatatt tctaatagtt taaaaaactt    2880
agttaaaatc ttttaatag tttgcttaaa tctttatata ataatgctat tatatcattt     2940
ttctaaatat tgattttatt atcagcaaaa cagtaaatga gccatcagaa taaccactgt    3000
agcctgtttc cctggccctc tgtccttcca tctgtctatc ttctctttt tttccttttt     3060 tgtgcctgtc atttagggca aagcatttta gtctctgaac aaaactttga aatttccaag    3120
taactcttgt ttatttgttg tgtctcatat tcaacccaag aaatattatt tactaactca    3180
tttaaaagca acaattataa cccactacat gttagcagaa aaacctattt gtttttattg    3240
agacgggatc acactagtaa gcactacatg gcatggcgtt cactgtgtag atcaggcagg    3300
ctggcttcgt gctcttgaca gtcctcctgt gttttgtctct cacttctgag tgctgggatt    3360
atagacatta ccaacacacc gatttggggg gttggggtac tgggatcagt ccagagttgc    3420
atggatgcta ggcaagcact ccaccaactt agctatatcc ctggtcataa atgtcataag    3480
gaaaaaaatt ccttatattt aaagaaattt taagaattgc attgtttaag atttcacaga    3540
tctctttgct atctggcaat ctttttgat attttgttt gttttaaaa atatgtggta      3600 tgtaaacaaa cttaaatatg aatgggacag ttccagatga gagtgaaaag ttaaatattt    3660
gggagaaaaa ttgataggtt tatctattat ggaaatttc agagatttta gtaaaatttg     3720
aaaatggagc tgggaggtct gaggtagtca tctaaagctg ccagttgtag agcgtgttgg    3780
agtgtggagt cagagggagt tactgataca cttgttgaaa ttgcccaggc ttcatgggaa    3840
gtgatgaggg gctgttactg tgactctggg cagggcttgt tagtttcctt tggatttagt    3900
ctcagtcaga gttgatacat agtttcctga ggacgtggct ttttggtaca gtgctgtgaa    3960
aaggcagaga agcaggtaaa cttagaaaat gtgtgttttt aaagtgatgt gttatgaaat    4020
cttacgtaag atgaataaag aaagaagtgg ggacactgag ggctcctgtt tctaaatgtt    4080
aaaagcaagg ctggaaacat tctttgaagg cccctgaagt cagagcccgt gtctctttg     4140 gttcccagga catttttgat attcccttac acatagcaaa tactaactag atctctgaca    4200
aatgcaggaa agctgtttat atttatatat atttatattg tatattttc tccttataaa     4260 ttctttaaaa gtctgtttta gtagttaatg ttatgattat tataaattac ttaattattt    4320
ttctaggcca aatagaataa tgagacttcg cttcaaccat tttgctacag aatgtagctg    4380
ggaccattta tatgtttatg atggggactc aatctacgca cctctgattg ctgcctttag    4440
gtaagccctg ctgcatttca tctcaggaag taagtgtgtc tccaggatgg agtccgtgct    4500
gcatttactt tattctgcag tcacactcat ctcatggaat tagttctgtt ctggtgagct    4560
acagttcact tggtttttat gtactgggtc gttttccatg tatactagta tgtagccacg    4620
gttagtcttg aacttctggt tctcctgcct ccaccttcca agtgctagga gtataggctt    4680
gtgccactgt gcctgactca tttcacattc ttgaactgtg aagttttgat aacactatta    4740
aatttacctg ctatttgtga ttttgttaaa gtttgcatta aaagttttt gactatattg     4800 ataatatttt tgtgacaaat ttaaatcaga aaccatacct ttcttgttct tgtatgtatt    4860
tcattccata ggcccttagg aataactttt ttcaatagta tatagttctc tcagtttgta    4920
tatatgtatt attagggata ggaggagctt tctggaagac tattttataaa ttggacaatg   4980 gctagctgtt gagagtgagg aatttgctag ttttgttttg taaatccctc cccaatgcat    5040
```

-continued

| | |
|---|---|
| ctgtattagt gatttaataa aataatgcaa ttttgtcagt tatatgggtt gcactgaatt | 5100 |
| tttgctattt tattttaaga aagattttg tgtgtctaca gtgtatatga gtgtatgata | 5160 |
| tgtgtgcgtg tgcatgtgtg tgtgtacttc tatgcaggta ctcacatgct atggtgtgca | 5220 |
| cgtaaggttg gagtgcagcc tcacatgttg atcattatat tccaccttgt tagagatagg | 5280 |
| ttgtctttgt tgtttgctgc ggcctggagc tggagctgga gctaacgagt ctcagccacc | 5340 |
| tgacatgggt actgggaacc aagagcagca agacctcttc ttcttcttct tctttttca | 5400 |
| ttttcggttt ttcaagacag ggtttctctg tatagccctg gctgtcctgg aactcactct | 5460 |
| gtagaccagg ctggcctcga actcagaaat ctgcctgcct ctgcctccca atgctggga | 5520 |
| ttaaaggtgt gtgccaccac cacccagcct aaaagatttt cttactaaaa tatatttcta | 5580 |
| aattaattag ttggaatctg gttcatactt cttttgaaa caaaaccagc atttttttc | 5640 |
| attctacata cagagacatt gacactgagc actggttatg agtagttact ataagaatgg | 5700 |
| gaaattattc caccttgta aaacttaata caactcctta tcaggctctg aagactttt | 5760 |
| aaaagcaaga attgtatata acacacagaa atgatttaga ctatttagat ctttattgca | 5820 |
| tgggatttta aaattattat tgtatttcgt gggcatgttt tgtctatgta gcatatgtgc | 5880 |
| ctgtagaggc aaccaccaag taggtcctgg gaatcaaacc tggtacccct gctcttaggt | 5940 |
| gttcttaact gctgagccat ctctccagtc ctc | 5973 |

<210> SEQ ID NO 5
<211> LENGTH: 90050
<212> TYPE: DNA
<213> ORGANISM: Mus musculus

<400> SEQUENCE: 5

| | |
|---|---|
| aggcaagaaa gagccagcga gcctccagac agaccattag aaattccaca gtcagcacaa | 60 |
| tagggagaac agtaaatctt acattaaaag aaggccaggg cctggtagca aaaggtttta | 120 |
| atttaagcac ttgagaggga gaggaggcaa atctctctga ttgggggttg gggttaatgg | 180 |
| tgaatgccat gacaccctgc tcagagttag ccttctcccc taaaaaaatt ttaaattcat | 240 |
| tttcaatgct gacacagtta atcatagaca ttgtatctca gacacctcaa catactccag | 300 |
| actgcagcac cagcccactg ctgaggctgt cgttcagttg gtagaaggca tgctcagcat | 360 |
| tcgcgaagca ccagacttca tccttagcac tacataaaac tgggtgtggt catgcacact | 420 |
| tataacttca gcaccatgga ggcagaggca ggatgatgag aacttgagga tcattctcag | 480 |
| ttacataggg agtttgaggt taagcagggg tacaggaggc ctgtctcaaa caaacagaca | 540 |
| aacagacaaa caaacaaact tcaaaaaact cttgaagtac taggcctagt acgtgctgag | 600 |
| attgtaggta tatgtcatca tgcctgttgt agaatgagtg agagcggact ccataggctt | 660 |
| atagatttga atcttggtgt ctgtctatgt catgtcatcc ctgcacaaaa gcccacacta | 720 |
| ggcccacaca ttctctctgt ctgctgcatg tgggttagat gtgagctctc agctgctgct | 780 |
| ccagtgccat gcctgcctgc tgccaggctc cagccatgac ggtcagggac taactctctg | 840 |
| aaactgtaac caagttccca atgaaatgct ttctttcata agttgccttg gtcatggtgt | 900 |
| ctgcttcaca gcaataacac ggtgactaag ataccctggct cctcccctcc ccaccccacc | 960 |
| attatttacc ataaagtaaa caatacacag ttggataaca tgatactgaa gttattttcc | 1020 |
| tgtttcctga tgtaacccaa ttttggacaa gattaagcct taaatagcaa gctgtgaggc | 1080 |
| aggataaaga aaagctcgc aggccaatgt ctgctttacc aaattctgtt cagcagtcta | 1140 |
| aagctgccgt cacctcgact cctgtgatgg catttccatc actatcttag atattccctg | 1200 |

-continued

```
ggtcacaacc ttttagtaca cagattgcaa ctctgatgga atggctgact gcttggctaa      1260
ttaaagcaag ctagagtttg tctggcttcc ttgtctgaat ggggaggtgg tatttacaaa      1320
attttgtaaa taaactacta tatttgcatg atgtatataa atttgatgtg gctgctttta      1380
aatcatttaa cctaaactgt cccacagaat catctgtttg attggaaaga ttgtagcttc      1440
aagagaattt ctgctgaacc tgaaatgatt cataatgatg tgtctgaaga atgtgtgcta      1500
tcacctacgg ttttgttt agttgatatt tgtactttaa gatttccttt atgtatgtgt       1560
gtgtgtgtgt atttatgtga atgtatacct catgtatgtg gtgctcaagg acacctgaag     1620
aagggctctg gagctggagt tacagggagt tgtgagtgct aggaaagaaa gctgggtaca     1680
ctgggaaatc aaaaggtgct tctaaccact gagaaatcct gccagcccct tggtttatta     1740
aaaatatcaa acaaaaccaa cactagttac ataagtatct ctctctcttt ctttctctct     1800
ttctttctct ctctcttct ctctctctct ctctgtcaca cacacacaca cacacacaca     1860
cacacacaca cacaaagg atccataata gttcttctgt atcccggtta aatataagtt      1920 cttagggct agagagatgg ctcagcagtt aagagtgctt gttgttcttc cagaggaccc      1980
aagttcagat cctagtacac acatcaggca gctcacagct acccatatct ccagctccag     2040
gaagaaccaa tcaatgccta tggcccatgc aagcaccagc acacatatgc tccacaaaca     2100
tccatatata tagctaaaag taataaaaat aaatcttcaa aaaattaatt ctggttgaac     2160
tgaaaaagat cacctaacat ttagaaaaag cagtttacta gtgaatagga cataaatcat     2220
ggtatcaaat attctgttgt taaggaagc aactagaaaa agcatgtgtt tgaaataacc      2280
aatggataca aaacaaatga ggcaacccca acatctgtca gtaccttgca aaccaacaca     2340
ataaatttga ttttatttaa atcgtagtta tttttcatgc tagtagtttt gaaacacaat     2400
aaatttgatt ttatttaaat cgtagttat tttcatgcta gtagttttga aaccaagatc      2460 tagatttgt atagccacat aaatacacat tagaattgca aactgatacg agcttcatct     2520
tcatcagtct ctcttcatga aaagcagtta cagggactga gacatgactc agcagttacg     2580
gcatgggctg ttcttccata cgacatggat tcaattctca gtgcccaaat gttggctcac     2640
aaccatttgt aactctggtc ccaggggatc tgacactctt cttggcttct atggccactg     2700
tattcatacg gtacacagac acatatgcag gcaaaactca acaaaaaaaa taaggtttaa     2760 aaaaagaat tagaacttaa aggcacttca ttccgtcagc actaaatcag cctctctgga      2820
gtcttcccac ttcatgagaa aatcgtcagc tctccactgc tgtctgtggc tgaggagcag     2880
gacctggaca acgttcagag attgtcagtg catctctttt cttctttggt ttgctgtcat     2940
caggttcact gtcacattcc ctttgtacca tccttccttt aacagccttt tgaaaatgca     3000
gaaatgttgg atgctgcctt cagttcacac aggctgtctt tttagctcct catctatcta     3060
tgcttaattt gttagtggtg ctcacccatg tatgtgttta tgtcatgaag ccacaagatg     3120
agccttgatt gagtcttgct gtcagtgtgg atcacagaaa tgacaccta tcatctttgc       3180 ttcctgcttg ttagaagtca ttgattctgc ttatactcaa ggcccacagt attatacttg     3240
ggtgtgaacc ccaggaagca gggaggtggg gggtgtcatg gatactactc agatatctga     3300
ctgttgtgat atttcatcag ttctcattgg tcctatcttt aaaatctgcc ctacatctag     3360
agctggctgt ggtggtgtgt gtggtggcat cagtatcaga acttggatta cagaggcagg     3420
aagattgtga ttttgaggc cagaataggt gcatacaaag atcctgtctg caaaagaaac      3480
aaatgtgcaa ataattataa ctactttact aatagcctaa ctaataacca ctgctagtgc     3540
```

```
tgtgtccacg aaaaggtgaa gtaaactgtg aaaatgactt cccctctgt gtgcacacg      3600
ccgtcatgtg atttacttg tgtctcatca ttgttttttcc ttctgtttgc atgtgtgaat    3660
gttcacatgt ggaagccaga agtcagtgtt gagtgtcttc ataattgatc tctattctct    3720
ttgttttgag acagggtttt gagactaagc ccagtgctca gtgattcatc cagtaaactg    3780
tagggagctt cctgtctctg cctccacagt gttgggatta caagcatgat ccaaattatg    3840
tgacaagcgc tttactaact tagccatgtc ctcagctccc cactcccctt ttcttttctt    3900
cttctttttt ttagacttac ttgtttattt ttatgaatgt cttgcctgca tgcatacaca    3960
cacacacaca cacacacaca cacacacaca ccccacatgc aagcaattcc agaagagggc    4020
attgaatccc tgaaactgga gttccagtta actgtgagcc tgtcatgtgc gtactgggag    4080
ctaaatccgg gttctctgga aggtcagcaa ggtcttacct gggagccgtc tctttagctc    4140
atgtgtttct ctcttgaagc aagaaaccta ggaatcattt tgaaacttcc ttcacagcct    4200
ttatcataac ttcacgtcaa tttttaccta ctctttcaac aaatacatgt tatattact     4260
tattttatg tttagcctgc tattggtttc tacttagcct cttgcagtag agttctgtca    4320
gatttatgtt tctattgctt ttaatttatt tgtaaggtg aatgggaaaa tatttaaaaa     4380
ttacagatcc catcattac tatattctta aaagccatgg ctagccaggc ttggttgtgc    4440
atgcttgtac tcccaggact ctgacaactc agtaaggagg agagtgaatc agaaaatagc    4500
gccagcctgt gctgcttagc aagaaacaga aacaagtaca atcacacaca tagaaaatcc    4560
cccattaata ccatcccatt agatataatg gtcctgtatg accattcaac cactgtttgt    4620
cctctgtact gcagtaacag tcttctgccc ttgcccgtga agcacgtgcg caccccgcct    4680
ccaagtgctt ttgcactggt gtcctccgtc tagatgtcct gttactatat gtaaggactg    4740
gtttctcctc ctctttacag ttcaatctaa ttgtctcatg aaaagatctt tcctgaccat    4800
ctggttcaga caggttctcc ctgttgttgt tttgtttttt gttttatagt tctaaattcc    4860
tttcaggaac ttttgcttat tttaaattcc ctgagtgcat acgtgtgctt gttgttgctc    4920
atgctcgttg tttgggctta ctttactatc agctctggat gtggttcaca gaaggtgctc    4980
agggagcac tctcagccac tcatctcaca cgggttatag atatatgtat tgatgctacg    5040
tttgcttgtg agccatgttt taaagattag aatatcttt ctatgtgtac tctatcaaaa     5100
cacatgttag ggctttatct attttataca gatattggtg ttcttgctttt actaattttc   5160
atggaatttc ggtgaatatt agtattttag ataggaagac ttgtctcaaa atgtagctca    5220
gctggttgag tgcctgcctg catgtagaaa gccctgtatt cactctccag cacctcagaa    5280
gtgggccatg tgcatatgc tgtcatctca gcactccgga gggagagaaa agagaatctg    5340
gagttcaagg ttatccttgg ctatataaca agtccaagat cagcctgggc tacatggcat    5400
cctgcctcaa aatcaaacac caaatcaaaa agctcacatc ttgatccaaa agaaggtaga    5460
gagaatacac tgggaaagtc tttgaaacct caaagctaac tccaagtgac agtgacacct    5520
ccttagcagg gccataaatt ctaatccttc cccaaagccc accaactgga gaccaagtat    5580
tcaaagataa gaatctatgc agtccattct ccttcaaact accacagtag ttttcttaa    5640
aaaaagaaaa aagaatattt taattgattg tgattattca gtattattca tgaataatca    5700
tgaactacat ggcaggacta taaactatta ttttttttaa agatttattt atttatttta    5760
tgtatgtgag tacactgtag ctgtcttcag acacaccaga agagagcatc aaatcccatt    5820
acagatggtt gtgagccacc aagtggttgc tgggaattga actcaggacc tctggaagaa    5880
cagtcagttc tcttaaccac taagccatct ctccagcccc tataaactat tattatattt    5940
```

```
ataaaatata aatccgtgag tctgtgcacc cctgtgtgca catggatggg acatctttga   6000
actggattat atcatactta gaagaataca agatactctg ttttgtcatt tgggtgaaaa   6060
tatggtctgt ttattttgca ggtatgacct gacttctagg gaatggcttc cactaaacca   6120
ttctgtgaac agtgtggttg taagatatgg tcattctttg gcattacata aggtaaacta   6180
tctcaactct tcaccaagca agaagttcaa ctcttcctgt tgctttatgt cattgaatac   6240
tatcgagctt tggttttagt tggtataagc tttgttttga tgtcatggag gtatataatt   6300
caccaagttg tcaccaagtt gtaattggaa attgaagtta gaacgatttt aatccatggt   6360
gtcttgcatt tggatactct gatcacagtt aacaatgaag attaaatagt gtcagcaagc   6420
ctatgcccat tatcaagtct agcatactgc atgcgtgtga ctgagtagcc attgttatct   6480
ccttgttttg agcgtatatt gtagaatgag gcaactgtat tttccacacc attttcgttc   6540
tgtaacacgt tcatgtaga gaaggtgatt tagagagggg aagaatgtga ttgtattggt   6600
tggttctttc tctatgctat tcctagcaag tcaccgaaga gctcatgtta ctcacacttc   6660
ttaagctggg atcacaatga gattgtgaac cactcattgt tgttttccaa tataattttt   6720
aaaaagatgt atttatttt attttatgtg tgtgggtgtt ttgcctgcat gtatgcctgt   6780
gtatactgtt cctccagagg tcagaagagg atggcatcag aactggtggc tgttagctgc   6840
catgtgggta ctaggaacta aacccgggtc tctgcaaga gcagcaagtg ttcataaact   6900
ctctctccag ccctagagtt gatttcttaa tggttttaaa aatcctgttt acatctttct   6960
tataggataa aatctacatg tatggaggaa aaattgattc aacagggaac gtgaccaatg   7020
agctgagagt atttcatatt cataatgaat catgggtatt gttaactccg aaagctaagg   7080
atcagtatgc agtggttgga cactcagcac acattgttac actggcatct ggccgtgtgg   7140
tcatgttggt catcttcggt cattgcccac tctatggata tataagcgtt gtgcaggaat   7200
atgacttggg tatgtatttt ttccagtgga ggcatcttga atatcatact gagaaccct   7260 gcccttatta ttaggacacc gtaacaaaat tcagcatgat cttgatccag taccttgtct   7320
tgaaatagta tcagtagata actggtgaga ttgaggttgt tgaagtccct gtgcaacagc   7380
tgtttcttac ttgtcaaggt ctagtcttgg cttgggaggg gttctgagga aaggggtgtc   7440
aaaaaaccca aaagtccaa ttgtaggtcc aagctggcag ctgtatattg cattaaggaa   7500
agctgaggga aatttgggat atttatttca tctattagtc tacatcaagc aagtcaagcg   7560
ctcacagtca acgtttgcac cctcaaatta gtaacaaaag agggggaact gaggagtcca   7620
gcatggtcct ggttgggaca gaatgacatg gttccagccc tgagacaggg gcagcaggtc   7680
cgggcctcca tggatgtcac actatggaca taaacctgtt tgtataataa tgtacatatt   7740
tcatgctcct cttctgagta atgtccttct gttaatgtga atgacttcat gataatcaga   7800
gccagtgtga gtctgggaag taaatggtgg gaccttcagg acagctctta aggctgtgga   7860
aaagaacatg agttcaaaac catatacttc ctcaactata caaaaataga aggatgcaat   7920
atgaattgta tgagggggctt cacagatcta aggaacaaa agcagcttcg ctgtgagcca   7980
acttgtcaga aagatattga gtaagcagtt aaagagattt agggagtgct gattgctaga   8040
ggaggccacc cagctaagtt tgtgcttaca aggcagaca aagtcctgag ttcagggtgg   8100
gcctggaaca gagcaaggtt agttagacct tggtgtggta gaaatggtaa tttccagaca   8160
ggatacccaa ctagtttttg tgcttaacag aggcaggtag atctctgaat tcttttgtaa   8220
tgttaaaagg aaatgtgtgc ttgttgtctc ccaagggggcc tgagtcccag gatgctgatt   8280
```

-continued

```
tataggaaac ctggagtaac tgggtttatg acctgcagga gacgagctat ccagaatgtt    8340
ttttgcaata gcaagagaga actgcctgga gaactgcctt cagcaaagaa tagcaagaga    8400
aagctgtcta gagagagagc tgtctgtaga gaaagccggt cagagagaaa gtagactgga    8460
aaactgtctc cagcttggac ccacaatttg acttttttgtt tttgttgaca agttgccctc    8520
ccccagaaac accttcctca ggaccccctcc caagccaagg cagggccttg cccttcttg    8580 tcagcttgca aggagccaaa gatagcatta aatgctttgg atatcaaaat aagcaaaatg    8640
caaaacagta aacactctaa ataattctg gctagtcctt taaatattag gccagtgcac    8700
tgttatttta ccttaatgta taatcttgtg ttacatttta ttgtttttat tgtataatag    8760
gaatgtcaga attataattt tgtaacattt gtttgacatt cctgtgaaaa tgcatctaaa    8820
gatcattaaa gtgcatctga agatcataag gactcactga ggagcacagg gaattaagtg    8880
tctgcttaag agaactttga atctttaatc tttagaattt gttttaaaaa tttgaatctt    8940
gccagtgtgg tggcgcatcc ctttggtccc agcactcaag gggcagaggc aggtgtatct    9000
ccattagtgt gaggccagcc tggtctacag agcaagttcc aggccaggca gggtacacag    9060 agaaaccccta gcttaacaaa acaaaacaaa atatgaatct ttaaaaactt gttctgtgaa    9120
aatttcatac atgtatacaa tatagcttgt tcatatccac cgccattcct tccagctcct    9180
ctaggctttc ccagtgcatc tccttcctag ccttatggcc tcccttttcag ggtgaaggtt    9240 agcacactga gtccagttag tgctgatccg atgcagtctt gtctagatgg tcttctttat    9300
aataaggtga agtatatcc taaacttccg tcttttgctc taaggtgttt agactttaaa    9360
ctaatgttta aatcgtttaa ataatttatt atttcataag aagaggagcc tgcaacattg    9420
actttaacta ttgtctctta tccagaaaag aacacatgga gtatattaca tactcagggt    9480
gctcttgtgc aaggggggtta tggccacagt agtgtttatg atgacaggac caaggctctg    9540
tacgttcatg gtgctacaa ggctttcagc gccaacaaat accggcttgc agatgacctc    9600
tacagatacg atgtggatac tcagatgtgg tgggtgtttt cctagagctt ccccttggta    9660
gtctagaatc tgcagaggca attgattaaa aatactgtgc tatggtttga cttttgttca    9720
gcattgtatg taacaaagtt aggagatcaa tacagtaata gagttaaggt actaatggtg    9780
ctgttgctgt ctgttagtgc ttagtgcttt agacctgatt cactgaactc tagcaaggtt    9840
tcctctcttc agaattctca gcaataaaag ctgtgctgat tttatccata cttaaaaagc    9900
atatccttcc ttttctcttt ttggtgttgg ggatcaaacc ttgtacatga ataggctata    9960
ccatctttat ccatttacat caccaaacag gatgctctcg tgcctatttg atagggtttt    10020
cactcacttc gaactgaaac ttgggttgta agagtatggt acttttagca aatgaaata    10080 aatttgagtt atgatgcaat tataaagcac tggtctctct gtatttccct cctccttcta    10140
ctccctccct cttcctttct gacccctct ctcaacatac attagagacc atgctttgac    10200
tgtcaattta tgctgtgctg aagatcaggt ctttagtggc tgtgaaccac ggagcctatg    10260
cagtggaagt tctggtctct ggcttttgcc ttactaataa aacactgagc ataaatttg    10320 atttgtattt cacaattctt acctggaatt cttaagtgga attatggagc catagagaat    10380
gaacatttta gggcttttaa tatagttttcc cgaaatttta acagattttc atgattgtta    10440
aaggaagtgg cttacgtata gggggaaatc aagtattgca catttgaatc taaagttata    10500
aagtaattac atttaaattg gcaaataagt attcttttaa aactaacctt atatttatta    10560
tttctaaata aactcaaaag gaccattctt aaggacagcc gattttttccg ttacttgcat    10620 acagctgtga tagtgagtgg aaccatgctg gtgtttggag ggaacacaca caatgacact    10680
```

```
tccatgagcc acggtgccaa atgcttctcc tcagacttca tggcttatga cattggtaag   10740
ctttccaaag atgttttagc ttcaggaata ttttctttgc tgatggaaag atcactatgt   10800
taaaataatt gcaccattta aaagaagtcc aggtggtaga atttgcattt aatttgagta   10860
gggttacaca tctattgaaa agcattattt tggattaaac tacattaaat tctttgtgaa   10920
atcactcttc ttaattgctt taattctttt tttaggttga gttaattggt atcttctttc   10980
ttataagtgc cttacatagt agtggtggta gttgtaacca ccagtgttat gttaagtttg   11040
atgggatatg ctgtttccta gaaacctggt tttacacatg ctgttgatgt caatatacat   11100
gtggccagaa gagggcagtg tctgtttatt cctggaaaat aaacatcagc tgctctgttg   11160
tgtaaatatc acccatgtga tgttcttcct gtttatttgt ctttgcattt tgagacagcc   11220
tcactatgta gtctaattgg ctgaagctca gtatatagat caaggtgacc ttgaacttag   11280
agaaatcctc ctgcctcttc tgagtgctaa gattaaagat gtgtactacg aatgaaaaaa   11340
aaaaatgtgt actaccacac ctgactagag attcatttta aaaattattc ttattgtgat   11400
aaaatgctca gaataacact caccatctta atgttttaag tagtttagat ttaaatatat   11460
tcctagtgtt attcatgtta taataccatc tgcttgccga cttcttgtaa aactgaaact   11520
ctgcccttaa acaatagttc ctctcttcat ccctcactcc agcctcttga aatcatttc   11580
tatatctcta tgattttgac tagtctaaat taggcatttt ttaaaaaaaa tattttgttt   11640
acttgtatgt gtatgagtgt tttgcatgca tgtatgttaa gcacaccatg tatattcagt   11700
gcccatagaa gccaaaagta ggcatagatt ccccagagct ggaattacag acttttgtga   11760
gccaccatgt gggtgctgga tactgtgccc aaatcctttg gaggaatagt gagtcttctt   11820
agctgttgag ccatcttgtc agccctagat gtttgttttt aacaaacgtg ttttttgccag   11880
ccattgagtt tttaaattga gaatgggggg tacactatag ttagtcctta gcttcaagct   11940
tgtggaagca gaaatgagaa gacaatataa tcttaactca ggaggattct tgctggctga   12000
aacaaagatg tgaaattacc tccgagcact cctaagccac tggggtgagc agggtggtct   12060
ggagaggcct tgaagagaag ctgtctgagc ttgttcctgg ggacactggg agtcaaatag   12120
acctcctggg caggggggatt tagtgcagac aagaggcagg aaagtacatg tcaaatattt   12180
aggacttttg aaccgctacc tttcttttgt catggtaaca cagaaggtag caggtgactg   12240
ttagactaga atgttcagat ctgattcaga gtgccaggga tcgttggttg gtcttgtgta   12300
aagtctcaca agtgatagaa tcatatgtgt gtcttagact tttttttgttg taggtatttt   12360
agattttttct tgttttttcct ttttgtaagt ctggccctca cactatggtc caggcaggct   12420
taagacttat ggtaaccatc ctactctgcc tttatgggcc accatgacca atttaagaag   12480
ctctcttggg tggcattgtg ataagtgatc tggaaggggc atattgacag ttagcaggct   12540
gctactgcag aagtcctaat taggtttgta tcaaggccat ggaaggagca gtgacttcta   12600
gtacctggct gttgtgtgtc ttgacaaaaa tataactgcc ctttcttccc aagtgtctac   12660
tatggaccac ctttgccaaa actaaaagca gattcagaga aaaacatatc atgattgcac   12720
atggctataa tccctgaact taggaggatg agaaatatgg caagattgag accagtctga   12780
actatctagt aagaccgtgt ctttaataaa aatagtaaaa attataaaat cagggagtag   12840
gatctgggaa gaagagaatg aagtaagtgt ggggcatatc caattggaga tgtctttagg   12900
acagagctga ttgctgagag gtggtttgtag gagaggtgag ttattgtggg gcataaaaga   12960
tgagcaagag tcagagacag ttggagaaca gagtctgaac aagagtagag actaaagaga   13020
```

-continued

```
gtgtcagaga agcagggaga aaataggtga gattgatgac ctgtgagata tgttaatggc    13080
cagaagagtg gctaaaaatg actggagaat ccttcagact tgtcaacaaa gaaatccttt    13140
agcctaattt agggtgcagg cggctgagga aggacatagg tgaaatatgt gctctgtgtg    13200
ttcattttta ttaaagctta tctgcaaagg cctcagattt gctgtgtact tgtagctgag    13260
gctcttttga actcctggtt ctcctggctc caccttccca agtgctagga ttacagatgt    13320
gtgccctagt taaaatagct gtatacctag cattaaaaat tttaagttag aaaatactgt    13380
ggtgctccgg ggatgcatct cagcagtaga gtgcttgcct gctatacaca aggccctggg    13440
actgatccct agcaccacaa atactaaagc agacattctg gtagggaaaa ctggtagaca    13500
gcagagtggt gaccatcagg agggggttg tgggtgatga atgactacat taattagaag    13560
ttctgtgcag tatatttatt tcatgccctg aaacattgct gctgctgttg ctgctttcct    13620
ttacacataa taacataact aaaagacaga caagcatgtg gtatgaggct gtggatgagg    13680
cattctttgt tttccttttt ttttttttt tgagacaggg tttctctgac ctggctgtct    13740
gaaactcagt aggtagaaca ggctggcctt gaatgcacag agaccctcct gcttctgcct    13800
tctgagtgct gggttcaaaa tttatgtttt tttctataaa gactgagagt tcacatggac    13860
tatatatgac aacctactct gaaatgtgtt tttctccccc ttagcttgtg accgatggtc    13920
agtgcttccc agacctgagc tccatcatga tgtcaacaga tttggccatt cagcagtctt    13980
gtacaacagg taattggaaa gcaaaggctc tattactgtc ttacatctta tattcattt    14040 taatatcaac ttcctaacag ttgtatctga atggtaagag gtttggggag aaaaaggag    14100 agaaggcagt tctaagtgca cgataaggta aggggaatag gactgggagg ttatggggtc    14160
aaagagcaag tctgaagtct gcactatatc caggtgtgtg ctcaggaata cttttctgac    14220
cagcagagct ctttttccat ttgctccagg aaccttagtc ctgtaaagga catgcaaagg    14280 actaggggttg tgggccagca atagagtgtt tatctagctt gcacaagatc ctgagttctg    14340
acctcagcat tttgccttct gcaaacacag catttgccat aagggacatg cagaatggcc    14400
attttaccta gtcacttgaa agtgtgcttt aagattgaga aacttaacag cctgctgatg    14460 ctgactttc ttattttgct tctgttactg cttctgctt cttcttaa tactctaatg    14520 cttacattat atagtcctac aggtattcaa attttctgtt ggagtttcct aatacaagta    14580
atttaacttg cattaggaaa aggataaaag tgccattctg gagttgtgaa gaatgaccgt    14640
ttagaagcta gatagtgggg aaagatgata tctttaatca tgtgattatt tagtgttta    14700 caagtatata ggggattgtg gcaagaccat tgtatgatta gagactaaag tggaaagatt    14760
ttttaaatat cttgttaact tgagtgttat cttaaattac aatctgatgc tttccttcag    14820
aaaaagccct aaatgcctct tgaggttttc atctggcaag tatcatgtca cctggccttg    14880
ctggtggaat ctgccccagc tcatgtgtgt tcttagtgtt ctcctagcac agagttaggc    14940
acgtgtgggc atttgcatac taatgtatag taatagtaac aattgaatga attgtctatt    15000
aaaacattct taagttttac ccaaacacag agaggtcgac aatttgtcat aaaatgtagt    15060
ttatccatga atcaaaatca ggaatgactg tctgaacagt gttttatttt ttattttat    15120 tttattttgt gtaatttctg tgatgtgttt gaatatctca gttttaggca ggattggaaa    15180
tgttagaggt tggtaagagg tcatggttgc agtttgatca tgagagaaat cgatggctct    15240
cccttcattg cagtgttgtc agtcagcagt gtgggatcac ctatgtctaa cagttgttct    15300
aattgagaga ggattacagg agggaaagca gtgagattgt gaggtgctag atgaggagat    15360
ggcatttacc tagcagcctt ctctcccgcc ctcccatcat gtgacctgag agattcacaa    15420
```

| | |
|---|---|
| tttctgaaga tatcagctgt gcttagttta agcaatagtt ttattaacta aatccaactt | 15480 |
| gattcatgtt attcccaggg aaccagtggt aggattaaaa atgaatccta gtgttctttt | 15540 |
| tggttattgg aatgtcaagt tttcagacac tgtaacgaat acagagccat acaatcacta | 15600 |
| tatttatttg gtcctttgtt gacttagaaa aattgaagcc cagtttaggt gagctaccaa | 15660 |
| atttctcatt gtggattagt attaaacttg cgtggagttg tgggatcttg gaagtggggg | 15720 |
| ctaagcatcc gtgtttgtca cagcccagaa ggaacagatg aggttccttt tgaggagtct | 15780 |
| tatgtcttta tgaacttgga cttagaaata tttgatgtgt ttaattctgc tgtagttttt | 15840 |
| taaactctag ctagtgagca tcttttcaca ggagcgcttg agtctgacct acagccattg | 15900 |
| tctgtctctg gtgtgcatat tacaaatgca ctgggagcgt tcttgacccc aaacatataa | 15960 |
| ttagattttt cttctaaaaa ggtctagttt gggaaggaat gaaagggatt agagaaatgt | 16020 |
| tgtgggtttg gtatttattt atttatttat ttatttattt aatgtatatg aatgatctat | 16080 |
| cttcatgtat acctgcatgc caaagagga catcagactc atgatggtga tgaaccatca | 16140 |
| tgtggttgct gggaattgaa ctcaagacct ctggaaaaac agctggtgat cttaactgct | 16200 |
| gaggcatctc tccagcccaa ttgttctgtt ttagtttgag gatgaacatc taatttagag | 16260 |
| atgccctgct tttccaaaag tgagttttaa acactaattt ccattgtcag tggattggtc | 16320 |
| ttttaagaat ataggtagtg gtggcacacg cctttaatcc cagcacttgg gaggcagagg | 16380 |
| caggtggatt tctgagttcg agaccagcct ggtttacaga gtgagttcca ggacagccag | 16440 |
| ggatacacag agaaaccctg tctcgaaaag caaacaaaca aaacaaaac aaacaaacaa | 16500 |
| aaacaaacaa aaagaatata ggttggaata ggttggaagc agccaatgat agtgcatacc | 16560 |
| tttaatccca gcacttgaga agcagaggca ggtggaactc tgagtttgag gccagcctag | 16620 |
| ttagtctaca gagtattttc ctggagagcc aaggctatat atagaaaccc tatcttgaaa | 16680 |
| ggccaaaaaa ggaggaaaaa aaaaaaaaag aaaagaaaaa agaaaaaaag aatgcaggtt | 16740 |
| gggcagtcag ggtaagtgtc taaggtaaga ggaattcttc aaggtggaaa gtcatgagtt | 16800 |
| ctgcgccagc ctaggctaca gagtactgaa aggggaagag actgtccatg tgtcagaccc | 16860 |
| tcatttctcc aaaagtcaca tgactatatt ttttctgtat tgcccactct tccatacatg | 16920 |
| cacctaacaa taaatattga agttcactct gtggcactat atctatgtga tagacttcta | 16980 |
| gaaaagtgat ttaaagttca aaaggtaaat acgtagtttt gtttcaagtt gccaaaatcc | 17040 |
| ctttagtaga ctcctacaat cttacatgcc cagtagcagt atagaagctt gcttgttgcc | 17100 |
| ttgaagcctc accaattcaa atattaggta acatttgtta catttttctt tgtcagctgg | 17160 |
| ataggtaatg aatgacacaa caatgtgttc ccatttttctc tgcattacta attgaagtcc | 17220 |
| tatcacccac agcagactga agagttcctt taatatttta tggactttga caaacctagg | 17280 |
| attcatagct tccatacaga gaggaatttc acaaatagca aagttgggct gttagaagaa | 17340 |
| taaaaagaga attctgagta cagcttctca aagaagagtc ccacgtaggt gtcctctggg | 17400 |
| atgtgcctag atgcagggtt attgtacagg agctcttctg tctgctctct gatacttgag | 17460 |
| attatagggt tgcagggaaa tgcattagat ggcattacaa actgataaga taaagttagg | 17520 |
| agctatcaga gatttaggac atggtttttc tctgtaaatg gggcttctgg tgagattcct | 17580 |
| agaaaatgct gttttatagct aggaatgggg ttatagctag gaatggggaa agaccttaag | 17640 |
| cagttgtgag ctgtggtgga atgcatgtgt tttcagtttg ctaaggcttc cgggaatact | 17700 |
| tttcctgtcg ataattttct ttcactctct ttgtagcctt ctttgtatta aaatcctctc | 17760 |

-continued

| | | | | | |
|---|---|---|---|---|---|
| tgcttgcttt | tgtgtgtgaa | tgtgtgtatg | tgtgtgtttg | tgtatgtgtg | tgtatgcatg | 17820 |
| tgcatgtagg | tccctacata | ggacagaaca | tatttcctgg | agttataggt | gcttgtgagc | 17880 |
| agcctttag | ggaaccaaac | tctgtcctct | ggaagagtag | cccctttaac | tgctgagtca | 17940 |
| tttcagcctc | aagaatcttc | tcttttccct | attagtagaa | gatgtcatct | tagctctagg | 18000 |
| aactacacca | cctctggcct | cagtggacac | ccatttacat | atgcatatac | agcagacaga | 18060 |
| catataacta | aagataaaat | aaatctttt | aaaatgtcat | ttccctgtgt | actaattttc | 18120 |
| catgtacaca | ctcacaggta | gatttttaaa | ctattctgag | tgatcacaaa | gcagagcaga | 18180 |
| aggtgaaatt | tgagagaata | gatgatatta | gtggattttg | agaccttgaa | aataatgtct | 18240 |
| cagagcatta | aattaatcac | tcatgtatgt | atgtatgtat | ataagtatgt | atgcatgtat | 18300 |
| tatgtggatg | ggggtgctgt | agcacatgtg | tggaagtcag | aggacaactt | tgtgaagtca | 18360 |
| tgtttctcct | tccatcttta | tatggttcca | gtgattgagc | tcagattgtc | tacctgtgta | 18420 |
| gcaagtgcct | tacctgctga | cctgtcgcac | tagccctctc | agaggacttt | taatatttgg | 18480 |
| aatatttcta | acgattgaca | gtcaaaagtt | tattgtgagc | caggcactta | aaatcctagc | 18540 |
| acttgtgaga | cacaagatgg | aggtcagtcc | agtctactga | gttctagacc | agcaagggct | 18600 |
| acacagtgaa | acctgtctca | aaaatttcaa | aagcggagct | agagaaatta | cccaaggagc | 18660 |
| taagggaac | tgcaacccta | taggtggaac | aacaatatga | actaaccagt | acctgggagc | 18720 |
| tcttgtcttt | agctgcatat | gtatcaaaag | atggcctagt | cggccatcac | tgcaaagaga | 18780 |
| ggcccattgg | acttgcaaac | tttatatgcc | ccagtacagg | ggaacgccag | ggccaaaaag | 18840 |
| ggggagtggg | tgggtagggg | attgggggg | tgggtatggg | gaacctttgg | gatagcattg | 18900 |
| aaaatgtaaa | cgaggaaaat | acctaataat | aaaaaaaaga | aatgatatca | gaaaaaaata | 18960 |
| aaaaataaa | aaataaaata | aaataaaatt | tcaaaagcaa | caactcaaac | cagccctacg | 19020 |
| tcgtgcctct | gagttctcag | taaattcctt | ctctctctcc | tctcagcacc | atgtatgtgt | 19080 |
| tcggcggctt | caacagcctc | ctcctcagtg | acgtcttggt | ctttacctcg | gagcagtgcg | 19140 |
| atgcacaccg | cagtgaagct | gcttgtgtgg | cagcaggacc | tggtatccgg | tgtctgtggg | 19200 |
| acacacagtc | gtctcgatgt | acctcctggg | agttggcaac | tgaagaacaa | gcagaaaagt | 19260 |
| taaaatcaga | gtgtttttct | aaaagaagta | tgttttttct | ctacttagaa | tttaaaaatc | 19320 |
| taattttatc | tgaattgtga | aggaacctag | tctctgtact | ttcctgttca | ccttactctc | 19380 |
| tagttatttc | ttaataaaaa | aatacacaag | atctttggat | gggaggaagc | atgtggctcc | 19440 |
| tggaagctgt | tagcaggtaa | taagttgtct | ttgaattaca | caggctttgt | gtaccaactc | 19500 |
| ctggtctggc | tgcaggtgat | ctgaagccat | agcacaatga | aatttgtttt | cattttggtt | 19560 |
| ttatgagaca | gggtcttgct | ctatagctca | tactggtcaa | gctccttgtc | agcctcctcc | 19620 |
| ttcagcctct | tgaatgctgg | ggttataggc | atgcatcact | ggcccactt | gggaaatatt | 19680 |
| ttgatgacag | acatgctata | tatttctttg | ttcagtttag | tagccactag | caatctgtta | 19740 |
| ttattagata | tttgaaatgt | ggctatgtaa | ctaaggggct | aactgttttc | ttttctttag | 19800 |
| tgtatgtagt | gaggcagatg | tagtagcaca | cgcctgcaat | ccagacactc | acgaggctga | 19860 |
| ggcaagaggc | agttctaggc | cagcctgggc | tgtgtaatga | gaccttgtct | caagagccaa | 19920 |
| aacatcaaca | ataaaagaac | agtatgtggc | tattggctgt | tatgttgatg | atgaaggtct | 19980 |
| agtgttaagg | ataagagcct | ctaatggtat | gatcacatat | agcaaattgc | tctggtagac | 20040 |
| agcagagagc | tgctgttctt | gaaaagtatt | tccagccccc | tttagctgta | tatagcaagc | 20100 |
| agtacagcat | aacagacaaa | ctatggtccc | ttcttctaga | gcccctggcg | tgctcttgtt | 20160 |

```
attttctct cctttgctac ttgcttagtg gttgctctga gcaccacttc accaactcag  20220
cgaagtaacg tgcaaaaatg tttggaaaat aagaatgcct ccaagatatt tgtccatatc  20280
aatctttaaa gtatgaaact acttccttat ctagttgttg cagttacatg agagttatat  20340
taggcagaga ctacttctgt ttttctggta tgtgttaaat aaagttgtgc agggacataa  20400
agctcctgag gctgtgctgt tgattagaat tttggttcat ttatggaaaa cagcttacca  20460
gaacctggta ggattcataa ttctcccgaa acagttagaa ttggtagaat aaccaaaatt  20520
taaagttaag cttaaatata cagtgcattg gaaataatat tatcttctga ggttcagtat  20580
gagcccatta gtttacctca ctttctgggt agacctaatc ctgtcagagt aaacttggca  20640
agaaaagcag cctacatgaa aactgatcag gcagggaagt ttctgtggcc tctcttcctg  20700
cttgtgtatg tcatattcat gaaatgattt atagatggca acatggcttt tagcttcttg  20760 tttgggatt taatgagaat tatgttaggt ctacaaagag tggaagttgt gaaatccaca  20820
ggtttggagt cacatgagta tatagagttc gagttagcaa gtgcctcctg tggggttgtg  20880
ggtcactggg tatacctgca cccaggtagg ccttgcattt gtaacaagga caaatgtatt  20940
ggtctctcat attgctttct taggcttctg cacagcttct ggtgttaatt ctgttgctag  21000
ttgatgtttg tcgtgggaag aaaagcatcc attacttctt agaagctata aaattaacag  21060
acctttgctt ttcactttct ggacactatg ggaggacagt tataaaacag tgtttctcgg  21120
attgtctgct tatatctgtt ttatttaac ctaaacatgg cactgctttt ttcctttcag  21180
tttgactata cactttgctt cctgactatt gttaggagct ttcctacctc agattataca  21240
taagagaggc tgccgcatag ttgatgggtt tgtcttctct ctgtagccct tgaccatgac  21300
agatgtgacc agcacacaga ttgttacagc tgcacagcca ataccaatga ctgccactgg  21360
tgcaatgatc actgtgtccc tgtgaaccac agctgcacag aaggccaggt cagatgctgt  21420
ttttcacgga ttttagggaa tagaaaaatg ctagatgagt gtgagtgtag ggcaaataat  21480
gagtagagtt ctttttaaaa tgggatatcg atttgaattc tactgttgct caggttttct  21540
cttaggaagg gatgctatat acatcctgat tccaaggatc gctcctgctg ctgaggtctt  21600
tgtgcagtgt ttccgaaagc atgttttaca gaatgcccctt ggcccatatc tgactcagca  21660
tgacatctgg gctaatcatg tatgatttgt tataggtgat aataggctat gagtaaggtg  21720 atccagctt tgctgtcttt gatggcttat gacattttt tctcaaagtt taatgcattt  21780
cataagaaat aagacttgag attgctatgg tgggcacggg ctgggaggag ctctggaaaa  21840
gcagcaggtt cagctttcac gttttacaga taagcattgg ctgaggcttg gtggtgccag  21900
tggttccgtt gggctgctag cttgccagct aaaagcatgt tagtgagaat acacactgtg  21960
gtattcacat tgcagtgctg cttcctgttc attctaattc tatcattcat ccatctacct  22020
atctctatct atctatctat ctatctatct atctacctac ctacctacct acctacctac  22080
ctacctacct acctaccact tatctaattc tatctgtctg tctgtctgtc tttctgtcta  22140
tctatcctcc atctaattct atctatctgt ccacctatct atcatctaat tttatacatc  22200
catccatcta tccatctatc tgtctgtcta tcatatatgt aattctaacc attcatctat  22260
ctatccactt atctgtctgt catctaattc catccatttta tgtatctatc tatatatcta  22320
attctatcta ttcaattctt ttcttttttt ctatctttct ttctgcagtt accattctca  22380
gttaattctc actgagttat ttgtgtgaat aacaaaacac ttctcccctg tgttccagat  22440
ctccattgcc aagtatgaga gttgccccaa ggataacccc atgtactact gcaataagaa  22500
```

```
aaccagctgc aggagctgtg ccctagacca gaactgccag tgggagcccc ggaatcaaga    22560
gtgcatcgcc ctgccgggta ggccttgcac agggatgtcc tctataaggt ccaagcttgg    22620
tcctccctcc tcagatcaag gtggacctag gaacaagatt gcttattctg tctatttagc    22680
cctctcacta ttggggggg ggggggcga tattttgtat gtttttaact taaatgtggt      22740
ttttatgtat gtatttacta gcctttgaaa gaaagtgaag tgtcagctca tgttctggag    22800
aattgggggg tagcttagat ccatgttaca aactgtgtcc cactgtcctt ccttctgctg    22860
tgaaggagaa cctggcacta gagctctgtg gtctcagcag cagtcaggaa cctgcaggaa    22920
gcacttactg acagttgtgt gagaagagat ttctgtacca gcatcatctc ccatgtgacc    22980
ttccttcccg actatttcag cagaggttgt tcagggtatt aacttaggtc ctgaggccag    23040
ctagccctga ctaaatctct atgatgtatt tgcttgatca ggatatccag gaagggagc    23100 ttctgtgctc tccaacatcg aggtttgagg ggaagttggt ctgactcttt tgaaagcatt    23160
ttatttagtt tgctgaatgg gctttagttt agccagtgtt ctattgctgt gaagagatac    23220
catttccaac gtgtaacttt tatgaaagga aacatttaag tggggcttg cagtctcaga     23280 agctattatc atcatgacag ggagcataga ggcacaaagg caggcattag agtggtagct    23340
gagagctaca tcctcatctg tgagcagagg cagacaaggt gtgaaaaaga cagaacctgg    23400
cctgggcttt tgagacctca aagtctacca cccccagtga cacttcct ccaacagctc      23460 ctgcaacaaa gctccatccc ccgatccttc tccagtcctg ccactccctg gtgaatgagc    23520
actcacatat atgagcctat gggggtcatt cttactcaag ccactacagg ctttgttttg    23580
tgtctcagac tttatgtcaa tagaatacct agacaccttg ttacaagaca ggcctggaaa    23640
gcctgcagtg ctgactccct gccagtagca cattctgagg agcaagtccc ttaagtcgct    23700
tacctgctct tacattacgc ctttccctga ccatttagtg agcactgttg gtgtccccaa    23760
cctgaacctg gttctgggga aacacttgct tattcacttc cgtgctaatg gccagggagc    23820
aagcatgctt tcatgcaaca ctgtgagttc agtacaacca caggaggaga ttgcagactt    23880
ccttcgtgta ctgtatcact atgaggtttt ccaaaccagt ctcccttca cctcattttt      23940 tggcatgcct tatgtacttg cttatacttt ctatcttatg acatgaaaac agagtggcat    24000
ttggaggctt aaatttatca cattcccaat tcaattccat tttcagttta ctctttctgt    24060
atatacatca gtgtgcagat aaatatctct ttgtgtgagc attggaggcc agaggttaac    24120
ctctggtata ttcttcctct atcactcttc acagggtcct ttgatgaatg tggagctcac    24180
tgattacata gactagctga ctcaaccctc aggcctcata accctgcctc tagccctcag    24240
atgagattac aagcaagcaa aactacgcct ggccttttat gtgggtgctt ggaatttgaa    24300
ctgggtactt atgcttgaca caagtatttt atccactgaa ccatctccca agcctccatt    24360
tgcagttttt tacctcaccc ttccaatata tatatttatt tgtatgccct ttgttcaaga    24420
ttttagtcac cttttacatt ttcttcaaa aataattgca ccaatttctt aataatggca     24480
cccaaaagta ggaacattag cctagagtat accctgtgag ccaggaaatg tgactggtga    24540
gacttgtaaa agggtctttt tattctggcc ctcagcggag gctcagcagt ggagcatgca    24600
tgctgttcct ctggaggacc cgaggtcccc aggggccagg tcacaaccac ttgtaacttt    24660
aactctgatc taatgccctc tatggctttt gtgctatagt ctcttgcact aacccacact    24720
caaggcacac atacacacat tctttaaaag ataaattatt ttattttcaa aggttttttt    24780
ctgcatatag aagttaataa tttgtctgtt atgctcacca gatcctaaca aagcacctga    24840
aattcaaatc aggatgagtt cagatgttca gtattttgaa ctagtaaacc gaactgcata    24900
```

```
attcctaaaa ctttgttttc tttcctcttc ccctttaaaa aagaaaatat ctgtggcaat    24960
ggctggcatt tggttggaaa ctcgtgtctg aaaatcacta ctgctaagga gaattatgac    25020
aatgctaaat tgtcctgtag gaaccacaat gccttttttgg cttccctcac atcccagaag   25080
aaggtggagt ttgtccttaa gcagcttcga ttaatgcaat catctcaaag tatggtgagt    25140
taatgtgttc agaactttgg tttctagggc acaacagcag ctcttatgta gaaggccaca    25200
gttgtatgtt atttgcctgg taagagaaag aattacaata aatgattaat aatatactgt    25260
gggcctctat ttcagaggct cttcttttga tacctttctt cttgtcttaa aaagttcagt    25320
actttgcata ttttattagt tgttattatt aagtaaatta taaggtatga acatatggaa    25380
tgaatggtaa tatgtgtaca tattctggtg acatcagatt attttgtact tgatttatat    25440
ctagattctg cttgggaaaa gggagagtaa aatgttagtt acctaggtgt cattaaagcc    25500
atctacagcc cctggaggta ttattatagc acatagtgta atcgtcagta agaaatgtaa    25560
aatctgccca ggttttatag ccttcttcct aaggcttctg aactcagaaa gttctcttac    25620
tctagagcca aactctcaaa tggcttgtag ttactatata gtctcatttg gtatttttct    25680
tggtaagtct aattctaaga cttgtgattt gactgtgatg cttcagtcaa ttagatattc    25740
acagagcagc ttttctgtct atgctggctg tggtacagag agatgtgagg gacatgtttt    25800
tgtctagcca ggagaagaca gaatgcagct cagcatctct catttggcac caccttcatg    25860
tgatgggatg ccggtatggt gtgggtcctg gttgttaaat ctcaggaagt ccatatatcc    25920
agaaatgacc tcaactatag gtggatttct ggcaattagg taaaagtcag cattccttgg    25980
gcacttggga aactggttac catctgcata aaggagtcat ttcccttcta tctggcagaa    26040
gggacatatg gctatctatt gtgcctgtca gcatggaagc acatgctagt ctccaggtcc    26100
ccccaatatc acaagtacct atagcagtga attagttaaa ctgatttggc tcccaatggg    26160
tcaagtacag ctgcacctgc ccaagagctc tttgggtttg caaatgagag acacatagtt    26220
aatttttata tgctttgact agttcagttg ctggacattt ctaatcctcc ctgcagtagc    26280
atacattaac ccctccaact ttcctgagtc aacttactaa ctcaacattt catctctgac    26340
accccagacc taatggcaga gtggccctta gagccacttt cccaattttt tttttatcag    26400
atattttctt tatttcatt tccaatgtcc cctttcctag tttccctgtc ctctccccct    26460
gctccccaac ccacccactc cctcttcctg gccttggcat tccctatac tggggcatag    26520 agccttcaca ggaccaagga cctctcctcc cattgatgac cgactaggcc atcctctgct    26580
gaatatacag ctagcaccac gagtcccacc atgtgttttc tttgattggt ggtttagtct    26640
cagggagctc tgggtactg gttagttcat attggtgttc actttcccaa attcttacat    26700
ggctggttta gttctttcct gcagctctta ggtctaatcc cttccttcc tctgtcatgg    26760 tgattgcctt cctctcctat ctcagttcct tgcctgctca atctaaaagt cccacctcca    26820
tctttctgcc cagccactgg ctgtatgcag ttctttatta tcagttgaag ccagctaggg   26880
gcagagacct tcaggtctgt aagtgctttg gggagcagaa ttaagacaaa gcattagaac    26940
caattcccaa caagtacctg ctatacattt caaagtccat attagtctcc tgggtcttcc    27000
cttccccagc tacttgtcct ccttgtaatc caaatgacaa gcttttttcac acatctcttt    27060 atctcacatt tccctagccc tggccatgtc cacttgttct tttactctct gctctgctct    27120 cttttccaatg cctctggata tttttctctct cttattcaca ataaaaacca aaccaaacca    27180
aacaaaaaac cttaccctaa taatggagtg gtcacgcctg aggtttcctt actgctcccc    27240
```

```
cttgcacacg tcttgtgtct gacacactgg caggctttta ttagcagcag gctctaggag    27300
ctgagagaag cagcaggcac ctctgaggtg gtagttacta gagtgattag aacagacagt    27360
ggagacgtgg ctggaaatat ggactctggt gtttggagcc aagtatggta ggcggcagaa    27420
gccagcagaa gcatgatcca caccttcacc aggttgcttc cattgggaaa ggctggaccc    27480
cttgggaagg ggtcccttg tgccttccta ggtgttcgga gccaggtgtg tgagggatac    27540
agtaaaggga ctgactgcat gactgctcca ttagggtgaa gggttttgtt gtgaatagga    27600
gaaacaaaat gtgcagaggc atctgggaga gagcagagca gagtgaaaag gaagcagtgt    27660
aggcatggtc agggctaggg acagcggaga cagcaagata gcgagtgggt gataaggtga    27720
gagagagtgt gtgtgtgcgg tgcacacatc acgtgcatta taaggaggct gagtagctag    27780 ctgggggag ggaagggcca gaaaactagc atgcactctg aaacgggtac ttgtgatgct    27840
gagggagctt gggggagaag ggcatgcctc aagaccagaa gagggagttg gagttacagt    27900
ttgtaagatg cctaatttga atgctgagat ccaaactctg atcctttggc tgaacatcat    27960
atctgctgag ccatctctcc agcccctaga aggtggtga tggtggttgt tcttgttttg    28020 ttttatttg tttaaatggg gagccaggta cagtacatca tgcctttaat cccagcagga    28080
gattcaggag atagagacag gtagatctct ttgagttcaa gggcaccttg gtgtgtatag    28140
gaaattccat ccacccaggg ctacagaagg gtaccttgtc tttaaaaaaa aaaaaagaa    28200 agaaagaaag aaaagaaaa aaaaagaga atgaaatttc agagttatgc aagataggag    28260
ctcagtggta gagtgtgtgc ccaggaagtg ctgggtttga ctcctcagaa caacagcagg    28320
ggcagaaact agtctacagg ttcatgagtg gtgttttgtt ttgttttaca taaaatgtgt    28380
tgaattagat aagtagataa aatgtgactc atacacagat aaatagataa aatgtgatac    28440
atgtacctgt acatagaaga ttatgatctc acctttaaaa aggaggaaat agagagtttt    28500
ggtagttaca ccacaggaaa actggaaaag aaaatgtata tatgaggctg tgccccatgg    28560
ctaaaggaac atgttttaa gtcatttgaa ttaccaaac agttttaggt aatgatatat    28620
ggttttgcat acaaccagta tttttataaat attagcaagg tcacatcatt tatgaaccaa    28680
catttaaact aaatttgtaa atcatcattt ctttatagca cttgtcatag aacataagta    28740
gtttaaaatg tgattattgc tttgctcttg atgtctgaaa atcttcatgt attctcttct    28800
ttgagccatt tttatgcttt gcagtactgg atgcatattg aagtgatcac ttatttaat    28860 ctaccttgcc tgagtttggg gaatagatgg tttccacatg tctgtgggtt atgcctaagc    28920
tagtggtttt tatgttagag cttgttttgg ggaaggcact ggttgcattc atagctgtgt    28980
ttcttttgcc tgtagtccaa gctcactctg actccatggg ttggtcttcg gaagatcaat    29040
gtgtcttact ggtgctggga ggatatgtct ccattcacaa atagtttgct gcagtggatg    29100
ccatctgagc ccagtgatgc tggcttctgt gggatcttgt cagagcctag tactcgggga    29160
ttaaaggctg caacctgcat caaccctctc aatggcagcg tctgtgaaag gcctggtaag    29220
gacatgggtg catatagtgc tccaggagga gccaagacag caaaggaggc acagctgaat    29280
gagcgctgag gtgatgaagt acttatggca gcagggagag gagcaccaat ttaggcatat    29340
gtatttcaaa cagaacccga ttccagatag tctttcttgg cctctgactg ctttaagcca    29400
tactgaaaac caaaataaa attgctgaaa gaacccagtt tatattgagc tgcactgttt    29460
cgttggtctc aaagtgttga gaattgttct agaagattat ttccttggtg ttggcagaga    29520
agtgctatgg aggaaacaac aacctgaaac caaagaaaca tttagaaaag cagcaagtca    29580
ggacactatt cagacactgc tggggtgggg ggagaggggc atggccaaag aagccgacag    29640
```

```
agccaacacc aggctgtggc aatgtcctgc gctgaggtta aggttagact ccatgaggcc    29700
aggcccagaa cagccataca caaatgagga ctccaaaaca agaggtgcaa gtgtagtgga    29760
gactccatcc ctgcaggtcc tgtttcagga aatgattgta ctttgcctga gtaatacagc    29820
ctaggagcta ctttctgata gggttttttta aatacttaca aagaattatt tatctttaat    29880
catgtggttt tgtatgtgtg tgcttgcaca tgcagtgctt gtgagagaga gtatgtgtga    29940
gagcatgcat gtatgagagt gtgagaatat atgtgagaga gtgtgagtgc atgtgtgcgt    30000
gtgtgcatct gtgtgtacag gtgtgtgtac atgcatgtgt gtataagagt atgtgagagt    30060
gtgggtgtgt gtgtgagagt atgtgagaat atatgtatga gtgtgtgtga gtatgagtgt    30120
atgtgcgtgc ctgcatgtgt gtgtgtgtgt gtgtgtgtgt gtgtgtgtgt gtgtgtgtgt    30180
agaagtggcc ttggaaaaca gagttgtcag atctcttaga gatatagttg cagttggttg    30240
tgagccatct catatgagcg ctggaagttg aaattgggtt ctctggaatc ctctgggttc    30300
cttgttgaag cctgaatatt ttgataaata tttatgtcat tatccctcaa aattgtaaat    30360
gtagaattta acaaactcag gtcttgagtc atctttgtcc caaggtttgt ttgtttggtt    30420
ttttgttccc ccaccttttc ttcagtgctt ttaaaaaaga gagtccattt tttcctaaat    30480
gtttaaatac agttgaggaa tagaacatct gactccaatt tcctgggttt ccctccatgt    30540
agtgtagtgc tgacctgatt tcagtgtgca ttgaaaactt tgatcacttg gaaggcagct    30600
atgctcacca ctatactacc aatgtctgca atcctatagg agaaacaaca atatgaacta    30660
actagtaccc cccagagctg tgtctctagt tgcatatgta gcagaggatg gcctagtcag    30720
ccatcattgg gaggagaggc ccttggtatt gcgaagatca tatgccccag tacaggggaa    30780
tgccaggacc aggaagcaag agtgggtggg ttggggagca gtgcgggggg ggggggtata    30840 ggggggttttg gggatagcat ttgaaatgta aatgaagaaa ataactaata aaaattgcct    30900
taaaaaaaaa caaaaagaa aagttttttga tcttagctga ccagtgtctc tttgggtctt    30960
aatttccagc aaaccacagt gccaagcagt gccggacacc atgtgccctg cggacagcgt    31020
gtggcgagtg cactagcagc agctcggagt gcatgtggtg cagtaacatg aagcagtgtg    31080
tggactccaa tgcctacgtg gcctccttcc cttttggcca gtgtatggaa tggtatacga    31140
tgagcagctg cccacgtaag tggaaggagc ttttgaacat ttgcaggcaa gttgggcttg    31200
actttctgct caagtccatg cagaagctgg tcgggccggc ccttccagat taacatgtat    31260
gtatagaatg cagcacagtg ttccatgcag taaatcagtt acatcaagga gaaggcacag    31320
ggtacagaaa tacctttttct tcttcagggt aatattataa ttcaatctgt ataatgtttc    31380
tacatcttaa tctaccagta tgtaaagtgc tttctagtag aggcctcccc agctcccttt    31440
ttcatccaac atcctgatat taaaggttg gaaaagtccc tgttatatat tatgtaaaat    31500
gtggggccct ttaaattatt tcagttcaat aatcactata gggtactatt tttaattcat    31560
ggaagttaaa tcatctgtta aaagaaaagg taataacagt aaattcaaat cttgtgatag    31620
tgaattacaa gttggattgt tttgccttgt tttttaatag ctgaaaattg ctctggctac    31680
tgtacctgca gccattgctt ggagcagcca ggctgtggtt ggtgtactga tcctagcaat    31740
actgggaaag gaaaatgtat tgagggcagc tataaaggac ctgtgaagat gccgtcacag    31800
gcctctgcag gaaatgtgta tccacagccc cttctgaact ccagcatgtg tctagaggac    31860
agcagataca actggtcttt cattcactgt ccaggtaaga tgcctgtgta tcctagttca    31920
aatctcgtac ataaactaga cgcccagatc ccttggctca cttgttttct tgactgtgtt    31980
```

```
tgagttctttt ctgtgttctg catcaccttg ttggatcata gctggcaaag gtgctctcct    32040
ttctgtgggc ttttcttta cttgattgat tgtttctttg gttgcacaga agcttttag     32100 ctttctgaag tcccatttgc cagttgtcct taattcctgg gcgagtagaa gcctcataaa    32160
aaaaagttcc ttcctacaca tgtatcatgt agggcactgc ctatgtttta ttccagaagt   32220
ttcagaggtt cgggttatgt ctttgatcca tttagggtta cttttgtga aaggtaatgg    32280 acacagttct gtttcattca ttattctaca tgtggacatc tacttttccc agcaccagtt   32340
ttgaagatgt tatcttttct gcaggttgtt gtttgcttg ttttgtctct tcagaaaatc     32400
ccagatggcg gtagctgtga gtgcttaggc ttggcctacc tgtttcatta tgttggcttg   32460
catgtctgtt ttgtgcagtg ccaccatatt gtcttaattg ctatagctct gcaatctatc   32520
ttgacatctg tgttggcaat cctgcagttt cgacccttct gctcagcagt gctttggcca   32580
tctggggtct tttctgggtt cataatgaat tttaggattt ttttttctat ttctgagaaa   32640
gtattgttga tattttgatt gcgattgaat tgaatctgta aattgcttt ggtagaatgg     32700 tcattttcac aatattaatt ttactgatcc atgaacatag gatgactcca gtctctcatg   32760
tctccctata gccctgtctt aagagatttg gagtcttcat tgtagaagtc cttcacctcc   32820
ttggttaagt ttatttctag atattgtatt gtctttggta ttataaatgg tagtatgtcc   32880
atgatcttgt tctcagtgtt ttttagttt agttttttt aatttatgtg tatgagtgtt     32940
tgttttatat atgtgtatat gtgcattcat gtcctctggg catcagatcc cctgggactg    33000
gatttacaga cagctttgag ctgcctgtag gtgctgagaa ttgaacccag gtcctctgca   33060
agaacagcca gtgctcctac tccccagccc cagaagtact aatttttaag agctgatttt   33120
ctacctttgc tgacattgtt gattgtttct agaagtttag tgatagagtt tttgagattt   33180
cttatatatc ttatgttatc tgtaaaaagg gataatttga ctccttttcc tatttatatc   33240
cttttatttc tttcatttgc catattgttc tagctagtgc ttcccgctca gtattgaaaa   33300
gagtggtgat tgtgaacagc ttttcttatt tcttatttta atgggattat tcacccattt   33360
aagataatgt tggttatggg tttgtcatac acagcccttc ttatattgag gtatgttcct   33420
tccagtcctg ttctctctag gactttttt tttttaatca agaaagcata ttgggttttt    33480
tgttgttgtt attttgtttt gtttttctag acaaggtttc tctgtgcagc cctggctgtc   33540
ctggaattca ctctgtagac caggctggcc ttgaactcag aaatccacct gcctctgcct   33600
cccgagtgct gggattaaag gcgtgcacca ccactgcctg gcacatgttg gttattttgc   33660
aagccctttc tacatctact aagatgagca tgtggtttca tctttgtctg tttatattgt   33720
ctgttgtatt tattgactta tgtgtgttga gccaacctga agttctggga taaaacccac   33780
atgctttgga tgattttgt gctatgtgct tatattgtgt ttgttagtgc tttattgagg    33840
acgtctgcat ccgtgttcat ctggggtact gtctgtagtt tgcttatttt gttgtctta     33900 cctgctctgc attttagagt aatcctggat ttatagaaag catttgggag tagtccttct   33960
gtttattaaa aaaaaaatt aagaatgatt ggttgttgtg tggtggaatt ctgctgtgaa    34020
cccatctggt tctggactct attcggaagg cttttttatta ctgtttcagt ctccttgttt  34080
gcagtgatct atttaggttg ctaatctcct tatgattcat ttggatgaat caagaaatta   34140
atccatctct ttagatttcc agcttaatgg aatatgagtg ttaaagtatt tctttatagc   34200
attctgtatt ttttgcatc tgttgtaata tttccctgtt ctttctgtta atctcttct      34260 ttcttgtggt tagttgggct aagaggctct tggttttttt tttttttttt tatctttta    34320 aaggaccagc tcttagattc attaattctt tgtattattt tccttgtttc tttttcactg   34380
```

```
atttcatttt agatttat  atttcttgcc atctactgcg tttgggttgg ttttagttat   34440
ttttccaaga ttttcagttt catcactaag tcattcattt gggctctttt gggtttcttc   34500
acgagaaccc acttgggact gttaccttcc cttttagacc tgcttttaat gtgcccaga   34560 gatttgttac attgtctttt cgatttaact tagtttcagg aatattttga tttcttcttt   34620
gacccattca tcattcggta atgagttgtt taatctctag tgagtttata catttattag   34680
aattttgttt actgatgatt ttaaggtgtt tggctttgtt tgtttgtttg tttgtttgtt   34740
tttcgagaca gggtttctct gttgtagctc tggctttctc tatgtagaac agtctgacct   34800
caaattcaca gagatccacc tgcctctgcc actgaagttc tgggattaaa ggtgtgtgcc   34860
accactacct ggctgatttt aagttttatt acataataga caggtagggt acatagattt   34920
tctacatttg tgaaggtttg cgttgtttgt cagcatgtaa ttctgtgtgc tgctgaggga   34980
atgtatgttg ttttgacagt taggtggaaa agtctgtaga catctgttag atccatttta   35040
catttcaaga agccatttaa ttctgaagtt tctctgctta ttttttccca ggtgacttac   35100
ctattggaga aaatagggtg ctaaaatcat ttactattat tgtttttttt aagaagaaaa   35160
taattaattt aaaaaaccct ggaaagaaag ataccaaatg tgaatcatgt ttcctggata   35220
gtggggttat atttgatcat ttattttcc tctcaaatac tgtgagtttt tacaatgaat   35280
aacaacataa atatttttat gttgctgtgg actttaactt tgctttgata atatatttgg   35340
ttttttgaga ctaatttctt tttgatattt tattttctca tactagtttt tagtaaactt   35400
tggttttgtt ttgtttgtat tttttagact ggccaccaac ttgctatgtt gtcaagggtg   35460
gccttaaaat ccacacccaa tactttgtcc tctctttctt tctttctttt ttttttttat   35520
tggaacaaaa tttctaggtg ggaatctcac tatgttaccc aggctgacct gaaacttctg   35580
ggcttaagca agatgggtgc acatgatcag agacgctgcg ctgcccgcct cagcccctgc   35640
tagttggaac tataggcaca gacagctgta cttcactcat ttcaatgatt taacatttag   35700
actatatgca aataaatatg aaatgtattc accaagttct cctatgggag aaacagagcc   35760
cttaagattt ttccttca gcttgccagt gcaacggaca cagcaaatgc atcaaccaga   35820
gtatctgtga gaagtgtgag gacctgacca cgggcaagca ctgcgagacc tgcatatctg   35880
gcttctatgg tgacccgact aatggaggca aatgtcagcg taagtcacac aggtcaagtt   35940
agtcacaagt caggtacaat agtacagtac ctgcagttga cttaaatatc ttaaagggaa   36000
aaggcctctt ggtttgggat attgcctttc ttaattatgt taaattgtta aaagtttaac   36060 tgagggcta gaaatgtggc tcagttggct aagaacactg actgttcttc tagaggaccg   36120
aggttcaatt cccagcaccc acatggcagc tcacaagtgc ttgtaacacc tgggatccaa   36180
caacctcata cagacataca tgcatgcaaa acactaatat acataaaata aatccattaa   36240
aaagtgtttg atgatgctgg aagaggaaaa aaggctcaac ttgtgggttt gggagcagtt   36300
agttaaagca acaaaccgac agtaaaggag ctaagctttt atttcttcag cagaggcata   36360
aacaaggggc cgaagtcact gaggcaccag ctgcctttat tccatttccc tcccatggaa   36420
gcacatcagc tcaagtcaag cagagcagcc tgggatggga ggtcatctca ttggagaagg   36480
aggcaggagg cattgtgagg ggagggagga caaggctggg aatgggaagt cctgagctca   36540
gaatcagaat gaggacaaga tcttcagttt ccttcttaat ataaagaggt atcacagagg   36600
tctctataga agtctactgg aagcctcaca caggcacaag ggtacatttg aaaaactgtg   36660
acagccaggg agagtcccct tctgaagtgt ccttcctcag agactgcagc acctgactgt   36720
```

-continued

```
gccccagtct gcaagaggtt tggggagagc aactgacctc ctgaggaccc cagatgaatc   36780
tttaagatgg cctgcttttg gttttggttg gttggttttt agacagatct aggagagttg   36840
gtgatgagct tgaattctct gtcctcctgc ctgacctcca aatgcccagc ttcacatggg   36900
ctcccattaa gttgtgagtt tcggtgtctg gctcctgctc tcacagccag tgcagtacat   36960
tgagctccat agagatagcg ccggggcaaa tgagagctgg acgggcactg ggtgactctg   37020
tgccttgtgc cggaaaatca actaaacatg gcaaaggag atcctaagaa gccgagaggc    37080
aaaatgtcct catatgcact ctttgtgaaa acctgctggg aggagcacaa gaagaagcac   37140
ccggatgctt ctgtcaactt ctcagagttc tccaagaagt gctcagagag gtggaagacc   37200
atgtctgcta agaaaaggg gaaatttgaa gatatggcaa aggctgacaa ggctcgttat    37260
gaaagagaaa tgaaaaccta catcccctgc ccccaaacag gagaccaaaa cgaagtacta   37320
ggaccccaat gcacccaatg ccttcttcgg ccttcttgtt ctgttctgag tacctcccca   37380
aaatcaaagg tgagcaccca gcttatccat tggtgatgtt gcaaagaaac taggagagat   37440
gtgaacaacg ctgcagcaga tgacaagcaa ccctaggaga agaaggctgc caagctgaag   37500
gaaaagtacg agaaggatat tgctgcctac agagctaaag gaaaacctga tgcagcaaaa   37560
aaaaaaaaaa gggggtggc caaggctgaa aagagcaaga aaagaagga agaggaagat    37620 gggaggagta tgaggaagag gaggaagaag aaagatgaag aagaatatga tgatgatgaa   37680
taagctggtt ctagtttttt tctcatctat aaagcattta accccctgt atacaattca    37740 ctcctttaa agaaaaaaat tgaaatgtaa gcctgtgtta gatttgtttt taaactttac    37800
agtgtctttt ttttgtataa ttaacatact gccgaatatg tctttagata gccctgttct   37860
ggtggtattt tcaatagcca gtaaccttgc ctggtacagt ctgggggttg taaattggca   37920
tggaaattta aagcaggttc ttgttggtgc acagcataaa ttagttatat atggggacag   37980
tagtttggtt ttggtttat ttttgggttt tttttttca tcttcagtcg cctctgatgc     38040
agcttatatg aatatgattg ttgttctgtt aactgaatac cactctgtaa ttgaaaaaaa   38100
aaaatcgtgg ctgtcttgac atcctgaatg tttctaagta aatacagttt tgttttatt    38160 aatattgtcc tttcgacagg tctgaaagtt ttcttcttga gggaaagcag tcttttgctt   38220
ttgtcccttt tgggtcacat gggttactgc agtgtgtatc ttttcatata gttagctgga   38280
agaaagcttt tgtccacaca ccctgcatat tgtggtaggg gtaacactt catccatatt    38340 caaagaatct ccaaaatcgt gatcagttgg ataagaaata ttatataacc tacttggcaa   38400
agcaaggtgt gatcaattct gtcacaccat gggatcatta gaatcaagca atctgaaaat   38460
ctgtccttaa aggactgata gaaaagtatt ttctaatcct tatacaaagg ctctccttta   38520
actgccactg ctatgtaatg acagttatgt tttgcagttt ccctactaaa aagacctga    38580 gaatgtatcc ccaaaagcgt gagcctaaac tacacaactg cagtactatt tgttgacctt   38640
agtcccagcg aaggctatca cgagaatgct agctataata taatgcctct gccctctat    38700 ctaaatatgg attgctcagg aaacttgact gcttaaaggt attttttca tattgttgtt    38760 cctcctatag ggttgcagac ccctttagct ccttgggtac tctctctatc tatctatcta   38820
tctatctatc tatctatcta tctatctatc tatctcttgt cagatttctt ttttcttttc   38880
tctttctttc tttcttttt taagatttat ttattattat ttctaagtac actgtagctg   38940
tcttcagatg caccagaaga gggtgtcaga tctcattacg gatggttgtg agccaccatg   39000
tggttgctgg gctttgaact caggaccttta ggaagagcag tcggtgctct taaccactga   39060
gccatctcta caacccttaa aggtattttt aagtagttga gtcagctttt aaaattatgc   39120
```

```
cagaagtgtc aaaagttcaa aagtttagga ccatcctcta ttgaagtaca gggtcatcct   39180
gggctacatg agaccctgcc ttaaaaccaa aatcaaacaa acaacaggaa aaacaagagt   39240
taagaaagag aaaaagaagc acttggaaac aaagatctgt ggagtatgta taggcttctc   39300
tacaacaggt gtatgtagga tcttgatggc ttttgagtct attaccctca aagaggtact   39360
gagaaaccta aatgtgatca ccgtggtctc tgaggggcac ctggcaggat tatgggagat   39420
aactaaagct tgctaatcac agagtttagg gagggaggac gtctctaagg caagttaact   39480
gtctggtttg agatgcttag gtgatgtctg aggaagtaat aaggcctgtc cattttcata   39540
cacactcagg ccttaagtct gggtaatggc tacttgaaca taaaatagtc ctctatgaaa   39600
ggaataatat ctctgtgtca gcagccttca cggctaatgt taattgtgca ggaaccctgc   39660
ttctcagtca gacagaagct caatcaggca ggggcaggac ttctttgcct ttcccatgtc   39720
cttgtaattt ccctggcttt tcatcttggt tcaaacatac ttacctgtta ggtaattata   39780
agaacaccaa atattactga ataaaatgtg tttatgactt tgtggtgact gccattcaag   39840
aattagatgc cttagccagc aatgatggca cacgccttta atcccagcac ttgggaggca   39900
gagataggca gatttctgag ttccaggaca gccagggcta cacagagaaa ccctgtctcg   39960
aaaaaacaaa acaaacaaac aaaaagattt cgatgtcttt atcacccaaa tcaagtaact   40020
ttccaaagtc tcacagtgag atgtagccta gttgggagcc acatctaata tatgctgatg   40080
atcttaacaa gtagcctgct tgtgtcttca ggtgaccacc ccggtgtcct cagctacctc   40140
tagaaagatc acactttcct ctgtggtctc tgcagggtcc ctgtatgatt ctggaacctt   40200
gctgtacttc tcagagtcct gattcataaa gcactgagtt tttgcttgtt tgtttgtttt   40260
gatactattg gtaagaatat atattgaacc ttgacatgcc tttttaaaat aacattattt   40320
ttacaatagt actttagcct tgattatgtt aactgcttac tgtttcagat gacattcgta   40380
catcttttaa tcctcaaacc agtcctatga gatggctagc atcattgtca catcatttag   40440
gcaaggaaac aggtcttggg ttaagcttca tgctcagagc tccttggaac acagtggact   40500
caagtgcaag cagactgacg cgactgggtt ttactaattc agtaagcctg tactctatgg   40560
aggaagagtt tctgaccact ggatgcagtc tgatgacctc tgactgttct gtttgaaagg   40620
tttctttcag tgatttttatt tttctccatg tggactttttt ttccagctttt taaaatatat   40680 atatatatct tattcgcttc acatcctgct cactgtcctc cctcccctgt catcccctcc   40740
tacaatcctt catatccccc cttaccttct gagcagctgg gagcccctct gggtatcccc   40800
acactcgggc acatcaagtc tgtgaggctg gacgcatctt cccccactgt ggccagacaa   40860
ggcagcccaa ctagaacata tcccacagac aggcaacagc ttttaggata gcccctgctc   40920
cagttgttca gcacccacat gaagaccaag ctgcacatct gctacatatg tgcagggagg   40980
cctaagttca gcccatgtat gttctttggt ttgtggttca gtctctgaga accccaagga   41040
tacaagttat ctgactctct taatcttcct atagagttcc tatctcctct ggggcccacg   41100
attggtgtcc ctattgcttc actgggattc ctgcctggct acacccacta tgaccaaggc   41160
aagtcttaga aaagacaaca tttaactggg gctggcttac aggttcagag gttcagttca   41220
gtatcatcaa ggcaggaaca tggcatcatc caagcaggca tagtatagaa agagctgaga   41280
gttctacaac ttatctgaag gctgctagca gaataccgac ttccaggcag ctaggatggg   41340
ggtcttcaga cccacaccca cagttggtgt ccctattgct tcactggggt tcctgcctgg   41400
ctacaggagg tagcctcttc aggttccata tccccaatgc tgtgagccac agttaaggtc   41460
```

```
acccactatt gattctaggg tgtctccctc atcccaggtc tctttcattg tggagatgcc   41520
ccccacttcc ccaccactgt cagttgcaga tttccattct cgggaccatc tggccatgcc   41580
ttctgtttct cctcacacct gatcccgaca ccccgccca ttccttctcc tacctagttc    41640
cctccctcca tatgcttcct atgactattt tattccccct tctaagtgag attcaagcat   41700
cctcacttgg gccggccttc ttgttttgtt tctttgggac tgtggagtgt agcttgggta   41760
tcccattttt ttatggctaa tatctgctta taagtgagta cataccattc gtgtccttt    41820 gggattgagt tacctcactc aggatggtat tcttaagttc tattcatttg cctgcaaaat   41880
tcatgatgtt tttgttttta gtaactgaat agtagtccac tgtatagatg taccacagtt   41940
tctttatcca ttcttcagtt gagtgaaatc taggttgttt ccagtttctg gctattacaa   42000
ataaagctgc tatgaacata gtggagcatg tgtccttgtg ggatggtaga gcatcttttg   42060
ggcatatgcc caggagtgat gatatagctg agtcttgaag tagaactatt cttagttttc   42120
taaaaaacca cgaaattgat ttccaaagta gttgtacaaa tttgcactcc ctctaaccaa   42180
gcaagtgaaa gatctgtatg acaagaacta caagtccctg aagaaataaa ctgaagaaga   42240
tatcaaaaga tggaaagatc tcccatgatc gtgaataggt aggattaaca aggtgaaact   42300
ggacatctta ccaaaagcaa tctagagatt cagtgcaatc cccatcaaaa ttccaacaca   42360 attttctgt agaccttgaa agagcaattc tcagtttcat ataggaaaac ataaagccca    42420
ggagagccaa aacagttctg agccataaac gaacttgtgg aggaatcacc atccctgacc   42480
ttaaagccgc actacagagc agtcgtgatt aaaacaacaa caaggctgc gcactttgg    42540 tacagaaaca gacgtgctga ccaatggcat ccaatccaag atccagaaag aaacccacac   42600
actatagttt ttttttaaat ataaagttct tcagcttaat gcttctcatt attcatgaga   42660
gaagaagact caacagcaaa gaaggtgaaa caagggtgac aagtaccaca gggctctcga   42720
gtgtctcttg tgatggacta gggagcccgt cagttctgaa tgctcaggaa tgtggttcac   42780
agtgtggcca cagtacagaa gatccccgag ataaggcaga agacagtcac cacaggtcat   42840
ctccacaggg caaggactca gtatatggca tattactaat gctcttaaat atttactgaa   42900
caaaggaaca aaatgctgag tctgtcacag agatgaaaat agccgttgct tcaggggaca   42960
gcagaagata gcctttttt ctccttgaat ggtagttaat ttaatgttgc ctctatatta    43020
ttagaaataa attacaagct gaaaaataat gagtcatacg cagtgatttc tcttgcttta   43080
ggctgtcttt actacaaacc catttcaggc taaatgattt tgtcttaatc acagtctatg   43140
gtaatctgtc aagccagttg tgacctgtct tcctttcctt cttcccagca tgcaagtgca   43200
atgggcacgc atcactgtgc aacaccaaca ccggcaagtg cttctgtacc accaaaggtg   43260
tcaaggggga cgagtgccag ctgtgagtac cacacacact ctgtgtctcc agtgggggac   43320
tgggccttgc agctgcctgg gccctgtcgg ccacctgctt gcctgggcat tgttgccctt   43380
cactcccagg gtctttgagt ggactagtgt ggaggtttac ctttttttcct tcagacaggt   43440 tatctcagtt actttaatat tgctctgata aaacatatga ccaaggcaac ttacaaaata   43500
aagcctttaa ttgggcttat gacttaagag cattggagtc tacattgagt tccagggcaa   43560
tagagctaca tagtaagact gtatcaatca atcaataaat aggactacat agtaagactg   43620
tatcaatcaa tcagtagatg aagagaaaga aagaaagaaa gaaagaaaga aagaaagaaa   43680
ggaaggaagg aaggaaggaa ggaaggaagg aaggaagggg aagaacaaaa caagcttaga   43740
taggaagaac aggatagaat gaatgacaaa tgcttgaaaa atgttttagc tgtacttta    43800 gaagcatact caatccacac agaagtaaaa atgttgttcc ttatgagtag tacctagcat   43860
```

```
tattacatat gtacttgcct gtgtccttgg gcaagtattt gtttatttgt tgtttttata   43920
ctgttgctgg tgtaaattac tgagcagtta gcagaaacat tcctgcaaat gggatagtct   43980
ctctgatctg aataatgata tagtttatgt aaaggattt acttggttta aaataaata    44040 tagagtctgt gctttaaatg tcaatagaag ataatttctt ttttccctag atgtgaggta   44100
gaaaatcgat accagggaaa ccctctcaaa ggaacatgct actgtaagtt tttgtaattg   44160
tttctagaga gtaattgaac aaaacgacat tgctttttt ttttaccatt gtctgagaat    44220
gataaatgct tgggggatga agcaaatact catagccatg cccctgactt ggtgaacact   44280
gttctaactg aggcatggtc tctgctggtc atccagagca gttagcaggg gtgctgtcct   44340
gcctgtcctt gttcagctcc cgcggaggcg tgctcattca ccattgccca gtgtagctta   44400
tcatgtccaa tcttcagaca gccaggaagg agtttctaag atagaggtgc gttccaccat   44460
tctctctgca gctgatttgt gctcacaaac aagtaaataa acaccaaat taataccttg     44520 gtgtgaaagt gaatctggta agcttacagc tttatcataa atatattttt tgtctatgag   44580
aatctacata gtaggttcta gactatagaa caataaaaaa aggaattaac atttggcata   44640
tgcagcataa tggtatatat aaattgtaga agaaaatgga tggttctaga cctgaaaaga   44700
caagaaaatt gcttgtgtgt aatctgggca ggtcttaagt tgtgaccttc aacatctgct   44760
tcccaagcag ctggaaccac caggcctaca gaattcttag ctatgattct aaaggtcatt   44820
catcaaatat aatgttaatg tgtattttat taaagtttca aacttctatc tttaataatc   44880
tgcaaatgta gctcagtaga ggagagctct cgctgtaagg tcctgtgttc tatccccagc   44940
acaacaaaac aagacattta agaaaaaatt aaaacaagtt ggctgtattg tctcagtatc   45000
tcatccttga gatagtgagg caggaggact tttagtttga ggcctatgtg ggttatgtag   45060
tgtgaaacct ttctcaaata atatttacac ttttttcttt aaaaaacaac ttttttctta   45120
atttatgtgt tttgcaacat gtaagtctgt gcaatgtgaa catatctgtt gcctttgaat   45180
gccagagagg gtttcagttt tcctggatct ggagttacca agggttgtga gctgccatag   45240
tgggtgctgg taatgaactg agtcctctgg aagagcagcc agtgctctta actgctgagc   45300
catctctgct gctaggtact ccccttccc cccttaaatt taagacaaag gtctcactgt     45360
gtagcctcag atggtctaga actcaatttg tagaatggtt gacctttgaa ctcacaaaac   45420
tctgcctgct tctgcctcct gagtgttgag attaaagttg tatgtcacca cacctgcccc   45480
tatgatttct atatttaata aagatcatga ctaggatata gagaacactt ttagaactga   45540
agaagaagac agttacagtt aaaagcaaaa caaaaacaaa aacaaaacaa aacccagaaa   45600
aaaaaagaat gaaaactagc actgaagaaa aaataaattt taaaaatagg caaagagtca   45660
ctattatatt gtgatggatg tgttatatgt ttaaaaccac aagtgagata caggcctgaa   45720
atgactttaa tcgaagctac accagcctgg ggtggtagtc cagttggtaa agttcttgct   45780
atgcaagcac aagaagctgg gtttgatgcc caggacccat gctgaaaccc aggagtgctg   45840
ctgagtgctt cagctctggg gtggcagggc tcactggcag gaagcctagg ctaagagaga   45900
ctctgtctcg aaaacaaagg ccgatggcac ctgatgaacg gcatctcagc atgacctttg   45960
ctcggcatat aatgtgtaca cacaaattca tagtttagta aagacaagt atgatctgct     46020 tttcatgaag tctgttgtaa tacgccttct ttagttaacc atagttgctt aaaaaagaa    46080 aaaaatcgac ctcactggac agaaaatgga tagagtgttc taatagccaa ttcaattcat   46140
catcattatc aaaacctata acttagggg ctggagagat ggctcagcgg gtaagagcac    46200
```

-continued

```
tgactcctct tctgaaggtc ctgagttcaa atcccagcaa ccagatggtg gctcacaacc    46260
atccataaag agatctgatg ccctcttctg gagtgtctga agacagctac agtgtactta    46320
cataaaataa ataaataaat ctttaaaaaa aaacacctat aacttaaact tatcaataac    46380
tttaactttc ctaccccatg cttcctagtt acccattctg ctttctgttt gtatgatcct    46440
gggtatggca tcttaatgga accacagtgt ttgactttgt atctacttaa tattaggcat    46500
gatgcctctg actctcatcc ctgatatagc acagttcaaa attgcctttc tttggtgctg    46560
tacatatagc tgagcgtttg agtgcttccc tgcatgcaca ggtttctgaa ttcaatcccc    46620
agcacaaaaa atgataaaaa gaaagcaaaa aggcttattt ttacagctgg acagatcatc    46680
ctgcattgtg cctgtcatgt tttgcttgtt cttctgtca gtggacactg tgttacttct     46740
accttttggt tgttgtcagg aatattgtaa acatgagtga atatacaccc agaagtacaa    46800
ctggatgtgg taattctatg agtgttttgt tttttgaggg atggttatta ttgtttccat    46860
acaataaatt acatttcctt acagttcatt acatttccaa aagccatgca tagcatttct    46920
gttgttctac attcttattg acaccagttt tcaatttaca tttattttgt gagttttta    46980 attggtaacc atcataatgg acataaaaaa tagctcattg tagttttggt atttgtattt    47040
cagtaatgct tggtgtgatt atcttttat attcttatta accattagtg tgtatctttt     47100
tttgaaaaaa cacctcttca agggtttac tatgtagctc tggctggcct ggaacttgtg     47160
cagaccaggc ttgcctccgg ttcccactgt cttaggtagg tttccattgc tgtgaagagg    47220
caccatgacc agagcaactc ttacgaagga catttaattg gggctggctt acagtttcag    47280
aggtttaatc cattatcatc atggcaggaa gcatggcagc atccaggcag atgtggtgct    47340
ggaggagccg agagagttct atatcttgat tcaaaaatag ccaggaaaag actgtctaca    47400
gcaggcaacc aggaggagac tgtcttccat attgggcaga acttgagcac taggagtgtt    47460
ccaaagccac ctacacagtg acacagtaca tccaaaaagg ccacacctat tccaacaagg    47520
ccacacctcc taatagttct acttctcatg ggccaagcat actcaaacca ctacatccac    47580
ctacttctgt ctcccgaatg ctgggattaa aggcatatgt tgccattacc caattttaaa    47640
ccagattatt attgttttt tgtacaacag acttttaagg ttaaagtttg cagcaatagg     47700 cattcttga agctgtatca cactgatata tgtctgttgt tttcttcctt cctagattaa     47760
aatagtacag tatattcaag tttcaattgt ccctttccat aagaagtcct ggtttctgtt    47820
ccattattag tttatatctt agtgttctta agtaaaaata ctcagtattt atagatgagt    47880
tagattagag ccaaacccca atcagggtat tggtaatgaa ggtttgctgg ataattcaaa    47940
ggatactgca aagatctggt ttctaatgga aagaacatgt aagttggcca ttagtggacc    48000
acacatctgt atttcttatt ctttggaacc ttgggcagga tagacagatg agctaagatt    48060
ccttcatagc tattgaattt gtgagaaaaa caaattgtgt ttccagaaac ctgctttagt    48120
ttgtatcaac acttactttc tttctgtgtg tggtgtgtgt gatgtgcctg taccattttc    48180
aagtttttct tccttctttc catagatacc cttctcattg actatcagtt cacctttagc    48240
ctgtcccagg aagacgaccg ctactacaca gccatcaact ttgtggctac tcctgatgaa    48300
gtaagctttt ctttaagct gtcttatttt gtgttaaatt ttgtataggt ttttttcttg     48360
gtcatcctgg acaaaagtac tacatagaag cagacagtat caggtggga atataaaagg     48420 caaccagttt ttaagtattt ttttatttac ttgttgacag ttttatatga ttatataatg    48480
tgcttgatga tattcaacct gtgaccttt gtctccctca tacttagttc cttctctccc     48540
caccaagtca ccttcactcc ctctcgtgtg tgtgtgtgtg tgtgtgtgtg tgtgtgtgtg    48600
```

```
tgtgtgtgag agagagagag agagagagag agagagagag agagagagaa agacagacag    48660
acagatagac agagagacag agattgattg attgattgat tgattgattg attgattgat    48720
ttacctacct agtttaccag ctgactgcag gagcatgctg ggtgggaagt tcttactgga    48780
gcatagacac attacagtga ctacaccact gaagaaagtg actccctctc aggtagtctt    48840
cactgccact aggtcctcag ggatcaagag aatgtttgga gtctacattt tatcttttt    48900 ccactcagaa ggcaaacatt actgaatgtt tttaagtagt agaataatgt tcatgatagt    48960
ctgtttaata ttaaattaag aatttgttcc taattataaa attttagaa gatagacaag    49020 aagacaaaat ttttgagtta acagtttgaa aggtttattt ttattttatt ttatatgtat    49080
gaatatttta gcttcttgta tccctgtgca tcatgtgtgt gcagtgcctg tggaggccag    49140
aaatagatat tggatccctg gaactagagt gatagatcat tgtgagccat catatgggtg    49200
ctagaaccaa cccagggtcc tctgcaagag cagtgagtgc tcttaactgc taggccattt    49260
ctttagcccc taaatgtgaa caactcttta aataaatgta agtgatctta aatactctgg    49320
agaaaaatct gtagctatac cttacttttt aaaaattatt ttgttttata ttatgagtgt    49380
tttgcctaca tatatgtgtg tctgatgcct gcagaggtca gaagagggtg ttggatcccc    49440
tagaactggg gttacagatg gctgtgagca gctatgtggt gcctgggagt tgaaccctgg    49500
ttctctgtta gggcaacaac tgcttttaac catcaaccca tctctttggc acatgggtgc    49560
attgttggtt tggctgcttg agttgtgtgt gaggggtgtg tgtgcataca tatgtgggtc    49620
catgcttatc cagtggaggc cagaggtcag agtcatgtat ctctctgtta cttcctacct    49680
tatgttttgg aagcaagatt agatagaccc ctgggacctt cctgtcttct cctcagcact    49740
aggactacaa gtccacacct gactttttac atggggcttc agatctaact cagtcccaac    49800
acttgtttca tttccttagc accttggcta gattcttagg attttagaag gagcttatag    49860
caaaatacca caagtgaaat ttactactgc cttagtcata agcaaatatt gaaggctcag    49920
tctttaaggg tataattgat agtgttcttt tttttttaa gtaaacaaat agcctgtcat    49980
ggtaactatc gctgtagtcc cattacttgt gagagatgtc agctcaaggc cagcctccgc    50040
tacataagta agggaagacc agcctgagct atatgggact ctatcaaaac aaataaacat    50100
tgtagaattt ttgtaatact tattagaagg tagctgatga tcatgagagt ctttagacat    50160
ttcttcattc cactgttttg tgtgtgtgtg tttcatgaca gatttcttac tagatttatc    50220
tctttgtgtg tgtgtgtgtg tgtgtgtgtt ttacaaaatg acaaagattt tagtccttct    50280
cgtggaaagt agttgctagt ggtcagcaga tacttgctag tataaataaa tgagcataga    50340
tctgcgcttg caaaggaaga caaagggaaa aaaggttttc ttgaacataa ttcctacttt    50400
gtgaaagaaa cttctcattt ggaaattaca ttttgaaaat aggtattgtg aatgtttcca    50460
ttgtggtttg tggtataact atcaaataac acttttttaa aaagaaaaat cttaattttc    50520
taagattttt aaatacccct ttaaaatgag catttccagc atggtttgat taatttgtaa    50580
aatgtaagaa tatagtatct aaggctacag aaatgactca gtggttaaga gcactggctg    50640
ctttacagag gacccaggtt ccatccccag caccctcatg acagttcaca gccatctgta    50700
tttctagttc cagggcatct gatgcccttc tctgattttc tccagtacta gtgacacaca    50760
gcatacattt gaacaaaacc actgatacac ataaaataaa ttgttttcaa gaaacaatat    50820
agcatctaat tagcttacaa aactaattat tgtttctgt actaattacg tttctattgg    50880
catgactaag gcaacttata agagaaagca tttaatttgg ggttcacact tctagtgcct    50940
```

-continued

```
tagattctat gagcatcatg gtagggagtg tggcagtagg caggcaggca tggtgctgga    51000
gcagaggctg agagctcaca tttgattttc tactagaaga cacagagaga gctaactgga    51060
aaaggcatgg gcttttcaaa cctcaaagcc cccctctagg aacacacacc tccaccaagg    51120
ccatacctcc taatcaaaca gtcctaccaa ctgaggacta accattcaga gatagatgag    51180
tctatggagg ccattgtcat ccaaaccacc acaggcccca agaaagattt gttagtgaaa    51240
tttcagtgaa aactaaaaca gcattagaat ttacctggca tagccagcaa tgatctcttc    51300
tgttcagtgc cacagatttc tttgagttaa aactcagttg ttaaaaccaa aaatcaaaat    51360
gtaattggca ctttaaattg ctataagggg aaacaaggtt ttcaaagcca tgaaaccata    51420
ttcagaataa ttttagcgag agaaatattt ttttcttttt ttgtcgtttc tttttttttct  51480 tggagagaaa tatttttatt attttatatt attttaatta catatttaat tattaaccat    51540
ttctgacaga gggcaaaagg tgaggatctt catggaacta atatctgata aagcaccaaa    51600
ttcttcccaa ctctgggatg caaatgacag ttcaacttca gtttattgct tgtattgaag    51660
aaaattgaca agaaatgtca tgtcttaaca taagcatgga tttcttttaa gatgtagaat    51720
agtctataat taatgttttt gagactagta agacctgatt attgttgtat cttaaaatct    51780
agaaggtact aacaattttc taatgtgtat tttttttttc atcagcaaaa cagggatttg    51840
gacatgttca tcaatgcctc caaaaacttc aacctcaaca tcacctgggc caccagcttc    51900
ccaggtacag acacacctag agagatggat tggcaagttt agtgtaggag ttggggaagg    51960
aggctctgaa ggctggtgag tgagttcaga gcccacctct gcctcttagt agccatggca    52020
ccttgaacaa gccatgcttg aacaagcatg tacaattccc tctctacctt aggctactca    52080
gagtgaggag tcacagctct tgcctccagc gttgctggtt caggttggtt ggatggctgc    52140
tccctgcttt gccaccacct tccagcacta tgactatctc tatgtttgtg cttcacaggg    52200
gaaaaactaa agtgactcat agttttaaga aatgaaaact cttaaggga aggggataa     52260 ctctaatatg tagaggtatt catactttgg gataactcct aaaagtacag cttttccatt    52320
cttgtttatc ttatagtgac tataaaattc tgatggccct aatgtagcag ttactataaa    52380
taaccactcc ataacttgat agccctgaag atagacctag gtttgaattt acctgcacgg    52440 tgttaacaa gttactgaag ctttcttttc tttgttttt aagtttgttt tattttatgt      52500
gtgtgtttgc ctttgcctgt atgtgtataa gtgtaccatg tatgtgcagt gcttgagaag    52560
gtcagaagag gacatcagct cccaccctc aacgagttac agacaattat gaactactat     52620
atctgtgctg gcaacagaac ccaggtcttc tgaaagagca accagtgctc ttaactgctg    52680
agccatctct ctctagcccc caagttacct aaactttctg atccagtttc cttctttata    52740
aaatgataca gtgaaaatag ctttgctatg tacagagata ttccaacttt ttaatattac    52800
aacatgacat ctacaaatat gttagccctc attcataatc ttgcctgaat tgtagagtgt    52860
tgcaaggaat aaatgaaata aggaggtac ttattataga gtttgaggtt tgccttcatg     52920
cataaagaga agcttttttg agtctgtact actcatgttc ttagccaatg gagtatataa    52980
aatatggtag aaccatttag aaatggagtc tcactgggta caggcctgaa tgcagtggta    53040
gcaggtagca gaaagaaggc ctgagtggct gcttgagcac cttctccatc aagacttgag    53100
gacctttctg cttaggaagt gatgagcgag taagtgtccc tgaacaggag ccttgagcat    53160
attctacagt gtgaagcaga aatacaaagg agttgaggta tcatgtgcaa aatgaatgca    53220
gtgtctgttt tatatgtatg attgttttac atacatgtat gtctgtgcat cgcttatata    53280
tctggagcct ctgagacaga ttacttaatc tattgggact tgagttttc caatctgtag     53340
```

```
atggagatag gaaggtgttg tgtgggttag agactgaagc tcataaggct atattctttt    53400
gacactgtaa gtgctcaata aacttttacc ctcattacta gtgcgcaaag attctttctg    53460
attggcatac ccgcctccca gtctttatt tttattcttg cttctttcta gccggaaccc    53520
agactggaga agaggtgcct gttgtttcaa aaaccaacat caaggaatac aaagatagct    53580
tctctaatga gaaatttgat tttcgcaacc atccaaacat cactttcttt gtttatgtca    53640
gtaatttcac ttggcccatc aaaattcagg taagaactgc ttttaactt cattcccgta    53700 aagatggtga catctcttta gtggagacta acttcactca tttggaatct gtggtgactg    53760
aaagatagtg ttgctttgcc tttgagggat ctttgccata gactgagtag caggtgagtg    53820
ctgttcttag gttggagaga tgttcagtga gtggagtgct tgctacacaa gcctgaggac    53880
atgcagttca tctgcagcct ctcatacaaa gcgggacacg cagggtgtgc ctgtcacctc    53940
agcactggac atgcagtgtg tgcctgtcac cccagcacag gacacgcagg gtgtgcctgt    54000
cacctcagca ctggacatgc agtgtgtgcc tgtcaccca gcacaggaca cgcagtgtgt    54060
gcctgtcacc ccagcactgg acacgcagtg tgtgcctgtc accccagcac tgggaagcag    54120
gggacagaaa gatcttgctt gctggccagc cactcaaagc tggatctgtg agttctagat    54180
tcagttagag accctgtctc aagtaaaata aggtagagag gaattgagga agacacctga    54240
ttacctctgg cttctgtatg catgtgcaca tatatatacc ttcacacata tacacactca    54300
gagaaaaaat tctgagagtg tcatatcact tgtgaagaaa gttttaaagc acttttaaaa    54360
gcaagatgaa agctatgcaa ggtatgcaag gtagtatact tttgtaatcc caggatgtgg    54420
aagaccaatg caggaggatc accctgagtt tgaggccata ggaagaccct gcctcaaaag    54480
gagggaagga gggagggagg gagagagaga aagagaaaga gaaagagaga gagaaagaga    54540
aagagaaaaa gaaagaaaga aagaaagaag gaaggaagga gaaagaaaat caaattgatt    54600
ggcatatagt tatgtgttta ttttttgagt aattgctatg taaaagcctt tagaaataca    54660 cagtttaat tatggaattg agtataaata aaacaagtac atgtttgtaa ccaataaagt    54720 ataaaatga cacataagat gtcaaagtgg tatgatggct ataatgtgga gtccatagag    54780
gaagcagtag gcagtatgag gtactgtgta aaaacacata gctttactat tgcacagaca    54840
agtgtggatt cttgttctgt gtgtggttca tggaggctct ccagtttgca gattctctgt    54900
gcatgtgtcc tgaaggattg gtcttcctgc tatgacctct ggtgttatta gcctgaactg    54960
agtcctaagg agacaggtag tggaaatgtt tgtattgcaa agacagtatg ggtagttgtt    55020
tttagaaaca ggagttcaac agaattgata gaacttgtga tcaagaagct aacagctgga    55080
ctgggatgta gctcagttga aagaacgctt gtctaacatt aagaagccct gggtaccatc    55140
actaccacag cataaactga gagtagtgac agactcatgt gtcccagcac tgggaaggta    55200
gaggtaggag gatcagaggc tgcccaggga ggttgagagt gacttacgct aggagataga    55260
tctaaaaatg aaaaggaaaa agaacttggt agctgctaga gctaccatga agagagtgga    55320
gcttaaggat tcagctgaag aatgtaaact gccttctgat gacaactgag agtcgctgag    55380
ttatttaaag tcaggaagtg aacaaagatc agtgtttcag aaagacctct gtggcaacag    55440
tattgactag aagtagcccc tcctatgtca ggtactggtt tagactgtat ttggaagtgt    55500
cctctttctt gatggccctc agacaccttt catggccact cctctgcatt tgtacccat    55560 agccacacac ttgatggttc tttattacat aaatagctcc ttataggcaa tgatagattt    55620 tatattttg ataattttaa gataaactct atgtcattgc atagaattta gtagttgtag    55680
```

```
gtactcagta aatgtatata ggatgaatac aaaagcttta gggtaacagt attttgttct   55740
tcttcccccg cattttaac  tatctcatag tagcacagac taacccataa ctgaccatga   55800
agccaaggat gaccttgaac tcctgtacct tctacctctt ccccgaaagt gctgaagtta   55860
ctggcatgtg ctgctcaccc aactaatagc aagttttct  tataaaggtg ctgatgccct   55920
ttccctgttt gtgttaattg ctgacactta aaagctcttt atcccaaccc acagtgttaa   55980
agagtttagt taaattttgt ggaaattttg tcccaaatga agtggttgat ggcaggcctg   56040
gtggctcctt cctataattc caacactcag gagacagagt caggacgatg gccaagaatt   56100
caaggccttg ggcctacaga gtagaagaga gaagaatgag gattcgaaca cctgattaaa   56160
tagataccat ttcctgctac caacctgtgc cttagctact cttctattgc cgtgacaaaa   56220 catcatacc  aaggcagctt ataaagaaa  gcatttatta ggactcacag tttcaagggt   56280
tatactccaa aaccatcatg gccgggagca ggcagcaggc aggaacatct gctgtgagga   56340
agagctgaga gctcacttct ttatccacaa ataggaggca gagagaaagc taactaggaa   56400
tagaatgagc tttgcagacc tcaaagccca cctccttccc aaacatttcc accaattggg   56460
aactaagtat tctaatctgt gagcctctgg aggcccattc ttatttaaac taccacactt   56520
tataagttaa tactacatgt gatgaggaaa ctggtatggg aattctgaaa agtagttcac   56580
aggagtggga ggggctgaac gtgagtagat gctagcatgt gtgtcaggag tgaagtgttc   56640
agagcattgc ctggtttgac ttctctccag agctgaggtg aacatgcttt gtgccaatac   56700
aaacccgtat taaagcggtg gtagttactg aaaatcagtg cagggctgtg gtctcaacac   56760
aatgtttgaa aaagaaaaca gggcatccac atcaggcagt gtacagctgc ttataattcc   56820
agtcctctgg cctctgctca catgcacata ccccccccata catacacaca tgattaaaca   56880
taatgaaaaa ttaaaaatta atgctataaa aatggaaaga gccgggcgtg gtggtgcatg   56940
cctttaatcc cagcacttgg gaggcagagg caggcggatt tctgagttcg aggccagcct   57000
gatctacaga gtgagttcca gtacagctag ggctacacag agaaaccctg tctcgaaaaa   57060
caaaaacaaa aacaaaaaca aaaaaaaaag tggaaagaaa ggttcactgt tcacaggaaa   57120
aactctgaga ggtgataatc caatcccagt ttaaaatata ctccatagtg cacacagcct   57180
ctcccatcct tggcaactga ggcctgtgag aagactcagt cctctcctgg cttccaacct   57240
tacagtgttc aaaactcttc tgcaagatcc acatggtcct accaagaccc tgaaggtcag   57300
gcatgctgat taggctgtct ctgggcctga agtgaaaggt aaacacttcc gagatctcca   57360
aagccttggg aagattctga aatgtatggg tgttggttca ggtagactct cagccttggt   57420
gaagctgccc ccggagctgt agggttatct gcagaaagtc agccaggtgc acttaccctg   57480
gaatcctctc ccattcacag acacctccct gaggctttgt ggcttcacct cactgtgcag   57540
ctagctcctg ttttacatgc ttatataatg aatggtcttg gtaaagaaga tgataaaggc   57600
aagctagagg cctttttttt cccctcttca aattttgatt ggcctttccc tactgttaca   57660
ctgtctactc aaggttttga gcatttactt tgtgtacata gtaaaagcaa agtacatatt   57720
tttaagtaga aagaaagca  tctgtggtct ttgatatagg tgcttttctt tatttaata   57780 gtaatactta ttccatgctt gttaagaaat tcattcacag cgtgttttca tagagacttt   57840
ctctatagag atatatagaa atctagacat gaggacagcc cactaaccca ctcttcagac   57900
actagctgct tctcttagag ccctgggctc tcacccttg  gaggacagcc atcctcactc   57960
atatgtgaca agcttagaca cagaataatc acagagactc cagcctcccc cacaaaccca   58020
caatgccaat atcccatatt cccaggaact tttaataagc catccactct aatactccat   58080
```

-continued

```
ctcttatctc aggcataggc cctggttttg gtttgcttca gagtactgcc tttctctac    58140 cacgcccttc ccactctttg ctgaccctcc agagatgtca tttccaaatg aaggggcttt    58200
ttggttctgt gggtgttttg tttttcagtg cagttcctta actgctattc aggggacgga    58260
gcaggcaaac cagatctcta acttctgagg cctgtgaaga gaagcatcag aacctcccag    58320
gggagctgta ggagcaggag tcaggcctag atatgactgt gagagagtgg ggaccattac    58380
cagtgtctta caaatgaggg gaaggactac cgtgctgggc cctgaaagat aaggaggacc    58440
aggcttcagg aaggtaggac acattctgct gactgtctgg gattgaggac agtaacacaa    58500
ctacttagac atactttgaa tgaaggacag acttagtgct tcagaactgt aaatccatta    58560
tatctttccc aagtcttagg ctagccaagt ttctcaacat ttatctacct catcccaaag    58620
ggttcccagg acaaatattt cttactcaaa catttgatgg gagttggaat caggttgagg    58680
aaatgcaggg gtgtagattt tagatttctg ggaatatgta tagatagcta ccttctgttg    58740
gatagaaaat gagattgtaa gttttcagt gttttttttac acgagtttgt gtgcccatgt     58800
atgcacatgt ggaggccacg ggtctacctt aggtgtcttc ttcaggaacc agccatctta    58860
tttttaagat gatctctctc cagacctcag ggctatcaac acacctcagg gatccatcct    58920
cctgactgta tgtccctagc atttgggtta ctgtaccacc atgctcaggt ctttgtgtag    58980
gtcctgggga tcacagttag gttctcatac tgcagggcaa gcactttgta acaactatc    59040 tcccctgcat atggaagtat taccactaaa ttacaacaag attttcttct attaaaatta    59100
tattttagaa gctggatata gtaatgcgtt ggggcaaaag gagggaggga aatgaagagg    59160
ataggaagag gggagggag aagggaaaga gtggaggcgg gatcagaagt ccaatgttat    59220
tcaagggcag cctgacctag ataaatccct attaaaaagt tttcagtata gaaacttctc    59280
atcaccttca ttatcagaaa agcccctaaa ttcagaacac tttttaatct taattagttg    59340
acaatttcat aaatgtatta tttatatata tgaataacat tttcctccta cctttttttc    59400
ccttcccctc tgatgattcc catcctccca accaagcccc ccttctgcat ttgtttgttg    59460
ctttaatgac ccactgagtt ccattgggct cacttccatg agtgtgacta aaagagctat    59520
ttatcagaat gtgggcaact taccagtagt gacactgatg aagaaagtgt ttccctctta    59580
cccagtaacc attaatggcc aggagctcct gggagggtg ggcgccttat gagccccttc    59640
tccaaaatgc tttcaaactg tgaccagcta tatttaatgt ttttattatg cctgtgtatc    59700
catgtgggac aagaaagctt gagagtatca tagcatgcat gtggaggtca aagaacaact    59760
gtgtaaagtc agatctcact tcccaccttc acatgggctc tggcactgaa ctcatgtcag    59820
tgacctgaga ggcactttat cctctaacac gcaccctgtg cccagcctaa aatttgacct    59880
ttgcaaggtt tagtgtgtgt tatctgactg tctgagtaag gatgacaaaa tgaaaccaaa    59940
cttatgggat aaagcttggt ggttgtatca gtacattttt attgttgtga taaaacatta    60000
tgaccaagac agcttataga agagtttatt tgggtgtata gttccagaga ggtaagagtc    60060
tgtcctgaca aggaagctgt ggcagcaagt ggcaggtatg gctacaggag caggaagcag    60120
aaagagcaaa ctagaaacag ttgaggtttt ttaataggaa agcccactcc cctaatgatg    60180
tccttcccct agcagaccac aagtcctaac cctcccctaca cagcaccacc agctggggag    60240
ttcaaatgtc tgggactgca ggggacatct cattcagacc acctcagtgg gagaatgctt    60300
gccttcatag tatgtgcaag gcctaggtt caattctagc caagaaaaga gaacatgagg    60360
aaagaaaaga aggtgggaga gagtagagaa agaagagaag aagaggaaaa aggaagggaa    60420
```

```
gggggagaca gaggaaagca gggaagcaga ggagaggaga agagaaagaa aagattaacc    60480
agcctggttt ttaatagcac ccctcccact ctcagtagtt cccaatttga gcattaagtt    60540
caagactgat agatatttct gggtgggtga ccagtgtggt cataaacatg gtgacttttg    60600
ctctccgtac aacttgtgat tatgaacttg ttagatgatc agcttcaaca ggagagggcc    60660
tcctttagtc tcaggtgccc cctccagcca ccctgggact cgcagcctct ctgtgatgag    60720
acacaggaca ttaactggta tggttctgct ttgccaaaac gtcagtccat ggttgaactc    60780
tccacaatga gaaagaagct ttgagaatca ttacatggca tcaggcaagc caggactgat    60840
ggagcctgag aaagggccag gagcatccgc aggttttggc acccagtact aactagtaaa    60900
agcacctcat aggtttcttt aaaatgcaaa cactaaggaa aatctaactt tttttttatt    60960
attaaggcca ttcattttat tttataagta ttttgcctgt atacatatgt accacatgca    61020
tacaaggtca aaagatagta ttgggtcttc gaactggagg tacagatgat tgtgagctgc    61080
catgtggatc ctcgaaattg aacctaggtc gtctacaaga gcaggaagtg ctcttaactt    61140
ctgagccatc tctccagctc cagaaaagct actcataaaa gtcaaatcta agccatgtgt    61200
ctggtgatgt acacctttaa ttgtagcaca tggaaggcgg aagtaggcgg attgttattc    61260
atccaaggcc agtcttctct taacagtgac aaaaacaaaa ccaaacccga aacctgttac    61320
tttgcacttt agagtataag tgatagagaa aagacacaga aatttttagaa tctataccct    61380 aaaatacctt atggcttata tgatactgtt gggaccatat ttacttatgg aatgcaaaaa    61440
aaaaaaaaaa aaaaaagat gggggggag ctgaaggtct cctttctatt ctgttgtaaa    61500
tctagctata aaaagagtaa gaggcatgag tgtgtctcag tggtagagca cctgcttagc    61560
ttgtgtggga ttgaatgatc ctcagcacca cagaagaagg gtggggcaat aaatttagga    61620
aaataagatg ctaatcattg actttcttga tttttttaaa aaagttatt atttttatgtt    61680 tattgtatat gtttatattt tctatgtgtg tttttgatgt gtgctggagg gatggggcc     61740 acttgctgaa cttcccaatt gttatcataa ctaccatctt tagtgaaaca gttaccatct    61800
acttagtaat tgtttcattc gaatagatac tgaacactct taatctgaaa ctaatgctca    61860
gaaagttcca ctttgccaag caagcaggat aatgtaagcc tataatttta gcactgggag    61920
ggtgaggcag aattgtgagc tcaagggcac cctgagcttt tgagatcctg tctcaaataa    61980
aattaaatta tatagatatc agattttcag aataggtgtg ttcagctgct gaataaatct    62040
aagcaaatat ccccaaagaa ccctgaaatc tgaaacgtat tagttctaag ccctatgttg    62100
tgtgtgtgtg tgtgtgtgtg tgtgtgtgtg tgtgtgtgtg tgtgtgtgtg taagatagat    62160
tctcactatg taaccctagc ttgcctggat cttgctatat agagagacca ggcatatgct    62220
atcgtgcctg ggagtcccaa acgttttaga tgaaagattt cagttgtacc attatcttcc    62280
taatgagggc tctggtctag tgaggcaggt gacattaggc cagtagtaag tattaggaat    62340
tggtgatgac ggtcaattct gagacacaca gtagatacat ctaatctacc aatacaacca    62400
atgatttaga aagaattagg ccatagttaa atttgcagtg ttttttcttct ccacaaaata    62460 atgttacttc tttcagttct tagttcaaat acagtaggaa tttttttatat tcttggtgct    62520 aaacactatt attttatagt aaagttagta agatagaaat gacgccctgt gggttgtctg    62580
gtcgtagtct gtagctgagg ccattttgct gagaagcagc gtaggctgtc actggctttg    62640
tcacccatat tttctgtatt tttgctgcag attgccttct cccagcacag caacttcatg    62700
gacctggtac agttcttcgt gactttcttc aggtaatttc tctatgctaa ttgtacacat    62760
tccatcgaga cagtccctta actgcagctt gctttgtata tccctacaaa gctgcttttc    62820
```

```
actcacagtg atgtaaattt agtctgatgt gataaaactc tccgtttgta tgattcggct   62880
ctttgcatgg ggagaggttt gggctcaagc agttattaat aatatagcta ctgctgtgag   62940
ctacatgtct taatctgtct taatcaagat atgactgtga ttttccatag ggaaaggtaa   63000
ggtttacttg caaactcctg gggttctcct tttttttatag ttttcttatt agtagggttt   63060
tttttttttt tgagaatact atgcagaaat gattgaaaag aacaaattag tcattgcata   63120
ttggtaagag aagcagcaag agccacctca cctccctctg ctctcccaa atagaaactg   63180 ctctgctgtg ctgcttctct accttcacac caatgctcgg cctgccaact cagttatctt   63240
tcctttcctt ttaagatagg gtctctcctt atagtagtta tgactgtcct ggaattctaa   63300
atagaagagg ttggctttca aatcacagat cctcctgcct ctgccttctg agtactgaa   63360 gtatggtgta tgccaccgtg ccacagctaa ctcagttatt ttttggtgtt ctataactgc   63420
cttacataca tacagaccag gtacacacaa aattcctttc cattaattta atagttatat   63480
cacaatgcat tgaccaacta aaaatcctaa aattgactta tgattctact tgctcatgtt   63540
ttaaaggaaa ggttactctt tgcttatctt aaatgtaata ttttccttt gcagttgctg   63600 tttaaatttt ccctataagt cgaccccaaa tttacatcta taatctggca aaacaaaaag   63660
acctctagtg atggttgtct cttagcttta gtctctcttg gactccattc cctccaccca   63720
taatgttcca tcctctgtcc ttaagtgtac tagtctccaa ggcctgctat gtggttgtca   63780
ttgttgtagt tacttttcta tgttgtgaca aagcaccctg acagtggcaa tttagaaagc   63840
atataatttg aggatcacag ttcctggtta gaatccatga ccatcttagc aaaggcagac   63900
aggcaggcct ggcactgaac aagtagctga gatcgtccat ctggtccaca agcataaggc   63960
agagaagcta attgggaatg gcatgggctt tggaaacctc agagtccact cttagtgata   64020
cctccttatc cttccaaaca gtattacaca ttcaaacttc aaatgtgtga gcctctgggg   64080
accactctca tttaaaccac cacagtgatc ttggcaactt cttttgtgtt cgtcccatgc   64140
cacagtcttt ccatgtattt ctccttttgc tggaactttt tccctcgaag gttcctgagg   64200
aaagaaacat agataacttt tgtatgtact tctacaactg aaagtatctt aattttgcc   64260 ctaacaaatt tttgtttgct tacttgcttg cttacttgat tctgcgtgca tgcatttatt   64320
tgtttgtttg tttgtttgtt tgtttgagac aagatctctc tttgtagttc tggctgcctc   64380
aaactcagag agattcatct gcctctgcct ccagaatgct gggataaagg catgctccac   64440
catacctaat ccaacctcac aatttttttaa gtgtgtattt atatgtgtgt gtggtatatg   64500
taaaggtgtg tgtgttcatg cacacatgtg cagagatcag aggagtcagg ttttctcatc   64560
tatcactctc tgccttatta ttttgagaca gggtctcttg ttcgatatta catatactag   64620
gtgagatagc ccaggagctt gtaggaattc tctcccattt ctaccttcca aatgtgtgct   64680
actgcatctg gctttaagca agttctggga atctgaggtc aggtccttac acctatgtag   64740
caactctgcc tactgagtca tcttactagt attcacaagg tcaaaggttg ggaccaacag   64800
ccaaggttgt cctcagatct ccacacagat gtacccacaa ttatacaaac actcaacata   64860
aacctattta cacacccaca tcacacgcac acacatacat gcacatacaa aaaatgctt   64920 tttgaaagaa gtagagaatg ctagatatgg tattacacgt atataatcca agccactctg   64980
gaagctgagg caggaggatt tcaagtttga aaccagcttg accacataat tataccatgc   65040
ctcaaaaatt gtatagagaa taagaatgaa tatgaatgag actaaagtca tatctcagtt   65100 actttttctat tgctgtggca aaacaccatg acaaaggtaa tttacagaag agattattgg   65160
```

```
ggcatatagt tcagagggt gagtccatga caattatgat atggcactga agtaatagct    65220
gagagcttaa atctggtcca caacattagg cagacagaga gctaactgga aatagccatg    65280
agattttgaa acctcaagcc ccactcctag tgatgtccca cacctcctaa tccttcccaa    65340
acagttccat cagctgggaa caagatattc aacatataag cctatggggg tcattctcat    65400
tcaaaccacc agtagtaatt attagagccc agcaaagaag gaagggatag aaagaaatga    65460
ttgatgggaa ctggggtgaa gtctgataca gagagatctt tatgtactgc agcgtagctc    65520
aggaagataa ctatggttaa ggacaattag ctaagtgatt agtagagagg attttaatat    65580
ttccaataca aagaaatgct gcaggcctga aatagggtac gtttcagtga cccagatctg    65640
attattacaa ctcatacact tgtaccaacc acataaatat gtacaataat tgtgtcagtt    65700
ttatattaaa taaaaatgtg gagcaagtta aaaaatgcct gttttaaact gatcacagtt    65760
atatgccagc ttttctttgc tgtgacaaaa taccataggg agtagtttat aaggaaagag    65820
atttcctcca gctcataatt ccagaatttt cagtctagag tcagttagtt ctatcatatt    65880
gggcccacag ctagaccaaa tacaatgatg gggagaatgt ggtaaagaaa agtatttacc    65940
tcagagtggt caggaggaac acaagacaaa atatacattt cagtcccata cctccagtga    66000
cttgcttcat ccaaacagac gccaccatcc aatagccatt aaaatacaag tcaaccagtt    66060
gattgacatc cattgatctt agtcatatcc ctaaattcaa cctctaagct ctgatgctct    66120
gggggccaag cctctattgc ataaatctct ggagcatatt tcataatatg aaatattaaa    66180
caggtctctc aggagctgtt tggtagactt agttgttttt tttttttttt tgtttaaggt    66240
ttttttggtt gggttttgtt ttgttttgtt ttgttttgtt tgtttgtttg tttgtttttt    66300
ttcgagaccg ggtttctctg tatagccctg gcggtcctgg aactcacttg tagaccaggc    66360
tggcctcgga ctcagaaatt tacctgcctc ctcctcccaa gtgctgggat taaaggtgtg    66420
cgacaccact gcctggccta gacttatttt tttaatcaga tttgagtctt tgcctctgga    66480
atcacagtag cttttcccat tcaacaccta gtttacagaa gaaagaaaac ccaattttt    66540 tttttataat cattagacaa ctagaagttt tccctcctat taagaaaaca tattaacggg    66600
ctggcgagat ggctcagtgg gtaagagcac ccgactgctc ttcccaaggt ccagagttca    66660
aatcccagca accacatggt ggctcacaac catccgtaac gagatctgac tccctcttct    66720
ggagtgtctg aagacagcta cagtgtactt acatataatc aataaataaa tcttttaaa    66780 aaaaaaaaaa aagaaaaaga aaagaaaac atattaacag tattgagaaa actgttggct    66840
taaatttgat gatttgaatt ttattttact aataaatgca tgtattgctg ggcatggcag    66900
cacatcccag cactcaggat tccgagataa gagatcataa gtccacgcta gctggaatag    66960
caaaataaaa tcttttttta aaaatatac atacatacat acatacatac atacatacat    67020
acatacacac acacacacac ttttctcagt agtacggcca attagttgac ttgtctaacg    67080
gagggaggaa gaggaggcag agagcatgct gttcagatca cgttctcttt tgcattcagt    67140
ctggaccccc agcccatagt gtggtgctgc ccacattgat tattggtatt cagttaaccc    67200
agtgtagaaa ctctctcaga gacatgccca gatgcttgcc tcataaccac tgtgtatgta    67260
tatatgctta cagaaaatat actcatcatt acacataaat ttcatccact tacctcttat    67320
gaaaagttga ttatttactg agatttttct cattctgaaa atccataaag tctaccacat    67380
tgattaaatt acttgttttt tacctgttat tgctcatgtt agaattgctt tccttatttg    67440
gggtaagctg tcgttggcca ctgtgagggg cttatcaaga agtcagaaat gggaacacct    67500
tctaggaagt caggactgga agcttagctg agccagcaag tgtttctcac actgcacttc    67560
```

```
ctgtgagcct acctgtgcgg catcaggaac tggagttggg accttgagga ttgttccctg   67620
gaggcagggg tggagtcagg cagggtgaa gctgactcac aagatggtct tgcctttcag    67680
ttgtttcctc tcgctgcttc tggtggctgc agtggtctgg aagatcaagc agagctgttg   67740
ggcatccagg cggagagagg taagcccaag tagacaaact ccacataaaa ctcattttt    67800 tccttctttc taggcagatc acttttacct gttgagtgat gactaatatt catatgagaa   67860
gcatgctgtt taacctgcat tctgtggttc cactatgtgc catcagtaga ttttaattat   67920
tcttgcataa agtgtcatta gttttgccac tgcttgattc aagtcttcct aagagtcttt   67980
cctaagaata tgagtgtaga gacaagttca gctcagtgac agagcacttg cctggcataa   68040
actgagtccc tggattctag tctcagcacc ctctaatagc acaacactag agacaaagct   68100
tctaacctgt gggtcttggg cagcaggtag gggaggggga tttaaaaaac aaaaacaaac   68160
ctctagctgt agcctgtgtc atttgttatg actaagcact agagtgggta ctagtagaca   68220
tgccatgtgg acattgagca cctctccatc ccaggcactg atccaggtgg ttctgcttta   68280
tcttcatctc caccctagga tataagggag gctacgtaac tacccatcac cacacagatg   68340
ctgaggtaca gaactgaggg gtaactagtg cctctgcctt cacagcacag gttcctaaac   68400
acgttttcta caaacacttc atttgttcta gtctgttcat ttaagaatct catgttctga   68460
ctgaatgagc tagacaactc accctagact atacattcta agaagggca acaaggcagt    68520 tttgttactg ttgagaagaa aacaaagtta tttccgtatg agttattgag atagaatagt   68580
agagatttgt ctgaatacaa aatagaaagt atataaaagt atataagtgg atcataaaga   68640
aagcaacaat caactgggaaa atatttgcag tatcatgaga gagagaaaac tagaagatga  68700
accccctcaa aaaggattt ttaaaatatg cttagactgt attcagtcag ctaataaact    68760 tttttttacct ttatttggaa tttacgaata gcactgaacc tgaccattgt aaatgcacga  68820
ggtcaggcat gacttgttcc cagtaggaag ttgtttttag ttcttgctgt ggcctgggtc   68880
ctgatggaag ttctttaccc accttatctc ctgtcctctt ggcagaggtt ctagaatagt   68940
gctgtgatgg ggtagcaact gtcttcctgt gaccctgcac ctagattatt acagaaccca   69000
gactgggttt gctgagttaa tggaaattct ttctaggttc agtagagaga tgtgctgaca   69060
catactaggc catctagttt ttcagtaatg ctcagagacc gcaataggat atgtaacagc   69120
aacaaaattt ttaacataaa atttcccttc taaaacagag tgatgattta tgtagcttca   69180
ggatcctgcc tcctagaaga tggtttgaag caaggccagt ttgtcttccc tagcataacc   69240
tcagaagacc tctcatatta ttgatggtat aggaatgaat gcccacattc tgtatttgag   69300
atgtgtgcta tagtatctca tctgacccaa catgaaaaca tttcaagcca tgtgtgcttg   69360
ggtaaggtag gagttcaaag tcatccagtg agttcaaggc cagcctgggc tgcatgagac   69420
actgtctcat aaacagacac ttgaatctca tttaaagaag acattgaaga cttgatactt   69480
tgaacaccta tcctaacgta tccacccca aatccagagt ccttcatgtt cttgtcctct    69540
gcagttccac tttcattgtg ttctcagcag cagctctctc cgaggagagt tgtctcccat   69600
cctatcagcc atctttttta ttgttgttgc tctgacaatg tctggttcag gttttaacac   69660
aaagcaagct agagtgattt taatctagca acaaaaaatat aaaaaggtaa gttttgccc   69720 ttttatatat tcaatcaaca gatatcatag cattatatcc tccactttaa cttttatttc   69780
ttactggtaa gggcttttta taaaaatata atagtgttac cacatgtaac aaaatttgat   69840
accttgtgct acctagcacc ttgtcatgtc cagtttctct cagctgtcac agaagcgaca   69900
```

```
ctgcatctga tcagtttgaa tcagagagag tgtagcatgt ctaatatcta gtattcacta    69960
ataaaatctc agtactaagc atattaataa tactatatta ttcattagca acttcttcgg    70020
gagatgcaac agatggccag ccgccccttt gcttctgtaa acgttgcctt ggaaacagat    70080
gaagaacctc ctgatctcat tgggggaagt ataaaggtga gaagtggctc aaaggtccat    70140
atagcttttc agaactcagg cctcagtttg ctaggctaca gacagcaagc gctctgtgtg    70200
tcactcctgt ctcctctcta acagttagtc agcagaagca accccgagcg accgtaaggg    70260
gctctgtgtg tggctttact tttcgagttg ttgcatgtca gattttaaca tgcaaattaa    70320
gcttgttatt cttactttgt ggcataatac tttatagttt ttatttggaa atatctaatc    70380
tgggctaggt gtgatggtgc acatctttaa tctcagttca gaggaggcag agacagaggc    70440
aggcaggatc tccttgagtt ctagaacagc tggtctacat aatgagaccc tatatgttag    70500
aaaaaaagaa agaggggtg ggggaaggca gctaacttta accattaatt gaaccaacac    70560
acacacattt tgttcagagc cccagtactc aattaaaagc caggcaggca tggtaacagt    70620
acttagggag tcagaaacag gattcccaga gtaagcagtc tgactaggct agcaggaaat    70680
ggtgagtttc aggttcagca agaggccctg cctcagtaag taaattgaag aacaactgag    70740
ggagacttgc atgtgcactt gtgcatgcac ccacacatgc acttgcacac ataccatatg    70800
tcaccatgct tagactataa aatgtagtca ctactggcag cacatgccta caatacagat    70860
gcaggagaat cactgcaaat ttgagatcag cctgggctac tggacaagat tttgtctcaa    70920
gaaaactaaa acaatacaaa agtgtactgg ggggttatt ctaatgccag tgtttatgac    70980
agcacattca gaactgacag taaaggcaat caaggactgt cagtggtggg tatatacata    71040
ggcagaggag caactgctac tagaaactgt ttatccttta aaagactaat gtatgctgca    71100
gcatagacaa acgttaagtt gtgttaagta aaagatgctg tatcattcca cttacccatc    71160
gagaataatc aaatacaaga cagagtaaaa tagtgactgc tagaggctta aaagaaaaga    71220 ccaggggtg gggaaaggga gggaaggaag tgggagaggg aggaagggag agagggaggg    71280
agggagccag actttgtggc ttacagcatc aagaggctga ggcagaaggg ttacaaattc    71340
aaggccctac tgggctacat agtgagaagt aggatttcct tgagctgtct ttctaggtca    71400
taatctctca ttgggggaag tcagggcagg gacttgaggc agaaaccatg gggaatgcta    71460
tttgctggct ccttcccagg ctcctctcta gctttgtttt ctcatttgt ttttactgtc    71520 tatgggtgtt ttacctgctt gtttttctgt gtaccatata catgcctgct acccacagag    71580
gcactgatgc ctggaactgg agttacagat ggttgcaggc tgccctgtga gtgctgggaa    71640
ctaaactcgg gtcctctaca tgagcaagtg ttcttaacca ttgagccatc tctccagcct    71700
ataaaattct tttttaaaaa taaagtctgc aacagaaaat gaatattttc tagagctgaa    71760
gcattcaatg agtggataaa gaatccattt gatgagctat ctacctttca caagctctta    71820 accctacag actcaggact tagtggctgg aagatgaatg taaaacaggt agctctctcc    71880
ataatatctg gtctgtttgt gccaggtgtg cagaactgtg caacaggtca ccatacaaac    71940
cggcgtgggc ctttcctgac actcacacag ctctcgggac agtgcccgtg gggacctctt    72000
attgacctta taagcacctg actgtgcagt gtagcaggga gttaaggtgc ttctgttttc    72060
ttcctccaga ccgttcctaa gcccattgcc ctggagccct gctttggtaa caaagccgca    72120
gtcctctctg tattcgtgag gctccctcga ggactgggag gaatccctcc tcctggtcag    72180
tcaggtgagt agacaggaga caatgacaga tattggtctg tgaaggactg agtcttagac    72240
acttcttctg gtatagaacc tgggtctggg cacagtgctt agtggtacag agctttggtg    72300
```

-continued

```
gaacaattct atagtcccca aactgtgttc tgagcactga cattcctgtc ctggggtgga   72360
agttcaggac cttcctcacg gtgcacagcg tcctcagaca ttcatgctct ggtccccttg   72420
actctattga tccctgcttt cttttttttt ttaacccctt gttcttatct caaatttagg   72480
cttttttctt cttgatacaa gctcctattc atctccatgc ctctggcttc agccatgtc   72540 ctcaaagctt gtgttgccaa gtacagagtt ctagtcatgc tccacatctt cttaaggtct   72600
tgctatgcag ccttagctgg acgagtgctc gttataggcc aggcagtggt ggtacacgcc   72660
ttatgtccta gcactgagga ggcagaggca ggcagatctc tgagttcaag accaccctgg   72720
tctacagagt aaattccagg acaaccagag ctacataggg aaaccctgtc tcaaaaaaat   72780
aaaaacaaca acaggaacaa ccccaaaaac tcattatatt gcccaggctg gcttcaaact   72840
catagttatc ctcctacttc agcctccaaa gtgctgggat tatgggtgtg acccttcatg   72900
cccagattgt cttaaatatg aggcatgaag aagtattatg aaaacataaa ggatattttg   72960
aaaattataa ttctactggg ttaatgcaga tccattttca tttcattgaa ataatgatac   73020
agcctttgga ggttagggga gcctctcctg ttttcaaact gactttgaac ttctgatcat   73080
cccgccacca ccgccacctc ctcctcctcc tcctcctccc cagtgctgag atacatcact   73140
actcctggtt tatgtggcac agaggctcaa acccagggcc tcatgcatgc taggcagaca   73200
ctctaccagc caacctaccc acagctccta gatgtgcacc gtattacaaa catttattct   73260
tcagcatgtt ttttttttttt tttcctaaaa atcatctcta caggaaacaa gtaccagtgg   73320
tgttttaggg caggaatagg aagaaaatat ttttactata tactcttttt ttttaatcat   73380
tttttagatt ttatttattt taaaatttat ttactattat taataagtac actgtagctg   73440
tcttcagaca acccagcaga gggcatcaga tctcattacg gatggttgtg agccaccacg   73500
tagttgctgg gatttgaact caggaccttt ggaagagcag tcagtgctct taactggtga   73560
gccatctctc cagcccctac tatatactct tttaaatgac ttatttgctt ttattttat   73620 gtgcattggt aatctgcctg catgtatgtc tctgagagag gatcagattc cttgaatttt   73680 gagttaccttt gtgggtgctg ggaattgaac ccaggtcctc tggaagaaca gccagtgctc   73740
ataactgctg agccgtctct gcagccccta ctatatactt tttttatagt tttgaatttt   73800 tttttcttt tgggtattgc taaggatcaa atatagatct actatttatt ttttataaca   73860
tccattagta ttttttataac ttactacata gtttgccaat tctttttatac atgtccatca   73920 aacatgtaag tcataattta tataaaccttt gtgttaaagc tggaggcaca gaaggaagat   73980
tgctacagag tgaagtctag actagccagg gctatatagt gggaccctgt tgcaaagaaa   74040
aagttctctc tttaaacaca aaggcagtat gaaaagacat accttgattc tgaagctgtg   74100
cataggaatg cctcacacag tgttctgctc aggactatac tcagatgcag tggtctgagg   74160
gacttggtgg tgtctcagcc aaaataacct ggagtttagt aggaaagtct cctttatccg   74220
tgtccagtcc tgaagggaag ccttatttat gtatgatgag tcaggaccca ttgtcttcat   74280
cttacttggc atcccccag cactgagtct ctgagttagc cttacttgga cagagtgact   74340
ctctgggcac tctggacagc atctcctgct tcaaagggc aagatcttta gaagacacag   74400
agatggagca ggtcttacat ggagatatag cagcttttcc ttcctgaccc ttgacccaat   74460
gcttctttgg aaatcctcat gaaaccctgc tcctttctgg agacccaccc cacagcaggg   74520
ttatccatgc caagcttcct gtactttctc tttttgagga agcacataca cacaaagttt   74580
tagtagctcg cacatctcac tgtgaagtag tgatactttc attgctatct tctggaaaca   74640
```

-continued

| | | | | | |
|---|---|---|---|---|---|
| ggcaggagta | ggcacacgct | cagagcatag | ctgcactctc | attcacttgc | cacccctgagg | 74700 |
| cagagcacac | gactttgtga | tctgctatgg | aggagagaga | aatgagtagt | taggtgtgta | 74760 |
| taaataagct | aacaccatca | ccccttatc | tttcactagg | gaaatgtaaa | aagaaatctg | 74820 |
| aaattatttt | gtaaaaaagt | aagctgcttc | atgacacatg | tccctcttg | tgggttcttc | 74880 |
| caaggtctcg | ctgtggccag | tgccctggtg | gacatttctc | agcagatgcc | aatagtgtac | 74940 |
| aaggagaagt | caggagctgt | aagaaaccgg | aagcagcagc | cgcctgcaca | gcctggaacc | 75000 |
| tgcatttgat | actggggcag | gaattcgccc | tcacagaggg | cgtgtggtcc | acgaagctgt | 75060 |
| ctacagggga | ggctgcaggc | aggaagcagg | cgtggggcag | aagactgggg | acccttgaag | 75120 |
| cgtccaactc | atgtgcatga | tcatgcaagc | tgttttcatg | gctcacccct | ctgtgtccag | 75180 |
| catctaacct | tttacttctg | tgtaggaaat | aatttaatta | caagtccagg | aatggtctgc | 75240 |
| tctactcatg | ggtggaggag | accagtgccg | accccgtgag | agctgaaggt | gatgctgagg | 75300 |
| tcccttgtgg | aagcctctct | tgggaatctc | aactgcagag | gagctgccct | ctgtcagcag | 75360 |
| ctctccagca | tggtcctctg | acactcctca | gatgaactgt | tctcatcgga | agcttgctgt | 75420 |
| cttttttacaa | gatgagcttt | tactctcttc | caggaagtag | cttttttttct | agctgagaat | 75480 |
| taataatggt | ctttctcttt | ggaagtcata | tcaaagtata | attgatgggg | gccttgtttt | 75540 |
| gttttgtttt | ggttttttgga | gacagggtct | cactgtgtag | tcctagctgg | cctggaactc | 75600 |
| actatgtaga | tcaggctgga | ctgaactcac | aaagatccac | ctgcctctgc | ctcacaaatg | 75660 |
| ctgggataaa | aagcatgaac | caccaggccc | agcaaagagg | gctattctaa | atgtcaaggt | 75720 |
| caatggagtt | agaatatata | taaaaaaatg | caattgataa | ttctctatag | aaacttgatt | 75780 |
| aattttaatc | cattctttcc | ttctctttct | ctcactctgt | cttacacaca | tgcacacata | 75840 |
| cacacacact | aagtgcctag | actttgaata | gatctagcaa | ttggacatta | gtaagcctaa | 75900 |
| gttttttacat | gattgcattc | ctacattctt | gtaaactttta | agtaactacc | attgcagttt | 75960 |
| gttctttttt | taaagtctaa | tttgcagcca | agaacgagta | attctcaccc | caagcaacat | 76020 |
| ctaatagga | ctgagtgacc | ccagcccagc | ctagtgtcac | tttaggcctg | acgtttgagc | 76080 |
| aaccctcggc | tcttgccaag | gcaccacaga | atgcacttgc | tcatgccctg | tgcctcttga | 76140 |
| gcagaaaaga | gcactgacaa | ctgggacacc | tggctctgtc | ttcctacagc | tgctcgcact | 76200 |
| gacctgtggg | aacctgtggg | tcatccccag | gctgaatgga | gtacacacta | gaagagggat | 76260 |
| gatgcctagc | attggggcag | catctgctca | gcacatggaa | agggacctgg | ttccatctcc | 76320 |
| cctgggcagg | agttggtcca | gcctcctccc | agacccagct | ggtggctgtg | aggaggtggg | 76380 |
| gaatgctaat | gagaatgaaa | agcacatggg | ttgatgggaa | gggacaagat | taccacgtta | 76440 |
| ggagggtgag | cagccctctg | ctatgtgccc | aggaccctgc | ctggacattg | catttcccca | 76500 |
| tttatggtgc | tccgtattct | ggcattatgc | agcagcctca | cacacctgtc | ctctccttct | 76560 |
| tcatgtccta | cagttctgct | atcacctgac | tagaatagcc | ctctaggcaa | cagtgctcaa | 76620 |
| atgtatgagt | ttggagaagt | taacaatcag | aagaacaaaa | actgtagtgt | ttcacctttta | 76680 |
| aatgcagtgt | tgaagaggga | gcctttctct | aagccctgca | ctaacccact | cctcccaaga | 76740 |
| ctcttgtgga | gtgacagttc | caagctgaac | cataaatcac | tgatgcacaa | aacactgcta | 76800 |
| gaaggctcac | ctctcaaaac | acgactcttt | gcatcactat | taaagagcag | aaagttctag | 76860 |
| aaatgatccc | agcctcatcc | cctatacagt | taggagctcc | ccacatctct | accaaaaccc | 76920 |
| agcacataag | tatctgcgtg | gtctagcctt | tcatctccgt | aacaagccag | gggactcttg | 76980 |
| gccaaaagaa | agaaagggaa | gttgcactag | ggcttgtccg | tccataagga | attcccctct | 77040 |

```
gctttgctca aaggaccaaa tttctttggc caaagaagtt gcttctatgt tagtcccata   77100
ccctgaagta atatgtacca tggctcccac ctacctgttt atgctctccc tgccccagg    77160 gaaactgttt attctttcaa aagaagcaaa cagcgttcat ttctgctcct gtaatggaga   77220
aacagccagc tcccctgcat cccttacagc caacagctcc cttcaggctt agagcagggg   77280
gaatggcagg gattaagagc tcagctcaga gccagttacc aagatggaat ggagttgtga   77340
cccagtaact gtgtcacgag agaccatgta tataaaatag tcatgacgac actgacctct   77400
tgcacttgta cataactata ctgtagtgtc cagaatgttc agacattcag ggtgtacata   77460
aacagaagag tatcataatg tattttatt aaacactaac atctgagttt cacctaatct    77520
gtttctgtgc catatactgg gtatccaagc tctgggaagt tatcctacca ggccctgatc   77580
tgttgataag gcactataca ccatgctggt gtgttctgta gccttgtgcc cattaggtaa   77640
ctgaacaatg attcagctct tagaatacct aggaagacag caagcagggt gacacacggc   77700
tgtgatctaa gcattcagaa gacagaggca ggaagaaaat tcaaaaatgg ggctggagag   77760
atggctcagt ggttaaaagc actggctgct cttggtcagg acactagttc agttcccagt   77820
acccacatgg tggctcacaa ccttctgtga ctacagttcc agataacctg acaccctcct   77880
ctggcctcct cgggtgcctg tggtggtcca cctggtgcac agacaaacac ccaatacaca   77940
caaaacaaaa gtaactcaag aatagcctgg gctacatagc aagagcctgt ctcaaaacaa   78000
acgaacctat gaagagccag gcagtctatc tatttacatg gcagtatact agagaaactc   78060
aggaagcaag agtgttcatc actgttgtaa tttcaaatgc tccttgtgat ttctggcatc   78120
tctgtggggt gaggtgttct gttactcttc acattcaaag actgtcaccc atgaacgtca   78180
gactttgcaa aggggctctc taagctgcac tgttgtggct ttgtctaaaa ttttaatgac   78240
gtttctgaga accatgttct ttttatacta aaatctgggg atgggagggc tcatttgttg   78300
ataaatagca ctattttccc acacctcagc ctcctgtccc cgtcctggtc ttccctacac   78360
agtctggaga gggctctgaa aggtccacag agtttgacag acacgaaagc aacccattgc   78420
cccgttgacc tgacctggaa gaagactgtc agcaaaagga aaataccaga atatctggaa   78480
agcttgaagt gtaagatggg atctcgttgg ggaattggat gaagaaaagc agagcgcctc   78540
tggtaggtga ctctgcagcc tgccagcgcc cgccctcttt ctacacagca gagtgtgcat   78600
ggcaaggaaa tgagtcacct ccttgggggga tggtgctgtt tttatgaaaa cctctgatcc   78660
ttggtgtcct ttaattgatc tgttcaacaa atatttacta aacacttcta agctaacatt   78720
agggcagtga ctgaggtgga aacccagctc tttagacagc tgtcatccta ggatagcttc   78780
ctggaagcag aaccaagaag ccagaaggtt cttcctaggg tggccttggc tccctgaagg   78840
aatctgaaat gctgaccctg tcacaacctc ccagcacagc tttggaatga gacatcagcc   78900
tggcctccag cagagcagag gctctggagc tccacatcct gcctgcaggg agccctcagg   78960
gtgccctcca gagtacaggg agaaactaaa ggcaataaca gaagctgctc tcagagcctg   79020
actgtgcaca aaacactagt gaagcctgct gaactaattc tgcctctgga aatcttttct   79080
ggttctttac agtttgttgt tttgtttttga tccaagctta gtttgttact atgtgtgatt   79140
tagcatctgt cgcacttgtg taaatatgga gtaagtattg taaactattt aattgctgcg   79200
attgttgggt tatacataca tttaggactg caattttttg gtattttttg tattgtaaaa   79260
taacagctaa tttcatcagg aacaagagaa ttaaggggg ctgcatttta aatgcagatg    79320
tgaagcactt gtatataaat aaaagtaaat actataatac aaagttcctt ctgaaataaa   79380
```

```
agtagatctg gtaaaaatgt gcgtgcgttt cgttctgaat gttcaatgct aattttgttt    79440
tattttatat ttacatttta gtccttattt tagcagtgag gagacaggca cagcagtgca    79500
ttctcacctt ggcagctgag gaatcccta gagtagactg caactcaaga ctcttggctt     79560
ccacactgaa aagagtttca gtttatgaag cagagtttag gaagtttagt gaggaattta    79620
aggacttctt ttaatgtttg tgtctacata tgtgggtaca tatatgacac agcatgcatg    79680
tggaaggcaa acaacacctt aatggaagtg gcctgaagaa caaactcagg acttcaatct    79740
tggcagcata aacctttacc taatgagtca tctccagtct atacgggtg tgtgtgtgaa     79800 cacatgtgca acagcacaca gtggaggtca gcacaactct gcgagtcaa ttctccctta    79860 ccttgtaaga cctagaattc cacattgccc aggctctgaa agttaggttg ggtccacact    79920
gggccatggc tgatgaaatg ttggaaaagt gataacacca aacttttgca cagaaaatat    79980
tttcatctgg ggccttccct ggagttcaca ggctaaagtg ttggaaggaa catgggtccc    80040
tgagccacca ctttcacaaa aactacctga tcaagaagaa ctattctggg tttctgttgc    80100
taaaattcct tcccagagag aaatgtaagc aatgtctgcc ccttcaaggg tcccagcaag    80160
aaaccaaggc acaattccac caaagttcac tagaaaacca gtgagtttat tgggcttccg    80220
tgcagaacat acatgagggg ttacttagag aagtgtggat actcctcccc ctaacaatcc    80280 acccctgaa aaagccttac ccagcaggga tgagggcttc cccagaccca cattgatggt     80340
gctcccattc cattttccc tggcatgcaa agagatagac agaaaatag attatatata      80400 atatacacat aaattagaaa aatagattat ataatataca cataaattat atattatata    80460
tataatatat aatacacaga tagattatat atgatatata aaacacacag aaatagggta    80520
tatataatat aaatacaca aactactcag ctattaaaaa cagtggattc atgaaattct      80580
taggcaaatg gatggaacta gaaaatattc tgagtgaggt aacccaatca caaagaaca     80640 cacatggtat gcactcactg ataagtggat attagcccag aagcttggaa tacccaagat    80700
accattcaca gaccacatga agctcaagaa aggaagatca acgtgtgggt gcttctgttc    80760
ttcttagagg aacaccctca taagtagtg gtggggggtg gggggagaca gaataggtgg     80820
tttccaggag aggaggaaaa caggaaaggg aataaataac atttgaaatg taaataaaga    80880
aaatacccaa taataaaaga aaaagaattt tgaaacagag ggtaaaaaat aatacacaaa    80940
ccaggtagat agattatata taatatatat aacacagaga tagatagata gatagataga    81000
tagatagata gatagataga tagatagata gatagatagg tcaactgctc gcccctccac    81060
taggtaacat gcagttaagg cagagctgca tacaacagat gttagggata ctcaggtgag    81120
aatctcaggc tttgctccat ccatctatgc tggggtgtaa gctgtcaaca gtttagctg     81180 ggatgatgct ttgcaagagg gcacagctga atgccctaag atggtagatg cttggctcaa    81240
aggagacact acagctctgc atcaaggcaa actaactgag atgagggcct ttatttccca    81300
gatctgtatc ctggagcatc attcacctgt tactacactg aaaacatttg gtgttggttt    81360
catggcagat gacaggcagt gagagaagta cagcagcgga ctgctagagg tggggttct    81420 gtcaggacgt gggaggctgt ttggttagta acttggaaag caacaagttt ttagctagag    81480
ggagaaaagc tggagataac tgtacttgct tgatttctta aatatcaaat tttattttat   81540
gcatatgggt attttgcttg catgtatggc tatacactac atgcttgtgg tgcccacaga    81600
gaccagagga agtagtgtga gcctctgaaa ctgaagttac agacattacg acttgagtgc    81660
ctgaaactga accttggtcc tctggaagaa cagccagggc tcctaaccac tgagctatct    81720
ctccagccct gacagaacat catgtactcc aggctggtct caaatttgct ttatagccaa    81780
```

```
gaacggtctt aaattctgat cctcctgttc tctcaagtag tggggttaca ggtctacact   81840
gccgttttct tgagcaaatc attacaaatt gagttctaag ccaggtgtaa tagttcatgt   81900
agtaacaatc tggaattttg gtctcttaaa aaaacaaata ttataagaat gtattttcat   81960
tttaatccca ggtgtatggc atatatcgaa ctgctttgga ctgactacag cagctatgat   82020
tttttcttgt tctagcagag gtatggtttt gccagctaca gatagtttct gtgattgtgt   82080
gacatttgga attctggaaa cttttcagat ggtatataaa tattagagcc ccaataggca   82140
gagttgatga ttgttggtca ttcaggggta ttggttgtgg ttagtagtct tgcttgaaga   82200
agaaacaaga acaaattaga ttcagagatc tctatatctc tctctatctt cctttctgtc   82260
ctatctagta ataggggta aaaccaggat gataaagggt tgggggaacc cacaaagtaa   82320
caaagactgg ctacaagtgg cacccaactt ggaactcaaa attgccatag aggaagcagc   82380
aggggatgaa ggaatggatt gtggctgttg ttgctgggat attcctcact ttgctcccag   82440
agggattttt tctgaggttt tgttgttttg ctttgctttg ctttggtttt cttctacata   82500
ttctgttttt taagtaagtt gaaataatag ccgagaagct ggaaaagttt ggtgtggaaa   82560
tggagcagcc tgagaaacaa acaatgtatg aaatgggaaa actaaagggg ccactcttct   82620
ctcttttctg aaaggcttgc agacttggtg gtgcacctgg agagtttatg gatggagatg   82680
gaagctctta ggagacaaga agcatggaaa aagagaacaa aggctcagtc ccagtgactg   82740
aagagagcag gagttttcca agaaggtgc atggagggc cactggtcag aaaaaaaagg   82800
ctgaaaaata ccaaaggaca atgtgctgaa atagcccatt tcaagagaaa gggttcatct   82860
caaaccagca ttctgacaga gtggaaggag gggtggctca gggttatgag atcaccatca   82920
gcttttccag ttttcccata tagcatatgc ctgctaatgg tatgaacaa gagtaaggca   82980 aaataggatg gtgtcctata gaatgatag ctctaaggtg ttttttaaaag gccttgattt   83040 catatggaat gcactctcct tatgtggaac ggatattaaa taaccggggt acacaaacta   83100
gaatcccttc ccaagattgg aagggattgg taacagctgt actagagact gtcagccgtt   83160
gcaatggtta acatgctgga ggaaagaagc tgtgaacatt gaacagtaaa acagagcaag   83220
gggtattaat atagtgaacg aacagctgct aggtgaaggg cggtactcta gtgtacaagc   83280
acagactcgg tgtcatgaaa ctactataga acaaggttgc ctcagtggct ataacacctt   83340
gggacaaagg aggagccagg aaaaagtcca gttcatttac aaagattata taaggctctg   83400
gagaagcctt cactgatttt ttttttttaca aagattagtc tcagctatga acaaagccat   83460
atcagaccct gacacaaggc aggtgttgat agagaccttg gtgtatgaca atgcaaatac   83520
caaatataaa aatgtcatta gacttttaaa ggcacaagta atgcctatgg atgagtggat   83580
aagggataag accaatatta gttctaatgt gtactgtgct aatatcattg atcaagctat   83640
agctagagat ctctgatgtc aaaatgcctt gtgcttcagt tgcagcaaat acagtaattt   83700
gcaaggagtc attgtggcca aaactaaagg tctcagatct caaaatgcct gatgctttgt   83760
gggaaatagg gtcatttgca acaaaaatgt gaacaagaca tctttaaggg caatggtttt   83820
tctaaatata aaccagaaag acggcctagg cttccaaggt tgtgctggcg atgtggccag   83880
ggttgccact ggaccaatga gtgtaggtcc aaaagagata ttcaaggtaa cgtattacca   83940
tcatgaaatg gtcttggggg cctatcttga ggccctgcag caaagagtat gagccattcc   84000
aaccagagag tggcatggag actcaaaacc ttcactgggc actggagatt taatgcacac   84060
tagctattgc aggcagcatg gctctagact tggccacaga taaacatctt gctctatccc   84120
```

```
ccaaaattca aagttataac atagctactg gagtgtatgg tcttttcccc tcagggacag    84180
taaggataat cttgggaagg agtggattga cttcctaaga attcactgtg catcaggaag    84240
tatagatgaa tatttcaaag gagaaattaa aattgtggca tatgtaaagg tagagctgca    84300
acttaacaca ggcgataggg ttgctcagct gctgctgttt ccctatatca aaggcaaagc    84360
aactgcagca gaaagaggag aggcctgaaa accttgggca ctgacacaaa aattgcttat    84420
ttcattgaaa atgtctgttt ataacttccc actatacagc acaacaggag ggggcttaaa    84480
acataatggg gaaaatgtca caattctgca attttttgttt ccttaaaaaa aacacacaca    84540
cagaatttta ataatgtgtt ctcatcttaa tcccgggtgt gggaattagg gctgctttgg    84600
accattccca gcagctgact atgatttgcc tcatgctcta gcagaagtat gattttttgcc   84660 acctgcagat agtttctggg attgtgtgac atttggaatt ttgggaactt ttctgaaggt    84720
atataaatgc taaggccctg gtggggaggg ttggtggttg gtggtcattc agggggtgg     84780 ttgtggttag tggtcttgct caaagaacaa acaagaaagt catttgattc agatgtatct    84840
ttcttccttc ccccactctt tctctcctcc ccccggcacc ctgccccctg cccgacctc     84900 taccctcctt tttctatcta gtgacaagga tgaaaccagg gggataaagg gtgggaaaaa    84960
gaagagccca caaagtaact caggttggct acaagttcat gccaagaatc ctaggacctt    85020
gttgtttaaa ggcttgtttt attttgtgaa catgaatgtt aaatgtacat acatgttaag    85080
tgtatgtatg tacaccatat gcatgcatac agaatccaga agaaagtaca ttataccctg    85140
gaatggaact tagagttgtg agacagcatg aggatgctgg gaactgaacc cagtttctcc    85200
acaagaggag tagttgctct tcactgctta acctttcctc cagccccaat cctagcattt    85260
tggaggctga tgtaggaaga ttatcccaag tgtgaggtca tcttgggctc cataataagt    85320
ttaagaccaa tctcagctcc agagtaggac cctgcctcaa aaacacacag gtggaaagat    85380
gggtcggcaa tgaagagcac acactgtgcc tccaggggac ccaagcttgg gtccaagcac    85440
ccttgttggg cagctcacaa ctgcctgtaa ctccacctcc agaggatcct aagccacctt    85500
ctggcttggc ttcatggagg gaacaggtat gtgggtatct gagtgtgacg aatgagcagc    85560
aagtgagtct cgctgtggct agcacaaagt atgggctgaa gagcaggagg acagctgaaa    85620
agtggccttt cctggtgact aagttggtct gagcagctga gtcagtttct tcctggctgc    85680
ttggctggtc tcagtgctta taagctgctc acttgtaagt cttttcctag gagcccagct    85740
tgtctagggg ttgtctttgc aactggcctt gtctgacagt gactttcagc agtcttagct    85800
gcttatatac acagtcttag gaaagaaggc tggtgaatct gatccatttc aggaactttc    85860
tgaagctatt ctgaatttac tttacaagct tacctgcagg atagaggatc tcagctcttt    85920
ataaacatcc tgtcctaaaa caccctgttg ttcctcttct cttttacatc ctgtgtcttg    85980
agaagtttgc ctccaggatg gaagttgttc aattcagagg acactgttgc acaagctccc    86040
agcacccaca tgtgagctca gtgctctcct tggctctagc tctgccctat gaggtttttt    86100
attttgtcat cataatcttt tcctatatcc ttccttgttc tgggaactca tctggttcat    86160
ttttttggca ttttgagaaa agctctcact atacaaatca ggctgcctcc aaatcatctt    86220
tttgccttaa cctcctcagt accaagatca cgagtggatc ttaacacttg actgactcgt    86280
ttaagtgtga ggaaatgtgg accaataaga gagcccagga aagcccagga gaatctgtag    86340
ccccatggct gttgtgtcag aacccagagt tttgtcaaca gaatttggtt cctaattttct   86400 ccactttata aaaacgagtg agagaaacag gaacctattc agatctggcg tctgagcaat    86460
cagtgggtga acatctagag atctgttctg catctcctcg ccagctggca gagcatgcgt    86520
```

```
aaggcgggag ggaacaaggg caatcactca ctctggggct caggcttgcc ccttgggtca   86580
ggtgtttctg agagacgtga tgtctgcttc tcttgttacc atccctcatc ctctcccctc   86640
cttctgtccc ctacttacca atttcactgg ccagtgtcca tatttcctgc aaaagcgatt   86700
tggtttaatg agcttgacta tgcccgactc ctttagggag ggtggggaaa gggcaacgag   86760
ggcagtaagt ggtttccaca accactttgc acccggctgc tgggcccaa gccagaggaa    86820 cgtgcatgag ccatgaagtt tccactgata aatccacaga tgcttctagc acctgccttt   86880
ctgactcagc ctcaccgtgc cgcctgccag ctgtgaaatc agtgccaaca acaggtaacc   86940
gagacccagg cgcagggcca ggacagctgt ctgacacttc cagacaggat gtggaggctg   87000
acagttgtga tggagaggag atggggagga cagagacggg ctcagcttta agacaccgag   87060
ccacagagca ccaaacaaaa gccagggcct tctgaggtag aagtaacaga aaccaaacag   87120
gcaattctac tagtttcctg ggactgtttg ctgcatttgc caatcttggt agttttaaaa   87180
aacaaaaaca gtttgttctc agcactggca gagctttcct cctctggagg ctccaggggt   87240
ccagactctc ctctgtggta cactggcttc agacatatct cttgcctatg gctgcctcac   87300
tctaaactct gcctgtcctt gaattacctc tctctgcact ggctttataa aggaaacatg   87360
agattgtgtt tagggcctgt ttgggtgacc tcctcaggat ctataacata atcacatctc   87420
taccgtatga agtgacgctt ccgtcccagt gtgtaataca tttgccggcg cctgtcctta   87480
ggacagtgac caccaccaac tgtggaactt gactatgtcc acgtcatctt cctactagct   87540
ttagaaggct tatacccaca ctttctatcc agaattgtat ttttatttag aatcattcct   87600
acttttaaaa aagtctctgt ggttaaaagc attgcagagg gcttgggttt tggtccccag   87660
gacccacatc aagtggctca cagtgtcctg gaactcttgt tccaatacccc tcttctggtc   87720 tccataggca ctacatacat atggcacata tatgtatact caggcacacg tgtaaatttt   87780
aatgtctact ttttatgcta aatatcaaag tcactcgagc agtggagttg agcacactca   87840
cataaggaaa tcatcagaca gacacttcat cctgtgttgg agccactttg tggctggagt   87900
aagcagggca gagtgatgtt ttcattactc tctggcccca gcaccccctg cctctcccca   87960
cccattcgtc catgcaggtg gggaagagaa ttctctttgt gaaattggaa gtttggaccc   88020
agcttcactc ttactctgcc cagtacctcc tgtgagaaac cctcctatcc caggtgacct   88080
gctggctgtg actctcctca gcaaaaggcc cgtgacccac actgcgccac taatgtatca   88140 tcccccaaatg ctgaaaagga agcgtgtctt cctctctctc tcttttttctt ttggtctttt   88200 tgagacagag tttctctgta tagccctggc tgtcctggaa ctcactttgt agaccaggct   88260
ggcctcgaac tcagaactcc gcctgcctct gcctcccgag tgctgggatt aaaggcgtgc   88320
atcaccactg cccggctgcg tgtctttctc ttagcggtct ctgtggagat gctgagtatg   88380
aagctcatcc tacccaccct tcagtggggc cttttctagc tactgagcag ctgtgtgagg   88440
actcgtgatc acaaggtcct ttgaaccctt gagacagatg tgcctgagcc cagtttgacc   88500
tgacaaaagc ctagagctca ctgataatgc cagcaaacac catctttgag tttgcaaagg   88560
aatcgcaaca catgcattca gtttccgttg ctggctgctg ctccagagat ggctatattc   88620
attctcaggt actcagactc aagagtagtt ctggccacac aggtctccac atttcgaggt   88680
caaatgacag aaaaccaggt tggtctcagt gcacatgggt ttattgagcc actgcaggtg   88740
ctggggaaac catggcaggg agatcctggg aagccagtgg ggtgctgagc aggagggacc   88800
tcagtctctc cttaatgtct acacactgtg tcataggtga caagccacgt cagtgctgtg   88860
```

-continued

| | |
|---|---|
| acacgggtaa gcttaatggt gagtaatggc taactgggag ggtatttagg cagccttgtc | 88920 |
| tgtcagcctg ttcatatgat ctccttagtg ccttgtcatc ttggaaaagg acagttccaa | 88980 |
| attctaggag cggggggctag tctctgtcct gctctgtaag cccaggggac ccaatgaggc | 89040 |
| ctcatctatg ggtgctcagc tctaggatgg ggaagaaaat ggacaagatg cctactgacg | 89100 |
| ggaacacagg cttttcagtc agaccctagc ctccagcccc caatccagag acagccaca | 89160 |
| cagggggtcca ggcctgcaaa gggcagcaga cctgagggca agggagtttc agctcagtga | 89220 |
| gcagtcatcg ggagacatgg cagtcagctg tgtcgtccac ggttcatgtt cctaatcaga | 89280 |
| gcagggcctg gagagccagg gcagtgagtg catacagcca ggacaccttg ggcgttagga | 89340 |
| caaaacaagg actgtttctg cctccagctc ttctcaggcc actcgtgcct tgcctaggaa | 89400 |
| gggtaagaga gcacagatgg gaaggattcg gaaactgtca actccctgtc ctctccccat | 89460 |
| acctacccgc gggaaacagc acccagcagt ctggtcctgc agaactgatg gctgcaagct | 89520 |
| gtcaaaggct tgtatggcac catctgcgga gtgcagagat ccagagaagg cttggccagg | 89580 |
| aaaccctaga aactaccccca ctcccttggg acaaaaaata agacacctg gaacctgcaa | 89640 |
| ggcatggcct gagatggaag gtcactgtgc taagaatgac ccacaaactg ctagtgaggt | 89700 |
| tgacaagggc tgccccctct cccttttacag gtgaacacaa tcggattaa taagagttta | 89760 |
| actctcagct actaagtggc agagacaggc ttcaaacaga ccccccagaaa tctggaactg | 89820 |
| agccattcca cccagaggca agaacagcag aggtaagttg ggcacacatg gaagaaaggg | 89880 |
| ccaccccatt agtgtcaaaa gggaggccaa cttcaggcca ttggacacgt tttaacgctg | 89940 |
| acttccaccc atgtaccatg gcatgtgcac actgtccatc gcccacacca aacatgatgc | 90000 |
| gacgtaaata agacccacgg gccaggcagc ttggattggg ccacagacat | 90050 |

<210> SEQ ID NO 6
<211> LENGTH: 226
<212> TYPE: DNA
<213> ORGANISM: Mus musculus

<400> SEQUENCE: 6

| | |
|---|---|
| agcgctattc agctgtgcct cctttgctgt cttggctcct cctggagcac tatatgcacc | 60 |
| catgtcctta ccaggccttt cacagacgct gccattgaga gggttgatgc aggttgcagc | 120 |
| ctttaatccc cgagtactag gctctgacaa gatcccacag aagccagcat cactgggctc | 180 |
| agatggcatc cactgcagca aactatttgt gaatggagac atatcc | 226 |

<210> SEQ ID NO 7
<211> LENGTH: 221
<212> TYPE: DNA
<213> ORGANISM: Mus musculus

<400> SEQUENCE: 7

| | |
|---|---|
| agcgctattc agctgtgcct cctttgctgt cttggctcct cctggagcac tatatgcacc | 60 |
| catgtcctta ccaggccttt cacagaccat tgagagggtt gatgcaggtt gcagccttta | 120 |
| atccccgagt actaggctct gacaagatcc cacagaagcc agcatcactg ggctcagatg | 180 |
| gcatccactg cagcaaacta tttgtgaatg gagacatatc c | 221 |

<210> SEQ ID NO 8
<211> LENGTH: 2419
<212> TYPE: DNA
<213> ORGANISM: Mus musculus

<400> SEQUENCE: 8

-continued

| | |
|---|---|
| gaattccggg cgaagggag ccggcgtgcg gggtgtgtat gtgttcgctg ggcgccggct | 60 |
| cagccccagg aagatggtgg cggtggcggc ggcggcggcg actgaggcgc ggctgagggg | 120 |
| gagcacgagg acgacagcag cgcctgcggg caggaagggc aggcagcacc gaccctgcac | 180 |
| cgcgacaggg gcctggaggc cgggaccgcg cgcccggctg tgtctcccgc gggtgctgtc | 240 |
| gcgggcgctg ccccgccgc cgctgctgcc gctgctcttt tcgctgctgc tgctgccgct | 300 |
| gccccgggag gccgaggccg ctgcggtggc ggcggcggtg tccggctcgg ccgcagccga | 360 |
| ggccaaggaa tgtgaccggc cgtgtgtcaa cggcggccgc tgcaaccctg gcaccggcca | 420 |
| gtgcgtctgc cccacgggct gggtgggcga gcaatgccag cactgcgggg gccgcttcag | 480 |
| gacatctgtc tcacgcctat aatcacagct gttcggaagg tgaggctgga ggaacagttc | 540 |
| gaggcaagct tcggctacag aataagttca agagtaacct ggggcaactt gggcttgtct | 600 |
| ccaaaaccaa aatgagcgaa aaggagcaag ctagagtctt ttgggaaaat tttagctgac | 660 |
| taattttca ccgagaacta actggctctt ctggatttgt aacagatgga cctgggaatt | 720 |
| ataaatataa gacgaagtgc acatggctca ttgaaggaca gccaaataga ataatgagac | 780 |
| ttcgcttcaa ccattttgct acagaatgta gctgggacca tttatatgtt tatgatgggg | 840 |
| actcaatcta cgcacctctg attgctgcct ttagtggcct cattgttcct gaaagagatg | 900 |
| gcaatgagac ggctcctgag gtcactgtca cttcaggtta tgcactgctg catttttca | 960 |
| gtgatgctgc ttataatctg actggattta atatcactta aattttgac atgtgtccga | 1020 |
| ataattgctc aggccgagga gagtgtaaga gcagtaacag cagcagcgct gttgagtgtg | 1080 |
| aatgttctga aaactggaaa ggggagtcgt gtgacattcc tcactgtaca gacaactgtg | 1140 |
| gctttcctca ccgaggcatc tgtaatgcaa gcgataccag agggtgctcc tgctttcctc | 1200 |
| actggcaggg tcctggatgt tcaattcctg tgccagctaa ccagtctttt tggactcgag | 1260 |
| aagaatattc tgatttaaag cttcccagag cctctcataa agctgtggtc aatggaaata | 1320 |
| taatgtgggt tgttggcgga tatatgttca accattcaga ttacagcatg gttttagcgt | 1380 |
| atgacctgac ttctagggaa tggcttccac taaaccattc tgtgaacagt gtggttgtaa | 1440 |
| gatatggtca ttctttggca ttacataagg ataaaatcta catgtatgga ggaaaaattg | 1500 |
| attcaacagg gaacgtgacc aatgagctga gagtatttca tattcataat gaatcatggg | 1560 |
| tattgttaac tccgaaagct aaggatcagt atgcagtggt tggacactca gcacacattg | 1620 |
| ttacactggc atctggccgt gtggtcatgt tggtcatctt cggtcattgc ccactctatg | 1680 |
| gatatataag cgttgtgcag gaatatgact tggaaaagaa cacatggagt atattacata | 1740 |
| ctcagggtgc tcttgtgcaa gggggttatg gccacagtag tgtttatgat gacaggacca | 1800 |
| aggctctgta cgttcatggt ggctacaagg cttttcagcgc caacaaatac cggcttgcag | 1860 |
| atgacctcta cagatacgat gtggatactc agatgtggac cattcttaag gacagccgat | 1920 |
| ttttccgtta cttgcataca gctgtgatag tgagtggaac catgctggtg tttggaggga | 1980 |
| acacacacaa tgacacttcc atgagccacg gtgccaaatg cttctcctcg gacttcatgg | 2040 |
| cttatgacat tgcttgtgac cgatggtcag tgcttcccag acctgagctc catcatgatg | 2100 |
| tcaacagatt tggccattca gcagtcttgt acaacagcac catgtatgtg ttcggcggct | 2160 |
| tcaacagcct cctcctcagt gacgtcttgg tctttacctc ggagcagtgc gatgcacacc | 2220 |
| gcagtgaagc tgcttgtgtg gcagcaggac ctggtatccg gtgtctgtgg gacacacagt | 2280 |
| cgtctcgatg tacctcctgg gagttggcaa ctgaagaaca agcagaaaag ttaaaatcag | 2340 |

-continued

```
agtgttttc taaaagaacc cttgaccatg acagatgtga ccagcacaca gattgttaca    2400
gctgcacagc caataccaa                                                 2419
```

<210> SEQ ID NO 9
<211> LENGTH: 549
<212> TYPE: PRT
<213> ORGANISM: Mus musculus
<220> FEATURE:
<221> NAME/KEY: SITE
<222> LOCATION: 549
<223> OTHER INFORMATION: Xaa=unknown amino acid

<400> SEQUENCE: 9

```
Met Arg Leu Arg Phe Asn His Phe Ala Thr Glu Cys Ser Trp Asp His
  1               5                  10                  15

Leu Tyr Val Tyr Asp Gly Asp Ser Ile Tyr Ala Pro Leu Ile Ala Ala
                 20                  25                  30

Phe Ser Gly Leu Ile Val Pro Glu Arg Asp Gly Asn Glu Thr Ala Pro
             35                  40                  45

Glu Val Thr Val Thr Ser Gly Tyr Ala Leu Leu His Phe Phe Ser Asp
 50                  55                  60

Ala Ala Tyr Asn Leu Thr Gly Phe Asn Ile Thr Tyr Asn Phe Asp Met
 65                  70                  75                  80

Cys Pro Asn Asn Cys Ser Gly Arg Gly Glu Cys Lys Ser Ser Asn Ser
                 85                  90                  95

Ser Ser Ala Val Glu Cys Glu Cys Ser Glu Asn Trp Lys Gly Glu Ser
            100                 105                 110

Cys Asp Ile Pro His Cys Thr Asp Asn Cys Gly Phe Pro His Arg Gly
            115                 120                 125

Ile Cys Asn Ala Ser Asp Thr Arg Gly Cys Ser Cys Phe Pro His Trp
130                 135                 140

Gln Gly Pro Gly Cys Ser Ile Pro Val Pro Ala Asn Gln Ser Phe Trp
145                 150                 155                 160

Thr Arg Glu Glu Tyr Ser Asp Leu Lys Leu Pro Arg Ala Ser His Lys
                165                 170                 175

Ala Val Val Asn Gly Asn Ile Met Trp Val Val Gly Gly Tyr Met Phe
            180                 185                 190

Asn His Ser Asp Tyr Ser Met Val Leu Ala Tyr Asp Leu Thr Ser Arg
            195                 200                 205

Glu Trp Leu Pro Leu Asn His Ser Val Asn Ser Val Val Arg Tyr
            210                 215                 220

Gly His Ser Leu Ala Leu His Lys Asp Lys Ile Tyr Met Tyr Gly Gly
225                 230                 235                 240

Lys Ile Asp Ser Thr Gly Asn Val Thr Asn Glu Leu Arg Val Phe His
                245                 250                 255

Ile His Asn Glu Ser Trp Val Leu Leu Thr Pro Lys Ala Lys Asp Gln
            260                 265                 270

Tyr Ala Val Val Gly His Ser Ala His Ile Val Thr Leu Ala Ser Gly
            275                 280                 285

Arg Val Val Met Leu Val Ile Phe Gly His Cys Pro Leu Tyr Gly Tyr
        290                 295                 300

Ile Ser Val Val Gln Glu Tyr Asp Leu Glu Lys Asn Thr Trp Ser Ile
305                 310                 315                 320

Leu His Thr Gln Gly Ala Leu Val Gln Gly Gly Tyr Gly His Ser Ser
                325                 330                 335
```

-continued

```
Val Tyr Asp Asp Arg Thr Lys Ala Leu Tyr Val His Gly Gly Tyr Lys
            340                 345                 350

Ala Phe Ser Ala Asn Lys Tyr Arg Leu Ala Asp Asp Leu Tyr Arg Tyr
        355                 360                 365

Asp Val Asp Thr Gln Met Trp Thr Ile Leu Lys Asp Ser Arg Phe Phe
    370                 375                 380

Arg Tyr Leu His Thr Ala Val Ile Val Ser Gly Thr Met Leu Val Phe
385                 390                 395                 400

Gly Gly Asn Thr His Asn Asp Thr Ser Met Ser His Gly Ala Lys Cys
                405                 410                 415

Phe Ser Ser Asp Phe Met Ala Tyr Asp Ile Ala Cys Asp Arg Trp Ser
            420                 425                 430

Val Leu Pro Arg Pro Glu Leu His His Asp Val Asn Arg Phe Gly His
        435                 440                 445

Ser Ala Val Leu Tyr Asn Ser Thr Met Tyr Val Phe Gly Gly Phe Asn
    450                 455                 460

Ser Leu Leu Leu Ser Asp Val Leu Val Phe Thr Ser Glu Gln Cys Asp
465                 470                 475                 480

Ala His Arg Ser Glu Ala Ala Cys Val Ala Ala Gly Pro Gly Ile Arg
                485                 490                 495

Cys Leu Trp Asp Thr Gln Ser Ser Arg Cys Thr Ser Trp Glu Leu Ala
            500                 505                 510

Thr Glu Glu Gln Ala Glu Lys Leu Lys Ser Glu Cys Phe Ser Lys Arg
        515                 520                 525

Thr Leu Asp His Asp Arg Cys Asp Gln His Thr Asp Cys Tyr Ser Cys
    530                 535                 540

Thr Ala Asn Thr Xaa
545
```

<210> SEQ ID NO 10
<211> LENGTH: 1051
<212> TYPE: DNA
<213> ORGANISM: Mus musculus

<400> SEQUENCE: 10

| | | |
|---|---|---|
| gaattccgga aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa aaaaaaaaaa aaaaaaaaaa | 120 |
| aaaaaaaaaa aaaaaaaagg agggcgaagg ggagccggcg tgcggggtgt gtatgtgttc | 180 |
| gctgggcgcc ggctcagccc caggaagatg gtggcggtgg cggcggcggc ggcgactgag | 240 |
| gcgcggctga gggggagcac gacgacgaca gcagcgcctg cgggcaggaa gggcaggcag | 300 |
| caccgaccct gcaccgcgac aggggcctgg aggccgggac cgcgcgcccg gctgtgtctc | 360 |
| ccgcgggtgc tgtcgcgggc gctgcccccg ccgccgctgc tgccgctgct cttttcgctg | 420 |
| ctgctgctgc cgctgccccg ggaggccgag gccgctgcgg tggcggcggc ggtgtccggc | 480 |
| tcggccgcag ccgaggccaa ggaatgtgac cggccgtgtg tcaacggcgg ccgctgcaac | 540 |
| cctggcaccg gccagtgcgt ctgccccacg ggctgggtgg gcgagcaatg ccagcactgc | 600 |
| gggggccgct tcagactaac tggctcttct ggatttgtaa cagatggacc tgggaattat | 660 |
| aaatataaga cgaagtgcac atggctcatt gaaggacagc caaatagaat aatgagactt | 720 |
| cgcttcaacc attttgctac agaatgtagc tgggaccatt tatatgttta tgatggggac | 780 |
| tcaatctacg cacctctgat tgctgccttt agtggcctca ttgttcctga aagagatggc | 840 |
| aatgagacgg ctcctgaggt cactgtcact tcaggttatg cactgctgca ttttttcagt | 900 |

```
gatgctgctt ataatctgac tggatttaat atcacttaca attttgacat gtgtccgaat      960
aattgctcag gccgaggaga gtgtaagagc agtaacagca gcagcgctgt tgagtgtgaa     1020
tgttctgaaa actggaaagg ggccggaatt c                                    1051
```

<210> SEQ ID NO 11
<211> LENGTH: 351
<212> TYPE: PRT
<213> ORGANISM: Mus musculus
<220> FEATURE:
<221> NAME/KEY: SITE
<222> LOCATION: 351
<223> OTHER INFORMATION: Xaa=unknown amino acid

<400> SEQUENCE: 11

```
Glu Phe Arg Lys Lys Lys Lys Lys Lys Lys Lys Lys Lys Lys Lys Lys
 1               5                  10                  15
Lys Lys Lys Lys Lys Lys Lys Lys Lys Lys Lys Lys Lys Lys Lys Lys
                20                  25                  30
Lys Lys Lys Lys Lys Lys Lys Lys Lys Lys Lys Lys Lys Gly Gly
                35                  40                  45
Arg Arg Gly Ala Gly Val Arg Gly Val Tyr Val Phe Ala Gly Arg Arg
50                  55                  60
Leu Ser Pro Arg Lys Met Val Ala Val Ala Ala Ala Ala Thr Glu
65                  70                  75                  80
Ala Arg Leu Arg Gly Ser Thr Thr Thr Ala Ala Pro Ala Gly Arg
                85                  90                  95
Lys Gly Arg Gln His Arg Pro Cys Thr Ala Thr Gly Ala Trp Arg Pro
                100                 105                 110
Gly Pro Arg Ala Arg Leu Cys Leu Pro Arg Val Leu Ser Arg Ala Leu
                115                 120                 125
Pro Pro Pro Leu Leu Pro Leu Leu Phe Ser Leu Leu Leu Pro
130                 135                 140
Leu Pro Arg Glu Ala Glu Ala Ala Ala Val Ala Ala Val Ser Gly
145                 150                 155                 160
Ser Ala Ala Glu Ala Lys Glu Cys Asp Arg Pro Cys Val Asn Gly
                165                 170                 175
Gly Arg Cys Asn Pro Gly Thr Gly Gln Cys Val Cys Pro Thr Gly Trp
                180                 185                 190
Val Gly Glu Gln Cys Gln His Cys Gly Gly Arg Phe Arg Leu Thr Gly
                195                 200                 205
Ser Ser Gly Phe Val Thr Asp Gly Pro Gly Asn Tyr Lys Tyr Lys Thr
210                 215                 220
Lys Cys Thr Trp Leu Ile Glu Gly Gln Pro Asn Arg Ile Met Arg Leu
225                 230                 235                 240
Arg Phe Asn His Phe Ala Thr Glu Cys Ser Trp Asp His Leu Tyr Val
                245                 250                 255
Tyr Asp Gly Asp Ser Ile Tyr Ala Pro Leu Ile Ala Ala Phe Ser Gly
                260                 265                 270
Leu Ile Val Pro Glu Arg Asp Gly Asn Glu Thr Ala Pro Glu Val Thr
                275                 280                 285
Val Thr Ser Gly Tyr Ala Leu Leu His Phe Phe Ser Asp Ala Ala Tyr
                290                 295                 300
Asn Leu Thr Gly Phe Asn Ile Thr Tyr Asn Phe Asp Met Cys Pro Asn
305                 310                 315                 320
```

-continued

```
Asn Cys Ser Gly Arg Gly Glu Cys Lys Ser Asn Ser Ser Ala
            325                 330                 335

Val Glu Cys Glu Cys Ser Glu Asn Trp Lys Gly Ala Gly Ile Xaa
            340                 345                 350
```

<210> SEQ ID NO 12
<211> LENGTH: 6370
<212> TYPE: DNA
<213> ORGANISM: Homo sapiens

<400> SEQUENCE: 12

| | | | | | |
|---|---|---|---|---|---|
| atgtactact | gtaacaagaa | gaccagctgc | aggagctgtg | ccctggacca | gaactgccag | 60 |
| tgggagcccc | ggaatcagga | gtgcattgcc | ctgcccgaaa | atatctgtgg | cattggctgg | 120 |
| catttggttg | gaaactcatg | tttgaaaatt | actactgcca | aggagaatta | tgacaatgct | 180 |
| aaattgttct | gtaggaacca | caatgccctt | tggcttctc | ttacaaccca | gaagaagta | 240 |
| gaatttgtcc | ttaagcagct | gcgaataatg | cagtcatctc | agagcatgtc | caagctcacc | 300 |
| ttaaccccat | gggtcgggcc | ttcgggaagg | tycaatgtgt | cctactkggt | gctggggaag | 360 |
| gatatgktcc | ccattttaca | aatagtttta | ctacagtggg | atgsccgtct | tgaggcccag | 420 |
| tgttgcttgg | rattctgtgg | gaattttatt | caggaaccca | gttacttcgg | ggactgaagg | 480 |
| ctgcaacctg | cattcaaccc | actymaatgg | tagtgtctgt | gaaaggcctg | caaaccacag | 540 |
| tgctaaggca | gtgccggaca | ccatgtgcct | tgaggacagc | atgtggagat | tgcaccagcg | 600 |
| gcagctctga | gtgcatgtgg | tgcagcaaca | tgaagcagtg | tgtggactcc | aatgcctatg | 660 |
| tggcctcctt | ccctttggc | cagtgtatgg | aatggtatac | gatgagcacc | tgcccccctg | 720 |
| aaaattgttc | aggctactgt | acctgtagtc | attgcttgga | gcaaccaggc | tgtggctggt | 780 |
| gtactgatcc | cagcaatact | ggcaaaggga | aatgcataga | gggttcctat | aaaggaccag | 840 |
| tgaagatgcc | ttcgcaagcc | cctacaggaa | atttctatcc | acagccctg | ctcaattcca | 900 |
| gcatgtgtct | agaggacagc | agatacaact | ggtctttcat | tcactgtcca | gcttgccaat | 960 |
| gcaacggcca | cagtaaatgc | atcaatcaga | gcatctgtga | aagtgtgag | aacctgacca | 1020 |
| caggcaagca | ctgcgagacc | tgcatatctg | gcttctacgg | tgatcccacc | aatggaggga | 1080 |
| aatgtcagc | atgcaagtgc | aatgggcacg | cgtctctgtg | caacaccaac | acgggcaagt | 1140 |
| gcttctgcac | caccaagggc | gtcaagggg | acgagtgcca | gctatgtgag | gtagaaaatc | 1200 |
| gataccaagg | aaaccctctc | agaggaacat | gttattatac | tcttcttatt | gactatcagt | 1260 |
| tcacctttag | tctatcccag | gaagatgatc | gctattacac | agctatcaat | tttgtggcta | 1320 |
| ctcctgacga | caaaacagg | gatttggaca | tgttcatcaa | tgcctccaag | aatttcaacc | 1380 |
| tcaacatcac | ctgggctgcc | agtttctcag | ctggaaccca | ggctggagaa | gagatgcctg | 1440 |
| ttgtttcaaa | aaccaacatt | aaggagtaca | agatagtttt | ctctaatgag | aagtttgatt | 1500 |
| ttcgcaacca | cccaaatatc | actttctttg | tttatgtcag | taatttcacc | tggcccatca | 1560 |
| aaattcagat | tgccttctct | cagcacagca | attttatgga | cctggtacag | ttcttcgtga | 1620 |
| ctttcttcag | ttgttcctc | tctttgctcc | tggtggctgc | tgtggtttgg | aagatcaaac | 1680 |
| aaagttgttg | ggcctccaga | cgtagagagc | aacttcttcg | agagatgcaa | cagatggcca | 1740 |
| gccgtccctt | tgcctctgta | aatgtcgcct | tggaaacaga | tgaggagcct | cctgatctta | 1800 |
| ttggggggag | tataaagact | gttcccaaac | ccattgcact | ggagccgtgt | tttggcaaca | 1860 |
| aagccgctgt | cctctctgtg | tttgtgaggc | tccctcgagg | cctgggtggc | atccctcctc | 1920 |
| ctgggcagtc | aggtcttgct | gtggccagcg | ccctggtgga | catttctcag | cagatgccga | 1980 |

```
tagtgtacaa ggagaagtca ggagccgtga gaaaccggaa gcagcagccc cctgcacagc      2040
ctgggacctg catctgatgc tggggccagg gactctccca cgcacgagct agtgagtggc      2100
acaccagagc catctgcagg gaagggcgtg gcggggaaat ggctgtgcgg tgcgggacgg      2160
aagactggaa accctcaaag catctgactc acctgcatga tcacaagctt tctttgacgg      2220
tttctcccat ccgtgttcca gcatctaacc ttttactttt gcataggaaa tacttgattt      2280
aattacaggt ccagggatga gctgatggtt gctggaggag gccagtgtag agccagtgag      2340
agaactagga atgacactca ggttcactgt ggaaaactgt tcttgggact gtctcaactg      2400
tgcaaaaaac aaaagatgga gtgtttacaa gtagacattc gtcatcagtt gttcttgaac      2460
atggtctttt aaaaactagt cagatgaatt aacttgtttt catctgaagc ctgctatctt      2520
ttttaaaaga tgtgctattt attcttgcac gatttaggca attatctctc ttccagggag      2580
tacctttttt tctagttgag aattaataat ggtccatctc ttttgatcat atcaagctag      2640
gatagaaggg gggctatttt aaatgtcaag gtcagcagtg ttactttgaa tgtaaactgg      2700
tataataggt agttttctat agtaacttga ttaatttagt cttaatccat ttgaaactct      2760
ctcttccttt ctctctgcct gtccctctcc ttctccatct caccctccct ctctcacaca      2820
tacacacaca aacacataca cacaacacta agtgcctaga cttaaatag atctagcaat       2880 tggaaagtta gtaagcctaa gttttacat aattgcattc ctacattctt gtaaaattta      2940
aatagctacc attggcaatc tgctttttt ctaaaatctg atttgcagcc aggaaagaat       3000
tttctcaccc aaggaacatt tgatctagca gcagggatga gaggaaagca gaaatgaatg      3060
aactgtgaaa gctcctgttt ttattatcaa aaaggacact gtcaagaagg cgcccctgc       3120 ccccaccccc gtgtcaccct aggcctgata agcgatcaga ggaaaggact cattcatgtc      3180
acgcttcctt gagcagaaaa gagcactgag agcacttggg acccctggat cagagagcat      3240
ctgtgtgtcc tgcagcctcc tctgaacttg tggttcattc tcaggctggg gtggactcag      3300
atgccaggaa agggacagcc tcccattgtc aggcagaagc tgcccaaagc ctggagaagg      3360
acttgtttgc cctctttccc ccaggagggg ctcgacccac ccaccctccc tctcagacca      3420
aggtggtggc tgtgaggagg gcagcaaatg ctgacaagga tgaaaagcac atggaaaaaa      3480
atggacgagg agggaaaact ctgccaaatg gaaaatgacc aaatttaaga gggtgggaca      3540 gtccctgct cctctcccag agggcactgc ttggaaattg tgttttcccc atttatggtg       3600
ctctgtattc tggcattatg cagcagcctc ccagaagctc tcttctgctt caaaacctgg      3660
gatctctggc attaccctat tgggatggac cgctggacag caatgctcga gtttgtgaat      3720
ttggagagat actcaaaaga gctaaaactg cagcattta cctttaaatg cagtgcctag       3780
agagagagta ttgtctcttc cccaacacta accccactcc catgaagaat tgcctggaaa      3840
gatgttttca aggaatttga accataaaac actatctgat gcacagaaca cctctacttt      3900
gagactcacc tctcataaag cttcttttc acattactgt taaagaccag acgttctaga       3960
aaagacccct cctctcatga gctcccccat ccctgctaca gaacacagca cccatggcgc      4020
ctgcagtgga ctggccccctt aattcccaca ggcccccca gcaaggccaa agggaggccc     4080
ctgggtattg tcctcctaca aggaagatcc tctttgtttg ttcaaaggac cagttttcct     4140
aggccaaaga agtctcttcc ccatgttagt cctatgcctt gaaatatcat gcaccatgac     4200
ccacagccat ctggttatgt cttattttt tcctaaaaga taatgtttat ttttaaaaag      4260
gaaggaagaa gcaagtgaag tttcattctg ctccagcggt ggggaagccg ctgaatccac     4320
```

```
ctgcttctcc tttgcaaccg acagcaaaca gctttctccg gcctcaggqc agaaaaaggg    4380 aatggcaggg agtaagaggc gctgggctcg gagcctgttt ccaagaagga attggttgtc    4440
atctggcagt gttgcgcgtc acaagagagc ctgtatataa attaaaatag tcaagacaac    4500
actgaccttg cacttgtaca taactataca gtagtgtcca gaatgttcag acattcggag    4560
tgtacataaa acagaaaaaa tcttcatgta tttttattaa atataacaat gtctgagttt    4620
cacctaagat gttttgtgc catatgctgg atatccaggt tctcgccagg ccccgataca     4680
tgaataacaa acccaagaaa cgcatcccca ttgtgtgatg tgttcagatg catctggcac    4740
caattaggta tttcttaaaa caggactcat ctgtcagagt gcacatgaaa atcaggcag    4800 ggaatcgaaa cgacagcgct ggaggagact caggaagcag aggcgtccct gccgctgccc    4860
ttggccctgc aagcacatca tgacccttc tggcagcctc ttggtgctct gggtagtgag     4920
ggatgaccag tcttgtcctg agaaatgttt ctcttagtct ttaagttcaa agactaacct    4980
gtagcaatca gactttccaa aagggggttc tccattttt gtagttttgt ctaaatttt     5040 aatgaccatt tcctggaatc agtttattat actgaaaact gggggtggga gtagggagct    5100
agtttgttga taaatagttc ccatttcccc gtggagaatt tgacataccc tggactcctg    5160
tgtgcctcct gccatccctg cacacagcct ggggagaagc ctgtgcctcc ccgtgtggag    5220
agaaggcaac cccagatccc ctgagctaac ccggaggaaa ggcagtcctg gacagaagac    5280
tgtcagcaga aggaaagtac tggactaccc gtgggtaagt cctgccattc aagactggag    5340
acacctggga aataaaaaga gcagggcact gctggtggga agaggcattt taccttccag    5400
tgcaaatcct gctccttga tttaatgggg tgtactgggg ccaggggctg attcacttcc     5460
ttgggagatg gtggtgtttt catgaacatc tttgatcctt ccatttcatt tattcatcca    5520
tccattcaac aagtatttgc taaacactaa cttaagctaa tgctagggta gtgactgaga    5580
tgtaaaaata gattttagaa ttaaaacaaa atccaagtcc tcacacccct gtcatcccag    5640
gagatctttc cttgtggtgg tttctgtgag aattggccat cctgaggaca cagccaggac    5700
ggcagaggcc tcctggcctc agggcatgcc ctgcctacct tctgaaatgt ttaccccatt    5760
gaccaaactt ggctccagcc attgcggtgg tttctagata gccaggccca ccaagagata    5820
ttgccccttg atgagagtca acaccctgc ctacaaggag atgttttgaa atggagagga     5880
aaattggcac ctcatctttt aaaggcagta atggaattga ttttcagtaa ctgaatttgt    5940
gcacaaaaca ttctaaacac tagtgaagcc tgtttcgttg aactaattct ggctctggaa    6000 atgttttgt tttatagtta tttacgattt cgtttgtttg gattcaagct tagtttgtta     6060
atatgtataa tttagcatct attacactca tgtaaatatg gagtaagtat tgtaaactat    6120
ttcattgcgg ggattgtggg tgttatacat acatttagga ctgcaatttt ttggtatttt    6180
ttgtattgta aaataacagc taatttaagc aggaacaaga gaactaaggg aggtctgtgc    6240
attttaaaca caaatgtgaa gaacttgtat ataaacaaaa gtaaatacta taatacaaac    6300
ttccttctga aataaaagta gatctggtaa aaaaaaaaa agaaaaaaaa aaaaaaaaa      6360 gggcggccgc                                                          6370
```

<210> SEQ ID NO 13
<211> LENGTH: 686
<212> TYPE: PRT
<213> ORGANISM: Homo sapiens
<220> FEATURE:
<221> NAME/KEY: SITE
<222> LOCATION: all "n" positions
<223> OTHER INFORMATION: Xaa=unknown amino acid

```
<400> SEQUENCE: 13

Met Tyr Tyr Cys Asn Lys Lys Thr Ser Cys Arg Ser Cys Ala Leu Asp
  1               5                  10                  15
Gln Asn Cys Gln Trp Glu Pro Arg Asn Gln Glu Cys Ile Ala Leu Pro
             20                  25                  30
Glu Asn Ile Cys Gly Ile Gly Trp His Leu Val Gly Asn Ser Cys Leu
         35                  40                  45
Lys Ile Thr Thr Ala Lys Glu Asn Tyr Asp Asn Ala Lys Leu Phe Cys
     50                  55                  60
Arg Asn His Asn Ala Leu Leu Ala Ser Leu Thr Thr Gln Lys Lys Val
 65                  70                  75                  80
Glu Phe Val Leu Lys Gln Leu Arg Ile Met Gln Ser Ser Gln Ser Met
                 85                  90                  95
Ser Lys Leu Thr Leu Thr Pro Trp Val Gly Pro Ser Gly Arg Xaa Asn
             100                 105                 110
Val Ser Tyr Xaa Val Leu Gly Lys Asp Met Xaa Pro Ile Leu Gln Ile
         115                 120                 125
Val Leu Leu Gln Trp Asp Xaa Arg Leu Glu Ala Gln Cys Cys Leu Xaa
    130                 135                 140
Phe Cys Gly Asn Phe Xaa Ser Gly Thr Gln Leu Leu Arg Gly Leu Lys
145                 150                 155                 160
Ala Ala Thr Cys Ile Gln Pro Thr Xaa Met Val Val Ser Val Lys Gly
                165                 170                 175
Leu Gln Thr Thr Val Leu Arg Gln Cys Arg Thr Pro Cys Ala Leu Arg
            180                 185                 190
Thr Ala Cys Gly Asp Cys Thr Ser Gly Ser Ser Glu Xaa His Val Val
        195                 200                 205
Gln Gln His Glu Xaa Ser Val Trp Thr Pro Met Pro Met Trp Pro Pro
    210                 215                 220
Ser Leu Leu Xaa Gln Cys Met Glu Trp Tyr Thr Met Ser Thr Cys Pro
225                 230                 235                 240
Pro Glu Asn Cys Ser Gly Tyr Cys Thr Cys Ser His Cys Leu Glu Gln
                245                 250                 255
Pro Gly Cys Gly Trp Cys Thr Asp Pro Ser Asn Thr Gly Lys Gly Lys
            260                 265                 270
Cys Ile Glu Gly Ser Tyr Lys Gly Pro Val Lys Met Pro Ser Gln Ala
        275                 280                 285
Pro Thr Gly Asn Phe Tyr Pro Gln Pro Leu Leu Asn Ser Ser Met Cys
    290                 295                 300
Leu Glu Asp Ser Arg Tyr Asn Trp Ser Phe Ile His Cys Pro Ala Cys
305                 310                 315                 320
Gln Cys Asn Gly His Ser Lys Cys Ile Asn Gln Ser Ile Cys Glu Lys
                325                 330                 335
Cys Glu Asn Leu Thr Thr Gly Lys His Cys Glu Thr Cys Ile Ser Gly
            340                 345                 350
Phe Tyr Gly Asp Pro Thr Asn Gly Gly Lys Cys Gln Pro Cys Lys Cys
        355                 360                 365
Asn Gly His Ala Ser Leu Cys Asn Thr Asn Thr Gly Lys Cys Phe Cys
    370                 375                 380
Thr Thr Lys Gly Val Lys Gly Asp Glu Cys Gln Leu Cys Glu Val Glu
385                 390                 395                 400
Asn Arg Tyr Gln Gly Asn Pro Leu Arg Gly Thr Cys Tyr Tyr Thr Leu
```

```
                    405                 410                 415
Leu Ile Asp Tyr Gln Phe Thr Phe Ser Leu Ser Gln Glu Asp Asp Arg
            420                 425                 430
Tyr Tyr Thr Ala Ile Asn Phe Val Ala Thr Pro Asp Glu Gln Asn Arg
            435                 440                 445
Asp Leu Asp Met Phe Ile Asn Ala Ser Lys Asn Phe Asn Leu Asn Ile
            450                 455                 460
Thr Trp Ala Ala Ser Phe Ser Ala Gly Thr Gln Ala Gly Glu Glu Met
465                 470                 475                 480
Pro Val Val Ser Lys Thr Asn Ile Lys Glu Tyr Lys Asp Ser Phe Ser
                485                 490                 495
Asn Glu Lys Phe Asp Phe Arg Asn His Pro Asn Ile Thr Phe Phe Val
            500                 505                 510
Tyr Val Ser Asn Phe Thr Trp Pro Ile Lys Ile Gln Ile Ala Phe Ser
            515                 520                 525
Gln His Ser Asn Phe Met Asp Leu Val Gln Phe Phe Val Thr Phe Phe
            530                 535                 540
Ser Cys Phe Leu Ser Leu Leu Val Ala Ala Val Val Trp Lys Ile
545                 550                 555                 560
Lys Gln Ser Cys Trp Ala Ser Arg Arg Arg Glu Gln Leu Leu Arg Glu
                565                 570                 575
Met Gln Gln Met Ala Ser Arg Pro Phe Ala Ser Val Asn Val Ala Leu
            580                 585                 590
Glu Thr Asp Glu Glu Pro Pro Asp Leu Ile Gly Gly Ser Ile Lys Thr
            595                 600                 605
Val Pro Lys Pro Ile Ala Leu Glu Pro Cys Phe Gly Asn Lys Ala Ala
            610                 615                 620
Val Leu Ser Val Phe Val Arg Leu Pro Arg Gly Leu Gly Ile Pro
625                 630                 635                 640
Pro Pro Gly Gln Ser Gly Leu Ala Val Ala Ser Ala Leu Val Asp Ile
                645                 650                 655
Ser Gln Gln Met Pro Ile Val Tyr Lys Glu Lys Ser Gly Ala Val Arg
            660                 665                 670
Asn Arg Lys Gln Gln Pro Pro Ala Gln Pro Gly Thr Cys Ile
            675                 680                 685

<210> SEQ ID NO 14
<211> LENGTH: 8589
<212> TYPE: DNA
<213> ORGANISM: Homo sapiens

<400> SEQUENCE: 14
atggtggcgg tggccgcagc ggcggcaact gaggcaaggc tgaggaggag gacggcggcg      60
acggcagcgc tcgcgggcag gagcggcggg ccgcaccgac cctgcaccgc gacaggggcc     120
tggaggccgg gaccgcgcgc ccggctgtgt ctcccgcggg tgctgtcgcg ggcgctgccc     180
ccgccgccgc tgctgccgct gctcttttcg ctgctgctgc tgccgctgcc ccgggaggcc     240
gaggccgctg cggtggcggc ggcggtgtcc ggctcggccg cagccgaggc caaggaatgt     300
gaccggccgt gtgtcaacgg cggtcgctgc aaccctggca ccggccagtg cgtctgcccc     360
gccggctggg tgggcgagca atgccagcac tgcggggggcc gcttcagact aactggatct     420
tctgggtttg tgacagatgg acctggaaat tataaataca aaacgaagtg cacgtggctc     480
attgaaggac agccaaatag aataatgaga cttcgtttca tcatttttgc tacagagtgt     540
```

-continued

```
agttgggacc atttatatgt ttatgatggg gactcaattt atgcaccgct agttgctgca      600
tttagtggcc tcattgttcc tgagagagat ggcaatgaga ctgtccctga ggttgttgcc      660
acatcaggtt atgccttgct gcatttttt agtgatgctg cttataattt gactggattt       720
aatattactt acagttttga tatgtgtcca ataactgct caggccgagg agagtgtaag       780
atcagtaata gcagcgatac tgttgaatgt gaatgttctg aaaactggaa aggtgaagca      840
tgtgacattc ctcactgtac agacaactgt ggttttcctc atcgaggcat ctgcaattca      900
agtgatgtca gaggatgctc ctgcttctca gactggcagg gtcctggatg ttcagttcct      960
gtaccagcta accagtcatt ttggactcga gaggaatatt ctaacttaaa gctccccaga     1020
gcatctcata aagctgtggt caatggaaac attatgtggg ttgttggagg atatatgttc     1080
aaccactcag attataacat ggttctagcg tatgaccttg cttctaggga gtggcttcca     1140
ctaaaccgtt ctgtgaacaa tgtggttgtt agatatggtc attctttggc attatacaag     1200
gataaaattt acatgtatgg aggaaaaatt gattcaactg gaatgtgac caatgagttg      1260 agagtttttc acattcataa tgagtcatgg gtgttgttga cccctaaggc aaaggagcag     1320
tatgcagtgg ttgggcactc tgcacacatt gttacactga agaatggccg agtggtcatg     1380
ctggtcatct ttggtcactg ccctctctat ggatatataa gcaatgtgca ggaatatgat     1440
ttggataaga acacatggag tatattacac acccagggtg cccttgtgca aggggttac     1500 ggccatagca gtgtttacga ccataggacc agggccctat acgttcatgg tggctacaag     1560
gctttcagtg ccaataagta ccggcttgca gatgatctct accgatatga tgtggatacc     1620
cagatgtgga ccattcttaa ggacagccga ttttccgtt acttgcacac agctgtgata     1680
gtgagtggaa ccatgctggt gttgggggga aacacacaca tgacacatc tatgagccat     1740 ggcgccaaat gcttctcttc agatttcatg gcctatgaca ttgcctgtga ccgctggtca     1800
gtgcttccca gacctgatct ccaccatgat gtcaacagat ttggccattc agcagtctta     1860
cacaacagca ccatgtatgt gttcggtggt ttcaatagtc tcctcctcag cgacatcctg     1920
gtattcacct cggaacagtg tgatgcgcat cggagtgaag ccgcttgttt agcagcagga     1980
cctggtattc ggtgtgtgtg gaacacaggg tcgtctcagt gtatctcgtg ggcgctggca     2040
actgatgaac aagaagaaaa gttaaaatca gaatgttttt ccaaaagaac tcttgaccat     2100
gacagatgtg accagcacac agattgttac agctgcacag ccaacaccaa tgactgccac     2160
tggtgcaatg accattgtgt ccccaggaac cacagctgct cagaaggcca gatctccatt     2220
tttaggtatg agaattgccc caaggataac cctatgtact actgtaacaa gaagaccagc     2280
tgcaggagct gtgccctgga ccagaactgc cagtgggagc cccggaatca ggagtgcatt     2340
gccctgcccg aaaatatctg tggcattggc tggcatttgg ttggaaactc atgtttgaaa     2400
attactactg ccaaggagaa ttatgacaat gctaaattgt tctgtaggaa ccacaatgcc     2460
cttttggctt ctcttacaac ccagaagaag gtagaatttg tccttaagca gctgcgaata     2520
atgcagtcat ctcagagcat gtccaagctc accttaaccc catgggtcgg ccttcggaag     2580
atcaatgtgt cctactggtg ctgggaagat atgtccccat ttacaaatag tttactacag     2640
tggatgccgt ctgagcccag tgatgctgga ttctgtggaa ttttatcaga acccagtact     2700
cggggactga aggctgcaac ctgcatcaac ccactcaatg gtagtgtctg tgaaaggcct     2760
gcaaaccaca gtgctaagca gtgccggaca ccatgtgcct tgaggacagc atgtggagat     2820
tgcaccagcg gcagctctga gtgcatgtgg tgcagcaaca tgaagcagtg tgtggactcc     2880
aatgcctatg tggcctcctt ccctttggc cagtgtatgg aatggtatac gatgagcacc     2940
```

-continued

```
tgcccccctg aaaattgttc aggctactgt acctgtagtc attgcttgga gcaaccaggc    3000
tgtggctggt gtactgatcc cagcaatact ggcaaaggga aatgcataga gggttcctat    3060
aaaggaccag tgaagatgcc ttcgcaagcc cctacaggaa atttctatcc acagcccctg    3120
ctcaattcca gcatgtgtct agaggacagc agatacaact ggtctttcat tcactgtcca    3180
gcttgccaat gcaacggcca cagtaaatgc atcaatcaga gcatctgtga gaagtgtgag    3240
aacctgacca caggcaagca ctgcgagacc tgcatatctg gcttctacgg tgatcccacc    3300
aatggaggga aatgtcagcc atgcaagtgc aatgggcacg cgtctctgtg caacaccaac    3360
acgggcaagt gcttctgcac caccaagggc gtcaagggcg acgagtgcca gctatgtgag    3420
gtagaaaatc gataccaagg aaaccctctc agaggaacat gttattatac tcttcttatt    3480
gactatcagt tcacctttag tctatcccag gaagatgatc gctattacac agctatcaat    3540
tttgtggcta ctcctgacga acaaaacagg gatttgaca tgttcatcaa tgcctccaag    3600
aatttcaacc tcaacatcac ctgggctgcc agtttctcag ctggaaccca ggctggagaa    3660
gagatgcctg ttgtttcaaa aaccaacatt aaggagtaca agatagtttt ctctaatgag    3720
aagtttgatt ttcgcaacca cccaaatatc actttctttg tttatgtcag taatttcacc    3780
tggcccatca aaattcagat tgccttctct cagcacagca attttatgga cctggtacag    3840
ttcttcgtga ctttcttcag ttgtttcctc tctttgctcc tggtggctgc tgtggtttgg    3900
aagatcaaac aaagttgttg ggcctccaga cgtagagagc aacttcttcg agagatgcaa    3960
cagatggcca gccgtccctt tgcctctgta aatgtcgcct tggaaacaga tgaggagcct    4020
cctgatctta ttgggggggag tataaagact gttcccaaac ccattgcact ggagccgtgt    4080
tttggcaaca agccgctgt cctctctgtg tttgtgaggc tccctcgagg cctgggtggc    4140
atccctcctc ctgggcagtc aggtcttgct gtggccagcg ccctggtgga catttctcag    4200
cagatgccga tagtgtacaa ggagaagtca ggagccgtga gaaaccggaa gcagcagccc    4260
cctgcacagc ctgggacctg catctgatgc tgggccagg gactctccca cgcacgagct    4320
agtgagtggc acaccagagc catctgcagg gaagggcgtg gcggggaaat ggctgtgcgg    4380
tgcgggacgg aagactggaa accctcaaag catctgactc acctgcatga tcacaagctt    4440
tctttgacgg tttctcccat ccgtgttcca gcatctaacc ttttactttt gcataggaaa    4500
tacttgattt aattacaggt ccagggatga gctgatggtt gctggaggag gccagtgtag    4560
agccagtgag agaactagga atgacactca ggttcactgt ggaaaactgt tcttgggact    4620
gtctcaactg tgcaaaaaac aaagatgga gtgtttacaa gtagacattc gtcatcagtt    4680
gttcttgaac atggtctttt aaaaactagt cagatgaatt aacttgtttt catctgaagc    4740
ctgctatctt ttttaaaaga tgtgctattt attcttgcac gatttaggca attatctctc    4800
ttccagggag tacttttttt tctagttgag aattaataat ggtccatctc ttttgatcat    4860
atcaagctag gatagaaggg gggctatttt aaatgtcaag gtcagcagtg ttactttgaa    4920
tgtaaactgg tataataggt agttttctat agtaacttga ttaatttagt cttaatccat    4980
ttgaaactct ctcttccttt ctctctgcct gtccctctcc ttctccatct caccctccct    5040
ctctcacaca tacacacaca aacacataca cacaacacta agtgcctaga ctttaaatag    5100
atctagcaat tggaaagtta gtaagcctaa gtttttacat aattgcattc ctacattctt    5160
gtaaaattta aatagctacc attggcaatc tgctttttt ctaaaatctg atttgcagcc    5220
aggaaagaat tttctcaccc aaggaacatt tgatctagca gcagggatga gaggaaagca    5280
```

```
gaaatgaatg aactgtgaaa gctcctgttt ttattatcaa aaaggacact gtcaagaagg    5340
cgcccctgc ccccaccccc gtgtcaccct aggcctgata agcgatcaga ggaaaggact    5400
cattcatgtc acgcttcctt gagcagaaaa gagcactgag agcacttggg acccctggat    5460
cagagagcat ctgtgtgtcc tgcagcctcc tctgaacttg tggttcattc tcaggctggg    5520
gtggactcag atgccaggaa agggacagcc tcccattgtc aggcagaagc tgcccaaagc    5580
ctggagaagg acttgtttgc cctctttccc ccaggagggg ctcgacccac ccaccctccc    5640
tctcagacca aggtggtggc tgtgaggagg cagcaaatg ctgacaagga tgaaaagcac     5700
atggaaaaaa atggacgagg agggaaaact ctgccaaatg gaaaatgacc aaatttaaga    5760
gggtgggaca gtcccctgct cctctcccag agggcactgc ttggaaattg tgttttcccc    5820
atttatggtg ctctgtattc tggcattatg cagcagcctc ccagaagctc tcttctgctt    5880
caaaacctgg gatctctggc attaccctat tgggatggac cgctggacag caatgctcga    5940
gtttgtgaat ttggagagat actcaaaaga gctaaaactg cagcatttta cctttaaatg    6000
cagtgcctag agagagagta ttgtctcttc cccaacacta accccactcc catgaagaat    6060
tgcctggaaa gatgttttca aggaatttga accataaaac actatctgat gcacagaaca    6120
cctctacttt gagactcacc tctcataaag cttcttttc acattactgt taaagaccag    6180
acgttctaga aaagaccccct cctctcatga gctcccccat ccctgctaca gaacacagca    6240
cccatggcgc ctgcagtgga ctggccccctt aattcccaca ggcccccca gcaaggccaa    6300
agggaggccc ctgggtattg tcctcctaca aggaagatcc tctttgttg ttcaaaggac     6360
cagttttcct aggccaaaga agtctcttcc ccatgttagt cctatgcctt gaaatatcat    6420
gcaccatgac ccacagccat ctggttatgt cttatttttt tcctaaaaga taatgtttat    6480
ttttaaaaag gaaggaagaa gcaagtgaag tttcattctg ctccagcggt ggggaagccg    6540
ctgaatccac ctgcttctcc tttgcaaccg acagcaaaca gctttctccg gcctcagggc    6600
agaaaagggg aatggcaggg agtaagaggc gctgggctcg gagcctgttt ccaagaagga    6660
attggttgtc atctggcagt gttgcgcgta caagagagc ctgtatataa attaaaatag     6720
tcaagacaac actgaccttg cacttgtaca taactataca gtagtgtcca gaatgttcag    6780
acattcggag tgtacataaa acagaaaaaa tcttcatgta tttttattaa atataacaat    6840
gtctgagttt cacctaagat gtttttgtgc catatgctgg atatccaggt tctcgccagg    6900
ccccgataca tgaataacaa acccaagaaa cgcatcccca ttgtgtgatg tgttcagatg    6960
catctggcac caattaggta tttcttaaaa caggactcat ctgtcagagt gcacatgaaa    7020
aatcaggcag ggaatcgaaa cgacagcgct ggaggagact caggaagcag aggcgtccct    7080
gccgctgccc ttggccctgc aagcacatca tgacccttc tggcagcctc ttggtgctct    7140
gggtagtgag ggatgaccag tcttgtcctg agaaatgttt ctcttagtct ttaagttcaa    7200
agactaacct gtagcaatca gactttccaa aaggggggttc tccatttttt gtagttttgt    7260
ctaaatttt aatgaccatt tcctggaatc agtttattat actgaaaact ggggtggga     7320
gtagggagct agtttgttga taaatagttc ccatttcccc gtggagaatt tgacataccc    7380
tggactcctg tgtgcctcct gccatccctg cacacagcct ggggagaagc ctgtgcctcc    7440
ccgtgtggag agaaggcaac cccagatccc ctgagctaac ccggaggaaa ggcagtcctg    7500
gacagaagac tgtcagcaga aggaaagtac tggactaccc gtgggtaagt cctgccattc    7560
aagactggag acacctggga aataaaaaga gcagggcact gctggtggga agaggcattt    7620
taccttccag tgcaaatcct gctcctttga tttaatgggg tgtactgggg ccaggggctg    7680
```

-continued

```
attcacttcc ttgggagatg gtggtgtttt catgaacatc tttgatcctt ccatttcatt    7740
tattcatcca tccattcaac aagtatttgc taaacactaa cttaagctaa tgctagggta    7800
gtgactgaga tgtaaaaata gattttagaa ttaaaacaaa atccaagtcc tcacacccct    7860
gtcatcccag gagatctttc cttgtggtgg tttctgtgag aattggccat cctgaggaca    7920
cagccaggac ggcagaggcc tcctggcctc agggcatgcc ctgcctacct tctgaaatgt    7980
ttacccatt gaccaaactt ggctccagcc attgcggtgg tttctagata gccaggccca     8040
ccaagagata ttgccccttg atgagagtca aacaccctgc ctacaaggag atgttttgaa    8100
atggagagga aaattggcac ctcatctttt aaaggcagta atggaattga ttttcagtaa    8160
ctgaatttgt gcacaaaaca ttctaaacac tagtgaagcc tgtttcgttg aactaattct    8220
ggctctggaa atgttttttgt tttatagtta tttacgattt cgtttgtttg gattcaagct   8280
tagtttgtta atatgtataa tttagcatct attcactca tgtaaatatg gagtaagtat     8340
tgtaaactat ttcattgcgg ggattgtggg tgttatacat acatttagga ctgcaatttt    8400
ttggtatttt ttgtattgta aaataacagc taatttaagc aggaacaaga gaactaaggg    8460
aggtctgtgc attttaaaca caaatgtgaa gaacttgtat ataaacaaaa gtaaatacta    8520
taatacaaac ttccttctga aataaaagta gatctggtaa aaaaaaaaaa agaaaaaaaa    8580
aaaaaaaaa                                                           8589
```

```
<210> SEQ ID NO 15
<211> LENGTH: 2787
<212> TYPE: PRT
<213> ORGANISM: Homo sapiens

<400> SEQUENCE: 15
```

```
Met Val Ala Val Ala Ala Ala Ala Thr Glu Ala Arg Leu Arg Arg
 1               5                  10                  15

Arg Thr Ala Ala Thr Ala Ala Leu Ala Gly Arg Ser Gly Pro His
                20                  25                  30

Arg Pro Cys Thr Ala Thr Gly Ala Trp Arg Pro Gly Pro Arg Ala Arg
                35                  40                  45

Leu Cys Leu Pro Arg Val Leu Ser Arg Ala Leu Pro Pro Pro Leu
     50                  55                  60

Leu Pro Leu Leu Phe Ser Leu Leu Leu Pro Leu Pro Arg Glu Ala
 65                  70                  75                  80

Glu Ala Ala Val Ala Ala Val Ser Gly Ser Ala Ala Glu
                85                  90                  95

Ala Lys Glu Cys Asp Arg Pro Cys Val Asn Gly Arg Cys Asn Pro
            100                 105                 110

Gly Thr Gly Gln Cys Val Cys Pro Ala Gly Trp Val Gly Glu Gln Cys
            115                 120                 125

Gln His Cys Gly Gly Arg Phe Arg Leu Thr Gly Ser Ser Gly Phe Val
            130                 135                 140

Thr Asp Gly Pro Gly Asn Tyr Lys Tyr Lys Thr Lys Cys Thr Trp Leu
145                 150                 155                 160

Ile Glu Gly Gln Pro Asn Arg Ile Met Arg Leu Arg Phe Asn His Phe
                165                 170                 175

Ala Thr Glu Cys Ser Trp Asp His Leu Tyr Val Tyr Asp Gly Asp Ser
            180                 185                 190

Ile Tyr Ala Pro Leu Val Ala Ala Phe Ser Gly Leu Ile Val Pro Glu
            195                 200                 205
```

```
Arg Asp Gly Asn Glu Thr Val Pro Glu Val Ala Thr Ser Gly Tyr
    210                 215                 220
Ala Leu Leu His Phe Phe Ser Asp Ala Ala Tyr Asn Leu Thr Gly Phe
225                 230                 235                 240
Asn Ile Thr Tyr Ser Phe Asp Met Cys Pro Asn Asn Cys Ser Gly Arg
                245                 250                 255
Gly Glu Cys Lys Ile Ser Asn Ser Ser Asp Thr Val Glu Cys Glu Cys
                260                 265                 270
Ser Glu Asn Trp Lys Gly Glu Ala Cys Asp Ile Pro His Cys Thr Asp
                275                 280                 285
Asn Cys Gly Phe Pro His Arg Gly Ile Cys Asn Ser Ser Asp Val Arg
            290                 295                 300
Gly Cys Ser Cys Phe Ser Asp Trp Gln Gly Pro Gly Cys Ser Val Pro
305                 310                 315                 320
Val Pro Ala Asn Gln Ser Phe Trp Thr Arg Glu Glu Tyr Ser Asn Leu
                325                 330                 335
Lys Leu Pro Arg Ala Ser His Lys Ala Val Val Asn Gly Asn Ile Met
                340                 345                 350
Trp Val Val Gly Gly Tyr Met Phe Asn His Ser Asp Tyr Asn Met Val
                355                 360                 365
Leu Ala Tyr Asp Leu Ala Ser Arg Glu Trp Leu Pro Leu Asn Arg Ser
            370                 375                 380
Val Asn Val Val Val Arg Tyr Gly His Ser Leu Ala Leu Tyr Lys
385                 390                 395                 400
Asp Lys Ile Tyr Met Tyr Gly Gly Lys Ile Asp Ser Thr Gly Asn Val
                405                 410                 415
Thr Asn Glu Leu Arg Val Phe His Ile His Asn Glu Ser Trp Val Leu
                420                 425                 430
Leu Thr Pro Lys Ala Lys Glu Gln Tyr Ala Val Val Gly His Ser Ala
            435                 440                 445
His Ile Val Thr Leu Lys Asn Gly Arg Val Val Met Leu Val Ile Phe
    450                 455                 460
Gly His Cys Pro Leu Tyr Gly Tyr Ile Ser Asn Val Gln Glu Tyr Asp
465                 470                 475                 480
Leu Asp Lys Asn Thr Trp Ser Ile Leu His Thr Gln Gly Ala Leu Val
                485                 490                 495
Gln Gly Gly Tyr Gly His Ser Ser Val Tyr Asp His Arg Thr Arg Ala
            500                 505                 510
Leu Tyr Val His Gly Gly Tyr Lys Ala Phe Ser Ala Asn Lys Tyr Arg
            515                 520                 525
Leu Ala Asp Asp Leu Tyr Arg Tyr Asp Val Asp Thr Gln Met Trp Thr
530                 535                 540
Ile Leu Lys Asp Ser Arg Phe Phe Arg Tyr Leu His Thr Ala Val Ile
545                 550                 555                 560
Val Ser Gly Thr Met Leu Val Phe Gly Gly Asn Thr His Asn Asp Thr
                565                 570                 575
Ser Met Ser His Gly Ala Lys Cys Phe Ser Ser Asp Phe Met Ala Tyr
            580                 585                 590
Asp Ile Ala Cys Asp Arg Trp Ser Val Leu Pro Arg Pro Asp Leu His
            595                 600                 605
His Asp Val Asn Arg Phe Gly His Ser Ala Val Leu His Asn Ser Thr
    610                 615                 620
```

-continued

```
Met Tyr Val Phe Gly Gly Phe Asn Ser Leu Leu Leu Ser Asp Ile Leu
625                 630                 635                 640

Val Phe Thr Ser Glu Gln Cys Asp Ala His Arg Ser Glu Ala Ala Cys
            645                 650                 655

Leu Ala Ala Gly Pro Gly Ile Arg Cys Val Trp Asn Thr Gly Ser Ser
            660                 665                 670

Gln Cys Ile Ser Trp Ala Leu Ala Thr Asp Glu Gln Glu Glu Lys Leu
            675                 680                 685

Lys Ser Glu Cys Phe Ser Lys Arg Thr Leu Asp His Asp Arg Cys Asp
690                 695                 700

Gln His Thr Asp Cys Tyr Ser Cys Thr Ala Asn Thr Asn Asp Cys His
705                 710                 715                 720

Trp Cys Asn Asp His Cys Val Pro Arg Asn His Ser Cys Ser Glu Gly
                725                 730                 735

Gln Ile Ser Ile Phe Arg Tyr Glu Asn Cys Pro Lys Asp Asn Pro Met
                740                 745                 750

Tyr Tyr Cys Asn Lys Lys Thr Ser Cys Arg Ser Cys Ala Leu Asp Gln
                755                 760                 765

Asn Cys Gln Trp Glu Pro Arg Asn Gln Glu Cys Ile Ala Leu Pro Glu
770                 775                 780

Asn Ile Cys Gly Ile Gly Trp His Leu Val Gly Asn Ser Cys Leu Lys
785                 790                 795                 800

Ile Thr Thr Ala Lys Glu Asn Tyr Asp Asn Ala Lys Leu Phe Cys Arg
                805                 810                 815

Asn His Asn Ala Leu Leu Ala Ser Leu Thr Thr Gln Lys Lys Val Glu
                820                 825                 830

Phe Val Leu Lys Gln Leu Arg Ile Met Gln Ser Ser Gln Ser Met Ser
            835                 840                 845

Lys Leu Thr Leu Thr Pro Trp Val Gly Leu Arg Lys Ile Asn Val Ser
850                 855                 860

Tyr Trp Cys Trp Glu Asp Met Ser Pro Phe Thr Asn Ser Leu Leu Gln
865                 870                 875                 880

Trp Met Pro Ser Glu Pro Ser Asp Ala Gly Phe Cys Gly Ile Leu Ser
                885                 890                 895

Glu Pro Ser Thr Arg Gly Leu Lys Ala Ala Thr Cys Ile Asn Pro Leu
            900                 905                 910

Asn Gly Ser Val Cys Glu Arg Pro Ala Asn His Ser Ala Lys Gln Cys
            915                 920                 925

Arg Thr Pro Cys Ala Leu Arg Thr Ala Cys Gly Asp Cys Thr Ser Gly
930                 935                 940

Ser Ser Glu Cys Met Trp Cys Ser Asn Met Lys Gln Cys Val Asp Ser
945                 950                 955                 960

Asn Ala Tyr Val Ala Ser Phe Pro Phe Gly Gln Cys Met Glu Trp Tyr
                965                 970                 975

Thr Met Ser Thr Cys Pro Pro Glu Asn Cys Ser Gly Tyr Cys Thr Cys
                980                 985                 990

Ser His Cys Leu Glu Gln Pro Gly Cys Gly Trp Cys Thr Asp Pro Ser
        995                 1000                1005

Asn Thr Gly Lys Gly Lys Cys Ile Glu Gly Ser Tyr Lys Gly Pro Val
        1010                1015                1020

Lys Met Pro Ser Gln Ala Pro Thr Gly Asn Phe Tyr Pro Gln Pro Leu
1025                1030                1035                1040

Leu Asn Ser Ser Met Cys Leu Glu Asp Ser Arg Tyr Asn Trp Ser Phe
```

-continued

```
                  1045              1050              1055

Ile His Cys Pro Ala Cys Gln Cys Asn Gly His Ser Lys Cys Ile Asn
            1060              1065              1070

Gln Ser Ile Cys Glu Lys Cys Glu Asn Leu Thr Thr Gly Lys His Cys
        1075              1080              1085

Glu Thr Cys Ile Ser Gly Phe Tyr Gly Asp Pro Thr Asn Gly Gly Lys
    1090              1095              1100

Cys Gln Pro Cys Lys Cys Asn Gly His Ala Ser Leu Cys Asn Thr Asn
1105              1110              1115              1120

Thr Gly Lys Cys Phe Cys Thr Thr Lys Gly Val Lys Gly Asp Glu Cys
            1125              1130              1135

Gln Leu Cys Glu Val Glu Asn Arg Tyr Gln Gly Asn Pro Leu Arg Gly
        1140              1145              1150

Thr Cys Tyr Tyr Thr Leu Leu Ile Asp Tyr Gln Phe Thr Phe Ser Leu
        1155              1160              1165

Ser Gln Glu Asp Asp Arg Tyr Tyr Thr Ala Ile Asn Phe Val Ala Thr
        1170              1175              1180

Pro Asp Glu Gln Asn Arg Asp Leu Asp Met Phe Ile Asn Ala Ser Lys
1185              1190              1195              1200

Asn Phe Asn Leu Asn Ile Thr Trp Ala Ala Ser Phe Ser Ala Gly Thr
            1205              1210              1215

Gln Ala Gly Glu Glu Met Pro Val Val Ser Lys Thr Asn Ile Lys Glu
            1220              1225              1230

Tyr Lys Asp Ser Phe Ser Asn Glu Lys Phe Asp Phe Arg Asn His Pro
        1235              1240              1245

Asn Ile Thr Phe Phe Val Tyr Val Ser Asn Phe Thr Trp Pro Ile Lys
        1250              1255              1260

Ile Gln Ile Ala Phe Ser Gln His Ser Asn Phe Met Asp Leu Val Gln
1265              1270              1275              1280

Phe Phe Val Thr Phe Phe Ser Cys Phe Leu Ser Leu Leu Val Ala
            1285              1290              1295

Ala Val Val Trp Lys Ile Lys Gln Ser Cys Trp Ala Ser Arg Arg Arg
            1300              1305              1310

Glu Gln Leu Leu Arg Glu Met Gln Gln Met Ala Ser Arg Pro Phe Ala
        1315              1320              1325

Ser Val Asn Val Ala Leu Glu Thr Asp Glu Glu Pro Pro Asp Leu Ile
    1330              1335              1340

Gly Gly Ser Ile Lys Thr Val Pro Lys Pro Ile Ala Leu Glu Pro Cys
1345              1350              1355              1360

Phe Gly Asn Lys Ala Ala Val Leu Ser Val Phe Val Arg Leu Pro Arg
            1365              1370              1375

Gly Leu Gly Gly Ile Pro Pro Gly Gln Ser Gly Leu Ala Val Ala
            1380              1385              1390

Ser Ala Leu Val Asp Ile Ser Gln Gln Met Pro Ile Val Tyr Lys Glu
        1395              1400              1405

Lys Ser Gly Ala Val Arg Asn Arg Lys Gln Gln Pro Ala Gln Pro
    1410              1415              1420

Gly Thr Cys Ile Cys Trp Gly Gln Gly Leu Ser His Ala Arg Ala Ser
1425              1430              1435              1440

Glu Trp His Thr Arg Ala Ile Cys Arg Glu Gly Arg Gly Glu Met
            1445              1450              1455

Ala Val Arg Cys Gly Thr Glu Asp Trp Lys Pro Ser Lys His Leu Thr
        1460              1465              1470
```

-continued

His Leu His Asp His Lys Leu Ser Leu Thr Val Ser Pro Ile Arg Val
        1475                1480                1485
Pro Ala Ser Asn Leu Leu Leu His Arg Lys Tyr Leu Ile Leu Gln
        1490                1495                1500
Val Gln Gly Ala Asp Gly Cys Trp Arg Pro Val Ser Gln Glu Asn
1505                1510                1515                1520
Glu His Ser Gly Ser Leu Trp Lys Thr Val Leu Gly Thr Val Ser Thr
            1525                1530                1535
Val Gln Lys Thr Lys Asp Gly Val Phe Thr Ser Arg His Ser Ser Ser
        1540                1545                1550
Val Val Leu Glu His Gly Leu Leu Lys Thr Ser Gln Met Asn Leu Val
        1555                1560                1565
Phe Ile Ser Leu Leu Ser Phe Leu Lys Asp Val Leu Phe Ile Leu Ala
        1570                1575                1580
Arg Phe Arg Gln Leu Ser Leu Phe Gln Gly Val Pro Phe Phe Leu Val
1585                1590                1595                1600
Glu Asn Trp Ser Ile Ser Phe Asp His Ile Lys Leu Gly Lys Gly Gly
            1605                1610                1615
Tyr Phe Lys Cys Gln Gly Gln Gln Cys Tyr Phe Glu Cys Lys Leu Val
        1620                1625                1630
Val Val Phe Tyr Ser Asn Leu Ile Asn Leu Val Leu Ile His Leu Lys
        1635                1640                1645
Leu Ser Leu Pro Phe Ser Leu Pro Val Pro Leu Leu His Leu Thr
        1650                1655                1660
Leu Pro Leu Ser His Ile His Thr Gln Thr His Thr His Asn Thr Lys
1665                1670                1675                1680
Cys Leu Asp Phe Lys Ile Gln Leu Glu Ser Ala Val Phe Thr Leu His
            1685                1690                1695
Ser Tyr Ile Leu Val Lys Phe Lys Leu Pro Leu Ala Ile Cys Phe Phe
        1700                1705                1710
Ser Lys Ile Phe Ala Ala Arg Lys Glu Phe Ser His Pro Arg Asn Ile
        1715                1720                1725
Ser Ser Ser Arg Asp Glu Arg Lys Ala Glu Met Asn Glu Leu Lys Leu
        1730                1735                1740
Leu Phe Leu Leu Ser Lys Arg Thr Leu Ser Arg Arg Arg Pro Leu Pro
1745                1750                1755                1760
Pro Pro Pro Cys His Pro Arg Asp Lys Arg Ser Glu Glu Arg Thr
            1765                1770                1775
His Ser Cys His Ala Ser Leu Ser Arg Lys Glu His Glu His Leu Gly
        1780                1785                1790
Pro Leu Asp Gln Arg Ala Ser Val Cys Pro Ala Ala Ser Ser Glu Leu
        1795                1800                1805
Val Val His Ser Gln Ala Gly Val Asp Ser Asp Ala Arg Lys Gly Thr
        1810                1815                1820
Ala Ser His Cys Gln Ala Glu Ala Ala Gln Ser Leu Glu Lys Asp Leu
1825                1830                1835                1840
Phe Ala Leu Phe Pro Pro Gly Gly Ala Arg Pro Thr His Pro Pro Ser
            1845                1850                1855
Gln Thr Lys Val Val Ala Val Arg Arg Ala Ala Asn Ala Asp Lys Asp
        1860                1865                1870
Glu Lys His Met Glu Lys Asn Gly Arg Gly Gly Lys Thr Leu Pro Asn
        1875                1880                1885

-continued

```
Gly Lys Pro Asn Leu Arg Gly Trp Asp Ser Pro Leu Leu Ser Gln
    1890                1895                1900

Arg Ala Leu Leu Gly Asn Cys Val Phe Pro Ile Tyr Gly Ala Leu Tyr
1905                1910                1915                1920

Ser Gly Ile Met Gln Gln Pro Pro Arg Ser Ser Leu Leu Gln Asn
            1925                1930                1935

Leu Gly Ser Leu Ala Leu Pro Tyr Trp Asp Gly Pro Leu Asp Ser Asn
            1940                1945                1950

Ala Arg Val Cys Glu Phe Gly Glu Ile Leu Arg Ala Lys Thr Ala
            1955                1960                1965

Ala Phe Tyr Leu Met Gln Cys Leu Glu Arg Glu Tyr Cys Leu Phe Pro
            1970                1975                1980

Asn Thr Asn Pro Thr Pro Met Lys Asn Cys Leu Glu Arg Cys Phe Gln
1985                1990                1995                2000

Gly Ile Thr Ile Lys His Tyr Leu Met His Arg Thr Pro Leu Leu Asp
            2005                2010                2015

Ser Pro Leu Ile Lys Leu Leu Phe His Ile Thr Val Lys Asp Gln Thr
            2020                2025                2030

Phe Lys Arg Pro Leu Leu Ser Ala Pro Pro Ser Leu Leu Gln Asn Thr
            2035                2040                2045

Ala Pro Met Ala Pro Ala Val Asp Trp Pro Leu Asn Ser His Arg Pro
    2050                2055                2060

Pro Gln Gln Gly Gln Arg Glu Ala Pro Gly Tyr Cys Pro Pro Thr Arg
2065                2070                2075                2080

Lys Ile Leu Phe Val Cys Ser Lys Asp Gln Phe Ser Ala Lys Glu Val
            2085                2090                2095

Ser Ser Pro Cys Ser Tyr Ala Leu Lys Tyr His Ala Pro Pro Thr Ala
            2100                2105                2110

Ile Trp Leu Cys Leu Ile Phe Phe Leu Lys Asp Asn Val Tyr Phe Lys
            2115                2120                2125

Gly Arg Lys Lys Gln Val Lys Phe His Ser Ala Pro Ala Val Gly Lys
            2130                2135                2140

Pro Leu Asn Pro Pro Ala Ser Pro Leu Gln Pro Thr Ala Asn Ser Phe
2145                2150                2155                2160

Leu Arg Pro Gln Gly Arg Lys Arg Glu Trp Gln Gly Val Arg Gly Ala
            2165                2170                2175

Gly Leu Gly Ala Cys Phe Gln Glu Gly Ile Gly Cys His Leu Ala Val
            2180                2185                2190

Leu Arg Val Thr Arg Glu Pro Val Tyr Lys Leu Lys Ser Arg Gln His
            2195                2200                2205

Pro Cys Thr Cys Thr Leu Tyr Ser Ser Val Gln Asn Val Gln Thr Phe
    2210                2215                2220

Gly Val Tyr Ile Lys Gln Lys Ser Ser Cys Ile Phe Ile Lys Tyr
2225                2230                2235                2240

Asn Asn Val Val Ser Pro Lys Met Phe Leu Cys His Met Leu Asp Ile
                2245                2250                2255

Gln Val Leu Ala Arg Pro Arg Tyr Met Asn Asn Lys Pro Lys Lys Arg
            2260                2265                2270

Ile Pro Ile Val Cys Val Gln Met His Leu Ala Pro Ile Arg Tyr Phe
            2275                2280                2285

Leu Lys Gln Asp Ser Ser Val Arg Val His Met Lys Asn Gln Ala Gly
            2290                2295                2300

Asn Arg Asn Asp Ser Ala Gly Gly Asp Ser Gly Ser Arg Gly Val Pro
```

-continued

```
2305                2310                2315                2320
Ala Ala Ala Leu Gly Pro Ala Ser Thr Ser Pro Phe Leu Ala Ser
                2325                2330                2335
Trp Cys Ser Gly Gly Met Thr Ser Leu Val Leu Arg Asn Val Ser Leu
                2340                2345                2350
Ser Leu Val Gln Arg Leu Thr Cys Ser Asn Gln Thr Phe Gln Lys Gly
            2355                2360                2365
Val Leu His Phe Leu Phe Cys Leu Asn Phe Pro Phe Pro Gly Ile Ser
        2370                2375                2380
Leu Leu Tyr Lys Leu Gly Val Gly Val Gly Ser Phe Val Asp Lys Phe
2385                2390                2395                2400
Pro Phe Pro Arg Gly Glu Phe Asp Ile Pro Trp Thr Pro Val Cys Leu
                2405                2410                2415
Leu Pro Ser Leu His Thr Ala Trp Gly Glu Ala Cys Ala Ser Pro Cys
                2420                2425                2430
Gly Glu Lys Ala Thr Pro Asp Pro Leu Ser Pro Gly Gly Lys Ala Val
                2435                2440                2445
Leu Asp Arg Arg Leu Ser Ala Glu Gly Lys Tyr Trp Thr Thr Arg Gly
                2450                2455                2460
Val Leu Pro Phe Lys Thr Gly Asp Thr Trp Glu Ile Lys Arg Ala Gly
2465                2470                2475                2480
His Cys Trp Trp Glu Glu Ala Phe Tyr Leu Pro Val Gln Ile Leu Leu
                2485                2490                2495
Leu Phe Asn Gly Val Tyr Trp Gly Gln Gly Leu Ile His Phe Leu Gly
                2500                2505                2510
Arg Trp Trp Cys Phe His Glu His Leu Ser Phe His Phe Ile Tyr Ser
                2515                2520                2525
Ser Ile His Ser Thr Ser Ile Cys Thr Leu Thr Ala Asn Ala Arg Val
        2530                2535                2540
Val Thr Glu Met Lys Ile Leu Glu Leu Lys Gln Asn Pro Ser Pro His
2545                2550                2555                2560
Thr Pro Val Ile Pro Gly Asp Leu Ser Leu Trp Trp Phe Leu Glu Leu
                2565                2570                2575
Ala Ile Leu Arg Thr Gln Pro Gly Arg Gln Arg Pro Gly Leu Arg
                2580                2585                2590
Ala Cys Pro Ala Tyr Leu Leu Lys Cys Leu Pro His Pro Asn Leu Ala
            2595                2600                2605
Pro Ala Ile Ala Val Val Ser Arg Pro Gly Pro Arg Asp Ile Ala
        2610                2615                2620
Pro Glu Ser Asn Thr Leu Pro Thr Arg Arg Cys Phe Glu Met Glu Arg
2625                2630                2635                2640
Lys Ile Gly Thr Ser Ser Phe Lys Gly Ser Asn Gly Ile Asp Phe Gln
                2645                2650                2655
Leu Asn Leu Cys Thr Lys His Ser Lys His Ser Leu Phe Arg Thr Asn
                2660                2665                2670
Ser Gly Ser Gly Asn Val Phe Val Leu Leu Phe Thr Ile Ser Phe Val
        2675                2680                2685
Trp Ile Gln Ala Phe Val Asn Met Tyr Asn Leu Ala Ser Ile Thr Leu
                2690                2695                2700
Met Ile Trp Ser Lys Tyr Cys Lys Leu Phe His Cys Gly Asp Cys Gly
2705                2710                2715                2720
Cys Tyr Thr Tyr Ile Asp Cys Asn Phe Leu Val Phe Val Leu Asn
                2725                2730                2735
```

```
Asn Ser Phe Lys Gln Glu Gln Glu Asn Gly Arg Ser Val His Phe Lys
        2740                2745                2750
His Lys Cys Glu Glu Leu Val Tyr Lys Gln Lys Ile Leu Tyr Lys Leu
        2755                2760                2765
Pro Ser Glu Ile Lys Val Asp Leu Val Lys Lys Lys Glu Lys Lys
        2770                2775                2780
Lys Lys Lys
2785

<210> SEQ ID NO 16
<211> LENGTH: 4072
<212> TYPE: DNA
<213> ORGANISM: Homo sapiens

<400> SEQUENCE: 16
atggtggcgg tggccgcagc ggcggcaact gaggcaaggc tgaggaggag gacggcggcg      60
acggcagcgc tcgcgggcag gagcggcggg ccgcaccgac cctgcaccgc gacaggggcc     120
tggaggccgg gaccgcgcgc ccggctgtgt ctcccgcggg tgctgtcgcg ggcgctgccc     180
ccgccgccgc tgctgccgct gctcttttcg ctgctgctgc tgccgctgcc ccgggaggcc     240
gaggccgctg cggtggcggc ggcggtgtcc ggctcggccg cagccgaggc caaggaatgt     300
gaccggccgt gtgtcaacgg cggtcgctgc aaccctggca ccggccagtg cgtctgcccc     360
gccggctggg tgggcgagca atgccagcac tgcgggggcc gcttcagact aactggatct     420
tctgggtttg tgacagatgg aacctggaaa tataaataca aaacgaagtg cacgtggctc     480
attgaaggac agccaaatag aataatgaga cttcgtttca atcattttgc tacagagtgt     540
agttgggacc atttatatgt ttatgatggg gactcaattt atgcaccgct agttgctgca     600
tttagtggcc tcattgttcc tgagagagat ggcaatgaga ctgtccctga ggttgttgcc     660
acatcaggtt atgccttgct gcattttttt agtgatgctg cttataattt gactggattt     720
aatattactt acagttttga tatgtgtcca ataactgct caggccgagg agagtgtaag     780
atcagtaata gcagcgatac tgttgaatgt gaatgttctg aaaactggaa aggtgaagca     840
tgtgacattc ctcactgtac agacaactgt ggttttcctc atcgaggcat ctgcaattca     900
agtgatgtca gaggatgctc ctgcttctca gactggcagg tcctggatg ttcagttcct     960
gtaccagcta accagtcatt ttggactcga gaggaatatt ctaacttaaa gctccccaga    1020
gcatctcata aagctgtggt caatggaaac attatgtggg ttgttggagg atatatgttc    1080
aaccactcag attataacat ggttctagcg tatgaccttg cttctaggga gtggcttcca    1140
ctaaaccgtt ctgtgaacaa tgtggttgtt agatatggtc attcttggc attatacaag    1200
gataaaattt acatgtatgg aggaaaaatt gattcaactg ggaatgtgac caatgagttg    1260
agagtttttc acattcataa tgagtcatgg gtgttgttga ccctaaggc aaaggagcag    1320
tatgcagtgg ttgggcactc tgcacacatt gttacactga gaatggccg agtggtcatg    1380
ctggtcatct ttggtcactg ccctctctat ggatatataa gcaatgtgca ggaatatgat    1440
ttggataaga acacatggag tatattacac acccagggtg cccttgtgca agggggttac    1500
ggccatagca gtgtttacga ccataggacc agggccctat acgttcatgg tggctacaag    1560
gctttcagtg ccaataagta ccggcttgca gatgatctct accgatatga tgtggatacc    1620
cagatgtgga ccattcttaa ggacagccga tttttccgtt acttgcacac agctgtgata    1680
gtgagtggaa ccatgctggt gtttggggga aacacacaca tgacacatc tatgagccat    1740
```

```
ggcgccaaat gcttctcttc agatttcatg gcctatgaca ttgcctgtga ccgctggtca    1800
gtgcttccca gacctgatct ccaccatgat gtcaacagat ttggccattc agcagtctta    1860
cacaacagca ccatgtatgt gttcggtggt ttcaatagtc tcctcctcag cgacatcctg    1920
gtattcacct cggaacagtg tgatgcgcat cggagtgaag ccgcttgttt agcagcagga    1980
cctggtattc ggtgtgtgtg gaacacaggg tcgtctcagt gtatctcgtg ggcgctggca    2040
actgatgaac aagaagaaaa gttaaaatca gaatgttttt ccaaaagaac tcttgaccat    2100
gacagatgtg accagcacac agattgttac agctgcacag ccaacaccaa tgactgccac    2160
tggtgcaatg accattgtgt ccccaggaac cacagctgct cagaaggcca gatctccatt    2220
tttaggtatg agaattgccc caaggataac cctatgtact actgtaacaa gaagaccagc    2280
tgcaggagct gtgccctgga ccagaactgc cagtgggagc cccggaatca ggagtgcatt    2340
gccctgcccg aaaatatctg tggcattggc tggcatttgg ttggaaactc atgtttgaaa    2400
attactactg ccaaggagaa ttatgacaat gctaaattgt tctgtaggaa ccacaatgcc    2460
cttttggctt ctcttacaac ccagaagaag gtagaatttg tccttaagca gctgcgaata    2520
atgcagtcat ctcagagcat gtccaagctc accttaaccc catgggtcgg ccttcggaag    2580
atcaatgtgt cctactggtg ctgggaagat atgtccccat ttacaaatag tttactacag    2640
tggatgccgt ctgagcccag tgatgctgga ttctgtggaa ttttatcaga acccagtact    2700
cggggactga aggctgcaac ctgcatcaac ccactcaatg gtagtgtctg tgaaaggcct    2760
gcaaaccaca gtgctaagca gtgccggaca ccatgtgcct tgaggacagc atgtggagat    2820
tgcaccagcg gcagctctga gtgcatgtgg tgcagcaaca tgaagcagtg tgtggactcc    2880
aatgcctatg tggcctcctt ccctttttggc cagtgtatgg aatggtatac gatgagcacc    2940 tgccccctg aaaattgttc aggctactgt acctgtagtc attgcttgga gcaaccaggc    3000
tgtggctggt gtactgatcc cagcaatact ggcaaaggga aatgcataga gggttcctat    3060
aaaggaccag tgaagatgcc ttcgcaagcc cctacaggaa atttctatcc acagcccctg    3120
ctcaattcca gcatgtgtct agaggacagc agatacaact ggtctttcat tcactgtcca    3180
gcttgccaat gcaacggcca cagtaaatgc atcaatcaga gcatctgtga aagtgtgag    3240 aacctgacca caggcaagca ctgcgagacc tgcatatctg gcttctacgg tgatcccacc    3300
aatggaggga atgtcagcc atgcaagtgc aatgggcacg cgtctctgtg caacaccaac    3360
acgggcaagt gcttctgcac caccaagggc gtcaagggg acgagtgcca gctatgtgag    3420
gtagaaaatc gataccaagg aaaccctctc agaggaacat gttattatac tcttcttatt    3480
gactatcagt tcacctttag tctatcccag gaagatgatc gctattacac agctatcaat    3540
tttgtggcta ctcctgacga acaaaacagg gatttggaca tgttcatcaa tgcctccaag    3600
aatttcaacc tcaacatcac ctgggctgcc agtttctcag ctggaaccca ggctggagaa    3660
gagatgcctg ttgtttcaaa aaccaacatt aaggagtaca agatagttt ctctaatgag    3720 aagtttgatt ttcgcaacca cccaaatatc actttctttg tttatgtcag taatttcacc    3780
tggcccatca aaattcaggt gcaaactgaa caatgaggac gcatggacac aggaagggga    3840
acatcacaca ccagggcctg ttgtggggtg ggggaaggg gaaggatag cattagggga    3900 tatacctaat gttaaatgac gagttaatgg gtgcagcaca ccaacatggc atatgtatac    3960
atatgtaaca aacctgcatg ttgtgcacat gtaccctaaa acttaaagta taattaaaaa    4020
aaaaaaaaga aaaaaaaaa aaaaaaaaa aaaaaaaaaa aaaaaaaaaa aa              4072
```

-continued

```
<210> SEQ ID NO 17
<211> LENGTH: 1350
<212> TYPE: PRT
<213> ORGANISM: Homo sapiens

<400> SEQUENCE: 17
```

| | | | | | | | | | | | | | | |
|---|---|---|---|---|---|---|---|---|---|---|---|---|---|---|
| Met | Val | Ala | Ala | Ala | Ala | Thr | Glu | Ala | Arg | Leu | Arg | Arg | Thr | |
| 1 | | | | 5 | | | | | 10 | | | | 15 | |
| Ala | Ala | Thr | Ala | Ala | Leu | Ala | Gly | Arg | Ser | Gly | Gly | Pro | His | Trp | Asp |
| | | 20 | | | | | 25 | | | | | 30 | | | |
| Trp | Asp | Val | Thr | Arg | Ala | Gly | Arg | Pro | Gly | Leu | Gly | Ala | Gly | Leu | Arg |
| | | 35 | | | | | 40 | | | | | 45 | | | |
| Leu | Pro | Arg | Leu | Leu | Ser | Pro | Pro | Leu | Arg | Pro | Arg | Leu | Leu | Leu | Leu |
| | 50 | | | | | 55 | | | | | 60 | | | | |
| Leu | Leu | Leu | Leu | Pro | Pro | Leu | Leu | Leu | Leu | Leu | Pro | Cys | Glu |
| 65 | | | | | 70 | | | | 75 | | | | 80 |
| Ala | Glu | Ala | Ala | Ala | Ala | Ala | Ala | Val | Ser | Gly | Ser | Ala | Ala | Ala |
| | | | | 85 | | | | | 90 | | | | | 95 |
| Glu | Ala | Lys | Glu | Cys | Asp | Arg | Pro | Cys | Val | Asn | Gly | Gly | Arg | Cys | Asn |
| | | | 100 | | | | | 105 | | | | | 110 | | |
| Pro | Gly | Thr | Gly | Gln | Cys | Val | Cys | Pro | Ala | Gly | Trp | Val | Gly | Glu | Gln |
| | | | 115 | | | | | 120 | | | | | 125 | | |
| Cys | Gln | His | Cys | Gly | Gly | Arg | Phe | Arg | Leu | Thr | Gly | Ser | Ser | Gly | Phe |
| 130 | | | | | 135 | | | | | 140 | | | | | |
| Val | Thr | Asp | Gly | Pro | Gly | Asn | Tyr | Lys | Tyr | Lys | Thr | Lys | Cys | Thr | Trp |
| 145 | | | | | 150 | | | | | 155 | | | | | 160 |
| Leu | Ile | Glu | Gly | Gln | Pro | Asn | Arg | Ile | Met | Arg | Leu | Arg | Phe | Asn | His |
| | | | | 165 | | | | | 170 | | | | | 175 | |
| Phe | Ala | Thr | Glu | Cys | Ser | Trp | Asp | His | Leu | Tyr | Val | Tyr | Asp | Gly | Asp |
| | | | 180 | | | | | 185 | | | | | 190 | | |
| Ser | Ile | Tyr | Ala | Pro | Leu | Val | Ala | Ala | Phe | Ser | Gly | Leu | Ile | Val | Pro |
| | | 195 | | | | | 200 | | | | | 205 | | | |
| Glu | Arg | Asp | Gly | Asn | Glu | Thr | Val | Pro | Glu | Val | Val | Ala | Thr | Ser | Gly |
| | 210 | | | | | 215 | | | | | 220 | | | | |
| Tyr | Ala | Leu | Leu | His | Phe | Phe | Ser | Asp | Ala | Ala | Tyr | Asn | Leu | Thr | Gly |
| 225 | | | | | 230 | | | | | 235 | | | | | 240 |
| Phe | Asn | Ile | Thr | Tyr | Ser | Phe | Asp | Met | Cys | Pro | Asn | Asn | Cys | Ser | Gly |
| | | | 245 | | | | | 250 | | | | | 255 | | |
| Arg | Gly | Glu | Cys | Lys | Ile | Ser | Asn | Ser | Ser | Thr | Val | Glu | Cys | Glu | Cys |
| | | | 260 | | | | | 265 | | | | | 270 | | |
| Ser | Glu | Asn | Trp | Lys | Gly | Glu | Ala | Cys | Asp | Ile | Pro | His | Cys | Thr | Asp |
| | | 275 | | | | | 280 | | | | | 285 | | | |
| Asn | Cys | Gly | Phe | Pro | His | Arg | Gly | Ile | Cys | Asn | Ser | Ser | Asp | Val | Arg |
| | 290 | | | | | 295 | | | | | 300 | | | | |
| Gly | Cys | Ser | Cys | Phe | Ser | Asp | Trp | Gln | Gly | Pro | Gly | Cys | Ser | Val | Pro |
| 305 | | | | | 310 | | | | | 315 | | | | | 320 |
| Val | Pro | Ala | Asn | Gln | Ser | Phe | Trp | Thr | Arg | Glu | Glu | Tyr | Ser | Asn | Leu |
| | | | 325 | | | | | 330 | | | | | 335 | | |
| Lys | Leu | Pro | Arg | Ala | Ser | His | Lys | Ala | Val | Val | Asn | Gly | Asn | Ile | Met |
| | | | 340 | | | | | 345 | | | | | 350 | | |
| Trp | Val | Val | Gly | Gly | Tyr | Met | Phe | Asn | His | Ser | Asp | Tyr | Asn | Met | Val |
| | | 355 | | | | | 360 | | | | | 365 | | | |
| Leu | Ala | Tyr | Asp | Leu | Ala | Ser | Arg | Glu | Trp | Leu | Pro | Leu | Asn | Arg | Ser |
| 370 | | | | | 375 | | | | | 380 | | | | | |

-continued

```
Val Asn Asn Val Val Arg Tyr Gly His Ser Leu Ala Leu Tyr Lys
385                 390                 395                 400

Asp Lys Ile Tyr Met Tyr Gly Lys Ile Asp Thr Gly Asn Val Thr
            405                 410                 415

Asn Glu Leu Arg Val Phe His Ile His Asn Glu Ser Trp Val Leu Leu
            420                 425                 430

Thr Pro Lys Ala Lys Glu Gln Tyr Ala Val Val Gly His Ser Ala His
            435                 440                 445

Ile Val Thr Leu Lys Asn Gly Arg Val Val Met Leu Val Ile Phe Gly
    450                 455                 460

His Cys Pro Leu Tyr Gly Tyr Ile Ser Asn Val Gln Glu Tyr Asp Leu
465                 470                 475                 480

Asp Lys Asn Thr Trp Ser Ile Leu His Thr Gln Gly Ala Leu Val Gln
                485                 490                 495

Gly Gly Tyr Gly His Ser Ser Val Tyr Asp His Arg Thr Arg Ala Leu
            500                 505                 510

Tyr Val His Gly Gly Tyr Lys Ala Phe Ser Ala Asn Lys Tyr Arg Leu
            515                 520                 525

Ala Asp Asp Leu Tyr Arg Tyr Asp Val Asp Thr Gln Met Trp Thr Ile
530                 535                 540

Leu Lys Asp Ser Arg Phe Phe Arg Tyr Leu His Thr Ala Val Ile Val
545                 550                 555                 560

Ser Gly Thr Met Leu Val Phe Gly Gly Asn Thr His Asn Asp Thr Ser
            565                 570                 575

Met Ser His Gly Ala Lys Cys Phe Ser Ser Asp Phe Met Ala Tyr Asp
            580                 585                 590

Ile Ala Cys Asp Arg Trp Ser Val Leu Pro Arg Pro Asp Leu His His
            595                 600                 605

Asp Val Asn Arg Phe Gly His Ser Ala Val Leu His Asn Ser Thr Met
            610                 615                 620

Tyr Val Phe Gly Gly Phe Asn Ser Leu Leu Ser Asp Ile Leu Val
625                 630                 635                 640

Phe Thr Ser Glu Gln Cys Asp Ala His Arg Ser Glu Ala Ala Cys Leu
            645                 650                 655

Ala Ala Gly Pro Gly Ile Arg Cys Val Trp Asn Thr Gly Ser Ser Gln
            660                 665                 670

Cys Ile Ser Trp Ala Leu Ala Thr Asp Glu Gln Glu Lys Leu Lys
            675                 680                 685

Ser Glu Cys Phe Ser Lys Arg Thr Leu Asp His Asp Arg Cys Asp Gln
            690                 695                 700

His Thr Asp Cys Tyr Ser Cys Thr Ala Asn Thr Asn Asp Cys His Trp
705                 710                 715                 720

Cys Asn Asp His Cys Val Pro Arg Asn His Ser Cys Ser Glu Gly Gln
                725                 730                 735

Ile Ser Ile Phe Arg Tyr Glu Asn Cys Pro Lys Asp Asn Pro Met Tyr
            740                 745                 750

Tyr Cys Asn Lys Lys Thr Ser Cys Arg Ser Cys Ala Leu Asp Gln Asn
            755                 760                 765

Cys Gln Trp Glu Pro Arg Asn Gln Glu Cys Ile Ala Leu Pro Glu Asn
    770                 775                 780

Ile Cys Gly Ile Gly Trp His Leu Val Gly Asn Ser Cys Leu Lys Ile
785                 790                 795                 800

Thr Thr Ala Lys Glu Asn Tyr Asp Asn Ala Lys Leu Phe Cys Arg Asn
```

-continued

```
                805                 810                 815
His Asn Ala Leu Leu Ala Ser Leu Thr Thr Gln Lys Lys Val Glu Phe
            820                 825                 830
Val Leu Lys Gln Leu Arg Ile Met Gln Ser Ser Gln Ser Met Ser Lys
            835                 840                 845
Leu Thr Leu Thr Pro Trp Val Gly Leu Arg Lys Ile Asn Val Ser Tyr
            850                 855                 860
Trp Cys Trp Glu Asp Met Ser Pro Phe Thr Asn Ser Leu Leu Gln Trp
865                 870                 875                 880
Met Pro Ser Glu Pro Ser Asp Ala Gly Phe Cys Gly Ile Leu Ser Glu
            885                 890                 895
Pro Ser Thr Arg Gly Leu Lys Ala Ala Thr Cys Ile Asn Pro Leu Asn
            900                 905                 910
Gly Ser Val Cys Glu Arg Pro Ala Asn His Ser Ala Lys Gln Cys Arg
            915                 920                 925
Thr Pro Cys Ala Leu Arg Thr Ala Cys Gly Asp Cys Thr Ser Gly Ser
            930                 935                 940
Ser Glu Cys Met Trp Cys Ser Asn Met Lys Gln Cys Val Asp Ser Asn
945                 950                 955                 960
Ala Tyr Val Ala Ser Phe Pro Phe Gly Gln Cys Met Glu Trp Tyr Thr
            965                 970                 975
Met Ser Thr Cys Pro Pro Glu Asn Cys Ser Gly Tyr Cys Thr Cys Ser
            980                 985                 990
His Cys Leu Glu Gln Pro Gly Cys Gly Trp Cys Thr Asp Pro Ser Asn
            995                 1000                1005
Thr Gly Lys Gly Lys Cys Ile Glu Gly Ser Tyr Lys Gly Pro Val Lys
            1010                1015                1020
Met Pro Ser Gln Ala Pro Thr Gly Asn Phe Tyr Pro Gln Pro Leu Leu
1025                1030                1035                1040
Asn Ser Ser Met Cys Leu Glu Asp Ser Arg Tyr Asn Trp Ser Phe Ile
            1045                1050                1055
His Cys Pro Ala Cys Gln Cys Asn Gly His Ser Lys Cys Ile Asn Gln
            1060                1065                1070
Ser Ile Cys Glu Lys Cys Glu Asn Leu Thr Thr Gly Lys His Cys Glu
            1075                1080                1085
Thr Cys Ile Ser Gly Phe Tyr Gly Asp Pro Thr Asn Gly Gly Lys Cys
            1090                1095                1100
Gln Pro Cys Lys Cys Asn Gly His Ala Ser Leu Cys Asn Thr Asn Thr
1105                1110                1115                1120
Gly Lys Cys Phe Cys Thr Thr Lys Gly Val Lys Gly Asp Glu Cys Gln
            1125                1130                1135
Leu Cys Glu Val Glu Asn Arg Tyr Gln Gly Asn Pro Leu Arg Gly Thr
            1140                1145                1150
Cys Tyr Tyr Thr Leu Leu Ile Asp Tyr Gln Phe Thr Phe Ser Leu Ser
            1155                1160                1165
Gln Glu Asp Asp Arg Tyr Tyr Thr Ala Ile Asn Phe Val Ala Thr Pro
            1170                1175                1180
Asp Glu Gln Asn Arg Asp Leu Asp Met Phe Ile Asn Ala Ser Lys Asn
1185                1190                1195                1200
Phe Asn Leu Asn Ile Thr Trp Ala Ala Ser Phe Ser Ala Gly Thr Gln
            1205                1210                1215
Ala Gly Glu Glu Met Pro Val Val Ser Lys Thr Asn Ile Lys Glu Tyr
            1220                1225                1230
```

```
Lys Asp Ser Phe Ser Asn Glu Lys Phe Asp Phe Arg Asn His Pro Asn
        1235                1240                1245

Ile Thr Phe Phe Val Tyr Val Ser Asn Phe Thr Trp Pro Ile Lys Ile
    1250                1255                1260

Gln Val Gln Thr Glu Gln Gly Arg Met Asp Thr Gly Arg Gly Thr Ser
1265                1270                1275                1280

His Thr Arg Ala Cys Cys Gly Val Gly Gly Arg Gly Arg Asp Ser Ile
                1285                1290                1295

Arg Gly Tyr Thr Cys Met Thr Ser Trp Val Gln His Thr Asn Met Ala
            1300                1305                1310

Tyr Val Tyr Ile Cys Asn Lys Pro Ala Cys Cys Ala His Val Pro Asn
        1315                1320                1325

Leu Lys Tyr Asn Lys Lys Lys Lys Lys Lys Lys Lys Lys Lys Lys Lys
        1330                1335                1340

Lys Lys Lys Lys Lys Lys
1345                1350

<210> SEQ ID NO 18
<211> LENGTH: 2625
<212> TYPE: DNA
<213> ORGANISM: Homo sapiens

<400> SEQUENCE: 18
atggtggcgg tggccgcagc ggcggcaact gaggcaaggc tgaggaggag gacggcggcg      60
acggcagcgc tcgcgggcag gagcggcggg ccgcaccgac cctgcaccgc gacaggggcc     120
tggaggccgg gaccgcgcgc ccggctgtgt ctcccgcggg tgctgtcgcg ggcgctgccc     180
ccgccgccgc tgctgccgct gctcttttcg ctgctgctgc tgccgctgcc ccgggaggcc     240
gaggccgctg cggtggcggc ggcggtgtcc ggctcggccg cagccgaggc caaggaatgt     300
gaccggccgt gtgtcaacgg cggtcgctgc aaccctggca ccggccagtg cgtctgcccc     360
gccggctggg tgggcgagca atgccagcac tgcggggggcc gcttcagact aactggatct     420
tctgggtttg tgacagatgg aacctggaaat tataaataca aaacgaagtg cacgtggctc     480
attgaaggac agccaaatag aataatgaga cttcgtttca atcattttgc tacagagtgt     540
agttgggacc atttatatgt ttatgatggg gactcaattt atgcaccgct agttgctgca     600
tttagtggcc tcattgttcc tgagagagat ggcaatgaga ctgtccctga ggttgttgcc     660
acatcaggtt atgccttgct gcatttttt agtgatgctg cttataattt gactggattt     720
aatattactt acagttttga tatgtgtcca aataactgct caggccgagg agagtgtaag     780
atcagtaata gcagcgatac tgttaatgt gaatgttctg aaaactggaa aggtgaagca     840
tgtgacattc tcactgtac agacaactgt ggttttcctc atcgaggcat ctgcaattca     900
agtgatgtca gaggatgctc ctgcttctca gactggcagg tcctggatg ttcagttcct     960 gtaccagcta accagtcatt ttggactcga gaggaatatt ctaacttaaa gctccccaga    1020
gcatctcata aagctgtggt caatggaaac attatgtggg ttgttggagg atatatgttc    1080
aaccactcag attataacat ggttctagcg tatgaccttg cttctaggga gtggcttcca    1140
ctaaaccgtt ctgtgaacaa tgtggttgtt agatatggtc attctttggc attatacaag    1200
gataaaattt acatgtatgg aggaaaaatt gattcaactg ggaatgtgac caatgagttg    1260 agagttttttc acattcataa tgagtcatgg gtgttgttga ccctaaggc aaaggagcag    1320 tatgcagtgg ttgggcactc tgcacacatt gttacactga agaatggccg agtggtcatg    1380
```

-continued

```
ctggtcatct ttggtcactg ccctctctat ggatatataa gcaatgtgca ggaatatgat   1440
ttggataaga acacatggag tatattacac acccagggtg cccttgtgca agggggttac   1500
ggccatagca gtgtttacga ccataggacc agggccctat acgttcatgg tggctacaag   1560
gctttcagtg ccaataagta ccggcttgca gatgatctct accgatatga tgtggatacc   1620
cagatgtgga ccattcttaa ggacagccga tttttccgtt acttgcacac agctgtgata   1680
gtgagtggaa ccatgctggt gtttggggga aacacacaca atgacacatc tatgagccat   1740
ggcgccaaat gcttctcttc agatttcatg gcctatgaca ttgcctgtga ccgctggtca   1800
gtgcttccca gacctgatct ccaccatgat gtcaacagat ttggccattc agcagtctta   1860
cacaacagca ccatgtatgt gttcggtggt ttcaatagtc tcctcctcag cgacatcctg   1920
gtattcacct cggaacagtg tgatgcgcat cggagtgaag ccgcttgttt agcagcagga   1980
cctggtattc ggtgtgtgtg gaacacaggg tcgtctcagt gtatctcgtg ggcgctggca   2040
actgatgaac aagaagaaaa gttaaaatca gaatgttttt ccaaaagaac tcttgaccat   2100
gacagatgtg accagcacac agattgttac agctgcacag ccaacaccaa tgactgccac   2160
tggtgcaatg accattgtgt ccccaggaac cacagctgct cagaaggcca gatctccatt   2220
tttaggtatg agaattgccc caaggataac cctatgtact actgtaacaa gaagaccagc   2280
tgcaggagct gtgccctgga ccagaactgc cagtgggagc cccggaatca ggagtgcatt   2340
gccctgcccg gtaggccttg cagggtcatc ttggtgtgtg tgggtccatt acttcagcct   2400
gcttccccca acactgtgca gcctaagttg aacctagcag aggggaagag ctaattctgt   2460
ccattcatcc cccacacgag tattatgggc ttttttgttt ttaactaaaa tacagttctt   2520
aagtatttgt tcctactgtc ctttgaaata aagtgaaaca tcctttgctg ctctgtaaaa   2580
aaaaaaaaaa aaaaaaaaaa aaaaaaaaaa aaaaaaaaaa aaaaa               2625
```

<210> SEQ ID NO 19
<211> LENGTH: 871
<212> TYPE: PRT
<213> ORGANISM: Homo sapiens

<400> SEQUENCE: 19

```
Met Val Ala Ala Ala Ala Thr Glu Ala Arg Leu Arg Arg Arg Thr
  1               5                  10                  15

Ala Ala Thr Ala Ala Leu Ala Gly Arg Ser Gly Gly Pro His Trp Asp
                 20                  25                  30

Trp Asp Val Thr Arg Ala Gly Arg Pro Gly Leu Gly Ala Gly Leu Arg
             35                  40                  45

Leu Pro Arg Leu Leu Ser Pro Pro Leu Arg Pro Arg Leu Leu Leu Leu
         50                  55                  60

Leu Leu Leu Leu Pro Pro Pro Leu Leu Leu Leu Leu Pro Cys Glu
 65                  70                  75                  80

Ala Glu Ala Ala Ala Ala Ala Ala Val Ser Gly Ser Ala Ala Ala
                 85                  90                  95

Glu Ala Lys Glu Cys Asp Arg Pro Cys Val Asn Gly Gly Arg Cys Asn
                100                 105                 110

Pro Gly Thr Gly Gln Cys Val Cys Pro Ala Gly Trp Val Gly Glu Gln
            115                 120                 125

Cys Gln His Cys Gly Gly Arg Phe Arg Leu Thr Gly Ser Ser Gly Phe
        130                 135                 140

Val Thr Asp Gly Pro Gly Asn Tyr Lys Tyr Lys Thr Lys Cys Thr Trp
145                 150                 155                 160
```

```
Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
                180                 185                 190

Ser Ile Tyr Ala Pro Leu Val Ala Ala Phe Ser Gly Leu Ile Val Pro
                195                 200                 205

Glu Arg Asp Gly Asn Glu Thr Val Pro Glu Val Val Ala Thr Ser Gly
                210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Thr Val Glu Cys Glu Cys
                260                 265                 270

Ser Glu Asn Trp Lys Gly Glu Ala Cys Asp Ile Pro His Cys Thr Asp
                275                 280                 285

Asn Cys Gly Phe Pro His Arg Gly Ile Cys Asn Ser Ser Asp Val Arg
                290                 295                 300

Gly Cys Ser Cys Phe Ser Asp Trp Gln Gly Pro Gly Cys Ser Val Pro
305                 310                 315                 320

Val Pro Ala Asn Gln Ser Phe Trp Thr Arg Glu Glu Tyr Ser Asn Leu
                325                 330                 335

Lys Leu Pro Arg Ala Ser His Lys Ala Val Val Asn Gly Asn Ile Met
                340                 345                 350

Trp Val Val Gly Gly Tyr Met Phe Asn His Ser Asp Tyr Asn Met Val
                355                 360                 365

Leu Ala Tyr Asp Leu Ala Ser Arg Glu Trp Leu Pro Leu Asn Arg Ser
                370                 375                 380

Val Asn Asn Val Val Arg Tyr Gly His Ser Leu Ala Leu Tyr Lys
385                 390                 395                 400

Asp Lys Ile Tyr Met Tyr Gly Gly Lys Ile Asp Thr Gly Asn Val Thr
                405                 410                 415

Asn Glu Leu Arg Val Phe His Ile His Asn Glu Ser Trp Val Leu Leu
                420                 425                 430

Thr Pro Lys Ala Lys Glu Gln Tyr Ala Val Val Gly His Ser Ala His
                435                 440                 445

Ile Val Thr Leu Lys Asn Gly Arg Val Val Met Leu Val Ile Phe Gly
                450                 455                 460

His Cys Pro Leu Tyr Gly Tyr Ile Ser Asn Val Gln Glu Tyr Asp Leu
465                 470                 475                 480

Asp Lys Asn Thr Trp Ser Ile Leu His Thr Gln Gly Ala Leu Val Gln
                485                 490                 495

Gly Gly Tyr Gly His Ser Ser Val Tyr Asp His Arg Thr Arg Ala Leu
                500                 505                 510

Tyr Val His Gly Gly Tyr Lys Ala Phe Ser Ala Asn Lys Tyr Arg Leu
                515                 520                 525

Ala Asp Asp Leu Tyr Arg Tyr Asp Val Asp Thr Gln Met Trp Thr Ile
530                 535                 540

Leu Lys Asp Ser Arg Phe Phe Arg Tyr Leu His Thr Ala Val Ile Val
545                 550                 555                 560

Ser Gly Thr Met Leu Val Phe Gly Gly Asn Thr His Asn Asp Thr Ser
                565                 570                 575
```

-continued

Met Ser His Gly Ala Lys Cys Phe Ser Asp Phe Met Ala Tyr Asp
              580                 585                 590

Ile Ala Cys Asp Arg Trp Ser Val Leu Pro Arg Pro Asp Leu His His
        595                 600                 605

Asp Val Asn Arg Phe Gly His Ser Ala Val Leu His Asn Ser Thr Met
    610                 615                 620

Tyr Val Phe Gly Gly Phe Asn Ser Leu Leu Ser Asp Ile Leu Val
625                 630                 635                 640

Phe Thr Ser Glu Gln Cys Asp Ala His Arg Ser Glu Ala Ala Cys Leu
                645                 650                 655

Ala Ala Gly Pro Gly Ile Arg Cys Val Trp Asn Thr Gly Ser Ser Gln
            660                 665                 670

Cys Ile Ser Trp Ala Leu Ala Thr Asp Glu Gln Glu Lys Leu Lys
        675                 680                 685

Ser Glu Cys Phe Ser Lys Arg Thr Leu Asp His Asp Arg Cys Asp Gln
    690                 695                 700

His Thr Asp Cys Tyr Ser Cys Thr Ala Asn Thr Asn Asp Cys His Trp
705                 710                 715                 720

Cys Asn Asp His Cys Val Pro Arg Asn His Ser Cys Ser Glu Gly Gln
                725                 730                 735

Ile Ser Ile Phe Arg Tyr Glu Asn Cys Pro Lys Asp Asn Pro Met Tyr
            740                 745                 750

Tyr Cys Asn Lys Lys Thr Ser Cys Arg Ser Cys Ala Leu Asp Gln Asn
        755                 760                 765

Cys Gln Trp Glu Pro Arg Asn Gln Glu Cys Ile Ala Leu Pro Gly Arg
    770                 775                 780

Pro Cys Arg Val Ile Leu Val Cys Val Gly Pro Leu Leu Gln Pro Ala
785                 790                 795                 800

Ser Pro Asn Thr Val Gln Pro Lys Leu Asn Leu Ala Glu Gly Lys Ser
                805                 810                 815

Phe Cys Pro Phe Ile Pro His Thr Ser Ile Met Gly Phe Val Phe
            820                 825                 830

Asn Asn Thr Val Leu Lys Tyr Leu Phe Leu Leu Ser Phe Glu Ile Lys
        835                 840                 845

Asn Ile Leu Cys Cys Ser Val Lys Lys Lys Lys Lys Lys Lys
    850                 855                 860

Lys Lys Lys Lys Lys Lys Lys
865                 870

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
tctcctagtt gtagtacatg ctgttg                                    26

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21

```
tctcctagtt gtagtacatg ctgttg                                                26

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
aggtcctgtc tcaagaaata gcaataac                                              28

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
tttgaaggcc cctgaagtca gag                                                   23

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
ttgagtcccc atcataaaca tataaatgg                                             29

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
ttctaggcca aatagaataa tgagacttc                                             29

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
agaactaatt ccatgagatg agtgtg                                                26

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
tgaagttgct gtaatctggt ctgtg                                                 25

<210> SEQ ID NO 28
<211> LENGTH: 22
<212> TYPE: DNA
<213> ORGANISM: Artificial Sequence
```

```
<220> FEATURE:
<223> OTHER INFORMATION: Primer

<400> SEQUENCE: 28
aaggagcctg actagaagcc tc                                          22

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
taaactccct acagttcact aactcag                                     27

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
agcgctgttg agtgtgaatg ttctg                                       25

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
aaagccacag ttgtctgtac agtgag                                      26

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
aggtctgcat tagttgcaat gttgc                                       25

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
tatacacccc cttatataca ctcag                                       25

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
agagcctctc ataaagctgt ggtc                                        24
```

```
<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
ttgaacatat atccgccaac aaccc                                              25

<210> SEQ ID NO 36
<211> LENGTH: 28
<212> TYPE: DNA
<213> ORGANISM: Artificial Sequence
<220> FEATURE:
<223> OTHER INFORMATION: Primer

<400> SEQUENCE: 36
cttggaatac tataaacttt caggctgc                                           28

<210> SEQ ID NO 37
<211> LENGTH: 29
<212> TYPE: DNA
<213> ORGANISM: Artificial Sequence
<220> FEATURE:
<223> OTHER INFORMATION: Primer

<400> SEQUENCE: 37
taaagcaaca ggaagagttg aacttcttg                                          29

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tgcaccctgt gtgcacatgg                                                    20

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
ttacggtgtc ctaataataa gggcag                                             26

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
aatcatgggt attgttaact ccgaaagc                                           28

<210> SEQ ID NO 41
<211> LENGTH: 24
<212> TYPE: DNA
<213> ORGANISM: Artificial Sequence
<220> FEATURE:
<223> OTHER INFORMATION: Primer
```

<400> SEQUENCE: 41
tgtaacaatg tgtgccgagt gtcc                                    24

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
tctctctcca gccctagagt tg                                      22

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
agaagaggag cctgcaacat tgac                                    24

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
tttgttggcg ctgaaagcct tg                                      22

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
tggccacagt agtgtttatg atgac                                   25

<210> SEQ ID NO 46
<211> LENGTH: 27
<212> TYPE: DNA
<213> ORGANISM: Artificial Sequence
<220> FEATURE:
<223> OTHER INFORMATION: Primer

<400> SEQUENCE: 46
ttaatcaatt gcctctgcag attctag                                 27

<210> SEQ ID NO 47
<211> LENGTH: 26
<212> TYPE: DNA
<213> ORGANISM: Artificial Sequence
<220> FEATURE:
<223> OTHER INFORMATION: Primer

<400> SEQUENCE: 47
tggcttacgt ataggggaa atcaag                                   26

<210> SEQ ID NO 48

```
<211> LENGTH: 24
<212> TYPE: DNA
<213> ORGANISM: Artificial Sequence
<220> FEATURE:
<223> OTHER INFORMATION: Primer

<400> SEQUENCE: 48
ttgtgtgtgt tccctccaaa cacc                                          24

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
ggaccattct taaggacagc cgat                                          24

<210> SEQ ID NO 50
<211> LENGTH: 26
<212> TYPE: DNA
<213> ORGANISM: Artificial Sequence
<220> FEATURE:
<223> OTHER INFORMATION: Primer

<400> SEQUENCE: 50
acatagtgat ctttccatca gcaaag                                        26

<210> SEQ ID NO 51
<211> LENGTH: 22
<212> TYPE: DNA
<213> ORGANISM: Artificial Sequence
<220> FEATURE:
<223> OTHER INFORMATION: Primer

<400> SEQUENCE: 51
tgaatgcaca gagaccctcc tg                                            22

<210> SEQ ID NO 52
<211> LENGTH: 26
<212> TYPE: DNA
<213> ORGANISM: Artificial Sequence
<220> FEATURE:
<223> OTHER INFORMATION: Primer

<400> SEQUENCE: 52
cctcttacca ttcagatact gttagg                                        26

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
agcaacaact caaaccagcc ctac                                          24

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
```
ttcttcagtt gccaactccc agg         23

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55
aagctgcttg tgtggcagca g           21

<210> SEQ ID NO 56
<211> LENGTH: 26
<212> TYPE: DNA
<213> ORGANISM: Artificial Sequence
<220> FEATURE:
<223> OTHER INFORMATION: Primer

<400> SEQUENCE: 56
agtaaggtga acaggaaagt acagag      26

<210> SEQ ID NO 57
<211> LENGTH: 24
<212> TYPE: DNA
<213> ORGANISM: Artificial Sequence
<220> FEATURE:
<223> OTHER INFORMATION: Primer

<400> SEQUENCE: 57
tacataagag aggctgccgc atag        24

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
ccctacactc acactcatct agc         23

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
ccctgtgttc cagatctcca ttg         23

<210> SEQ ID NO 60
<211> LENGTH: 24
<212> TYPE: DNA
<213> ORGANISM: Artificial Sequence
<220> FEATURE:
<223> OTHER INFORMATION: Primer

<400> SEQUENCE: 60
ttcctaggtc caccttgatc tgag        24

<210> SEQ ID NO 61
<211> LENGTH: 26
<212> TYPE: DNA

<213> ORGANISM: Artificial Sequence
<220> FEATURE:
<223> OTHER INFORMATION: Primer

<400> SEQUENCE: 61
agcacctgaa ttcaaatcag gatgag                                    26

<210> SEQ ID NO 62
<211> LENGTH: 29
<212> TYPE: DNA
<213> ORGANISM: Artificial Sequence
<220> FEATURE:
<223> OTHER INFORMATION: Primer

<400> SEQUENCE: 62
aaaccaaagt tctgaacaca ttaactcac                                 29

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
ctggttgcat tcatagctgt gtttc                                     25

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
acagaagcca gcatcactgg g                                         21

<210> SEQ ID NO 65
<211> LENGTH: 24
<212> TYPE: DNA
<213> ORGANISM: Artificial Sequence
<220> FEATURE:
<223> OTHER INFORMATION: Primer

<400> SEQUENCE: 65
ttactggtgc tgggaggata tgtc                                      24

<210> SEQ ID NO 66
<211> LENGTH: 26
<212> TYPE: DNA
<213> ORGANISM: Artificial Sequence
<220> FEATURE:
<223> OTHER INFORMATION: Primer

<400> SEQUENCE: 66
ataagtactt catcacctca gcgctc                                    26

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
ttgatcttag ctgaccagtg tctc                                      24

<210> SEQ ID NO 68
<211> LENGTH: 25
<212> TYPE: DNA
<213> ORGANISM: Artificial Sequence
<220> FEATURE:
<223> OTHER INFORMATION: Primer

<400> SEQUENCE: 68
tctgcatgga cttgagcaga aagtc                                          25

<210> SEQ ID NO 69
<211> LENGTH: 30
<212> TYPE: DNA
<213> ORGANISM: Artificial Sequence
<220> FEATURE:
<223> OTHER INFORMATION: Primer

<400> SEQUENCE: 69
caaatcttgt gatagtgaat tacaagttgg                                     30

<210> SEQ ID NO 70
<211> LENGTH: 27
<212> TYPE: DNA
<213> ORGANISM: Artificial Sequence
<220> FEATURE:
<223> OTHER INFORMATION: Primer

<400> SEQUENCE: 70
tttatagctg ccctcaatac attttcc                                        27

<210> SEQ ID NO 71
<211> LENGTH: 22
<212> TYPE: DNA
<213> ORGANISM: Artificial Sequence
<220> FEATURE:
<223> OTHER INFORMATION: Primer

<400> SEQUENCE: 71
tgtacctgca gccattgctt gg                                             22

<210> SEQ ID NO 72
<211> LENGTH: 25
<212> TYPE: DNA
<213> ORGANISM: Artificial Sequence
<220> FEATURE:
<223> OTHER INFORMATION: Primer

<400> SEQUENCE: 72
ggatctgggc tctagtttat gtacg                                          25

<210> SEQ ID NO 73
<211> LENGTH: 24
<212> TYPE: DNA
<213> ORGANISM: Artificial Sequence
<220> FEATURE:
<223> OTHER INFORMATION: Primer

<400> SEQUENCE: 73
ttgaactata ggcacagaca gctg                                           24

<210> SEQ ID NO 74
<211> LENGTH: 23
<212> TYPE: DNA
<213> ORGANISM: Artificial Sequence
<220> FEATURE:

<223> OTHER INFORMATION: Primer

<400> SEQUENCE: 74
aacttgacct gtgtgactta cgc                                     23

<210> SEQ ID NO 75
<211> LENGTH: 26
<212> TYPE: DNA
<213> ORGANISM: Artificial Sequence
<220> FEATURE:
<223> OTHER INFORMATION: Primer

<400> SEQUENCE: 75
tcacagtcta tggtaatctg tcaagc                                  26

<210> SEQ ID NO 76
<211> LENGTH: 22
<212> TYPE: DNA
<213> ORGANISM: Artificial Sequence
<220> FEATURE:
<223> OTHER INFORMATION: Primer

<400> SEQUENCE: 76
aagggcaaca atgccctggc aa                                      22

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
ttcctgcaaa tgggatagtc tctctg                                  26

<210> SEQ ID NO 78
<211> LENGTH: 26
<212> TYPE: DNA
<213> ORGANISM: Artificial Sequence
<220> FEATURE:
<223> OTHER INFORMATION: Primer

<400> SEQUENCE: 78
atcccccaag catttatcat tctcag                                  26

<210> SEQ ID NO 79
<211> LENGTH: 28
<212> TYPE: DNA
<213> ORGANISM: Artificial Sequence
<220> FEATURE:
<223> OTHER INFORMATION: Primer

<400> SEQUENCE: 79
tgtgtttcca gaaacctgct ttagtttg                                28

<210> SEQ ID NO 80
<211> LENGTH: 26
<212> TYPE: DNA
<213> ORGANISM: Artificial Sequence
<220> FEATURE:
<223> OTHER INFORMATION: Primer

<400> SEQUENCE: 80
tagtactttt gtccaggatg accaag                                  26

<210> SEQ ID NO 81
<211> LENGTH: 30
<212> TYPE: DNA
<213> ORGANISM: Artificial Sequence
<220> FEATURE:
<223> OTHER INFORMATION: Primer

<400> SEQUENCE: 81
tgacaagaaa tgtcatgtct taacataagc                           30

<210> SEQ ID NO 82
<211> LENGTH: 22
<212> TYPE: DNA
<213> ORGANISM: Artificial Sequence
<220> FEATURE:
<223> OTHER INFORMATION: Primer

<400> SEQUENCE: 82
ttcagagcct ccttccccaa ct                                   22

<210> SEQ ID NO 83
<211> LENGTH: 25
<212> TYPE: DNA
<213> ORGANISM: Artificial Sequence
<220> FEATURE:
<223> OTHER INFORMATION: Primer

<400> SEQUENCE: 83
tagtctgtag ctgaggccat tttgc                                25

<210> SEQ ID NO 84
<211> LENGTH: 25
<212> TYPE: DNA
<213> ORGANISM: Artificial Sequence
<220> FEATURE:
<223> OTHER INFORMATION: Primer

<400> SEQUENCE: 84
aagcaagctg cagttaaggg actgt                                25

<210> SEQ ID NO 85
<211> LENGTH: 23
<212> TYPE: DNA
<213> ORGANISM: Artificial Sequence
<220> FEATURE:
<223> OTHER INFORMATION: Primer

<400> SEQUENCE: 85
ttgggacctt gaggattgtt ccc                                  23

<210> SEQ ID NO 86
<211> LENGTH: 26
<212> TYPE: DNA
<213> ORGANISM: Artificial Sequence
<220> FEATURE:
<223> OTHER INFORMATION: Primer

<400> SEQUENCE: 86
cactcaacag gtaaaagtga tctgcc                               26

<210> SEQ ID NO 87
<211> LENGTH: 27
<212> TYPE: DNA
<213> ORGANISM: Artificial Sequence
<220> FEATURE:
<223> OTHER INFORMATION: Primer

<400> SEQUENCE: 87
tgcatctgat cagtttgaat cagagag                                    27

<210> SEQ ID NO 88
<211> LENGTH: 26
<212> TYPE: DNA
<213> ORGANISM: Artificial Sequence
<220> FEATURE:
<223> OTHER INFORMATION: Primer

<400> SEQUENCE: 88
aaactgaggc ctgagttctg aaaagc                                     26

<210> SEQ ID NO 89
<211> LENGTH: 24
<212> TYPE: DNA
<213> ORGANISM: Artificial Sequence
<220> FEATURE:
<223> OTHER INFORMATION: Primer

<400> SEQUENCE: 89
caccaaagct ctgtaccact aagc                                       24

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
tgactgtgca gtgatgcagg g                                          21

<210> SEQ ID NO 91
<211> LENGTH: 27
<212> TYPE: DNA
<213> ORGANISM: Artificial Sequence
<220> FEATURE:
<223> OTHER INFORMATION: Primer

<400> SEQUENCE: 91
ttgaccttga catttagaat agccctc                                    27

<210> SEQ ID NO 92
<211> LENGTH: 30
<212> TYPE: DNA
<213> ORGANISM: Artificial Sequence
<220> FEATURE:
<223> OTHER INFORMATION: Primer

<400> SEQUENCE: 92
gctgagaatt aataatggtc tttctctttg                                 30

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
tacacagtga gaccctgtct cc                                         22

<210> SEQ ID NO 94
<211> LENGTH: 22

```
<212> TYPE: DNA
<213> ORGANISM: Artificial Sequence
<220> FEATURE:
<223> OTHER INFORMATION: Primer

<400> SEQUENCE: 94
tagctgaggt cccttgtgga ag                                            22

<210> SEQ ID NO 95
<211> LENGTH: 21
<212> TYPE: DNA
<213> ORGANISM: Artificial Sequence
<220> FEATURE:
<223> OTHER INFORMATION: Primer

<400> SEQUENCE: 95
agtgtcagag gaccatgctg g                                             21

<210> SEQ ID NO 96
<211> LENGTH: 23
<212> TYPE: DNA
<213> ORGANISM: Artificial Sequence
<220> FEATURE:
<223> OTHER INFORMATION: Primer

<400> SEQUENCE: 96
cttgaagcgt ccaactcatg tgc                                           23

<210> SEQ ID NO 97
<211> LENGTH: 26
<212> TYPE: DNA
<213> ORGANISM: Artificial Sequence
<220> FEATURE:
<223> OTHER INFORMATION: Primer

<400> SEQUENCE: 97
aactcataca tttgagcact gttgcc                                        26

<210> SEQ ID NO 98
<211> LENGTH: 23
<212> TYPE: DNA
<213> ORGANISM: Artificial Sequence
<220> FEATURE:
<223> OTHER INFORMATION: Primer

<400> SEQUENCE: 98
tgaggaggtg gggaatgcta atg                                           23

<210> SEQ ID NO 99
<211> LENGTH: 21
<212> TYPE: DNA
<213> ORGANISM: Artificial Sequence
<220> FEATURE:
<223> OTHER INFORMATION: Primer

<400> SEQUENCE: 99
acatagcaga gggctgctca c                                             21

<210> SEQ ID NO 100
<211> LENGTH: 21
<212> TYPE: DNA
<213> ORGANISM: Artificial Sequence
<220> FEATURE:
<223> OTHER INFORMATION: Primer

<400> SEQUENCE: 100
```

```
actgacctgt gggaacctgt g                                              21
```

<210> SEQ ID NO 101
<211> LENGTH: 26
<212> TYPE: DNA
<213> ORGANISM: Artificial Sequence
<220> FEATURE:
<223> OTHER INFORMATION: Primer

<400> SEQUENCE: 101

```
aatgctaggc atcatccctc ttctag                                         26
```

<210> SEQ ID NO 102
<211> LENGTH: 26
<212> TYPE: DNA
<213> ORGANISM: Artificial Sequence
<220> FEATURE:
<223> OTHER INFORMATION: Primer

<400> SEQUENCE: 102

```
aacatctaat agggactgag tgaccc                                         26
```

<210> SEQ ID NO 103
<211> LENGTH: 22
<212> TYPE: DNA
<213> ORGANISM: Artificial Sequence
<220> FEATURE:
<223> OTHER INFORMATION: Primer

<400> SEQUENCE: 103

```
ttctgtggtg ccttggcaag ag                                             22
```

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104

```
cacacataca cacacactaa gtgcc                                          25
```

<210> SEQ ID NO 105
<211> LENGTH: 32
<212> TYPE: DNA
<213> ORGANISM: Artificial Sequence
<220> FEATURE:
<223> OTHER INFORMATION: Primer

<400> SEQUENCE: 105

```
tggtagttac ttaaagttta caagaatgta gg                                  32
```

<210> SEQ ID NO 106
<211> LENGTH: 28
<212> TYPE: DNA
<213> ORGANISM: Artificial Sequence
<220> FEATURE:
<223> OTHER INFORMATION: Primer

<400> SEQUENCE: 106

```
aaatgctggg ataaaaagca tgaaccac                                       28
```

<210> SEQ ID NO 107
<211> LENGTH: 25
<212> TYPE: DNA
<213> ORGANISM: Artificial Sequence
<220> FEATURE:
<223> OTHER INFORMATION: Primer

<400> SEQUENCE: 107
ttcagttacc taatgggcac aaggc                          25

<210> SEQ ID NO 108
<211> LENGTH: 23
<212> TYPE: DNA
<213> ORGANISM: Artificial Sequence
<220> FEATURE:
<223> OTHER INFORMATION: Primer

<400> SEQUENCE: 108
acgacactga cctcttgcac ttg                            23

<210> SEQ ID NO 109
<211> LENGTH: 26
<212> TYPE: DNA
<213> ORGANISM: Artificial Sequence
<220> FEATURE:
<223> OTHER INFORMATION: Primer

<400> SEQUENCE: 109
tgtacaccct gaatgtctga acattc                         26

<210> SEQ ID NO 110
<211> LENGTH: 25
<212> TYPE: DNA
<213> ORGANISM: Artificial Sequence
<220> FEATURE:
<223> OTHER INFORMATION: Primer

<400> SEQUENCE: 110
gcgttcattt ctgctcctgt aatgg                          25

<210> SEQ ID NO 111
<211> LENGTH: 24
<212> TYPE: DNA
<213> ORGANISM: Artificial Sequence
<220> FEATURE:
<223> OTHER INFORMATION: Primer

<400> SEQUENCE: 111
tgagctctta atccctgcca ttcc                           24

<210> SEQ ID NO 112
<211> LENGTH: 22
<212> TYPE: DNA
<213> ORGANISM: Artificial Sequence
<220> FEATURE:
<223> OTHER INFORMATION: Primer

<400> SEQUENCE: 112
tagggcttgt ccgtccataa gg                             22

<210> SEQ ID NO 113
<211> LENGTH: 25
<212> TYPE: DNA
<213> ORGANISM: Artificial Sequence
<220> FEATURE:
<223> OTHER INFORMATION: Primer

<400> SEQUENCE: 113
tgttacggag atgaaaggct agacc                          25

```
<210> SEQ ID NO 114
<211> LENGTH: 22
<212> TYPE: DNA
<213> ORGANISM: Artificial Sequence
<220> FEATURE:
<223> OTHER INFORMATION: Primer

<400> SEQUENCE: 114
taagccctgc actaacccac tc                                      22

<210> SEQ ID NO 115
<211> LENGTH: 25
<212> TYPE: DNA
<213> ORGANISM: Artificial Sequence
<220> FEATURE:
<223> OTHER INFORMATION: Primer

<400> SEQUENCE: 115
tgttttgaga ggtgagcctt ctagc                                   25

<210> SEQ ID NO 116
<211> LENGTH: 25
<212> TYPE: DNA
<213> ORGANISM: Artificial Sequence
<220> FEATURE:
<223> OTHER INFORMATION: Primer

<400> SEQUENCE: 116
catgtcctac agttctgcta tcacc                                   25

<210> SEQ ID NO 117
<211> LENGTH: 26
<212> TYPE: DNA
<213> ORGANISM: Artificial Sequence
<220> FEATURE:
<223> OTHER INFORMATION: Primer

<400> SEQUENCE: 117
cttttcttca tccaattccc cacgag                                  26

<210> SEQ ID NO 118
<211> LENGTH: 24
<212> TYPE: DNA
<213> ORGANISM: Artificial Sequence
<220> FEATURE:
<223> OTHER INFORMATION: Primer

<400> SEQUENCE: 118
tctctaagct gcactgttgt ggct                                    24

<210> SEQ ID NO 119
<211> LENGTH: 24
<212> TYPE: DNA
<213> ORGANISM: Artificial Sequence
<220> FEATURE:
<223> OTHER INFORMATION: Primer

<400> SEQUENCE: 119
tggaagccaa gagtcttgag ttgc                                    24

<210> SEQ ID NO 120
<211> LENGTH: 28
<212> TYPE: DNA
<213> ORGANISM: Artificial Sequence
<220> FEATURE:
<223> OTHER INFORMATION: Primer
```

<400> SEQUENCE: 120
gtctgcattt taaatgcaga gtgtaagc    28

<210> SEQ ID NO 121
<211> LENGTH: 25
<212> TYPE: DNA
<213> ORGANISM: Artificial Sequence
<220> FEATURE:
<223> OTHER INFORMATION: Primer

<400> SEQUENCE: 121
cgaaacgcac gcacattttt accag    25

<210> SEQ ID NO 122
<211> LENGTH: 26
<212> TYPE: DNA
<213> ORGANISM: Artificial Sequence
<220> FEATURE:
<223> OTHER INFORMATION: Primer

<400> SEQUENCE: 122
gtgtgattta gcatctgtcg cacttg    26

<210> SEQ ID NO 123
<211> LENGTH: 26
<212> TYPE: DNA
<213> ORGANISM: Artificial Sequence
<220> FEATURE:
<223> OTHER INFORMATION: Primer

<400> SEQUENCE: 123
tgtatgtata acccaacaat cgctgc    26

<210> SEQ ID NO 124
<211> LENGTH: 26
<212> TYPE: DNA
<213> ORGANISM: Artificial Sequence
<220> FEATURE:
<223> OTHER INFORMATION: Primer

<400> SEQUENCE: 124
tccagagtac agggagaaac taaagg    26

<210> SEQ ID NO 125
<211> LENGTH: 94
<212> TYPE: PRT
<213> ORGANISM: Homo sapiens
<220> FEATURE:
<223> OTHER INFORMATION: Primer

<400> SEQUENCE: 125

Phe Arg Asn His Pro Asn Ile Thr Phe Phe Val Tyr Val Ser Asn Phe
1               5                   10                  15

Thr Trp Pro Ile Lys Ile Gln Ile Ala Phe Ser Gln His Ser Asn Phe
            20                  25                  30

Met Asp Leu Val Gln Phe Phe Val Thr Phe Phe Ser Cys Phe Leu Ser
        35                  40                  45

Leu Leu Leu Val Ala Ala Val Val Trp Lys Ile Lys Gln Ser Cys Trp
    50                  55                  60

Ala Ser Arg Arg Arg Glu Gln Leu Leu Arg Glu Met Gln Gln Met Ala
65                  70                  75                  80

Ser Arg Pro Phe Ala Ser Val Glu Thr Leu Pro Trp Asn Arg

```
                    85                  90

<210> SEQ ID NO 126
<211> LENGTH: 113
<212> TYPE: PRT
<213> ORGANISM: Homo sapiens

<400> SEQUENCE: 126

Phe Arg Ser Asn Pro Asn Ile Thr Phe Tyr Val Tyr Val Ser Asn Phe
 1               5                  10                  15

Ser Trp Pro Ile Lys Ile Gln Ile Ala Phe Ser Gln His Asn Thr Ile
            20                  25                  30

Met Asp Leu Val Gln Phe Phe Val Thr Phe Phe Ser Cys Phe Leu Ser
        35                  40                  45

Leu Leu Leu Val Ala Ala Val Val Trp Lys Ile Lys Gln Thr Cys Trp
    50                  55                  60

Ala Ser Arg Arg Arg Glu Gln Leu Leu Arg Glu Arg Gln Gln Met Ala
65                  70                  75                  80

Ser Arg Pro Phe Ala Ser Val Asp Val Ala Leu Glu Val Gly Ala Glu
                85                  90                  95

Gln Thr Glu Phe Leu Arg Gly Pro Leu Glu Gly Ala Pro Lys Pro Ile
            100                 105                 110

Ala

<210> SEQ ID NO 127
<211> LENGTH: 100
<212> TYPE: PRT
<213> ORGANISM: Homo sapiens

<400> SEQUENCE: 127

Phe Gly Pro Asp Ser Asn Thr Thr Phe Phe Val Arg Val Tyr Asn Phe
 1               5                  10                  15

Asn Thr Pro Val Gln Ile Val Val Ser Phe Ala Gln Ser Pro Pro Ile
            20                  25                  30

Asn Trp Val Leu Phe Phe Val Ile Phe Ala Ala Cys Phe Ile Val Leu
        35                  40                  45

Leu Val Val Ala Gly Leu Leu Trp Met Ile Lys Val Arg Ile Glu Ala
    50                  55                  60

Tyr Arg Arg Asn Gln Arg Arg Ile Asp Glu Ile Glu His Met Ala Ser
65                  70                  75                  80

Arg Pro Phe Ala Ser Thr Lys Met Glu Leu Ser Met Leu Ser Gln Phe
                85                  90                  95

Ser Ser Ala Gly
            100

<210> SEQ ID NO 128
<211> LENGTH: 118
<212> TYPE: PRT
<213> ORGANISM: Homo sapiens

<400> SEQUENCE: 128

Leu Lys Ser Ser Arg Phe Tyr Leu Leu Leu Gly Val Gly Asp Pro
 1               5                  10                  15

Ser Gly Pro Gly Ala Asn Gly Ser Ala Asp Ser Gln Gly Leu Leu Phe
            20                  25                  30

Phe Arg Gln Asp Gln Ala His Ile Asp Leu Phe Val Phe Phe Ser Val
        35                  40                  45
```

```
Phe Phe Ser Cys Phe Phe Leu Phe Leu Ser Leu Cys Val Leu Leu Trp
     50                  55                  60

Lys Ala Lys Gln Ala Leu Asp Gln Arg Gln Glu Gln Arg Arg His Leu
 65                  70                  75                  80

Gln Glu Met Thr Lys Met Ala Ser Arg Pro Phe Ala Lys Val Thr Val
                 85                  90                  95

Cys Phe Pro Pro Asp Pro Thr Pro Ala Ser Ala Trp Lys Pro Ala
                100                 105                 110

Gly Leu Pro Pro Pro Ala
            115
```

<210> SEQ ID NO 129
<211> LENGTH: 11
<212> TYPE: DNA
<213> ORGANISM: Artificial Sequence
<220> FEATURE:
<223> OTHER INFORMATION: Primer

<400> SEQUENCE: 129
ttcctcactg g         11

<210> SEQ ID NO 130
<211> LENGTH: 10
<212> TYPE: DNA
<213> ORGANISM: Artificial Sequence
<220> FEATURE:
<223> OTHER INFORMATION: Primer

<400> SEQUENCE: 130
ggacacacag         10

<210> SEQ ID NO 131
<211> LENGTH: 1429
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid

<400> SEQUENCE: 131

```
Met Val Ala Val Ala Ala Ala Ala Thr Glu Ala Arg Leu Arg Gly
 1               5                  10                  15

Ser Thr Thr Thr Thr Ala Ala Pro Ala Gly Arg Lys Gly Arg Gln His
                 20                  25                  30

Arg Pro Cys Thr Ala Thr Gly Ala Trp Arg Pro Gly Pro Arg Ala Arg
                 35                  40                  45

Leu Cys Leu Pro Arg Val Leu Ser Arg Ala Leu Pro Pro Pro Leu
     50                  55                  60

Leu Pro Leu Leu Phe Ser Leu Leu Leu Pro Leu Pro Arg Glu Ala
 65                  70                  75                  80

Glu Ala Ala Ala Val Ala Ala Val Ser Gly Ser Ala Ala Ala Glu
                 85                  90                  95

Ala Lys Glu Cys Asp Arg Pro Cys Val Asn Gly Gly Arg Cys Asn Pro
                100                 105                 110

Gly Thr Gly Gln Cys Val Cys Pro Thr Gly Trp Val Gly Glu Gln Cys
            115                 120                 125

Gln His Cys Gly Gly Arg Phe Arg Leu Thr Gly Ser Ser Gly Phe Val
        130                 135                 140

Thr Asp Gly Pro Gly Asn Tyr Lys Tyr Lys Thr Lys Cys Thr Trp Leu
```

```
                                              -continued
145                 150                 155                 160
Ile Glu Gly Gln Pro Asn Xaa Ile Met Arg Leu Arg Phe Asn His Phe
                    165                 170                 175
Ala Thr Glu Cys Ser Trp Asp His Leu Tyr Val Tyr Asp Gly Asp Ser
                180                 185                 190
Ile Tyr Ala Pro Leu Ile Ala Ala Phe Ser Gly Leu Ile Val Pro Glu
                195                 200                 205
Arg Asp Gly Asn Glu Thr Ala Pro Glu Val Thr Ala Thr Ser Gly Tyr
                210                 215                 220
Ala Leu Leu His Phe Phe Ser Asp Ala Ala Tyr Asn Leu Thr Gly Phe
225                 230                 235                 240
Asn Ile Thr Tyr Asn Phe Asp Met Cys Pro Asn Asn Cys Ser Gly Arg
                    245                 250                 255
Gly Glu Cys Lys Ser Ser Asn Ser Ser Ser Xaa Val Glu Cys Glu Cys
                260                 265                 270
Ser Glu Asn Trp Lys Gly Xaa Ala Cys Asp Ile Pro His Cys Thr Asp
                275                 280                 285
Asn Cys Gly Phe Pro His Arg Gly Ile Cys Asn Xaa Ser Asp Xaa Arg
                290                 295                 300
Gly Cys Ser Cys Phe Ser Asp Trp Gln Gly Pro Gly Cys Ser Val Pro
305                 310                 315                 320
Val Pro Ala Asn Gln Ser Phe Trp Thr Arg Glu Glu Tyr Ser Asn Leu
                    325                 330                 335
Lys Leu Pro Arg Ala Ser His Lys Ala Val Val Asn Gly Asn Ile Met
                340                 345                 350
Trp Val Val Gly Gly Tyr Met Phe Asn His Ser Asp Tyr Asn Met Val
                355                 360                 365
Leu Ala Tyr Asp Leu Ala Ser Arg Glu Trp Leu Pro Leu Asn Arg Ser
                370                 375                 380
Val Asn Asn Val Val Val Arg Tyr Gly His Ser Leu Ala Leu Tyr Lys
385                 390                 395                 400
Asp Lys Ile Tyr Met Tyr Gly Gly Lys Ile Asp Ser Thr Gly Asn Val
                    405                 410                 415
Thr Asn Glu Leu Arg Val Phe His Ile His Asn Glu Ser Trp Val Leu
                420                 425                 430
Leu Thr Pro Lys Ala Lys Glu Gln Tyr Ala Val Val Gly His Ser Ala
                435                 440                 445
His Ile Val Thr Leu Lys Asn Gly Arg Val Val Met Leu Val Ile Phe
                450                 455                 460
Gly His Cys Pro Leu Tyr Gly Tyr Ile Ser Asn Val Gln Glu Tyr Asp
465                 470                 475                 480
Leu Asp Lys Asn Thr Trp Ser Ile Leu His Thr Gln Gly Ala Leu Val
                    485                 490                 495
Gln Gly Gly Tyr Gly His Ser Ser Val Tyr Asp His Arg Thr Arg Ala
                500                 505                 510
Leu Tyr Val His Gly Gly Tyr Lys Ala Phe Ser Ala Asn Lys Tyr Arg
                515                 520                 525
Leu Ala Asp Asp Leu Tyr Arg Tyr Asp Val Asp Thr Gln Met Trp Thr
                530                 535                 540
Ile Leu Lys Asp Ser Arg Phe Phe Arg Tyr Leu His Thr Ala Val Ile
545                 550                 555                 560
Val Ser Gly Thr Met Leu Val Phe Gly Gly Asn Thr His Asn Asp Thr
                    565                 570                 575
```

```
Ser Met Ser His Gly Ala Lys Cys Phe Ser Ser Asp Phe Met Ala Tyr
            580                 585                 590

Asp Ile Ala Cys Asp Arg Trp Ser Val Leu Pro Arg Pro Asp Leu His
            595                 600                 605

His Asp Val Asn Arg Phe Gly His Ser Ala Val Leu His Asn Ser Thr
            610                 615                 620

Met Tyr Val Phe Gly Gly Phe Asn Ser Leu Leu Leu Ser Asp Ile Leu
625                 630                 635                 640

Val Phe Thr Ser Glu Gln Cys Asp Ala His Arg Ser Glu Ala Ala Cys
                    645                 650                 655

Leu Ala Ala Gly Pro Gly Ile Arg Cys Val Trp Asn Thr Gly Ser Ser
                660                 665                 670

Gln Cys Ile Ser Trp Ala Leu Ala Thr Asp Glu Gln Glu Glu Lys Leu
            675                 680                 685

Lys Ser Glu Cys Phe Ser Lys Arg Thr Leu Asp His Asp Arg Cys Asp
            690                 695                 700

Gln His Thr Asp Cys Tyr Ser Cys Thr Ala Asn Thr Asn Asp Cys His
705                 710                 715                 720

Trp Cys Asn Asp His Cys Val Pro Arg Asn His Ser Cys Ser Glu Gly
                725                 730                 735

Gln Ile Ser Ile Phe Arg Tyr Glu Asn Cys Pro Lys Asp Asn Pro Met
                740                 745                 750

Tyr Tyr Cys Asn Lys Lys Thr Ser Cys Arg Ser Cys Ala Leu Asp Gln
            755                 760                 765

Asn Cys Gln Trp Glu Pro Arg Asn Gln Glu Cys Ile Ala Leu Pro Glu
770                 775                 780

Asn Ile Cys Gly Ile Gly Trp His Leu Val Gly Asn Ser Cys Leu Lys
785                 790                 795                 800

Ile Thr Thr Ala Lys Glu Asn Tyr Asp Asn Ala Lys Leu Phe Cys Arg
                805                 810                 815

Asn His Asn Ala Leu Leu Ala Ser Leu Thr Thr Gln Lys Lys Val Glu
            820                 825                 830

Phe Val Leu Lys Gln Leu Arg Ile Met Gln Ser Ser Gln Ser Met Ser
            835                 840                 845

Lys Leu Thr Leu Thr Pro Trp Val Gly Leu Arg Lys Ile Asn Val Ser
850                 855                 860

Tyr Trp Cys Trp Glu Asp Met Ser Pro Phe Thr Asn Ser Leu Leu Gln
865                 870                 875                 880

Trp Met Pro Ser Glu Pro Ser Asp Ala Gly Phe Cys Gly Ile Leu Ser
                885                 890                 895

Glu Pro Ser Thr Arg Gly Leu Lys Ala Ala Thr Cys Ile Asn Pro Leu
            900                 905                 910

Asn Gly Ser Val Cys Glu Arg Pro Ala Asn His Ser Ala Lys Gln Cys
            915                 920                 925

Arg Thr Pro Cys Ala Leu Arg Thr Ala Cys Gly Asp Cys Thr Ser Gly
            930                 935                 940

Ser Ser Glu Cys Met Trp Cys Ser Asn Met Lys Gln Cys Val Asp Ser
945                 950                 955                 960

Asn Ala Tyr Val Ala Ser Phe Pro Phe Gly Gln Cys Met Glu Trp Tyr
                965                 970                 975

Thr Met Ser Thr Cys Pro Pro Glu Asn Cys Ser Gly Tyr Cys Thr Cys
                980                 985                 990
```

-continued

Ser His Cys Leu Glu Gln Pro Gly Cys Gly Trp Cys Thr Asp Pro Ser
        995                 1000                1005

Asn Thr Gly Lys Gly Lys Cys Ile Glu Gly Ser Tyr Lys Gly Pro Val
     1010                1015                1020

Lys Met Pro Ser Gln Ala Pro Thr Gly Asn Phe Tyr Pro Gln Pro Leu
1025                1030                1035                1040

Leu Asn Ser Ser Met Cys Leu Glu Asp Ser Arg Tyr Asn Trp Ser Phe
             1045                1050                1055

Ile His Cys Pro Ala Cys Gln Cys Asn Gly His Ser Lys Cys Ile Asn
             1060                1065                1070

Gln Ser Ile Cys Glu Lys Cys Glu Asn Leu Thr Thr Gly Lys His Cys
        1075                1080                1085

Glu Thr Cys Ile Ser Gly Phe Tyr Gly Asp Pro Thr Asn Gly Gly Lys
        1090                1095                1100

Cys Gln Pro Cys Lys Cys Asn Gly His Ala Ser Leu Cys Asn Thr Asn
1105                1110                1115                1120

Thr Gly Lys Cys Phe Cys Thr Thr Lys Gly Val Lys Gly Asp Glu Cys
             1125                1130                1135

Gln Leu Cys Glu Val Glu Asn Arg Tyr Gln Gly Asn Pro Leu Arg Gly
        1140                1145                1150

Thr Cys Tyr Tyr Thr Leu Leu Ile Asp Tyr Gln Phe Thr Phe Ser Leu
        1155                1160                1165

Ser Gln Glu Asp Asp Arg Tyr Tyr Thr Ala Ile Asn Phe Val Ala Thr
        1170                1175                1180

Pro Asp Glu Gln Asn Arg Asp Leu Asp Met Phe Ile Asn Ala Ser Lys
1185                1190                1195                1200

Asn Phe Asn Leu Asn Ile Thr Trp Ala Ala Ser Phe Ser Ala Gly Thr
             1205                1210                1215

Gln Ala Gly Glu Glu Met Pro Val Val Ser Lys Thr Asn Ile Lys Glu
        1220                1225                1230

Tyr Lys Asp Ser Phe Ser Asn Glu Lys Phe Asp Phe Arg Asn His Pro
        1235                1240                1245

Asn Ile Thr Phe Phe Val Tyr Val Ser Asn Phe Thr Trp Pro Ile Lys
        1250                1255                1260

Ile Gln Ile Ala Phe Ser Gln His Ser Asn Phe Met Asp Leu Val Gln
1265                1270                1275                1280

Phe Phe Val Thr Phe Phe Ser Cys Phe Leu Ser Leu Leu Val Ala
             1285                1290                1295

Ala Val Val Trp Lys Ile Lys Gln Ser Cys Trp Ala Ser Arg Arg Arg
             1300                1305                1310

Glu Gln Leu Leu Arg Glu Met Gln Gln Met Ala Ser Arg Pro Phe Ala
        1315                1320                1325

Ser Val Asn Val Ala Leu Glu Thr Asp Glu Pro Pro Asp Leu Ile
        1330                1335                1340

Gly Gly Ser Ile Lys Thr Val Pro Lys Pro Ile Ala Leu Glu Pro Cys
1345                1350                1355                1360

Phe Gly Asn Lys Ala Ala Val Leu Ser Val Phe Val Arg Leu Pro Arg
             1365                1370                1375

Gly Leu Gly Gly Ile Pro Pro Gly Gln Ser Gly Leu Ala Val Ala
             1380                1385                1390

Ser Ala Leu Val Asp Ile Ser Gln Gln Met Pro Ile Val Tyr Lys Glu
        1395                1400                1405

Lys Ser Gly Ala Val Arg Asn Arg Lys Gln Gln Pro Pro Ala Gln Pro

-continued

```
             1410              1415              1420
Gly Thr Cys Ile Asn
1425

<210> SEQ ID NO 132
<211> LENGTH: 1198
<212> TYPE: PRT
<213> ORGANISM: Homo sapiens

<400> SEQUENCE: 132

Met Val Ala Ala Ala Ala Thr Glu Ala Arg Leu Arg Arg Arg Thr
 1               5                  10                  15

Ala Ala Thr Ala Ala Leu Ala Gly Arg Ser Gly Gly Pro His Cys Val
                20                  25                  30

Asn Gly Gly Arg Cys Asn Pro Gly Thr Gly Gln Cys Val Cys Pro Ala
                35                  40                  45

Gly Trp Val Gly Glu Gln Cys Gln His Cys Gly Gly Arg Phe Arg Leu
    50                  55                  60

Thr Gly Ser Ser Gly Phe Val Thr Asp Gly Pro Gly Asn Tyr Lys Tyr
65                  70                  75                  80

Lys Thr Lys Cys Thr Trp Leu Ile Glu Gly Gln Pro Asn Arg Ile Met
                85                  90                  95

Arg Leu Arg Phe Asn His Phe Ala Thr Glu Cys Ser Trp Asp His Leu
                100                 105                 110

Tyr Val Tyr Asp Gly Asp Ser Ile Tyr Ala Pro Leu Val Ala Ala Phe
                115                 120                 125

Ser Gly Leu Ile Val Pro Glu Arg Asp Gly Asn Glu Thr Val Pro Glu
    130                 135                 140

Val Val Ala Thr Ser Gly Tyr Ala Leu Leu His Phe Phe Ser Asp Ala
145                 150                 155                 160

Ala Tyr Asn Leu Thr Gly Phe Asn Ile Thr Tyr Ser Phe Asp Met Cys
                165                 170                 175

Pro Asn Asn Cys Ser Gly Arg Gly Glu Cys Lys Ile Ser Asn Ser Ser
                180                 185                 190

Asp Thr Val Glu Cys Glu Cys Ser Glu Asn Trp Lys Gly Glu Ala Cys
                195                 200                 205

Asp Ile Pro His Cys Thr Asp Asn Cys Gly Phe Pro His Arg Gly Ile
    210                 215                 220

Cys Asn Ser Ser Asp Val Arg Gly Cys Ser Cys Phe Ser Asp Trp Gln
225                 230                 235                 240

Gly Pro Gly Cys Ser Val Pro Val Pro Ala Asn Gln Ser Phe Trp Thr
                245                 250                 255

Arg Glu Glu Tyr Ser Asn Leu Lys Leu Pro Arg Ala Ser His Lys Ala
                260                 265                 270

Val Val Asn Gly Asn Ile Met Trp Val Val Gly Gly Tyr Met Phe Asn
                275                 280                 285

His Ser Asp Tyr Asn Met Val Leu Ala Tyr Asp Leu Ala Ser Arg Glu
    290                 295                 300

Trp Leu Pro Leu Asn Arg Ser Val Asn Val Val Arg Tyr Gly
305                 310                 315                 320

His Ser Leu Ala Leu Tyr Lys Asp Lys Ile Tyr Met Tyr Gly Gly Lys
                325                 330                 335

Ile Asp Ser Thr Gly Asn Val Thr Asn Glu Leu Arg Val Phe His Ile
                340                 345                 350
```

-continued

```
His Asn Glu Ser Trp Val Leu Leu Thr Pro Lys Ala Lys Glu Gln Tyr
            355                 360                 365

Ala Val Val Gly His Ser Ala His Ile Val Thr Leu Lys Asn Gly Arg
            370                 375                 380

Val Val Met Leu Val Ile Phe Gly His Cys Pro Leu Tyr Gly Tyr Ile
385                 390                 395                 400

Ser Asn Val Gln Glu Tyr Asp Leu Asp Lys Asn Thr Trp Ser Ile Leu
            405                 410                 415

His Thr Gln Gly Ala Leu Val Gln Gly Gly Tyr Gly His Ser Ser Val
            420                 425                 430

Tyr Asp His Arg Thr Arg Ala Leu Tyr Val His Gly Tyr Lys Ala
            435                 440                 445

Phe Ser Ala Asn Lys Tyr Arg Leu Ala Asp Asp Leu Tyr Arg Tyr Asp
            450                 455                 460

Val Asp Thr Gln Met Trp Thr Ile Leu Lys Asp Ser Arg Phe Phe Arg
465                 470                 475                 480

Tyr Leu His Thr Ala Val Ile Val Ser Gly Thr Met Leu Val Phe Gly
            485                 490                 495

Gly Asn Thr His Asn Asp Thr Ser Met Ser His Gly Ala Lys Cys Phe
            500                 505                 510

Ser Ser Asp Phe Met Ala Tyr Asp Ile Ala Cys Asp Arg Trp Ser Val
            515                 520                 525

Leu Pro Arg Pro Asp Ser Thr Met Met Ser Thr Asp Leu Ala Ile Pro
            530                 535                 540

Ala Val Leu His Asn Ser Thr Met Tyr Val Phe Gly Gly Phe Asn Ser
545                 550                 555                 560

Leu Leu Leu Ser Asp Ile Leu Val Phe Thr Ser Glu Gln Cys Asp Ala
            565                 570                 575

His Arg Ser Glu Ala Ala Cys Leu Ala Ala Gly Pro Gly Ile Arg Cys
            580                 585                 590

Val Trp Asn Thr Gly Ser Ser Gln Cys Ile Ser Trp Ala Leu Ala Thr
            595                 600                 605

Asp Glu Gln Glu Glu Lys Leu Lys Ser Glu Cys Phe Ser Lys Arg Thr
            610                 615                 620

Leu Asp His Asp Arg Cys Asp Gln His Thr Asp Cys Tyr Ser Cys Thr
625                 630                 635                 640

Ala Asn Thr Asn Asp Cys His Trp Cys Asn Asp His Cys Val Pro Arg
            645                 650                 655

Asn His Ser Cys Ser Glu Gly Gln Ile Ser Ile Phe Arg Tyr Glu Asn
            660                 665                 670

Cys Pro Lys Asp Asn Pro Met Tyr Tyr Cys Asn Lys Lys Thr Ser Cys
            675                 680                 685

Arg Ser Cys Ala Leu Asp Gln Asn Cys Gln Trp Glu Pro Arg Asn Gln
            690                 695                 700

Glu Cys Ile Ala Leu Pro Glu Asn Ile Cys Gly Ile Gly Trp His Leu
705                 710                 715                 720

Val Gly Asn Ser Cys Leu Lys Ile Thr Thr Ala Lys Glu Asn Tyr Asp
            725                 730                 735

Asn Ala Lys Leu Phe Cys Arg Asn His Asn Ala Leu Leu Ala Ser Leu
            740                 745                 750

Thr Thr Gln Lys Lys Val Glu Phe Val Leu Lys Gln Leu Arg Ile Met
            755                 760                 765

Gln Ser Ser Gln Ser Met Ser Lys Leu Thr Leu Thr Pro Trp Val Gly
```

-continued

```
            770              775              780
Leu Arg Lys Ile Asn Val Ser Tyr Trp Cys Trp Glu Asp Met Ser Pro
785              790              795              800
Phe Thr Asn Ser Leu Leu Gln Trp Met Pro Ser Glu Pro Ser Asp Ala
             805              810              815
Gly Phe Cys Gly Ile Leu Ser Glu Pro Ser Thr Arg Gly Leu Lys Ala
             820              825              830
Ala Thr Cys Ile Asn Pro Leu Asn Gly Ser Val Cys Glu Arg Pro Ala
             835              840              845
Asn His Ser Ala Lys Gln Cys Arg Thr Pro Cys Ala Leu Arg Thr Ala
             850              855              860
Cys Gly Asp Cys Thr Ser Gly Ser Ser Glu Cys Met Trp Cys Ser Asn
865              870              875              880
Met Lys Gln Cys Val Asp Ser Asn Ala Tyr Val Ala Ser Phe Pro Phe
             885              890              895
Gly Gln Cys Met Glu Trp Tyr Thr Met Ser Thr Cys Pro Pro Glu Asn
             900              905              910
Cys Ser Gly Tyr Cys Thr Cys Ser His Cys Leu Glu Gln Pro Gly Cys
             915              920              925
Gly Trp Cys Thr Asp Pro Ser Asn Thr Gly Lys Gly Lys Cys Ile Glu
             930              935              940
Gly Ser Tyr Lys Gly Pro Val Lys Met Pro Ser Gln Ala Pro Thr Gly
945              950              955              960
Asn Phe Tyr Pro Gln Pro Leu Leu Asn Ser Ser Met Cys Leu Glu Asp
             965              970              975
Ser Arg Tyr Asn Trp Ser Phe Ile His Cys Pro Ala Cys Gln Cys Asn
             980              985              990
Gly His Ser Lys Cys Ile Asn Gln Ser Ile Cys Glu Lys Cys Glu Asn
             995              1000             1005
Leu Thr Thr Gly Lys His Cys Glu Thr Cys Ile Ser Gly Phe Tyr Gly
             1010             1015             1020
Asp Pro Thr Asn Gly Gly Lys Cys Gln Pro Cys Lys Cys Asn Gly His
1025             1030             1035             1040
Ala Ser Leu Cys Asn Thr Asn Thr Gly Lys Cys Phe Cys Thr Thr Lys
             1045             1050             1055
Gly Val Lys Gly Asp Glu Cys Gln Leu Cys Glu Val Glu Asn Arg Tyr
             1060             1065             1070
Gln Gly Asn Pro Leu Arg Gly Thr Cys Tyr Tyr Thr Leu Leu Ile Asp
             1075             1080             1085
Tyr Gln Phe Thr Phe Ser Leu Ser Gln Glu Asp Asp Arg Tyr Tyr Thr
             1090             1095             1100
Ala Ile Asn Phe Val Ala Thr Pro Asp Glu Gln Asn Arg Asp Leu Asp
1105             1110             1115             1120
Met Phe Ile Asn Ala Ser Lys Asn Phe Asn Leu Asn Ile Thr Trp Ala
             1125             1130             1135
Ala Ser Phe Ser Ala Gly Thr Gln Ala Gly Glu Glu Met Pro Val Val
             1140             1145             1150
Ser Lys Thr Asn Ile Lys Glu Tyr Lys Asp Ser Phe Ser Asn Glu Lys
             1155             1160             1165
Phe Asp Phe Arg Asn His Pro Asn Ile Thr Phe Phe Val Tyr Val Ser
             1170             1175             1180
Asn Phe Thr Trp Pro Ile Lys Ile Gln Val Gln Thr Glu Gln
1185             1190             1195
```

<210> SEQ ID NO 133
<211> LENGTH: 504
<212> TYPE: DNA
<213> ORGANISM: Soares Mouse
<220> FEATURE:
<221> NAME/KEY: misc_feature
<222> LOCATION: (1)..(504)
<223> OTHER INFORMATION: n = a, c, g or t

<400> SEQUENCE: 133

| | | | | | |
|---|---|---|---|---|---|
| caaagaatga | ccatatctta | caaccacact | gttcacagaa | tggtttagtg | gaagccattc | 60 |
| cctagaagtc | aggtcatacg | ctaaaaccat | gctgtaatct | gaatggttga | acatatatcc | 120 |
| gccaacaacc | cacattatat | ttccattgac | cacagcttta | tgagaggctc | tgggaagctt | 180 |
| taaatcagaa | tattcttctc | gagtccaaaa | agactggtta | gctggcacag | gaattgagca | 240 |
| tccaggaccc | tgccagtgag | gaaagcagga | gcaccctctg | gtatcgcttg | cattacagat | 300 |
| gcctcggtga | ggaaagccac | agttgtctgt | acagtgagga | atgtcacacg | actcccettt | 360 |
| ccagttttca | gaacattcac | actcaacagc | gctgctgctg | ttactgctct | tacactctcc | 420 |
| tcgggctgag | caattattcg | gacacatggt | caaattgtaa | gtgatattaa | atccagtcag | 480 |
| attataagca | gcatcactga | aaaa | | | | 504 |

<210> SEQ ID NO 134
<211> LENGTH: 396
<212> TYPE: DNA
<213> ORGANISM: Homo sapiens
<220> FEATURE:
<221> NAME/KEY: misc_feature
<222> LOCATION: (1)..(396)
<223> OTHER INFORMATION: n = a, c, g or t

<400> SEQUENCE: 134

| | | | | | |
|---|---|---|---|---|---|
| tatgatttgg | ataagaacac | atggagtata | ttacacaccc | agggtgccct | tgtgcaaggg | 60 |
| ggttacggcc | atagcagtgt | ttacgaccat | aggaccaggg | ccctatacgt | tnatggtggc | 120 |
| tacaaggctt | tcagtgccaa | taagtaccgg | cttgcagatg | atctctaccg | atatgatgtg | 180 |
| gatacccaga | tgtggaccat | tcttaaggac | agccgatttt | tccgttactt | gcacacagct | 240 |
| gtgatagtga | gtggaaccat | gctggtgttt | ggaggaaaca | cacacaatga | cacatctatg | 300 |
| agccatggcg | ccaaatgctt | ctcttcagat | ttcatggcct | atgacattgc | ctgtgaccgc | 360 |
| tggtcagtgc | ttnccagacc | tgatcttcac | catgat | | | 396 |

<210> SEQ ID NO 135
<211> LENGTH: 416
<212> TYPE: DNA
<213> ORGANISM: Homo Sapiens
<220> FEATURE:
<221> NAME/KEY: misc_feature
<222> LOCATION: (1)..(416)
<223> OTHER INFORMATION: n = a, c, g or t

<400> SEQUENCE: 135

| | | | | | |
|---|---|---|---|---|---|
| atgtactact | gtaacaagaa | gaccagctgc | aggagctgtg | ccctggacca | gaactgccag | 60 |
| tgggagcccc | ggaatcagga | gtgcattgcc | ctgcccgaaa | atatctgtgg | cattggctgg | 120 |
| catttggttg | gaaactcatg | tttgaaaatt | actactgcca | aggagaatta | tgacaatgct | 180 |
| aaattgttct | gtaggaacca | caatgccctt | tggcttctc | ttacaaccca | gaagaaggta | 240 |
| ggaatttgtc | cttaaggcag | gctgcgaata | atgcaggtca | tctcagaggc | atgtccaagg | 300 |

| | |
|---|---|
| ctcaccttaa ccccatgggg tcgggccttc gggnaggtcc aatgtgtncc tacttggtgc | 360 |
| tngggagga tattgtcccc cttttaccaa ataggtttta ctacagtggg gtgccc | 416 |

<210> SEQ ID NO 136
<211> LENGTH: 517
<212> TYPE: DNA
<213> ORGANISM: Homo Sapiens
<220> FEATURE:
<221> NAME/KEY: misc_feature
<222> LOCATION: (1)..(517)
<223> OTHER INFORMATION: n = a, c, g or t

<400> SEQUENCE: 136

| | |
|---|---|
| agggagctgt nccntggacc agaactgcca gtgggagccc cggaatcagg agtgcattcc | 60 |
| ctgcccgaaa atatctgtgg cattggctgg catttggttg gaaactcatg tttgaaaatt | 120 |
| actactgcca aggagaatta tgacaatgct aaattgttct gtaggaacca caatgccctt | 180 |
| ttggcttctc ttacaaccca gaagaagta gaatttgtcc ttaagcagct gcganataat | 240 |
| gcagtcatct cagagcatgt ccaagctcac cttaacccca tgggtccggg ccttcgggaa | 300 |
| ggntcaattg tgtcctactg ggtgctgggg aaggatatgt tccccatttt acaantagtt | 360 |
| ttacttacag tnggatggcc gtcttgaggc ccagttgatg cttgganttc tgttggggat | 420 |
| ttttattcag gaacccagtt acttcggggg gattnaaggg gctggcaacc ntgcattcaa | 480 |
| anccactca ntgggtangt tttctgttgn aaagggc | 517 |

<210> SEQ ID NO 137
<211> LENGTH: 355
<212> TYPE: DNA
<213> ORGANISM: Homo Sapiens
<220> FEATURE:
<221> NAME/KEY: misc_feature
<222> LOCATION: (1)..(355)
<223> OTHER INFORMATION: n = a, c, g or t

<400> SEQUENCE: 137

| | |
|---|---|
| tagaatttgt ccttaagcag ctncnnataa tgcagtcatc tcagagcatg tccaagctca | 60 |
| ccttaaccccc atggtcggcc ttcggaagat caatgtgtcc tactggtgct gggaagatat | 120 |
| gtccccattt acaaatagtt tactacagtg atgccgtct gagcccagtg atgctggatt | 180 |
| ctgtggaatt ttatcagaac ccagtacttc ggggactgaa ggctgcaacc tgcattcaac | 240 |
| ccacttcaat ggtagtgtct gtgaaaaggc ctggcaaacc acagtggtta agcagtnccg | 300 |
| gnacaccatg gtgccctttg agggacagca tgtgggaaga tttgtcacca gcggg | 355 |

<210> SEQ ID NO 138
<211> LENGTH: 527
<212> TYPE: DNA
<213> ORGANISM: Homo Sapiens
<220> FEATURE:
<221> NAME/KEY: misc_feature
<222> LOCATION: (1)..(527)
<223> OTHER INFORMATION: n = a, c, g or t

<400> SEQUENCE: 138

| | |
|---|---|
| gggattctgt gggaatttta ttcaggaacc cagttacttc ggggactgaa ggctgncaac | 60 |
| ctgncattca acccacttca atggtagtgt ctgtgaaagg cctgcaaacc acagtgctaa | 120 |
| ggcagtgccg gacaccatgt gcctgaggac agcatgtgga gattgcacca gcggcanttc | 180 |
| tgagtggcat gtggtgcagc aacatgaagg cagtgtgtgg actccaatgc ctatgtggcc | 240 |
| tccttccctt ttgggccagt gtatggaatg gtatacgatg aggcacctgc cccctgaaa | 300 |

```
attgttcagg ctactgtacc tgtagtcatt gcttggagca accagggctg tngctggtgt      360
actgatccca gcaatactgg caaagggaaa tgcatagagg gttcctataa aggaccagtg      420
aagatgcctt cgcaagcccc tacangaaat ttctatccac agcccctgct caattncagc      480
atgtgtctag aggncagcag gtacaacttg gctttcatta ctttcca                   527
```

<210> SEQ ID NO 139
<211> LENGTH: 400
<212> TYPE: DNA
<213> ORGANISM: Homo Sapiens
<220> FEATURE:
<221> NAME/KEY: misc_feature
<222> LOCATION: (1)..(400)
<223> OTHER INFORMATION: n = a, c, g or t

<400> SEQUENCE: 139

```
gggcttgcga aggcatcttc actggtcctt tataggaacc ctctatgcat ttcccttcgc       60
cagtattgct gggatcagta caccagccac agcctggttg ctccaagcaa tgactacagg      120
tacagtagcc tgaacaattt tcaggggggc aggtgctcat cgtataccat tccatacact      180
ggccaaaagg gaaggaggcc acataggcat tggagtccac acactgcttc atgttgctgc      240
accacatgca ctcagagctn ccgctggtgc aatctccaca tgctgtcctc aaggcacatg      300
gtgtccggca ctgcttagca ctgtggtttg caggnctttn acagacacta ccatttgagt      360
gggttgatgc aggttgcagc ctttcagtnc ccgnggtact                            400
```

<210> SEQ ID NO 140
<211> LENGTH: 230
<212> TYPE: DNA
<213> ORGANISM: Homo Sapiens
<220> FEATURE:
<221> NAME/KEY: misc_feature
<222> LOCATION: (1)..(230)
<223> OTHER INFORMATION: n = a, c, g or t

<400> SEQUENCE: 140

```
ctcaatggta gtntctgtga aaggcctgca aaccacagtg ctaagcagtg ccggacacca       60
tgtgccttga ggacagcatg tggagattgc accagcggca gctctgagtg catgtggtgc      120
agcaacatga agcagtntgt ggactccaat gcctatntgg cctccttccc ttttggccag      180
tgtatggaat ngtatacgat gagcacctgc cccctgaaa attttttcagg                 230
```

<210> SEQ ID NO 141
<211> LENGTH: 5632
<212> TYPE: DNA
<213> ORGANISM: Homo Sapiens
<220> FEATURE:
<221> NAME/KEY: misc_feature
<222> LOCATION: (1)..(5632)
<223> OTHER INFORMATION: n = a, c, g or t

<400> SEQUENCE: 141

```
atacgatgag cacctgcccc cctgaaaatt gttcaggcta ctgtacctgt agtcattgct       60
tggagcaacc aggctgtggc tggtgtactg atcccagcaa tactggcaaa gggaaatgca      120
tagagggttc ctataaagga ccagtgaaga tgccttcgca agcccctaca ggaaatttct      180
atccacagcc cctgctcaat tccagcatgt gtctagagga cagcagatac aactggtctt      240
tcattcactg tccagcttgc caatgcaacg gccacagtaa atgcatcaat cagagcatct      300
gtgagaagtg tgagaacctg accacaggca agcactgcga gacctgcata tctggcttct      360
```

```
acgtgatcc caccaatgga gggaaatgtc agccatgcaa gtgcaatggg cacgcgtctc    420
tgtgcaacac caacacgggc aagtgcttct gcaccaccaa gggcgtcaag ggggacgagt    480
gccagctatg tgaggtagaa aatcgatacc aaggaaaccc tctcagagga acatgttatt    540
atactcttct tattgactat cagttcacct ttagtctatc ccaggaagat gatcgctatt    600
acacagctat caattttgtg ctactcctg acgaacaaaa cagggatttg acatgttca     660 tcaatgcctc caagaatttc aacctcaaca tcacctgggc tgccagtttc tcagctggaa    720
cccaggctgg agaagagatg cctgttgttt caaaaaccaa cattaaggag tacaaagata    780
gtttctctaa tgagaagttt gattttcgca accacccaaa tatcactttc tttgtttatg    840
tcagtaattt cacctggccc atcaaaattc agattgcctt ctctcagcac agcaatttta    900
tggacctggt acagttcttc gtgactttct tcagttgttt cctctctttg ctcctggtgg    960
ctgctgtggt ttggaagatc aaacaaagtt gttgggcctc cagacgtaga gagcaacttc   1020
ttcgagagat gcaacagatg gccagccgtc cctttgcctc tgtaaatgtc gccttggaaa   1080
cagatgagga gcctcctgat cttattgggg ggagtataaa gactgttccc aaacccattg   1140
cactggagcc gtgttttggc aacaaagccg ctgtcctctc tgtgtttgtg aggctccctc   1200
gaggcctggg tggcatccct cctcctgggc agtcaggtct tgctgtggcc agcgccctgg   1260
tggacatttc tcagcagatg ccgatagtgt acaaggagaa gtcaggagcc gtgagaaacc   1320
ggaagcagca gccccctgca cagcctggga cctgcatctg atgctggggc cagggactct   1380
cccacgcacg agctagtgag tggcacacca gagccatctg cagggaaggg cgtggcgggg   1440
aaatggctgt gcggtgcggg acggaagact ggaaaccctc aaagcatctg actcacctgc   1500
atgatcacaa gctttctttg acggtttctc ccatccgtgt tccagcatct aaccttttac   1560
ttttgcatag gaaatacttg atttaattac aggtccaggg atgagctgat ggttgctgga   1620
ggaggccagt gtagagccag tgagagaact aggaatgaca ctcaggttca ctgtggaaaa   1680
ctgttcttgg gactgtctca actgtgcaaa aaacaaaaga tggagtgttt acaagtagac   1740
attcgtcatc agttgttctt gaacatggtc ttttaaaaac tagtcagatg aattaacttg   1800
ttttcatctg aagcctgcta ctttttttaa aagatgtgct atttattctt gcacgattta   1860
ggcaattatc tctcttccag ggagtacctt tttttctagt tgagaattaa taatggtcca   1920
tctcttttga tcatatcaag ctaggataga aggggggcta ttttaaatgt caaggtcagc   1980
agtgttactt tgaatgtaaa ctggtataat aggtagtttt ctatagtaac ttgattaatt   2040
tagtcttaat ccatttgaaa ctctctcttc cttctctct gcctgtccct ctccttctcc    2100 atctcacccct ccctctctca cacatacaca cacaaacaca tacacacaac actaagtgcc   2160
tagactttaa atagatctag caattggaaa gttagtaagc ctaagttttt acataattgc   2220
attcctacat tcttgtaaaa tttaaatagc taccattggc aatctgcttt ttttctaaaa   2280
tctgatttgc agccaggaaa gaattttctc acccaaggaa catttgatct agcagcaggg   2340
atgagaggaa agcagaaatg aatgaactgt gaaagctcct gttttattta tcaaaaagga   2400
cactgtcaag aaggcgcccc ctgcccccac ccccgtgtca ccctaggcct gataagcgat   2460
cagaggaaag gactcattca tgtcacgctt ccttgagcag aaaagagcac tgagagcact   2520
tgggacccct ggatcagaga gcatctgtgt gtcctgcagc ctcctctgaa cttgtggttc   2580
attctcaggc tggggtggac tcagatgcca ggaaagggac agcctcccat tgtcaggcag   2640
aagctgccca agcctggag aaggacttgt ttgccctctt tcccccagga ggggctcgac    2700
ccacccaccc tccctctcag accaaggtgg tggctgtgag gagggcagca aatgctgaca   2760
```

```
aggatgaaaa gcacatggaa aaaaatggac gaggagggaa aactctgcca aatggaaaat    2820
gaccaaattt aagagggtgg gacagtcccc tgctcctctc ccagagggca ctgcttggaa    2880
attgtgtttt ccccatttat ggtgctctgt attctggcat tatgcagcag cctcccagaa    2940
gctctcttct gcttcaaaac ctgggatctc tggcattacc ctattgggat ggaccgctgg    3000
acagcaatgc tcgagtttgt gaatttggag agatactcaa aagagctaaa actgcagcat    3060
tttaccttta aatgcagtgc ctagagagag agtattgtct cttccccaac actaacccca    3120
ctcccatgaa gaattgcctg gaaagatgtt ttcaaggaat ttgaaccata aaacactatc    3180
tgatgcacag aacacctcta ctttgagact cacctctcat aaagcttctt tttcacatta    3240
ctgttaaaga ccagacgttc tagaaaagac ccctcctctc atgagctccc ccatccctgc    3300
tacagaacac agcacccatg gcgcctgcag tggactggcc ccttaattcc cacaggcccc    3360
cccagcaagg ccaaagggag gcccctgggt attgtcctcc tacaaggaag atcctctttg    3420
tttgttcaaa ggaccagttt tcctaggcca agaagtctc ttccccatgt tagtcctatg    3480
ccttgaaata tcatgcacca tgacccacag ccatctggtt atgtcttatt ttttttcctaa    3540 aagataatgt ttatttttaa aaaggaagga agaagcaagt gaagtttcat tctgctccag    3600
cggtggggaa gccgctgaat ccacctgctt ctcctttgca accgacagca aacagctttc    3660
tccggcctca gggcagaaaa agggaatggc agggagtaag aggcgctggg ctcggagcct    3720
gtttccaaga aggaattggt tgtcatctgg cagtgttgcg cgtcacaaga gagcctgtat    3780
ataaattaaa atagtcaaga caacactgac cttgcacttg tacataacta tacagtagtg    3840
tccagaatgt tcagacattc ggagtgtaca taaaacagaa aaaatcttca tgtattttta    3900
ttaaatataa caatgtctga gtttcaccta agatgttttt gtgccatatg ctggatatcc    3960
aggttctcgc caggccccga tacatgaata acaaacccaa gaaacgcatc cccattgtgt    4020
gatgtgttca gatgcatctg gcaccaatta ggtatttctt aaaacaggac tcatctgtca    4080
gagtgcacat gaaaaatcag gcagggaatc gaaacgacag cgctggagga gactcaggaa    4140
gcagaggcgt ccctgccgct gcccttggcc ctgcaagcac atcatgaccc tttctggcag    4200
cctcttggtg ctctgggtag tgagggatga ccagtcttgt cctgagaaat gtttctctta    4260
gtctttaagt tcaaagacta acctgtagca atcagacttt ccaaaagggg gttctccatt    4320
ttttgtagtt ttgtctaaat ttttaatgac catttcctgg aatcagttta ttatactgaa    4380 aactggggt gggagtaggg agctagtttg ttgataaata gttcccattt ccccgtggag    4440
aatttgacat accctggact cctgtgtgcc tcctgccatc cctgcacaca gcctggggag    4500
aagcctgtgc ctccccgtgt ggagagaagg caacccccaga tcccctgagc taacccggag    4560
gaaaggcagt cctggacaga agactgtcag cagaaggaaa gtactggact acccgtgggt    4620
aagtcctgcc attcaagact ggagacacct gggaaataaa aagagcaggg cactgctggt    4680
gggaagaggc attttacctt ccagtgcaaa tcctgctcct ttgatttaat ggggtgtact    4740
ggggccaggg gctgattcac ttccttggga gatggtggtg ttttcatgaa catctttgat    4800
ccttccattt catttattca tccatccatt caacaagtat ttgctaaaca ctaacttaag    4860
ctaatgctag ggtagtgact gagatgtaaa aatagatttt agaattaaaa caaaatccaa    4920
gtcctcacac ccctgtcatc ccaggagatc tttccttgtg gtggtttctg tgagaattgg    4980
ccatcctgag gacacagcca ggacggcaga ggcctcctgg cctcagggca tgccctgcct    5040
accttctgaa atgtttaccc cattgaccaa acttggctcc agccattgcg gtggtttcta    5100
```

```
gatagccagg cccaccaaga gatattgccc cttgatgaga gtcaaacacc ctgcctacaa    5160
ggagatgttt tgaaatggag aggaaaattg gcacctcatc ttttaaaggc agtaatggaa    5220
ttgattttca gtaactgaat ttgtgcacaa aacattctaa acactagtga agcctgtttc    5280
gttgaactaa ttctggctct ggaaatgttt ttgttttata gttatttacg atttcgtttg    5340
tttggattca agcttagttt gttaatatgt ataatttagc atctattaca ctcatgtaaa    5400
tatggagtaa gtattgtaaa ctatttcatt gcggggattg tgggtgttat acatacattt    5460
aggactgcaa ttttttggta tttttttgtat tgtaaaataa cagctaattt aagcaggaac    5520
aagagaacta agggaggtct gtgcatttta aacacaaatg tgaagaactt gtatataaac    5580
aaaagtaaat actataatac aaacttcctt ctgaaataaa gtagatctg gt             5632
```

<210> SEQ ID NO 142
<211> LENGTH: 279
<212> TYPE: DNA
<213> ORGANISM: Homo Sapiens
<220> FEATURE:
<221> NAME/KEY: misc_feature
<222> LOCATION: (1)..(279)
<223> OTHER INFORMATION: n = a, c, g or t

<400> SEQUENCE: 142

```
agcacctgcc cccctgaaaa ttgttcaggc tactgtacct ntagtcattg cttggagcaa     60
ccaggctgtg gctggtgtac tgatcccagc aatactggca aagggaaatg catagagggt    120
tcctataaag gaccagtgaa gatgccttcg caagccccta caggaaattt ntatccacag    180
cccctgctca attccagcat gtnctagag gacagcagat acaactgggt ctttcatttc     240
actgtnccag tttgccaatg gaacgggcca cagtaaatg                            279
```

<210> SEQ ID NO 143
<211> LENGTH: 319
<212> TYPE: DNA
<213> ORGANISM: Homo Sapiens
<220> FEATURE:
<221> NAME/KEY: misc_feature
<222> LOCATION: (1)..(319)
<223> OTHER INFORMATION: n = a, c, g or t

<400> SEQUENCE: 143

```
ctgatccca gcaatactgg caaagggaaa tgcatagagg gttcctataa aggaccagtg       60
agatgccttt cgcaagcccc tacaggaaat ttntatccac agccctgct caattccagc      120 tgtntctag aggacagcag atacaactgg tctttcattc actgtccagc ttgccaatgc      180 acggccaca gtaaatgcat caatcagagc atctntgaga agtgtgagaa cctgaccaca      240 gcaagcact gcgagacctg catatctggc ttctacgggt gatnccacca attggaggga      300 atgtcagcc atgcaagtg                                                    319
```

<210> SEQ ID NO 144
<211> LENGTH: 464
<212> TYPE: DNA
<213> ORGANISM: Homo Sapiens
<220> FEATURE:
<221> NAME/KEY: misc_feature
<222> LOCATION: (1)..(464)
<223> OTHER INFORMATION: n = a, c, g or t

<400> SEQUENCE: 144

```
tttttttc tttttttttt ttttaattat actttaagtt ttaggttaca tgtgcacaac       60 tgcaggttt gttacatatg tatacatatg ccatgttggt gtgctgcacc cattaactcg     120
```

```
catttaaca ttaggtatat cccctaatgc tatcccttcc ccttcccccc accccacaac      180 ggccctggt gtgtgatgtt ccccttcctg tgtccatgcg tcctcattgt tcagtttgca      240 ctgaattt  gatgggccag gtgaaattac tgacataaac aaagaaagtg atatttggt       300 gttgcgaaa atcaaacttc tcattagaga aactatcttt gtactcctta atgttggttt      360 tgaaacaac aggcatctct tctccagcct gggttccagc tgagaaactg gcagcccagg      420 gatgttgag gttgaaattc ttggaggcat tgatgaacat gtcc                      464

<210> SEQ ID NO 145
<211> LENGTH: 370
<212> TYPE: DNA
<213> ORGANISM: Homo Sapiens
<220> FEATURE:
<221> NAME/KEY: misc_feature
<222> LOCATION: (1)..(370)
<223> OTHER INFORMATION: n =  a, c, g or t

<400> SEQUENCE: 145
tttttttttt tttctttttt tttttttaat tatactttaa gttttagggt acatgtgcac       60
aacatgcagg tttgttacat atgtatacat atgccatgtt ggtgtgctgc acccattaac      120
tcgtcattta acattaggta tatcccctaa tgctatccct tccccttccc cccaccccac      180
aacaggccct ggtgtgtgat gttccccttc ctgtgtccat gcgtcctcat tgttcagttt      240
gcacctgaat tttgatgggc caggtgaaat tactgacata aacaaagaaa gtgatatttg      300
ggtggttgcg aaaatcaaac ttctcattag agaaactatc tttgtactcc ttaatgttgg      360
tttttgaaac                                                            370

<210> SEQ ID NO 146
<211> LENGTH: 316
<212> TYPE: DNA
<213> ORGANISM: Homo Sapiens
<220> FEATURE:
<221> NAME/KEY: misc_feature
<222> LOCATION: (1)..(316)
<223> OTHER INFORMATION: n =  a, c, g or t

<400> SEQUENCE: 146
atactttaag ttttagggta catgtgcaca acatgcaggt ttgttacata tgtatacata       60
tgccatgttg gtgtgctgca cccattaact cgtcatttaa cattaggtat atcccctaat      120
gctatccctt ccccttcccc ccaccccaca acaggccctg gtgtgtgatg ttccccttcc      180
tgtgtccatg cgtcctcatt gttcagtttg cacctgaatt ttgatgggcc aggtgaaatt      240
actgacataa acaaagaaag tgatatttgg ggtggttgcg aaaatcaaac ttctcattag      300
agaaactatc tttgta                                                     316

<210> SEQ ID NO 147
<211> LENGTH: 308
<212> TYPE: DNA
<213> ORGANISM: Homo Sapiens
<220> FEATURE:
<221> NAME/KEY: misc_feature
<222> LOCATION: (1)..(308)
<223> OTHER INFORMATION: n =  a, c, g or t

<400> SEQUENCE: 147
ggtggccagc gccctggtgg acattttctc agcagatgcc gatagtgtac acaggagaag       60
tcaggagccg tgagaaaccg gaagcagcag ccccctgcac agmctgggac ctgcatctga      120
```

-continued

```
tgctggggcc agggcactct cccacgsacg cagctagats agtcgcacac cagagccatc      180
tgcagggaag ggcgtcgcgg ggaaatggct gtccggtgcg ggacggaaga ctggaaaccc      240
tcaaagcatc tgactcacct gcatgatcac aagstttctt tgacggtttc tcccatccgt      300
gttccagc                                                               308
```

<210> SEQ ID NO 148
<211> LENGTH: 342
<212> TYPE: DNA
<213> ORGANISM: Homo Sapiens
<220> FEATURE:
<221> NAME/KEY: misc_feature
<222> LOCATION: (1)..(342)
<223> OTHER INFORMATION: n = a, c, g or t

<400> SEQUENCE: 148

```
gctattttaa atgtcaaggt cagcagtgtt actttgaatg taaactggta taataggtag       60
ttttctatag taacttgatt aatttagtct taatccattt gaaactctct cttcctttct      120
ctctgcctgt ccctctcctt ctccatctca ccctccctct ctcacacata cacacacaaa      180
cacatacaca caacactaag tgcctagact ttaaatagat ctagcaattg gaaagttagt      240
aagcctaagt ttttacataa ttgcattcct acattcttgt aaaatttaaa tagctaccat      300
tggcaatctg ctttttttct aaaatctgat ttgcagccag gg                        342
```

<210> SEQ ID NO 149
<211> LENGTH: 305
<212> TYPE: DNA
<213> ORGANISM: Homo Sapiens
<220> FEATURE:
<221> NAME/KEY: misc_feature
<222> LOCATION: (1)..(305)
<223> OTHER INFORMATION: n = a, c, g or t

<400> SEQUENCE: 149

```
aagaagaaag catagaggtt gattggggtg ggggcagggg gcgccttctt gacagtgtcc       60
tttttgataa taaaaacagg rgctttcaca gttcattcat ttctgctttc ctctcatccc      120
tgctgctaga tcaaatgttc cttgggtgag aaaattcttt cctggctgca aatcagattt      180
tagaaaaama gcagattscc aatggtagct atttaamtyt yacaagaatg taggaatgca      240
attatgtaaa amcttaggct tactaactty ccagttgcta gayctattta avgtctaggc      300
actta                                                                  305
```

<210> SEQ ID NO 150
<211> LENGTH: 267
<212> TYPE: DNA
<213> ORGANISM: Homo Sapiens
<220> FEATURE:
<221> NAME/KEY: misc_feature
<222> LOCATION: (1)..(267)
<223> OTHER INFORMATION: n = a, c, g or t

<400> SEQUENCE: 150

```
gatcctcttt gtttgtncaa aggaccagtt ttcctaggcc aaagaagtct ctnccccatg       60 taagnccta tgccttnaaat atcatgcacc atgacccaca gccatctggt tatgtcttat      120
ttttttccta aaagataatg tttatnntta aaaggaagg anggagcaag tgaagtttca      180
ttctgctcca gcggtgggg angccgctga atccacctgn ttctccttt gcaaccgnca      240 gcangcagct tttctccggg cnncagg                                          267
```

-continued

```
<210> SEQ ID NO 151
<211> LENGTH: 173
<212> TYPE: DNA
<213> ORGANISM: Homo Sapiens
<220> FEATURE:
<221> NAME/KEY: misc_feature
<222> LOCATION: (1)..(173)
<223> OTHER INFORMATION: n =  a, c, g or t

<400> SEQUENCE: 151
ctgggctcgg agcctgtttc caagaaggaa ttggttgtca tntngcagtg ttgcgcgtca      60
caagagagcc ngtatataan ttaaaatagt caagacaaca ctgaccttgc acttgtacat     120
aactatacag tagtgtccag aatgttcaga cattcggagt gtacataaaa cag            173

<210> SEQ ID NO 152
<211> LENGTH: 416
<212> TYPE: DNA
<213> ORGANISM: Homo Sapiens
<220> FEATURE:
<221> NAME/KEY: misc_feature
<222> LOCATION: (1)..(416)
<223> OTHER INFORMATION: n =  a, c, g or t

<400> SEQUENCE: 152
cttttatttc agaaggaagt ttgtattata gnatttactt tngtttatat acaagttctt      60
cacanttgng tttaaaatgc acagacctcc cttagntctc tngttcctgc ttaaattagc     120
tgttatttta caatacaaaa aataccaaaa aatngcagnc ctaaatgtat gnataacacc     180
cacaatcccc gcgatgaaat agnttacaat acttactcca tatttacatg agngtaatag    240
ntgctaaatn atacatatta acaaactaag gcttgaatcc aaacaaacgg aatcgnaaat    300
aactataaaa caaaaacatt tccagaggcc aganttaggg tcaacgnaac gggcttcact    360
aggngtttag gnatgttttg gggcacaaat tcaggntacc gnaaatccaa ttccct        416

<210> SEQ ID NO 153
<211> LENGTH: 258
<212> TYPE: DNA
<213> ORGANISM: Homo Sapiens
<220> FEATURE:
<221> NAME/KEY: misc_feature
<222> LOCATION: (1)..(258)
<223> OTHER INFORMATION: n =  a, c, g or t

<400> SEQUENCE: 153
tttttttttt tttcatttt accagatcta cttttatttc agaaggaagt ttgtattata      60
gtatttactt ttgtttatat acaagttctt cacatttgtg tttaaaatgc acagacctcc    120
cttagttctc tngttcctgc ttaaattagc tgttatttta caatacaaaa aataccaaaa    180
aattgcagtc ctaaatgtat gtataacacc cacaatcccc gcaatgaaat agtttacaat    240
acttacncca tatttaca                                                  258
```